US010464896B2

(12) United States Patent
Dreier et al.

(10) Patent No.: US 10,464,896 B2
(45) Date of Patent: Nov. 5, 2019

(54) EFFLUX-PUMP INHIBITORS AND THERAPEUTIC USES THEREOF

(71) Applicants: Basilea Pharmaceutica International AG, Basel (CH); MME Muller-Regush, Strasbourg (FR)

(72) Inventors: Jürg Dreier, Basel (CH); Berangere Gaucher, Basel (CH); Eric Desarbre, Basel (CH); Marc Muller

(73) Assignee: Basilea Pharmaceutica International AG, Basel (CH)

( * ) Notice: Subject to any disclaimer, the term of this patent is extended or adjusted under 35 U.S.C. 154(b) by 0 days.

(21) Appl. No.: 15/580,008

(22) PCT Filed: Jun. 13, 2016

(86) PCT No.: PCT/EP2016/063487
§ 371 (c)(1),
(2) Date: Dec. 6, 2017

(87) PCT Pub. No.: WO2016/198691
PCT Pub. Date: Dec. 15, 2016

(65) Prior Publication Data
US 2018/0179158 A1 Jun. 28, 2018

(30) Foreign Application Priority Data
Jun. 11, 2015 (EP) ...................... 15001729

(51) Int. Cl.
C07D 211/26 (2006.01)
C07D 403/12 (2006.01)
(Continued)

(52) U.S. Cl.
CPC .......... *C07D 211/26* (2013.01); *A61K 31/397* (2013.01); *A61K 31/40* (2013.01);
(Continued)

(58) Field of Classification Search
CPC ................................................... C07D 211/26
(Continued)

(56) References Cited

U.S. PATENT DOCUMENTS 4,038,412 A 7/1977 Grisar et al.
4,140,770 A 2/1979 Repplinger et al.
(Continued)

FOREIGN PATENT DOCUMENTS

CA 2024581 A1 3/1991
CA 2033190 C 4/2003
(Continued)

OTHER PUBLICATIONS

Lorthior et al. Analytical Chemistry, 73(5), 963-970 (2001).*
(Continued)

*Primary Examiner* — Kahsay Habte

(57) ABSTRACT

The present invention relates to compounds of formula I or pharmaceutically acceptable salt, solvate or hydrate thereof, wherein ASC is —N(R8)(R9)ASC-1 ASC-1 is Ring A represents a 4- to 6-membered saturated ring containing carbon atoms as ring members in addition to the nitrogen atom and wherein one CH2 moiety in ring A is optionally replaced by CH(R21) and wherein one carbon atom in ring A that is not adjacent to the nitrogen atom is optionally replaced by O, and wherein ring A is connected to X via a carbon atom; X represents a bond, —CH2- or —C(=O)—; AR1, AR2 represent independently phenyl or a 5- to 6-membered heteroaryl ring containing one to three heteroatoms selected from O, S and N, wherein AR1 is connected to L1 via a carbon atom, and wherein AR2 is connected to L1 and L2 via a carbon atom; R1, R2, R3 represent independently hydrogen, halogen, cyano, hydroxyl, C1-C6alkyl, C1-C6haloalkyl, C3-C8cycloalkyl, C1-C6alkoxy, C1-C6haloalkoxy, —C1-C6alkylene-N(R12)R13, —N(R12)R13, —C(O)OR111, —C(O)N(R12)R13, —S(O)OR11 or phenyl; R4 represents hydroxyl, hydrogen, halogen, nitro, cyano, amino, C1-C6alkyl optionally substituted by 1 to 5 R14, C2-C6alkenyl optionally substituted by 1 to 5 R14, C2-C6alkynyl optionally substituted by 1 to 5 R14, C1-C6alkoxy optionally substituted by 1 to 5 R14, C2-C6alkenyloxy optionally substituted by 1 to 5 R14, C2-C6alkynyloxy optionally substituted by 1 to 5 R14, —C(O)OR15, —CHO, —C(O)N(R16)R17, —C1-C6alkylene-N(R9)(R16)R17, —O-Cycle-P or —O-Cycle-Q; R5, R6, R7 represent independently hydrogen, halogen, cyano, C1-C6alkyl, C1-C6haloalkyl, C1-C6alkoxy or C1-C6haloalkoxy; R8 represents hydrogen, methyl or ASC-1; R9 is methyl or absent, and wherein when R9 is present the respective nitrogen atom carries a positive charge; R10 represents hydrogen or methyl; R11 represents independently at each occurrence hydrogen or C1-C6alkyl; R12, R13 represent independently at each occurrence hydrogen or C1-C6alkyl; R14 represents independently at each occurrence halogen, cyano, hydroxyl, C1-C6alkoxy, C1-C6haloalkoxy, C3-C8cycloalkyl, —C(O)OR11, —CHO, —C(O)N(R12)R13, —C1-C6alkylene-N(R12)R13, Cycle-P, O-Cycle-P, Cycle-Q or O-Cycle-Q; Cycle-P represents independently at each occurrence a saturated or partially unsaturated C3-C8 carbocyclic ring optionally substituted by 1 to 3 R18, or a saturated or partially unsaturated C3-C8 heterocyclic ring optionally substituted by 1 to 3 R18 containing carbon atoms as ring members and one or two ring members independently selected from N(R9)(R12), N(R9) and O; Cycle-Q represents independently at each occurrence phenyl optionally substituted by 1 to 3 R19 or a 5- to 6-membered heteroaryl ring containing one to four heteroatoms selected from O, S and N, optionally substituted by 1 to 3 R19; R15 represents independently at each occurrence hydrogen or C1-C6alkyl optionally substituted by 1 to 5 R14; R16 and R17 represent independently at each
(Continued)

occurrence hydrogen or C1-C6alkyl optionally substituted by 1 to 5 R14; R18 and R19 represent independently at each occurrence halogen, cyano, hydroxyl, oxo, amino, C1-C4alkyl, C1-C4haloalkyl, C1-C4alkoxy, C1-C4haloalkoxy or —CO(O)R11; R20 represents independently at each occurrence hydrogen or methyl; R21 represents N(R20)2 or CH2-N(R20)2; LI represents —CH═CH—, —CH2-O—, —O—CH2-, —CH2-O—CH2-, —CH2-S—, —S—CH2-, —CH2-S(O)—, —CH2-S(O2)-, —S(O)—CH2-; —S(O2)-CH2-, —C(CH3)(CH3)-, —C(═O)—NH—, —NH—C(═O)—, —CH2-CH2-, —CH═CH—CH2-, —CH2-NH—C(═O)—, —C(═O)—NH—CH2, —C≡C—, —S(O2)-NH—CH2-, —S(O2)-NH, —O—CH2-CH2-O—, —O—, —NH— CH2-, —CH2-NH—, —CH2-CH2-O—, or —NH—C(═O)—CH2-O—, or a bond; L2 represents C1-C7alkylene, wherein one or more CH2 moieties in the alkylene are optionally replaced independently by —N(R9)(R20)-, —CH(N(R9)(R20)(R20))-, or —C(═O)—, wherein within L2 there are no adjacent C(═O) moieties or adjacent —N(R9)(R20)— moieties, and wherein the terminal moiety of L2 is not —N(R9)(R20)-, or L2 represents —O—C1-C6alkylene-, or L2 represents a bond, providing that X represents —CH2- when L2 is a bond; as well as methods of using the compounds of formula I for treating or preventing bacterial infections.

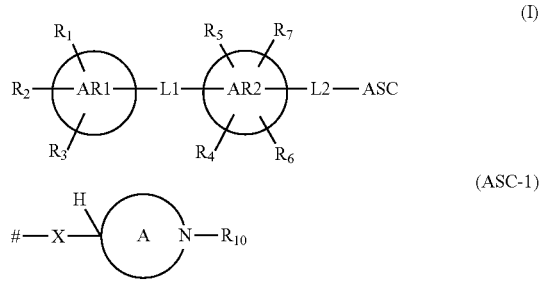

(I)

(ASC-1)

48 Claims, No Drawings

(51) Int. Cl.

| C07D 401/12 | (2006.01) |
|---|---|
| C07D 405/12 | (2006.01) |
| C07D 409/12 | (2006.01) |
| C07D 413/12 | (2006.01) |
| C07D 417/12 | (2006.01) |
| C07D 417/14 | (2006.01) |
| C07D 205/04 | (2006.01) |
| C07D 265/30 | (2006.01) |
| C07D 207/09 | (2006.01) |
| A61P 31/04 | (2006.01) |
| A61K 31/397 | (2006.01) |
| A61K 31/40 | (2006.01) |
| A61K 31/4025 | (2006.01) |
| A61K 31/4155 | (2006.01) |
| A61K 31/4178 | (2006.01) |
| A61K 31/4245 | (2006.01) |
| A61K 31/427 | (2006.01) |
| A61K 31/4439 | (2006.01) |
| A61K 31/444 | (2006.01) |
| A61K 31/4465 | (2006.01) |
| A61K 31/4468 | (2006.01) |
| A61K 31/5375 | (2006.01) |
| A61K 31/5377 | (2006.01) |
| A61K 31/65 | (2006.01) |
| C07D 207/14 | (2006.01) |
| C07D 207/16 | (2006.01) |
| C07D 211/58 | (2006.01) |
| C07D 401/14 | (2006.01) |
| C07D 413/14 | (2006.01) |

(52) U.S. Cl.
CPC ...... *A61K 31/4025* (2013.01); *A61K 31/4155* (2013.01); *A61K 31/4178* (2013.01); *A61K 31/427* (2013.01); *A61K 31/4245* (2013.01); *A61K 31/444* (2013.01); *A61K 31/4439* (2013.01); *A61K 31/4465* (2013.01); *A61K 31/4468* (2013.01); *A61K 31/5375* (2013.01); *A61K 31/5377* (2013.01); *A61K 31/65* (2013.01); *A61P 31/04* (2018.01); *C07D 205/04* (2013.01); *C07D 207/09* (2013.01); *C07D 207/14* (2013.01); *C07D 207/16* (2013.01); *C07D 211/58* (2013.01); *C07D 265/30* (2013.01); *C07D 401/12* (2013.01); *C07D 401/14* (2013.01); *C07D 403/12* (2013.01); *C07D 405/12* (2013.01); *C07D 409/12* (2013.01); *C07D 413/12* (2013.01); *C07D 413/14* (2013.01); *C07D 417/12* (2013.01); *C07D 417/14* (2013.01)

(58) Field of Classification Search
USPC .......................................................... 514/154
See application file for complete search history.

(56) References Cited

U.S. PATENT DOCUMENTS

| 5,212,182 | A | 5/1993 | Musser et al. |
|---|---|---|---|
| 5,945,454 | A | 8/1999 | Pevarello et al. |
| 6,087,135 | A | 7/2000 | Kierulff |
| 6,399,629 | B1 | 6/2002 | Chamberland et al. |
| 6,538,137 | B1 | 3/2003 | Nakada et al. |
| 6,649,619 | B1* | 11/2003 | Hickey ............... C07D 239/56 514/258.1 |
| 6,706,745 | B1 | 3/2004 | Hara et al. |
| 7,358,249 | B2 | 4/2008 | Murai et al. |
| 7,429,609 | B2 | 9/2008 | Ohi et al. |
| 7,511,136 | B2 | 3/2009 | Amici et al. |
| 7,968,748 | B2 | 6/2011 | Napolitano et al. |
| 8,093,266 | B2 | 1/2012 | Dahmann et al. |
| 8,153,647 | B2 | 4/2012 | Bocskei et al. |
| 8,193,237 | B2 | 6/2012 | Enomoto et al. |
| 8,399,449 | B2 | 3/2013 | Fujii et al. |
| 8,445,539 | B2 | 5/2013 | Izzo et al. |
| 8,889,665 | B2 | 11/2014 | Sapountzis et al. |
| 8,962,648 | B2 | 2/2015 | Nakamura et al. |
| 9,145,425 | B2 | 9/2015 | Hisakawa et al. |
| 9,163,013 | B2 | 10/2015 | Alisi et al. |
| 9,238,657 | B2 | 1/2016 | Nishitani et al. |
| 9,359,298 | B2 | 6/2016 | Li et al. |
| 9,359,346 | B2 | 6/2016 | Lee et al. |
| 9,422,285 | B2 | 8/2016 | Vakalopoulos et al. |
| 9,447,090 | B2 | 9/2016 | Koga et al. |
| 2002/0032238 | A1 | 3/2002 | Priepke et al. |
| 2003/0186963 | A1 | 10/2003 | Dorwald |
| 2003/0225076 | A1 | 12/2003 | Biwersi |
| 2004/0053967 | A1 | 3/2004 | Hara et al. |
| 2004/0224967 | A1 | 11/2004 | Chen |
| 2005/0101675 | A1 | 5/2005 | Hara et al. |
| 2007/0015832 | A1 | 1/2007 | Laughlin |
| 2007/0142455 | A1 | 7/2007 | Thaler et al. |
| 2007/0275968 | A1 | 11/2007 | Kurata et al. |
| 2009/0197871 | A1 | 8/2009 | Callahan et al. |
| 2011/0172230 | A1 | 7/2011 | Ishii et al. |

(56) References Cited

U.S. PATENT DOCUMENTS

| | | |
|---|---|---|
| 2012/0046301 A1 | 2/2012 | Frank et al. |
| 2012/0082713 A1 | 4/2012 | Meyering et al. |
| 2014/0023611 A1 | 1/2014 | Lewis et al. |
| 2015/0133465 A1 | 5/2015 | LaVoie et al. |
| 2015/0274719 A1 | 10/2015 | Vakalopoulos et al. |

FOREIGN PATENT DOCUMENTS

| | | | |
|---|---|---|---|
| CN | 103130791 A | | 6/2013 |
| EP | 1652839 A2 | | 5/2006 |
| EP | 2277861 A1 | | 1/2011 |
| GB | 2039276 A | | 8/1980 |
| JP | 2013112657 A | | 6/2013 |
| WO | 9511240 A1 | | 4/1995 |
| WO | 9605729 A1 | | 2/1996 |
| WO | 9610999 A2 | | 4/1996 |
| WO | 9611192 A1 | | 4/1996 |
| WO | 9807692 A1 | | 2/1998 |
| WO | 9856771 A1 | | 12/1998 |
| WO | 0117995 A1 | | 3/2001 |
| WO | 0149288 A1 | | 7/2001 |
| WO | 0155111 A1 | | 8/2001 |
| WO | WO-0160805 A1 * | | 8/2001 ........... C07D 239/56 |
| WO | 0185695 A1 | | 11/2001 |
| WO | 0217712 A2 | | 3/2002 |
| WO | 0224649 A1 | | 3/2002 |
| WO | 0230904 A1 | | 4/2002 |
| WO | 0230911 A1 | | 4/2002 |
| WO | 02051831 A1 | | 7/2002 |
| WO | 02069901 A2 | | 9/2002 |
| WO | 02083641 A2 | | 10/2002 |
| WO | 03024928 A2 | | 3/2003 |
| WO | 03037271 A2 | | 5/2003 |
| WO | 03041641 A2 | | 5/2003 |
| WO | 03068418 A2 | | 8/2003 |
| WO | 03080573 A1 | | 10/2003 |
| WO | 03104198 A1 | | 12/2003 |
| WO | 2004004720 A1 | | 1/2004 |
| WO | 2004005267 A2 | | 1/2004 |
| WO | 04062601 A2 | | 7/2004 |
| WO | 04076412 A2 | | 9/2004 |
| WO | 2004081005 A1 | | 9/2004 |
| WO | 04092123 A2 | | 10/2004 |
| WO | 05002673 A1 | | 1/2005 |
| WO | 2005003118 A1 | | 1/2005 |
| WO | 05011573 A2 | | 2/2005 |
| WO | 05011675 A1 | | 2/2005 |
| WO | 05012270 A2 | | 2/2005 |
| WO | 2005047249 A1 | | 5/2005 |
| WO | 05066163 A1 | | 7/2005 |
| WO | 05087236 A1 | | 9/2005 |
| WO | 2005115972 A1 | | 12/2005 |
| WO | 06055553 A1 | | 5/2006 |
| WO | 2006057845 A1 | | 6/2006 |
| WO | 2006063791 A1 | | 6/2006 |
| WO | 2006063813 A2 | | 6/2006 |
| WO | 2006086705 A1 | | 8/2006 |
| WO | 2006089100 A1 | | 8/2006 |
| WO | 2006138475 A2 | | 12/2006 |
| WO | 2007056338 A2 | | 5/2007 |
| WO | 2007136680 A2 | | 11/2007 |
| WO | 2008071387 A1 | | 6/2008 |
| WO | 2008084223 A2 | | 7/2008 |
| WO | 2008100618 A2 | | 8/2008 |
| WO | 2008101195 A2 | | 8/2008 |
| WO | 2008103613 A2 | | 8/2008 |
| WO | 2008111299 A1 | | 9/2008 |
| WO | 2009002495 A1 | | 12/2008 |
| WO | 2009048547 A1 | | 4/2009 |
| WO | 2009049305 A2 | | 4/2009 |
| WO | 2009100167 A1 | | 8/2009 |
| WO | 2009130469 A1 | | 10/2009 |
| WO | 2009158375 A1 | | 12/2009 |
| WO | 2010033643 A2 | | 3/2010 |
| WO | 2010052448 A2 | | 5/2010 |
| WO | 2010111353 A1 | | 9/2010 |
| WO | 2010141817 A1 | | 12/2010 |
| WO | 2011025838 A1 | | 3/2011 |
| WO | 2011054841 A1 | | 5/2011 |
| WO | 2012028676 A1 | | 3/2012 |
| WO | 2012054110 A2 | | 4/2012 |
| WO | 2012068589 A2 | | 5/2012 |
| WO | 2012079154 A1 | | 6/2012 |
| WO | 2013064543 A1 | | 5/2013 |
| WO | 2013070657 A1 | | 5/2013 |
| WO | 2013151991 A1 | | 10/2013 |
| WO | 2014068388 A1 | | 5/2014 |
| WO | 2014165143 A1 | | 10/2014 |
| WO | 2014190096 A1 | | 11/2014 |
| WO | 2015002915 A1 | | 1/2015 |
| WO | 2015034820 A1 | | 3/2015 |
| WO | 2016077818 A1 | | 5/2016 |

OTHER PUBLICATIONS

The International Search Report and Written Opinion, dated Aug. 2, 2016, in the corresponding PCT Appl. No. PCT/EP2016/063487.
STN Registry No. 1216651-00-1, entered STN: Apr. 4, 2010. XP002744631.
STN Registry No. 1216785-78-2, entered STN: Apr. 5, 2010. XP002744632.
STN Registry No. 1377769-70-4, entered STN: Jun. 13, 2012. XP002744633.
STN Registry No. 1280889-95-3, entered STN: Apr. 17, 2011. XP002744634.
STN Registry No. 1427551-24-3, entered STN: Apr. 9, 2013. XP002744635.
STN Registry No. 1568462-40-7, entered STN: Mar. 14, 2014. XP002744636.
STN Registry No. 1572002-48-2, entered STN: Mar. 21, 2014. XP002744637.
STN Registry No. 1572341-88-8, entered STN: Mar. 24, 2014. XP002744638.
STN Registry No. 1574781-10-4, entered STN: Mar. 27, 2014. XP002744639.
STN Registry No. 1581213-53-7, entered STN: Apr. 7, 2014. XP002744640.
STN Registry No. 1603803-68-4, entered STN: May 13, 2014. XP002744641.
STN Registry No. 1588390-29-7, entered STN: Apr. 22, 2014. XP002744642.
STN Registry No. 1591119-57-1, entered STN: Apr. 27, 2014. XP002744643.
STN Registry No. 1593686-48-6, entered STN: Apr. 30, 2014. XP002744644.
STN Registry No. 1597507-21-5, entered STN: May 5, 2014. XP002744645.
STN Registry No. 1601311-25-4, entered STN: May 9, 2014. XP002744646.
STN Registry No. 1606103-17-6, entered STN: May 16, 2014. XP002744647.
STN Registry No. 1606582-40-4, entered STN: May 19, 2014. XP002744648.
STN Registry No. 1606950-21-3, entered STN: May 19, 1921. XP002744649.
STN Registry No. 1648046-67-6, entered STN: Feb. 16, 2015. XP002744650.
STN Registry No. 1215818-94-2, entered STN: Apr. 2, 2010. XP002744651.
STN Registry No. 1605157-65-0, entered STN: May 14, 2015. XP002744652.
STN Registry No. 1604590-29-5, entered STN: May 14, 2014. XP002744653.
STN Registry No. 1590291-81-8, entered STN: Apr. 25, 2014. XP002744654.
STN Registry No. 1585964-69-7, entered STN: Apr. 17, 2014. XP002744655.

(56) References Cited

OTHER PUBLICATIONS

STN Registry No. 1585140-32-4, entered STN: Apr. 16, 2014. XP002744656.
STN Registry No. 924855-69-6, entered STN: Mar. 5, 2017. XP002744657.
STN Registry No. 1583636-04-7, entered STN: Apr. 13, 2014. XP002744658.
STN Registry No. 1583255-90-6, entered STN: Apr. 11, 2014. XP002744659.
STN Registry No. 1297503-65-1, entered STN: May 19, 2011. XP002744660.
STN Registry No. 1252112-09-6, entered STN: Nov. 9, 2010. XP002744661.
STN Registry No. 1216980-58-3, entered STN: Apr. 5, 2010. XP002744662.
STN Registry No. 1216483-68-9, entered STN: Apr. 4, 2010. XP002744663.
STN Registry No. 1215759-26-4, entered STN: Apr. 2, 2010. XP002744664.
STN Registry No. 1197605-94-9, entered STN: Dec. 16, 2009. XP002744665.
STN Registry No. 1050502-78-7, entered STN: Sep. 19, 2008. XP002744666.
STN Registry No. 1031184-55-0, entered STN: Jun. 27, 2008. XP002744667.
Search results from the Reaxys database, Jan. 23, 2015. Total 20 pages.
SureChembl Citations, Feb. 2015. Total 16 pages.
Registry citations, entered STN: prior to Sep. 22, 2014. Total 173 pages.
HCAPLUS citations, prior to 2012. Total 9 pages.
Chemical structures from the Scifinder database, Apr. 2015. Total 283 pages.
Ayesa et al. "An Expeditious Library Synthesis of N-Monoalkylated Aminopiperidines and -pyrrolidines", European Journal of Organic Chemistry 12, 2723-2737, 2004.
Zhang et al. Identification and characterization of small molecule inhibitors of signal transducer and activator of transcription 3 (STATJ) signaling pathway by virtual screening 2, Bioorganic & Medicinal Chemistry Letters 23(7), 2225-2229, 2013.
Buemi et al., "Indole derivatives as dual-effective agents for the treatment of neurodegenerative diseases: Synthesis, biological evaluation, and molecular modeling studies", Bioorganic & Medicinal Chemistry 21(15), 4575-4580, 2013.
Kratz et al., "Experimentally Validated hERG Pharmacophore Models as Cardiotoxicity Prediction Tools", Journal of Chemical Information and Modeling 54(10), 2887-2901, 2014.
Moser et al., "PENG: A Neural Gas-Based Approach for Pharmacophore Elucidation. Method Design, Validation, and Virtual Screening for Novel Ligands of LTA4H" Journal of Chemical Information and Modeling 55(2), 284-293, 2015.
Brown et al., "Serendipity in drug-discovery: A new series of 2-(benzyloxy)benzamides as TRPMS antagonists", Bioorganic & Medicinal Chemistry Letters 23(22), 6118-6122, 2013.
Jenkins et al., "Design, Synthesis, and Evaluation of Naphthalene-Sulfonamide Antagonists of Human CCR5", Journal of Medicinal Chemistry 50(3), 566-584, 2007.
Ballell et al, "Fueling Open-Source Drug Discovery: 177 Small-Molecule Leads against Tuberculosis", ChemMedChem 8(2), 313-321, 2013.
Fish et al., "Derivatives of (35)-N-(biphenyl-2-ylmethyl)pyrrolidin-3-amine as selective noradrenaline reuptake inhibitors: Reducing P-gp mediated efflux by modulation of H-bond acceptor capacity", Bioorganic & Medicinal Chemistry Letters 18(15), 4355-4359, 2008.
Akahane et al, "A new chiral synthesis of wieland-miescher ketone catalyzed by a combination of (s)-n-benzyl-n-(2-pyrrolidinylmethy)amine derivative and bronsted acid", Heterocycles 77(2), 1065-1078, 2009.

Budzik et al., "2' Biaryl amides as novel and subtype selective M1 agonists. Part II: Further optimization and profiling", Bioorganic & Medicinal Chemistry Letters 20(12), 3545-3549, 2010.
Murchie et al., "Structure-based Drug Design Targeting an Inactive RNA Conformation: Exploiting the Flexibility of HIV-1 TAR RNA", Journal of Molecular Biology 336(3), 625-638, 2004.
Lu et al., "CCR5 receptor antagonists: Discovery and SAR of novel 4-hydroxypiperidine derivatives" Bioorganic and Medicinal Chemistry Letters 17(7) 1883-1887, 2007.
Keith et al., "Heteroarylureas with spirocyclic diamine cores as inhibitors of fatty acid amide hydrolase" Bioorganic and Medicinal Chemistry Letters 24(3) 737-741, 2014.
Crowley et al., "Diels-alder active-template synthesis of rotaxanes and metal-ion-switchable molecular shuttles" Journal of the American Chemical Society 132(14) 5309-5314, 2010.
Yang et al., "Synthesis of 2-(4-substituted benzyl-1,4-diazepan-1-yl)-N-(3,4-dihydro-3- oxo-2H benzo[b][1,4]oxazin-7-yl)acetamides and their positive inotropic evaluation" Bioorganic and Medicinal Chemistry Letters 20(15) 4464-4467, 2010.
Zhou et al., "Structural optimization and biological evaluation of substituted bisphenol a derivatives as β-amyloid peptide aggregation" Journal of Medicinal Chemistry 53(15) 5449-5466, 2010.
Fujita et al., "A recyclable dendritic osmium catalyst for homogeneous dihydroxylation of olefins", Tetrahedron 66(44), 8536-8543, 2010.
Fujita et al., "Homogeneous dihydroxylation of olefins catalyzed by a recyclable OsO42—core dendrimer", Tetrahedron Letters 51(5), 808-810, 2010.
Sugimoto et al., "Template-assisted control of porphyrin aggregation by ladder-type supramolecular assemblies", Tetrahedron Letters 46(32), 5347-5350, 2005.
Briere et al., "Synthesis of a Heterocyclic Amine and Acid Receptor", Tetrahedron 56(44), 8679-8688, 2000.
Briere et al., "Regioselective Reductions of Various 3-Aminosuccinimides; Application to the Synthesis of two Heterocyclic Systems.", Tetrahedron 53(6), 2075-2086, 1997.
Carrieri et al., "Biological profiling of anti-HIV agents and insight into CCR5 antagonist binding using in silico techniques", ChemMedChem 4(7), 1153-1163, 2009.
Nasveschuk et al., "Discovery and optimization of tetramethylpiperidinyl benzamides as inhibitors of EZH2", ACS Medicinal Chemistry Letters 5(4), 378-383, 2014.
Nenad et al., "Ring-opening reactions of 1,4-diazabicyclo[2.2.2]octane (DABCO) derived quaternary ammonium salts with phenols and related nucleophiles", Organic and Biomolecular Chemistry 10(6) 1300-1310, 2012.
Okabe et al., "Curing reaction of epoxy resin composed of mixed base resin and curing agent: Experiments and molecular simulation", Polymer (United Kingdom) 54(17) 4660-4668, 2013.
Vanhoutte et al., "Thermospray liquid chromatography-mass spectrometry of the DNA adducts formed between 2' deoxynucleosides and bisphenol A diglycidyl ether", Journal of Mass Spectrometry 30(10) 1453-1461, 1995.
Li et al., Synthesis and Positive Intropic Evaluatoin of 2-(4-(4-Substituted benzyloxy)-3-methoxybenzyl)-1,4-diazepan-1-yl)-N-(4,5-dihydro-1-methyl[1,2,4] triazolo[4,3-a]quinolin-7-yl)-acetamides, Archiv der Pharmazie 341(12), 794-799, 2008.
Ore et al., "Cyclic Compounds from the Reaction of Bisphenol A Diglycidyl Ether with Amines", Ada Chemica Scandinavica (1947-1973), 24, 2397-2407, 1970.
Song et al. "Preparation of Functionated POSS Nano-particle Bearing the Perfluoro Aryl Ether Dendron", Advanced Materials Research 148-149, 1212-1216, 2011.
Hankovsky et al., "New Antiarrhythmic Agents. 2,2,5,5-Tetramethyl-3-pyrroline-3-carboxamides and 2,2,5,5-Tetramethylpyrrolidine-3-carboxamides", New Journal of Medicinal Chemistry 29(7), 1138-52, 1986.
Hamada et al., (N-Substituted Imidazolines and Ethylenediamines and Their Action on alpha-and beta-Adrenergic Receptors, Journal of Medicinal Chemistry 28(9), 1269-73, 1985.

* cited by examiner

EFFLUX-PUMP INHIBITORS AND THERAPEUTIC USES THEREOF

This application is a National Stage Application of PCT/EP2016/063487 filed Jun. 13, 2016, which claims priority from European Patent Application No. 15001729.1, filed on Jun. 11, 2015. The priority of both said PCT and European Patent Application are claimed. Each of the prior mentioned applications is hereby incorporated by reference herein in its entirety.

The invention relates to compounds that act in combination with antimicrobial agents to enhance their potency, in particular inhibitors of microbial efflux pumps and use of these compounds in combination with antimicrobial compounds, in particular antibiotics, for treatment of bacterial and other microbial diseases. Antibiotics are important and effective drugs to treat bacterial infections in many clinical settings. The introduction of antibiotics to treat infectious diseases greatly improved public health in the twentieth century. Early on, bacteria started to develop resistance mechanisms to evade the action of antibacterial agents. The widespread use of various antibacterial agents promoted the evolution of multi-drug resistant pathogens and their global spread. Nowadays, increased occurrence of resistant pathogens, especially in hospitals and care centers, causes problems for the treatment of infections and leads to higher morbidity and mortality, longer treatment durations and increased costs (e.g. Gootz T. D. 2010. Critical Rev. Immunol. 30(1):79-93; Silver L. L. 2011. Clin. Microbiol. Rev. 24(1): 71-109; Denis G. A. and Relich R. F. Clin Lab Med 2014. 34: 257-270).

Bacteria achieve resistance by different mechanisms. Some mechanisms are specific for a drug or a class of antibiotics whereas other mechanisms are non-specific and affect several unrelated classes of antibiotics. Specific mechanisms can be modification of the drug target or inactivation of the drug by degradation or by enzymatic alteration. Non-specific mechanisms can be reduced uptake of a drug by lower permeability, by transport of drugs out of the bacterial cell or by combinations of both. The result is that drug concentrations that would normally kill bacterial cells are reduced at the target site to levels that allow the survival of the bacteria (Enzyme-Mediated Resistance to Antibiotics. Bonomo R. A. and Tolmasky M. Eds. ASM Press 2007; Martinez and Baquero 2014. Upsala J. Med. Sci. 119: 68-77; Piddock L. J. V. 2006. Clin. Microbiol. Rev. 19(2):382-402; Olivares et al. 2013. Front. Microbiol. 4, 103: doi 10.3389/fmicb.2013.00103). Active transport of antibiotics out of a bacterial cell can confer resistance and contribute significantly to high-level resistances. Multidrug efflux pumps can expel a large variety of chemically different substances including medically important antibiotics and disinfectants. Such systems are perceived as the predominant underlying mechanism of multi-drug resistance in bacteria (e.g. Li et al. 2015. Clin. Microbiol. Rev. 28(2): 337-418; Nikaido 2011. Adv. Enzymol. Relat. Areas Mol. Biol. 77:1-60; Poole 2005. J. Antimicrob. Chemother. 56: 20-51); Olivares et al. 2013. Front. Microbiol. 4:103).

Active drug transporters are divided into two major classes according to their mechanism of energization. Primary transporters like the ABC-type transporters hydrolyze ATP (a primary cellular energy source) to power drug efflux. Most bacterial drug-efflux systems known today belong to the class of secondary transporters using energy stored in the transmembrane electrochemical potential of protons or sodium. Transporters driven by this proton motive force (PMF) can be further divided into four groups based on size as well as structural features. These groups are the major facilitator superfamily (MFS), the small multidrug resistance family (SMR), the resistance nodulation division family (RND), and the multidrug and toxic compound extrusion family (MATE) (for reviews see: Microbial Efflux Pumps Wu, Zhang, Brown Eds. Caister Academic Press 2013; Sun et al. 2014 Biochem. Biophys. Res. Commun. 453(2):254-267). Members of the RND family are highly relevant in terms of multidrug efflux and resistance since they accept a wide variety of substrates. RND pumps are found in Gram-negative bacteria including the clinically relevant Enterobacteriaceae and glucose non-fermenters. Well described members are AcrAB-TolC in *Escherichia coli* and MexAB-OprM in *Pseudomonas aeruginosa*. X-ray structures of AcrAB-TolC and MexAB-OprM subunits were the first to be solved and boosted the understanding of the function of tripartite RND pumps (Nikaido H. 2011 Adv. Enzymol. Relat Areas Mol. Biol. 77:1-60; Murakami S. 2008. Curr. Opin. Struct. Biol. 18:459-465; Ruggerone et al. 2013. Curr. Top Med. Chem. 13(24):3079-100). Models for the structure of a complete RND complex were published on the example of AcrAB-TolC and for MexAB-OprM (Kim et al. 2015. Mol. Cells. 38(2): 180-186; Du et al. 2015. Trends Microbiol. 23: 311-319; Du et al. 2014. Nature 509:512-515; Trépout et al. 2010. Biochim. Biophys. Acta 1798: 1953-1960; Symmons et al. 2009. Proc. Natl. Acad. Sci. 106: 7173-7178). Pathways for substrate translocation through the assembled pump complex were described on the basis of X-ray crystal structures. Binding sites for a few substrates and inhibitors could be determined and computational simulation were used to describe dynamic interactions of substrates and inhibitors with efflux pumps (reviewed in Yamaguchi et al. 2015. Front Microbiol. 6:327; Ruggerone et al. 2013 Curr. Topics Med. Chem. 13(24):3079-3100).

The expression of RND pumps is regulated in response to environmental stress such as the presence of antibiotics (Morita et al. 2014. Front. Microbiol. 4, 422: doi: 10.3389/fmicb.2013.00422; Poole 2014. Can. J. Microbiol. 60:783-791). Enhanced efflux gene expression was found to cause antibiotic resistance. Many antibiotics lack activity against Gram-negative bacteria because of active drug efflux. Overexpression of MexAB-OprM for example, contributes substantially to fluoroquinolone- and β-lactam-resistance. MexXY, another RND pump from *P. aeruginosa*, contributes to decreased amikacin susceptibility and co-resistance to fluoroquinolones, carbapenems, and the cephalosporin antibiotic ceftazidime. Reduced or even lost activity due to efflux can be restored by efflux-pump inhibitors. Efflux pumps play a role in biofilm formation, quorum sensing, virulence and invasiveness. Hence, efflux pump inhibitors may be useful to combat several aspects of infections (e.g. Soto S. M. 2013. Virulence 4(3): 223-229; Hirakata et al. 2009. Int. J. Antimicrob. Agents. 34: 343-346).

Increased resistance occurrence and the fact that the number of new antibiotics that are developed dramatically declined in the recent years led to a need for new treatment options. Combination therapy is a proven approach to combat resistant pathogens. Efflux pumps are considered to be targets for inhibitors that can boost the activity of existing antimicrobial agents. Molecules of different sources like natural products (e.g. Piddock L. et al. 2010 J. Antimicrob. Chemother. 65:1215-1223; Starvi et al. 2007 J. Antimicrob. Chemother. 59(6): 1247-60; Li et al. 2015. Clin. Microbiol. Rev. 28(2): 337-418), inhibitors of human efflux pumps or new chemical entities were tested and described (reviewed in Van Bambeke et al. 2010. Frontiers in Anti-infective Drug Discovery 1:138-175; Van Bambeke et al. 2006. Recent patents on Anti-infective Drug Discovery; Zechini B. and Versace I. 2009. 4:37-50; Opperman and Nguyen 2015. Front. Microbiol. 6, 421: doi 10.3389/fmicb.2015.00421). Phenylalanine-arginine beta-naphthylamide (MC-207,110 or PAβN) from a series of peptidomimetic compounds and the pyridopyrimidine derivative D13-9001 are well studied examples of efflux-pump inhibitors.

EP1652839 and U.S. Pat. No. 6,399,629 describe drug efflux pump inhibitors.

The present invention provides new compounds and methods for treating bacterial infections.

In a first aspect the invention provides a compound of formula I for use in a method of treating a subject with a microbial infection or susceptible to a microbial infection, said method comprising administering the compound of formula I to said subject, wherein said subject is receiving the compound of formula I in combination with an antimicrobial agent and wherein the compound of formula I is

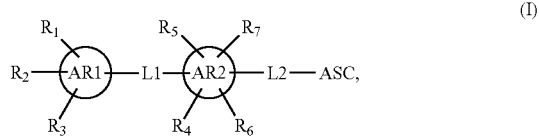

wherein
ASC is —N(R8)(R9)ASC-1;
ASC-1 is

Ring A represents a 4- to 6-membered saturated ring containing carbon atoms as ring members in addition to the nitrogen atom and wherein one CH2 moiety in ring A is optionally replaced by CH(R21) and wherein one carbon atom in ring A that is not adjacent to the nitrogen atom is optionally replaced by O;
X represents a bond, —CH2- or —C(=O)—, and wherein ring A is connected to X via a carbon atom; AR1, AR2 represent independently phenyl or a 5- to 6-membered heteroaryl ring containing one to three heteroatoms selected from O, S and N, wherein AR1 is connected to L1 via a carbon atom, and wherein AR2 is connected to L1 and L2 via a carbon atom;
R1, R2, R3 represent independently hydrogen, halogen, cyano, hydroxyl, C1-C6alkyl, C1-C6haloalkyl, C3-C8cycloalkyl, C1-C6alkoxy, C1-C6haloalkoxy, —C1-C6alkylene-N(R12)R13, —N(R12)R13, —C(O)OR11, —C(O)N(R12)R13, —S(O)OR11 or phenyl;
R4 represents hydrogen, halogen, hydroxyl, nitro, cyano, amino, C1-C6alkyl optionally substituted by 1 to 5 R14, C2-C6alkenyl optionally substituted by 1 to 5 R14, C2-C6alkynyl optionally substituted by 1 to 5 R14, C1-C6alkoxy optionally substituted by 1 to 5 R14, C2-C6alkenyloxy optionally substituted by 1 to 5 R14, C2-C6alkynyloxy optionally substituted by 1 to 5 R14, —C(O)OR15, —CHO, —C(O)N(R16)R17, —C1-C6alkylene-N(R9)(R16)R17, —O-Cycle-P or —O-Cycle-Q;

R5, R6, R7 represent independently hydrogen, halogen, cyano, C1-C6alkyl, C1-C6haloalkyl, C1-C6alkoxy or C1-C6haloalkoxy;
R8 represents hydrogen, methyl or ASC-1;
R9 is methyl or absent, and wherein when R9 is present the respective nitrogen atom carries a positive charge, i.e. to generate a quaternary amine;
R10 represents hydrogen or methyl;
R11 represents independently at each occurrence hydrogen or C1-C6alkyl;
R12, R13 represent independently at each occurrence hydrogen or C1-C6alkyl;
R14 represents independently at each occurrence halogen, cyano, hydroxyl, C1-C6alkoxy, C1-C6haloalkoxy, C3-C8cycloalkyl, —C(O)OR11, —CHO, —C(O)N(R12)R13, —C1-C6alkylene-N(R12)R13, Cycle-P, O-Cycle-P, Cycle-Q or O-Cycle-Q;
Cycle-P represents independently at each occurrence a saturated or partially unsaturated C3-C8 carbocyclic ring optionally substituted by 1 to 3 R18, or a saturated or partially unsaturated C3-C8 heterocyclic ring optionally substituted by 1 to 3 R18 containing carbon atoms as ring members and one or two ring members independently selected from N(R9)(R12) and O;
Cycle-Q represents independently at each occurrence phenyl optionally substituted by 1 to 3 R19 or a 5- to 6-membered heteroaryl ring containing one to four heteroatoms selected from O, S and N, optionally substituted by 1 to 3 R19;
R15 represents independently at each occurrence hydrogen or C1-C6alkyl optionally substituted by 1 to 5 R14;
R16 and R17 represent independently at each occurrence hydrogen or C1-C6alkyl optionally substituted by 1 to 5 R14;
R18 and R19 represent independently at each occurrence halogen, cyano, hydroxyl, oxo, amino, C1-C4alkyl, C1-C4haloalkyl, C1-C4alkoxy, C1-C4haloalkoxy or —CO(O)R11;
R20 represents independently at each occurrence hydrogen or methyl;
R21 represents N(R20)2 or CH2-N(R20)2; L1 represents —CH=CH— (Z, E or Z/E), —CH2-O—, —O—CH2-, —CH2-O—CH2—, —CH2-S—, —S—CH2-, —CH2-S(O)—, —CH2-S(O2)-, —S(O)—CH2-, —S(O2)-CH2-, —C(CH3)(CH3)-, —C(=O)—NH—, —NH—C(=O)—, —CH2-CH2-, —CH=CH—CH2- (Z, E or Z/E), —CH2-NH—C(=O)—, —C(=O)—NH—CH2, —C≡C—, —S(O2)-NH—CH2-, —S(O2)-NH, —O—CH2-CH2-O—, —O—, —NH—CH2-, —CH2-NH—, —CH2-CH2-O—, —NH—C(=O)—CH2-O— or a bond;
L2 represents C1-C7alkylene, wherein one or more CH2 moieties in the alkylene are optionally replaced independently by —N(R9)(R20)-, —CH(N(R9)(R20)(R20))—, or —C(=O)—, wherein within L2 there are no adjacent C(=O) moieties or adjacent —N(R9)(R20)- moieties, and wherein the terminal moiety of L2 is not —N(R9)(R20)-, or L2 represents —O—C1-C6alkylene- or L2 represents a bond, providing that X represents —CH2- when L2 is a bond;
including pharmaceutically acceptable salts, solvates, and hydrates of said compounds.

The compound of formula I is generally administered to the subject as a component of a combined therapy with an antimicrobial agent. The subject may have been treated with the antimicrobial agent prior to administration with the compound of formula I, or the treatment with the antimicrobial agent may be simultaneous with, or after administration of the compound of formula I.

In a further aspect the invention provides a compound of formula I for use in a method of treating a subject with a microbial infection or susceptible to a microbial infection, said method comprising administering the compound of formula I to said subject. In this case the subject will have received, is receiving or will receive additionally an antimicrobial agent in order to complete the treatment of the microbial infection. In a further aspect the invention provides a compound of formula I for use in a method for preventing or treating a microbial infection in a subject in combination with an antimicrobial agent.

In a further aspect the invention provides a compound of formula I for use in a method of treating a subject with a microbial infection or susceptible to a microbial infection, said method comprising administering the compound of formula I in combination with an antimicrobial agent to said subject.

In a further aspect the invention provides use of a compound of formula I in the manufacture of a medicament for treating a subject with a microbial infection or susceptible to a microbial infection, said method comprising administering the compound of formula I to said subject. In this case, the subject will have received, is receiving or will receive additionally an antimicrobial agent in order to complete the treatment of the microbial infection.

In a further aspect the invention provides a compound of formula I in the manufacture of a medicament for preventing or treating a microbial infection in a subject in combination with an antimicrobial agent.

In a further aspect the invention provides use of a compound of formula I in the manufacture of a medicament for treating a subject with a microbial infection or susceptible to a microbial infection, said method comprising administering the compound of formula I to said subject, and wherein said subject is receiving the compound of formula I in combination with an antimicrobial agent.

In a further aspect the invention provides use of a compound of formula I in the manufacture of a medicament for treating a subject with a microbial infection or susceptible to a microbial infection, said method comprising administering the compound of formula I in combination with an antimicrobial agent.

In a further aspect the invention provides a pharmaceutical product comprising a compound of formula I and an antimicrobial agent. In a further aspect the invention provides a method of treating a subject with a microbial infection or susceptible to a microbial infection, said method comprising administering the compound of formula I to said subject. In this case, the subject will have received, is receiving or will receive additionally an antimicrobial agent in order to complete the treatment of the microbial infection.

In a further aspect the invention provides a method of treating a subject with a microbial infection or susceptible to a microbial infection, said method comprising administering the compound of formula I to said subject, and wherein said subject is receiving the compound of formula I in combination with an antimicrobial agent.

In a further aspect the invention provides a method of treating a subject with a microbial infection or susceptible to a microbial infection, said method comprising administering the compound of formula I in combination with an antimicrobial agent to said subject.

Reference to microbial infections preferably refers to bacterial infections, and reference to microbial agents preferably refers to antibiotics.

Although many compounds of formula I are new, some compounds of formula I are known for uses other than as compounds for use in combination treatments with antimicrobial agents, i.e. as anti-bacterial efflux pump inhibitors, and in a further aspect the invention provides compounds of formula I as described above with the following provisos:

when L2 is C(=O), then R8 is ASC-1;

when L1 is a bond, then R1 is Br or C2-C6alkyl, and/or R4 is O—C2-C6alkenyl, O—C1-C6alkylene-Cycle-P1 or O—C1-C6alkylene-Cycle-Q1, wherein Cycle-P1 represents a saturated or partially unsaturated C3-C8 heterocyclic ring optionally substituted by 1 to 3 R18 containing carbon atoms as ring members and one or two ring members independently selected from N(R9)(R12) and O and Cycle-Q1 represents a 5- to 6-membered heteroaryl ring containing one to four heteroatoms selected from O, S and N, optionally substituted by 1 to 3 R19, preferably when L1 is a bond, then R1 is Br or C2-C6alkyl, and/or R4 is O—C2-C6alkenyl;

when L1 is —CH2-O— or —NH—C(=O)—CH2-O—, L2 is C1-C7alkylene as defined above, AR1 and AR2 are phenyl, ring A is a 6-membered ring, and R8 is hydrogen or methyl, then R1 is Br or C2-C6alkyl, and/or R4 is O—C2-C6alkenyl, O—C1-C6alkylene-Cycle-P1 or O—C1-C6alkylene-Cycle-Q1, preferably when L1 is —CH2-O— or —NH—C(=O)—CH2-O—, L2 is C1-C7alkylene as defined above, AR1 and AR2 are phenyl, ring A is a 6-membered ring, and R8 is hydrogen or methyl, then R1 is Br or C2-C6alkyl, and/or R4 is O—C2-C6alkenyl;

when L1 is —CH2-O— or —NH—C(=O)—CH2-O—, L2 is —CH2- or CH2-CH2-, AR1 and AR2 are phenyl, ring A is a 4- or 5-membered ring, X is C(=O) and R8 is hydrogen or methyl, then R1 is Br or C2-C6alkyl, and/or R4 is O—C2-C6alkenyl, O—C1-C6alkylene-Cycle-P1 or O—C1-C6alkylene-Cycle-Q1, preferably when L1 is —CH2-O—, L2 is —CH2- or CH2-CH2-, AR1 and AR2 are phenyl, ring A is a 4- or 5-membered ring, X is C(=O) and R8 is hydrogen or methyl, then R1 is Br or C2-C6alkyl, and/or R4 is O—C2-C6alkenyl;

when L1 is —O—CH2-, —CH2-O—CH2-, —C(=O)—NH—, —NH—C(=O)—, —CH2-NH—C(=O)—, —C≡C—, —O—CH2-CH2-O— or —O—, L2 is —CH2-, AR1 and AR2 are phenyl, X is C(=O) and R8 is hydrogen or methyl, then R1 is Br or C2-C6alkyl, and/or R4 is O—C2-C6alkenyl, O—C1-C6alkylene-Cycle-P1 or O—C1-C6alkylene-Cycle-Q1, preferably when L1 is —O—CH2-, —CH2-O—CH2-, —C(=O)—NH—, —NH—C(=O)—, —CH2-NH—C(=O)—, —C≡C—, —O—CH2-CH2-O— or —O—, L2 is —CH2-, AR1 and AR2 are phenyl, X is C(=O) and R8 is hydrogen or methyl, then R1 is Br or C2-C6alkyl, and/or R4 is O—C2-C6alkenyl;

when L1 is —O— and AR1 and AR2 are phenyl, then ring A is a 4- or 5-membered ring;

wherein the compound of formula I is not

2-Pyrrolidinemethanamine, N-[[4-[(4-bromophenyl)methoxy]-3-methoxyphenyl]methyl]-1-methyl- (e.g. CAS1648057-81-1);

2-Pyrrolidinemethanamine, N-[[3-bromo-4-(phenylmethoxy)phenyl]methyl]-1-methyl- (e.g. CAS1647489-16-4);

2-Pyrrolidinemethanamine, N-[[3-[(2-chlorophenyl)methoxy]phenyl]methyl]-1-methyl- (e.g. CAS1647358-80-2);

2-Pyrrolidinemethanamine, N-[[3-methoxy-4-[[3 (trifluoromethyl)phenyl]methoxy]phenyl]methyl]-1-methyl- (e.g. CAS1647019-78-0);

2-Pyrrolidinemethanamine, N-[[4-[(4-chlorophenyl) methoxy]-3-methoxyphenyl]methyl]-1-methyl- (e.g. CAS1646939-45-8);
Benzamide, N-(2,4-difluorophenyl)-3-[[methyl(3-piperidinylmethyl)amino]methyl]- (e.g. CAS 1269196-81-7);
Benzamide, N-(4-hydroxy[1,1'-biphenyl]-3-yl)-4-[[methyl [(1-methyl-4-piperidinyl)methyl]amino]methyl]- (e.g. CAS1095165-15-3);
Benzamide, N-(4-hydroxy[1,1'-biphenyl]-3-yl)-4-[[[(1-methyl-3-pyrrolidinyl)methyl]amino]methyl]- (e.g. CAS1095165-05-1);
2-Furancarboxylic acid, 5-[[4-[[methyl[(1-methyl-2-piperidinyl)methyl]amino]methyl]phenoxy]methyl]- (e.g. CAS1609874-75-0);
3-Pyrrolidinemethanamine, N, 1-dimethyl-N-[[2-(2-pyridinylmethoxy)phenyl]methyl]- (e.g. CAS1011355-74-0);
2-Pyrrolidinemethanamine, 1-methyl-N-[(3-phenoxyphenyl)methyl]- (e.g. CAS1647976-69-9);
2-Pyrrolidinemethanamine, N-[[4-(4-chloro-2-nitrophenoxy)phenyl]methyl]-1-methyl- e.g. CAS1646460-90-3);
3-Azetidinamine, N-methyl-N-[(3-phenoxyphenyl)methyl]- (e.g. CAS1465772-35-3);
3-Pyrrolidinamine, N-methyl-N-[(3-phenoxyphenyl) methyl]- (e.g. CAS1408147-14-7);
3-Pyrrolidinamine, 1-methyl-N-[(3-phenoxyphenyl) methyl]- (e.g. CAS1305392-54-4);
2-Pyrrolidinemethanamine, N-[[4-(4-bromophenoxy)phenyl]methyl]-N-methyl- (e.g. CAS943816-92-0);
3-Pyrrolidinecarboxamide, N-[[2-(3-methoxyphenoxy)-3-pyridinyl]methyl]- (e.g. CAS1572909-23-9),
4-Piperidinecarboxamide, N-[[6-(2,5-dimethylphenoxy)-3-pyridinyl]methyl]- (e.g. CAS1581476-55-2),
2-Pyrrolidinecarboxamide, N-[[2-(3,4-dimethylphenoxy)-4-pyridinyl]methyl]- (e.g. CAS1581023-85-9),
4-Piperidinamine, N-[[5-bromo-2-(2-pyridinylmethoxy) phenyl]methyl]-1-methyl- (e.g. CAS1031184-55-0).

A known compound in which L1 is C(=O) is Benzamide, 4-[(3-fluorophenyl)methoxy]-N-methyl-N-4-piperidinyl- (e.g. CAS1008853-73-3).

A known compound in which L1 is a bond is 2-Pyrrolidinecarboxamide, N-[(4'-methoxy[1,1'-biphenyl]-4-yl) methyl]- (e.g. CAS 1607531-64-5).

A known compound in which L1 is —CH2-O—, L2 is C1-C7alkylene, AR1 and AR2 are phenyl, ring A is a 6-membered ring, and R8 is hydrogen or methyl is 4-Piperidinemethanamine, N-[[3-bromo-4-[(2-chlorophenyl) methoxy]-5-methoxyphenyl]methyl]- (e.g. CAS1219151-95-7).

A known compound in which L1 is —O—, and AR1 and AR2 are phenyl is 4-Piperidinamine, N,1-dimethyl-N-[(3-phenoxyphenyl)methyl]- (e.g. CAS414889-26-2).

Known compounds in which L1 is —CH2-O— or —NH—C(=O)—CH2-O—, L2 is —CH2- or CH2-CH2-, AR1 and AR2 are phenyl, ring A is a 4- or 5-membered ring, X is C(=O) and R8 is hydrogen or methyl are 3-Azetidinecarboxamide, N-[[3-(phenylmethoxy)phenyl]methyl]- (e.g. CAS 1880445-58-8) and 3-Azetidinecarboxamide, N-[2-[4-[2-[(3-methylphenyl)amino]-2-oxoethoxy]phenyl]ethyl]- (e.g. CAS 1839264-91-3).

Known compounds in which L1 is —O—CH2-, —CH2-O—CH2-, —C(=O)—NH—, —NH—C(=O)—, —CH2-NH—C(=O)—, —C≡C—, —O—CH2-CH2-O— or —O—, L2 is —CH2-, AR1 and AR2 are phenyl, X is C(=O) and R8 is hydrogen or methyl are 3-Azetidinecarboxamide, N-[[2-[(2-chlorophenoxy)methyl]phenyl] methyl]- (e.g. CAS 1834496-54-6), 3-Piperidinecarboxamide, N-[[2-[(phenylmethoxy)methyl]phenyl]methyl]- (e.g. CAS1833723-16-2), 3-Piperidinecarboxamide, N-[[3-[(4-methylbenzoyl)amino]phenyl]methyl]- (e.g. CAS1838466-03-7), 3-Piperidinecarboxamide, N-[[4-[[(4-fluorophenyl) amino]carbonyl]phenyl]methyl]- (e.g. CAS1836686-73-7), 3-Piperidinecarboxamide, N-[[3-[[[(4-methylphenyl) methyl]amino]carbonyl]phenyl]methyl]- (e.g. CAS1832096-07-7), 3-Azetidinecarboxamide, N-[[4-[2-(4-chlorophenoxy)ethoxy]phenyl]methyl]- (e.g. CAS1838287-45-8) and 3-Pyrrolidinecarboxamide, N-[[4-(4-fluorophenoxy)-3-methylphenyl]methyl]- (e.g. CAS1840459-92-8).

In view of the above, it is generally preferred in all embodiments of the invention that ASC is —N(R8a)ASC-1 or —N(R8)(R9)ASC-1;

ring A represents a 4- to 5-membered saturated ring containing carbon atoms (in particular CH2 moieties) as ring members in addition to the nitrogen atom;

X represents CH2;

L1 represents —CH=CH—, —CH2-O—, —O—CH2-, —CH2-O—CH2-, —CH2-S—, —S—CH2-, —CH2-S (O)—, —CH2-S(O2)-, —S(O)—CH2-, —S(O2)-CH2-, —C(CH3)(CH3)-, —C(=O)—NH—, —NH—C(=O)—, —CH2-CH2-, —CH=CH—CH2-, —CH2-NH—C (=O)—, —C(=O)—NH—CH2, —C≡C—, —S(O2)-NH—CH2-, —S(O2)-NH—, —O—CH2-CH2-O—, —O—, —NH—CH2-, —CH2-NH—, —CH2-CH2-O—, or —NH—C(=O)—CH2-O—;

R8a represents hydrogen or ASC-1;

R8b represents methyl or ASC-1;

R9 represents methyl; and

R10 represents hydrogen.

Each alkyl moiety either alone or as part of a larger group such as alkoxy is a straight or branched chain and is preferably C1-C6alkyl, more preferably C1-C4alkyl. Examples include methyl, ethyl, n-propyl, prop-2-yl, n-butyl, but-2-yl, 2-methyl-prop-1-yl or 2-methyl-prop-2-yl.

Each alkylene moiety is a straight or branched chain and is, for example, —CH2-, —CH2-CH2-, —CH(CH3)-, —CH2-CH2-CH2-, —CH(CH3)-CH2-, or —CH (CH2CH3)-.

Each alkenyl moiety either alone or as part of a larger group such as alkenyloxy is a straight or branched chain and is preferably C2-C6alkenyl, more preferably C2-C4alkenyl. Each moiety can be of either the (E)- or (Z)-configuration. Examples include vinyl and allyl.

Each alkynyl moiety either alone or as part of a larger group such as alkynyloxy is a straight or branched chain and is preferably C2-C6alkynyl, more preferably C2-C4alkynyl. Examples are ethynyl and propargyl.

Each haloalkyl moiety either alone or as part of a larger group such as haloalkoxy is an alkyl group substituted by one or more of the same or different halogen atoms. Examples include difluoromethyl, trifluoromethyl, chlorodifluoromethyl and 2,2,2-trifluoro-ethyl. Haloalkyl moieties include for example 1 to halo substituents, or 1 to 3 halo substituents.

Each haloalkenyl moiety either alone or as part of a larger group such as haloalkenyloxy is an alkenyl group substituted by one or more of the same or different halogen atoms. Examples include, 2-difluoro-vinyl and 1,2-dichloro-2-fluoro-vinyl. Haloalkenyl moieties include for example 1 to 5 halo substituents, or 1 to 3 halo substituents.

Each cycloalkyl moiety can be in mono- or bi-cyclic form and preferably contains 3 to 8 carbon atoms, more preferably 3 to 6 carbon atoms. Examples of monocyclic cycloalkyl groups include cyclopropyl, cyclobutyl and cyclohexyl. An example of a bicyclic cycloalkyl group is bicyclo[2.2.1]heptan-2-yl. Halogen is fluorine, chlorine, bromine, or iodine.

The term "heteroaryl" refers to an aromatic ring system containing at least one heteroatom, and preferably up to four, more preferably three, heteroatoms selected from nitrogen, oxygen and sulfur as ring members. Heteroaryl rings do not contain adjacent oxygen atoms, adjacent sulfur atoms, or adjacent oxygen and sulfur atoms within the ring. Examples include pyridinyl, pyrimidinyl, pyrazinyl, pyridazinyl, pyrrolyl, pyrazolyl, imidazolyl, triazolyl, isoxazolyl, oxazolyl, isothiazolyl, thiazolyl, tetrazolyl, furanyl, and thiophenyl.

The term "heterocyclic ring" refers to a saturated or partially unsaturated carbocyclic ring containing one to four heteroatoms selected from nitrogen, oxygen and sulfur as ring members. Such rings do not contain adjacent oxygen atoms, adjacent sulfur atoms, or adjacent oxygen and sulfur atoms within the ring. Examples include tetrahydrofuranyl, pyrrolidinyl, piperidinyl, piperazinyl, dioxanyl and morpholinyl. Where a group is said to be optionally substituted, preferably there are optionally 1-5 substituents, more preferably optionally 1-3 substituents.

In respect of depictions of moieties given for L1 the bond on the left hand side of each moiety as depicted is connected to AR1 and the bond on the right hand side is connected to AR2. Likewise, in respect of depictions of moieties given for L2, the left hand side of each moiety as depicted is connected to Ar2 and the right hand side is connected to ASC.

Reference to "the terminal moiety of L2" refers to both termini of L2.

When a moiety is said to be optionally substituted the moiety is substituted or unsubstituted with said optional substituents.

Reference to compounds of the invention includes pharmaceutically acceptable salts of said compounds. Certain compounds of formula I may contain one or two or more centers of chirality and such compounds may be provided as pure enantiomers or pure diastereoisomers as well as mixtures thereof in any ratio. The compounds of the invention also include all cis/trans-isomers (for example where —C═C— moiety is present) as well as mixtures thereof in any ratio. The compounds of the invention also include all tautomeric forms of the compounds of formula I. The compounds of formula I may also be solvated, especially hydrated, which are also included in the compounds of formula I. Solvation and hydration may take place during the preparation process.

Examples of pharmacologically acceptable salts of the compounds of formula (I) are salts of physiologically acceptable mineral acids, such as hydrochloric acid, sulfuric acid and phosphoric acid, or salts of organic acids, such as methane-sulfonic acid, p-toluenesulfonic acid, lactic acid, acetic acid, trifluoroacetic acid, citric acid, succinic acid, fumaric acid, maleic acid and salicylic acid. Further examples of pharmacologically acceptable salts of the compounds of formula (I) are alkali metal and alkaline earth metal salts such as, for example, sodium, potassium, lithium, calcium or magnesium salts, ammonium salts or salts of organic bases such as, for example, methylamine, dimethylamine, triethylamine, piperidine, ethylenediamine, lysine, choline hydroxide, meglumine, morpholine or arginine salts.

The following preferred substituent definitions may be combined in any combination. Preferably ASC is —N(R8a)ASC-1 or —N(R8b)(R9)ASC-1, wherein R8a represents hydrogen or ASC-1 and R8b represents methyl or ASC-1 and R9 represents methyl, more preferably ASC is —N(R8a)ASC-1;

In ASC-1 ring A preferably represents a 4- to 6-membered saturated ring containing carbon atoms as ring members in addition to the nitrogen atoms. More preferably ASC-1 is ASC-1a

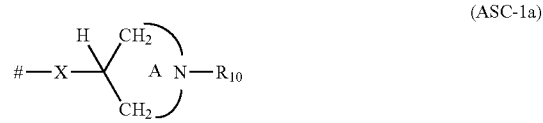

wherein ring A represents a 4- to 6-membered saturated ring containing carbon atoms as ring members in addition to the nitrogen atom;

or ASC-1b

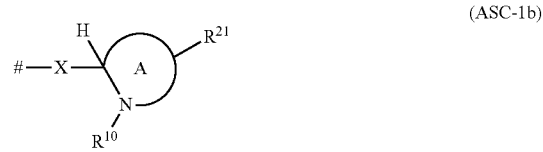

wherein ring A represents a 4- to 6-membered saturated ring containing carbon atoms as ring members in addition to the nitrogen atom. In ASC-1b the nitrogen atom in ring A is adjacent to the carbon atom that is bonded to X.

Even more preferably ASC-1 is ASC-1a wherein ring A represents a 4- to 5-membered saturated ring containing carbon atoms as ring members in addition to the nitrogen atom.

In all embodiments of the invention it is generally preferred that ring A contains only CH2 moieties as ring members in addition to the nitrogen atom, i.e. no CH2 moiety in ring A is replaced by CH(R21).

X preferably represents —CH2- or —C(═O)—, more preferably X represents —CH2-.

Examples of ASC include —NH—CH2-azetidinyl, —NH—CH2-pyrrolidinyl, —N(CH2-azetidinyl)2, —NH—piperidinyl, —N(CH3)-CH2-(N-methyl)azetidinyl, —N(CH3)-CH2-azetidinyl, —N+(CH3)2-CH2-azetidinyl, —N+(CH3)2-CH2-pyrrolidinyl, —NH—CH2-(2R)-pyrrolidinyl-2-amine, —NH—CH2-(N-methyl)azetidinyl, —NH—CH2-morpholinyl, —NH—CH2-piperidinyl, —NH—CH2-pyrrolidin-2-ylmethanamine, —NH—CO-azetidinyl, —NH—CO-piperidinyl, —NH—CO-pyrrolidinyl, and —NH-pyrrolidinyl.

More specific examples of ASC include ASC-a to ASC-q

ASC-a

ASC-b

ASC-c

ASC-a, ASC-g and ASC-o are particularly preferred. ASC is preferably ASC-o when R8 is ASC-1. ASC is preferably ASC-a or ASC-g when R8 is not ASC-1.

AR1 preferably represents phenyl or a 5- to 6-membered heteroaryl ring containing one to two heteroatoms selected from O, S and N. Specific examples of heteroaryl rings include pyridinyl, pyrimidinyl, pyrazinyl, pyridazinyl, pyrrolyl, pyrazolyl, imidazolyl, triazolyl, isoxazolyl, oxazolyl, isothiazolyl, thiazolyl, furanyl, or thiophenyl, in particular pyridinyl, thiazolyl, thiophenyl. More preferably AR1 represents phenyl, pyridinyl or thiazolyl, even more preferably phenyl or pyridinyl.

AR2 preferably represents phenyl or a 5- to 6-membered heteroaryl ring containing one to two heteroatoms selected from O, S and N. Specific examples of heteroaryl rings include pyridinyl, pyrimidinyl, pyrazinyl, pyridazinyl, pyrrolyl, pyrazolyl, imidazolyl, triazolyl, isoxazolyl, oxazolyl, isothiazolyl, thiazolyl, furanyl, or thiophenyl. More preferably AR2 represents phenyl, pyridinyl or furanyl, even more preferably phenyl or pyridinyl.

R1 preferably represents hydrogen, halogen, cyano, C1-C6alkyl, C1-C6haloalkyl, C3-C8cycloalkyl, C1-C6alkoxy, C1-C6haloalkoxy, —C(O)OR11, —C(O)N(R12)R13, more preferably R1 represents hydrogen, halogen, $C_1$-$C_6$alkyl, $C_1$-$C_6$haloalkyl, $C_1$-$C_6$alkoxy, or $C_1$-$C_6$haloalkoxy, more preferably R1 represents hydrogen, halogen, $C_1$-$C_6$alkyl or $C_1$-$C_6$haloalkyl. Specific examples of R1 include hydrogen, F, Cl, Br, I, OH, CF3, CN, NH2, —O-methyl, —O-ethyl, —O-propyl, O-butyl, —C(=O)OH, —C(=O)O-methyl, —C(=O)NH2, —C(=O)N(CH3)2, —C(=O)NH(CH3), —S(O)2-methyl, methyl, ethyl, propyl, butyl, —CH2-NH2, —CH2-N(CH3)2, —CH2-NH(CH3), —CH2OH, phenyl.

R2 preferably represents hydrogen, halogen, cyano, C1-C6alkyl, C1-C6haloalkyl, C3-C8cycloalkyl, C1-C6alkoxy, C1-C6haloalkoxy, —C(O)OR11, —C(O)N(R12)R13, more preferably R2 represents hydrogen, halogen, $C_1$-$C_6$alkyl, $C_1$-$C_6$haloalkyl, $C_1$-$C_6$alkoxy, or $C_1$-$C_6$haloalkoxy, more preferably R2 represents hydrogen, halogen, $C_1$-$C_6$alkyl or $C_1$-$C_6$haloalkyl. Specific examples of R2 include hydrogen, F, Cl, Br, I, OH, CF3, CN, NH2, —O-methyl, —O-ethyl, —O-propyl, O-butyl, —C(=O)OH, —C(=O)O-methyl, —C(=O)NH2, —C(=O)N(CH3)2, —C(=O)NH(CH3), —S(O)2-methyl, methyl, ethyl, propyl, butyl, —CH2-NH2, —CH2-N(CH3)2, —CH2-NH(CH3), —CH2OH, phenyl.

R3 preferably represents hydrogen, halogen, cyano, C1-C6alkyl, C1-C6haloalkyl, C3-C8cycloalkyl, C1-C6alkoxy, C1-C6haloalkoxy, —C(O)OR11, —C(O)N(R12)R13, more preferably R3 represents hydrogen, halogen, $C_1$-$C_6$alkyl, $C_1$-$C_6$haloalkyl, $C_1$-$C_6$alkoxy, or $C_1$-$C_6$haloalkoxy, more preferably R3 represents hydrogen, halogen, $C_1$-$C_6$alkyl or $C_1$-$C_6$haloalkyl. Specific examples of R3 include hydrogen, F, Cl, Br, I, OH, CF3, CN, NH2, —O-methyl, —O-ethyl, —O-propyl, O-butyl, —C(=O)OH, —C(=O)O-methyl, —C(=O)NH2, —C(=O)N(CH3)2, —C(=O)NH(CH3), —S(O)2-methyl, methyl, ethyl, propyl, butyl, —CH2-NH2, —CH2-N(CH3)2, —CH2-NH(CH3), —CH2OH, phenyl. More preferably R3 represents hydrogen.

R4 preferably represents hydrogen, halogen, cyano, C1-C6alkyl, C1-C6haloalkyl, or O—R22, wherein R22 represents C1-C6alkyl, C2-C6alkenyl, C1-C6haloalkyl, C2-C6haloalkenyl, C1-C6alkyl-Cycle-P, C1-C6alkyl-Cycle-Q, C2-C6alkenyl-Cycle-P, C2-C6alkenyl-Cycle-Q, and preferably wherein Cycle-P represents independently at each occurrence cylopropyl, cyclobutyl, cyclohexyl, tetrahydrofuranyl, pyrrolidinyl, piperidinyl, piperazinyl, dioxanyl, or morpholinyl, each optionally substituted by 1 to 3 R18 and wherein a nitrogen atom on pyrrolidinyl, piperidinyl, piperazinyl, and morpholinyl may be substituted by R9 to form a quaternary positively charged nitrogen atom, i.e. a quaternary amine; and preferably wherein Cycle-Q represents independently at each occurrence phenyl, pyridinyl, pyrimidinyl, pyrazinyl, pyridazinyl, pyrrolyl, pyrazolyl, imidazolyl, triazolyl, isoxazolyl, oxazolyl, isothiazolyl, thiazolyl, tetrazolyl, furanyl, or thiophenyl, each optionally substituted by 1 to 3 R19, and preferably wherein R18 and R19 represent independently at each occurrence halogen, cyano, methyl, halomethyl, methoxy, halomethoxy.

In one embodiment R4 represents O—R22 and wherein R22 is C3-C6alkyl, C2-C6alkenyl, C1-C6alkyl-Cycle-P1, C1-C6alkyl-Cycle-Q1, preferably wherein R22 is C2-C6alkenyl.

Specific examples of R4 include hydrogen, F, Cl, Br, I, OH, methyl, ethyl, propyl, butyl, —O-methyl, —O— ethyl, —O-propyl, —O-butyl, —C(═O)—NH—(CH2)3-O—CH3, —C(═O)—NH2, —C(═O)—NH-benzyl, —CF3, —CH═CH—C(═O)O-ethyl, —CH═CH-furanyl, —CH2-N(CH3)-CH2-C(═O)OH, —CH2-N+(CH3)2-CH2-C(═O)OH, —CH2-NH—CH2-azetidinyl, —CH2-O—(N+(CH3)2-pyrrolidinyl-2-carboxylic acid), —CH2-O—(N-methyl-pyrrolidinyl-2-carboxylic acid), —CH2-O—(N+(CH3)2-pyrrolidinyl), —CH2-OH, —CH2-O-methyl, —CHO, COOH, —NO2, —O—(CH2)2-(N+(CH3)2-pyrrolidine-2-carboxylic acid), —O—(CH2)2-(N-methyl-pyrrolidine-2-carboxylic acid), —O—(CH2)2-C(O)—NH2, —O-allyl, —O-benzyl, —O—CH2-(2-aminothiazolyl), —O—CH2-(2-methylthiazolyl), —O—CH2-(3H-1,3,4-oxadiazol-2-onyl), —O—CH2-(5-methylisoxazolyl), —O—CH2-(p-chloro-o-bromo-phenyl), —O—CH2-C(O)—NH2, —O—CH2-(p-C(═O)OH-phenyl), —O—CH2-(p-C(═O)O(methyl)-phenyl), —O—CH2-CH2-(3,5-dimethyl-1H-pyrazolyl), —O—CH2-CH2-(3,5-dimethylisoxazolyl), —O—CH2-(3H-1,3,4-oxadiazol-2-onyl), —O—CH2-CH2-(3H-1,3,4-oxadiazol-2-onyl), —O—CH2-CH2-imidazolyl, —O—CH2-CH2-morpholinyl, —O—CH2-CH2-pyridinyl, —O—CH2-CH2-tetrazolyl, —O—CH2-cyclopropyl, —O—CH2-imidazolyl, —O—CH2-N-methyl-imidazolyl, —O—CH2-pyridinyl, —O—CH2-CH(CH3)2, —O—CH2-(5-methylisoxazolyl).

R5 preferably represents hydrogen or halogen, more preferably hydrogen.

R6 preferably represents hydrogen or halogen, more preferably hydrogen.

R7 preferably represents hydrogen or halogen, more preferably hydrogen.

R8 preferably represents hydrogen or ASC-1.

R10 preferably represents hydrogen.

When Cycle-P represents a saturated or partially unsaturated C3-C8 heterocyclic ring optionally substituted by 1 to 3 R18 containing carbon atoms as ring members and one or two ring members independently selected from N(R9)(R12), and O, it will be clear that when the nitrogen atom is the point of attachment then R12 is absent. Cycle-P preferably represents independently at each occurrence cylopropyl, cyclobutyl, cyclohexyl, tetrahydrofuranyl, pyrrolidinyl, piperidinyl, piperazinyl, dioxanyl, or morpholinyl, each optionally substituted by 1 to 3 R18, and wherein a nitrogen atom on pyrrolidinyl, piperidinyl, piperazinyl, and morpholinyl may be substituted by R9 to form a quaternary positively charged nitrogen atom, i.e. a quaternary amine. In one embodiment Cycle-P is Cycle-P1, wherein Cycle-P1 represents a saturated or partially unsaturated C3-C8 heterocyclic ring optionally substituted by 1 to 3 R18 containing carbon atoms as ring members and one or two ring members independently selected from N(R9)(R12) and O.

Cycle-Q preferably represents independently at each occurrence phenyl, pyridinyl, pyrimidinyl, pyrazinyl, pyridazinyl, pyrrolyl, pyrazolyl, imidazolyl, triazolyl, isoxazolyl, oxazolyl, isothiazolyl, thiazolyl, tetrazolyl, furanyl, or thiophenyl, each optionally substituted by 1 to 3 R19.

In one embodiment Cycle-Q is Cycle-Q1, wherein Cycle-Q1 represents a 5- to 6-membered heteroaryl ring containing one to four heteroatoms selected from O, S and N, optionally substituted by 1 to 3 R19; R21 preferably represents CH2-N(R20)2, e.g. CH2-NH2, CH2-N(Me)2 or CH2-NHMe.

L1 preferably represents —CH═CH— (Z, E or Z/E), —CH2-O—, —O—CH2-, —CH═CH—CH2- (Z, E or Z/E), —CH2-O—CH2-, —C(CH3)(CH3)-, or —NH—CH2-, more preferably —CH═CH— (Z, E or Z/E), —CH2-O—, or —C(CH3)(CH3)-.

L2 preferably represents C1-C7alkylene, wherein one or more, preferably one or two, CH2 moieties in the alkylene are optionally replaced independently by —N(R9)(R20)-, —CH(N(R9)(R20)(R20))—, or —C(═O)⁻, wherein within L2 there are no adjacent C(═O) moieties or adjacent —N(R9)(R20)- moieties, and wherein the terminal moiety of L2 is not —N(R9)(R20)-, or L2 represents —O—C1-C6alkylene-, more preferably L2 represents —CH2-, —CH2-CH2-, —CH2-CH2-CH2-, —CH(CH3)-, —CH2-NH—CH2-CH2-, —C(═O)—, —C(═O)—CH2, —C(═O)—NH—CH2-C(═O)—, —C(═O)—NH—CH2-CH2-, —CH2-N+(CH3)2-CH2-C(═O)—, —CH2-NH—C(═O)—CH2-, —CH2-NH—CH2-C(═O)—, —O—CH2-CH2- or O—CH2-CH2-CH2- or —O—CH2-CH2-CH2-, even more preferably —CH2-, —CH2-CH2-, —CH(CH3)-, —CH2-CH2-CH2-, —CH2-NH—CH2-CH2-, —C(═O)—, —O—CH2-CH2-, —O—CH2-CH2-CH2- or —O—CH2-CH2-CH2-CH2-. It is generally preferred in all embodiments that the terminal moiety of L2 connected to ASC is —CH2-. It is also generally preferred that the terminal moiety of L2 connected to ASC is —CH2- and X is —CH2-.

In one embodiment L2 represents —CH2- or C2-C7alkylene, wherein one or more, preferably one or two, CH2 moieties in the alkylene are optionally replaced independently by —N(R9)(R20)-, —CH(N(R9)(R20)(R20))—, or —C(═O)—, wherein within L2 there are no adjacent C(═O) moieties or adjacent —N(R9)(R20)- moieties, and wherein the terminal moiety of L2 is not —N(R9)(R20)- and preferably wherein the terminal moiety of L2 connected to ASC is —CH2-, or L2 represents —O—C1-C6alkylene-.

In one embodiment L2 represents C1-C7alkylene, wherein one or two CH2 moieties in the alkylene are optionally replaced independently by —N(R9)(R20)- or —C(═O)—, and wherein the terminal moiety of L2 connected to ASC is —CH2-.

In one embodiment L2 represents —O—C1-C6alkylene, i.e. —O—CH2-, —O—CH2-CH2-, —O—CH2-CH2-CH2-, —O—CH2-CH2-CH2-CH2-, —O—CH2-CH2-CH2-CH2-CH2- or —O—CH2-CH2-CH2-CH2-CH2-CH2-.

In one embodiment L2 represents —C(═O)—.

When R8 is ASC-1, preferably ring A in both ASC-1 groups is a four-membered ring, and more preferably both ASC-1 groups are —CH2-Azetidinyl.

When AR1 represents a heteroaryl group having less than 3 available substituent positions in addition to the substituent position occupied by L1, R3 may be absent, or R2 and R3 may be absent. Likewise, when AR2 represents a heteroaryl group having less than 3 available substituent positions in addition to the substituent positions occupied by L1 and L2, R7 may be absent, or R6 and R7 may be absent, or R5, R6 and R7 may be absent, or R4, R5, R6 and R7 may be absent when there are no available substituent positions.

In ASC-1 the carbon atom within the ring that is bound to X is not substituted, i.e. the hydrogen atom indicated is not substituted (not replaced). In ASC-1a the CH2 moieties indicated are adjacent to the carbon atom that is bonded to X. In ASC-1b the N(R10) moiety is adjacent to the carbon atom that is bonded to X.

The following embodiments may be combined with each other and with any of the substituent definitions set out above.

In one embodiment R8 is hydrogen or methyl, preferably hydrogen.

In one embodiment R8 is ASC-1.

In one embodiment at least one, preferably only one, R9 is present and the respective nitrogen atom carries a positive charge i.e. to generate a quaternary amine.

In one embodiment each R9 is absent.

In one embodiment R1 is Br.

In one embodiment R1 is C2-C6alkyl.

In one embodiment R4 is O—R22, wherein R22 is C2-C6alkenyl, e.g. allyl.

In one embodiment L2 is at the meta position on AR2 with respect to the position of L1.

In one embodiment L2 and R4 are at the meta positions on AR2 with respect to the position of L1 and R4 is not hydrogen.

In one embodiment R5, R6, R7 are hydrogen, L2 and R4 are at the meta positions on AR2 with respect to the position of L1, and R4 is not hydrogen.

In one embodiment R3, R5, R6 and R7 are hydrogen.

In one embodiment R3, R5, R6, R7 are hydrogen, L2 and R4 are at the meta positions on AR2 with respect to the position of L1, and R4 is not hydrogen.

In one embodiment R1 and R2 are not hydrogen and are at the meta positions on AR1 with respect to L1, R3, R5, R6, R7 are hydrogen, R4 is not hydrogen, and L2 and R4 are at the meta positions on AR2 with respect to the position of L1.

In one embodiment R1 is not hydrogen and is at the para position on AR1 with respect to L1, R2, R3, R5, R6, R7 are hydrogen, R4 is not hydrogen, and L2 and R4 are at the meta positions on AR2 with respect to the position of L1.

In one embodiment R1 is not hydrogen and is at the para position on AR1 with respect to L1, and R2, R3, R4, R5, R6, R7 are hydrogen and L2 is at the meta positions on AR2 with respect to the position of L1.

In all embodiments of the invention it is preferred that ring A is a 4- to 6-membered saturated ring containing only CH2 moieties as ring members in addition to the nitrogen atom; and L2 represents C1-C7alkylene, wherein one or more, preferably one or two, CH2 moieties in the alkylene are optionally replaced independently by —N(R9)(R20)-, —CH(N(R9)(R20)(R20))—, or —C(=O)—, wherein within L2 there are no adjacent C(=O) moieties or adjacent —N(R9)(R20)- moieties, and wherein the terminal moiety of L2 is not —N(R9)(R20)-, or L2 represents —O—C1-C6alkylene-:

and more preferably wherein ring A is a 4- to 6-membered saturated ring containing only CH2 moieties as ring members in addition to the nitrogen atom.

X represents CH2; and

L2 represents C1-C7alkylene, wherein one or more, preferably one or two, CH2 moieties in the alkylene are optionally replaced independently by —N(R9)(R20)-, —CH(N(R9)(R20)(R20))—, or —C(=O)—, wherein within L2 there are no adjacent C(=O) moieties or adjacent —N(R9)(R20)- moieties, and wherein the terminal moiety of L2 is not —N(R9)(R20)- and wherein the terminal moiety of L2 connected to ASC is —CH2-, or L2 represents —O—C1-C6alkylene-;

or wherein L2 is —C(=O)— and R8 is ASC-1.

In other words, it is generally preferred that L2 is not a bond, and in one preferred group of compounds the nitrogen atom of the ASC group that is connected to L2 is not part of an amide group. In another preferred group of compounds L2 is —C(=O)— and R8 is ASC-1.

In embodiment A1 the compound of the invention is a compound of formula I wherein ASC-1 is ASC-1a or ASC-1b

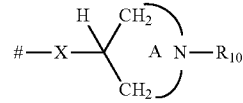

(ASC-1a)

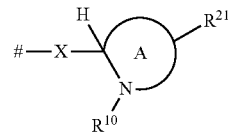

(ASC-1b)

ring A represents a 4- to 6-membered saturated ring containing carbon atoms as ring members in addition to the nitrogen atom;

X represents —CH2- or —C(=O)—;

AR1 represents phenyl, pyridinyl or thiazolyl;

AR2 represents phenyl or pyridinyl;

R10 represents hydrogen;

L1 represents —CH=CH— (Z, E or Z/E), —CH2-O—, —O—CH2-, —CH=CH—CH2- (Z, E or Z/E), —CH2-O—CH2-, —C(CH3)(CH3)-, or —NH—CH2-;

L2 represents —CH2-, —CH2-CH2-, —CH2-CH2-CH2-, —CH(CH3)-, —CH2-NH—CH2-CH2-, —C(=O)—, —C(=O)—CH2, —C(=O)—NH—CH2-C(=O)—, —C(=O)—NH—CH2-CH2-, —CH2-N(CH3)2-CH2-C(=O)—, —CH2-NH—C(=O)—CH2-, —CH2-NH—CH2-C(=O)—, —O—CH2-CH2-, —O—CH2-CH2-CH2- or —O—CH2-CH2-CH2-CH2-.

In embodiment A2 the compound of the invention is a compound of formula I wherein ASC-1 is ASC-1a or ASC-1b

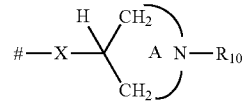

(ASC-1a)

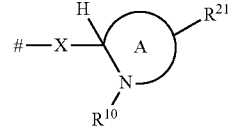

(ASC-1b)

ring A represents a 4- to 6-membered saturated ring containing carbon atoms as ring members in addition to the nitrogen atom;
X represents —CH2- or —C(=O)—;
AR1 represents phenyl, pyridinyl or thiazolyl;
AR2 represents phenyl or pyridinyl;
R1 and R2 represent independently hydrogen, halogen, cyano, C1-C6alkyl, C1-C6haloalkyl, C3-C8cycloalkyl, C1-C6alkoxy, C1-C6haloalkoxy, —C(O)OR11, —C(O)N(R12)R13;
R3 is hydrogen;
R4 represents hydrogen, halogen, cyano, C1-C6alkyl, C1-C6haloalkyl, or O—R22;
R5, R6, R7 are hydrogen or halogen;
R8 represents hydrogen or methyl or ASC-1;
R9 is methyl or absent;
R10 represents hydrogen;
R11 represents independently at each occurrence hydrogen or C1-C6alkyl;
R12 and R13 represent independently at each occurrence hydrogen or C1-C6alkyl;
R18 and R19 represent independently at each occurrence halogen, cyano, methyl, halomethyl, methoxy, halomethoxy;
R22 represents C1-C6alkyl, C2-C6alkenyl, C1-C6haloalkyl, C2-C6haloalkenyl, C1-C6alkyl-Cycle-P, C1-C6alkyl-Cycle-Q, C2-C6alkenyl-Cycle-P or C2-C6alkenyl-Cycle-Q;
Cycle-P represents independently at each occurrence cylopropyl, cyclobutyl, cyclohexyl, tetrahydrofuranyl, pyrrolidinyl, piperidinyl, piperazinyl, dioxanyl, or morpholinyl, each optionally substituted by 1 to 3 R18, and wherein a nitrogen atom on pyrrolidinyl, piperidinyl, piperazinyl, and morpholinyl may be substituted by R9 to form a quaternary positively charged nitrogen atom;
Cycle-Q represents independently at each occurrence phenyl, pyridinyl, pyrimidinyl, pyrazinyl, pyridazinyl, pyrrolyl, pyrazolyl, imidazolyl, triazolyl, isoxazolyl, oxazolyl, isothiazolyl, thiazolyl, tetrazolyl, furanyl, or thiophenyl, each optionally substituted by 1 to 3 R19;
L1 represents —CH=CH— (Z, E or Z/E), —CH2-O—, —O—CH2-, —CH=CH—CH2- (Z, E or Z/E), —CH2-O—CH2-, —C(CH3)(CH3)-, or —NH—CH2-;
L2 represents —CH2-, —CH2-CH2-, —CH2-CH2-CH2-, —CH(CH3)-, —CH2-NH—CH2-CH2-, —C(=O)—, —C(=O)—CH2, —C(=O)—NH—CH2-C(=O)—, —C(=O)—NH—CH2-CH2-, —CH2-N(CH3)2-CH2-C(=O)—, —CH2-NH—C(=O)—CH2-, —CH2-NH—CH2-C(=O)—, —O—CH2-CH2-, —O—CH2-CH2-CH2-, or —O—CH2-CH2-CH2-CH2-.

In embodiment A3 the compound of the invention is a compound of formula I wherein ASC-1 is ASC-1a

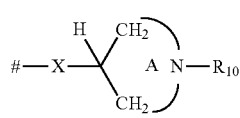
(ASC-1a)

ring A represents a 4- to 5-membered saturated ring containing carbon atoms as ring members in addition to the nitrogen atom;
X represents CH2;
AR1 represents phenyl or pyridinyl;
AR2 represents phenyl or pyridinyl;
R1 and R2 represent independently hydrogen, halogen, cyano, C1-C6alkyl, C1-C6haloalkyl, C3-C8cycloalkyl, C1-C6alkoxy, C1-C6haloalkoxy, —C(O)OR11 or —C(O)N(R12)R13;
R3 is hydrogen;
R4 represents hydrogen, halogen, cyano, C1-C6alkyl, C1-C6haloalkyl, or O—R22;
R5, R6, R7 are hydrogen or halogen;
R8 represents hydrogen, methyl or ASC-1;
R9 is methyl or absent;
R10 represents hydrogen;
R11 represents independently at each occurrence hydrogen or C1-C6alkyl;
R12 and R13 represent independently at each occurrence hydrogen or C1-C6alkyl;
R18 and R19 represent independently at each occurrence halogen, cyano, methyl, halomethyl, methoxy or halomethoxy;
R22 represents C1-C6alkyl, C2-C6alkenyl, C1-C6haloalkyl, C2-C6haloalkenyl, C1-C6alkyl-Cycle-P, C1-C6alkyl-Cycle-Q, C2-C6alkenyl-Cycle-P or C2-C6alkenyl-Cycle-Q;
Cycle-P represents independently at each occurrence tetrahydrofuranyl, pyrrolidinyl, piperidinyl, piperazinyl, dioxanyl, or morpholinyl, each optionally substituted by 1 to 3 R18;
Cycle-Q represents independently at each occurrence phenyl, pyridinyl, pyrimidinyl, pyrazinyl, pyridazinyl, pyrrolyl, pyrazolyl, imidazolyl, triazolyl, isoxazolyl, oxazolyl, isothiazolyl, thiazolyl, tetrazolyl, furanyl, or thiophenyl, each optionally substituted by 1 to 3 R19;
L1 represents —CH=CH— (Z, E or Z/E), —CH2-O—, or —C(CH3)(CH3)-;
L2 represents —CH2-, —CH2-CH2-, —CH(CH3)-, —CH2-CH2-CH2-, —CH2-NH—CH2-CH2-, —C(=O)—, C(=O)—NH—CH2-CH2, —O—CH2, —O—CH2-CH2-, —O—CH2-CH2-CH2- or —O—CH2-CH2-CH2-CH2-,
and preferably wherein ASC is ASC-o when R8 is ASC-1 and preferably wherein ASC is ASC-a or ASC-g when R8 is not ASC-1.

Further embodiments of compounds of the invention are represented by embodiments B1 to B44, wherein, in each case, AR1, AR2, R1, R2, R3, R4, R5, R6, R7 and L1 are as defined for compounds of formula I.

| | L2 | ASC |
|---|---|---|
| B1 | — | NH—CH2-azetidinyl |
| B2 | (CH2)3 | NH—CH2-azetidinyl |
| B3 | (CH2)3 | NH—CH2-pyrrolidinyl |
| B4 | C(=O) | N(CH2-azetidinyl)2 |
| B5 | C(=O) | NH—CH2-azetidinyl |
| B6 | C(=O)NHCH2C(=O) | NH—CH2-azetidinyl |
| B7 | C(=O)NHCH2 | N(CH2-azetidinyl)2 |
| B8 | C(=O)NHCH2CH2 | NH—CH2-azetidinyl |
| B9 | C(=O)NHCH2CH2 | NH—CO-azetidinyl |
| B10 | C(O) | NH-piperidinyl |
| B11 | C(O)—CH2 | NH—CH2-azetidinyl |
| B12 | C(O)—CH2 | NH—CH2-pyrrolidinyl |
| B13 | CH(CH3) | NH—CH2-azetidinyl |
| B14 | CH2 | N(CH2-azetidinyl)2 |
| B15 | CH2 | N(CH3)—CH2-(N-methyl)azetidinyl |
| B16 | CH2 | N(CH3)—CH2-azetidinyl |
| B17 | CH2 | N + (CH3)2—CH2-azetidinyl |
| B18 | CH2 | N + (CH3)2—CH2-pyrrolidinyl |
| B19 | CH2 | NH—CH2-(2R)-pyrrolidinyl-2-amine |
| B20 | CH2 | NH—CH2-(N-methyl)azetidinyl |
| B21 | CH2 | NH—CH2-azetidinyl |
| B22 | CH2 | NH—CH2-morpholinyl |

|     | L2           | ASC                        |
| --- | ------------ | -------------------------- |
| B23 | CH2          | NH—CH2-piperidinyl         |
| B24 | CH2          | NH—CH2-pyrrolidin-2-ylmethanamine |
| B25 | CH2          | NH—CH2-pyrrolidinyl        |
| B26 | CH2NHCOCH2   | NH—CH2-azetidinyl          |
| B27 | CH2          | NH—CO-piperidinyl          |
| B28 | CH2          | NH—CO-pyrrolidinyl         |
| B29 | CH2          | NH—piperidinyl             |
| B30 | CH2          | NH—pyrrolidinyl            |
| B31 | CH2—CH2      | NH—CH2-azetidinyl          |
| B32 | CH2—CH2      | NH—CH2-pyrrolidinyl        |
| B33 | CH2NHC(=O)CH2 | NH—CH2-azetidinyl         |
| B34 | CH2NHCH2CH2  | N(CH2-azetidinyl)2         |
| B35 | CH2NHCH2CH2  | NH—CO-azetidinyl           |
| B36 | O—(CH2)2     | NH—CH2-azetidinyl          |
| B37 | O—(CH2)2     | NH—CH2-piperidinyl         |
| B38 | O—(CH2)2     | NH—CH2-pyrrolidinyl        |
| B39 | O—(CH2)3     | NH—CH2-azetidinyl          |
| B40 | O—(CH2)3     | NH—CH2-piperidinyl         |
| B41 | O—(CH2)3     | NH—CH2-pyrrolidinyl        |
| B42 | O—(CH2)3     | NH—CO-azetidinyl           |
| B43 | O—(CH2)4     | NH—CH2-azetidinyl          |
| B44 | O—(CH2)4     | NH—CO-azetidinyl           |

Further embodiments of compounds of the invention are represented by embodiments Ba1-Ba44, which correspond to embodiments B1 to B44, but wherein the AR1, AR2, R1, R2, R3, R4, R5, R6, R7 and L1 are as defined for compounds of formula I in embodiment A1.

Further embodiments of compounds of the invention are represented by embodiments Bb1-Bb44, which correspond to embodiments B1 to B44, but wherein the AR1, AR2, R1, R2, R3, R4, R5, R6, R7 and L1 are as defined for compounds of formula I in embodiment A2.

Further embodiments of compounds of the invention are represented by embodiments Bc1-Bc44, which correspond to embodiments B1 to B44, but wherein the AR1, AR2, R1, R2, R3, R4, R5, R6, R7 and L1 are as defined for compounds of formula I in embodiment A3.

Further embodiments of compounds of the invention are represented by embodiments C1 to C42, wherein, in each case, R1, R2, R3, R4, R5, R6, R7, L2 and ASC are as defined for compounds of formula I.

|     | AR1    | L1         | AR2      |
| --- | ------ | ---------- | -------- |
| C1  | phenyl | —          | phenyl   |
| C2  | phenyl | C(CH3)2    | phenyl   |
| C3  | phenyl | C(O)—NH    | phenyl   |
| C4  | phenyl | C(O)—NH—CH2 | phenyl  |
| C5  | phenyl | CH=CH      | phenyl   |
| C6  | phenyl | CH=CH      | pyridinyl |
| C7  | phenyl | CH=CH—CH2  | phenyl   |
| C8  | phenyl | CH2—CH2    | phenyl   |
| C9  | phenyl | CH2—NH     | phenyl   |
| C10 | phenyl | CH2—NH—C(O) | phenyl  |
| C11 | phenyl | CH2—O      | phenyl   |
| C12 | phenyl | CH2—O      | pyridinyl |
| C13 | phenyl | CH2—O—CH2  | phenyl   |
| C14 | phenyl | CH2—S      | phenyl   |
| C15 | phenyl | CH2—SO     | phenyl   |
| C16 | phenyl | CH2—SO2    | phenyl   |
| C17 | phenyl | NH—C(O)    | phenyl   |
| C18 | phenyl | NH—CH2     | phenyl   |
| C19 | phenyl | O          | phenyl   |
| C20 | phenyl | O—(CH2)2—O | phenyl   |
| C21 | phenyl | O—CH2      | phenyl   |
| C22 | phenyl | O—CH2      | Furan    |
| C23 | phenyl | S—CH2      | phenyl   |
| C24 | phenyl | SO2—NH     | phenyl   |
| C25 | phenyl | SO2—NH—CH2 | phenyl   |
| C26 | phenyl | C≡C        | phenyl   |
| C27 | isoxazolyl | CH2—O  | phenyl   |
| C28 | pyridinyl | (CH2)2—O | phenyl   |
| C29 | pyridinyl | C(O)—NH  | phenyl   |
| C30 | pyridinyl | C(O)—NH—CH2 | phenyl |
| C31 | pyridinyl | CH=CH    | phenyl   |
| C32 | pyridinyl | CH=CH    | pyridinyl |
| C33 | pyridinyl | CH2—NH—C(O) | phenyl |
| C34 | pyridinyl | CH2—O    | phenyl   |
| C35 | pyridinyl | NH—C(O)  | phenyl   |
| C36 | pyridinyl | bond     | phenyl   |
| C37 | thiazolyl | C(O)—NH  | phenyl   |
| C38 | thiazolyl | C(O)—NH—CH2 | phenyl |
| C39 | thiazolyl | CH=CH    | phenyl   |
| C40 | thiazolyl | NH—C(O)  | phenyl   |
| C41 | thiophenyl | CH=CH   | phenyl   |
| C42 | pyridinyl | CH2—SO2  | phenyl   |

Further embodiments of compounds of the invention are represented by embodiments Ca1 to Ca42, which correspond to embodiments C1 to C42, but wherein, in each case, R1, R2, R3, R4, R5, R6, R7, L2 and ASC are as defined for compounds of formula I in embodiment A1.

Further embodiments of compounds of the invention are represented by embodiments Cb1 to Cb42, which correspond to embodiments C1 to C42, but wherein, in each case, R1, R2, R3, R4, R5, R6, R7, L2 and ASC are as defined for compounds of formula I in embodiment A2.

Further embodiments of compounds of the invention are represented by embodiments Cc1 to Cc42, which correspond to embodiments C1 to C42, but wherein, in each case, R1, R2, R3, R4, R5, R6, R7, L2 and ASC are as defined for compounds of formula I in embodiment A3.

Further embodiments of compounds of the invention are represented by embodiments D1 to D133, wherein, in each case, R1, R2, R3, R4, R5, R6 and R7 are as defined for compounds of formula I.

|     | AR1    | L1       | AR2    | L2       | ASC                 |
| --- | ------ | -------- | ------ | -------- | ------------------- |
| D1  | phenyl | —        | phenyl | CH2      | NH—CH2-azetidinyl   |
| D2  | phenyl | —        | phenyl | CH2      | NH—CH2-pyrrolidinyl |
| D3  | phenyl | C(CH3)2  | phenyl | CH2      | NH—CH2-azetidinyl   |
| D4  | phenyl | C(CH3)2  | phenyl | CH2      | NH—CH2-piperidinyl  |
| D5  | phenyl | C(CH3)2  | phenyl | CH2      | NH—CH2-pyrrolidinyl |
| D6  | phenyl | C(CH3)2  | phenyl | O—(CH2)2 | NH—CH2-azetidinyl   |
| D7  | phenyl | C(CH3)2  | phenyl | O—(CH2)2 | NH—CH2-piperidinyl  |
| D8  | phenyl | C(CH3)2  | phenyl | O—(CH2)2 | NH—CH2-pyrrolidinyl |
| D9  | phenyl | C(CH3)2  | phenyl | O—(CH2)3 | NH—CH2-azetidinyl   |
| D10 | phenyl | C(CH3)2  | phenyl | O—(CH2)3 | NH—CH2-piperidinyl  |
| D11 | phenyl | C(CH3)2  | phenyl | O—(CH2)3 | NH—CH2-pyrrolidinyl |
| D12 | phenyl | C(O)—NH  | phenyl | CH2      | NH—CH2-azetidinyl   |
| D13 | phenyl | C(O)—NH  | phenyl | CH2      | NH—CH2-pyrrolidinyl |

-continued

|   | AR1 | L1 | AR2 | L2 | ASC |
|---|---|---|---|---|---|
| D14 | phenyl | C(O)—NH—CH2 | phenyl | CH2 | NH—CH2-azetidinyl |
| D15 | phenyl | C(O)—NH—CH2 | phenyl | CH2 | NH—CH2-pyrrolidinyl |
| D16 | phenyl | CH=CH | phenyl | C(O) | N(CH2-azetidinyl)2 |
| D17 | phenyl | CH=CH | phenyl | C(O) | NH—CH2-azetidinyl |
| D18 | phenyl | CH=CH | phenyl | C(O)—NH—CH2—C(O) | NH—CH2-azetidinyl |
| D19 | phenyl | CH=CH | phenyl | C(O)—NH—CH2—CH2 | N(CH2-azetidinyl)2 |
| D20 | phenyl | CH=CH | phenyl | C(O)NH—CH2—CH2 | NH—CH2-azetidinyl |
| D21 | phenyl | CH=CH | phenyl | C(O)NH—CH2—CH2 | NH—CO-azetidinyl |
| D22 | phenyl | CH=CH | phenyl | CH2 | N(CH2-azetidinyl)2 |
| D23 | phenyl | CH=CH | phenyl | CH2 | N + (CH3)2—CH2-azetidinyl |
| D24 | phenyl | CH=CH | phenyl | CH2 | N + (CH3)2—CH2-pyrrolidinyl |
| D25 | phenyl | CH=CH | phenyl | CH2 | NH—CH2-(2R)-pyrrolidinyl-2-amine |
| D26 | phenyl | CH=CH | phenyl | CH2 | NH—CH2-azetidinyl |
| D27 | phenyl | CH=CH | phenyl | CH2 | NH—CH2-piperidinyl |
| D28 | phenyl | CH=CH | phenyl | CH2 | NH—CH2-pyrrolidin-2-ylmethanamine |
| D29 | phenyl | CH=CH | phenyl | CH2 | NH—CH2-pyrrolidinyl |
| D30 | phenyl | CH=CH | phenyl | CH2—NH—CO—CH2 | NH—CH2-azetidinyl |
| D31 | phenyl | CH=CH | phenyl | CH2 | NH—CO-piperidinyl |
| D32 | phenyl | CH=CH | phenyl | CH2 | NH—CO-pyrrolidinyl |
| D33 | phenyl | CH=CH | phenyl | CH2 | NH-piperidinyl |
| D34 | phenyl | CH=CH | phenyl | CH2—CH2 | NH—CH2-azetidinyl |
| D35 | phenyl | CH=CH | phenyl | CH2—CH2 | NH—CH2-pyrrolidinyl |
| D36 | phenyl | CH=CH | phenyl | CH2—NH—C(O)—CH2 | NH—CH2-azetidinyl |
| D37 | phenyl | CH=CH | phenyl | CH2—NH—CH2—CH2 | N(CH2-azetidinyl)2 |
| D38 | phenyl | CH=CH | phenyl | O—(CH2)2 | NH—CH2-azetidinyl |
| D39 | phenyl | CH=CH | phenyl | O—(CH2)2 | NH—CH2-pyrrolidinyl |
| D40 | phenyl | CH=CH | phenyl | O—(CH2)3 | NH—CH2-azetidinyl |
| D41 | phenyl | CH=CH | phenyl | O—(CH2)3 | NH—CH2-pyrrolidinyl |
| D42 | phenyl | CH=CH | phenyl | O—(CH2)3 | NH—CO-azetidinyl |
| D43 | phenyl | CH=CH | phenyl | O—(CH2)4 | NH—CH2-azetidinyl |
| D44 | phenyl | CH=CH | phenyl | O—(CH2)4 | NH—CO-azetidinyl |
| D45 | phenyl | CH=CH | pyridinyl | CH2 | NH—CH2-pyrrolidinyl |
| D46 | phenyl | CH=CH | pyridinyl | CH2 | NH—CH2-azetidinyl |
| D47 | phenyl | CH=CH—CH2 | phenyl | CH2 | NH—CH2-azetidinyl |
| D48 | phenyl | CH=CH—CH2 | phenyl | CH2 | NH—CH2-pyrrolidinyl |
| D49 | phenyl | CH2—CH2 | phenyl | CH2 | NH—CH2-azetidinyl |
| D50 | phenyl | CH2—NH | phenyl | CH2 | NH—CH2-azetidinyl |
| D51 | phenyl | CH2—NH—C(O) | phenyl | CH2 | NH—CH2-azetidinyl |
| D52 | phenyl | CH2—NH—C(O) | phenyl | CH2 | NH—CH2-pyrrolidinyl |
| D53 | phenyl | CH2—O | phenyl | — | NH—CH2-azetidinyl |
| D54 | phenyl | CH2—O | phenyl | (CH2)3 | NH—CH2-azetidinyl |
| D55 | phenyl | CH2—O | phenyl | (CH2)3 | NH—CH2-pyrrolidinyl |
| D56 | phenyl | CH2—O | phenyl | C(O) | NH-piperidinyl |
| D57 | phenyl | CH2—O | phenyl | C(O)—CH2 | NH—CH2-azetidinyl |
| D58 | phenyl | CH2—O | phenyl | C(O)—CH2 | NH—CH2-pyrrolidinyl |
| D59 | phenyl | CH2—O | phenyl | CH(CH3) | NH—CH2-azetidinyl |
| D60 | phenyl | CH2—O | phenyl | CH2 | N(CH3)—CH2-(N-Methyl)azetidinyl |
| D61 | phenyl | CH2—O | phenyl | CH2 | N(CH3)—CH2-azetidinyl |
| D62 | phenyl | CH2—O | phenyl | CH2 | N + (CH3)2—CH2-azetidinyl |
| D63 | phenyl | CH2—O | phenyl | CH2 | N + (CH3)2—CH2-pyrrolidine |
| D64 | phenyl | CH2—O | phenyl | CH2 | NH—CH2-(2R)-pyrrolidinyl-2-amine |
| D65 | phenyl | CH2—O | phenyl | CH2 | NH—CH2-(N-methyl)azetidinyl |
| D66 | phenyl | CH2—O | phenyl | CH2 | NH—CH2-azetidinyl |
| D67 | phenyl | CH2—O | phenyl | CH2 | NH—CH2-piperidinyl |
| D68 | phenyl | CH2—O | phenyl | CH2 | NH—CH2-pyrrolidin-2-ylmethanamine |
| D69 | phenyl | CH2—O | phenyl | CH2 | NH—CH2-pyrrolidinyl |
| D70 | phenyl | CH2—O | phenyl | CH2 | NH—CO-piperidinyl |
| D71 | phenyl | CH2—O | phenyl | CH2 | NH—CO-pyrrolidinyl |
| D72 | phenyl | CH2—O | phenyl | CH2 | NH-piperidinyl |
| D73 | phenyl | CH2—O | phenyl | CH2—CH2 | NH—CH2-azetidinyl |
| D74 | phenyl | CH2—O | phenyl | CH2—CH2 | NH—CH2-pyrrolidinyl |
| D75 | phenyl | CH2—O | pyridinyl | CH2 | NH—CH2-azetidinyl |
| D76 | phenyl | CH2—O | pyridinyl | CH2 | NH—CH2-pyrrolidinyl |
| D77 | phenyl | CH2—O—CH2 | phenyl | CH2 | NH—CH2-azetidinyl |
| D78 | phenyl | CH2—O—CH2 | phenyl | CH2 | NH—CH2-pyrrolidinyl |
| D79 | phenyl | CH2—S | phenyl | CH2 | NH—CH2-azetidinyl |

-continued

| | AR1 | L1 | AR2 | L2 | ASC |
|---|---|---|---|---|---|
| D80 | phenyl | CH2—S | phenyl | CH2 | NH—CH2-pyrrolidinyl |
| D81 | phenyl | CH2—SO | phenyl | CH2 | NH—CH2-pyrrolidinyl |
| D82 | phenyl | CH2—SO2 | phenyl | CH2 | NH—CH2-azetidinyl |
| D83 | phenyl | CH2—SO2 | phenyl | CH2 | NH—CH2-pyrrolidinyl |
| D84 | phenyl | NH—C(O) | phenyl | CH2 | NH—CH2-azetidinyl |
| D85 | phenyl | NH—C(O) | phenyl | CH2 | NH—CH2-pyrrolidinyl |
| D86 | phenyl | NH—CH2 | phenyl | CH2 | NH—CH2-azetidinyl |
| D87 | phenyl | O | phenyl | CH2 | NH—CH2-azetidinyl |
| D88 | phenyl | O | phenyl | CH2 | NH—CH2-piperidinyl |
| D89 | phenyl | O | phenyl | CH2 | NH—CH2-pyrrolidinyl |
| D90 | phenyl | O—(CH2)2—O | phenyl | CH2 | NH—CH2-azetidinyl |
| D91 | phenyl | O—CH2 | phenyl | (CH2)3 | NH—CH2-azetidinyl |
| D92 | phenyl | O—CH2 | phenyl | CH2 | NH—CH2-azetidinyl |
| D93 | phenyl | O—CH2 | phenyl | CH2 | NH—CH2-morpholinyl |
| D94 | phenyl | O—CH2 | phenyl | CH2 | NH-piperidinyl |
| D95 | phenyl | O—CH2 | phenyl | CH2 | NH-pyrrolidinyl |
| D96 | phenyl | O—CH2 | phenyl | CH2—CH2 | NH—CH2-azetidinyl |
| D97 | phenyl | O—CH2 | phenyl | O—(CH2)3 | NH—CH2-azetidinyl |
| D98 | phenyl | O—CH2 | furanyl | CH2 | NH—CH2-azetidinyl |
| D99 | phenyl | S—CH2 | phenyl | CH2 | NH—CH2-azetidinyl |
| D100 | phenyl | S—CH2 | phenyl | CH2 | NH—CH2-pyrrolidinyl |
| D101 | phenyl | SO2—NH | phenyl | CH2 | NH—CH2-pyrrolidinyl |
| D102 | phenyl | SO2—NH—CH2 | phenyl | CH2 | NH—CH2-azetidinyl |
| D103 | phenyl | SO2—NH—CH2 | phenyl | CH2 | NH—CH2-pyrrolidinyl |
| D104 | phenyl | —C≡C— | phenyl | CH2 | NH—CH2-azetidinyl |
| D105 | phenyl | —C≡C— | phenyl | CH2 | NH—CH2-pyrrolidinyl |
| D106 | isoxazolyl | CH2—O | phenyl | CH2 | NH—CH2-azetidinyl |
| D107 | isoxazolyl | CH2—O | phenyl | CH2 | NH—CH2-pyrrolidinyl |
| D108 | pyridinyl | (CH2)2—O | phenyl | CH2 | NH—CH2-azetidinyl |
| D109 | pyridinyl | (CH2)2—O | phenyl | CH2 | NH—CH2-pyrrolidinyl |
| D110 | pyridinyl | C(O)—NH | phenyl | CH2 | NH—CH2-pyrrolidinyl |
| D111 | pyridinyl | C(O)—NH | phenyl | C(O)—CH2 | NH—CH2-pyrrolidinyl |
| D112 | pyridinyl | C(O)—NH—CH2 | phenyl | CH2 | NH—CH2-pyrrolidinyl |
| D113 | pyridinyl | C(O)—NH—CH2 | phenyl | CH2 | NH—CH2-azetidinyl |
| D114 | pyridinyl | C(O)—NH—CH2 | phenyl | C(O)—NH—CH2—CH2 | N(CH2-azetidinyl)2 |
| D115 | pyridinyl | CH=CH | phenyl | CH2 | NH—CH2-azetidinyl |
| D116 | pyridinyl | CH=CH | phenyl | CH2 | NH—CH2-pyrrolidinyl |
| D117 | pyridinyl | CH=CH | phenyl | C(O)—CH2 | NH—CH2-pyrrolidinyl |
| D118 | pyridinyl | CH=CH | pyridinyl | CH2 | NH—CH2-pyrrolidinyl |
| D119 | pyridinyl | CH2—NH—C(O) | phenyl | CH2 | NH—CH2-pyrrolidinyl |
| D120 | pyridinyl | CH2—O | phenyl | CH2 | NH—CH2-azetidinyl |
| D121 | pyridinyl | CH2—O | phenyl | CH2 | NH—CH2-pyrrolidinyl |
| D122 | pyridinyl | CH2—O | phenyl | C(O)—NH—CH2—CH2 | N(CH2-azetidinyl)2 |
| D123 | pyridinyl | NH—C(O) | phenyl | CH2 | NH—CH2-pyrrolidinyl |
| D124 | pyridinyl | CH2—SO2 | phenyl | CH2 | NH—CH2-pyrrolidinyl |
| D125 | thiazolyl | C(O)—NH | phenyl | CH2 | NH—CH2-pyrrolidinyl |
| D126 | thiazolyl | C(O)—NH—CH2 | phenyl | CH2 | NH—CH2-azetidinyl |
| D127 | thiazolyl | C(O)—NH—CH2 | phenyl | CH2 | NH—CH2-pyrrolidinyl |
| D128 | thiazolyl | CH=CH | phenyl | CH2 | NH—CH2-azetidinyl |
| D129 | thiazolyl | CH=CH | phenyl | CH2 | NH—CH2-pyrrolidinyl |
| D130 | thiazolyl | NH—C(O) | phenyl | CH2 | NH—CH2-azetidinyl |
| D131 | thiazolyl | NH—C(O) | phenyl | CH2 | NH—CH2-pyrrolidinyl |
| D132 | thiophenyl | CH=CH | phenyl | CH2 | NH—CH2-azetidinyl |
| D133 | thiophenyl | CH=CH | phenyl | CH2 | NH—CH2-pyrrolidinyl |

Further embodiments of compounds of the invention are represented by embodiments Da1 to Da133, which correspond to embodiments D1 to D133, but wherein, in each case, R1, R2, R3, R4, R5, R6, and R7 are as defined for compounds of formula I in embodiment A1.

Further embodiments of compounds of the invention are represented by embodiments Db1 to Db133, which correspond to embodiments D1 to D133, but wherein, in each case, R1, R2, R3, R4, R5, R6, and R7 are as defined for compounds of formula I in embodiment A2.

Further embodiments of compounds of the invention are represented by embodiments Dc1 to Dc133, which correspond to embodiments D1 to D133, but wherein, in each case, R1, R2, R3, R4, R5, R6, and R7 are as defined for compounds of formula I in embodiment A3.

Further embodiments of the invention are represented by compounds of formula I-1 to I-18, wherein in each case R1, R2, R4, L1, L2 and ASC are as defined for compounds of formula I.

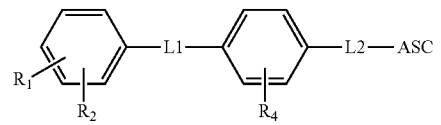

I-1

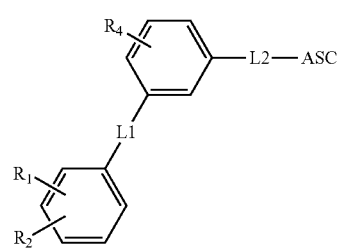

I-2

I-3
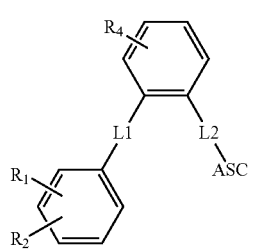
I-4
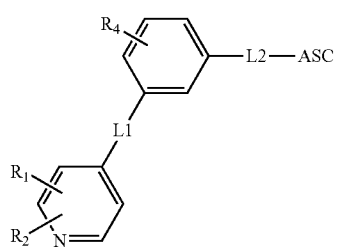
I-5
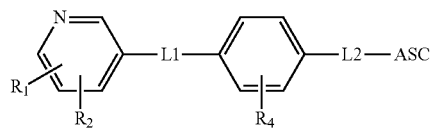
I-6
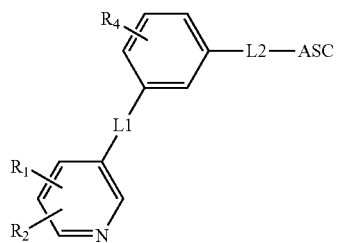
I-7
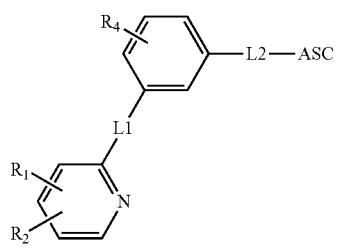
I-8
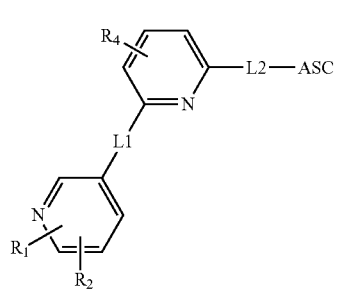
I-9
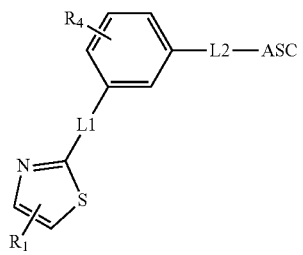
I-10
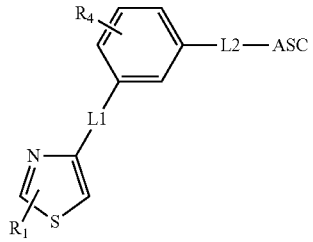
I-11
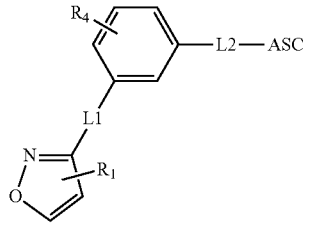
I-12
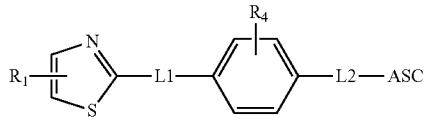
I-13
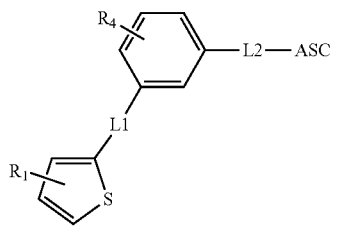
I-14
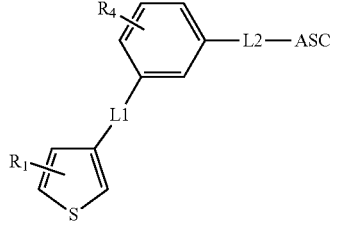
I-15
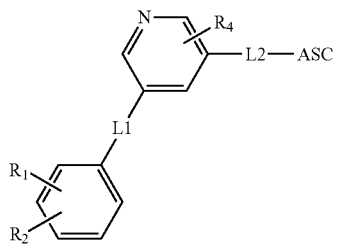

I-16

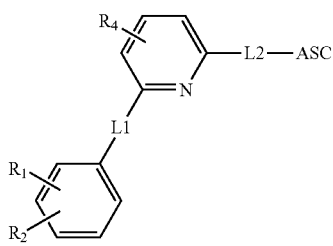

I-17

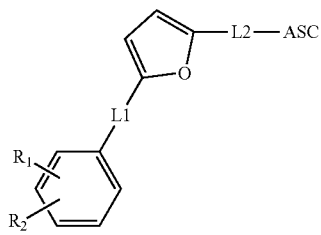

I-18

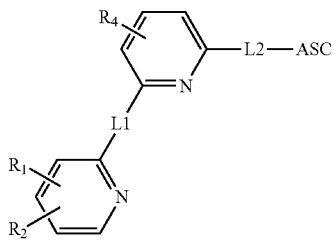

Further embodiments of the invention are represented by compounds of formula Ia-1 to Ia-18, which correspond to compounds of formula I-1 to L-18, but wherein in each case R1, R2, R4, L1, L2 and ASC are as defined for compounds of formula I in embodiment A1.

Further embodiments of the invention are represented by compounds of formula Ib-1 to Ib-18, which correspond to compounds of formula I-1 to L-18, but wherein in each case R1, R2, R4, L1, L2 and ASC are as defined for compounds of formula I in embodiment A2.

Further embodiments of the invention are represented by compounds of formula Ic-1 to Ic-18, which correspond to compounds of formula I-1 to L-18, but wherein in each case R1, R2, R4, L1, L2 and ASC are as defined for compounds of formula I in embodiment A3.

In a further embodiment the compound of formula I is a compound of formula I-20

(I-20)

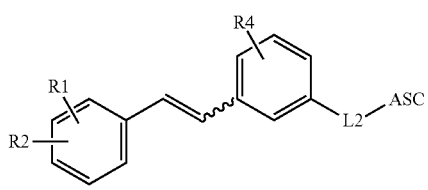

wherein R1, R2, R4, L1 and ASC are as defined in Embodiment A3.

In a further embodiment the compound of formula I is a compound of formula I-21

(I-21)

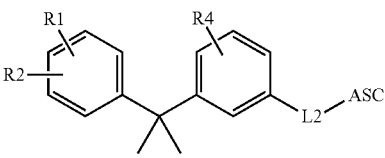

wherein R1, R2, R4, L1 and ASC are as defined in Embodiment A3.

In a further embodiment the compound of formula I is a compound of formula I-22

(I-22)

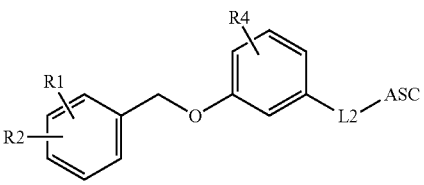

wherein R1, R2, R4, L1 and ASC are as defined in Embodiment A3.

In a further embodiment the compound of formula I is a compound of formula I-23

(I-23)

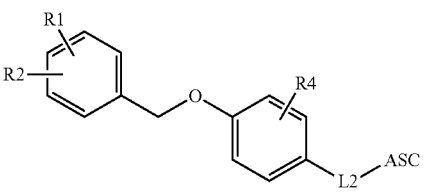

wherein R1, R2, R4, L1 and ASC are as defined in Embodiment A3.

In a further embodiment the compound of formula I is a compound of formula I-24

(I-24)

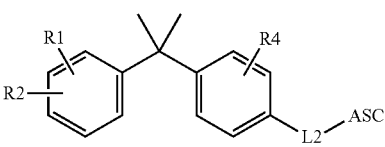

wherein R1, R2, R4, L1 and ASC are as defined in Embodiment A3.

In a further embodiment the compound of formula I is a compound of formula I-25

(I-25)

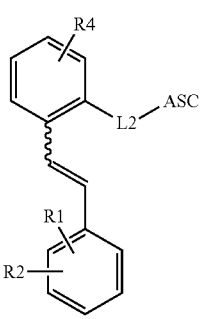

wherein R1, R2, R4, L1 and ASC are as defined in Embodiment A3.

In a further embodiment the compound of formula I is a compound of formula I-26

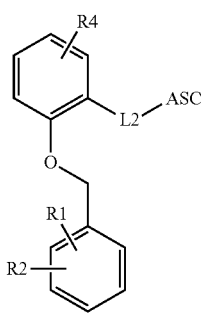
(I-26)

wherein R1, R2, R4, L1 and ASC are as defined in Embodiment A3.

In a further embodiment the compound of formula I is a compound of formula I-27

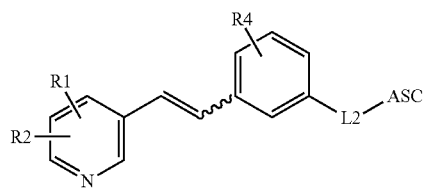
(I-27)

wherein R1, R2, R4, L1 and ASC are as defined in Embodiment A3.

In a further embodiment the compound of formula I is a compound of formula I-28

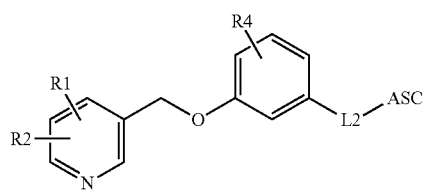
(I-28)

wherein R1, R2, R4, L1 and ASC are as defined in Embodiment A3.

In a further embodiment the compound of formula I is a compound of formula I-29

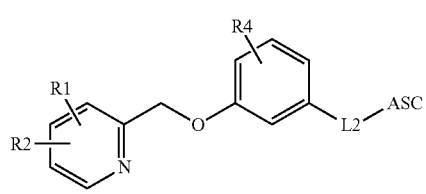
(I-29)

wherein R1, R2, R4, L1 and ASC are as defined in Embodiment A3.

In a further embodiment the compound of formula I is a compound of formula I-30

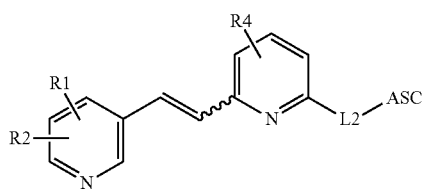
(I-30)

wherein R1, R2, R4, L1 and ASC are as defined in Embodiment A3.

In a further embodiment the compound of formula I is a compound of formula I-31

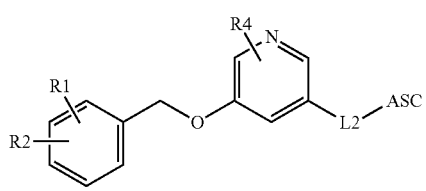
(I-31)

wherein R1, R4, L1 and ASC are as defined in Embodiment A3.

In a further embodiment the compound of formula I is a compound of formula I-32

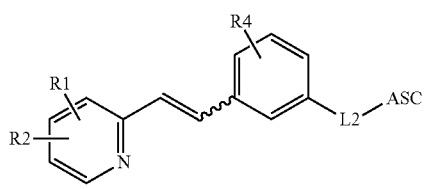
(I-32)

wherein R1, R2, R4, L1 and ASC are as defined in Embodiment A3.

In a further embodiment the compound of formula I is a compound of formula I-33

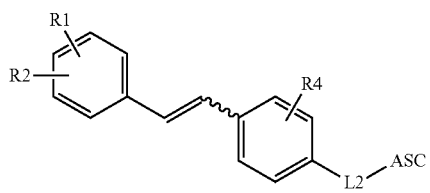
(I-33)

wherein R1, R2, R4, L1 and ASC are as defined in Embodiment A3.

In a further embodiment the compound of formula I is a compound of formula I-34

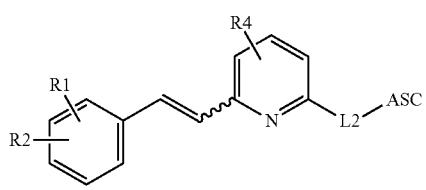
(I-34)

wherein R1, R2, R4, L1 and ASC are as defined in Embodiment A3.

In a further embodiment the compound of formula I is a compound of formula I-35

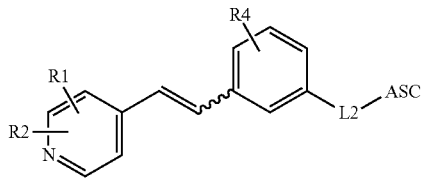
(I-35)

wherein R1, R2, R4, L1 and ASC are as defined in Embodiment A3.

In a further embodiment the compound of formula I is a compound of formula I-36

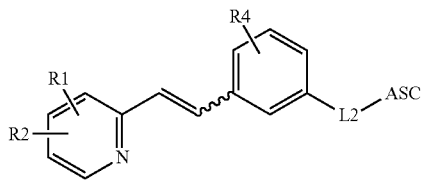
(I-36)

wherein R1, R2, R4, L1 and ASC are as defined in Embodiment A3.

In a further embodiment the compound of formula I is a compound of formula I-37

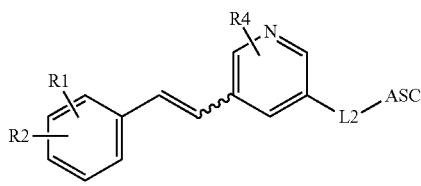
(I-37)

wherein R1, R2, R4, L1 and ASC are as defined in Embodiment A3.

In a further embodiment the compound of formula I is a compound of formula I-38

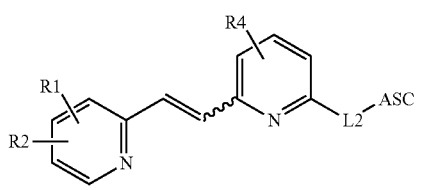
(I-38)

wherein R1, R2, R4, L1 and ASC are as defined in Embodiment A3.

The methods of the invention include administering the compound of formula I in combination with the antimicrobial agent. Administering the compound of formula I in combination with an antimicrobial agent means, for example, that the compound of formula I and antimicrobial agent are administered simultaneously, separately or sequentially, preferably simultaneously. The compounds of formula I may be administered in combination with more than one antimicrobial agent if desired.

The pharmaceutical products comprising the compound of formula I and an antimicrobial agent may include instructions for simultaneous, separate or sequential administration.

The compound of formula I and the antimicrobial agent may be provided in different dosage units or may be combined in the same dosage unit e.g. for simultaneous administration. In one embodiment the pharmaceutical product may comprise one or more than one dosage unit comprising the compound of formula I, and one or more than one dosage unit comprising the antimicrobial agent. In a further embodiment the pharmaceutical product may comprise one or more than one dosage units comprising the compound of formula I and the antimicrobial agent.

The invention also provides a compound of formula I for use in a method of enhancing the antimicrobial agent efficacy of an antimicrobial agent comprising contacting a microbe with the compound of formula I and said antimicrobial agent. In a further embodiment the invention provides a method for enhancing the sensitivity of a microorganism to an antimicrobial agent, which comprises the step of contacting a microorganism with a compound of formula I.

In addition to an antibiotic, or as an alternative to, the compounds of formula I may be administered in combination with an antifungal agent, an antiviral agent, an anti-inflammatory agent or an anti-allergic agent. The antimicrobial agents to be used in combination with the compounds of the invention are preferably antibiotics. Whilst antimicrobial agents are agents that are able to kill or inhibit growth of microbes in a general sense, antibiotics are agents that are able to kill or inhibit the growth of bacteria, i.e. antibacterial agents. Various antibacterial agents can be used in combination with the compounds of formula I, including quinolones, fluoroquinolones, tetracyclines, glycopeptides, aminoglycosides, β-lactams, rifamycins, macrolides and ketolides, oxazolidinones, coumermycins, phenicols (including chloramphenicol), fusidic acid, and novel bacterial topoisomerase inhibitors (NBTI). These are described in more detail below. Bacterial Topoisomerase inhibitors: e.g. GSK2140944, Ross et al. 2014. J. Clin. Microbiol. 52(7): 2629, NXL101, Reck et al. 2014. Bioorg. Med. Chem. Epub ahead of print, Surivet et al. 2013 J. Med. Chem. 56(18): 7396, Singh et al. 2014. Med. Chem. Lett. 5:609.

Beta-lactams: Beta-lactam antibiotics include but are not limited to, Biapenem, Doripenem, Ertapenem, Imipenem, Meropenem, or Panipenem, Pivampicillin, Hetacillin, Bacampicillin, Metampicillin, Talampicilli), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometacillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (Dicloxacillin, Flucloxacillin), Oxacillin, Meticillin, Nafcillin, Faropenem, Biapenem, Doripenem, Ertapenem, Imipenem, Meropenem, Panipenem, Tomopenem, Razupenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftazidime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, Ceftolozane (CXA-101), RWJ-54428, MC-04,546, ME1036, BAL30072, SYN 2416, Ceftiofur, Cefquinome, Cefovecin, Aztreonam, Tigemonam, Carumonam, Tebipenem, Tomopenem, RWJ-442831, RWJ-333441, BAL30072, or RWJ-333442.

Macrolides: Macrolides include but are not limited to azithromycin, clarithromycin, erythromycin, oleandomycin, rokitamycin, rosaramicin, roxythromycin, spiramycin, or troleandomycin. Ketolides: Ketolides include but are not limited to telithromycin, solithromycin, or cethromycin. Quinolones: Quinolones include but are not limited to amifloxacin, besifloxacin, cinoxacin, ciprofloxacin, enoxacin, finafloxacin, fleroxacin, flumequine, lomefloxacine, nalidixic acid, nemonoxacin, norfloxacin, ofloxacin, levofloxacin, oxolinic acid, pefloxacin, rosoxacin, temafloxacin, tosufloxacin, sparfloxacin, clinafloxacin, moxifloxacin, gemifloxacin, garenofloxacin, delafloxacin, PD131628, PD138312, PD140248, Q-35, AM-1155, NM394, T-3761, rufloxacin, OPC-17116, DU-6859a (AAC 37:1419), JNJ-Q2, or DV-7751a (AAC 37:2212).

Tetracyclines and glycylcyclines: Tetracyclines and glycylcyclines include but are not limited to tetracycline, minocycline, chlortetracycline, demeclocycline, doxycycline, lymecycline, methacycline, omadacycline, oxytetracycline, tigecycline, or eravacycline.

Oxazolidinones: Oxazolidinones include but are not limited to linezolid, tedizolid, eperozolid, or radezolid. Aminoglycosides:Aminoglycosides include but are not limited to amikacin, arbekacin, butirosin, dibekacin, fortimicins, gentamicin, kanamycin, neomycin, netilmicin, plazomicin, robostamycin, sisomicin, spectinomycin, streptomycin, or tobramycin.

Lincosamides: Lincosamides include but are not limited to clindamycin, or lincomycin. Glycopeptides: Glycopeptides include but are not limited to vancomycin, teicoplanin, telavancin, bleomycin, ramoplanin, dalbavancin, oritavancin, or decaplanin.

Pleuromutilins: Pleuromutilins include but are not limited to retapamulin, valnemulin, tiamulin, azamulin, or BC-3781 Other antibiotics: Other antibiotics include but are not limited to trimethoprim, sulfamethoxazole, rifampicin, fusidic acid, puromycin, novobiocin, coumermycin, thiamphenicol, or thiolactomycin, ETX0914 (AZD0914) (see Huband et al. AAC 2015. 59(1): 467), VXc-486 (see Locher et al. AAC 2015. 59(3):1455 and Grillot et al. J. Med. Chem. 2014. 57:8792).

Compositions comprising the compound of formula I and an antimicrobial agent may comprise the compound of formula I and an antibiotic in the weight ratio of, for example, 1:10 to 10:1, 1:5 to 5:1, 2:1 to 2:1, for example about 1:1.

The compounds of the present invention may be administered in combination with two or more antimicrobial agents as desired, and likewise, compositions may comprise the compound of formula I and two or more antimicrobial agents. Examples of such combinations include compounds of formula I and two or more beta lactam antibiotics, e.g. ceftolozane/tazobactam, ceftazidime/avibactam, and the corresponding triple beta lactam combinations.

The microorganism and microbial infections to be treated by the present invention are preferably bacteria and bacterial infections. Bacteria that may be treated using the present invention include but are not limited to *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella enterica* (including all subspecies and serotypes some of which are also known as *Salmonella typhimurium, Salmonella typhi, Salmonella paratyphi, Salmonella enteritidis) Salmonella bongori* (including all subspecies and serotypes), *Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

Of particular interest are *Pseudomonas aeruginosa, Pseudomonas fluorescens, Stenotrophomonas maltophilia, Escherichia coli, Citrobacter freundii, Salmonella enterica* (including all subspecies and serotypes some of which are also known as *Salmonella typhimurium, Salmonella typhi, Salmonella paratyphi, Salmonella enteritidis), Salmonella bongori* (including all subspecies and serotypes), *Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii,* or *Bacteroides splanchnicus.*

A particularly suitable example of a bacterium that can be treated by the present invention is the pathogenic bacterial species *Pseudomonas aeruginosa*, which is intrinsically resistant to many commonly used antibiotics. Co-administration of compound of formula I with an antibacterial agent can reduce the export of the antibacterial agent out of the cell leading to intracellular accumulation to levels higher than the ones otherwise maintained in the absence of the compound of formula I.

Thus, the compounds and compositions of the invention are particularly useful for treating subjects infected with or susceptible to infection with bacteria that are resistant to one or several antibiotics. The methods of the invention may comprise administering the compound of formula I in combination with an antibiotic to which the bacteria show resistance. The resistance may be intermediate or complete resistance according to guidelines such as issued by the Clinical Laboratory Standards Institute in the US and European Committee on Antimicrobial Susceptibility Testing (EUCAST) in Europe, e.g. exposure of the bacteria to the antibiotic results in reduced or in no growth inhibition, In further embodiments the invention provides a method for eliminating resistance of a microorganism with intrinsic or acquired resistance to an antimicrobial agent, which comprises the step of contacting the microorganism, which is being exposed to the antimicrobial agent, with an effective amount of a compound of formula I. The invention also provides a method for inhibiting acquisition of resistance to an antimicrobial agent by a microorganism, which is being exposed to the antimicrobial agent, which comprises the step of contacting a microorganism with an effective amount of a compound of formula I. Other bacterial and microbial species may have broad substrate spectrum efflux pumps similar to *Pseudomonas aeruginosa* and may therefore be appropriate targets too.

A compound according to the invention is not only for the (prophylactic and preferably therapeutic) management of human subjects, but also for veterinary use for the treatment of other warm-blooded animals, for example of commercially useful animals, for example cattle, horses, pigs, chickens, sheep, dogs, cats, rodents, such as mice, rabbits or rats, or guinea-pigs. Such a compound may also be used as a reference standard to permit a comparison with other compounds. Treatment of humans is preferred.

In general, compounds of formula (I) are administered either individually, or optionally also in combination with another desired therapeutic agent as described herein, using the known and acceptable methods. Such therapeutically useful agents may be administered, for example, by one of the following routes: orally, for example in the form of dragees, coated tablets, pills, semi-solid substances, soft or hard capsules, solutions, emulsions or suspensions; parenterally, for example in the form of an injectable solution; rectally in the form of suppositories; by inhalation, for example in the form of a powder formulation or a spray; transdermally or intranasally. Routes of administration include parenteral, enteral and topical.

The compositions comprise the active ingredient, preferably together with a pharmaceutically acceptable carrier, which may be selected from conventional carriers and excipients known to the person skilled in the art.

For the preparation of such tablets, pills, semi-solid substances, coated tablets, dragees and hard gelatine capsules, the therapeutically usable product may be mixed with pharmacologically inert, inorganic or organic pharmaceutical carrier substances, for example with lactose, sucrose, glucose, gelatine, malt, silica gel, starch or derivatives thereof, talcum, stearic acid or salts thereof, skimmed milk powder, and the like. For the preparation of soft capsules, pharmaceutical carrier substances such as, for example, vegetable oils, petroleum, animal or synthetic oils, wax, fat and polyols may be used.

For the preparation of liquid solutions and syrups, pharmaceutical carrier substances such as, for example, water, alcohols, aqueous saline solution, aqueous dextrose solution, polyols, glycerol, vegetable oils, petroleum and animal or synthetic oils may be used.

For suppositories, pharmaceutical carrier substances such as, for example, vegetable oils, petroleum, animal or synthetic oils, wax, fat and polyols may be used.

For aerosol formulations, compressed gases that are suitable for this purpose, such as, for example, oxygen, nitrogen and carbon dioxide may be used. The pharmaceutically acceptable agents may also comprise additives for preserving and stabilizing, emulsifiers, sweeteners, flavourings, salts for altering the osmotic pressure, buffers, encapsulation additives and antioxidants.

The compositions of the invention may be provided in a sterile container, e.g. as a powder for reconstitution. In this case the invention provides a method of preparing a pharmaceutical composition for administration, comprising reconstituting the contents of the sterile container using a pharmaceutically acceptable diluent. The reconstituted solution may be administered intravenously to a patient.

The pharmaceutical compositions of the invention comprise the compound of formula I and/or the antimicrobial agent in a pharmaceutically effective amount, and the methods of the invention comprise administering the active compounds in pharmaceutically effective amounts. The pharmaceutical compositions may comprise from approximately 1% to approximately 95% active ingredient.

The dosage of the active ingredient depends upon the disease to be treated and upon the species, its age, weight, and individual condition, the individual pharmacokinetic data, and the mode of administration. The pharmaceutical compositions of the present invention are prepared in a manner known per se, for example by means of conventional mixing, granulating, coating, dissolving or lyophilizing processes. The compositions may be provided in solid or liquid form.

The activity of antibacterial agents to treat infections caused by drug-resistant pathogens can be restored and enhanced by co-administration with efflux-pump inhibitor compounds. The invention provides methods to overcome antibiotic resistance of bacteria that express efflux pumps, which transport antibiotics out of the cell.

The compounds according to the present invention, as well as pharmaceutically acceptable salts, solvates, hydrates thereof can be prepared e.g. by one of the processes (a), (b), (c), (d), (e), (f), (g) or (h) described below; followed, if necessary, by removing any protecting groups, forming a pharmaceutically acceptable salt, or forming a pharmaceutically acceptable solvate or hydrate.

Process (a):

This process variant can be used for the manufacture of compounds of formula I as defined above, wherein L1 is $-(CH_2)_m-O-(CH_2)_n-$, $-(CH_2)_m-NH-(CH_2)_n-$, $-(CH_2)_m-S-(CH_2)_n-$, $-(CH_2)_m-SO-(CH_2)_n-$ or $-(CH_2)_m-SO_2-(CH_2)_n-$, in which formulae m is 1, 2 or 3 and n is 0, 1, 2 or 3 within the limits defined by the claims.

In this process a compound of formula II-1

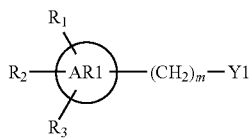
(II-1)

is reacted with a compound of formula III

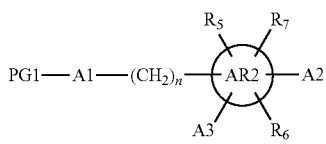
(III)

to generate a compound of formula IV-1

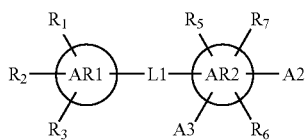
(IV-1)

in which formulae
AR1, AR2, $R_1$, $R_2$, $R_3$, $R_5$, $R_6$, $R_7$ are as in formula I,
m is 1, 2 or 3,
n is 0, 1, 2 or 3,
Y1 is —OH, a halogen atom or a leaving group like mesylate, tosylate, triflate,
A1 is —O—, —S— or —NH—,
PG1 is a hydrogen atom or an amino protecting group (such as allyloxycarbonyl, benzyloxycarbonyl, 9-fluorenylmethylcarbonyl, tert-butoxycarbonyl or benzyl),
A2 is —(CH$_2$)$_o$—Y2,
wherein o is 0, 1, 2 or 3,
Y2 is —OH, a halogen atom, a leaving group like mesylate, tosylate, triflate, —COOH, —CHO, —C(O)—CH$_2$—X or —NH-PG2,
wherein X is a halogen atom and PG2 is a hydrogen atom or an amino protecting group,
A3 is as $R_4$ in formula I or is a halogen atom, —OH, —CHO, —CH$_2$OH or —COOH.

When A3 is a halogen atom, the compound of formula IV-1 is further reacted with a compound of formula V

(V)

wherein X is —CH$_2$—OH,
to generate a compound of formula VI-1

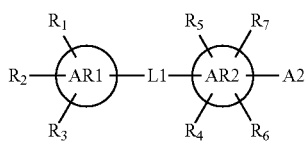
(VI-1)

wherein $R_4$ is an ether group.

When A3 is —OH, the compound of formula IV-1 is further reacted with a compound of formula V wherein X is —OH, a halogen atom or a leaving group like mesylate, tosylate, triflate, to generate a compound of formula VI-1 wherein $R_4$ is an ether group.

When A3 is —CHO, the compound of formula IV-1 can further react with a compound of formula V wherein X is a phosphonium salt or a phosphonate, to generate a compound of formula VI-1 wherein $R_4$ is a $C_2$-$C_6$-alkenyl group.

When A3 is —CHO, the compound of formula IV-1 can further react with a compound of formula V wherein X is —NHE or —NH$_2$, E being an amino protecting group, to generate compound of formula VI-1 wherein $R_4$ is an amino group.

When A3 is —CH$_2$OH, the compound of formula IV-1 can be converted to the corresponding halide, mesylate, tosylate, triflate compound, and further react with a compound of formula V wherein X is —OH, —SH, —NHE or —NH$_2$, E being an amino protecting group, to generate compound of formula VI-1 wherein $R_4$ is an ether, a thiol or an amine group, respectively.

When A3 is —COOH, the compound of formula IV-1 can further react with a compound of formula V wherein X is —NHE or —NH$_2$, E being an amino protecting group, to generate compound of formula VI-1 wherein $R_4$ is an amide group.

When Y2 is a halogen atom, a leaving group like mesylate, tosylate, triflate, —CHO, —C(O)—CH$_2$—X or —COOH, compound of formula VI-1 is reacted with a compound of formula VII

ASC'-A4  (VII)

wherein A4 is —NHE or —NH$_2$, E being an amino protecting group, to generate compound of formula I-1 wherein L2 is —(CH$_2$)$_o$—, —(CH$_2$)$_p$—, —(CH$_2$)$_o$—C(O)—CH$_2$—, —(CH$_2$)$_o$—C(O)—, respectively, wherein p is 1, 2, 3 or 4.

When Y2 is —NH-PG2, PG2 amino protecting group is removed and the deprotected intermediate is reacted with a compound of formula VII wherein A4 is —CH$_2$—X or —CHO, with X as a halogen atom or a leaving group like mesylate, tosylate, or triflate, to generate compound of formula I-1 wherein L2 is —(CH$_2$)$_o$—. Alternatively, when Y2 is —NH-PG2, PG2 amino protecting group can be removed and the deprotected intermediate is reacted with a compound of formula VII wherein A4 is —COOH, to generate compound of formula I-1 wherein L2 is —(CH$_2$)$_o$—. Or the amino protecting group PG2 can be removed after reaction of a compound of formula VI-1 with a compound of formula VII.

When Y2 is —OH, the compound of formula IV-1 can be converted to the corresponding halide, mesylate, tosylate, triflate compound, and further react with a compound of VII wherein A4 is —NHE or —NH$_2$, E being an amino protecting group, to generate compound of formula I-1 wherein L2 is —(CH$_2$)$_o$—.

Alternatively, when Y2 is —OH, the compound of formula IV-1 can react with a compound of VII wherein A4 is —(CH$_2$)$_q$—X, with X as a halogen atom or a leaving group like mesylate, tosylate, or triflate and q being comprised between 1 and 4 to generate compound of formula I-1 wherein L2 is —(CH$_2$)$_o$—O—(CH$_2$)$_q$.

In certain cases, Y2 may require appropriate activation to allow a reaction of compounds of formulae VI-1 and VII as described in more detail below.

Additionally, when L1 is —(CH$_2$)$_m$—S—(CH$_2$)$_n$— compounds of formulae IV-1, VI-1 or I-1 can be oxidized to generate compounds of formulae VI-1, I-1 or I-2, respectively, wherein L1 is —(CH$_2$)$_m$—SO—(CH$_2$)$_n$— or —(CH$_2$)$_m$—SO$_2$—(CH$_2$)$_n$—.

Process (b)

This process variant can be used for the manufacture of compounds of formula I as defined above, wherein L1 is —O—(CH$_2$)$_n$—, —S—(CH$_2$)$_n$—, —NH—(CH$_2$)$_n$—, —SO—(CH$_2$)$_n$— or —SO$_2$—(CH$_2$)$_n$—, in which formulae n is 0, 1, 2 or 3 within the limits defined by the claims.

In this process a compound of formula VIII

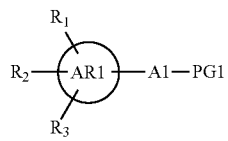
(VIII)

is reacted with a compound of formula IX

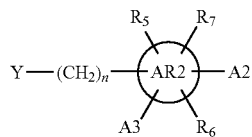
(IX)

to generate a compound of formula IV-2

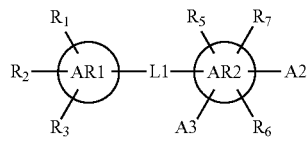
(IV-2)

in which formulae
AR1, AR2, R$_1$, R$_2$, R$_3$, R$_5$, R$_6$, R$_7$ are as in formula I,
n is 0, 1, 2 or 3,
A1 is —O—, —S—, —NH—,
PG1 is a hydrogen atom or an amino protecting group,
Y is a halogen atom or a leaving group like mesylate, tosylate, triflate,
A2 and A3 have the same meaning as in formulae III and IV-1.

Following procedures already described in process (a), the compound of formula IV-2 can react with a compound of formula V

R'$_4$—X      (V)

to generate a compound of formula VI-2

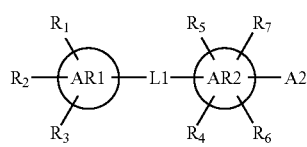
(VI-2)

wherein R$_4$ is as in formula I.

Further coupling with a compound of formula VII, followed by a deprotection step allow the generation of a compound of formula I-3, applying procedures already described in process (a).

Additionally, when L1 is —S—(CH$_2$)$_n$— compounds of formulae IV-2, VI-2 or I-3 can be oxidized to generate compounds of formulae VI-2, I-3 or I-4, respectively, wherein L1 is —SO—(CH$_2$)$_n$— or —SO$_2$—(CH$_2$)$_n$—.

Process (c)

This process variant can be used for the manufacture of compounds of formula I as defined above, wherein L1 is —CH═CH—(CH$_2$)$_m$— (double bond Z, E or Z/E) or —(CH$_2$)$_{m+2}$—, with m being 0 or 1.

In this process a compound of formula II-2

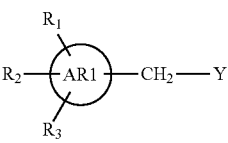
(II-2)

is reacted with a compound of formula X

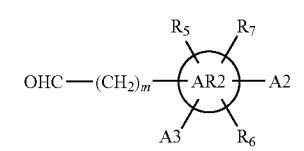
(X)

to generate a compound of formula IV-3

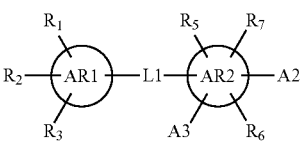
(IV-3)

in which formulae
AR1, AR2, R$_1$, R$_2$, R$_3$, R$_5$, R$_6$, R$_7$ are as in formula I,
Y is a phosphonium salt or a phosphonate,
m is 0 or 1
L1 is —CH═CH—(CH$_2$)$_m$— (double bond Z, E or Z/E),
A2 and A3 have the same meaning as in formulae III and IV-1.

Following procedures already described in process (a), the compound of formula IV-3 can react with a compound of formula V

R'$_4$—X      (V)

to generate a compound of formula VI-3

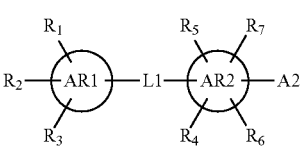
(VI-3)

wherein R$_4$ is as in formula I.

Further coupling with a compound of formula VII, followed by a deprotection step allow the generation of a compound of formula I-5, applying procedures already described in process (a).

When L1 is —CH=CH—$(CH_2)_m$— (double bond Z, E or Z/E), compounds of formulae IV-3, VI-3 or I-5 can further be reduced to generate compounds of formulae VI-3, I-5 or I-6, respectively, wherein L1 is —$(CH_2)_{m+2}$—.

Process (d)

This process variant can be used for the manufacture of compounds of formula I as defined above, wherein L1 is —C≡C—.

In this process a compound of formula XII

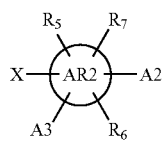
(XII)

is first reacted with trimethylsilylacetylene. Further trimethylsilyl removal allowed the generation of a compound of formula XIII

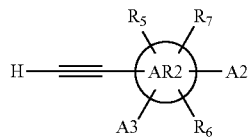
(XIII)

which is then reacted with a compound of formula XI

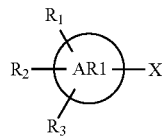
(XI)

to generate a compound of formula IV-4

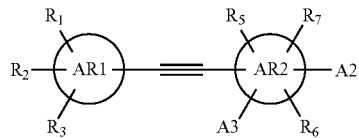
(IV-4)

in which formulae
X is a halogen atom or a triflate,
AR1, AR2, $R_1$, $R_2$, $R_3$, $R_5$, $R_6$, $R_7$ are as in formula I,
A2 and A3 have the same meaning as in formulae III and IV-1.

Alternatively, a compound of formula XI can first react with trimethylsilylacetylene. Further trimethylsilyl removal allowed the preparation of an intermediate which can react with a compound of formula XII to generate a compound of formula IV-4.

Following procedures already described in process (a), the compound of formula IV-4 can react with a compound of formula V

R'$_4$—X (V)

to generate a compound of formula VI-4

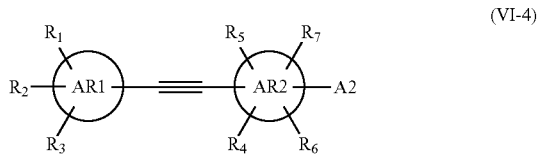
(VI-4)

wherein $R_4$ is as in formula I.

Further coupling with a compound of formula VII, followed by a deprotection step allow the generation of a compound of formula I-7, applying procedures already described in process (a).

Process (e):

This process variant can be used for the manufacture of compounds of formula I as defined above, wherein L1 is —$(CH_2)_m$—NH—C(O)— with m being 0 or 1.

In this process a compound of formula XIV

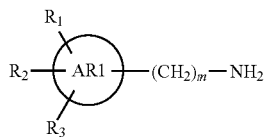
(XIV)

is reacted with a compound of formula XV

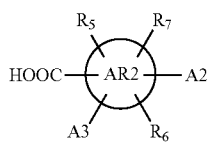
(XV)

to generate a compound of formula IV-5

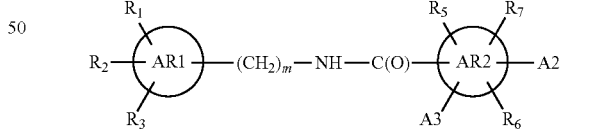
(IV-5)

in which formulae
AR1, AR2, $R_1$, $R_2$, $R_3$, $R_5$, $R_6$, $R_7$ are as in formula I,
m is 0, 1 or 2,
A2 and A3 have the same meaning as in formulae III and IV-1.

Following procedures already described in process (a), the compound of formula IV-5 can react with a compound of formula V

R'$_4$—X (V)

to generate a compound of formula VI-5

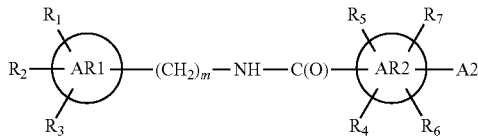
(VI-5)

wherein $R_4$ is as in formula I.

Further coupling with a compound of formula VII, followed by a deprotection step allow the generation of a compound of formula I-8, applying procedures already described in process (a).

Process (f)

This process variant can be used for the manufacture of compounds of formula I as defined above, wherein L1 is —C(O)—NH—(CH$_2$)$_n$— or —SO$_2$—NH—(CH$_2$)$_n$— with n being 0 or 1.

In this process a compound of formula XVI

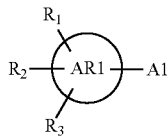
(XVI)

is reacted with a compound of formula XVII

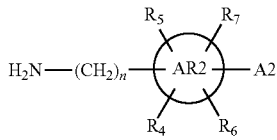
(XVII)

to generate a compound of formula IV-6

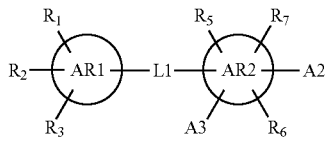
(IV-6)

in which formulae
AR1, AR2, $R_1$, $R_2$, $R_3$, $R_5$, $R_6$, $R_7$ are as in formula I,
A1 is —COOH or —SO$_2$Cl,
n is 0 or 1,
A2 and A3 have the same meaning as in formulae III and IV-1.

Following procedures already described in process (a), the compound of formula IV-6 can react with a compound of formula V

(V)

to generate a compound of formula VI-6

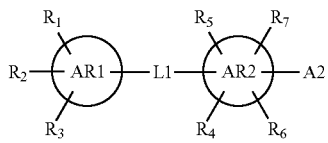
(VI-6)

wherein $R_4$ is as in formula I.

Further coupling with a compound of formula VII, followed by a deprotection step allow the generation of a compound of formula I-9, applying procedures already described in process (a).

Process (g)

This process variant can be used for the manufacture of compounds of formula I as defined above, wherein L1 is absent or is —O—.

In this process a compound of formula XVIII

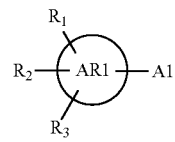
(XVIII)

is reacted with a compound of formula XIX

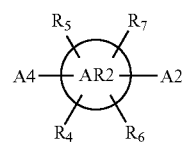
(XIX)

to generate a compound of formula IV-7

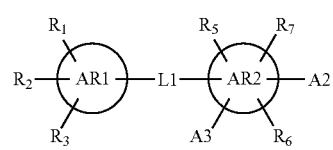
(IV-7)

in which formulae
AR1, AR2, $R_1$, $R_2$, $R_3$, $R_5$, $R_6$, $R_7$ are as in formula I,
A1 is —OH, a halogen atom or a triflate,
A4 is a halogen atom, a boronic acid, a boronic ester or —SnBu$_3$,
A2 and A3 have the same meaning as in formulae III and IV-1.

When A1 is —OH, said compound of formula XVIII can react with a compound of formula XIX wherein A4 is a fluorine atom, a boronic acid or a boronic ester to generate a compound of formula IV-7 wherein L1 is —O—.

When A1 is a halogen atom or a triflate, said compound of formula XVIII can react with a compound of formula XIX wherein A4 a boronic acid, a boronic ester or —SnBu$_3$ to generate a compound of formula IV-7 wherein L1 is absent.

Following procedures already described in process (a), the compound of formula IV-6 can react with a compound of formula V

(V)

to generate a compound of formula VI-7

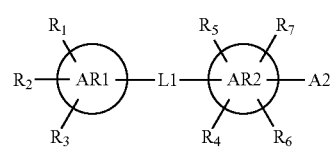
(VI-7)

wherein $R_4$ is as in formula I.

Further coupling with a compound of formula VII, followed by a deprotection step allow the generation of a compound of formula I-10, applying procedures already described in process (a).

Process (h)

This process variant can be used for the manufacture of compounds of formula I as defined above, that present a quaternary amine. These molecules can be obtained by reacting a $C_1$-$C_6$-alkyl halide or the corresponding mesylate, tosylate or triflate with any compound of formula I or VI for which a free secondary amine is present.

The necessary starting materials for the synthetic methods as described herein, if not commercially available, may be made by procedures which are described in the scientific literature, or may be made from commercially available compounds using adaptations of processes reported in the scientific literature. The reader is further referred to *Advanced Organic Chemistry*, $5^{th}$ Edition, by J. March and M. Smith, published by John Wiley & Sons, 2001, for general guidance on reaction conditions and reagents.

Furthermore in some of the reactions mentioned herein it may be necessary or desirable to protect any sensitive groups in compounds. Conventional protecting groups may be used in accordance with standard practice (for illustration see *Protective Groups in Organic Synthesis*, $3^{rd}$ Edition, by T. W. Greene and P. G. M. Wuts, published by John Wiley & Sons, 1999).

The protecting groups may be removed at any convenient stage in the synthesis using conventional techniques well known in the art, or they may be removed during a later reaction step or work-up.

The compounds of formula I wherein L1 is —$(CH_2)_m$—O—$(CH_2)_n$—, —$(CH_2)_m$—NH—$(CH_2)_n$—, —$(CH_2)_m$—S—$(CH_2)_n$—, —$(CH_2)_m$—SO—$(CH_2)_n$— or —$(CH_2)_m$—$SO_2$—$(CH_2)_n$—, with m being 1, 2 or 3 and n being 0, 1, 2 or 3 (within the limits defined by the claims), can be obtained as summarized in Scheme 1.

In Scheme 1, all the symbols have the same meanings as previously described in process (a).

When A1 is —NH— and PG1 is an amino protecting group, compounds of formula III are usually obtained by reacting the corresponding free amine with allyl, fluorenylmethyl or benzyl chloroformate or with di-tert-butyl dicarbonate in presence of a base such as sodium hydroxide, sodium hydrogencarbonate, triethylamine, 4-dimethylaminopyridine or imidazole. They can also be protected as N-benzyl derivatives by reaction with benzyl bromide or chloride in presence of a base such as sodium carbonate or triethylamine. Alternatively, N-benzyl derivatives can be obtained through reductive amination in presence of benzaldehyde. Further strategies to introduce other amino protecting groups have been described in *Protective Groups in Organic Synthesis*, $3^{rd}$ Edition, by T. W. Greene and P. G. M. Wuts, published by John Wiley & Sons, 1999. Compounds of formula IV-1 (Scheme 1) wherein L1 is —$(CH_2)_m$—O—$(CH_2)_n$— can be obtained from compounds of formula II-1 wherein Y1 is —OH via a Mitsunobu coupling (as reviewed in O. Mitsunobu, Synthesis 1981, 1) with compounds of formula III for which A1-PG1 is a hydroxyl group. The reaction is for example performed in the presence of diethyl or diisopropyl azodicarboxylate and triphenylphosphine, in a wide range of solvents such as N,N-dimethylformamide, tetrahydrofuran, 1,2-dimethoxyethane or dichloromethane and within a wide range of temperatures (between −20° C. and 60° C.). The reaction might also be performed using polymer-supported triphenylphosphine.

An alternative route to form compounds of formula IV-1 wherein L1 is —$(CH_2)_m$—O—$(CH_2)_n$— consists of reacting compounds of formula III wherein A1-PG1 is a hydroxyl group with compounds of formula II-1 for which Y1 is a hydroxyl group, which needs to be activated prior to the reaction as described below, or a halogen atom in presence of an inorganic base such as sodium hydride, potassium carbonate or the like in a solvent such as dichloromethane or N,N-dimethylformamide at a temperature ranging between −20° C. and 80° C. Activation of the hydroxyl group of compounds of formula II-1 wherein Y1 is —OH as for

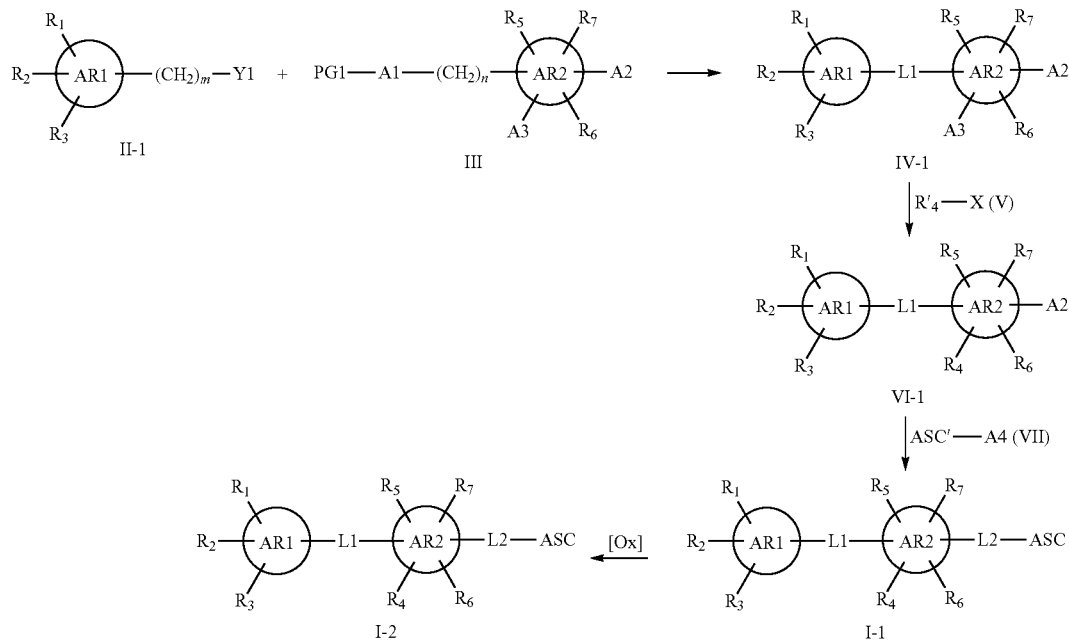

Scheme 1.

example a mesylate, a tosylate or a triflate can be achieved by reacting the corresponding alcohol with methanesulfonyl chloride or methanesulfonic anhydride, p-toluenesulfonyl chloride, trifluoromethanesulfonyl chloride or trifluoromethanesulfonic anhydride, respectively, in presence of a base such as triethylamine or the like in a dry aprotic solvent such as pyridine, acetonitrile, tetrahydrofuran or dichloromethane between −30° C. and 80° C.

The same procedure can also be applied to generate compounds of formula IV-1 wherein L1 is —$(CH_2)_m$—S—$(CH_2)_n$— or —$(CH_2)_m$—NH—$(CH_2)_n$— starting from compounds of formula II-1 wherein Y1 is a halogen atom and compounds of formula III wherein A1-PG1 is a thiol group or an amino group (protected or not), respectively.

When A3 is a fluorine atom, compounds of formula IV-1 can react with a compound of formula V for which X is —$CH_2$—OH, in presence of an inorganic base such as sodium hydride or the like in a solvent such as tetrahydrofuran or N,N-dimethylformamide at a temperature ranging between −20° C. and 80° C., to generate compounds of formula VI-1 wherein $R_4$ is an ether group.

Alternatively, when A3 is a hydroxyl group, a Mitsunobu coupling between compounds of formula IV-1 and compounds of formula V for which X is —$CH_2$—OH can lead to the generation of compounds of formula IV-1 wherein $R_4$ is an ether group.

Additionally, when A3 is a hydroxyl group, compounds of formula IV-1 can react with a compound of formula V for which X is a halogen atom or a leaving group, in presence of an inorganic base such as sodium hydride or the like in a solvent such as tetrahydrofuran or N,N-dimethylformamide at a temperature ranging between −20° C. and 80° C., to generate compounds of formula VI-1 wherein $R_4$ is an ether group.

When A3 is —CHO, compounds of formula IV-1 can react with compounds of formula V for which X is a phosphonium salt or a phosphonate via a Wittig or Horner-Wadsworth-Emmons reaction, respectively, to generate compounds of formula VI-1 for which R4 is a $C_2$-$C_6$-alkenyl group.

The Wittig reaction is the reaction of an aldehyde with a triphenyl phosphonium ylide to afford an alkene and triphenylphosphine oxide. The Wittig reagent is usually prepared from a phosphonium salt, which is, in turn, prepared by alkylation of triphenylphosphine with a benzyl halide. To form the Wittig reagent (benzyl ylide), the phosphonium salt is suspended in a solvent such as diethyl ether or tetrahydrofuran and a strong base such as n-butyl lithium is added. With simple ylides, the product is usually mainly the Z-isomer, although a lesser amount of the E-isomer also is often formed. If the reaction is performed in N,N-dimethylformamide in the presence of lithium or sodium iodide, the product is almost exclusively the Z-isomer. If the Z-isomer is the desired product, the Schlosser modification may be used.

Alternatively the Horner-Wadsworth-Emmons reaction produces predominantly E-alkenes. The Horner-Wadsworth-Emmons reaction is the condensation of stabilized phosphonate carbanions with aldehydes in presence of a base such as sodium hydride or sodium methylate in a solvent such as diethyl ether or tetrahydrofuran, between 0° C. and 50° C. In contrast to phosphonium ylides used in the Wittig reaction, phosphonate-stabilized carbanions are more nucleophilic and more basic. Diethyl benzylphosphonates can be easily prepared from readily available benzyl halides.

When A3 is —CHO, compounds of formula IV-1 can react with compounds of formula V for which X is —$NH_2$ or —NHE, E being an amino protecting group, via a reductive amination reaction, to generate compounds of formula VI-1 for which $R_4$ is an amine group. The reductive amination reaction between the amine and the aldehyde to form an intermediate imine is conducted in a solvent system allowing the removal of the formed water through physical or chemical means (e.g. distillation of the solvent-water azeotrope or presence of drying agents such as molecular sieves, magnesium sulfate or sodium sulfate). Such solvent is typically toluene, n-hexane, tetrahydrofuran, dichloromethane N,N-dimethylformamide, N,N-dimethylacetamide, acetonitrile, 1,2-dichloroethane or mixture of solvents such as methanol-1,2-dichloroethane. The reaction can be catalyzed by traces of acid (usually acetic acid). The intermediate imine is reduced subsequently or simultaneously with a suitable reducing agent (e.g. sodium borohydride, sodium cyanoborohydride, sodiumtriacetoxyborohydride; R. O. and M. K. Hutchins, *Comprehensive Organic Synthesis*, B. M. Trost, I. Fleming, Eds; Pergamon Press: New York (1991), vol. 8, p. 25-78) or through hydrogenation over a noble metal catalyst such as palladium on activated carbon. The reaction is usually carried out between −10° C. and 110° C., preferably between 0° C. and 60° C. The reaction can also be carried out in one pot. It can also be performed in protic solvents such as methanol or water in presence of a picoline-borane complex (Tetrahedron, 2004, 60, 7899).

When A3 is —$CH_2OH$, compounds of formula IV-1 can be converted to the corresponding halide, mesylate, tosylate, triflate compounds and further react with compounds of formula V for which X is a hydroxyl group, a thiol group or an amino group (protected or not) to generate compounds of formula VI-1 for which R4 is an ether, a thiol or amine group, respectively. The substitution reaction can proceed at a temperature between −20° C. and 100° C. in a dry aprotic solvent like dichloromethane, acetonitrile, N,N-dimethylformamide, dimethyl sulfoxide or tetrahydrofuran without or with an inorganic base such as potassium carbonate or cesium carbonate, or an organic base such as triethylamine or N,N-diisopropylethylamine.

When A3 is —COOH, compounds of formula IV-1 can react with compounds of formula V for which X is —$NH_2$ or —NHE, E being an amino protecting group, via a peptidic coupling reaction, to generate compounds of formula VI-1 for which $R_4$ is an amide group. The reaction takes place in the presence of an activating agent such as N,N'-dicyclohexylcarbodiimide or N-(3-dimethylaminopropyl)-N'-ethylcarbodiimide hydrochloride, with the optional addition of 1-hydroxybenzotriazole. Other suitable coupling agents may be utilized such as, O-(7-azabenzotriazol-1-yl)-N,N,N',N'-tetramethyluronium hexafluorophosphate, 2-ethoxy-1-ethoxycarbonyl-1,2-dihydroquinoline, carbonyldiimidazole or diethylphosphorylcyanide. Optionally, a base like triethylamine, N,N-diisopropylethylamine or pyridine can be added to perform the coupling. The peptidic coupling is conducted at a temperature comprised between −20° C. and 80° C., in an inert solvent, preferably a dry aprotic solvent like dichloromethane, acetonitrile or N,N-dimethylformamide and chloroform. Alternatively, the carboxylic acid can be activated by conversion into its corresponding acid chloride or its corresponding activated ester, such as the N-hydroxysuccinimidyl ester (Org. Process Res. & Dev., 2002, 863) or the benzothiazolyl thioester (J. Antibiotics, 2000, 1071). The generated activated entity can react at a temperature comprised between −20° C. and 80° C. with compound of formula II-1 in an aprotic solvent like dichloromethane, chloroform, acetonitrile, N,N-dimethylformamide and tetrahydrofuran to generate compound of formula I-1. Optionally, a base like triethylamine, N,N-diisopropylethylamine, pyridine, sodium hydroxide, sodium carbonate, potassium carbonate can be added to perform the coupling.

For the generation of compounds of formula I-1, when Y2 is a halogen atom, a leaving group or —C(O)—$CH_2$—X, with X being a halogen atom, compounds of formula VI-1 can react with compounds of formula VII for which A4 is —$NH_2$ or —NHE, E being an amino protecting group, via a substitution reaction as previously described above, to generate compounds of formula I-1 wherein L2 is —$(CH_2)_o$— or —$(CH_2)_o$—C(O)—$CH_2$—, respectively.

Additionally, when Y2 is —CHO, compounds of formula VI-1 can react with compounds of formula VII for which A4 is —$NH_2$ or —NHE, E being an amino protecting group, via a reductive amination reaction as previously described above, to generate compounds of formula I-1 for which L2 is —$(CH_2)_p$—, wherein p is comprised between 1 and 4.

In certain cases, compounds of formula VI-1 for which Y2 is —CHO can be generated from the corresponding compounds for which Y2 is an ester group or a carboxylic acid function. The ester derivatives are further reduced into their corresponding alcohol. This reduction is performed with a reducing agent like boron or aluminium hydride reducing agent such as lithium aluminium hydride, lithium borohydride, sodium borohydride in a solvent such as tetrahydrofuran between $-20°$ C. and $80°$ C. Alternatively, the ester function is hydrolyzed into its corresponding carboxylic acid using an alkali hydroxide such as sodium hydroxide, potassium hydroxide or lithium hydroxide in water or in a mixture of water with polar protic or aprotic organic solvents such as dioxane, tetrahydrofuran or methanol between $-10°$ C. and $80°$ C. The resulting carboxylic acid is further reduced into the corresponding alcohol using a borane derivative such as borane-tetrahydrofuran complex in a solvent such as tetrahydrofuran between $-10°$ C. and $80°$ C. The generated alcohol is then transformed into its corresponding aldehyde through oxidation under Swern, Dess Martin, Sarett or Corey-Kim conditions respectively. Further methods are described in Comprehensive Organic Transformations. A guide to functional Group Preparations; $2^{nd}$ Edition, R. C. Larock, Wiley-VC; New York, Chichester, Weinheim, Brisbane, Singapore, Toronto, 1999. Section aldehydes and ketones, p. 1235-1236 and 1238-1246.

When Y2 is —COOH, compounds of formula VI-1 can react with compounds of formula VII for which A4 is —$NH_2$ or —NHE, E being an amino protecting group, via a peptidic coupling reaction as previously described above, to generate compounds of formula I-1 wherein L2 is —$(CH_2)_o$—C(O)—.

Alternatively, when Y2 is —NH-PG2, PG2 being an amino protecting group, the protecting group can first be removed under standard conditions. For example the benzyl carbamates are deprotected by hydrogenolysis over a noble metal catalyst (e.g. palladium or palladium hydroxide on activated carbon). The Boc group is removed under acidic conditions such as hydrochloric acid in an organic solvent such as methanol, dioxane or ethyl acetate, or trifluoroacetic acid neat or diluted in a solvent such as dichloromethane. The Alloc group is removed in presence of a palladium salt such as palladium acetate or tetrakis(triphenylphosphine) palladium(0) and an allyl cation scavenger such as morpholine, pyrrolidine, dimedone or tributylstannane between $0°$ C. and $70°$ C. in a solvent such as tetrahydrofuran. The N-benzyl protected amines are deprotected by hydrogenolysis over a noble metal catalyst (e.g. palladium hydroxide on activated carbon). The Fmoc protecting group is removed under mild basic conditions such as diluted morpholine or piperidine in N,N-dimethylformamide or acetonitrile. Further general methods to remove amine protecting groups have been described in Protective Groups in Organic Synthesis, $3^{rd}$ Edition, by T. W. Greene and P. G. M. Wuts, published by John Wiley & Sons, 1999.

The corresponding free amine can then react with compounds of formula VII for which A4 is —$CH_2$—X or —CHO via a substitution or a reductive amination, respectively, to generate compounds of formula I-1 wherein L2 is —$(CH_2)_o$—.

The corresponding free amine can also react with compounds of formula VII for which A4 is —COOH via a peptidic coupling, to generate compounds of formula I-1 wherein L2 is —$(CH_2)_o$—.

Alternatively, the amino protecting group PG2 can also be removed only after the substitution, the reductive amination or the peptidic coupling reactions, following standard procedure described above.

For the generation of compounds of formula I-1 for which L2 is —$(CH_2)_o$—, compounds of formula VI-1 wherein Y2 is a hydroxyl group, can be converted to the corresponding halide, mesylate, tosylate or triflate compound and react with compounds of formula VII for which A4 is —$NH_2$ or —NHE, E being an amino protecting group, via a substitution reaction as previously described above.

In addition and following substitution reaction conditions described above, compounds of formula I-1 for which L2 is —$(CH_2)_o$—O—$(CH_2)_q$— can be obtained by reacting compounds of formula VI-1 wherein Y2 is a hydroxyl group with compounds of formula VII for which A4 is —$(CH_2)_q$—X, X being a halogen atom or a leaving group and q being comprised between 1 and 4.

Finally, compounds of formulae VI-1, I-1 and I-2 for which L1 is —$(CH_2)_m$—SO—$(CH_2)_n$— or —$(CH_2)_m$—$SO_2$—$(CH_2)_n$— can be generated by oxidation of compounds of formulae IV-1, VI-1 and I-1, respectively, for which L1 is —$(CH_2)_m$—S—$(CH_2)_n$— in presence of a peroxide such as dihydrogen peroxide or meta-chloroperbenzoic acid or the like in a solvent such as dichloromethane, acetonitrile or ethyl acetate at a temperature ranging between $-20°$ C. and $60°$ C.

In certain cases, when A3 or Y2 are hydroxyl groups, protection of this function is required and is carried out under standard conditions. For example the benzyl or the allyl groups are introduced with an alkaline solution of benzyl or allyl halide, respectively; the tetrahydropyranyl group is introduced with dihydropyran under acidic conditions; the hydroxyl groups are protected as silyl ethers by reacting with the required silyl chloride reagent in presence of a base such as imidazole or pyridine. Further general methods to introduce hydroxyl protecting groups have been described in Protective Groups in Organic Synthesis, $3^{rd}$ Edition, by T. W. Greene and P. G. M. Wuts, published by John Wiley & Sons, 1999.

Such hydroxyl protecting groups can be removed at any convenient step of the process. The benzyl group is removed by hydrogenolysis over a noble metal catalyst (e.g. palladium or palladium hydroxide on activated carbon); the tetrahydropyranyl group is removed in presence of para-toluenesulfonic acid with a pH of 3, between $40°$ C. and $70°$ C. in a solvent such as methanol; the silyl ether groups are removed either using fluoride anion sources such as tetra-n-butylammonium fluoride in a solvent such as tetrahydrofuran or N,N-dimethylformamide between $0°$ C. and $40°$ C. or in hydrofluoric acid in acetonitrile between $0°$ C. and $40°$ C. or using acidic conditions such as acetic acid in tetrahydrofuran-methanol or hydrochloric acid in methanol. Further general methods to remove hydroxyl protecting groups have been described in Protective Groups in Organic Synthesis, $3^{rd}$ Edition, by T. W. Greene and P. G. M. Wuts, published by John Wiley & Sons, 1999. In Scheme 1, the amino protecting groups PG1, PG2 and E can be removed at any convenient step of the process.

The compounds of formula I wherein L1 is —O—$(CH_2)_n$—, —S—$(CH_2)_n$—, —NH—$(CH_2)_n$—, —SO—$(CH_2)_n$— or —$SO_2$—$(CH_2)_n$—, with n being 0, 1, 2 or 3 (within the limits defined by the claims), can be obtained as summarized in Scheme 2.

Scheme 2.

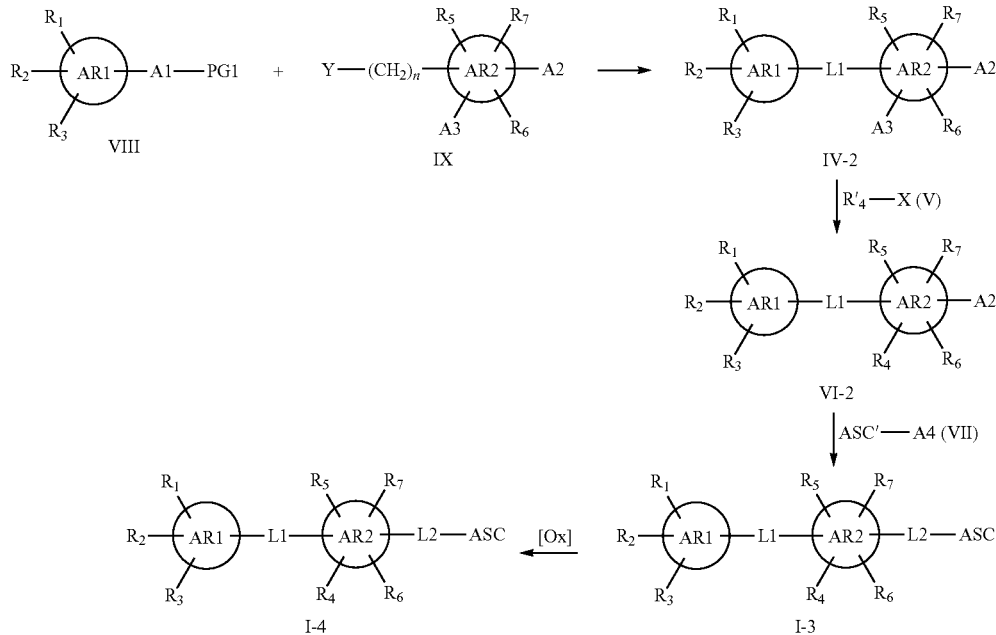

In Scheme 2, all the symbols have the same meanings as previously described in process (b).

Compounds of formula IV-2 wherein L1 is —O—$(CH_2)_n$—, —S—$(CH_2)_n$— or —NH—$(CH_2)$— can be obtained via a substitution reaction between compounds of formula VIII for which -A1-PG1 is —OH, —SH, —$NH_2$ or NHE, respectively, E being an amino protecting group, with compounds of formula IX, following procedures previously described above in Scheme 1.

Alternatively, compounds of formula IV-2 wherein L1 is —O—$(CH_2)_n$—, can be obtained from compounds of formula VIII wherein -A1-PG1 is —OH via a Mitsunobu coupling (as reviewed in O. Mitsunobu, Synthesis 1981, 1) with compounds of formula IX for which Y is a hydroxyl group, following procedures previously described above in Scheme 1.

Further conversion of compounds of formula IV-2 into compounds of formula I-3 and I-4 is performed following methods described above in Scheme 1 for the preparation of compounds of formula I-1 and I-2.

In Scheme 2, the amino protecting groups PG1, PG2 and E can be removed at any convenient step of the process.

The compounds of formula I wherein L1 is —CH=CH—$(CH_2)_m$— (double bond Z, E or Z/E) or —$(CH_2)_{m+2}$—, with m being 0 or 1, can be obtained as summarized in Scheme 3.

Scheme 3.

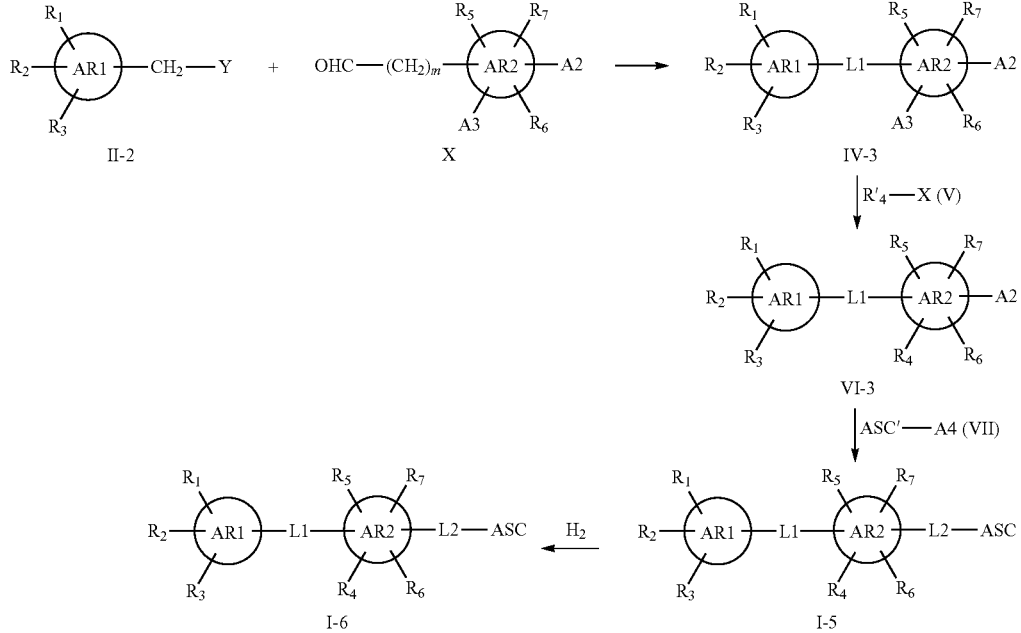

In Scheme 3, all the symbols have the same meanings as previously described in process (c).

Compounds of formula IV-3 wherein L1 is —CH=CH—$(CH_2)_m$— (double bond Z, E or Z/E), with m being 0 or 1, can be obtained via a Wittig or Horner-Wadsworth-Emmons reaction between compounds of formula II-2 for which X is a phosphonium salt or a phosphonate and compounds of formula X, following procedures previously described above in Scheme 1.

Further conversion of compounds of formula IV-3 into compounds of formula I-5 is performed following methods described above in Scheme 1 for the preparation of compounds of formula I-1.

Compounds of formulae IV-2, VI-2 and I-5 for which L1 is —CH=CH—$(CH_2)_m$— (double bond Z, E or Z/E), with m being 0 or 1, can also be converted into compounds of formulae VI-2, I-5 and I-6, respectively, for which L1 is or —$(CH_2)_{m+2}$— via hydrogenolysis over a noble metal catalyst (palladium or palladium hydroxide on activated carbon; Chem. Eur. J., 1999, 5, 1055).

In Scheme 3, the amino protecting groups PG1, PG2 and E can be removed at any convenient step of the process.

The compounds of formula I wherein L1 is —C≡C— can be obtained as summarized in Scheme 4.

In Scheme 4, all the symbols have the same meanings as previously described in process (d).

In Scheme 4, compounds of formula XII are first converted into compounds of formula XIII, via a Sonogashira cross-coupling reaction with the commercially available trimethylsilylacetylene, followed by a desylilation step.

The Sonogashira reaction is a cross-coupling of terminal alkynes with aryl or vinyl halides that is carried out in presence of a palladium catalyst such as palladium(II) acetate, palladium(II) chloride, tetrakis(triphenylphosphine) palladium(0) or the like, a copper(I) cocatalyst such as copper(I) iodide and an amine base such as diethylamine, triethylamine, diisoppropylamine, diisopropylethylamine, N-butylamine or the like in an inert solvent such as tetrahydrofuran or N,N-dimethylformamide, at a temperature comprised between 0° C. and 120° C. Other bases such as potassium carbonate or cesium carbonate are occasionally used.

Desilylation is then carried out under standard conditions in presence of a base such as potassium carbonate in a solvent such as methanol, or in presence of tetrabutylammonium fluoride in tetrahydrofuran. Further general methods to remove the trimethylsilyl group have been described in *Protective Groups in Organic Synthesis*, 3$^{rd}$ Edition, by T. W. Greene and P. G. M. Wuts, published by John Wiley & Sons, 1999.

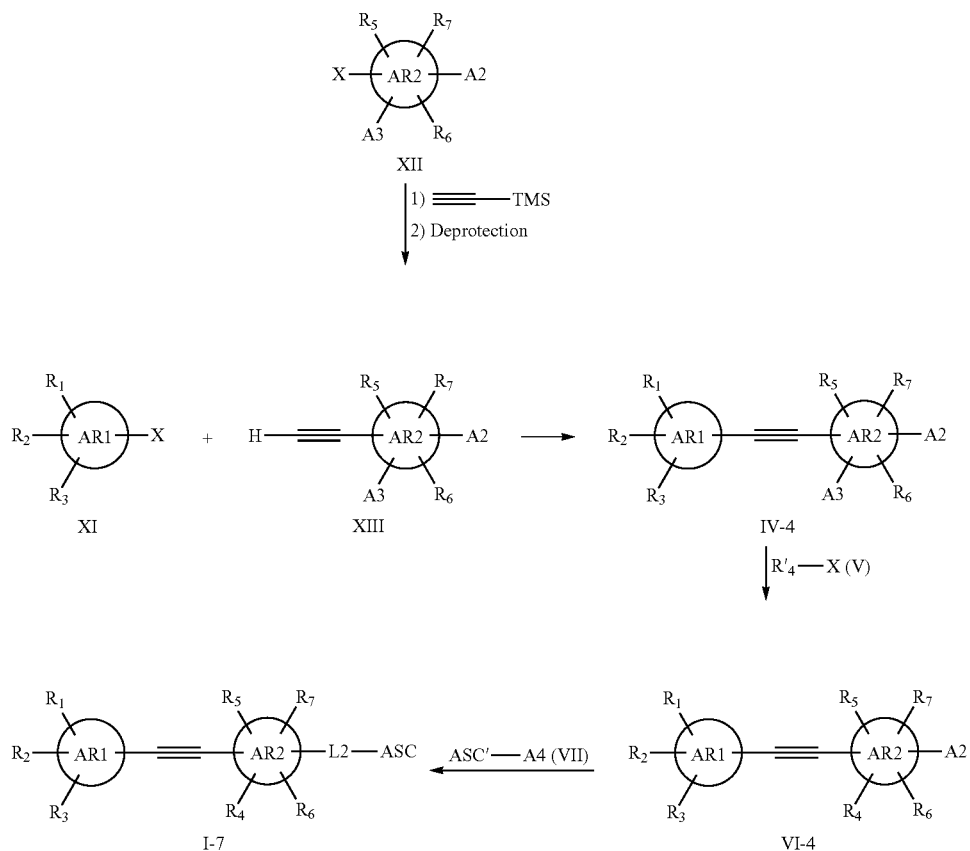

Scheme 4.

Compounds of formula IV-4 are then obtained via a second Sonogashira cross-coupling reaction between compounds of formula XI and the generated compounds of formula XIII.

Further conversion of compounds of formula IV-4 into compounds of formula I-7 is performed following methods described above in Scheme 1 for the preparation of compounds of formula I-1. In Scheme 4, the amino protecting groups PG1, PG2 and E can be removed at any convenient step of the process.

The compounds of formula I wherein L1 is —(CH$_2$)$_m$—NH—C(O)—, with m being 0 or 1, can be obtained as summarized in Scheme 5.

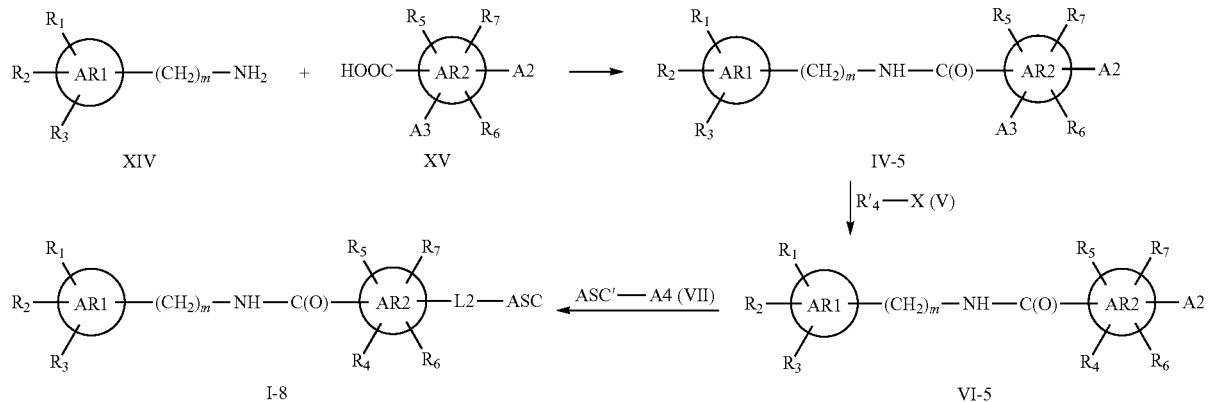

Scheme 5.

In Scheme 5, all the symbols have the same meanings as previously described in process (e).

Compounds of formula IV-5 can be prepared via a peptidic coupling reaction between compounds of formula XIV and compounds of formula XV, following procedures previously described above in Scheme 1.

Further conversion of compounds of formula IV-5 into compounds of formula I-8 is performed following methods described above in Scheme 1 for the preparation of compounds of formula I-1.

In Scheme 5, the amino protecting groups PG1, PG2 and E can be removed at any convenient step of the process.

The compounds of formula I wherein L1 is —C(O)—NH—(CH$_2$)$_n$— or —SO$_2$—NH—(CH$_2$)$_n$— with n being 0 or 1, can be obtained as summarized in Scheme 6.

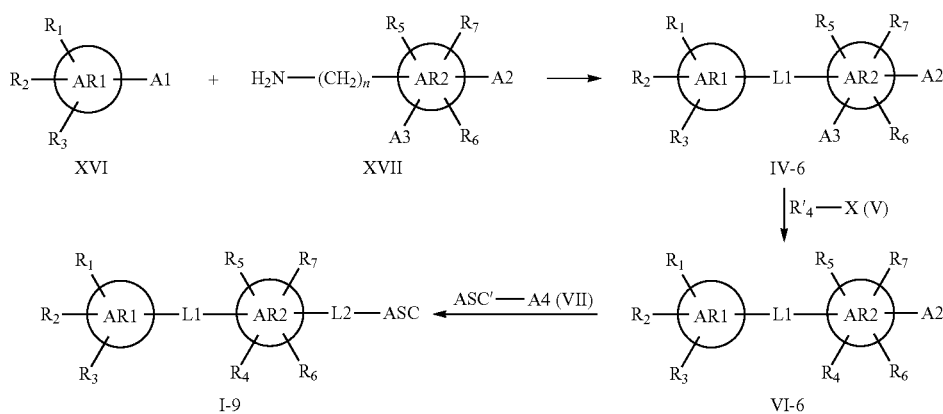

Scheme 6.

In Scheme 6, all the symbols have the same meanings as previously described in process (f).

When A1 is —COOH, compounds of formula IV-6 can be prepared via a peptidic coupling reaction between compounds of formula XVI and compounds of formula XVII, following procedures previously described above in Scheme 1.

When A1 is —SO$_2$Cl, compounds of formula IV-6 can be prepared following substitution reaction conditions previously described above in Scheme 1.

Further conversion of compounds of formula IV-6 into compounds of formula I-9 is performed following methods described above in Scheme 1 for the preparation of compounds of formula I-1.

In Scheme 6, the amino protecting groups PG1, PG2 and E can be removed at any convenient step of the process.

The compounds of formula I wherein L1 is absent or is —O— can be obtained as summarized in Scheme 7.

can be carried out in a variety of organic solvents including toluene, tetrahydrofuran, dioxane, 1,2-dichloroethane, N,N-dimethylformamide, dimethylsulfoxide and acetonitrile, aqueous solvents and under biphasic conditions. Reactions are typically run from room temperature to 150° C. Additives such as cesium fluoride, potassium fluoride, potassium hydroxide or sodium ethylate frequently accelerate the coupling. Potassium trifluoroborates and organoboranes or boronate esters may be used in place of boronic acids. Although there are numerous components in the Suzuki reaction such as the particular palladium catalyst, the ligand, additives, solvent, temperature, numerous protocols have been identified. One skilled in the art will be able to identify a satisfactory protocol without undue experimentation.

Alternatively the Stille coupling is a versatile palladium-catalyzed coupling reaction between organostannanes and

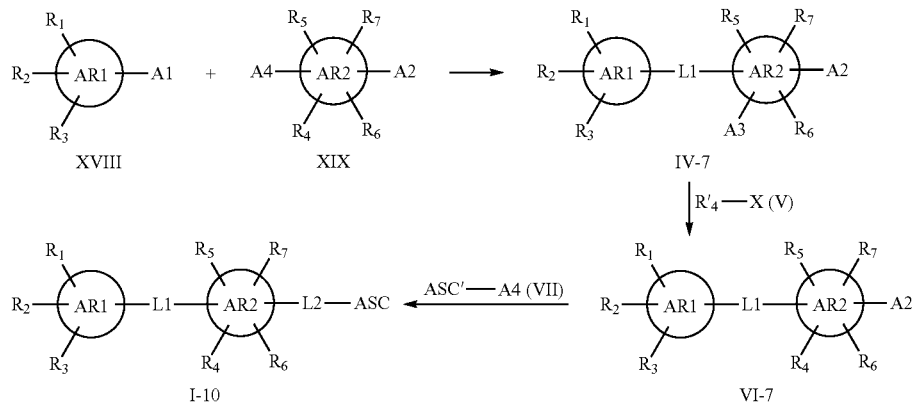

Scheme 7.

In Scheme 7, all the symbols have the same meanings as previously described in process (g).

When A1 is —OH, compounds of formula XVIII can react with compounds of formula XIX for which A4 is a fluorine atom, under basic conditions in presence of potassium carbonate, cesium carbonate or the like in a solvent such as N,N-dimethylformamide, at a temperature between 20° C. and 120° C., to generate compounds of formula IV-7 wherein L1 is —O—.

Alternatively, compounds of formula IV-7 wherein L1 is —O— can be obtained by reacting compounds of formula XVIII for which A1 is —OH with compounds of formula XIX for which A4 is a boronic acid or a boronic ester in presence of copper(II) acetate and triethylamine in a solvent such as dichloromethane under dry conditions and at a temperature between 0° C. and 80° C.

When A1 is a halogen atom or a triflate, compounds of formula XVIII can react with compounds of formula XIX for which A4 is a boronic acid, a boronic ester or —SnBu$_3$ via a Suzuki or a Stille cross coupling reaction, to generate compounds of formula VI-7 wherein L1 is absent.

The Suzuki reaction is a palladium-catalyzed cross coupling between organoboronic acids and aryl or vinyl halides or triflates. Typical catalysts include palladium(II) acetate, tetrakis(triphenylphosphine)palladium(0), bis(triphenylphosphine)palladium(II) dichloride and [1,1'bis(diphenylphosphino)ferrocene]dichloropalladium(II). The reaction halides or pseudohalides. In comparison to the Suzuki reaction, the main drawback is the toxicity of the tin compounds used, and their low polarity, which makes them poorly soluble in water.

Further conversion of compounds of formula IV-7 into compounds of formula I-10 is performed following methods described above in Scheme 1 for the preparation of compounds of formula I-1.

In Scheme 7, the amino protecting groups PG1, PG2 and E can be removed at any convenient step of the process.

Finally, some compounds of formula I present a quaternary amine. These compounds can be obtained by reacting a C$_1$-C$_6$-alkyl halide or the corresponding mesylate, tosylate or triflate with any compounds of formula I or VI for which a free amine is present, in presence of a base such as sodium hydrogen carbonate, potassium carbonate, cesium carbonate, sodium hydroxide, triethylamine, in a variety of organic solvents including methanol, acetonitrile, acetone, dichloromethane and N,N-dimethylformamide, aqueous solvents and under biphasic conditions. Reactions are typically run from 0° C. to 150° C.

Unless otherwise stated the required starting compounds of formula II, III, V, VII to XII, XIV to XIX are prepared following or adapting procedures described in the scientific literature.

When an optically active form of a compound of the invention is required, it may be obtained by carrying out one of the above procedures using a pure enantiomer or diastereomer as a starting material, or by resolution of a mixture of the enantiomers or diastereomers of the final product or intermediate using a standard procedure. The resolution of enantiomers may be achieved by chromatography on a chiral stationary phase, such as REGIS PIRKLE COVALENT (R-R) WHELK-02, 10 μm, 100 Å, 250×21.1 mm column. Alternatively, resolution of stereoisomers may be obtained by preparation and selective crystallization of a diastereomeric salt of a chiral intermediate or chiral product with a chiral acid, such as camphorsulfonic acid.

Alternatively a method of stereoselective synthesis may be employed, for example by using a chiral variant of a protecting group, a chiral catalyst or a chiral reagent where appropriate in the reaction sequence. Enzymatic techniques may also be used for the preparation of optically active compounds and/or intermediates.

The invention will now be described by way of non-limiting examples.

EXAMPLES

Particular embodiments of the invention are described in the following Examples, which serve to illustrate the invention in more detail All reagents and solvents are generally used as received from the commercial supplier; reactions are routinely performed with anhydrous solvents in well-dried glassware under an argon or nitrogen atmosphere;
evaporations are carried out by rotary evaporation under reduced pressure and work-up procedures are carried out after removal of residual solids by filtration;
all temperatures are given in ° C.; unless otherwise noted, operations are carried out at room temperature, that is typically in the range 18-25° C.;
column chromatography (by the flash procedure) is used to purify compounds and is performed using Merck silica gel 60 (70-230 mesh ASTM) unless otherwise stated;
in general, the course of reactions is followed by TLC, HPLC, or LC/MS and reaction times are given for illustration only; yields are given for illustration only and are not necessarily the maximum attainable; the structure of the final products of the invention is generally confirmed by NMR or HPLC and mass spectral techniques.

HPLC of final products are generated using a Dionex Ultimate 3000 instrument and the following conditions:

| | |
|---|---|
| Mobile Phase A: | 50 mM Ammonium acetate aqueous solution |
| Mobile Phase B: | Acetonitrile |
| Column: | YMC Triart C18 5 μm 12 nm 100 × 4.6 mm |
| Column Temperature: | 50° C. |
| Detection: | UV 250 nm |
| Injection: | 2 μL of 20 mM sample DMSO solution |
| Flow: | 1.6 mL/min |

| Gradient | Time (min) | % Mobile Phase B |
|---|---|---|
| | 0 | 5 |
| | 8 | 95 |
| | 10 | 95 |
| 3 min equilibration | | |

Proton NMR spectra are recorded on a Brucker 400 MHz spectrometer. Chemical shifts (δ) are reported in ppm relative to Me$_4$Si as internal standard, and J values are in Hertz (Hz). Each peak is denoted as a broad singlet (br), singlet (s), doublet (d), triplet (t), quadruplet (q), doublet of doublets (dd), triplet of doublets (td) or multiplet (m).

Mass spectra are generated using a q-Tof Ultima (Waters AG) mass spectrometer in the positive ESI mode.

The system is equipped with the standard Lockspray interface;
each intermediate is purified to the standard required for the subsequent stage and is characterized in sufficient detail to confirm that the assigned structure is correct;
analytical and preparative HPLC on non-chiral phases are performed using RP-C18 based columns; the following abbreviations may be used:
CDCl$_3$: Deuterated chloroform
CD$_3$OD: Deuterated methanol
DMSO-d6: Deuterated dimethyl sulphoxide
D$_2$O: Deuterated water
ELSD: Evaporative light scattering detection
ESI: Electrospray ionization
HPLC: High performance liquid chromatography
J: Coupling constant
LC/MS: Liquid chromatography coupled to mass spectroscopy Me$_4$Si:
Me$_4$Si: Tetramethylsilane
MS: Mass spectroscopy
NMR: Nuclear magnetic resonance
TLC: Thin layer chromatography The following Examples refer to the compounds of formula I as indicated in Table 1:

TABLE 1

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 1 | (structure: 2-chlorobenzyl ether linked to phenyl-CH$_2$-NH-CH$_2$-piperidine) | 1 | Ex 37 | Commercially Available [924855-44-7] | 345.3 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 2 | | 1 | Ex 37 | Commercially Available [924855-67-4] | 325.4 [M + H]$^+$ |
| 3 | | 1 | Ex 37 | Commercially Available [924866-17-1] | 345.3 [M + H]$^+$ |
| 4 | | 1 | Ex 37 | Commercially Available [915902-83-9] | 375.3 [M + H]$^+$ |
| 5 | | 1 | Ex 37 | Commercially Available [924866-16-0] | 345.3 [M + H]$^+$ |
| 6 | | 1 | Ex 37 | Commercially Available [919013-66-4] | 375.3 [M + H]$^+$ |
| 7 | | 1 | Ex 37 | Commercially Available [924855-55-0] | 345.3 [M + H]$^+$ |
| 8 | | 1 | Ex 37 | Commercially Available [915875-61-5] | 345.3 [M + H]$^+$ |
| 9 | | 1 | Ex 37 | Commercially Available- [915926-22-6] | 345.3 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 10 | | 1 | Ex 37 | Commercially Available [924855-42-5] | 311.4 [M + H]⁺ |
| 11 | | 1 | Ex 37 | Commercially Available [924855-46-9] | 375.3 [M + H]⁺ |
| 12 | | 1 | Ex 37 | Commercially Available [725211-65-4] | 311.2 [M + H]⁺ |
| 13 | | 1 | Ex 37 | DMSO + D$_2$O: 7.45 (m, 4H), 7.35 (t, J = 8.0 Hz, 1H), 7.14 (d, J = 1.6 Hz, 1H), 7.07 (m, 2H), 5.11 (s, 2H), 4.08 (s, 2H), 3.99 (m, 2H), 3.84 (m, 2H), 3.20 (m, 3H) | 317.1 [M + H]⁺ |
| 14 | | 1 | — | DMSO: 7.30-7.55 (m, 7H), 7.05 (d, J = 8.7 Hz, 2H), 5.15 (s, 2H), 3.25 (m, 2H), 2.98 (m, 2H), 2.80 (m, 1H), 1.70 (m, 2H), 1.15 (m, 2H) | 311.3 [M + H]⁺ |
| 15 | | 7 | Ex 37 | DMSO: 9.46 (br, 2H), 9.04 (br, 2H), 7.63 (m, 2H), 7.43 (m, 2H), 7.19 (m, 1H), 7.04 (m, 4H), 4.11 (s, 2H), 3.25 (m, 2H), 2.84 (m, 4H), 2.08 (m, 1H), 1.95 (m, 2H), 1.43 (m, 2H) | 297.3 [M + H]⁺ |
| 16 | | 3 | Ex 37 | DMSO: 9.55 (br, 2H), 9.20 (br, 1H), 8.90 (br, 1H), 7.65 (m, 6H), 7.41 (m, 2H), 7.30 (m, 3H), 4.14 (s, 2H), 3.26 (m, 2H), 2.82 (m, 4H), 2.10 (m, 1H), 1.97 (m, 2H), 1.43 (m, 2H) | 307.4 [M + H]⁺ |
| 17 | | 1 | Ex 37 | DMSO: 10.00 (br, 3H), 7.50 (m, 4H), 7.36 (m, 2H), 7.10 (m, 2H), 5.15 (s, 2H), 4.04 (m, 2H), 4.00 (m, 2H), 3.95 (m, 2H), 3.20 (m, 3H), 2.78 (s, 3H) | 331.1 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 18 | | 1 | Ex 37 | DMSO: 9.53 (br, 2H), 9.00 (br, 2H), 7.86 (d, J = 2.0 Hz, 1H), 7.63 (d, J = 8.4 Hz, 1H), 7.56 (dd, J = 2.0 Hz, 8.4 Hz, 1H), 7.39 (t, J = 8.0 Hz, 1H), 7.09 (dd, J = 8.0, 2.0 Hz, 1H), 5.15 (s, 2H), 4.11 (m, 2H), 3.99 (m, 2H), 3.88 (m, 2H), 3.22 (m, 3H) | 395.1, 397.1 [M + H]+ |
| 19 | | 1 | Ex 37 | DMSO: 11.25 (br, 1H), 10.66 (br, 1H), 10.48 (br, 1H), 7.50 (m, 4H), 7.39 (m, 2H), 7.14 (m, 2H), 5.16 (s, 2H), 4.00-4.30 (m, 4H), 3.70-3.95 (m, 2H), 3.45 (m, 3H), 2.84 (m, 3H), 2.57 (m, 3H) | 345.2 [M + H]+ |
| 20 | | 1 | Ex 37 | DMSO: 11.19 (br, 1H), 9.11, 8.87 (2br, H), 7.49 (m, 4H), 7.38 (m, 2H), 7.13 (m, 2H), 5.15 (s, 2H), 4.23 (m, 2H), 4.00 (m, 2H), 3.84 (m, 2H), 3.34 (m, 3H), 2.51 (s, 3H) | 331.1 [M + H]+ |
| 21 | | 1 | Ex 37 | DMSO: 9.42 (br, 2H), 9.02 (br, 2H), 7.45 (m, 6H), 7.05 (m, 2H), 5.15 (s, 2H), 4.05 (m, 2H), 3.97 (m, 2H), 3.82 (m, 2H), 3.20 (m, 3H) | 317.1 [M + H]+ |
| 22 | | 1 | Ex 37 | DMSO. 9.41 (br, 2H), 9.10 (br, 2H), 7.35-7.65 (m, 6H), 7.15 (m, 1H), 7.02 (m, 1H), 5.20 (s, 2H), 4.10 (m, 2H), 3.95 (m, 2H), 3.83 (m, 2H), 3.23 (m, 3H) | 317.1 [M + H]+ |
| 23 | | 1 | Ex 37, 158 | DMSO + D2O: 7.44 (m, 4H), 7.04 (m, 1H), 6.32 (m, 3H), 5.02 (s, 2H), 3.95 (m, 2H), 3.70 (m, 2H), 3.28 (m, 2H), 3.00 (m, 1H) | 303.1 [M + H]+ |
| 24 | | 1 | Ex 37 | DMSO: 8.97 (br, 2H), 8.79 (br, 1H), 8.62 (br, 1H), 7.36 (m, 3H), 7.15 (s, 1H), 7.06 (m, 2H), 6.96 (m, 2H), 5.03 (s, 2H), 4.11 (m, 2H), 3.98 (m, 2H), 3.83 (m, 2H), 3.76 (s, 3H), 3.22 (m, 2H), 3.15 (m, 1H) | 313.3 [M + H]+ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 25 | | 7 | Ex 37 | DMSO: 9.73 (br, 2H), 9.21 (br, 2H), 7.74 (m, 6H), 7.55 (m, 2H), 4.16 (s, 2H), 3.98 (m, 2H), 3.90 (m, 2H), 3.26 (m, 3H) | 287.2 [M + H]+ |
| 26 | | 1 | Ex 37 | DMSO: 8.93 (br, 2H), 8.74 (br, 1H), 8.59 (br, 1H), 7.58 (d, J = 7.6 Hz, 1H), 7.57 (d, J = 1.2 Hz, 1H), 7.48 (dd, J = 1.2 Hz, 7.6 Hz, 1H), 7.39 (t, J = 8.0 Hz, 1H), 7.18 (s, 1H), 7.08 (m, 2H), 5.15 (s, 2H), 4.13 (m, 2H), 3.98 (m, 2H), 3.90 (s, 3H), 3.83 (m, 2H), 3.22 (m, 2H), 3.14 (m, 1H) | 338.0 [M + H]+ |
| 27 | | 7 | Ex 37, 158, 183 | DMSO + D2O: 7.48 (m, 3H), 7.23 (m, 1H), 7.15 (m, 1H), 7.00-7.10 (m, 3H), 4.11 (s, 2H), 4.00 (m, 2H), 3.78 (m, 2H), 3.22 (m, 2H), 3.12 (m, 1H) | 303.0 [M + H]+ |
| 28 | | 1 | Ex 37 | DMSO + D2O: 7.47 (m, 4H), 7.26 (m, 1H), 6.90 (m, 3H), 5.08 (s, 2H), 4.00 (m, 2H), 3.83 (m, 2H), 3.25 (m, 2H), 3.13 (m, 3H), 2.88 (m, 2H) | 331.0 [M + H]+ |
| 29 | | 1 | Ex 37 & 51 | DMSO + D2O: 7.10-7.30 (m, 7H), 6.85 (d, J = 8.8 Hz, 2H), 4.02 (m, 4H), 3.85 (m, 2H), 3.25 (m, 2H), 3.15 (m, 1H), 3.03 (m, 2H), 2.06 (m, 2H), 1.60 (s, 6H) | 339.2 [M + H]+ |
| 30 | | 1 | Ex 37 | DMSO + D2O: 7.82 (d, J = 2.0 Hz, 1H), 7.60 (d, J = 8.0 Hz, 1H), 7.52 (dd, J = 2.0, 8.0 Hz, 1H), 7.39 (dd, J = 8.0 Hz, 1H), 7.23 (s, 1H), 7.10 (m, 2H), 5.11 (s, 2H), 4.12 (s, 2H), 3.35 (m, 1H), 3.25 (m, 1H), 3.13 (m, 1H), 3.05 (m, 2H), 2.92 (m, 1H), 2.60 (m, 1H), 2.15 (m, 1H), 1.65 (m, 1H) | 409.0, 411.0 [M + H]+ |
| 31 | | 1 | Ex 37 & 51 | DMSO + D2O: 7.10-7.30 (m, 7H), 6.82 (m, 2H), 4.00 (m, 2H), 3.25 (m, 2H), 3.05 (m, 2H), 2.85 (m, 4H), 2.05 (m, 2H), 1.95 (m, 1H), 1.88 (m, 2H), 1.60 (s, 6H), 1.37 (m, 2H) | 367.3 [M + H]+ |
| 32 | | 1 | Ex 37 & 51 | DMSO + D2O: 7.10-7.30 (m, 7H), 6.82 (m, 2H), 4.00 (m, 2H), 3.35 (m, 1H), 3.25 (m, 1H), 3.00-3.17 (m, 5H), 2.90 (m, 1H), 2.58 (m, 1H), 2.00-2.18 (m, 3H), 1.68 (m, 1H), 1.60 (s, 6H) | 353.2 [M + H]+ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 33 | | 1 | Ex 37 | DMSO + D₂O: 7.84 (d, J = 2.0 Hz, 1H), 7.63 (d, J = 8.0 Hz, 1H), 7.53 (dd, J = 2.0 Hz, 8.0 Hz, 1H), 7.44 (m, 2H), 7.15 (d, J = 8.0 Hz, 1H), 7.06 (dd, J = 7.6 Hz, 1H), 5.19 (s, 2H), 4.13 (m, 2H), 3.99 (m, 2H), 3.76 (m, 2H), 3.22 (m, 2H), 3.14 (m, 1H) | 395.0, 397.1 [M + H]⁺ |
| 34 | | 1 | Ex 37 | DMSO + D₂O: 7.59 (m, 1H), 7.38 (dd, J = 8.0 Hz, 1H), 7.26 (m, 1H), 7.18 (s, 1H), 7.10 (m, 3H), 5.09 (s, 2H), 4.08 (s, 2H), 4.02 (m, 2H), 3.80 (m, 2H), 3.20 (m, 2H), 3.15 (m, 1H) | 319.1 [M + H]⁺ |
| 35 | | 1 | Ex 37 | DMSO + D₂O: 7.82 (d, J = 2.0 Hz, 1H), 7.59 (d, J = 8.4 Hz, 1H), 7.52 (dd, J = 2.0 Hz, 8.4 Hz, 1H), 7.38 (dd, J = 8.0 Hz, 1H), 7.21 (s, 1H), 7.10 (m, 2H), 5.11 (s, 2H), 4.11 (s, 2H), 3.27 (m, 2H), 2.82 (m, 4H), 2.00 (m, 1H), 1.95 (m, 2H), 1.31 (m, 2H) | 423.0, 425.0 [M + H]⁺ |
| 36 | | 1 | Ex 37 | DMSO + D₂O: 7.80 (d, J = 2.0 Hz, 1H), 7.57 (d, J = 8.4 Hz, 1H), 7.50 (dd, J = 2.0 Hz, 8.4 Hz, 1H), 7.42 (d, J = 8.8 Hz, 2H), 7.06 (d, J = 8.8 Hz, 2H), 5.13 (s, 2H), 4.04 (m, 2H), 4.01 (m, 2H), 3.79 (m, 2H), 3.21 (m, 2H), 3.15 (m, 1H) | 395.0, 397.0 [M + H]⁺ |
| 37 | | 1 | — | DMSO + D₂O: 7.82 (d, J = 2.0 Hz, 1H), 7.59 (d, J = 8.4 Hz, 1H), 7.52 (dd, J = 2.0 Hz, 8.4 Hz, 1H), 7.14-7.22 (m, 3H), 5.12 (s, 2H), 4.09 (s, 2H), 4.00 (m, 2H), 3.83 (m, 2H), 3.24 (m, 2H), 3.15 (m, 1H) | 429.0, 430.9 [M + H]⁺ |
| 38 | | 2 | Ex 37 | DMSO + D₂O: 7.69 (d, J = 2.4 Hz, 1H), 7.47-7.55 (m, 4H), 7.40 (dd, J = 2.4 Hz, 8.8 Hz, 1H), 7.21 (d, J = 8.8 Hz, 1H), 5.19 (s, 2H), 4.12 (s, 2H), 4.02 (m, 2H), 3.85 (m, 2H), 3.23 (m, 2H), 3.15 (m, 1H) | 395.0, 397.0 [M + H]⁺ |
| 39 | | 1 | Ex 37 & 51 | DMSO + D₂O: 7.10-7.30 (m, 7H), 6.88 (m, 2H), 4.20 (m, 2H), 3.20-3.35 (m, 4H), 2.80-2.95 (m, 4H), 2.00 (m, 1H), 1.90 (m, 2H), 1.59 (s, 6H), 1.37 (s, 2H), | 353.2 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 40 | (3,5-dichlorobenzyl-O-phenyl-CH2-NH-CH2-azetidine) | 1 | Ex 37 | DMSO + D₂O: 7.55 (dd, J = 1.6 Hz, 1H), 7.46 (d, J = 1.6 Hz, 2H), 7.38 (d, J = 8.0 Hz, 1H), 7.13 (s, 1H), 7.06 (m, 2H), 5.14 (s, 2H), 4.08 (s, 2H), 4.02 (m, 2H), 3.78 (m, 2H), 3.22 (m, 2H), 3.14 (m, 1H) | 351.1 [M + H]⁺ |
| 41 | (2-bromobenzyl-O-phenyl-CH2-NH-CH2-azetidine) | 1 | Ex 37 | DMSO + D₂O: 7.69 (d, J = 7.6 Hz, 1H), 7.57 (d, J = 7.6 Hz, 1H), 7.38-7.46 (m, 2H), 7.33 (dd, J = 8.0 Hz, 1H), 7.16 (s, 1H), 7.06-7.13 (m, 2H), 5.13 (s, 2H), 4.12 (s, 2H), 4.02 (m, 2H), 3.79 (m, 2H), 3.24 (m, 2H), 3.15 (m, 1H) | 361.1, 363.1 [M + H]⁺ |
| 42 | (cumyl-phenyl-O-CH2CH2-NH-CH2-pyrrolidine) | 1 | Ex 37 & 51 | DMSO + D₂O: 7.10-7.30 (m, 7H), 6.90 (m, 2H), 4.20 (m, 2H), 3.35 (m, 3H), 3.25 (m, 1H), 3.15 (m, 3H), 2.92 (m, 1H), 2.65 (m, 1H), 2.15 (m, 1H), 1.68 (m, 1H), 1.60 (s, 6H) | 339.2 [M + H]⁺ |
| 43 | (3,5-difluorobenzyl-O-phenyl-CH2-NH-CH2-azetidine) | 1 | Ex 37 | DMSO + D₂O: 7.37 (dd, J = 8.0 Hz, 1H), 7.14 (m, 4H), 7.06 (d, J = 8.4 Hz, 2H), 5.15 (s, 2H), 4.07 (s, 2H), 4.02 (m, 2H), 3.79 (m, 2H), 3.22 (m, 2H), 3.15 (m, 1H) | 319.1 [M + H]⁺ |
| 44 | (cumyl-phenyl-CH2-NH-CH2-pyrrolidine) | 1 | Ex 37 | DMSO + D₂O: 7.40 (m, 2H), 7.27 (m, 4H), 7.18 (m, 3H), 4.07 (s, 2H), 3.35 (m, 1H), 3.25 (m, 1H), 3.00-3.15 (m, 3H), 2.90 (m, 1H), 2.60 (m, 1H), 2.13 (m, 1H), 1.67 (m, 1H), 1.62 (s, 6H) | 309.1 [M + H]⁺ |
| 45 | (cumyl-phenyl-CH2-NH-CH2-azetidine) | 1 | Ex 37 | DMSO + D₂O: 7.27 (m, 2H), 7.25 (m, 4H), 7.18 (m, 3H), 4.05 (s, 2H), 3.98 (m, 2H), 3.85 (m, 2H), 3.24 (m, 2H), 3.15 (m, 1H), 1.62 (s, 6H) | 295.2 [M + H]⁺ |
| 46 | (cumyl-phenyl-CH2-NH-CH2-piperidine) | 1 | Ex 37 | DMSO + D₂O: 7.28 (m, 2H), 7.10-7.30 (m, 7H), 4.06 (s, 2H), 3.25 (m, 2H), 2.85 (m, 4H), 1.97 (m, 1H), 1.87 (m, 2H), 1.63 (s, 6H), 1.33 (m, 2H) | 323.2 [M + H]⁺ |
| 47 | (4-bromo-2-trifluoromethylbenzyl-O-phenyl-CH2-NH-CH2-azetidine) | 1 | Ex 37 | DMSO + D₂O: 7.95 (m, 2H), 7.69 (d, J = 8.4 Hz, 1H), 7.39 (t, J = 8.0 Hz, 1H), 7.16 (s, 1H), 7.08 (m, 2H), 5.18 (s, 2H), 4.09 (s, 2H), 4.02 (m, 2H), 3.79 (m, 2H), 3.23 (m, 2H), 3.15 (m, 1H) | 429.0, 430.9 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 48 | | 1 | Ex 37 | DMSO + D$_2$O: 9.77 (br, 2H), 9.26 (br, 2H), 8.42 (m, 1H), 8.05 (m, 1H), 7.53 (m, 1H), 7.40 (m, 2H), 7.22 (m, 1H), 7.09 (m, 1H), 5.18 (2s, 2H), 4.11 (m, 2H), 3.97 (m, 2H), 3.87 (m, 2H), 3.25 (m, 3H) | 362.3, 364.3 [M + H]$^+$ |
| 49 | | 1 | Ex 37 | DMSO + D$_2$O: 7.94 (s, 1H), 7.80 (m, 2H), 7.40 (t, J = 8.0 Hz, 1H), 7.24 (s, 1H), 7.12 (m, 2H), 5.25 (s, 2H), 4.11 (s, 2H), 4.02 (m, 2H), 3.81 (m, 2H), 3.24 (m, 2H), 3.18 (m, 1H) | 385.0 [M + H]$^+$ |
| 50 | | 1 | Ex 37 & 51 | DMSO + D$_2$O: 7.26 (m, 2H), 7.15 (m, 5H), 6.88 (m, 2H), 4.15 (m, 2H), 3.98 (m, 2H), 3.83 (m, 2H), 3.25 (m, 4H), 3.15 (m, 1H), 1.59 (s, 6H) | 325.1 [M + H]$^+$ |
| 51 | | 1 | Ex 37 | DMSO + D$_2$O: 7.74 (d, J = 2.0 Hz, 1H), 7.50 (s, 1H), 7.27-7.40 (m, 5H), 4.29 (s, 2H), 4.08 (s, 2H), 4.02 (m, 2H), 3.81 (m, 2H), 3.23 (m, 2H), 3.15 (m, 1H) | 410.9, 412.9 [M + H]$^+$ |
| 52 | | 1 | Ex 37 | DMSO: 9.44 (br, 2H), 9.10 (br, 2H), 7.62 (dd, J = 1.9, 9.7 Hz, 1H), 7.50 (m, 4H), 7.07 (d, J = 8.7 Hz, 2H), 5.15 (s, 2H), 4.06 (s, 2H), 3.23 (m, 2H), 2.80 (m, 4H), 2.07 (m, 1H), 1.93 (m, 2H), 1.43 (m, 2H) | 407.1, 409.1 [M + H]$^+$ |
| 53 | | 2 | Ex 37 & 183 | DMSO + D$_2$O: 7.72 (d, J = 2.5 Hz, 1H), 7.66 (s, 1H), 7.62 (m, 1H), 7.47-7.57 (m, 2H), 7.43 (dd, J = 2.6 Hz, 8.8 Hz, 1H), 7.26 (d, J = 8.9 Hz, 1H), 5.22 (s, 2H), 4.20 (s, 2H), 3.38 (m, 3H), 2.94 (m, 2H), 2.29 (m, 2H), 1.94 (m, 2H) | 409.0, 410.9 [M + H]$^+$ |
| 54 | | 2 | Ex 37 & 183 | D$_2$O: 7.58 (d, J = 1.6 Hz, 1H), 7.50 (d, J = 7.6 Hz, 1H), 7.35-7.46 (m, 3H), 7.20 (dd, J = 1.6 Hz, 8.8 Hz, 1H), 6.99 (d, J = 8.8 Hz, 1H), 5.17 (s, 2H), 4.22 (m, 2H), 4.00 (m, 1H), 3.68 (m, 1H), 3.48 (m, 1H), 3.30 (m, 2H), 2.45 (m, 1H), 2.10 (m, 1H) | 395.0, 397.0 [M + H]$^+$ |
| 55 | | 1 | Ex 37 | DMSO: 9.45 (br, 4H), 7.62 (dd, J = 1.8 Hz, 9.7 Hz, 1H), 7.50 (m, 4H), 7.07 (d, J = 8.7 Hz, 2H), 5.15 (s, 2H), 4.06 (m, 2H), 3.35 (m, 1H), 3.23 (m, 1H), 3.10 (m, 1H), 3.00 (m, 2H), 2.92 (m, 1H), 2.70 (m, 1H), 2.10 (m, 1H), 1.70 (m, 1H) | 393.2, 395.2 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 56 | Br-C6H3(F)-CH2-O-C6H4-CH2-NH-CH2-azetidine-NH | 1 | Ex 37 | DMSO: 9.60 (br, 2H), 9.20 (br, 2H), 7.62 (dd, J = 1.9 Hz, 9.7 Hz, 1H), 7.50 (m, 4H), 7.07 (d, J = 8.7 Hz, 2H), 5.15 (s, 2H), 4.04 (s, 2H), 3.97 (m, 2H), 3.85 (m, 2H), 3.25 (m, 1H), 3.20 (m, 2H) | 379.1, 381.1 [M + H]+ |
| 57 | t-Bu-C6H4-CH2-O-C6H4-CH2-NH-CH2-piperidine-NH | 1 | Ex 37 | HPLC: 3.05 min | 367.5 [M + H]+ |
| 58 | Cl-C6H3(Br)-O-CH2-C6H4-CH2CH2-NH-CH2-azetidine-NH | 2 | Ex 37, 165, 183 | DMSO + D2O: 7.70 (d, J = 2.4 Hz, 1H), 7.38 (m, 4H), 7.22 (m, 2H), 5.16 (s, 2H), 4.00 (m, 2H), 3.80 (m, 2H), 3.23 (m, 2H), 3.13 (m, 3H), 2.89 (m, 2H) | 409.0, 411.1 [M + H]+ |
| 59 | t-Bu-C6H4-CH2-O-C6H4-CH2-NH-piperidine-NH | 1 | Ex 37 | DMSO: 9.35 (br, 4H), 7.53 (d, J = 8.7 Hz, 2H), 7.40 (m, 4H), 7.05 (d, J = 8.7 Hz, 2H), 5.10 (s, 2H), 4.05 (m, 2H), 3.25 (m, 3H), 2.90 (m, 2H), 2.25 (m, 2H), 1.90 (m, 2H), 1.29 (s, 9H) | 353.2 [M + H]+ |
| 60 | Br-C6H3(F)-CH2-O-C6H4-CH2-NH-piperidine-NH | 1 | Ex 37 | DMSO: 9.45 (br, 4H), 7.45-7.65 (m, 5H), 7.06 (d, J = 8.8 Hz, 2H), 5.15 (s, 2H), 4.07 (s, 2H), 3.25 (m, 3H), 2.90 (m, 2H), 2.25 (m, 2H), 1.90 (m, 2H) | 393.1, 395.1 [M + H]+ |
| 61 | Cl-C6H3(Br)-CH=CH-C6H4-CH2-NH-CH2-azetidine-NH | 3 | Ex 37, 64, 236 | DMSO + D2O: 7.85 (d, J = 8.4 Hz, 1H), 7.79 (d, J = 2.0 Hz, 1H), 7.75 (s, 1H), 7.63 (d, J = 7.6 Hz, 1H), 7.50 (m, 2H), 7.40 (m, 2H), 7.28 (d, J = 16.4 Hz, 1H), 4.15 (s, 2H), 4.00 (m, 2H), 3.80 (m, 2H), 3.25 (m, 2H), 3.15 (m, 1H) | 391.1, 393.1 [M + H]+ |
| 62 | biphenyl(Cl, Br)-CH2-NH-CH2-pyrrolidine-NH | 7 | Ex 37 & 68 | DMSO + D2O: 7.86 (d, J = 2.0 Hz, 1H), 7.58 (m, 3H), 7.45 (m, 2H), 7.36 (m, 1H), 4.19 (s, 2H), 3.40 (m, 1H), 3.25 (m, 1H), 3.13 (m, 3H), 2.92 (m, 1H), 2.65 (m, 1H), 2.15 (m, 1H), 1.68 (m, 1H) | 379.0, 381.0 [M + H]+ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 63 | | 1 | Ex 37 | DMSO + D$_2$O: 7.80 (d, J = 2.0 Hz, 1H), 7.57 (d, J = 8.4 Hz, 1H), 7.50 (dd, J = 2.0 Hz, 8.4 Hz, 1H), 7.43 (d, J = 8.8 Hz, 2H), 7.06 (d, J = 8.8 Hz, 2H), 5.14 (s, 2H), 4.06 (s, 2H), 3.35 (m, 1H), 3.25 (m, 1H), 3.12 (m, 1H), 3.05 (m, 2H), 2.87 (m, 1H), 2.57 (m, 1H), 2.13 (m, 1H), 1.65 (m, 1H) | 409.1, 411.1 [M + H]$^+$ |
| 64 | | 3 | Ex 37, 236 | DMSO + D$_2$O: 7.70 (d, J = 2.0 Hz, 1H), 7.26-7.40 (m, 6H), 4.10 (s, 2H), 4.00 (m, 2H), 3.80 (m, 2H), 3.23 (m, 2H), 3.15 (m, 1H), 2.95 (m, 2H), 2.85 (m, 2H) | 393.1, 395.0 [M + H]$^+$ |
| 65 | | 2 | Ex 37 & 183 | DMSO + D$_2$O: 7.70 (d, J = 2.8 Hz, 1H), 7.39-7.53 (m, 5H), 7.21 (d, J = 8.8 Hz, 1H), 5.19 (s, 2H), 4.11 (s, 2H), 3.98 (m, 2H), 3.65 (m, 1H), 3.20 (m, 2H), 2.90-3.10 (m, 3H), 2.85 (m, 1H) | 425.1, 427.0 [M + H]$^+$ |
| 66 | | 1 | Ex 37 | DMSO: 9.50 (br, 2H), 9.15 (br, 2H), 7.73 (d, J = 2.0 Hz, 1H), 7.68 (d, J = 8.3 Hz, 1H), 7.53 (m, 2H), 7.46 (dd, J = 2.0 Hz, 8.3 Hz, 1H), 7.07 (m, 2H), 5.17 (s, 2H), 4.04 (s, 2H), 3.95 (m, 2H), 3.85 (m, 2H), 3.10-3.25 (m, 3H) | 351.2 [M + H]$^+$ |
| 67 | | 1 | Ex 37 | DMSO: 9.60 (br, 2H), 9.30 (br, 2H), 7.73 (d, J = 1.9 Hz, 1H), 7.67 (d, J = 8.2 Hz, 1H), 7.56 (d, J = 8.6 Hz, 2H), 7.46 (dd, J = 2.0 Hz, 8.3 Hz, 1H), 7.05 (d, J = 8.6 Hz, 2H), 5.16 (s, 2H), 4.04 (s, 2H), 3.20 (m, 2H), 2.75 (m, 4H), 2.07 (m, 1H), 1.93 (m, 2H), 1.43 (m, 2H) | 379.2 [M + H]$^+$ |
| 68 | | 7 | Ex 37, 158 | DMSO: 8.99 (br, 2H), 8.78, 8.63 (2br, 2H), 7.92 (d, J = 2.0 Hz, 1H), 7.58 (m, 3H), 7.49 (d, J = 8.0 Hz, 2H), 7.39 (d, J = 8.0 Hz, 1H), 4.20 (m, 2H), 3.99 (m, 2H), 3.86 (m, 2H), 3.25 (m, 2H), 3.15 (m, 1H) | 365.0, 367.0 [M + H]$^+$ |
| 69 | | 7 | Ex 37 & 68 | DMSO + D$_2$O: 7.89 (d, J = 2.0 Hz, 1H), 7.73 (m, 1H), 7.55 (m, 3H), 7.40 (m, 1H), 7.22 (m, 1H), 4.05 (m, 1H), 3.75 (m, 1H), 3.32 (m, 1H), 3.20 (m, 1H), 3.07 (m, 1H), 2.85 (m, 3H), 2.55 (m, 1H), 2.05 (m, 1H), 1.60 (m, 1H) | 379.0, 381.0 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 70 | | 1 | Ex 37 | DMSO: 9.40 (br, 4H), 7.73 (d, J = 2.0 Hz, 1H), 7.68 (d, J = 8.3 Hz, 1H), 7.53 (d, J = 6.8 Hz, 2H), 7.46 (dd, J = 2.0 Hz, 8.3 Hz, 1H), 7.07 (d, J = 8.4 Hz, 2H), 5.17 (s, 2H), 4.05 (m, 2H), 3.35 (m, 1H), 3.25 (m, 1H), 3.12 (m, 1H), 3.00 (m, 3H), 2.70 (m, 1H), 2.10 (m, 1H), 1.70 (m, 1H) | 365.2 [M + H]+ |
| 71 | | 1 | Ex 37 | DMSO: 9.30 (br, 4H), 7.70 (dd, J = 1.2 Hz, 8.0 Hz, 1H), 7.58 (m, 3H), 7.44 (td, J = 1.2 Hz, 7.5 Hz, 1H), 7.33 (td, J = 1.8 Hz, 7.7 Hz, 1H), 7.08 (d, J = 8.7 Hz, 2H), 5.15 (s, 2H), 4.10 (s, 2H), 3.30 (m, 3H), 2.90 (m, 2H), 2.27 (m, 2H), 1.90 (m, 2H) | 375.2, 377.2 [M + H]+ |
| 72 | | 1 | Ex 37 | DMSO: 9.40 (br, 2H), 9.05 (br, 2H), 7.70 (dd, J = 1.3 Hz, 8.0 Hz, 1H), 7.58 (m, 3H), 7.44 (td, J = 1.3 Hz, 7.5 Hz, 1H), 7.33 (td, J = 1.8 Hz, 7.6 Hz, 1H), 7.08 (d, J = 8.7 Hz, 2H), 5.15 (s, 2H), 4.07 (s, 2H), 3.25 (m, 2H), 2.80 (m, 4H), 2.08 (m, 1H), 1.94 (m, 2H), 1.44 (m, 2H) | 389.2, 391.2 [M + H]+ |
| 73 | | 2 | Ex 37, 165, 183 | DMSO + D2O: 7.70 (d J = 2.4 Hz, 1H), 7.19-7.41 (m, 6H), 5.16 (s, 2H), 4.00 (m, 2H), 3.80 (m, 2H), 3.18 (m, 2H), 3.08 (m, 1H), 2.91 (m, 2H), 2.65 (m, 2H), 1.86 (m, 2H) | 423.1, 425.1 [M + H]+ |
| 74 | | 7 | Ex 37 & 68 | DMSO + D2O: 7.89 (d, J = 2.0 Hz, 1H), 7.55 (m, 5H), 7.40 (m, 1H), 4.21 (s, 2H), 3.37 (m, 1H), 3.25 (m, 1H), 3.10 (m, 3H), 2.90 (m, 1H), 2.60 (m, 1H), 2.15 (m, 1H), 1.65 (m, 1H) | 379.1, 381.1 [M + H]+ |
| 75 | | 7 | Ex 37 & 68 | DMSO + D2O: (d, J = 2.0 Hz, 1H), 7.55 (m, 5H), 7.40 (m, 1H), 4.19 (s, 2H), 3.98 (m, 2H), 3.82 (m, 2H), 3.25 (m, 2H), 3.15 (m, 1H) | 365.1, 367.0 [M + H]+ |
| 76 | | 1 | Ex 37 | DMSO + D2O: 7.83 (d, J = 8.4 Hz, 2H), 7.61 (d, J = 8.4 Hz, 2H), 7.41 (d, J = 8.8 Hz, 2H), 7.05 (d, J = 8.8 Hz, 2H), 5.22 (s, 2H), 4.03 (s, 2H), 3.97 (m, 2H), 3.82 (m, 2H), 3.25 (m, 2H), 3.15 (m, 1H) | 308.2 [M + H]+ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 77 | | 1 | Ex 37 | DMSO + D₂O: 7.98 (d, J = 8.4 Hz, 2H), 7.58 (d, J = 8.4 Hz, 2H), 7.36 (dd, J = 8.0 Hz, 1H), 7.19 (d, J = 2.0 Hz, 1H), 7.07 (m, 2H), 5.20 (s, 2H), 4.08 (s, 2H), 4.00 (m, 2H), 3.80 (m, 5H), 3.24 (m, 2H), 3.15 (m, 1H) | 341.2 [M + H]⁺ |
| 78 | | 1 | Ex 37 | DMSO + D₂O: 8.02 (d, J = 1.6 Hz, 1H), 7.91 (dd, J = 1.6 Hz, 8.0 Hz, 1H), 7.83 (d, J = 8.0 Hz, 1H), 7.44 (d, J = 8.4 Hz, 2H), 7.10 (d, J = 8.4 Hz, 2H), 5.26 (s, 2H), 4.05 (s, 2H), 3.97 (m, 2H), 3.82 (m, 2H), 3.25 (m, 2H), 3.15 (m, 1H) | 395.2 [M + H]⁺ |
| 79 | | 7 | Ex 37 & 68 | HPLC: 4.98 min | 365.1, 367.1 [M + H]⁺ |
| 80 | | 1 | Ex 37 | DMSO + D₂O: 7.69 (dd, J = 1.2 Hz, 7.9 Hz, 1H), 7.58 (dd, J = 1.8 Hz, 7.6 Hz, 1H), 7.53 (m, 2H), 7.44 (td, J = 1.2 Hz, 7.5 Hz, 1H), 7.33 (td, J = 1.8 Hz, 7.7 Hz, 1H), 7.08 (d, J = 8.7 Hz, 2H), 5.15 (s, 2H), 4.09 (s, 2H), 3.38 (m, 1H), 3.25 (m, 1H), 3.12 (m, 1H), 3.03 (m, 2H), 2.97 (m, 1H), 2.69 (m, 1H), 2.14 (m, 1H), 1.70 (m, 1H) | 375.2, 377.2 [M + H]⁺ |
| 81 | | 7 | Ex 27 & 37 | DMSO + D₂O: 7.93 (d, J = 2.5 Hz, 1H), 7.52 (m, 3H), 7.12 (d, J = 8.7 Hz, 1H), 7.03 (m, 2H), 4.12 (s, 2H), 4.00 (m, 2H), 3.85 (m, 2H), 3.25 (m, 2H), 3.16 (m, 1H) | 381.1, 383.1 [M + H]⁺ |
| 82 | | 7 | Ex 27 & 37 | DMSO + D₂O: 7.88 (d, J = 2.8 Hz, 1H), 7.50 (m, 3H), 7.12 (m, 1H), 6.98 (m, 2H), 4.10 (s, 2H), 3.35 (m, 1H), 3.25 (m, 1H), 3.10 (m, 3H), 2.90 (m, 1H), 2.60 (m, 1H), 2.12 (m, 1H), 1.65 (m, 1H) | 395.1, 397.1 [M + H]⁺ |
| 83 | | 1 | Ex 37 | DMSO + D₂O: 7.94 (d, J = 8.4 Hz, 2H), 7.70 (d, J = 8.4 Hz, 2H), 7.37 (dd, J = 8.0 Hz, 1H), 7.21 (s, 1H), 7.08 (m, 2H), 5.24 (s, 2H), 4.09 (s, 2H), 4.00 (m, 2H), 3.83 (m, 2H), 3.26 (m, 3H) | 361.2 [M + H]⁺ |
| 84 | | 7 | Ex 27 & 37 | DMSO + D₂O: 7.90 (d, J = 2.4 Hz, 1H), 7.62 (m, 1H), 7.53 (m, 1H), 7.40 (m, 1H), 7.20 (m, 2H), 6.66 (m, 1H), 4.27 (s, 2H), 3.37 (m, 1H), 3.25 (m, 1H), 3.10 (m, 3H), 2.90 (m, 1H), 2.65 (m, 1H), 2.15 (m, 1H), 1.65 (m, 1H) | 395.1, 397.1 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 85 | [structure] | 1 | Ex 37 | DMSO + D$_2$O: 8.29 (s, 2H, formic acid), 8.20 (d, J = 1.6 Hz, 1H), 7.87 (dd, J = 1.6 Hz, 8.0 Hz, 1H), 7.71 (d, J = 8.0 Hz, 1H), 7.29 (d, J = 8.4 Hz, 2H), 6.98 (d, J = 8.4 Hz, 2H), 5.15 (s, 2H), 3.95 (m, 2H), 3.65 (m, 4H), 2.92 (m, 1H), 2.80 (m, 2H) | 386.1, 388.1 [M + H]$^+$ |
| 86 | [structure] | 1 | Ex 37 | DMSO + D$_2$O: 7.92 (d, J = 8.4 Hz, 2H), 7.69 (d, J = 8.4 Hz, 2H), 7.41 (d, J = 8.8 Hz, 2H), 7.06 (d, J = 8.8 Hz, 2H), 5.25 (s, 2H), 4.03 (s, 2H), 3.99 (m, 2H), 3.82 (m, 2H), 3.20 (m, 6H) | 361.1 [M + H]$^+$ |
| 87 | [structure] | 1 | Ex 37 | DMSO + D$_2$O: 8.14 (d, J = 1.2 Hz, 1H), 7.97 (dd, J = 1.2 Hz, 8.0 Hz, 1H), 7.70 (d, J = 8.0 Hz, 1H), 7.43 (d, J = 8.8 Hz, 2H), 7.08 (d, J = 8.8 Hz, 2H), 5.19 (s, 2H), 4.04 (s, 2H), 3.98 (m, 2H), 3.80 (m, 5H), 3.21 (m, 2H), 3.15 (m, 1H) | 419.1, 421.1 [M + H]$^+$ |
| 88 | [structure] | 7 | Ex 37, 236 | DMSO + D$_2$O: 7.88 (d, J = 2.4 Hz, 1H), 7.48 (m, 2H), 7.28 (m, 1H), 7.17 (m, 1H), 7.08 (m, 1H), 6.99 (m, 1H), 4.13 (s, 2H), 3.37 (m, 1H), 3.22 (m, 1H), 3.00-3.15 (m, 3H), 2.90 (m, 1H), 2.60 (m, 1H), 2.15 (m, 1H), 1.65 (m, 1H) | 395.1, 397.1 [M + H]$^+$ |
| 89 | [structure] | 7 | Ex 27 & 37 | DMSO + D$_2$O: 7.90 (d, J = 2.4 Hz, 1H), 7.55 (m, 2H), 7.40 (m, 1H), 7.22 (m, 2H), 6.66 (m, 1H), 4.24 (s, 2H), 4.00 (m, 2H), 3.83 (m, 2H), 3.30 (m, 2H), 3.15 (m, 1H) | 381.1, 383.1 [M + H]$^+$ |
| 90 | [structure] | 7 | Ex 37 & 88 | DMSO + D$_2$O: 7.88 (d, J = 2.8 Hz, 1H), 7.48 (m, 2H), 7.23 (m, 1H), 7.10 (m, 2H), 7.00 (m, 1H), 4.09 (s, 2H), 3.97 (m, 2H), 3.81 (m, 2H), 3.21 (m, 2H), 3.10 (m, 1H) | 381.1, 383.1 [M + H]$^+$ |
| 91 | [structure] | 1 | Ex 37 | DMSO + D$_2$O: 7.83 (d, J = 8.0 Hz, 2H), 7.62 (d, J = 8.0 Hz, 2H), 7.29 (dd, J = 8.0 Hz, 1H), 7.07 (s, 1H), 6.95 (m, 2H), 5.19 (s, 2H), 3.72-3.96 (m, 6H), 3.00 (m, 1H), 2.90 (m, 2H) | 308.1 [M + H]$^+$ |
| 92 | [structure] | 1 | Ex 37 | DMSO + D$_2$O: 8.16 (d, J = 1.6 Hz, 1H), 7.99 (dd, J = 1.6 Hz, 8.0 Hz, 1H), 7.72 (d, J = 8.0 Hz, 1H), 7.40 (dd, J = 8.0 Hz, 1H), 7.21 (s, 1H), 7.10 (m, 2H), 5.19 (s, 2H), 4.10 (s, 2H), 4.02 (m, 2H), 3.83 (m, 5H), 3.23 (m, 2H), 3.15 (m, 1H) | 419.1, 421.1 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 93 | [structure: 4-chloro-2-bromo-phenoxymethyl-furan-methyl-NH-CH2-azetidine] | 2 | Ex 37 | DMSO + D₂O: 7.68 (d, J = 2.4 Hz, 1H), 7.41 (dd, J = 2.4 Hz, 8.8 Hz, 1H), 7.28 (d, J = 8.8 Hz, 1H), 6.80 (d, J = 3.2 Hz, 1H), 6.62 (d, J = 3.2 Hz, 1H), 5.14 (s, 2H), 4.21 (s, 2H), 4.00 (m, 2H), 3.75 (m, 2H), 3.21 (m, 2H), 3.10 (m, 1H) | 385.1, 387.1 [M + H]⁺ |
| 94 | [structure: 3-biphenyl-CH2-O-phenyl-CH2-NH-CH2-azetidine] | 1 | Ex 37 | DMSO + D₂O: 7.00-7.70 (m, 13H), 5.18 (s, 2H), 4.08 (s, 2H), 4.00 (m, 2H), 3.80 (m, 2H), 3.22 (m, 2H), 3.12 (m, 1H) | 359.3 [M + H]⁺ |
| 95 | [structure: 4-biphenyl-CH2-O-phenyl-CH2-NH-CH2-azetidine] | 1 | Ex 37 | DMSO + D₂O: 7.02-7.67 (m, 13H), 5.14 (s, 2H), 4.08 (s, 2H), 4.00 (m, 2H), 3.80 (m, 2H), 3.22 (m, 2H), 3.14 (m, 1H) | 359.2 [M + H]⁺ |
| 96 | [structure: 4-chloro-2-bromo-phenoxy-CH2CH2-O-phenyl-CH2-NH-CH2-azetidine] | 1 & 2 | Ex 37, 183, 354 | DMSO + D₂O: 7.67 (d, J = 2.8 Hz, 1H), 7.40 (m, 3H), 7.19 (d, J = 9.2 Hz, 1H), 7.04 (m, 2H), 4.36 (m, 4H), 4.05 (s, 2H), 3.98 (m, 2H), 3.80 (m, 2H), 3.19 (m, 2H), 3.12 (m, 1H) | 425.1, 427.1 [M + H]⁺ |
| 97 | [structure: 4-chloro-2-bromo-benzyl-O-phenyl(2-Br)-CH2-NH-CH2-azetidine] | 1 | Ex 37 | DMSO + D₂O: 7.80 (d, J = 2.0 Hz, 1H), 7.63 (d, J = 8.8 Hz, 1H), 7.57 (d, J = 8.4 Hz, 1H), 7.50 (dd, J = 2.0 Hz, 8.4 Hz, 1H), 7.30 (d, J = 2.8 Hz, 1H), 7.07 (dd, J = 3.2 Hz, 8.8 Hz, 1H), 5.10 (s, 2H), 4.20 (s, 2H), 4.00 (m, 2H), 3.85 (m, 2H), 3.34 (m, 2H), 3.21 (m, 1H) | 473.0, 475.0 [M + H]⁺ |
| 98 | [structure: bis(4-chloro-2-bromo-benzyl-O)-phenyl-CH2-NH-CH2-azetidine] | 1 | Ex 37 | DMSO + D₂O: 7.79 (m, 2H), 7.50 (m, 4H), 6.78 (m, 2H), 6.71 (d, J = 2.0 Hz, 1H), 5.08 (s, 4H), 4.02 (m, 4H), 3.82 (m, 2H), 3.23 (m, 2H), 3.15 (m, 1H) | 615.0, 617.0 [M + H]⁺ |
| 99 | [structure: 4-chloro-2-bromo-benzyl-O-phenyl(4-F)-CH2-NH-CH2-azetidine] | 1 | Ex 37 | DMSO + D₂O: 7.81 (d, J = 2.0 Hz, 1H), 7.60 (d, J = 8.4 Hz, 1H), 7.52 (dd, J = 2.0 Hz, 8.4 Hz, 1H), 7.44 (d, J = 7.6 Hz, 1H), 7.29 (dd, J = 8.4 Hz, 11.2 Hz, 1H), 7.10 (m, 1H), 5.15 (s, 2H), 4.09 (s, 2H), 4.00 (m, 2H), 3.82 (m, 2H), 3.27 (m, 2H), 3.15 (m, 1H) | 413.1, 415.1 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 100 | | 1 | Ex 37 & 51 | DMSO + D$_2$O: 7.79 (d, J = 2.0 Hz, 1H), 7.55 (d, J = 8.4 Hz, 1H), 7.48 (dd, J = 2.0 Hz, 8.4 Hz, 1H), 7.19 (d, J = 8.4 Hz, 2H), 6.96 (d, J = 8.4 Hz, 2H), 5.06 (s, 2H), 4.04 (m, 2H), 3.79 (m, 2H), 3.23 (m, 2H), 3.15 (m, 1H), 3.07 (m, 2H), 2.85 (m, 2H) | 409.1, 411.1 [M + H]$^+$ |
| 101 | | 1 | Ex 37 | DMSO + D$_2$O: 8.20 (d, J = 1.6 Hz, 1H), 7.88 (dd, J = 1.6 Hz, 8.0 Hz, 1H), 7.72 (d, J = 8.0 Hz, 1H), 7.40 (dd, J = 8.0 Hz, 1H), 7.05-7.15 (m, 3H), 5.17 (s, 2H), 4.09 (s, 2H), 4.00 (m, 2H), 3.80 (m, 2H), 3.22 (m, 2H), 3.15 (m, 1H) | 386.1, 388.1 [M + H]$^+$ |
| 102 | | 1 | Ex 37 | DMSO + D$_2$O: 8.03 (d, J = 1.6 Hz, 1H), 7.93 (dd, J = 1.6 Hz, 8.0 Hz, 1H), 7.85 (d, J = 8.0 Hz, 1H), 7.40 (dd, J = 8.0 Hz, 1H), 7.21 (s, 1H), 7.09-7.14 (m, 2H), 5.25 (s, 2H), 4.09 (s, 2H), 3.99 (m, 2H), 3.83 (m, 2H), 3.25 (m, 5H), 3.15 (m, 1H) | 395.2 [M + H]$^+$ |
| 103 | | 1 | Ex 37 & 136 | DMSO + D$_2$O: 7.82 (d, J = 2.0 Hz, 1H), 7.59 (d, J = 8.4 Hz, 1H), 7.52 (dd, J = 2.0 Hz, 8.0 Hz, 1H), 7.03 (s, 1H), 6.99 (m, 2H), 5.11 (s, 2H), 4.10 (s, 2H), 4.00 (m, 2H), 3.83 (m, 2H), 3.23 (m, 2H), 3.16 (m, 1H) | 413.1, 415.1 [M + H]$^+$ |
| 104 | | 1 | Ex 37 & 136 | DMSO + D$_2$O: 7.83 (d, J = 2.0 Hz, 1H), 7.62 (d, J = 8.4 Hz, 1H), 7.53 (dd, J = 2.0 Hz, 8.4 Hz, 1H), 7.49 (d, J = 9.2 Hz, 2H), 7.43 (s, 1H), 5.19 (s, 2H), 4.19 (s, 2H), 4.00 (m, 2H), 3.83 (m, 2H), 3.14 (m, 1H), 2.60 (m, 2H) | 463.1, 465.0 [M + H]$^+$ |
| 105 | | 1 | Ex 37 | DMSO + D$_2$O: 7.81 (d, J = 2.0 Hz, 1H), 7.57 (d, J = 8.4 Hz, 1H), 7.50 (dd, J = 2.0 Hz, 8.4 Hz, 1H), 7.40 (d, J = 8.8 Hz, 2H), 7.08 (d, J = 8.4 Hz, 2H), 5.10 (s, 2H), 4.26 (d, J = 1H), 3.95 (m, 2H), 3.75 (m, 2H), 3.15 (m, 1H), 3.00 (m, 1H), 2.92 (m, 1H), 1.50 (d, J = 6.8 Hz, 3H) | 409.2, 411.2 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 106 | | 1 | Ex 37 | HPLC: 5.73 min | 451.2, 453.2 [M + H]⁺ |
| 107 | | 1 | Ex 37 & 136 | DMSO + D₂O: 7.84 (d, J = 2.0 Hz, 1H), 7.58 (d, J = 8.4 Hz, 1H), 7.53 (dd, J = 2.0 Hz, 8.4 Hz, 1H), 7.23 (s, 2H), 7.09 (s, 1H), 5.10 (s, 2H), 4.11 (s, 4H), 4.00 (m, 4H), 3.85 (m, 4H), 3.25 (m, 4H), 3.15 (m, 2H) | 493.2, 495.2 [M + H]⁺ |
| 108 | | 1 | Ex 37 | DMSO: 9.60 (br, 2H), 9.40 (br, 2H), 7.86 (d, J = 2.1 Hz, 1H), 7.63 (d, J = 8.3 Hz, 1H), 7.56 (dd, J = 2.1 Hz, 8.3 Hz, 1H), 6.93 (s, 2H), 6.67 (s, 1H), 6.06 (m, 1H), 5.42 (m, 1H), 5.28 (m, 1H), 5.13 (s, 2H), 4.60 (m, 2H), 4.08 (s, 2H), 2.90-3.45 (m, 6H), 2.70 (m, 1H), 2.15 (m, 1H), 1.70 (m, 1H) | 465.1, 467.1 [M + H]⁺ |
| 109 | | 1 | Ex 37 | DMSO: 9.63 (br, 2H), 9.10 (br, 2H), 7.85 (d, J = 2.1 Hz, 1H), 7.63 (d, J = 2.1 Hz, 8.3 Hz, 1H), 6.95 (s, 2H), 6.66 (s, 1H), 6.05 (m, 1H), 5.42 (m, 1H), 5.28 (m, 1H), 5.12 (s, 2H), 4.59 (m, 2H), 4.06 (s, 2H), 3.25 (m, 2H), 2.80 (m, 4H), 2.09 (m, 1H), 1.95 (m, 2H), 1.43 (m, 2H) | 479.1, 481.1 [M + H]⁺ |
| 110 | | 1 | Ex 37, 51, 130, 263 | DMSO + D₂O: 7.81 (d, J = 2.0 Hz, 1H), 7.70 (s, 1H), 7.55 (m, 3H), 7.37 (s, 1H), 5.15 (s, 2H), 4.15 (s, 2H), 3.98 (m, 2H), 3.82 (m, 2H), 3.24 (m, 2H), 3.13 (m, 1H) | 437.2, 439.2 [M + H]⁺ |
| 111 | | 1 | Ex 37 & 51 | DMSO + D₂O: 7.80 (d, J = 2.0 Hz, 1H), 7.57 (d, J = 8.4 Hz, 1H), 7.50 (dd, J = 2.0 Hz, 8.4 Hz, 1H), 7.24 (t, J = 8.0 Hz, 1H), 6.84 (m, 3H), 5.06 (s, 2H), 4.02 (m, 2H), 3.75 (m, 2H), 3.09-3.18 (m, 3H), 2.86 (m, 2H), 2.60 (m, 2H), 1.86 (m, 2H) | 423.1, 425.0 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 112 | | 1 | Ex 37 & 51 | DMSO + D₂O: 7.81 (d, J = 2.4 Hz, 1H), 7.58 (d, J = 8.4 Hz, 1H), 7.51 (dd, J = 2.0 Hz, 1H), 7.25 (t, J = 8.0 Hz, 1H), 6.85 (m, 3H), 5.07 (s, 2H), 3.35 (m, 1H), 3.22 (m, 1H), 3.13 (m, 1H), 3.10 (m, 2H), 2.86 (m, 3H), 2.50-2.65 (m, 3H), 2.10 (m, 1H), 1.90 (m, 2H), 1.62 (m, 1H) | 437.1, 439.1 [M + H]⁺ |
| 113 | | 1 | Ex 37 & 51 | DMSO + D₂O: 7.82 (d, J = 2.4 Hz, 1H), 7.60 (d, J = 8.0 Hz, 1H), 7.52 (dd, J = 2.0 Hz, 8.4 Hz, 1H), 7.20 (m, 2H), 7.03 (d, J = 8.0 Hz, 1H), 6.93 (t, J = 7.2 Hz, 1H), 5.10 (s, 2H), 4.00 (m, 2H), 3.78 (m, 2H), 3.15 (m, 2H), 3.10 (m, 1H), 2.85 (m, 2H), 2.64 (m, 2H), 1.85 (m, 2H) | 423.1, 425.1 [M + H]⁺ |
| 114 | | 1 | Ex 37 & 51 | DMSO + D₂O: 7.81 (d, J = 2.0 Hz, 1H), 7.59 (d, J = 8.4 Hz, 1H), 7.51 (dd, J = 2.0 Hz, 8.4 Hz, 1H), 7.20 (m, 2H), 7.03 (d, J = 8.0 Hz, 1H), 6.93 (t, J = 7.6 Hz, 1H), 5.09 (s, 2H), 3.33 (m, 1H), 3.23 (m, 1H), 3.12 (m, 1H), 2.97 (m, 2H), 2.87 (m, 3H), 2.65 (m, 2H), 2.53 (m, 1H), 2.10 (m, 1H), 1.85 (m, 2H), 1.62 (m, 1H) | 437.1, 439.1 [M + H]⁺ |
| 115 | | 1 | Ex 37, 51, 130, 263, 399 | DMSO + D₂O: 7.83 (s, 1H), 7.65 (m, 3H), 7.53 (dd, J = 2.0 Hz, 8.4 Hz, 1H), 7.30 (s, 1H), 5.15 (s, 2H), 4,13 (s, 2H), 4.00 (m, 2H), 3.82 (m, 2H), 3.24 (m, 2H), 3.15 (m, 1H) | 438.1, 440.1 [M + H]⁺ |
| 116 | | 1 | Ex 37 & 51 | DMSO + D₂O: 7.79 (d, J = 2.0 Hz, 1H), 7.56 (d, J = 8.0 Hz, 1H), 7.49 (dd, J = 2.0 Hz, 8.4 Hz, 1H), 7.15 (d, J = 8.4 Hz, 2H), 6.94 (d, J = 8.4 Hz, 2H), 5.05 (s, 2H), 4.02 (m, 2H), 3.79 (m, 2H), 3.17 (m, 2H), 3.10 (m, 1H), 2.86 (m, 2H), 2.57 (m, 2H), 1.83 (m, 2H) | 423.1, 425.1 [M + H]⁺ |
| 117 | | 1 | Ex 37 & 51 | DMSO + D₂O: 7.80 (d, J = 2.0 Hz, 1H), 7.56 (d, J = 8.0 Hz, 1H), 7.49 (dd, J = 2.0 Hz, 8.4 Hz, 1H), 7.15 (d, J = 8.4 Hz, 2H), 6.94 (d, J = 8.8 Hz, 2H), 5.05 (s, 2H), 3.35 (m, 1H), 3.23 (m, 1H), 3.12 (m, 1H), 3.00 (m, 2H), 2.88 (m, 2H), 2.58 (m, 2H), 2.52 (m, 2H), 2.12 (m, 1H), 1.87 (m, 2H), 1.65 (m, 1H) | 437.1, 439.1 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 118 | | | 1 | Ex 37, 51, 119, 130, 263 | DMSO + D$_2$O: 7.83 (s, 1H), 7.60 (d, J = 8.0 Hz, 1H), 7.55 (m, 3H), 7.28 (s, 1H), 5.15 (s, 2H), 4.14 (s, 2H), 4.00 (m, 2H), 3.82 (m, 2H), 3.35 (m, 2H), 3.30 (m, 2H), 3.25 (m, 2H), 3.21 (s, 3H), 3.13 (m, 1H), 1.75 (m, 2H) | 510.1 512.1 [M + H]$^+$ |
| 119 | | | 1 | Ex 51, 130 | DMSO + D$_2$O: 7.84 (s, 1H), 7.61 (m, 3H), 7.53 (d, J = 8.4 Hz, 1H), 7.35 (m, 5H), 7.25 (m, 1H), 5.17 (s, 2H), 4.47 (s, 2H), 4.15 (s, 2H), 4.00 (m, 2H), 3.82 (m, 2H), 3.25 (m, 2H), 3.17 (m, 1H) | 528.1, 530.1 [M + H]$^+$ |
| 120 | | | 3 | Ex 37, 130, 168 | DMSO + D$_2$O: 7.55 (m, 3H), 7.15-7.40 (m, 7H), 4.21 (m, 2H), 4.00 (m, 2H), 3.84 (m, 2H), 3.24 (m, 2H), 3.11 (m, 3H), 2.10 (m, 2H) | 401.2, 403.2 [M + H]$^+$ |
| 121 | | | 1 | Ex 37 & 51 | DMSO + D$_2$O: 7.81 (d, J = 2.0 Hz, 1H), 7.58 (d, J = 8.4 Hz, 1H), 7.51 (dd, J = 2.0 Hz, 8.4 Hz, 1H), 7.28 (t, J = 8.0 Hz, 1H), 6.90 (m, 3H), 5.08 (s, 2H), 4.04 (m, 2H), 3.82 (m, 2H), 3.24 (m, 2H), 3.13 (m, 3H), 2.89 (m, 2H) | 409.1, 411.1 [M + H]$^+$ |
| 122 | | | 1 | Ex 37 & 51 | DMSO + D$_2$O: 7.82 (d, J = 2.0 Hz, 1H), 7.59 (d, J = 8.4 Hz, 1H), 7.52 (dd, J = 1.6 Hz, 8.0 Hz, 1H), 7.29 (t, J = 7.6 Hz, 1H), 6.92 (m, 3H), 5.09 (s, 2H), 3.38 (m, 1H), 3.25 (m, 1H), 3.00-3.20 (m, 5H), 2.92 (m, 3H), 2.63 (m, 1H), 2.12 (m, 1H), 1.70 (m, 1H) | 423.1, 425.1 [M + H]$^+$ |
| 123 | | | 1 | Ex 37 & 51 | DMSO + D$_2$O: 7.84 (d, J = 2.0 Hz, 1H), 7.65 (d, J = 8.4 Hz, 1H), 7.53 (dd, J = 2.0 Hz, 8.4 Hz, 1H), 7.27 (m, 2H), 7.08 (m, 1H), 6.97 (m, 1H), 5.13 (s, 2H), 2.85-3.50 (m, 10H), 2.55 (m, 1H), 2.10 (m, 1H), 1.65 (m, 1H) | 423.1, 425.1 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 124 | | 1 | Ex 37, 51, 130, 387 | DMSO + D$_2$O: 7.81 (s, 1H), 7.58 (d, J = 8.0 Hz, 1H), 7.51 (d, J = 8.0 Hz, 1H), 6.95 (s, 1H), 6.92 (s, 1H), 6.88 (s, 1H), 5.08 (s, 2H), 4.37 (s, 2H), 3.93 (m, 2H), 3.67 (m, 4H), 3.28 (s, 3H), 2.93 (m, 1H), 2.80 (m, 2H) | 439.3, 441.3 [M + H]$^+$ |
| 125 | | 1 | Ex 37 & 51 | DMSO + D$_2$O: 7.84 (d, J = 1.6 Hz, 1H), 7.65 (d, J = 8.4 Hz, 1H), 7.54 (dd, J = 2.0 Hz, 8.4 Hz, 1H), 7.28 (t, J = 8.0 Hz, 1H), 6.97 (t, J = 7.6 Hz, 1H), 5.12 (s, 2H), 4.01 (m, 2H), 3.79 (m, 2H), 3.21 (m, 2H), 3.12 (m, 3H), 2.92 (m, 2H) | 409.1, 411.1 [M + H]$^+$ |
| 126 | | 2 | Ex 37 & 51 | DMSO + D$_2$O: 7.69 (d, J = 2.4 Hz, 1H), 7.59 (d, J = 8.0 Hz, 1H), 7.39 (dd, J = 2.4 Hz, 8.8 Hz, 1H), 7.19 (m, 2H), 7.00 (d, J = 8.4 Hz, 1H), 5.15 (s, 2H), 4.13 (m, 2H), 3.99 (m, 2H), 3.81 (m, 2H), 3.23 (m, 2H), 3.10 (m, 3H), 2.08 (m, 2H) | 517.0, 519.0 [M + H]$^+$ |
| 127 | | 1 | Ex 37, 51, 130 | DMSO + D$_2$O: 9.98 (s, 1H), 7.84 (s, 1H), 7.52-7.66 (m, 5H), 5.20 (s, 2H), 4.20 (s, 2H), 4.00 (m, 2H), 3.84 (m, 2H), 3.27 (m, 2H), 3.18 (m, 1H) | 423.1, 425.1 [M + H]$^+$ |
| 128 | | 1 | Ex 37, 51, 130 | DMSO + D$_2$O: 7.83 (s, 1H), 7.58 (d, J = 8.0 Hz, 1H), 7.52 (d, J = 8.0 Hz, 1H), 7.07 (s, 1H), 7.05 (s, 1H), 7.04 (s, 1H), 5.09 (s, 2H), 4.50 (s, 2H), 4.08 (s, 2H), 3.98 (m, 2H), 3.82 (m, 2H), 3.23 (m, 2H), 3.14 (m, 1H) | 425.1, 427.1 [M + H]$^+$ |
| 129 | | 1 | Ex 119 | DMSO + D$_2$O: 7.82 (s, 1H), 7.62 (m, 2H), 7.53 (d, J = 8.0 Hz, 1H), 7.51 (s, 1H), 7.48 (s, 1H), 7.18 (s, 1H), 6.68 (d, J = 16.4 Hz, 1H), 5.15 (s, 2H), 4.20 (q, J = 7.2 Hz, 2H), 4.12 (s, 2H), 3.98 (m, 2H), 3.82 (m, 2H), 3.24 (m, 2H), 3.14 (m, 1H), 1.24 (t, J = 7.2 Hz, 3H) | 493.1, 495.1 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 130 | | 1 | Ex 37, 51, 158 | DMSO + D$_2$O: 7.83 (d, J = 2.0 Hz, 1H), 7.67 (d, J = 1.3 Hz, 1H), 7.61 (d, J = 8.2 Hz, 1H), 7.52 (dd, J = 2.0 Hz, 8.2 Hz, 1H), 7.31 (s, 1H), 7.25 (s, 1H), 7.17 (d, J = 16.0 Hz, 1H), 7.02 (s, 1H), 6.97 (d, J = 16.0 Hz, 1H), 6.57 (m, 1H), 6.45 (m, 1H), 5.14 (s, 2H), 4.09 (s, 2H), 3.98 (m, 2H), 3.82 (m, 2H), 3.25 (m, 2H), 3.12 (m, 1H) | 487.1, 489.1 [M + H]$^+$ |
| 131 | | 1 | Ex 37 | DMSO + D$_2$O: 7.75-7.90 (m, 3H), 7.40 (t, J = 8.0 Hz, 1H), 7.12 (m, 3H), 5.23 (s, 2H), 4.13 (s, 2H), 3.98 (m, 2H), 3.80 (m, 2H), 3.23 (m, 2H), 3.14 (m, 1H) | 385.1 [M + H]$^+$ |
| 132 | | 1 | Ex 37 | DMSO + D$_2$O: 7.75-7.90 (m, 3H), 7.40 (t, J = 8.0 Hz, 1H), 7.12 (m, 3H), 5.20 (s, 2H), 4.12 (s, 2H), 3.35 (m, 1H), 3.25 (m, 1H), 3.11 (m, 1H), 3.05 (m, 2H), 2.87 (m, 1H), 2.57 (m, 1H), 2.13 (m, 1H), 1.64 (m, 1H) | 399.1 [M + H]$^+$ |
| 133 | | 1 | Ex 37 & 136 | DMSO + D$_2$O: 7.75 (d, J = 2.0 Hz, 1H), 7.40 (m, 6H), 4.30 (s, 2H), 4.07 (s, 2H), 3.98 (m, 2H), 3.81 (m, 2H), 3.21 (m, 2H), 3.12 (m, 1H) | 411.1, 413.1 [M + H]$^+$ |
| 134 | | 1 | Ex 37 & 136 | DMSO + D$_2$O: 7.75 (d, J = 2.0 Hz, 1H), 7.40 (m, 6H), 4.30 (s, 2H), 4.10 (s, 2H), 3.35 (m, 1H), 3.25 (m, 1H), 3.12 (m, 1H), 3.03 (m, 2H), 2.86 (m, 1H), 2.56 (m, 1H), 2.12 (m, 1H), 1.63 (m, 1H) | 425.1, 427.2 [M + H]$^+$ |
| 135 | | 1 | Ex 136 & 158 | DMSO + D$_2$O: 7.82 (d, J = 2.0 Hz, 1H), 7.47-7.62 (m, 5H), 7.42 (dd, J = 1.6 Hz, 8.0 Hz, 1H), 5.17 (s, 2H), 4.70 (s, 2H), 4.05 (m, 2H), 3.80 (m, 2H), 3.28 (m, 2H), 3.20 (m, 1H) | 423.2, 425.2 [M + H]$^+$ |
| 136 | | 1 | Ex 37 | DMSO + D$_2$O: 7.75 (s, 1H), 7.30-7.50 (m, 6H), 4.29 (s, 2H), 4.10 (s, 2H), 3.35 (m, 1H), 3.25 (m, 1H), 3.00-3.20 (m, 3H), 2.85 (m, 1H), 2.55 (m, 1H), 2.15 (m, 1H), 1.60 (m, 1H) | 425.3, 427.3 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 137 | [structure] | 1 | Ex 37 & 136 | DMSO + D$_2$O: 7.50-7.80 (m, 5H), 7.41 (dd, J = 2.0 Hz, 8.4 Hz, 1H), 7.18 (d, J = 8.4 Hz, 1H), 4.27-4.37 (m, 2H), 4.21 (s, 2H), 3.37 (m, 1H), 3.25 (m, 1H), 3.00-3.20 (m, 3H), 2.87 (m, 1H), 2.55 (m, 1H), 2.15 (m, 1H), 1.65 (m, 1H) | 441.1, 443.2 [M + H]$^+$ |
| 138 | [structure] | 1 | Ex 37, 136, 137, 141 | DMSO + D$_2$O: 7.76 (m, 2H), 7.70 (m, 3H), 7.48 (dd, J = 2.0 Hz, 8.4 Hz, 1H), 7.37 (d, J = 8.4 Hz, 1H), 4.79 (s, 2H), 4.24 (s, 2H), 4.00 (m, 2H), 3.80 (m, 2H), 3.24 (m, 2H), 3.14 (m, 1H) | 443.2, 445.1 [M + H]$^+$ |
| 139 | [structure] | 1 | Ex 37 & 135 | DMSO + D$_2$O: 7.97 (d, J = 9.2 Hz, 2H), 7.82 (d, J = 2.0 Hz, 1H), 7.59 (d, J = 8.4 Hz, 1H), 7.51 (dd, J = 2.0 Hz, 8.4 Hz, 1H), 7.20 (d, J = 9.2 Hz, 2H), 5.21 (s, 2H), 4.65 (s, 2H), 4.05 (m, 2H), 3.85 (m, 2H), 3.30 (m, 2H), 3.20 (m, 1H) | 423.3, 425.3 [M + H]$^+$ |
| 140 | [structure] | 1 | Ex 37 & 135 | DMSO + D$_2$O: 7.98 (d, J = 9.2 Hz, 2H), 7.82 (d, J = 2.0 Hz, 1H), 7.60 (d, J = 8.0 Hz, 1H), 7.51 (dd, J = 2.0 Hz, 8.0 Hz, 1H), 7.20 (d, J = 9.2 Hz, 2H), 5.22 (s, 2H), 4.70 (s, 2H), 3.40 (m, 1H), 3.27 (m, 1H), 3.10 (m, 3H), 2.90 (m, 1H), 2.65 (m, 1H), 2.20 (m, 1H), 1.65 (m, 1H) | 437.2, 439.2 [M + H]$^+$ |
| 141 | [structure] | 1 | Ex 37 | DMSO + D$_2$O: 7.92 (s, 1H), 7.82 (d, J = 6.8 Hz, 1H), 7.68 (m, 3H), 7.46 (d, J = 8.4 Hz, 1H), 7.31 (d, J = 8.4 Hz, 1H), 4.77 (s, 2H), 4.21 (s, 2H), 3.35 (m, 1H), 3.00-3.30 (m, 4H), 2.85 (m, 1H), 2.55 (m, 1H), 2.10 (m, 1H), 1.60 (m, 1H) | 457.1, 459.1 [M + H]$^+$ |
| 142 | [structure] | 3 | Ex 37, 136, 165, 168 | DMSO + D$_2$O: 7.84 (d, J = 8.4 Hz, 1H), 7.78 (d, J = 2.0 Hz, 1H), 7.68 (m, 2H), 7.48 (m, 3H), 7.39 (d, J = 16.4 Hz, 1H), 7.29 (d, J = 16.4 Hz, 1H), 4.12 (s, 2H), 4.00 (m, 2H), 3.80 (m, 2H), 3.23 (m, 2H), 3.13 (m, 1H) | 391.2, 393.2 [M + H]$^+$ |
| 143 | [structure] | 1 | Ex 37 & 135 | DMSO + D$_2$O: 7.82 (d, J = 2.0 Hz, 1H), 7.40-7.60 (m, 6H), 5.18 (s, 2H), 4.75 (s, 2H), 3.40 (m, 1H), 3.25 (m, 1H), 3.12 (m, 3H), 2.90 (m, 1H), 2.65 (m, 1H), 2.20 (m, 1H), 1.70 (m, 1H) | 437.1, 439.1 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 144 | | 1 | Ex 37 & 158 | DMSO + D₂O: 8.47 (s, 1H), 8.36 (s, 1H), 7.85 (s, 1H), 7.80 (s, 1H), 7.64 (d, J = 8.4 Hz, 1H), 7.54 (d, J = 8.4 Hz, 1H), 5.21 (s, 2H), 4.20 (s, 2H), 4.00 (m, 2H), 3.85 (m, 2H), 3.27 (m, 2H), 3.20 (m, 1H) | 396.1, 398.1 [M + H]⁺ |
| 145 | | 1 | Ex 37 & 135 | DMSO + D₂O: 7.88 (m, 2H), 7.70 (m, 2H), 7.53 (dd, J = 2.0 Hz, 8.4 Hz, 1H), 7.31 (d, J = 8.8 Hz, 1H), 7.17 (t, J = 7.6 Hz, 1H), 5.32 (s, 2H), 4.42 (s, 2H), 4.00 (m, 2H), 3.80 (m, 2H), 3.18 (m, 2H), 3.10 (m, 1H) | 423.1, 425.1 [M + H]⁺ |
| 146 | | 1 | Ex 37 & 158 | DMSO + D₂O: 8.47 (s, 1H), 8.37 (s, 1H), 7.84 (s, 1H), 7.81 (s, 1H), 7.63 (d, J = 8.0 Hz, 1H), 7.53 (d, J =8.4 Hz, 1H), 5.21 (s, 2H), 4.22 (s, 2H), 3.38 (m, 1H), 3.25 (m, 1H), 3.12 (m, 3H), 2.92 (m, 1H), 2.62 (m, 1H), 2.15 (m, 1H), 1.68 (m, 1H) | 410.2, 412.2 [M + H]⁺ |
| 147 | | 3 | Ex 37, 136, 168 | DMSO + D₂O: 7.86 (d, J = 8.4 Hz, 1H), 7.79 (d, J = 2.0 Hz, 1H), 7.69 (dd, J = 2.0 Hz, 8.4 Hz, 2H), 7.50 (m, 3H), 7.39 (d, J = 16.4 Hz, 1H), 7.30 (d, J = 16.4 Hz, 1H), 4.16 (s, 2H), 3.35 (m, 1H), 3.25 (m, 1H), 3.14 (m, 1H), 3.05 (m, 2H), 2.88 (m, 1H), 2.57 (m, 1H), 2.13 (m, 1H), 1.66 (m, 1H) | 405.2, 407.1 [M + H]⁺ |
| 148 | | 1 | Ex 37 | HPLC: 5.43 min | 454.0, 456.0 [M + H]⁺ |
| 149 | | 4 | Ex 37 & 136 | DMSO + D₂O: 7.92 (d, J = 2.0 Hz, 1H), 7.72 (s, 1H), 7.65 (m, 2H), 7.55 (m, 3H), 4.16 (s, 2H), 4.00 (m, 2H), 3.80 (m, 2H), 3.25 (m, 2H), 3.15 (m, 1H) | 389.2, 391.1 [M + H]⁺ |
| 150 | | 4 | Ex 37 & 149 | DMSO + D₂O: 7.92 (d, J = 2.0 Hz, 1H), 7.74 (s, 1H), 7.65 (m, 2H), 7.55 (m, 3H), 4.18 (s, 2H), 3.36 (m, 1H), 3.25 (m, 1H), 3.14 (m, 1H), 3.08 (m, 2H), 2.88 (m, 1H), 2.58 (m, 1H), 2.15 (m, 1H), 1.65 (m, 1H) | 403.2, 405.2 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 151 | (structure) | 6 | Ex 23, 37, 119, 130 | DMSO + D$_2$O: 7.88 (s, 1H), 7.77 (m, 2H), 7.55 (m, 3H), 4.17 (s, 2H), 3.37 (m, 1H), 3.25 (m, 1H), 3.15 (m, 1H), 3.10 (m, 2H), 2.92 (m, 1H), 2.65 (m, 1H), 2.15 (m, 1H), 1.70 (m, 1H) | 456.2, 458.2 [M + H]$^+$ |
| 152 | (structure) | 6 | Ex 27, 37, 119, 130 | DMSO + D$_2$O: 7.75 (m, 3H), 7.50-7.60 (m, 3H), 4.17 (s, 2H), 3.35 (m, 1H), 3.25 (m, 1H), 3.15 (m, 1H), 3.10 (m, 2H), 2.90 (m, 1H), 2.60 (m, 1H), 2.15 (m, 1H), 1.65 (m, 1H) | 412.2, 414.2 [M + H]$^+$ |
| 153 | (structure) | 6 | Ex 23, 37, 119, 130 | DMSO + D$_2$O: 7.95 (d, J = 2.0 Hz, 1H), 7.91 (d, J = 8.0 Hz, 1H), 7.75 (m, 3H), 7.54 (d, J = 8.4 Hz, 1H), 4.17 (s, 2H), 3.35 (m, 1H), 3.25 (m, 1H), 3,15 (m, 1H), 3.10 (m, 2H), 2.95 (m, 1H), 2.65 (m, 1H), 2.15 (m, 1H), 1.70 (m, 1H) | 446.2, 448.2 [M + H]$^+$ |
| 154 | (structure) | 1 | Ex 37 & 135 | DMSO + D$_2$O: 7.88 (m, 2H), 7.80 (m, 2H), 7.52 (dd, J = 2.0 Hz, 8.0 Hz, 1H), 7.33 (d, J = 8.4 Hz, 1H), 7.18 (t, J = 7.6 Hz, 1H), 5.32 (s, 2H), 4.43 (s, 2H), 3.35 (m, 1H), 3.25 (m, 1H), 3.12 (m, 1H), 2.98 (m, 2H), 2.85 (m, 1H), 2.50 (m, 1H), 2.10 (m, 1H), 1.60 (m, 1H) | 437.0, 439.0 [M + H]$^+$ |
| 155 | (structure) | 6 | Ex 23, 37, 119, 130 | DMSO + D$_2$O: 8.20 (m, 2H), 7.95 (d, J = 8.0 Hz, 1H), 7.75 (m, 2H), 7.51 (m, 1H), 4.14 (s, 2H), 4.00 (m, 2H), 3.85 (m, 2H), 3.25 (m, 2H), 3.15 (m, 1H) | 466.2 [M + H]$^+$ |
| 156 | (structure) | 6 | Ex 23, 37, 119, 130 | DMSO + D$_2$O: 7.75 (m, 3H), 7.48-7.55 (m, 3H), 4.14 (s, 2H), 4.00 (m, 2H), 3.85 (m, 2H), 3.25 (m, 2H), 3.15 (m, 1H) | 398.1, 400.1 [M + H]$^+$ |
| 157 | (structure) | 3 | Ex 37, 136, 168, 387 | DMSO + D$_2$O: 7.84 (d, J = 8.4 Hz, 1H), 7.82 (d, J = 2.4 Hz, 1H), 7.72 (m, 2H), 7.52 (m, 2H), 7.43 (d, J = 16.4 Hz, 1H), 7.28 (d, J = 16.4 Hz, 1H), 4.19 (s, 2H), 3.37 (m, 1H), 3.25 (m, 1H), 3.11 (m, 3H), 2.89 (m, 1H), 2.59 (m, 1H), 2.15 (m, 1H), 1.68 (m, 1H) | 439.1, 441.1 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 158 | | 1 | Ex 37 | DMSO + D$_2$O: 7.74 (d, J = 2.0 Hz, 1H), 7.40 (dd, J = 2.0 Hz, 8.0 Hz, 1H), 7.31 (d, J = 8.4 Hz, 1H), 7.14 (m, 1H), 6.65 (d, J = 8.0 Hz, 1H), 6.59 (s, 1H), 6.55 (dd, J = 2.0 Hz, 8.0 Hz, 1H), 4.27 (s, 2H), 3.98 (m, 4H), 3.77 (m, 2H), 3.19 (m, 2H), 3.11 (m, 1H) | 394.2, 396.2 [M + H]$^+$ |
| 159 | | 3 | Ex 37, 165, 168 | DMSO + D$_2$O: 7.83 (d, J = 8.8 Hz, 1H), 7.81 (d, J = 2.4 Hz, 1H), 7.71 (m, 2H), 7.52 (m, 2H), 7.43 (d, J = 16.4 Hz, 1H), 7.27 (d, J = 16.4 Hz, 1H), 4.17 (s, 2H), 3.99 (m, 2H), 3.83 (m, 2H), 3.26 (m, 2H), 3.13 (m, 1H) | 425.1, 427.1 [M + H]$^+$ |
| 160 | | 6 | Ex 23, 37, 119, 130 | DMSO + D$_2$O: 8.22 (m, 2H), 7.96 (d, J = 7.6 Hz, 1H), 7.76 (m, 2H), 7.55 (d, J = 8.0 Hz, 1H), 4.17 (s, 2H), 3.37 (m, 1H), 3.25 (m, 1H), 3,13 (m, 1H), 3.07 (m, 2H), 2.93 (m, 1H), 2.63 (m, 1H), 2.15 (m, 1H), 1.68 (m, 1H) | 480.2 [M + H]$^+$ |
| 161 | | 6 | Ex 23, 37, 119, 130 | DMSO + D$_2$O: 7.94 (s, 1H), 7.88 (d, J = 8.4 Hz, 1H), 7.72 (m, 3H), 7.50 (d, J = 8.4 Hz, 1H), 4.14 (s, 2H), 4.00 (m, 2H), 3.85 (m, 2H), 3.25 (m, 2H), 3.15 (m, 1H) | 432.2 [M + H]$^+$ |
| 162 | | 6 | Ex 23, 37, 119, 130 | DMSO + D$_2$O: 7.86 (d, J = 2.0 Hz, 1H), 7.75 (d, J = 8.4 Hz, 1H), 7.71 (s, 1H), 7.58 (m, 2H), 7.49 (dd, J = 2.0 Hz, 8.4 Hz, 1H), 4.14 (s, 2H), 4.03 (m, 2H), 3.86 (m, 2H), 3.25 (m, 2H), 3.15 (m, 1H) | 442.0, 444.0 [M + H]$^+$ |
| 163 | | 1 | Ex 37 | DMSO + D$_2$O: 7.83 (d, J = 2.1 Hz, 1H), 7.61 (d, J = 8.3 Hz, 1H), 7.53 (dd, J = 2.1 Hz, 8.3 Hz, 1H), 6.84 (s, 1H), 6.82 (s, 1H), 6.58 (s, 1H), 5.10 (s, 2H), 4.63 (m, 1H), 4.08 (s, 2H), 3.39 (m, 1H), 3.25 (m, 1H), 3.13 (m, 1H), 3.04 (m, 2H), 2.97 (m, 1H), 2.70 (m, 1H), 2.14 (m, 1H), 1.70 (m, 1H), 1.27 (d, J = 6.0 Hz, 6H) | 467.0, 469.0 [M + H]$^+$ |
| 164 | | 3 | Ex 37, 165, 168 | DMSO + D$_2$O: 7.84 (d, J = 8.8 Hz, 1H), 7.78 (d, J = 2.4 Hz, 1H), 7.50 (m, 3H), 7.39 (m, 1H), 7.23-7.37 (m, 3H), 3.36 (m, 1H), 3.27 (m, 1H), 3.12-3.21 (m, 3H), 3.07 (m, 2H), 2.95 (m, 2H), 2.88 (m, 1H), 2.54 (m, 1H), 2.14 (m, 1H), 1.64 (m 1H) | 419.1, 421.1 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 165 | | 3 | Ex 37, 158, 168 | DMSO: 7.84 (d, J = 8.4 Hz, 1H), 7.78 (d, J = 2.0 Hz, 1H), 7.50 (m, 3H), 7.39 (m, 1H), 7.22-7.32 (m, 3H), 4.00 (m, 2H), 3.80 (m, 2H), 3.24 (m, 2H), 3.15 (m, 3H), 2.92 (m, 2H) | 405.1, 407.0 [M + H]+ |
| 166 | | 1 | Ex 37 | DMSO: 9.50 (br, 2H), 8.98 (br, 2H), 7.72 (d, J = 2.1 Hz, 1H), 7.64 (d, J = 8.3 Hz, 1H), 7.52 (dd, J = 2.1 Hz, 8.3 Hz, 1H), 6.88 (s, 1H), 6.84 (s, 1H), 6.65 (s, 1H), 5.15 (s, 2H), 4.05 (m, 2H), 3.98 (m, 2H), 3.86 (m, 4H), 3.21 (m, 3H), 1.24 (m, 1H), 0.59 (m, 2H), 0.32 (m, 2H) | 421.2, 423.2 [M + H]+ |
| 167 | | 1 | Ex 37 & 158 | DMSO: 7.86 (d, J = 2.1 Hz, 1H), 7.62 (d, J = 8.3 Hz, 1H), 7.55 (dd, J = 2.1 Hz, 8.3 Hz, 1H), 6.77 (m, 3H), 5.15 (s, 2H), 4.66 (m, 1H), 4.46 (m, 2H), 3.67 (m, 1H), 3.25-3.50 (m, 9H), 3.11 (m, 1H), 2.85 (m, 1H), 2.71 (m, 1H), 2.04 (m, 1H), 1.50 (m, 1H), 1.29 (d, J = 6.0 Hz, 6H) | 495.1, 497.1 [M + H]+ |
| 168 | | 3 | Ex 37 & 158 | DMSO + D2O: 7.73 (m, 1H), 7.64 (d, J = 8.4 Hz, 1H), 7.25-7.50 (m, 5H), 6.68 (d, J = 15.6 Hz, 1H), 6.45 (m, 1H), 4.08 (m, 2H), 3.96 (m, 2H), 3.80 (m, 2H), 3.60 (m, 2H), 3.21 (m, 2H), 3.11 (m, 1H) | 405.0, 407.0 [M + H]+ |
| 169 | | 3 | Ex 37 & 168 | DMSO + D2O: 7.73 (m, 1H), 7.64 (d, J = 8.4 Hz, 1H), 7.30-7.50 (m, 5H), 6.68 (d, J = 15.6 Hz, 1H), 6.45 (m, 1H), 4.11 (m, 2H), 3.59 (m, 2H), 3.35 (m, 1H), 3.25 (m, 1H), 3.10 (m, 1H), 3.05 (m, 2H), 2.85 (m, 1H), 2.55 (m, 1H), 2.10 (m, 1H), 1.60 (m, 1H) | 419.0, 421.1 [M + H]+ |
| 170 | | 2 | Ex 37 & 158 | DMSO + D2O: 7.48 (d, J = 2.4 Hz, 1H), 7.32 (m, 2H), 7.27 (m, 2H), 7.09 (dd, J = 2.4 Hz, 8.8 Hz, 1H), 6.47 (d, J = 8.8 Hz, 1H), 4.38 (s, 2H), 3.95 (m, 2H), 3.90 (s, 2H), 3.75 (m, 2H), 3.01 (m, 3H) | 394.1, 396.1 [M + H]+ |
| 171 | | 3 | Ex 37, 51, 168 | DMSO + D2O: 7.78 (m, 3H), 7.66 (d, J = 7.6 Hz, 1H), 7.44-7.53 (m, 3H), 7.39 (d, J = 16.4 Hz, 1H), 7.30 (d, J = 16.4 Hz, 1H), 4.22 (m, 2H), 4.01 (m, 1H), 3.92 (m, 1H), 3.58-3.67 (m, 1H), 3.18-3.27 (m, 3H), 2.20 (m, 1H), 2.11 (m, 1H) | 420.1, 422.1 [M + H]+ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 172 | | 1 | Ex 37 & 51 | DMSO: 9.23 (br, 2H), 8.20 (br, 2H), 7.87 (d, J = 2.0 Hz, 1H), 7.61 (d, J = 8.4 Hz, 1H), 7.55 (dd, J = 2.0 Hz, 8.4 Hz, 1H), 7.41 (m, 1H), 7.19 (s, 1H), 7.12 (m, 2H), 5.13 (s, 2H), 4.16 (m, 2H), 3.93-4.05 (m, 2H), 3.21 (m, 4H), 2.08-2.20 (m, 2H) | 424.1, 426.1 [M + H]+ |
| 173 | | 1 | Ex 158 | DMSO + D$_2$O: 7.74 (d, J = 2.0 Hz, 1H), 7.35-7.55 (m, 6H), 4.61 (s, 2H), 4.56 (s, 2H), 4.11 (s, 2H), 3.98 (m, 2H), 3.80 (m, 2H), 3.23 (m, 2H), 3.13 (m, 1H) | 409.2, 411.2 [M + H]+ |
| 174 | | 1 | Ex 37 & 158 | DMSO + D$_2$O: 7.75 (d, J = 2.0 Hz, 1H), 7.35-7.55 (m, 6H), 4.67 (s, 2H), 4.62 (s, 2H), 4.14 (s, 2H), 3.35 (m, 1H), 3.25 (m, 1H), 3.10 (m, 1H), 3.05 (m, 2H), 2.87 (m, 1H), 2.55 (m, 1H), 2.12 (m, 1H), 1.62 (m, 1H) | 423.2, 425.2 [M + H]+ |
| 175 | | 1 | Ex 37 & 51 | DMSO: 9.38 (br, 1H), 8.20 (br, 3H), 7.87 (d, J = 2.0 Hz, 1H), 7.62 (d, J = 8.4 Hz, 1H), 7.55 (dd, J = 2.0 Hz, 8.4 Hz, 1H), 7.25 (s, 1H), 7.21 (s, 1H), 7.14 (s, 1H), 5.15 (s, 2H), 4.12 (m, 2H), 3.96 (m, 2H), 3.20 (m, 4H), 2.19 (m, 1H), 2.10 (m, 1H) | 458.1, 460.1 [M + H]+ |
| 176 | | 1 | Ex 37 | DMSO: 8.80 (br, 3H), 7.73 (d, J = 2.1 Hz, 1H), 7.64 (d, J = 8.3 Hz, 1H), 7.52 (dd, J = 2.1 Hz, 8.3 Hz, 1H), 7.39 (t, J = 7.9 Hz, 1H), 7.19 (m, 1H), 7.09 (m, 2H), 5.17 (s, 2H), 4.10 (s, 2H), 3.39 (m, 1H), 3.26 (m, 1H), 3.15 (m, 1H), 2.98 (m, 2H), 2.91 (m, 1H), 2.58 (m, 1H), 2.12 (m, 1H), 1.66 (m, 1H) | 365.2 [M + H]+ |
| 177 | | 1 | Ex 37 | DMSO: 8.80 (br, 3H), 7.73 (d, J = 2.1 Hz, 1H), 7.64 (d, J = 8.3 Hz, 1H), 7.52 (dd, J = 2.1 Hz, 8.3 Hz, 1H), 7.39 (m, 1H), 7.19 (t, J = 2.0 Hz, 1H), 7.10 (m, 2H), 5.17 (s, 2H), 4.10 (s, 4H), 4.00 (m, 2H), 3.83 (m, 2H), 3.17 (m, 3H) | 351.2 [M + H]+ |
| 178 | | 3 | Ex 37, 51, 158, 168, 183, 399 | DMSO + D$_2$O: 7.84 (d, J = 8.8 Hz, 1H), 7.80 (d, J = 2.0 Hz, 1H), 7.50 (dd, J = 2.0 Hz, 8.8 Hz, 1H), 7.37 (m, 2H), 7.15-7.30 (m, 2H), 7.13 (s, 1H), 6.05 (m, 1H), 5.45 (m, 1H), 5.28 (m, 1H), 4.63 (m, 2H), 4.15 (s, 2H), 3.37 (m, 1H), 3.25 (m, 1H), 3.13 (m, 1H), 3.07 (m, 2H), 2.92 (m, 1H), 2.65 (m 1H), 2.15 (m, 1H), 1.65 (m, 1H) | 461.1, 463.1 [M + H]+ |
| 179 | | 1 | Ex 37 & 387 | DMSO + D$_2$O: 7.83 (d, J = 2.0 Hz, 1H), 7.60 (d, J = 8.0 Hz, 1H), 7.53 (dd, J = 2.0 Hz, 8.0 Hz, 1H), 7.36 (s, 1H), 7.26 (s, 1H), 5.16 (s, 2H), 4.40 (s, 2H), 4.05 (m, 2H), 3.95 (m, 2H), 3.62 (m, 2H), 3.55 (m, 1H), 2.90 (s, 6H) | 457.0, 459.0 [M + H]+ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 180 | | 3 | Ex 37, 165, 168, 183 | DMSO + D$_2$O: 7.80 (m, 2H), 7.50 (d, J = 8.4 Hz, 1H), 7.20-7.40 (m, 4H), 7.03 (s, 1H), 6.04 (m, 1H), 5.40 (m, 1H), 5.30 (m, 1H), 4.62 (m, 2H), 4.12 (s, 2H), 4.00 (m, 2H), 3.80 (m, 2H), 3.25 (m, 2H), 3.15 (m, 1H) | 447.1, 449.1 [M + H]$^+$ |
| 181 | | 3 | Ex 37, 51, 183 | DMSO + D$_2$O: 7.83 (d, J = 8.8 Hz, 1H), 7.79 (d, J = 2.0 Hz, 1H), 7.15-7.50 (m, 11H), 5.17 (s, 2H), 4.15 (s, 2H), 3.37 (m, 1H), 3.25 (m, 1H), 3.15 (m, 1H), 3.10 (m, 2H), 2.90 (m, 1H), 2.62 (m, 1H), 2.15 (m, 1H), 1.65 (m, 1H) | 511.4, 513.4 [M + H]$^+$ |
| 182 | | 3 | Ex 37, 51, 183 | DMSO + D$_2$O: 7.82 (m, 2H), 7.50 (dd, J = 2.0 Hz, 8.4 Hz, 1H), 7.25-7.39 (m, 3H), 7.17 (s, 1H), 7.08 (s, 1H), 4.14 (s, 2H), 3.80 (m, 2H), 3.35 (m, 1H), 3.25 (m, 1H), 3.15 (m, 1H), 3.10 (m, 2H), 2.90 (m, 1H), 2.62 (m, 1H), 2.15 (m, 1H), 2.00 (m, 1H), 1.65 (m, 1H), 0.98 (d, J = 6.4 Hz, 6H) | 477.2, 479.2 [M + H]$^+$ |
| 183 | | 2 | Ex 37, 51, 158 | DMSO + D$_2$O: 7.78 (s, 1H), 7.65 (s, 2H), 6.97 (m, 3H), 6.00 (m, 1H), 5.34 (m, 1H), 5.25 (m, 1H), 4.51 (m, 2H), 4.31 (s, 2H), 4.05 (s, 2H), 4.00 (m, 2H), 3.80 (m, 2H), 3.20 (m, 2H), 3.13 (m, 1H) | 457.1 [M + H]$^+$ |
| 184 | | 2 | Ex 37, 51, 183 | DMSO + D$_2$O: 7.75 (s, 1H), 7.67 (s, 2H), 6.95-7.10 (m, 3H), 6.00 (m, 1H), 5.35 (m, 1H), 5.22-5.32 (m, 1H), 4.52 (m, 2H), 4.32 (s, 2H), 4.07 (s, 2H), 3.35 (m, 1H), 3.25 (m, 1H), 3.12 (m, 1H), 3.03 (m, 2H), 2.87 (m, 1H), 2.60 (m, 1H), 2.15 (m, 1H), 1.65 (m, 1H) | 471.1 [M + H]$^+$ |
| 185 | | 3 | Ex 37, 51, 201 | DMSO + D$_2$O: 7.83 (d, J = 8.8 Hz, 1H), 7.77 (d, J = 2.4 Hz, 1H), 7.61 (d, J = 8.4 Hz, 1H), 7.48 (m, 2H), 7.29 (d, J = 16.4 Hz, 1H), 7.13 (d, J = 2.0 Hz, 1H), 7.07 (dd, J = 2.0 Hz, 8.0 Hz, 1H), 4.17 (m, 2H), 3.35 (m, 1H), 3.25 (m, 1H), 3.00-3.15 (m, 5H), 2.90 (m, 1H), 2.60 (m, 1H), 2.05-2.20 (m, 3H), 1.68 (m, 1H) | 483.1, 485.1 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 186 | (structure) | 3 | Ex 36, 130, 201 | DMSO + D$_2$O: 7.83 (d, J = 8.8 Hz, 1H), 7.79 (d, J = 2.0 Hz, 1H), 7.64 (d, J = 2.4 Hz, 1H), 7.52 (d, J = 16.4 Hz, 1H), 7.49 (dd, J = 2.0 Hz, 8.8 Hz, 1H), 7.35 (dd, J = 2.4 Hz, 9.0 Hz, 1H), 7.29 (d, J = 16.4 Hz, 1H), 7.10 (d, J = 9.0 Hz, 1H), 4.16 (m, 2H), 3.35 (m, 1H), 3.25 (m, 1H), 3.00-3.15 (m, 5H), 2.90 (m, 1H), 2.55 (m, 1H), 2.05-2.20 (m, 3H), 1.65 (m, 1H) | 483.1, 485.1 [M + H]$^+$ |
| 187 | (structure) | 3 | Ex 37, 51, 201 | DMSO + D$_2$O: 7.84 (d, J = 8.4 Hz, 1H), 7.79 (d, J = 1.6 Hz, 1H), 7.62 (d, J = 8.4 Hz, 1H), 7.46 (m, 2H), 7.30 (d, J = 16.4 Hz, 1H), 7.13 (d, J = 1.6 Hz, 1H), 7.08 (dd, J = 1.6 Hz, 8.2 Hz, 1H), 4.18 (m, 2H), 3.98 (m, 2H), 3.80 (m, 2H), 3.24 (m, 2H), 3.10 (m, 3H), 2.15 (m, 2H) | 469.1, 471.1 [M + H]$^+$ |
| 188 | (structure) | 3 | Ex 37, 130, 201 | DMSO + D$_2$O: 7.82 (d, J = 8.4 Hz, 1H), 7.80 (d, J = 2.0 Hz, 1H), 7.50 (dd, J = 2.0 Hz, 8.6 Hz, 1H), 7.36 (d, J = 16.4 Hz, 1H), 7.28 (s, 1H), 7.21 (d, J = 16.4 Hz, 1H), 7.13 (s, 1H), 6.99 (s, 1H), 4.12 (m, 2H), 4.05 (m, 2H), 3.80 (m, 2H), 3.25 (m, 2H), 3.15 (m, 1H), 3.05 (m, 2H), 2.05 (m, 2H) | 469.1, 471.1 [M + H]$^+$ |
| 189 | (structure) | 3 | Ex 37, 130, 201 | DMSO + D$_2$O: 7.82 (d, J = 8.8 Hz, 1H), 7.80 (d, J = 2.0 Hz, 1H), 7.51 (dd, J = 2.0 Hz, 8.8 Hz, 1H), 7.37 (d, J = 16.4 Hz, 1H), 7.29 (s, 1H), 7.22 (d, J = 16.4 Hz, 1H), 7.13 (s, 1H), 6.99 (s, 1H), 4.14 (m, 2H), 3.37 (m, 1H), 3.25 (m, 1H), 3.00-3.20 (m, 5H), 2.90 (m, 1H), 2.55 (m, 1H), 2.05-2.20 (m, 3H), 1.65 (m, 1H) | 483.0, 485.0 [M + H]$^+$ |
| 190 | (structure) | 3 | Ex 37, 51, 183 | DMSO + D$_2$O: 7.81 (m, 2H), 7.50 (dd, J = 2.0 Hz, 8.4 Hz, 1H), 7.20-7.40 (m, 3H), 7.17 (s, 1H), 7.02 (s, 1H), 4.12 (s, 2H), 4.00 (m, 2H), 3.80 (m, 4H), 3.25 (m, 2H), 3.15 (m, 1H), 2.02 (m, 1H), 0.98 (d, J = 6.8 Hz, 6H) | 463.2, 465.1 [M + H]$^+$ |
| 191 | (structure) | 3 | Ex 23, 37, 51, 168 | DMSO + D$_2$O: 7.77-7.85 (m, 3H), 7.65 (d, J = 7.6 Hz, 1H), 7.52 (d, J = 8.4 Hz, 1H), 7.46 (m, 2H), 7.39 (d, J = 16.4 Hz, 1H), 7.30 (d, J = 16.4 Hz, 1H), 4.24 (m, 2H), 3.74 (m, 2H), 3.24 (m, 2H), 3.00 (m, 2H), 2.08 (m, 2H), 1.70 (m, 2H) | 434.2, 436.1 [M + H]$^+$ |
| 192 | (structure) | 1 | Ex 23, 37, 51 | DMSO: 9.20 (br, 2H), 8.20 (br, 2H), 7.86 (d, J = 2.0 Hz, 1H), 7.58 (d, J = 8.4 Hz, 1H), 7.52 (dd, J = 2.0 Hz, 8.4 Hz, 1H), 7.41 (dd, J = 8.0 Hz, 8.8 Hz, 1H), 7.21 (s, 1H), 7.12 (m, 2H), 5.13 (s, 2H), 4.19 (m, 2H), 3.75 (m, 2H), 3.02-3.21 (m, 4H), 2.08 (m, 2H), 1.71 (m, 2H) | 438.2, 440.2 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 193 | | 1 | Ex 23, 37, 51 | DMSO: 8.09 (br, 2H), 7.87 (d, J = 2.0 Hz, 1H), 7.62 (d, J = 8.4 Hz, 1H), 7.55 (d, J = 2.0 Hz, 8.4 Hz, 1H), 7.27 (s, 1H), 7.23 (s, 1H), 7.16 (s, 1H), 5.16 (s, 2H), 4.17 (m, 2H), 2.98 (m, 4H), 2.02 (m, 2H), 1.69 (m, 2H) (2 protons masked under water peak) | 472.0, 474.1 [M + H]+ |
| 194 | | 2 | Ex 37, 51, 183 | DMSO + D2O: 7.73 (s, 1H), 7.40 (m, 2H), 7.12 (m, 1H), 7.05 (m, 2H), 6.00 (m, 1H), 5.37 (m, 1H), 5.25 (m, 1H), 4.55 (m, 2H), 4.26 (s, 2H), 4.08 (s, 2H), 3.35 (m, 1H), 3.25 (m, 1H), 3.12 (m, 1H), 3.03 (m, 2H), 2.90 (m, 1H), 2.62 (m, 1H), 2.12 (m, 1H), 1.65 (m, 1H) | 481.1, 483.1 [M + H]+ |
| 195 | | 1 | Ex 37 | HPLC: 4.84 min | 409.1 [M + H]+ |
| 196 | | 2 | Ex 37, 51, 183 | DMSO + D2O: 7.74 (s, 1H), 7.39 (m, 2H), 7.05 (m, 2H), 6.97 (s, 1H), 6.00 (m, 1H), 5.35 (m, 1H), 5.26 (m, 1H), 4.53 (m, 2H), 4.25 (s, 2H), 4.05 (s, 2H), 4.00 (m, 2H), 3.80 (m, 2H), 3.23 (m, 2H), 3.12 (m, 1H) | 467.1, 469.1 [M + H]+ |
| 197 | | 1 | Ex 37 | DMSO + D2O: 7.99 (d, J = 8.3 Hz, 2H), 7.83 (d, J = 2.1 Hz, 1H), 7.59 (m, 3H), 7.52 (dd, J = 2.1 Hz, 8.3 Hz, 1H), 6.92 (s, 1H), 6.88 (s, 1H), 6.76 (s, 1H), 5.23 (s, 2H), 5.11 (s, 2H), 4.10 (s, 2H), 3.86 (s, 3H), 3.40 (m, 1H), 3.25 (m, 1H), 3.15 (m, 1H), 3.05 (m, 2H), 2.95 (m, 1H), 2.65 (m, 1H), 2.15 (m, 1H), 1.70 (m, 1H) | 573.1, 575.1 [M + H]+ |

TABLE 1-continued

Exemplified compounds

The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 198 | | 3 | Ex 37, 51, 183 | DMSO + D$_2$O: 7.85 (d, J = 8.8 Hz, 1H), 7.79 (d, J = 2.0 Hz, 1H), 7.20-7.50 (m, 10H), 7.10 (s, 1H), 5.16 (s, 2H), 4.12 (s, 2H), 4.00 (m, 2H), 3.80 (m, 2H), 3.25 (m, 2H), 3.12 (m, 1H) | 497.2, 499.2 [M + H]$^+$ |
| 199 | | 3 | Ex 37, 130, 201 | DMSO + D$_2$O: 7.85 (d, J = 8.8 Hz, 1H), 7.79 (d, J = 2.0 Hz, 1H), 7.64 (d, J = 2.0 Hz, 1H), 7.52 (d, J = 16.4 Hz, 1H), 7.50 (dd, J = 2.0 Hz, 8.4 Hz, 1H), 7.35 (dd, J = 2.0 Hz, 8.8 Hz, 1H), 7.30 (d, J = 16.4 Hz, 1H), 7.10 (d, J = 8.4 Hz, 1H), 4.16 (m, 2H), 4.00 (m, 2H), 3.80 (m, 2H), 3.25 (m, 2H), 3.10 (m, 3H), 2.15 (m, 2H) | 469.0, 471.0 [M + H]$^+$ |
| 200 | | 3 | Ex 37, 130, 201, 263 | DMSO + D$_2$O: 7.82 (m, 2H), 7.59 (dd, J = 1.4 Hz, 7.8 Hz, 1H), 7.30-7.50 (m, 4H), 6.95-7.10 (m, 2H), 4.15 (m, 2H), 4.00 (m, 2H), 3.85 (m, 2H), 3.25 (m, 2H), 3.10 (m 3H), 2.15 (m, 2H) | 435.0, 437.1 [M + H]$^+$ |
| 201 | | 3 | Ex 37, 51, 158, 183 | DMSO + D$_2$O: 7.77-7.85 (m, 2H), 7.48 (dd, J = 2.2 Hz, 8.6 Hz, 1H), 7.20-7.36 (m, 4H), 7.13 (s, 1H), 6.91 (dd, J = 2.0 Hz, 8.0 Hz, 1H), 4.09 (m, 2H), 4.02 (m, 2H), 3.87 (m, 2H), 3.24 (m, 2H), 3.00-3.20 (m, 3H), 2.06 (m, 2H) | 435.2, 437.2 [M + H]$^+$ |
| 202 | | 3 | Ex 37, 51, 201 | DMSO + D$_2$O: 7.84 (d, J = 8.8 Hz, 1H), 7.79 (s, 1H), 7.49 (dd, J = 2.2 Hz, 8.6 Hz, 1H), 7.20-7.40 (m, 4H), 7.14 (s, 1H), 6.92 (dd, J = 2.4 Hz, 8.0 Hz, 1H), 4.11 (m, 2H), 3.35 (m, 1H), 3.25 (m, 1H), 3.00-3.20 (m, 5H), 2.90 (m, 1H), 2.55 (m, 1H), 2.10 (m, 3H) 1.65 (m, 1H) | 449.1, 451.1 [M + H]$^+$ |
| 203 | | 3 | Ex 37, 130, 201, 263 | DMSO + D$_2$O: 7.85 (d, J = 8.8 Hz, 1H), 7.78 (d, J = 2.4 Hz, 1H), 7.60 (dd, J = 2.4 Hz, 8.8 Hz, 1H), 7.30-7.50 (m, 4H), 7.05 (m, 2H), 4.16 (m, 2H), 3.35 (m, 1H), 3.25 (m, 1H), 3.00-3.20 (m, 5H), 2.90 (m, 1H), 2.55 (m, 1H), 2.05-2.20 (m, 3H), 1.65 (m, 1H) | 449.1, 451.1 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 204 | | 1 | Ex 37 | DMSO + D$_2$O: 8.00 (d, J = 8.3 Hz, 2H), 7.83 (d, J = 2.0 Hz, 1H), 7.58 (m, 3H), 7.52 (dd, J = 2.1 Hz, 8.3 Hz, 1H), 6.82 (s, 1H), 6.78 (m, 2H), 5.22 (s, 2H), 5.11 (s, 2H), 4.10 (s, 2H), 4.00 (m, 2H), 3.86 (s, 3H), 3.80 (m, 2H), 3.25 (m, 2H), 3.18 (m, 1H) | 558.9, 560.9 [M + H]$^+$ |
| 205 | | 1 | Ex 37 | DMSO + D$_2$O: 7.92 (d, J = 7.9 Hz, 2H), 7.81 (d J = 2.1 Hz, 1H), 7.57 (d, J = 8.3 Hz, 1H), 7.51 (dd, J = 2.1 Hz, 8.3 Hz, 1H), 7.44 (d, J = 7.9 Hz, 2H), 6.67 (s, 1H), 6.63 (s, 1H), 6.57 (s, 1H), 5.12 (s, 2H), 5.07 (s, 2H), 3.68 (s, 2H), 3.25 (m, 1H), 3.18 (m, 1H), 3.10 (m, 1H), 2.83 (m, 1H), 2.47 (m, 2H), 2.38 (m, 1H), 1.99 (m, 1H), 1.55 (m, 1H) | 558.9, 560.9 [M + H]$^+$ |
| 206 | | 1 | Ex 37 | DMSO + D$_2$O: 7.76 (d, J = 7.8 Hz, 2H), 7.34 (m, 2H), 7.27 (d, J = 7.9 Hz, 2H), 7.13 (d, J = 7.4 Hz, 1H), 7.03 (d, J = 7.2 Hz, 1H), 5.10 (s, 2H), 4.09 (s, 2H), 3.98 (m, 2H), 3.87 (m, 2H), 3.24 (m, 3H) | 409.1 [M + H]$^+$ |
| 207 | | 1 | Ex 37 | DMSO: 9.70 (br, 2H), 9.51 (br, 2H), 7.77 (d, J = 7.8 Hz, 2H), 7.33 (m, 4H), 7.17 (d, J = 7.4 Hz, 1H), 7.04 (dd, J = 2.2 Hz, 8.1 Hz, 1H), 5.12 (s, 2H), 4.10 (m, 2H), 2.90-3.45 (m, 6H), 2.75 (m, 1H), 2.11 (m, 1H), 1.70 (m, 1H) | 423.1 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 208 | | 1 | Ex 37 | HPLC: 4.96 min | 545.0, 547.0 [M + H]⁺ |
| 209 | | 3 | Ex 37, 130, 168, 263 | DMSO + D₂O: 7.90 (m, 1H), 7.80 (m, 1H), 7.70 (m, 1H), 7.48 (m, 2H), 7.37 (m, 2H), 7.12 (d, J = 8.8 Hz, 1H), 4.30 (t, J = 4.8 Hz, 2H), 4.00 (m, 2H), 3.83 (m, 2H), 3.41 (t, J = 4.8 Hz, 2H), 3.32 (m, 2H), 3.20 (m, 1H) | 455.1, 457.1 [M + H]⁺ |
| 210 | | 3 | Ex 37, 130, 168, 263 | DMSO + D₂O: 7.88 (m, 1H), 7.79 (m, 1H), 7.74 (m, 1H), 7.35-7.50 (m, 4H), 7.12 (d, J = 8.8 Hz, 1H), 4.32 (t, J = 4.8 Hz, 2H), 3.42 (t, J = 4.8 Hz, 2H), 3.35 (m, 1H), 3.25 (m, 1H), 3.12 (m, 3H), 2.90 (m, 1H), 2.63 (m, 1H), 2.12 (m, 1H), 1.65 (m, 1H) | 469.1, 471.1 [M + H]⁺ |
| 211 | | 3 | Ex 37, 130, 168, 263 | DMSO + D₂O: 7.89 (d, J = 8.4 Hz, 1H), 7.77 (m, 1H), 7.50 (m, 2H), 7.32 (m, 1H), 7.22 (s, 1H), 7.04 (d, J = 8.8 Hz, 1H), 6.94 (d, J = 8.8 Hz, 1H), 5.98 (m, 1H), 5.39 (m, 1H), 5.26 (m, 1H), 4.56 (m, 2H), 4.25 (t, J = 5.2 Hz, 2H), 3.40 (m, 3H), 3.25 (m, 1H), 3.12 (m, 3H), 2.90 (m, 1H), 2.65 (m, 1H), 2.12 (m, 1H), 1.65 (m, 1H) | 491.3, 493.3 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 212 | | 3 | Ex 37, 130, 168, 263 | DMSO + D$_2$O: 7.88 (d, J = 8.8 Hz, 1H), 7.77 (d, J = 2.4 Hz, 1H), 7.50 (m, 2H), 7.33 (m, 1H), 7.22 (d, J = 2.8 Hz, 1H), 7.04 (m, 1H), 6.93 (m, 1H), 6.00 (m, 1H), 5.39 (m, 1H), 5.26 (m, 1H), 4.56 (m, 2H), 4.21 (t, J = 4.8 Hz, 2H), 4.00 (m, 2H), 3.82 (m, 2H), 3.39 (t, J = 4.8 Hz, 2H), 3.32 (m, 2H), 3.18 (m, 1H) | 477.0, 479.0 [M + H]$^+$ |
| 213 | | 3 | Ex 37, 130, 168 | DMSO + D$_2$O: 7.81 (d, J = 8.4 Hz, 1H), 7.77 (d, J = 2.4 Hz, 1H), 7.48 (m, 2H), 7.30 (d, J = 16.4 Hz, 1H), 7.16 (s, 1H), 7.00 (d, J = 8.8 Hz, 1H), 6.91 (d, J = 8.8 Hz, 1H), 6.00 (m, 1H), 5.38 (m, 1H), 5.25 (m, 1H), 4.55 (m, 2H), 4.08 (m, 2H), 3.35 (m, 1H), 3.25 (m, 1H), 3.00-3.15 (m, 5H), 2.90 (m, 1H), 2.55 (m, 1H), 2.15 (m, 3H), 1.65 (m, 1H) | 505.3, 507.3 [M + H]$^+$ |
| 214 | | 3 | Ex 37, 130, 168, 263 | DMSO + D$_2$O: 7.83 (d, J = 8.4 Hz, 1H), 7.78 (d, J = 2.4 Hz, 1H), 7.59 (s, 2H), 7.30 (d, J = 16.4 Hz, 1H), 7.17 (d, J = 2.8 Hz, 1H), 7.00 (m, 1H), 6.92 (m, 1H), 6.03 (m, 1H), 5.39 (m, 1H), 5.26 (m, 1H), 4.55 (m, 2H), 4.10 (m, 2H), 3.99 (m, 2H), 3.83 (m, 2H), 3.25 (m, 2H), 3.10 (m, 3H), 2.12 (m, 2H) | 491.0, 493.0 [M + H]$^+$ |
| 215 | | 1 | Ex 37 | DMSO + D$_2$O: 7.38 (m, 6H), 7.03 (m, 2H), 5.06 (s, 2H), 4.04 (s, 2H), 3.35 (m, 1H), 3.23 (m, 1H), 3.12 (m, 1H), 3.02 (m, 2H), 2.88 (m, 1H), 2.57 (m, 1H), 2.10 (m, 1H), 1.65 (m, 1H), 1.25 (s, 9H) | 353.2 [M + H]$^+$ |
| 216 | | 1 | Ex 37 | DMSO + D$_2$O: 7.33-7.40 (m, 5H), 7.18 (s, 1H), 7.05 (m, 2H), 5.05 (s, 2H), 4.10 (s, 2H), 3.38 (m, 1H), 3.25 (m, 1H), 3.15 (m, 1H), 3.05 (m, 2H), 2.88 (m, 1H), 2.59 (m, 1H), 2.15 (m, 1H), 1.65 (m, 1H), 1.25 (s, 9H) | 353.2 [M + H]$^+$ |
| 217 | | 1 | Ex 37 | DMSO: 9.60 (br, 4H), 7.85 (d, J = 2.1 Hz, 1H), 7.65 (d, J = 8.3 Hz, 1H), 7.55 (dd, J = 2.1 Hz, 8.3 Hz, 1H), 7.23 (s, 1H), 7.14 (s, 1H), 6.94 (s, 1H), 5.14 (s, 2H), 4.09 (m, 2H), 3.42 (m, 1H), 3.22 (m, 1H), 2.95-3.15 (m, 4H), 2.85 (m, 1H), 2.75 (m, 1H), 2.14 (m, 1H), 1.70 (m, 1H), 1.22 (d, J = 6.9 Hz, 6H) | 451.1, 453.1 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 218 | | | 1 | Ex 37 | DMSO: 9.48 (br, 2H), 9.36 (br, 2H), 7.83 (d, J = 2.1 Hz, 1H), 7.64 (d, J = 8.3 Hz, 1H), 7.53 (dd, J = 2.2 Hz, 8.3 Hz, 1H), 7.28 (s, 1H), 7.18 (s, 1H), 7.01 (s, 1H), 5.13 (s, 2H), 4.12 (m, 2H), 3.40 (m, 1H), 3.25 (m, 1H), 3.12 (m, 1H), 3.06 (m, 2H), 3.00 (m, 1H), 2.75 (m, 1H), 2.15 (m, 1H), 1.70 (m, 1H), 1.28 (s, 9H) | 465.0, 467.0 [M + H]+ |
| 219 | | | 1 | Ex 37 | DMSO: 9.15 (br, 4H), 7.84 (m, 1H), 7.72 (m, 1H), 7.49 (m, 1H), 7.34 (m, 2H), 7.23 (t, J = 7.8 Hz, 1H), 7.13 (m, 1H), 7.03 (dd, J = 2.5 Hz, 8.0 Hz, 1H), 5.12 (s, 2H), 4.03 (m, 2H), 3.98 (m, 2H), 3.84 (m, 2H), 3.20 (m, 1H), 3.13 (m, 2H) | 408.9 [M + H]+ |
| 220 | | | 1 | Ex 37 | DMSO: 9.10 (br, 2H), 8.95 (br, 2H), 7.71 (dd, J = 1.2 Hz, 8.0 Hz, 1H), 7.61 (dd, J = 1.8 Hz, 7.7 Hz, 1H), 7.30-7.50 (m, 3H), 7.23 (m, 1H), 7.12 (m, 2H), 5.15 (s, 2H), 4.18 (m, 2H), 3.40 (m, 1H), 3.27 (m, 1H), 3.15 (m, 1H), 3.08 (m, 2H), 2.93 (m, 1H), 2.63 (m, 1H), 2.15 (m, 1H), 1.67 (m, 1H) | 375.2, 377.2 [M + H]+ |
| 221 | | | 1 | Ex 37 | DMSO: 7.84 (m, 1H), 7.71 (m, 1H), 7.48 (m, 1H), 7.22 (m, 2H), 7.01 (m, 1H), 6.91 (m, 1H), 6.87 (m, 1H), 5.08 (s, 2H), 3.66 (s, 2H), 3.10 (m, 1H), 2.90-3.05 (m, 2H), 2.68 (m, 1H), 2.45 (m, 2H), 2.27 (m, 1H), 1.90 (m, 1H), 1.48 (m, 1H) | 423.1 [M + H]+ |
| 222 | | | 1 | Ex 37 | DMSO + D2O: 7.33-7.42 (m, 5H), 7.19 (s, 1H), 7.05 (m, 2H), 5.05 (s, 2H), 4.08 (s, 2H), 3.99 (m, 2H), 3.84 (m, 2H), 3.10-3.25 (m, 3H), 1.26 (s, 9H) | 339.2 [M + H]+ |
| 223 | | | 1 | Ex 37 | DMSO + D2O: 7.37 (m, 5H), 7.22 (s, 1H), 7.06 (m, 2H), 5.06 (s, 2H), 4.13 (s, 2H), 3.37 (m, 3H), 2.92 (m, 2H), 2.26 (m, 2H), 1.80 (m, 2H), 1.26 (s, 9H) | 353.2 [M + H]+ |
| 224 | | | 1 | Ex 37 | DMSO: 7.84 (d, J = 2.1 Hz, 1H), 7.62 (d, J = 8.3 Hz, 1H), 7.54 (dd, J = 2.1 Hz, 8.3 Hz, 1H), 6.82 (s, 2H), 6.75 (s, 1H), 5.09 (s, 2H), 3.60-3.80 (m, 4H), 3.45 (m, 2H), 2.70-2.85 (m, 2H), 2.65 (m, 2H), 1.19 (d, J = 6.9 Hz, 6H) | 437.1, 439.1 [M + H]+ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 225 | | 1 | Ex 37 | DMSO: 7.84 (d, J = 2.1 Hz, 1H), 7.62 (d, J = 8.3 Hz, 1H), 7.54 (dd, J = 2.1 Hz, 8.3 Hz, 1H), 6.97 (d, J = 1.5 Hz, 1H), 6.84 (m, 2H), 5.10 (s, 2H), 3.60-3.80 (m, 4H), 3.42 (m, 2H), 2.76 (m, 1H), 2.65 (m 2H), 1.26 (s, 9H) | 450.9, 452.9 [M + H]+ |
| 226 | | 1 | Ex 37 | DMSO + D2O: 7.34-7.42 (m, 4H), 7.17 (m, 3H), 5.07 (s, 2H), 4.13 (s, 2H), 3.35 (m, 3H), 2.93 (m, 2H), 2.25 (m, 2H), 1.72-1.85 (m, 2H), 1.25 (s, 9H) | 387.1 [M + H]+ |
| 227 | | 1 | Ex 37 | DMSO + D2O: 7.34-7.42 (m, 4H), 7.18 (m, 3H), 5.08 (s, 2H), 4.10 (s, 2H), 3.38 (m, 1H), 3.25 (m, 1H), 3.12 (m, 3H), 2.90 (m, 1H), 2.65 (m, 1H), 2.15 (m, 1H), 1.65 (m, 1H), 1.25 (s, 9H) | 387.2 [M + H]+ |
| 228 | | 1 | Ex 37 | DMSO + D2O: 7.33-7.42 (m, 4H), 7.15 (m, 3H), 5.07 (s, 2H), 4.08 (s, 2H), 4.00 (m, 2H), 3.83 (m, 2H), 3.22 (m, 2H), 3.15 (m, 1H), 1.25 (s, 9H) | 373.1 [M + H]+ |
| 229 | | 1 | Ex 37 | HPLC: 5.27 min | 442.9 [M + H]+ |
| 230 | | 1 | Ex 37 | DMSO + D2O: 8.00 (t, J = 1.2 Hz, 1H), 7.53 (d, J = 1.3 Hz, 2H), 7.25 (t, J = 7.8 Hz, 1H), 7.00 (s, 1H), 6.93 (d, J = 7.5 Hz, 1H), 6.87 (m, 1H), 5.02 (s, 2H), 3.66 (s, 2H), 3.15 (m, 1H), 2.95-3.10 (m, 2H), 2.71 (m, 1H), 2.45 (m, 2H), 2.30 (m, 1H), 1.92 (m, 1H), 1.49 (m, 1H) | 456.9 [M + H]+ |
| 231 | | 1 | Ex 37 | DMSO + D2O: 7.38 (m, 6H), 7.04 (m, 2H), 5.06 (s, 2H), 4.02 (s, 2H), 3.98 (m, 2H), 3.80 (m, 2H), 3.20 (m, 2H), 3.13 (m, 1H), 1.25 (s, 9H) | 339.2 [M + H]+ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 232 | [structure: 4-Cl-2-Br-benzyl ether linked to benzene with CH2-NH-CH2-azetidine and CH2-N+(Me)2-CH2-COOH substituents] | 1 | Ex 37, 51, 130, 387 | DMSO + D2O: 7.84 (s, 1H), 7.62 (d, J = 8.4 Hz, 1H), 7.53 (d, J = 8.4 Hz, 1H), 7.44 (s, 1H), 7.28 (s, 1H), 7.22 (s, 1H), 5.16 (s, 2H), 4.68 (s, 2H), 4.24 (s, 2H), 4.16 (s, 2H), 4.00 (m, 2H), 3.85 (m, 2H), 3.28 (m, 2H), 3.22 (m, 1H), 3.18 (s, 6H) | 510.0, 512.0 [M + H]+ |
| 233 | [structure: t-Bu-phenyl-CH=CH-phenyl-CH2-NH-CH2-pyrrolidine] | 3 | Ex 37 & 236 | DMSO + D2O: 7.73 (s, 1H), 7.63 (d, J = 7.6 Hz, 1H), 7.53 (d, J = 8.4 Hz, 2H), 7.44 (m, 1H), 7.40 (d, J = 8.4 Hz, 2H), 7.38 (m, 1H), 7.16-7.27 (AB-like, J = 16.4 Hz, 2H), 4.15 (s, 2H), 3.38 (m, 1H), 3.25 (m, 1H), 3.05-3.20 (m, 3H), 2.92 (m, 1H), 2.65 (m, 1H), 2.15 (m, 1H), 1.67 (m, 1H), 1.26 (s, 9H) | 349.3 [M + H]+ |
| 234 | [structure: t-Bu-phenyl-CH=CH-phenyl-CH2-NH-CH2-azetidine] | 3 | Ex 37 & 236 | DMSO + D2O: 7.62 (s, 1H), 7.60 (d, J = 7.6 Hz, 1H), 7.52 (d, J = 8.8 Hz, 2H), 7.43 (m, 1H), 7.40 (d, J = 8.8 Hz, 2H), 7.33 (d, J = 7.6 Hz, 1H), 7.20 (AB-like, J = 16.4 Hz, 2H), 4.10 (s, 2H), 4.00 (m, 2H), 3.80 (m, 2H), 3.23 (m, 2H), 3.14 (m, 1H), 1.26 (s, 9H) | 335.3 [M + H]+ |
| 235 | [structure: cis-t-Bu-phenyl-CH=CH-phenyl-CH2-NH-piperidine] | 3 | Ex 37 & 236 | DMSO + D2O: 7.39 (s, 1H), 7.34 (d, J = 7.6 Hz, 1H), 7.27 (m, 1H), 7.25 (m, 3H), 7.15 (d, J = 8.4 Hz, 2H), 6.62 (AB-like, J = 12.4 Hz, 2H), 4.11 (s, 2H), 3.37 (m, 3H), 2.92 (m, 2H), 2.24 (m, 2H), 1.80 (m, 2H), 1.22 (s, 9H) | 349.3 [M + H]+ |
| 236 | [structure: cis-t-Bu-phenyl-CH=CH-phenyl-CH2-NH-CH2-pyrrolidine] | 3 | Ex 37 & 236 | DMSO + D2O: 7.10-7.40 (m, 8H), 6.60 (AB-like, J = 12.4 Hz, 2H), 4.05 (s, 2H), 3.35 (m, 1H), 3.25 (m, 1H), 3.12 (m, 1H), 3.00 (m, 2H), 2.88 (m, 1H), 2.55 (m, 1H), 2.12 (m, 1H), 1.65 (m, 1H), 1.22 (s, 9H) | 349.3 [M + H]+ |
| 237 | [structure: cis-t-Bu-phenyl-CH=CH-phenyl-CH2-NH-CH2-azetidine] | 3 | Ex 37 & 236 | DMSO + D2O: 7.32 (s, 1H), 7.31 (m, 2H), 7.27 (m, 1H), 7.25 (d, J = 8.4 Hz, 2H), 7.14 (d, J = 8.4 Hz, 2H), 6.60 (AB-like, J = 12.4 Hz, 2H), 4.06 (s, 2H), 3.97 (m, 2H), 3.80 (m, 2H), 3.23 (m, 2H), 3.12 (m, 1H), 1.22 (s, 9H) | 335.3 [M + H]+ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 238 | | 1 | Ex 37 | DMSO + D₂O: 7.84 (d, J = 2.0 Hz,1H), 6.60 (d, J = 8.4 Hz, 1H, 7.53 (dd, J = 2.0 Hz, 1H), 6.88 (s, 1H), 6.85 (s, 1H), 6.73 (s, 1H), 5.10 (s, 2H), 4.38 (t, J = 4.8 Hz, 2H), 4.09 (s, 2H), 3.95 (m, 2H), 3.75 (m, 2H), 3.56 (t, J = 4.8 Hz, 2H), 3.45 (m, 1H), 3.25 (m, 4H), 3.15 (m, 2H), 3.05 (m, 2H), 2.92 (m, 1H), 2.65 (m, 1H), 2.15 (m, 2H) 1.68 (m, 1H), 0.96 (m, 2H), 0.70 (m, 2H) | 538.1, 540.1 [M + H]⁺ |
| 239 | | 1 | Ex 37 | DMSO + D₂O: 7.82 (d, J = 2.0 Hz, 1H), 7.59 (d, J = 8.0 Hz, 1H), 7.52 (dd, J = 2.0 Hz, 8.0 Hz, 1H), 6.82 (s, 1H), 6.78 (s, 1H), 6.71 (s, 1H), 5.09 (s, 2H), 4.30 (m, 2H), 4.02 (m, 4H), 3.83 (m, 4H), 3.13-3.41 (m, 11H) | 523.3, 526.3 [M + H]⁺ |
| 240 | | 3 | Ex 37 & 236 | DMSO + D₂O: 7.56 (s, 1H), 7.51 (d, J = 8.4 Hz, 2H), 7.47 (d, J = 7.6 Hz, 1H), 7.39 (d, J = 8.4 Hz, 2H), 7.32 (m, 1H), 7.24 (m, 1H), 7.12-7.22 (AB-like, J = 16.4 Hz, 2H), 3.77 (s, 2H), 3.24 (m, 2H), 2.78-2.87 (m, 3H), 2.00 (m, 2H), 1.53 (m, 2H), 1.26 (s, 9H) | 349.3 [M + H]⁺ |
| 241 | | 3 | Ex 37 & 236 | DMSO + D₂O: 7.83 (d, J = 2.0 Hz, 1H), 7.31 (dd, J = 2.0 Hz, 8.4 Hz, 1H), 7.13 (d, J = 8.4 Hz, 1H), 7.12 (s, 1H), 6.92 (s, 1H), 6.78 (d, J = 12.0 Hz, 1H), 6.71 (s, 1H), 6.63 (d, J = 12.0 Hz, 1H), 4.23 (t, J = 4.8 Hz, 2H), 4.01 (s, 2H), 3.65-4.05 (m, 4H), 3.50 (t, J = 4.8 Hz, 2H), 2.85-3.45 (m, 10H), 2.60 (m, 1H), 2.10 (m, 1H), 1.65 (m, 1H) | 534.4, 536.4 [M + H]⁺ |
| 242 | | 3 | Ex 37 & 236 | DMSO + D₂O: 7.83 (d, J = 1.6 Hz, 1H), 7.30 (d, J = 8.4 Hz, 1H), 7.10 (m, 2H), 6.91 (s, 1H), 6.76 (d, J = 12.0 Hz, 1H), 6.68 (s, 1H), 6.62 (d, J = 12.0 Hz, 1H), 4.20 (m, 2H), 3.75-4.00 (m, 10H), 3.46 (m, 2H), 3.10-3.40 (m, 7H) | 520.3, 522.3 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 243 | | 3 | Ex 37 & 236 | DMSO + D₂O: 7.82 (m, 2H), 7.51 (dd, J = 2.0 Hz, 8.4 Hz, 1H), 7.39 (m, 2H), 7.25 (m, 2H), 7.05 (s, 1H), 4.37 (t, J = 4.6 Hz, 2H), 4.14 (s, 2H), 3.75-4.00 (m, 8H), 3.55 (m, 2H), 3.10-3.40 (m, 7H) | 520.3, 522.2 [M + H]⁺ |
| 244 | | 1 | Ex 37, 51, 119, 130, 232 | DMSO + D₂O: 7.84 (s, 1H), 7.60 (d, J = 8.0 Hz, 1H), 7.53 (d, J = 8.0 Hz, 1H), 7.27 (s, 1H), 7.25 (s, 1H), 7.14 (s, 1H), 5.12 (s, 2H), 4.25 (s, 2H), 4.13 (s, 2H), 4.00 (m, 2H), 3.87 (m, 2H), 3.75 (m, 2H), 3.24 (m, 2H), 3.12 (m, 1H), 2.73 (s, 3H) | 496.2, 498.2 [M + H]⁺ |
| 245 | | 1 | Ex 37, 119, 130, 263, 387 | DMSO + D₂O: 7.82 (d, J = 2.0 Hz, 1H), 7.58 (d, J = 8.4 Hz, 1H), 7.52 (dd, J = 2.0 Hz, 8.4 Hz, 1H), 6.72 (m, 3H), 5.09 (s, 2H), 4.05-4.25 (m, 5H), 3.70-3.80 (m, 4H), 3.35 (m, 1H), 3.25 (m, 1H), 3.00-3.20 (m, 4H), 2.90 (m, 1H), 2.80 (s, 3H), 2.60 (m, 1H), 2.40 (m, 1H), 2.15 (m, 1H), 2.05 (m, 1H), 1.65 (m, 1H) | 596.2, 598.2 [M + H]⁺ |
| 246 | | 3 | Ex 37 & 236 | DMSO + D₂O: 7.81 (m, 2H), 7.51 (dd, J = 2.0 Hz, 8.4 Hz, 1H), 7.39 (m, 2H), 7.24 (m, 2H), 7.07 (s, 1H), 4.38 (t, J = 4.8 Hz, 2H), 4.16 (s, 2H), 3.70-4.00 (m, 4H), 3.58 (t, J = 4.8 Hz, 2H), 3.20-3.50 (m, 6H), 3.15 (m, 1H), 3.09 (m, 2H), 2.87 (m, 1H), 2.60 (m, 1H), 2.15 (m, 1H), 1.65 (m, 1H) | 534.2, 536.2 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 247 | | 1 | Ex 37, 119, 130, 263, 387 | DMSO + D₂O: 7.82 (d, J = 2.4 Hz, 1H), 7.58 (d, J = 8.4 Hz, 1H), 7.52 (dd, J = 2.0 Hz, 8.4 Hz, 1H), 6.70 (m, 3H), 5.08 (s, 2H), 4.33 (m, 2H), 4.10 (m, 4H), 3.75 (m, 4H), 3.05-3.35 (m, 12H), 2.88 (m, 2H), 2.55 (m, 1H), 2.13 (m, 1H), 1.65 (m, 1H) | 610.4, 612.3 [M + H]⁺ |
| 248 | | 1 | Ex 37, 119, 130, 263, 387 | DMSO + D₂O: 7.82 (d, J = 2.0 Hz, 1H), 7.57 (d, J = 8.4 Hz, 1H), 7.52 (dd, J = 2.0 Hz, 8.0 Hz, 1H), 6.70 (m, 3H), 5.07 (s, 2H), 4.25-4.45 (m, 2H), 4.10 (m, 2H), 4.04 (s, 2H), 3.60-4.00 (m, 8H), 3.05-3.30 (m, 9H), 2.80 (m, 1H), 2.25 (m, 1H) | 596.3, 598.3 [M + H]⁺ |
| 249 | | 1 | Ex 37, 119, 130, 263, 387 | DMSO + D₂O: 7.82 (d, J = 2.0 Hz, 1H), 7.57 (d, J = 8.4 Hz, 1H), 7.51 (dd, J = 2.0 Hz, 8.4 Hz, 1H), 6.75 (m, 3H), 5.08 (s, 2H), 3.90-4.30 (m, 8H), 3.70-3.90 (m, 5H), 3.10-3.25 (m, 4H), 2.88 (s, 3H), 2.45 (m, 1H), 2.10 (m, 1H) | 582.3, 584.2 [M + H]⁺ |

TABLE 1-continued

Exemplified compounds

The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 250 | | 1 | Ex 37, 119, 130, 263, 387 | DMSO + D$_2$O: 7.82 (d, J = 2.0 Hz, 1H), 7.57 (d, J = 8.0 Hz, 1H), 7.51 (dd, J = 2.0, 8.0 Hz, 1H), 6.60-6.73 (m, 3H), 5.08 (s, 2H), 3.90-4.20 (m, 8H), 3.50-3.90 (m, 5H), 3.10-3.30 (m, 4H), 2.84 (s, 3H), 2.48 (m, 1H), 2.15 (m, 1H) | 582.3, 584.2 [M + H]$^+$ |
| 251 | | 1 | Ex 37, 130, 354 | DMSO + D$_2$O: 8.96 (d, J = 1.6 Hz, 1H), 7.83 (d, J = 2.0 Hz, 1H), 7.59 (d, J = 8.0 Hz, 1H), 7.52 (dd, J = 2.0 Hz, 8.0 Hz, 1H), 7.49 (d, J = 1.2 Hz, 1H), 6.82 (s, 1H), 6.78 (s, 1H), 6.69 (s, 1H), 5.09 (s, 2H), 4.24 (t, J = 6.4 Hz, 2H), 4.07 (s, 2H), 3.36 (m, 1H), 3.25 (m, 1H), 3.13 (m, 3H), 3.04 (t, J = 6.4 Hz, 2H), 2.91 (m, 1H), 2.63 (m, 1H), 2.13 (m, 1H), 1.66 (m, 1H) | 519.4, 521.3 [M + H]$^+$ |
| 252 | | 1 | Ex 37, 130, 354 | DMSO + D$_2$O: 8.94 (s, 1H), 7.82 (d, J = 2.0 Hz, 1H), 7.58 (d J = 8.4 Hz, 1H), 7.52 (dd, J = 2.0 Hz, 8.4 Hz, 1H), 7.47 (s, 1H), 6.80 (s, 1H), 6.76 (s, 1H), 6.67 (s, 1H), 5.08 (s, 2H), 4.23 (t, J = 6.2 Hz, 2H), 4.04 (s, 2H), 3.99 (m, 2H), 3.84 (m, 2H), 3.11-3.24 (m, 5H) | 505.3, 507.2 [M + H]$^+$ |
| 253 | | 3 | Ex 37, 158, 236, 354 | DMSO + D$_2$O: 8.77 (d, J = 6.4 Hz, 2H), 7.90 (d, J = 6.4 Hz, 2H), 7.80 (d, J = 2.0 Hz, 1H), 7.28 (dd, J = 2.0 Hz, 8.4 Hz, 1H), 7.11 (d, J = 8.4 Hz, 1H), 7.03 (s, 1H), 6.89 (s, 1H), 6.75 (d, J = 12.4 Hz, 1H), 6.61 (d, J = 12.4 Hz, 1H), 6.56 (s, 1H), 4.15 (t, J = 6.0 Hz, 2H), 3.99 (s, 2H), 3.35 (m, 2H), 3.25 (m, 2H), 3.13 (m, 1H), 2.90 (m, 1H), 2.98 (m, 2H), 2.59 (m, 1H), 2.10 (m, 1H), 1.63 (m, 1H) | 526.2, 528.2 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 254 | | 3 | Ex 37, 158, 236, 354 | DMSO + D$_2$O: 8.76 (d, J = 6.4 Hz, 2H), 7.95 (d, J = 6.4 Hz, 2H), 7.82 (m, 2H), 7.50 (dd, J = 2.0 Hz, 8.4 Hz, 1H), 7.37 (m, 2H), 7.23 (d, J = 16.4 Hz, 1H), 7.18 (s, 1H), 7.12 (s, 1H), 4.42 (t, J = 6.0 Hz, 2H), 4.14 (s, 2H), 3.36 (m, 3H), 3.25 (m, 1H), 3.15 (m, 1H), 3.12 (m, 2H), 2.92 (m, 1H), 2.55 (m, 1H), 2.15 (m, 1H), 1.67 (m, 1H) | 526.4, 528.4 [M + H]$^+$ |
| 255 | | 3 | Ex 37, 158, 236, 354 | DMSO + D$_2$O: 8.95 (d, J = 1.2 Hz, 1H), 7.81 (d, J = 2.0 Hz, 1H), 7.40 (d, J = 1.2 Hz, 1H), 7.30 (dd, J = 2.0 Hz, 8.4 Hz, 1H), 7.12 (d, J = 8.4 Hz, 1H), 7.02 (s, 1H), 6.88 (s, 1H), 6.75 (d, J = 12.4 Hz, 1H), 6.61 (m, 2H), 4.00 (m, 6H), 3.82 (m, 2H), 3.15 (m, 3H), 3.04 (t, J = 6.4 Hz, 2H) | 501.3, 503.3 [M + H]$^+$ |
| 256 | | 1 | Ex 37 & 354 | DMSO + D$_2$O: 8.79 (d, J = 6.4 Hz, 2H), 8.01 (d, J = 6.4 Hz, 2H), 7.82 (d, J = 2.0 Hz, 1H), 7.47 (d, J = 8.4 Hz, 1H), 7.50-7.59 (dd, J = 2.0 Hz, 8.4 Hz, 1H), 6.79 (s, 1H), 6.74 (s, 1H), 6.65 (s, 1H), 5.07 (s, 2H), 4.36 (t, J = 6.0 Hz, 2H), 4.03 (s, 2H), 3.99 (m, 2H), 3.83 (m, 2H), 3.35 (t, J = 6.0 Hz, 2H), 3.20 (m, 3H) | 516.3, 518.3 [M + H]$^+$ |
| 257 | | 3 | Ex 37, 158, 236, 354 | DMSO + D$_2$O: 8.80 (d, J = 6.4 Hz, 2H), 7.95 (d, J = 6.4 Hz, 2H), 7.80 (d, J = 2.0 Hz, 1H), 7.29 (dd, J = 2.0 Hz, 8.4 Hz, 1H), 7.11 (d, J = 8.4 Hz, 1H), 7.02 (s, 1H), 6.89 (s, 1H), 6.74 (d, J = 12.0 Hz, 1H), 6.61 (d, J = 12.0 Hz, 1H), 6.54 (s, 1H), 3.16 (t, J = 6.2 Hz, 2H), 3.99 (m, 4H), 3.83 (m, 2H), 3.27 (t, J = 6.2 Hz, 2H), 3.16 (m, 3H) | 512.3, 514.2 [M + H]$^+$ |
| 258 | | 1 | Ex 37 & 354 | DMSO + D$_2$O: 8.80 (d, J = 6.8 Hz, 2H), 8.05 (d, J = 6.8 Hz, 2H), 7.81 (d, J = 2.0 Hz, 1H), 7.58 (d, J = 8.0 Hz, 1H), 7.52 (dd, J = 2.0 Hz, 8.0 Hz, 1H), 6.82 (s, 1H), 6.78 (s, 1H), 6.64 (s, 1H), 5.07 (s, 2H), 4.37 (t, J = 6.0 Hz, 2H), 4.06 (s, 2H), 3.37 (m, 2H), 3.25 (m, 2H), 3.14 (m, 1H), 3.05 (m, 2H), 2.93 (m, 1H), 2.64 (m, 1H), 2.13 (m, 1H), 1.66 (m, 1H) | 530.3, 532.3 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 259 | 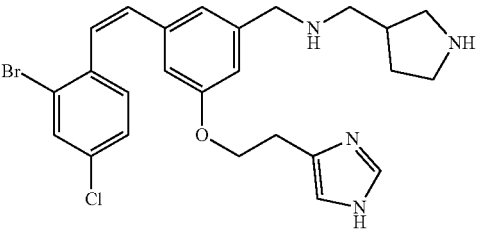 [SMILES: Clc1ccc(/C=C\c2cc(CNCC3CCNC3)cc(OCCc3c[nH]cn3)c2)c(Br)c1] | 3 | Ex 37, 158, 236, 354 | DMSO + D$_2$O: 8.93 (d, J = 1.6 Hz, 1H), 7.80 (d, J = 2.0 Hz, 1H), 7.40 (d, J = 1.6 Hz, 1H), 7.29 (dd, J = 2.0 Hz, 8.4 Hz, 1H), 7.13 (d, J = 8.4 Hz, 1H), 7.05 (s, 1H), 6.87 (s, 1H), 6.75 (d, J = 12.4 Hz, 1H), 6.61 (m, 2H), 4.03 (m, 4H), 3.35 (m, 1H), 3.25 (m, 1H), 3.14 (m, 1H), 3.05 (t, J = 6.4 Hz, 2H), 2.97 (m, 2H), 2.90 (m 1H), 2.59 (m, 1H), 2.12 (m, 1H), 1.64 (m, 1H) | 515.3, 517.3 [M + H]$^+$ |
| 260 | 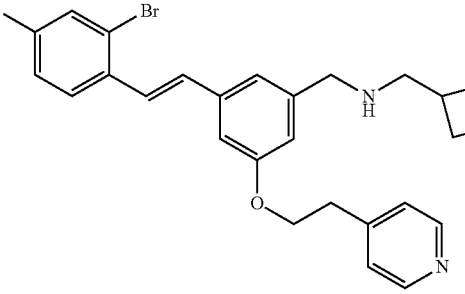 | 3 | Ex 37, 158, 236, 354 | DMSO + D$_2$O: 8.82 (d, J = 6.8 Hz, 2H), 8.07 (d, J = 6.8 Hz, 2H), 7.81 (m, 2H), 7.50 (dd, J = 2.2 Hz, 8.6 Hz, 1H), 7.39 (s, 1H), 7.35 (s, 1H), 7.13-7.25 (m, 3H), 4.44 (t, J = 6.0 Hz, 2H), 4.11 (s, 2H), 3.99 (m, 2H), 3.87 (m, 2H), 3.40 (t, J = 6.0 Hz, 2H), 3.26 (m, 3H) | 512.3, 514.3 [M + H]$^+$ |
| 261 | 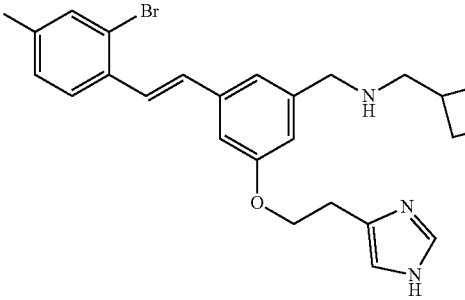 | 3 | Ex 37, 158, 236, 354 | DMSO + D$_2$O: 8.95 (d, J = 1.2 Hz, 1H), 7.81 (m, 2H), 7.50 (m, 2H), 7.37 (m, 2H), 7.22 (m, 2H), 7.10 (s, 1H), 4.29 (t, J = 6.2 Hz, 2H), 4.12 (s, 2H), 4.00 (m, 2H), 3.85 (m, 2H), 3.25 (m, 2H), 3.13-3.22 (m, 3H) | 501.3, 503.3 [M + H]$^+$ |
| 262 | 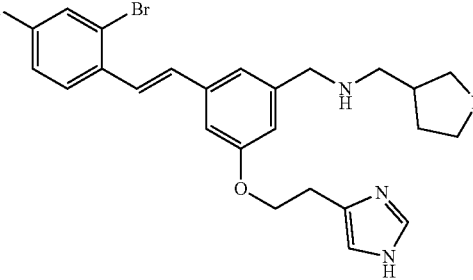 | 3 | Ex 37, 158, 236, 354 | DMSO + D$_2$O: 8.95 (d, J = 1.2 Hz, 1H), 7.84 (d, J = 8.4 Hz, 1H), 7.79 (d, J = 2.4 Hz, 1H), 7.50 (m, 2H), 7.41 (s, 1H), 7.38 (d, J = 16.4 Hz, 1H), 7.26 (s, 1H), 7.20 (m, 2H), 4.31 (t, J = 6.2 Hz, 2H), 4.15 (s, 2H), 3.38 (m, 1H), 3.25 (m, 1H), 3.17 (t, J = 6.2 Hz, 2H), 3.10 (m, 2H), 2.95 (m, 2H), 2.67 (m, 1H), 2.15 (m, 1H), 1.69 (m, 1H) | 515.3, 517.3 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 263 | | 1 | Ex 136, 158, 387 | DMSO + D₂O: 7.83 (d, J = 2.0 Hz, 1H), 7.59 (d, J = 8.4 Hz, 1H), 7.52 (dd, J = 2.0 Hz, 8.0 Hz, 1H), 7.19 (s, 1H), 7.12 (s, 1H), 7.06 (s, 1H), 5.12 (s, 2H), 4.40-4.60 (m, 3H), 4.12 (s, 2H), 4.00 (m, 1H), 3.72 (m, 1H), 3.00-3.40 (m, 13H), 2.90 (m, 2H), 2.65 (m, 1H), 2.15 (m, 1H), 1.68 (m, 1H) | 580.1, 582.0 [M + H]⁺ |
| 264 | | 1 | Ex 37 & 130 | DMSO + D₂O: 7.76 (d, J = 8.0 Hz, 2H), 7.66 (d, J = 8.0 Hz, 2H), 6.80, (s, 1H), 6.74 (s, 1H), 6.63 (s, 1H), 5.21 (s, 2H), 4.06 (s, 2H), 3.73 (m, 2H), 3.35 (m, 1H), 3.25 (m, 1H), 3.10 (m, 1H), 3.05 (m, 2H), 2.95 (m, 1H), 2.70 (m, 1H), 2.13 (m, 1H), 2.00 (m, 1H), 1.65 (m, 1H), 0.95 (d, J = 6.8 Hz, 6H) | 437.1 [M + H]⁺ |
| 265 | | 1 | Ex 37 & 130 | DMSO + D₂O: 8.13 (m, 2H), 8.01 (m, 1H), 6.77 (m, 2H), 6.64 (s, 1H), 5.31 (s, 2H), 4.07 (s, 2H), 3.74 (m, 2H), 3.37 (m, 1H), 3.25 (m, 1H), 3.12 (m, 1H), 3.04 (m, 2H), 2.90 (m, 1H), 2.60 (m, 1H), 2.15 (m, 1H), 1.97 (m, 1H), 165 (m, 1H), 0.95 (d, J = 6.8 Hz, 6H) | 505.5 [M + H]⁺ |
| 266 | | 1 | Ex 37 & 130 | DMSO + D₂O: 7.43-7.57 (m, 3H), 6.73 (s, 1H), 6.69 (s, 1H), 6.60 (s, 1H), 5.10 (s, 2H), 4.04 (s, 2H), 3.86 (s, 3H), 3.72 (m, 2H), 3.35 (m, 1H), 3.25 (m, 1H), 3.12 (m, 1H), 3.02 (m, 2H), 2.85 (m, 1H), 2.58 (m, 1H), 2.13 (m, 1H), 1.95 (m, 1H), 1.65 (m, 1H), 0.95 (d, J = 6.8 Hz, 6H) | 424.3 [M + H]⁺ |
| 267 | | 1 | Ex 37 & 130 | DMSO + D₂O: 8.60 (d, J = 2.4 Hz, 1H), 7.96 (dd, J = 2.4 Hz, 8.4 Hz, 1H), 7.56 (d, J = 8.4 Hz, 1H), 6.62-6.72 (m, 3H), 5.16 (s, 2H), 4.05 (s, 2H), 3.72 (m, 2H), 3.35 (m, 1H), 3.25 (m, 1H), 3.10 (m, 1H), 3.02 (m, 2H), 2.90 (m, 1H), 2.60 (m, 1H), 2.13 (m, 1H), 1.95 (m, 1H), 1.65 (m, 1H), 0.94 (d, J = 6.8 Hz, 6H) | 404.1 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 268 | | 1 | Ex 37 & 130 | DMSO + D$_2$O: 7.63 (m, 2H), 7.31 (m, 1H), 6.75 (m, 2H), 6.63 (m, 1H), 5.08 (s, 2H), 4.07 (s, 2H), 3.74 (m, 2H), 3.35 (m, 1H), 3.25 (m, 1H), 3.10 (m, 1H), 3.03 (m, 2H), 2.90 (m, 1H), 2.63 (m, 1H), 2.13 (m, 1H), 1.97 (m, 1H), 1.65 (m, 1H), 0.96 (d, J = 6.8 Hz, 6H) | 465.0, 466.9 [M + H]$^+$ |
| 269 | | 1 | Ex 37 & 130 | DMSO + D$_2$O: 8.48 (d, J = 2.0 Hz, 1H), 7.92 (dd, J = 2.0 Hz, 8.0 Hz, 1H), 7.55 (d, J = 8.0 Hz, 1H), 6.62-6.80 (m, 3H), 5.15 (s, 2H), 4.05 (s, 2H), 3.74 (m, 2H), 3.35 (m, 1H), 3.25 (m, 1H), 3.10 (m, 1H), 3.02 (m, 2H), 2.90 (m, 1H), 2.65 (m, 1H), 2.15 (m, 1H), 1.97 (m, 1H), 1.66 (m, 1H), 0.95 (d, J = 6.8 Hz, 6H) | 404.1 [M + H]$^+$ |
| 270 | | 1 | Ex 37 & 130 | DMSO + D$_2$O: 8.05-8.32 (m, 2H), 7.22 (dd, J = 2.4, 8.4 Hz, 1H), 6.64-6.72 (m, 3H), 5.14 (s, 2H), 4.06 (s, 2H), 3.74 (m, 2H), 3.36 (m, 1H), 3.25 (m, 1H), 3.14 (m, 1H), 3.02 (m, 2H), 2.90 (m, 1H), 2.60 (m, 1H), 2.14 (m, 1H), 1.97 (m, 1H), 1.65 (m, 1H), 0.95 (d, J = 6.8 Hz, 6H) | 388.1 [M + H]$^+$ |
| 271 | | 1 | Ex 37 & 130 | DMSO + D$_2$O; 7.63-7.78 (m, 3H), 6.76 (s, 1H), 6.72 (s, 1H), 6.66 (s, 1H), 5.20 (s, 2H), 4.06 (s, 2H), 3.74 (m, 2H), 3.35 (m, 1H), 3.25 (m, 1H), 3.13 (m, 1H), 3.03 (m, 2H), 2.87 (m, 1H), 2.58 (m, 1H), 2.13 (m, 1H), 1.98 (m, 1H), 1.65 (m, 1H), 0.95 (d, J = 6.8 Hz, 6H) | 455.1 [M + H]$^+$ |
| 272 | | 3 | Ex 37, 130, 158, 168, 183, 263 | DMSO + D$_2$O: 7.62 (m, 2H), 7.18-7.29 (m, 5H), 7.15 (d, J = 16.4 Hz, 1H), 7.01 (s, 1H), 6.05 (m, 1H), 5.41 (m, 1H), 5.28 (m, 1H), 4.61 (m, 2H), 4.09 (s, 2H), 4.00 (m, 2H), 3.86 (m, 2H), 3.25 (m, 2H), 3.18 (m, 1H) | 353.1 [M + H]$^+$ |
| 273 | | 1 | Ex 37, 130, 158 | DMSO + D$_2$O: 7.35-7.45 (m, 7H), 5.12 (s, 2H), 4.16 (s, 2H), 3.98 (m, 2H), 3.80 (m, 2H), 3.25 (m, 2H), 3.15 (m, 1H), 1.25 (s, 9H) | 407.1 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 274 | | 1 | Ex 37 | DMSO + D$_2$O: 7.40 (d, J = 8.0 Hz, 2H), 7.34 (d, J = 8.0 Hz, 2H), 6.69 (s, 1H), 6.64 (s, 1H), 6.60 (s, 1H), 5.03 (s, 2H), 4.03 (s, 2H), 3.98 (m, 2H), 3.80 (m, 2H), 3.70 (m, 2H), 3.22 (m, 2H), 3.15 (m, 1H), 1.95 (m, 1H), 1.26 (s, 9H), 0.94 (d, J = 6.4 Hz, 6H) | 411.2 [M + H]$^+$ |
| 275 | | 3 | Ex 37, 158, 168, 183, 263 | DMSO + D$_2$O: 7.80 (d, J = 8.0 Hz, 2H), 7.73 (d, J = 8.4 Hz, 2H), 7.36 (s, 2H), 7.29 (m, 2H), 7.02 (s, 1H), 6.05 (m, 1H), 5.41 (m, 1H), 5.29 (m, 1H), 4.62 (m, 2H), 4.10 (s, 2H), 4.00 (m, 2H), 3.82 (m, 2H), 3.24 (m, 2H), 3.15 (m, 1H) | 403.1 [M + H]$^+$ |
| 276 | | 3 | Ex 37, 158, 168, 183, 263 | DMSO + D$_2$O: 7.31 (m, 2H), 7.24 (m, 3H), 7.16 (m, 2H), 7.02 (s, 1H), 6.87 (dd, J = 2.4 Hz, 8.4 Hz, 1H), 6.05 (m, 1H), 5.41 (m, 1H), 5.29 (m, 1H), 4.61 (m, 2H), 4.10 (s, 2H), 4.00 (m, 2H), 3.84 (m, 2H), 3.74 (s, 3H), 3.26 (m, 2H), 3.18 (m, 1H) | 365.1 [M + H]$^+$ |
| 277 | | 1 | Ex 37 | DMSO + D$_2$O: 7.41 (d, J = 8.4 Hz, 2H), 7.34 (d, J = 8.4 Hz, 2H), 6.78 (s, 1H), 6.70 (s, 1H), 6.66 (s, 1H), 5.02 (s, 2H), 4.29 (t, J = 4.8 Hz, 2H), 4.04 (s, 2H), 3.98 (m, 2H), 3.70-3.95 (m, 6H), 3.51 (t, J = 4.8 Hz, 2H), 3.15-3.45 (m, 6H), 3.12 (m, 1H), 1.25 (s, 9H) | 468.3 [M + H]$^+$ |
| 278 | | 1 | Ex 37 & 130 | DMSO + D$_2$O: 8.37 (dd, J = 1.6 Hz, 4.8 Hz, 1H), 7.97 (dd, J = 1.6 Hz, 7.6 Hz, 1H), 7.51 (dd, J = 4.8 Hz, 7.6 Hz, 1H), 6.79 (s, 1H), 6.76 (s, 1H), 6.65 (s, 1H), 5.10 (s, 2H), 4.07 (s, 2H), 3.70 (m, 2H), 3.36 (m, 1H), 3.25 (m, 1H), 3.13 (m, 1H), 3.04 (m, 2H), 2.90 (m, 1H), 2.62 (m, 1H), 2.14 (m, 1H), 2.00 (m, 1H), 1.65 (m, 1H), 0.96 (d, J = 6.8 Hz, 6H) | 448.1, 450.1 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 279 | | 3 | Ex 37, 158, 168, 183, 263 | DMSO + D₂O: 7.30 (s, 1H), 7.20 (m, 3H), 7.02 (s, 1H), 6.89 (s, 2H), 6.06 (m, 1H), 5.41 (m, 1H), 5.29 (m, 1H), 4.62 (m, 2H), 4.10 (s, 2H), 4.00 (m, 2H), 3.84 (m, 8H), 3.66 (s, 3H), 3.26 (m, 2H), 3.20 (m, 1H) | 425.1 [M + H]⁺ |
| 280 | | 1 | Ex 37 & 130 | DMSO + D₂O: 7.60-7.80 (m, 3H), 6.75 (s, 2H), 6.61 (s, 1H), 5.16 (s, 2H), 4.06 (d, J = 6.4 Hz, 2H), 3.73 (m, 2H), 3.37 (m, 1H), 3.25 (m, 1H), 3.12 (m, 1H), 3.04 (m, 2H), 2.90 (m, 1H), 2.65 (m, 1H), 2.15 (m, 1H), 1.97 (m, 1H), 1.66 (m, 1H), 0.95 (d, J = 6.4 Hz, 6H) | 455.1 [M + H]⁺ |
| 281 | | 1 | Ex 37 & 130 | DMSO + D₂O: 7.75-7.87 (m, 3H), 6.76 (s, 2H), 6.60 (s, 1H), 5.18 (s, 2H), 4.06 (s, 2H), 3.73 (m, 2H), 3.37 (m, 1H), 3.25 (m, 1H), 3.13 (m, 1H), 3.04 (m, 2H), 2.90 (m, 1H), 2.63 (m, 1H), 2.15 (m, 1H), 1.95 (m, 1H), 1.65 (m, 1H), 0.94 (d, J = 6.8 Hz, 6H) | 471.1 [M + H]⁺ |
| 282 | | 1 | Ex 37 & 130 | DMSO + D₂O: 8.05 (s, 1H), 7.79 (m, 2H), 6.76 (s, 1H), 6.73 (s, 1H), 6.64 (s, 1H), 5.18 (s, 2H), 4.05 (s, 2H), 3.74 (m, 2H), 3.36 (m, 1H), 3.24 (m, 1H), 3.10 (m, 1H), 3.03 (m, 2H), 2.88 (m, 1H), 2.60 (m, 1H), 2.13 (m, 1H), 2.00 (m, 1H), 1.65 (m, 1H), 0.95 (d, J = 6.8 Hz, 6H) | 515.4, 517.3 [M + H]⁺ |
| 283 | | 1 | Ex 37 & 130 | DMSO + D₂O: 8.28 (m, 1H), 7.21 (dd, J = 2.4, 8.4 Hz, 1H), 6.65-6.75 (m, 3H), 5.23 (s, 2H), 4.06 (s, 2H), 3.74 (m, 2H), 3.35 (m, 1H), 3.25 (m, 1H), 3.10 (m, 1H), 3.02 (m, 2H), 2.90 (m, 1H), 2.63 (m, 1H), 2.14 (m, 1H), 2.00 (m, 1H), 1.65 (m, 1H), 0.96 (d, J = 6.8 Hz, 6H) | 406.4 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 284 | 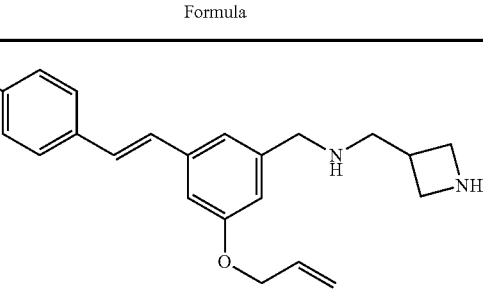 | 3 | Ex 37, 158, 168, 183, 263 | DMSO + D$_2$O: 7.79 (m, 4H), 7.32-7.43 (m, 3H), 7.27 (s, 1H), 7.06 (s, 1H), 6.05 (m, 1H), 5.41 (m, 1H), 5.29 (m, 1H), 4.62 (m, 2H), 4.11 (s, 2H), 4.02 (m, 2H), 3.85 (m, 2H), 3.26 (m, 2H), 3.19 (m, 1H) | 360.3 [M + H]$^+$ |
| 285 | 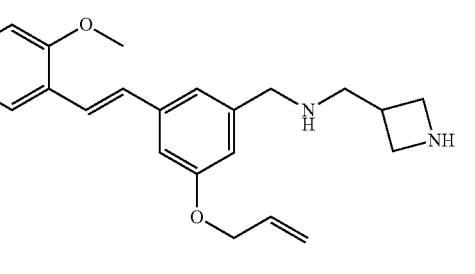 | 3 | Ex 37, 158, 168, 183, 263 | DMSO + D$_2$O: 7.62 (dd, J = 1.6 Hz, 1H), 7.45 (d, J = 16.8 Hz, 1H), 7.30 (m, 2H), 7.18 (d, J = 16.8 Hz, 1H), 7.14 (s, 1H), 7.04 (m, 1H), 6.97 (m, 2H), 6.05 (m, 1H), 5.41 (m, 1H), 5.28 (m, 1H), 4.61 (m, 2H), 4.10 (s, 2H), 4.01 (m, 2H), 3.76-3.86 (m, 5H), 3.26 (m, 2H), 3.17 (m, 1H) | 365.4 [M + H]$^+$ |
| 286 | 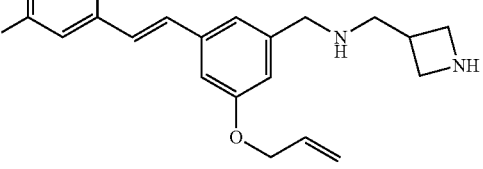 | 3 | Ex 37, 158, 168, 183, 263 | DMSO + D$_2$O: 7.28 (s, 1H), 7.21 (m, 3H), 7.08 (m, 2H), 6.99 (s, 1H), 6.96 (d, J = 8.4 Hz, 1H), 6.05 (m, 1H), 5.41 (m, 1H), 5.28 (m, 1H), 4.62 (m, 2H), 4.09 (s, 2H), 4.01 (m, 2H), 3.85 (m, 2H), 3.75 (s, 3H), 3.73 (s, 3H), 3.26 (m, 2H), 3.18 (m, 1H) | 395.4 [M + H]$^+$ |
| 287 | 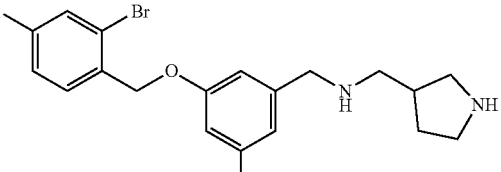 | 1 | Ex 37, 130, 136, 263, 387 | DMSO + D$_2$O: 7.83 (d, J = 2.0 Hz, 1H), 7.60 (d, J = 8.4 Hz, 1H), 7.53 (dd, J = 2.0 Hz, 8.4 Hz, 1H), 7.18 (s, 1H), 7.06 (s, 1H), 7.04 (s, 1H), 5.11 (s, 2H), 4.30-4.55 (m, 4H), 4.11 (s, 2H), 3.82 (m, 1H), 3.35 (m, 1H), 3.25 (m, 2H), 2.90-3.20 (m, 4H), 2.90 (s, 3H), 2.70 (m, 2H), 2.30 (m, 1H), 2.17 (m, 1H), 1.65 (m, 1H) | 566.4, 568.3 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 288 | | 1 | Ex 37, 130, 136, 263, 387 | DMSO + D₂O: 7.84 (t, J = 2.0 Hz, 1H), 7.63 (dd, J = 3.2 Hz, 8.3 Hz, 1H), 7.54 (td, J = 1.9 Hz, 8.3 Hz, 1H), 7.30 (s, 1H), 7.20, 7.24 (2s, 1H), 7.05, 7.07 (2s, 1H), 5.13 (s, 2H), 4.85, 4.70 (2m, 1H), 4.40-4.60 (m, 3H), 3.95-4.20 (m, 5H), 3.75-3.95 (m, 4H), 3.10-3.40 (m, 8H), 2.95, 2.75 (2m, 1H), 2.45 (m, 1H) | 566.3, 568.3 [M + H]⁺ |
| 289 | | 1 | Ex 37 & 130 | DMSO + D₂O: 8.97 (s, 1H), 8.28 (d, J = 8.4 Hz, 1H), 7.75 (d, J = 8.4 Hz, 1H), 6.65-6.83 (m, 3H), 5.30 (s, 2H), 4.06 (s, 2H), 3.74 (m, 2H), 3.36 (m, 1H), 3.25 (m, 1H), 3.12 (m, 1H), 3.02 (m, 2H), 2.85 (m, 1H), 2.65 (m, 1H), 2.15 (m, 1H), 1.97 (m, 1H), 1.65 (m, 1H), 0.95 (d J = 6.4 Hz, 6H) | 438.4 [M + H]⁺ |
| 290 | | 1 | Ex 37 & 130 | DMSO + D₂O: 7.61 (d, J = 2.0 Hz, 1H), 7.49 (d, J = 8.0 Hz, 1H), 7.44 (dd, J = 2.0 Hz, 8.0 Hz, 1H), 6.76 (s, 1H), 6.73 (s, 1H), 6.62 (s, 1H), 3.25 (m, 1H), 3.12 (m, 1H), 3.05 (m, 2H), 2.90 (m, 1H), 2.60 (m, 1H), 2.12 (m, 1H), 1.98 (m, 1H), 1.65 (m, 1H), 1.25 (s, 9H), 0.96 (d, J = 6.4 Hz, 6H) | 503.5, 505.5 [M + H]⁺ |
| 291 | | 1 | Ex 37 & 130 | DMSO + D₂O: 8.83 (s, 1H), 8.14 (d, J = 8.0 Hz, 1H), 7.95 (d J = 8.0 Hz, 1H), 6.66-6.78 (m, 3H), 5.28 (s, 2H), 4.05 (s, 2H), 3.74 (m, 2H), 3.36 (m, 1H), 3.25 (m, 1H), 3.10 (m, 1H), 3.01 (m, 2H), 2.88 (m, 1H), 2.60 (m, 1H), 2.13 (m, 1H), 1.97 (m, 1H), 1.65 (m, 1H), 0.95 (d, J = 6.4 Hz, 6H) | 438.4 [M + H]⁺ |
| 292 | | 3 | Ex 37, 158, 168, 183, 263 | DMSO + D₂O: 7.51 (d, J = 8.4 Hz, 2H), 7.40 (d, J = 8.4 Hz, 2H), 7.24 (m, 3H), 7.14 (d, J = 16.4 Hz, 1H), 6.96 (s, 1H), 6.05 (m, 1H), 5.41 (m, 1H), 5.29 (m, 1H), 4.62 (m, 2H), 4.10 (s, 2H), 3.99 (m, 2H), 3.82 (m, 2H), 3.25 (m, 2H), 3.15 (m, 1H), 1.27 (s, 9H) | 391.5 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 293 | | 1 | Ex 37, 130, 136, 263, 387 | DMSO + D$_2$O: 7.82 (d, J = 2.4 Hz, 1H), 7.60 (d, J = 8.4 Hz, 1H), 7.53 (dd, J = 2.4 Hz, 8.4 Hz, 1H), 7.16 (s, 1H), 7.04 (m, 2H), 5.10 (s, 2H), 4.50 (m, 1H), 4.40 (m, 2H), 4.30 (m, 1H), 4.09 (s, 2H), 4.00 (m, 2H), 3.85 (m, 2H), 3.75 (m, 1H), 3.15-3.30 (m, 4H), 2.91 (s, 3H), 2.72 (m, 1H), 2.28 (m, 1H) | 552.3, 554.3 [M + H]$^+$ |
| 294 | | 3 | Ex 37, 158, 168, 183, 263 | DMSO + D$_2$O: 7.53 (d, J = 8.8 Hz, 2H), 7.18-7.32 (m, 3H), 7.05 (m, 2H), 6.96 (d, J = 8.8 Hz, 2H), 6.05 (m, 1H), 5.42 (m, 1H), 5.29 (m, 1H), 4.62 (m, 2H), 4.10 (s, 2H), 4.00 (m, 2H), 3.85 (m, 2H), 3.76 (s, 3H), 3.27 (m, 2H), 3.20 (m, 1H) | 365.5 [M + H]$^+$ |
| 295 | | 1 | Ex 37 | DMSO + D$_2$O: 7.41 (d, J = 8.0 Hz, 2H), 7.36 (d, J = 8.0 Hz, 2H), 7.06 (s, 1H), 7.02 (s, 1H), 6.96 (s, 1H), 5.04 (s, 2H), 4.08 (s, 2H), 3.98 (m, 2H), 3.82 (m, 2H), 3.24 (m, 2H), 3.15 (m, 1H), 1.26 (s, 9H), 1.25 (s, 9H) | 395.2 [M + H]$^+$ |
| 296 | | 1 | Ex 37 | DMSO + D$_2$O: 7.42 (d, J = 8.4 Hz, 2H), 7.35 (d, J = 8.4 Hz, 2H), 6.70 (s, 1H), 6.64 (s, 1H), 6.62 (s, 1H), 5.97 (m, 1H), 5.37 (m, 1H), 5.25 (m, 1H), 5.02 (s, 2H), 4.52 (m, 2H), 4.03 (s, 2H), 3.97 (m, 2H), 3.80 (m, 2H), 3.22 (m, 2H), 3.13 (m, 1H), 1.25 (s, 9H) | 395.2 [M + H]$^+$ |
| 297 | | 1 | Ex 37 | DMSO + D$_2$O: 7.30-7.45 (m, 9H), 6.71 (m, 3H), 5.07 (s, 2H), 5.02 (s, 2H), 4.02 (m, 4H), 3.80 (m, 2H), 3.22 (m, 2H), 3.12 (m, 1H), 1.25 (s, 9H) | 445.4 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 298 | | 3 | Ex 37, 130, 158, 168 | DMSO + D$_2$O: 7.80 (m, 4H), 7.35 (m, 3H), 7.28 (s, 1H), 7.09 (s, 1H), 6.05 (m, 1H), 5.42 (m, 1H), 5.29 (m, 1H), 4.63 (m, 2H), 4.13 (s, 2H), 3.38 (m, 1H), 3.24 (m, 1H), 3.12 (m, 1H), 3.07 (m, 2H), 2.90 (m, 1H), 2.60 (m, 1H), 2.15 (m, 1H), 1.66 (m, 1H) | 374.2 [M + H]$^+$ |
| 299 | | 3 | Ex 37, 51, 130, 136, 158, 168 | DMSO + D$_2$O: 8.16 (s, 1H), 8.12 (d, J = 8.0 Hz, 1H), 8.07 (d, J = 8.0 Hz, 1H), 7.60 (d, J = 16.4 Hz, 1H), 7.45 (d, J = 16.4 Hz, 1H), 7.36 (s, 1H), 7.31 (s, 1H), 7.12 (s, 1H), 6.08 (m, 1H), 5.43 (m, 1H), 5.20 (m, 1H), 4.64 (m, 2H), 4.11 (s, 2H), 4.00 (m, 2H), 3.83 (m, 2H), 3.25 (m, 2H), 3.15 (m, 1H) | 428.2 [M + H]$^+$ |
| 300 | | 3 | Ex 37, 51, 130, 136, 158, 168 | DMSO + D$_2$O:8.18 (s, 1H), 8.14 (d, J = 8.0 Hz, 1H), 8.07 (d, J = 8.0 Hz, 1H), 7.61 (d, J = 16.4 Hz, 1H), 7.49 (d, J = 16.4 Hz, 1H), 7.39 (s, 1H), 7.32 (s, 1H), 7.16 (s, 1H), 6.06 (m, 1H), 5.44 (m, 1H), 5.30 (m, 1H), 4.64 (m, 2H,), 4.14 (s, 2H), 3.40 (m, 1H), 3.25 (m, 1H), 3.15 (m, 1H), 3.07 (m, 2H), 2.93 (m, 1H), 2.65 (m, 1H), 2.15 (m, 1H), 1.68 (m, 1H) | 442.2 [M + H]$^+$ |
| 301 | | 3 | Ex 37, 51, 130, 136, 158, 168 | DMSO + D$_2$O: 8.19 (s, 1H), 8.14 (d, J = 8.0 Hz, 1H), 8.09 (d J = 8.0 Hz, 1H), 7.83 (s, 1H), 7.73 (m, 1H), 7.66 (d, J = 16.4 Hz, 1H), 7.42-7.55 (m, 3H), 4.18 (s, 2H), 3.37 (m, 1H), 3.25 (m, 1H), 3.13 (m, 1H), 3.10 (m, 2H), 2.93 (m, 1H), 2.65 (m, 1H), 2.15 (m, 1H), 1.66 (m, 1H) | 386.1 [M + H]$^+$ |
| 302 | | 3 | Ex 37, 130, 158, 168 | DMSO + D$_2$O: 7.99 (d, J = 8.4 Hz, 1H), 7.85 (d, J = 9.2 Hz, 1H), 7.74 (m, 1H), 7.38-7.52 (m, 4H), 7.25 (s, 1H), 7.17 (s, 1H), 6.06 (m, 1H), 5.44 (m, 1H), 5.34 (m, 1H), 4.64 (m, 2H), 4.17 (s, 2H), 3.38 (m, 1H), 3.25 (m, 1H), 3.10 (m, 3H), 2.90 (m, 1H), 2.65 (m, 1H), 2.15 (m, 1H), 1.65 (m, 1H) | 374.2 [M + H]$^+$ |
| 303 | | 3 | Ex 37, 130, 158, 168 | DMSO + D$_2$O: 8.64 (d, J = 4.8 Hz, 1H), 8.42 (d, J = 8.4 Hz, 1H), 7.75 (m, 1H), 7.58 (d, J = 16.4 Hz, 1H), 7.37 (d, J = 16.4 Hz, 1H), 7.35 (s, 1H), 7.27 (s, 1H), 7.19 (s, 1H), 6.05 (m, 1H), 5.43 (m, 1H), 5.30 (m, 1H), 4.65 (m, 2H), 4.17 (s, 2H), 3.40 (m, 1H), 3.25 (m, 1H), 3.10 (m, 3H), 2.95 (m, 1H), 2.64 (m, 1H), 2.15 (m, 1H), 1.65 (m, 1H) | 375.1 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 304 | | 3 | Ex 37, 130, 158, 168 | DMSO + D$_2$O: 8.03 (t, J = 7.6 Hz, 1H), 7.87 (m, 2H), 7.70 (d, J = 16.0 Hz, 1H), 7.42 (s, 1H), 7.40 (d, J = 17.2 Hz, 1H), 7.34 (s, 1H), 7.13 (s, 1H), 6.07 (m, 1H), 5.42 (m, 1H), 5.27 (m, 1H), 4.64 (m, 2H), 4.13 (s, 2H), 3.38 (m, 1H), 3.25 (m, 1H), 3.10 (m, 3H), 2.92 (m, 1H), 2.65 (m, 1H), 2.15 (m, 1H), 1.68 (m, 1H) | 375.2 [M + H]$^+$ |
| 305 | | 3 | Ex 37, 130, 158, 168 | DMSO + D$_2$O: 8.05 (s, 1H), 7.92 (d, J = 8.0 Hz, 1H), 7.72 (d, J = 8.0 Hz, 1H), 7.60 (t, J = 8.0 Hz, 1H), 7.34 (m, 4H), 7.25 (s, 1H), 7.11 (s, 1H), 6.06 (m, 1H), 5.43 (m, 1H), 5.29 (m, 1H), 4.63 (m, 2H), 4.13 (s, 2H), 3.37 (m, 1H), 3.25 (m, 1H), 3.10 (m, 3H), 2.90 (m, 1H), 2.63 (m, 1H), 2.16 (m, 1H), 1.69 (m, 1H) | 374.2 [M + H]$^+$ |
| 306 | | 3 | Ex 37, 130, 158, 168 | DMSO + D$_2$O: 8.99 (s, 1H), 8.80 (d, J = 5.6 Hz, 1H), 7.97 (d, J = 5.6 Hz, 1H), 7.79 (d, J = 16.4 Hz, 1H), 7.47 (s, 1H), 7.34 (d, J = 16.4 Hz, 1H), 7.31 (s, 1H), 7.24 (s, 1H), 6.07 (m, 1H), 5.44 (m, 1H), 5.30 (m, 1H), 4.65 (m, 2H), 4.18 (s, 2H), 3.40 (m, 1H), 3.25 (m, 1H), 3.10 (m, 3H), 2.92 (m, 1H), 2.66 (m, 1H), 2.15 (m, 1H), 1.69 (m, 1H) | 375.2 [M + H]$^+$ |
| 307 | | 3 | Ex 37, 130, 158, 168 | DMSO + D$_2$O: 8.97 (d, J = 2.0 Hz, 1H), 8.26 (dd, J = 2.0 Hz, 1H), 7.79 (d, J = 16.0 Hz, 1H), 7.71 (d, J = 8.4 Hz, 1H), 7.45 (m, 2H), 7.35 (s, 1H), 7.18 (s, 1H), 6.05 (m, 1H), 5.43 (m, 1H), 5.29 (m, 1H), 4.64 (m, 2H), 4.15 (s, 2H), 3.35 (m, 1H), 3.25 (m, 1H), 3.12 (m, 3H), 2.95 (m, 1H), 2.65 (m, 1H), 2.10 (m, 1H), 1.65 (m, 1H) | 375.1 [M + H]$^+$ |
| 308 | | 3 | Ex 37, 51, 130, 136, 158, 168 | DMSO + D$_2$O: 8.19 (s, 1H), 8.15 (d, J = 8.0 Hz, 1H), 8.09 (d, J = 8.0 Hz, 1H), 7.82 (s, 1H), 7.65-7.75 (m, 2H), 7.42-7.53 (m, 3H), 4.16 (s, 2H), 4.00 (m, 2H), 3.85 (m, 2H), 3.28 (m, 2H), 3.20 (m, 1H) | 372.1 [M + H]$^+$ |
| 309 | | 3 | Ex 37, 51, 130, 136, 158, 168 | DMSO + D$_2$O: 8.36 (s, 1H), 8.25 (s, 1H), 8.17 (s, 1H), 7.55 (d, J = 16.4 Hz, 1H), 7.40 (d, J = 16.4 Hz, 1H), 7.31 (s, 1H), 7.28 (s, 1H), 7.08 (s, 1H), 6.05 (m, 1H), 5.42 (m, 1H), 5.30 (m, 1H), 4.62 (m, 2H), 4.10 (s, 2H), 4.00 (m, 2H), 3.34 (m, 2H), 3.25 (m, 2H), 3.15 (m, 1H) | 428.2 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 310 | | 3 | Ex 37, 51, 130, 136, 158, 168 | DMSO + D$_2$O: 8.27 (s, 1H), 8.15 (m, 2H), 7.50 (d, J = 16.4 Hz, 1H), 7.37 (m, 2H), 7.23 (s, 1H), 7.16 (s, 1H), 6.06 (m, 1H), 5.43 (m, 1H), 5.30 (m, 1H), 4.64 (m, 2H), 4.14 (s, 2H), 4.00 (m, 2H), 3.85 (m, 2H), 3.26 (m, 2H), 3.17 (m, 1H) | 428.2 [M + H]$^+$ |
| 311 | | 3 | Ex 37, 51, 130, 136, 158, 168 | DMSO + D$_2$O: 8.31 (s, 1H), 8.19 (d, J = 8.4 Hz, 1H), 8.08 (d, J = 8.4 Hz, 1H), 7.64 (d, J = 16.4 Hz, 1H), 7.45 (d, J = 16.4 Hz, 1H), 7.41 (s, 1H), 7.29 (s, 1H), 7.15 (s, 1H), 6.05 (m, 1H), 5.45 (m, 1H), 5.30 (m, 1H), 4.65 (m, 2H), 4.15 (s, 2H), 4.00 (m, 2H), 3.85 (m, 2H), 3.27 (m, 2H), 3.15 (m, 1H) | 428.2 [M + H]$^+$ |
| 312 | | 3 | Ex 37, 51, 130, 136, 158, 168 | DMSO + D$_2$O: 8.17 (s, 1H), 8.15 (m, 2H), 7.77 (s, 1H), 7.67 (m, 1H), 7.50 (m, 3H), 7.40 (d, J = 16.4 Hz, 1H), 4.18 (s, 2H), 4.00 (m, 2H), 3.85 (m, 2H), 3.27 (m, 2H), 3.16 (m, 1H) | 372.1 [M + H]$^+$ |
| 313 | | 3 | Ex 37, 51, 130, 136, 158, 168 | DMSO + D$_2$O: 8.27 (s, 1H), 8.16 (m, 2H), 7.50 (d, J = 16.0 Hz, 1H), 7.38 (m, 2H), 7.24 (s, 1H), 7.19 (s, 1H), 6.05 (m, 1H), 5.45 (m, 1H), 5.30 (m, 1H), 4.64 (m, 2H), 4.16 (s, 2H), 3.36 (m, 1H), 3.25 (m, 1H), 3.13 (m, 1H), 3.07 (m, 2H), 2.94 (m, 1H), 2.65 (m, 1H), 2.15 (m, 1H), 1.66 (m, 1H) | 442.2 [M + H]$^+$ |
| 314 | | 3 | Ex 37, 51, 130, 136, 158, 168 | DMSO + D$_2$O: 8.27 (s, 1H), 8.20 (d, J = 8.4 Hz, 1H), 8.15 (d, J = 8.4 Hz, 1H), 7.81 (s, 1H), 7.68 (m, 1H), 7.55 (m, 3H), 7.40 (d, J = 16.4 Hz, 1H), 4.20 (s, 2H), 3.36 (m, 1H), 3.25 (m, 1H), 3.13 (m, 1H), 3.08 (m, 2H), 2.94 (m, 1H), 2.65 (m, 1H), 2.15 (m, 1H), 1.66 (m, 1H) | 386.1 [M + H]$^+$ |
| 315 | | 3 | Ex 37, 130, 158, 168 | DMSO + D$_2$O: 8.84 (dd, J = 1.6 Hz, 4.8 Hz, 1H), 8.28 (dd, J = 1.6 Hz, 7.6 Hz, 1H), 7.95 (d, J = 15.6 Hz, 1H), 7.48 (m, 3H), 7.33 (s, 1H), 7.20 (s, 1H), 6.05 (m, 1H), 5.44 (m, 1H), 5.30 (m, 1H), 4.66 (m, 2H), 4.18 (s, 2H), 3.40 (m, 1H), 3.25 (m, 1H), 3.10 (m, 3H), 2.95 (m, 1H), 2.62 (m, 1H), 2.15 (m, 1H), 1.70 (m, 1H) | 375.2 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 316 | | 3 | Ex 37, 130, 158, 168 | DMSO + D₂O: 9.21 (s, 1H), 8.68 (d, J = 5.2 Hz, 1H), 7.85 (d, J = 5.2 Hz, 1H), 7.64 (d, J = 16.8 Hz, 1H), 7.35 (d, J = 16.4 Hz, 1H), 7.34 (s, 1H), 7.29 (s, 1H), 7.19 (s, 1H), 6.05 (m, 1H), 5.44 (m, 1H), 5.30 (m, 1H), 4.65 (m, 2H), 4.17 (s, 2H), 3.40 (m, 1H), 3.25 (m, 1H), 3.10 (m, 3H), 2.90 (m, 1H), 2.65 (m, 1H), 2.15 (m, 1H), 1.68 (m, 1H) | 375.1 [M + H]⁺ |
| 317 | | 3 | Ex 37, 158, 168, 183, 263 | DMSO + D₂O: 7.48 (m, 2H), 7.24 (m, 3H), 7.08 (dd, J = 3.6 Hz, 5.2 Hz, 1H), 7.02 (s, 1H), 6.90 (d, J = 16.4 Hz, 1H), 6.05 (m, 1H), 5.41 (m, 1H), 5.29 (m, 1H), 4.61 (m, 2H), 4.09 (s, 2H), 4.00 (m, 2H), 3.85 (m, 2H), 3.25 (m, 2H), 3.18 (m, 1H) | 341.1 [M + H]⁺ |
| 318 | | 3 | Ex 37, 158, 168, 183, 263 | DMSO + D₂O: 7.57 (m, 2H), 7.47 (dd, 1.6 Hz, 5.2 Hz, 1H), 7.30 (m, 2H), 7.17 (s, 1H), 7.05 (m, 2H), 6.05 (m, 1H), 5.41 (m, 1H), 5.29 (m, 1H), 4.62 (m, 2H), 4.09 (s, 2H), 4.00 (m, 2H), 3.85 (m, 2H), 3.25 (m, 2H), 3.17 (m, 1H) | 341.1 [M + H]⁺ |
| 319 | | 3 | Ex 37, 158, 168, 183, 263 | DMSO + D₂O: 7.49 (m, 2H), 7.24 (m, 3H), 7.08 (dd, J = 3.6 Hz, 5.2 Hz, 1H), 7.02 (s, 1H), 6.91 (d, J = 16.0 Hz, 1H), 6.05 (m, 1H), 5.42 (m, 1H), 5.29 (m, 1H), 4.62 (m, 2H), 4.09 (s, 2H), 3.35 (m, 1H), 3.25 (m, 1H), 3.17 (m, 1H), 3.02 (m, 2H), 2.90 (m, 1H), 2.61 (m, 1H), 2.15 (m, 1H), 1.67 (m, 1H) | 355.2 [M + H]⁺ |
| 320 | | 3 | Ex 37, 158, 168, 183, 263 | DMSO + D₂O: 7.57 (m, 2H), 7.47 (dd, J = 1.6 Hz, 5.2 Hz, 1H), 7.30 (m, 2H), 7.17 (s, 1H), 7.05 (m, 2H), 6.05 (m, 1H), 5.42 (m, 1H), 5.29 (m, 1H), 4.62 (m, 2H), 4.09 (s, 2H), 3.35 (m, 1H), 3.25 (m, 1H), 3.00-3.20 (m, 3H), 2.92 (m, 1H), 2.61 (m, 1H), 2.14 (m, 1H), 1.68 (m, 1H) | 355.2 [M + H]⁺ |
| 321 | | 3 | Ex 37, 51, 130, 136, 158, 168 | DMSO + D₂O: 8.37 (s, 1H), 8.08 (d, J = 8.4 Hz, 1H), 8.00 (d, J = 8.4 Hz, 1H), 7.55 (d, J = 16.4 Hz, 1H), 7.40 (d, J = 16.4 Hz, 1H), 7.35 (s, 1H), 7.29 (s, 1H), 7.12 (s, 1H), 6.05 (m, 1H), 5.42 (m, 1H), 5.31 (m, 1H), 4.64 (m, 2H), 4.12 (s, 2H), 4.00 (m, 2H), 3.85 (m, 2H), 3.26 (m, 2H), 3.17 (m, 1H) | 428.2 [M + H]⁺ |

TABLE 1-continued

Exemplified compounds

The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 322 | | 3 | Ex 37, 158, 168, 183, 263 | DMSO + D$_2$O: 7.01 (d, J = 8.4 Hz, 1H), 6.96 (d, J = 2.0 Hz, 1H), 6.93 (s, 1H), 6.81 (s, 1H), 6.52 (d, J = 2.4 Hz, 1H), 6.41 (dd, J = 2.4 Hz, 8.4 Hz, 1H), 6.03 (m, 1H), 5.38 (m, 1H), 5.26 (m, 1H), 4.54 (m, 2H), 4.05 (s, 2H), 4.00 (m, 2H), 3.85 (m, 2H), 3.76 (s, 3H), 3.71 (s, 3H), 3.23 (m, 2H), 3.17 (m, 1H), 2.75 (s, 4H) | 397.2 [M + H]$^+$ |
| 323 | | 3 | Ex 37, 158, 168, 183, 263 | HPLC: 5.28 min | 395.3 [M + H]$^+$ |
| 324 | | 3 | Ex 37, 130, 158, 168 | DMSO + D$_2$O: 8,70 (d, J = 5.2 Hz, 1H), 8.21 (d, J = 1.6 Hz, 1H), 7.84 (dd, J = 1.6 Hz, 5.2 Hz, 1H), 7.65 (d, J = 16.8 Hz, 1H), 7.30 (m, 3H), 7.11 (s, 1H), 6.05 (m, 1H), 5.42 (m, 1H), 5.30 (m, 1H), 4.63 (m, 2H), 4.15 (s, 2H), 3.35 (m, 1H), 3.25 (m, 1H), 3.10 (m, 3H), 2.88 (m, 1H), 2.55 (m, 1H), 2.10 (m, 1H), 1.65 (m, 1H) | 375.2 [M + H]$^+$ |
| 325 | | 3 | Ex 37, 130, 158, 168 | DMSO + D$_2$O: 9.01 (s, 1H), 8.87 (s, 1H), 8.52 (s, 1H), 7.49 (d, J = 16.8 Hz, 1H), 7.32 (m, 3H), 7.07 (s, 1H), 6.05 (m, 1H), 5.42 (m, 1H), 5.29 (m, 1H), 4.63 (m, 2H), 4.14 (s, 2H), 3.37 (m, 1H), 3.25 (m, 1H), 3.10 (m, 3H), 2.87 (m, 1H), 2.55 (m, 1H), 2.15 (m, 1H), 1.65 (m, 1H) | 375.2 [M + H]$^+$ |
| 326 | | 3 | Ex 37, 130, 158, 168 | DMSO + D$_2$O: 8.95 (s, 1H), 8.24 (d, J = 8.4 Hz, 1H), 8.02 (d, J = 8.0 Hz, 1H), 7.56 (d, J = 16.4 Hz, 1H), 7.41 (m, 2H), 7.31 (s, 1H), 7.16 (s, 1H), 6.06 (m, 1H), 5.43 (m, 1H), 5.30 (m, 1H), 4.64 (m, 2H), 4.15 (s, 2H), 3.40 (m, 1H), 3.25 (m, 1H), 3.10 (m, 3H), 2.95 (m, 1H), 2.65 (m, 1H), 2.15 (m, 1H), 1.65 (m, 1H) | 375.2 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 327 | | 3 | Ex 37, 158, 168, 183, 263 | DMSO + D₂O: 7.51 (s, 1H), 7.27 (m, 3H), 7.22 (s, 1H), 7.06 (s, 1H), 6.05 (m, 1H), 5.42 (m, 1H), 5.29 (m, 1H), 4.63 (m, 2H), 4.10 (s, 2H), 4.00 (m, 2H), 3.85 (m, 2H), 3.17-3.35 (m, 4H), 1.34 (d, J = 6.8 Hz, 6H) | 384.2 [M + H]⁺ |
| 328 | | 3 | Ex 37, 51, 130, 136, 158, 168 | DMSO + D₂O: 8.21 (d, J = 8.0 Hz, 1H), 8.11 (d, J = 8.0 Hz, 1H), 7.74 (d, J = 8.0 Hz, 1H), 7.44 (d, J = 16.4 Hz, 1H), 7.35 (s, 1H), 7.28 (s, 1H), 7.15 (m, 2H), 6.05 (m, 1H), 5.44 (m, 1H), 5.30 (m, 1H), 4.64 (m, 2H), 4.13 (s, 2H), 3.85 (m, 2H), 4.00 (m, 2H), 3.25 (m, 2H), 3.17 (m, 1H) | 428.1 [M + H]⁺ |
| 329 | | 3 | Ex 37, 130, 158, 168 | DMSO + D₂O: 8.78 (d, J = 4.8 Hz, 1H), 7.98 (s, 1H), 7.73 (d, J = 16.0 Hz, 1H), 7.69 (dd, J = 1.6 Hz, 4.8 Hz, 1H), 7.39 (m, 2H), 7.31 (s, 1H), 7.14 (s, 1H), 6.05 (m, 1H), 5.42 (m, 1H), 5.27 (m, 1H), 4.64 (m, 2H), 4.15 (s, 2H), 3.40 (m, 1H), 3.25 (m, 1H), 3.12 (m, 3H), 2.90 (m, 1H), 2.63 (m, 1H), 2.15 (m, 1H), 1.68 (m, 1H) | 375.3 [M + H]⁺ |
| 330 | | 3 | Ex 37, 158, 168, 183, 263 | DMSO + D₂O: 7.51 (s, 1H), 7.30 (m, 3H), 7.22 (s, 1H), 7.06 (s, 1H), 6.05 (m, 1H), 5.42 (m, 1H), 5.29 (m, 1H), 4.63 (m, 2H), 4.12 (s, 2H), 3.20-3.40 (m, 3H), 3.00-3.20 (m, 3H), 2.92 (m, 1H), 2.64 (m, 1H), 2.15 (m, 1H), 1.68 (m, 1H), 1.34 (d, J = 6.8 Hz, 6H) | 398.2 [M + H]⁺ |
| 331 | | 3 | Ex 37, 51, 130, 136, 158, 168, 399 | DMSO + D₂O: 8.08 (s, 1H), 7.74 (m, 2H), 7.47 (m, 1H), 7.30 (m, 2H), 7.19 (s, 1H), 7.12 (s, 1H), 6.90 (s, 1H), 3.80 (m, 4H), 3.30 (m, 1H), 3.20 (m, 1H), 3.10 (m, 1H), 2.85 (m, 1H), 2.70 (m, 2H), 2.45 (m, 1H), 2.05 (m, 2H), 1.60 (m, 1H), 0.99 (d, J = 6.8 Hz, 6H) | 408.3 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 332 | | 3 | Ex 37, 51, 130, 136, 158, 168, 399 | DMSO + D₂O: 8.84 (d, J = 1.6 Hz, 1H), 8.56 (dd, J = 1.6 Hz, 4.8 Hz, 1H), 8.28 (d, J = 8.0 Hz, 1H), 7.64 (dd, J = 4.8 Hz, 8.0 Hz, 1H), 7.43 (d, J = 16.4 Hz, 1H), 7.35 (d, J = 16.4 Hz, 1H), 7.28 (s, 1H), 7.27 (s, 1H), 7.06 (s, 1H), 4.14 (s, 2H), 3.81 (m, 2H), 3.38 (m, 1H), 3.25 (m, 1H), 3.10 (m, 3H), 2.88 (m, 1H), 2.55 (m, 1H), 2.15 (m, 1H), 2.05 (m, 1H), 1.65 (m, 1H), 0.99 (d, J = 6.4 Hz, 6H) | 366.2 [M + H]⁺ |
| 333 | | 3 | Ex 37, 51, 130, 136, 158, 168, 399 | DMSO + D₂O: 8.55 (s, 1H), 7.80 (m, 1H), 7.60 (m, 2H), 7.15-7.35 (m, 4H), 6.97 (s, 1H), 3.96 (s, 2H), 3.80 (m, 2H), 3.35 (m, 1H), 3.25 (m, 1H), 3.12 (m, 1H), 2.90 (m, 3H), 2.55 (m, 1H), 1.95-2.15 (m, 2H), 1.65 (m, 1H), 0.99 (d, J = 6.8 Hz, 6H) | 366.2 [M + H]⁺ |
| 334 | | 3 | Ex 37, 51, 130, 136, 158, 168, 399 | DMSO + D₂O: 8.62 (d, J = 6.0 Hz, 2H), 7.77 (d, J = 6.0 Hz, 1H), 7.63 (d, J = 16.4 Hz, 1H), 7.35 (m, 3H), 7.10 (s, 1H), 4.14 (s, 2H), 3.81 (m, 2H), 3.35 (m, 1H), 3.25 (m, 1H), 3.10 (m, 3H), 2.90 (m, 1H), 2.60 (m, 1H), 2.15 (m, 1H), 2.05 (m, 1H), 1.65 (m, 1H), 0.99 (d, J = 6.8 Hz, 6H) | 366.2 [M + H]⁺ |
| 335 | | 3 | Ex 37, 51, 130, 136, 158, 168, 399 | DMSO + D₂O: 8.74 (s, 1H), 8.45 (dd, J = 1.2 Hz, 4.8 Hz, 1H), 8.04 (m, 1H), 7.42 (m, 1H), 7.34 (d, J = 16.4 Hz, 1H), 7.28 (d, J = 16.4 Hz, 1H), 7.24 (s, 1H), 7.19 (s, 1H), 6.96 (s, 1H), 6.06 (m, 1H), 5.41 (m, 1H), 5.28 (m, 1H), 4.61 (m, 2H), 3.97 (m, 2H), 3.90 (s, 2H), 3.75 (m, 2H), 3.00 (m, 3H) | 336.3 [M + H]⁺ |
| 336 | | 3 | Ex 37, 51, 130, 136, 158, 168, 399 | DMSO + D₂O: 8.56 (d, J = 4.0 Hz, 1H), 7.80 (m, 1H), 7.61 (d, J = 16.4 Hz, 1H), 7.55 (m, 1H), 7.20-7.35 (m, 4H), 6.97 (s, 1H), 6.06 (m, 1H), 5.42 (m, 1H), 5.29 (m, 1H), 4.62 (m, 2H), 3.97 (m, 2H), 3.92 (s, 2H), 3.76 (m, 2H), 3.00 (m, 3H) | 336.3 [M + H]⁺ |
| 337 | | 3 | Ex 37, 51, 130, 136, 158, 168, 399 | DMSO + D₂O: 7.86 (d, J = 8.4 Hz, 2H), 7.66 (d, J = 8.4 Hz, 2H), 7.30 (m, 2H), 7.16 (s, 1H), 7.07 (s, 1H), 6.87 (s, 1H), 3.80 (m, 2H), 3.75 (s, 2H), 3.27 (m, 1H), 3.18 (m, 1H), 3.08 (m, 1H), 2.84 (m, 1H), 2.58 (m, 2H), 2.40 (m, 1H), 2.02 (m, 2H), 1.58 (m, 1H), 0.99 (d, J = 6.4 Hz, 6H) | 408.3 [M + H]⁺ |

US 10,464,896 B2

171                                                                                 172

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 338 | 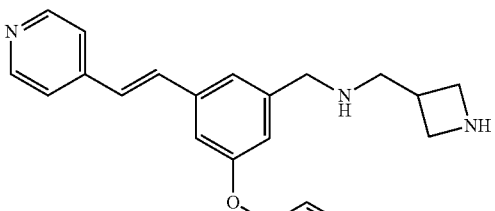 | 3 | Ex 37, 51, 130, 136, 158, 168, 399 | DMSO + D$_2$O: 8.67 (d, J = 6.4 Hz, 2H), 7.83 (d, J = 6.4 Hz, 2H), 7.69 (d, J = 16.4 Hz, 1H), 7.38 (m, 3H), 7.11 (s, 1H), 6.07 (m, 1H), 5.45 (m, 1H), 5.28 (m, 1H), 4.64 (m, 2H), 4.14 (s, 2H), 4.00 (m, 2H), 3.85 (m, 2H), 3.26 (m, 2H), 3.15 (m, 1H) | 336.2 [M + H]$^+$ |
| 339 | 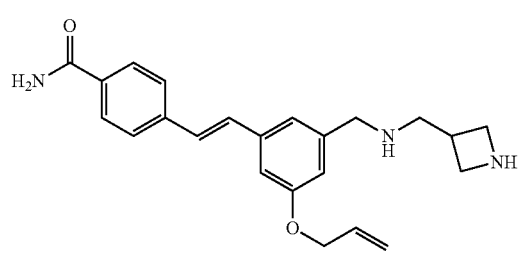 [SMILES: C=CCOc1cc(/C=C/c2ccc(C(N)=O)cc2)cc(CNCC2CNC2)c1] | 3 | Ex 37, 51, 130, 136, 158, 168, 399 | DMSO + D$_2$O: 7.85 (d, J = 8.4 Hz, 2H), 7.66 (d, J = 8.4 Hz, 2H), 7.27 (s, 2H), 7.21 (s, 1H), 7.14 (s, 1H), 6.92 (s, 1H), 6.05 (m, 1H), 5.41 (m, 1H), 5.28 (m, 1H), 4.60 (m, 2H), 3.95 (m, 2H), 3.80 (m, 2H), 3.73 (m, 2H), 2.95 (m, 1H), 2.78 (m, 2H) | 378.3 [M + H]$^+$ |
| 340 | 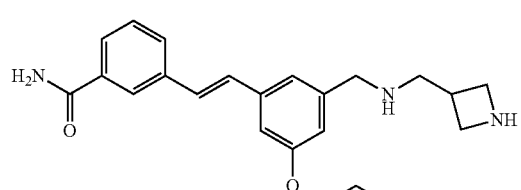 | 3 | Ex 37, 51, 130, 136, 158, 168, 399 | DMSO + D$_2$O: 8,08 (s, 1H), 7.73 (m, 2H), 7.47 (m, 1H), 7.31 (d, J = 16.8 Hz, 1H), 7.26 (d, J = 16.8 Hz, 1H), 7.20 (s, 1H), 7.14 (s, 1H), 6.91 (s, 1H), 6.05 (m, 1H), 5.41 (m, 1H), 5.28 (m, 1H), 4.61 (m, 2H), 3.95 (m, 2H), 3.80 (m, 2H), 3.73 (m, 2H), 2.98 (m, 1H), 2.85 (m, 2H) | 378.3 [M + H]$^+$ |
| 341 | 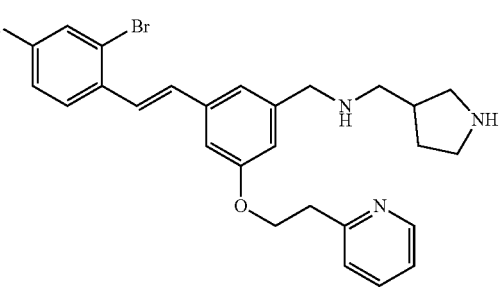 | 3 | Ex 37, 130, 136, 158, 168, 183, 354 | DMSO + D$_2$O: 8.69 (m, 1H), 8.26 (m, 1H), 7.82 (m, 3H), 7.70 (m, 1H), 7.51 (dd, J = 2.0 Hz, 8.4 Hz, 1H), 7.38 (s, 1H), 7.36 (d, J = 16.0 Hz, 1H), 7.24 (d, J = 16.0 Hz, 1H), 7.17 (s, 1H), 7.10 (s, 1H), 4.45 (t, J = 6.0 Hz, 2H), 4.13 (s, 2H), 3.40 (m, 3H), 3.25 (m, 1H), 3.15 (m, 1H), 3,05 (m, 2H), 2.90 (m, 1H), 2.65 (m, 1H), 2.15 (m, 1H), 1.68 (m, 1H) | 526.2, 528.2 [M + H]$^+$ |
| 342 | 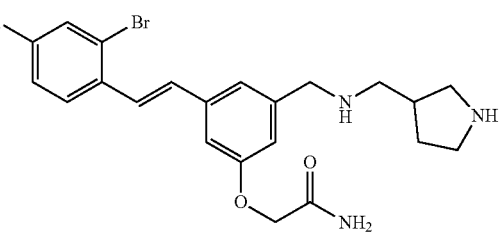 | 3 | Ex 37, 130, 136, 158, 168, 183 | DMSO + D$_2$O: 7.82 (d, J = 8.4 Hz, 1H), 7.78 (d, J = 2.0 Hz, 1H), 7.49 (dd, J = 2.0 Hz, 8.4 Hz, 1H), 7.39 (s, 1H), 7.35 (s, 1H), 7.22 (m, 2H), 7.04 (s, 1H), 4.51 (s, 2H), 4.14 (s, 2H), 3.37 (m, 1H), 3.26 (m, 1H), 3.13 (m, 1H), 3.07 (m, 2H), 2.87 (m, 1H), 2.58 (m, 1H), 2.16 (m, 1H), 1.62 (m, 1H) | 478.1, 480.1 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 343 | | 1 | Ex 37, 119, 158, 168, 354 | DMSO + D₂O: 7.81 (d, J = 2.0 Hz, 1H), 7.52 (m, 2H), 6.46 (m, 3H), 6.00 (m, 1H), 5.35 (m, 1H), 5.24 (m, 1H), 5.05 (s, 2H), 4.51 (m, 2H), 4.22 (m, 2H), 3.05-3.35 (m, 5H), 2.17 (m, 1H), 1.90 (m, 1H) | 479.1, 481.1 [M + H]⁺ |
| 344 | | 3 | Ex 37, 130, 136, 158, 168, 183, 354 | DMSO + D₂O: 8.87 (s, 1H), 7.82 (m, 2H), 7.71 (s, 1H), 7.51 (dd, 1H, J = 2.0 Hz, 8.4 Hz, 1H), 7.23-7.41 (m, 4H), 7.10 (s, 1H), 5.20 (s, 2H), 4.16 (s, 2H), 3.37 (m, 1H), 3.26 (m, 1H), 3.13 (m, 1H), 3.07 (m, 2H), 2.87 (m, 1H), 2.60 (m, 1H), 2.15 (m 1H), 1.65 (m, 1H) | 501.2, 503.2 [M + H]⁺ |
| 345 | | 3 | Ex 37, 130, 136, 158, 168, 183 | DMSO + D₂O: 8.91 (s, 1H), 7.81 (m, 2H), 7.74 (s, 1H), 7.53 (m, 1H), 7.29-7.41 (m, 4H), 7.09 (s, 1H), 5.17 (s, 2H), 4.16 (s, 2H), 3.84 (s, 3H), 3.38 (m, 1H), 3.26 (m, 1H), 3.13 (m, 1H), 3.08 (m, 2H), 2.88 (m, 1H), 2.60 (m, 1H), 2.15 (m, 1H), 1.65 (m, 1H) | 515.2, 517.2 [M + H]⁺ |
| 346 | | 3 | Ex 37, 130, 136, 158, 168, 183 | DMSO + D₂O: 8.63 (d, J = 8.0 Hz, 1H), 8.00 (t, J = 8.0 Hz, 1H), 7.82 (m, 2H), 7.67 (d, J = 8.0 Hz, 1H), 7.50 (m, 2H), 7.23-7.41 (m, 5H), 5.30 (s, 2H), 4.16 (s, 2H), 3.37 (m, 1H), 3.25 (m, 1H), 3.13 (m, 1H), 3.06 (m, 2H), 2.90 (m, 1H), 2.60 (m, 1H), 2.13 (m, 1H), 1.65 (m, 1H) | 512.1, 514.1 [M + H]⁺ |
| 347 | | 3 | Ex 37, 130, 136, 158, 168, 183 | DMSO + D₂O: 7.81 (m, 2H), 7.50 (dd, J = 2.0 Hz, 8.8 Hz, 1H), 7.26-7.41 (m, 4H), 7.18 (s, 1H), 6.35 (s, 1H), 5.20 (s, 2H), 4.15 (s, 2H), 3.37 (m, 1H), 3.26 (m, 1H), 3.13 (m, 1H), 3.07 (m, 2H), 2.91 (m, 1H), 2.65 (m, 1H), 2.40 (s, 3H), 2.15 (m, 1H), 1.65 (m, 1H) | 516.1, 518.1 [M + H]⁺ |
| 348 | | 3 | Ex 37, 51, 130, 136, 158, 168 | DMSO + D₂O: 8.41 (s, 1H), 7.58 (m, 2H), 7.37 (m, 2H), 7.08 (s, 1H), 6.05 (m, 1H), 5.41 (m, 1H), 5.29 (m, 1H), 4.63 (m, 2H), 4.12 (s, 2H), 4.00 (m, 2H), 3.82 (m, 2H), 3.22 (m, 2H), 3.14 (m, 1H) | 410.2 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 349 | 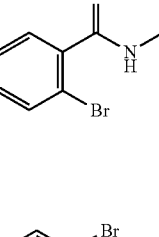 | 6 | Ex 37, 119, 130, 158, 354 | DMSO + D$_2$O: 9.05 (t, J = 6.0 Hz, 1H), 7.81 (d, J = 2.0 Hz, 1H), 7.54 (dd, J = 2.0 Hz, 8.4 Hz, 1H), 7.45 (d, J = 8.4 Hz, 1H), 7.02 (m, 3H), 6.08 (m, 1H), 5.40 (m, 1H), 5.27 (m, 1H), 4.57 (m, 2H), 4.42 (d, J = 6.0 Hz, 2H), 4.10 (s, 2H), 3.36 (m, 1H), 3.25 (m, 1H), 3.13 (m, 1H), 3.04 (m, 2H), 2.90 (m, 1H), 2.62 (m, 1H), 2.12 (m, 1H), 1.68 (m, 1H) | 492.1, 494.1 [M + H]$^+$ |
| 350 | 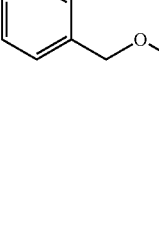 | 1 | Ex 37, 119, 158, 168, 354 | DMSO + D$_2$O: 7.79 (d, J = 2.4 Hz, 1H), 7.53 (m, 2H), 6.44 (m, 3H), 5.99 (m, 1H), 5.34 (m, 1H), 5.24 (m, 1H), 5.04 (s, 2H), 4.50 (m, 2H), 4.18 (m, 2H), 3.28 (m, 2H), 2.87 (m, 2H), 2.51 (m, 1H), 1.87 (m, 2H), 1.73 (m, 2H) | 493.1, 495.0 [M + H]$^+$ |
| 351 | 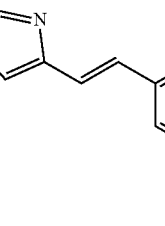 | 3 | Ex 37, 158, 168, 183, 263 | DMSO + D$_2$O: 7.48 (s, 1H), 7.31 (m, 3H), 7.21 (s, 1H), 7.10 (s, 1H), 6.05 (m, 1H), 5.43 (m, 1H), 5.29 (m, 1H), 4.63 (m, 2H), 4.12 (s, 2H), 3.38 (m, 1H), 3.25 (m, 1H), 3.00-3.17 (m, 3H), 2.95 (m, 1H), 2.68 (m, 4H), 2.15 (m, 1H), 1.70 (m, 1H) | 370.2 [M + H]$^+$ |
| 352 | 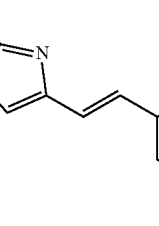 | 3 | Ex 37, 158, 168, 183, 263 | DMSO + D$_2$O: 7.47 (s, 1H), 7.30 (m, 3H), 7.20 (s, 1H), 7.03 (s, 1H), 6.05 (m, 1H), 5.41 (m, 1H), 5.29 (m, 1H), 4.62 (m, 2H), 4.09 (s, 2H), 4.00 (m, 2H), 3.85 (m, 2H), 3.26 (m, 2H), 3.18 (m, 1H), 2.67 (s, 3H) | 356.1 [M + H]$^+$ |
| 353 | 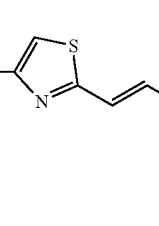 | 3 | Ex 37, 158, 168, 183, 263 | DMSO + D$_2$O: 7.30-7.50 (m, 4H), 7.24 (s, 1H), 7.05 (s, 1H), 6.03 (m, 1H), 5.41 (m, 1H), 5.29 (m, 1H), 4.63 (m, 2H), 4.13 (s, 2H), 3.37 (m, 1H), 3.25 (m, 1H), 2.95-3.20 (m, 4H), 2.88 (m, 1H), 2.59 (m, 1H), 2.14 (m, 1H), 1.66 (m, 1H), 1.24 (d, J = 6.8 Hz, 6H) | 398.3 [M + H]$^+$ |
| 354 | 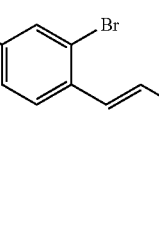 | 3 | Ex 37, 158, 168 | DMSO + D$_2$O: 7.82 (d, J = 8.4 Hz, 1H), 7.78 (d, J = 2.4 Hz, 1H), 7.48 (dd, J = 2.0 Hz, 8.4 Hz, 1H), 7.29 (d, J = 16.4 Hz, 1H), 7.21 (d, J = 16.0 Hz, 1H), 7.06 (s, 1H), 7.03 (s, 1H), 6.78 (s, 1H), 6.04 (m, 1H), 5.39 (m, 1H), 5.27 (m, 1H), 4.58 (m, 2H), 4.26 (s, 2H), 3.29 (m, 2H), 2.91 (m, 2H), 2.50 (m, 1H), 1.91 (m, 2H), 1.77 (m, 2H) | 489.2, 491.1 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 355 | | 3 | Ex 37, 158, 168, 183, 263 | DMSO + D$_2$O: 7.39 (d, J = 16.0 Hz, 1H), 7.32 (d, J = 16.0 Hz, 1H), 7.20 (s, 2H), 7.13 (s, 1H), 6.91 (s, 1H), 6.03 (m, 1H), 5.40 (m, 1H), 5.26 (m, 1H), 4.59 (m, 2H), 3.68 (s, 2H), 3.28 (m, 1H), 3.17 (m, 1H), 3.05 (m, 1H), 2.82 (m, 1H), 2.52 (m, 2H), 2.40 (m, 1H), 2.05 (m, 2H), 1.58 (m, 1H), 0.90 (m, 2H), 0.81 (m, 2H) | 396.2 [M + H]$^+$ |
| 356 | | 3 | Ex 37, 158, 168, 183, 263 | DMSO + D$_2$O: 7.43 (d, J = 16.0 Hz, 1H), 7.35 (d, J = 16.0 Hz, 1H), 7.32 (s, 1H), 7.30 (s, 1H), 7.22 (s, 1H), 7.02 (s, 1H), 6.05 (m, 1H), 5.40 (m, 1H), 5.28 (m, 1H), 4.62 (m, 2H), 4.08 (s, 2H), 4.00 (m, 2H), 3.81 (m, 2H), 3.23 (m, 2H), 3.15 (m, 1H), 2.08 (m, 1H), 0.91 (m, 2H), 0.80 (m, 2H) | 382.3 [M + H]$^+$ |
| 357 | | 6 | Ex 37, 119, 130, 158, 354 | DMSO + D$_2$O: 7.79 (dd, J = 2.0 Hz, 8.4 Hz, 2H), 7.48 (d, J = 2.0 Hz, 8.0 Hz, 2H), 6.98 (m, 3H), 6.00 (m, 1H), 5.36 (m, 1H), 5.24 (m, 1H) 4.54 (m, 2H), 4.44 (s, 2H), 4.07 (s, 2H), 3.36 (m, 1H), 3.23 (m, 1H), 3.12 (m, 1H), 3.03 (m, 2H), 2.89 (m, 1H), 2.59 (m, 1H), 2.11 (m, 1H), 1.67 (m, 1H), 1.27 (s, 9H) | 436.3 [M + H]$^+$ |
| 358 | | 6 | Ex 37, 119, 130, 158, 354 | DMSO + D$_2$O: 8.85 (d, J = 2.4 Hz, 1H), 8.26 (dd, J = 2.4 Hz, 8.4 Hz, 1H), 7.64 (d, J = 8.4 Hz, 1H), 7.05 (s, 1H), 7.02 (s, 1H), 6.96 (s, 1H), 6.00 (m, 1H), 5.37 (m, 1H), 5.24 (m, 1H), 4.55 (m, 2H), 4.46 (s, 2H), 4.08 (s, 2H), 3.37 (m, 1H), 3.25 (m, 1H), 3.12 (m, 1H), 3.03 (m, 2H), 2.90 (m, 1H), 2.64 (m, 1H), 2.13 (m, 1H), 1.67 (m, 1H) | 415.3 [M + H]$^+$ |
| 359 | | 3 | Ex 37, 130, 136, 158, 168, 183 | DMSO + D$_2$O: 7.83 (d, J = 8.4 Hz, 1H), 7.78 (d, J = 2.4 Hz, 1H), 7.54 (s, 1H), 7.48 (dd, J = 2.0 Hz, 8.8 Hz, 1H), 7.18-7.32 (m, 3H), 7.12 (s, 1H), 6.98 (s, 1H), 5.12 (s, 2H), 3.70 (s, 2H), 3.27 (m, 1H), 3.17 (m, 1H), 3.08 (m, 1H), 2.85 (m, 1H), 2.64 (s, 3H), 2.55 (m, 2H), 2.38 (m, 1H), 2.02 (m, 1H), 1.54 (m, 1H) | 532.1, 534.1 [M + H]$^+$ |
| 360 | | 3 | Ex 37, 130, 136, 158, 168, 183 | DMSO + D$_2$O: 8.56 (d, J = 6.0 Hz, 2H), 7.82 (d, J = 8.4 Hz, 1H), 7.78 (d, J = 2.0 Hz, 1H), 7.47 (m, 3H), 7.18-7.32 (m, 3H), 7.12 (s, 1H), 6.99 (s, 1H), 5.22 (s, 2H), 3.74 (s, 2H), 3.27 (m, 1H), 3.18 (m, 1H), 3.09 (m, 1H), 2.82 (m, 1H), 2.55 (m, 2H), 2.41 (m, 1H), 2.03 (m, 1H), 1.53 (m, 1H) | 512.1, 514.1 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 361 | | 3 | Ex 37, 130, 136, 158, 168, 183 | DMSO + D$_2$O: 7.83 (d, J = 8.4 Hz, 1H), 7.77 (d, J = 2.0 Hz, 1H), 7.48 (dd, J = 2.0 Hz, 8.4 Hz, 1H), 7.18-7.32 (m, 3H), 7.08 (s, 1H), 6.95 (s, 1H), 6.60 (s, 1H), 4.87 (s, 2H), 3.70 (s, 2H), 3.27 (m, 1H), 3.17 (m, 1H), 3.08 (m, 1H), 2.83 (m, 1H), 2.55 (m, 2H), 2.38 (m, 1H), 2.02 (m, 1H), 1.56 (m, 1H) | 533.2, 535.2 [M + H]$^+$ |
| 362 | | 3 | Ex 37, 158, 168, 183, 263 | DMSO + D$_2$O: 7.30-7.52 (m, 4H), 7.25 (s, 1H), 7.04 (s, 1H), 6.05 (m, 1H), 5.41 (m, 1H), 5.29 (m, 1H), 4.63 (m, 2H), 4.11 (s, 2H), 4.00 (m, 2H), 3.82 (m, 2H), 3.25 (m, 2H), 3.15 (m, 1H), 3.02 (m, 1H), 1.25 (d, J = .8 Hz, 6H) | 384.3 [M + H]$^+$ |
| 363 | | 3 | Ex 37, 51, 130, 136, 158, 168 | DMSO + D$_2$O: 8.41 (s, 1H), 7.58 (m, 2H), 7.37 (m, 2H), 7.10 (s, 1H), 6.05 (m, 1H), 5.42 (m, 1H), 5.29 (m, 1H), 4.63 (m, 2H), 4.14 (s, 2H), 3.38 (m, 1H), 3.25 (m, 1H), 3.00-3.20 (m, 3H), 2.875 (m, 1H), 2.57 (m, 1H), 2.15 (m, 1H), 1.66 (m, 1H) | 424.3 [M + H]$^+$ |
| 364 | | 6 | Ex 37, 130, 158, 354, 369 | DMSO + D$_2$O: 7.69 (d, J = 8.8 Hz, 2H), 7.57 (d, J = 8.8 Hz, 2H), 7.00 (s, 1H), 6.96 (s, 1H), 6.83 (s, 1H), 6.02 (m, 1H), 5.38 (m, 1H), 5.27 (m, 1H), 4.49 (m, 2H), 4.06 (s, 2H), 3.96 (s, 2H), 3.35 (m, 1H), 3.25 (m, 1H), 3.13 (m, 1H), 3.03 (m, 2H), 2.90 (m, 1H), 2.60 (m, 1H), 2.10 (m, 1H), 1.65 (m, 1H), 1.29 (s, 9H) | 472.4 [M + H]$^+$ |
| 365 | | 6 | Ex 37, 130, 158, 354, 369 | DMSO + D$_2$O: 7.82 (d, J = 6.4 Hz, 1H), 7.73 (s, 1H), 7.53 (d, J = 6.4 Hz, 1H), 6.96 (s, 1H), 6.86 (s, 1H), 6.80 (s, 1H), 6.00 (m, 1H), 5.38 (m, 1H), 5.28 (m, 1H), 4.48 (m, 2H), 4.09 (s, 2H), 4.02 (m, 2H), 3.37 (m, 1H), 3.25 (m, 1H), 3.13 (m, 1H), 3.03 (m, 2H), 2.90 (m, 1H), 2.60 (m, 1H), 2.13 (m, 1H), 1.65 (m, 1H) | 484.2 [M + H]$^+$ |
| 366 | | 3 | Ex 37, 119, 158, 168, 354 | DMSO + D$_2$O: 7.82 (d, J = 8.0 Hz, 1H), 7.77 (d, J = 2.0 Hz, 1H), 7.48 (dd, J = 2.4 Hz, 8.4 Hz, 1H), 7.30 (d, J = 16.4 Hz, 1H), 7.20 (d, J = 16.4 Hz, 1H), 7.08 (s, 1H), 7.03 (s, 1H), 6.79 (s, 1H), 6.02 (m, 1H), 5.39 (m, 1H), 5.27 (m, 1H), 4.58 (m, 2H), 4.28 (m, 2H), 3.31 (m, 2H), 3.22 (m, 3H), 2.23 (m, 1H), 1.95 (m, 1H) | 475.2, 477.2 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 367 | | 3 | Ex 37, 119, 158, 168, 354 | DMSO + D$_2$O: 7.83 (d, J = 8.4 Hz, 1H), 7.78 (d, J = 2.4 Hz, 1H), 7.49 (dd, J = 2.0 Hz, 8.4 Hz, 1H), 7.30 (d, J = 16.0 Hz, 1H), 7.22 (d, J = 16.4 Hz, 1H), 7.08 (s, 1H), 7.04 (s, 1H), 6.80 (s, 1H), 6.02 (m, 1H), 5.40 (m, 1H), 5.27 (m, 1H), 4.59 (m, 2H), 4.59 (m, 2H), 4.29 (m, 2H), 3.31 (m, 2H), 3.18 (m, 3H), 2.21 (m, 1H), 1.96 (m, 1H) | 475.1, 477.0 [M + H]$^+$ |
| 368 | | 6 | Ex 37, 119, 130, 136, 354 | DMSO + D$_2$O: 9.19 (t, J = 6.50 Hz, 1H), 7.53 (s, 1H), 6.96 (s, 3H), 6.00 (m, 1H), 5.36 (m, 1H), 5.25 (m, 1H), 4.54 (m, 2H), 4.42 (m, 2H), 4.05 (s, 2H), 4.00 (m, 2H), 3.80 (m, 2H), 3.22 (m, 2H), 3.12 (m, 1H), 2.10 (m, 1H), 0.95 (m, 2H), 0.85 (m, 2H) | 413.3 [M + H]$^+$ |
| 369 | | 6 | Ex 37, 130, 136, 158, 354 | DMSO + D$_2$O: 7.68 (m, 2H), 7.56 (m, 2H), 6.91 (m, 2H), 6.83 (s, 1H), 6.00 (m, 1H), 5.36 (m, 1H), 5.26 (m, 1H), 4.46 (m, 2H), 3.95-4.05 (m, 6H), 3.80 (m, 2H), 3.21(m, 2H), 3.13 (m, 1H), 1.28 (s, 9H) | 458.4 [M + H]$^+$ |
| 370 | | 5 | Ex 37, 119, 130, 158, 263 | DMSO + D$_2$O: 9.13 (t, J = 5.6 Hz, 1H), 7.76 (d, J = 2.0 Hz, 1H), 7.55 (d, J = 1.6 Hz, 1H), 7.54 (d, J = 1.6 Hz, 1H), 7.45 (dd, J = 2.4 Hz, 8.4 Hz, 1H), 7.31 (d, J = 8.4 Hz, 1H), 7.26 (t, J = 1.6 Hz, 1H), 6.05 (m, 1H), 5.42 (m, 1H), 5.30 (m, 1H), 4.63 (m, 2H), 4.47 (d, J = 5.6 Hz, 2H), 4.14 (s, 2H), 3.98 (m, 2H), 3.82 (m, 2H), 3.24 (m, 2H), 3.14 (m, 1H) | 478.2, 480.2 [M + H]$^+$ |
| 371 | | 3 | Ex 37, 119, 130, 158, 168, 354 | DMSO + D$_2$O: 7.81 (d, J = 8.4 Hz, 1H), 7.79 (d, J = 2.0 Hz, 1H), 7.50 (dd, J = 2.0 Hz, 8.4 Hz, 1H), 7.34 (d, J = 16.4 Hz, 1H), 7.21 (d, J = 16.4 Hz, 1H), 7.13 (s, 1H), 7.08 (s, 1H), 6.84 (s, 1H), 6.03 (m, 1H), 5.42 (m, 1H), 5.29 (m, 1H), 4.59 (m, 2H), 4.35 (s, 2H), 4.01 (m, 2H), 3.82 (m, 4H), 3.24 (m, 2H), 3.13 (m, 1H) | 504.3, 506.3 [M + H]$^+$ |
| 372 | | 6 | Ex 37, 119, 130, 158, 354 | DMSO + D$_2$O: 7.52 (s, 1H), 6.84 (s, 1H), 6.82 (s, 1H), 6.77 (s, 1H), 6.00 (m, 1H), 5.35 (m, 1H), 5.22 (m, 1H), 4.51 (m, 2H), 4.37 (s, 2H), 3.64 (s, 2H), 3.25 (m, 1H), 3.15 (m, 1H), 3.05 (m, 1H), 2.80 (m, 1H), 2.45 (m, 2H), 2.36 (m, 1H), 2.10 (m, 1H), 1.95 (m, 1H), 1.55 (m, 1H), 0.95 (m, 2H), 0.84 (m, 2H) | 427.4 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 373 | (structure) | 5 | Ex 37, 119, 130, 158, 263 | DMSO + D₂O: 7.87 (d, J = 2.0 Hz, 1H), 7.65 (m, 2H), 7.53 (m, 2H), 7.34 (s, 1H), 6.08 (m, 1H), 5.44 (m, 1H), 5.31 (m, 1H), 4.67 (m, 2H), 4.20 (m, 2H), 3.38 (m, 1H), 3.25 (m, 1H), 3.15 (m, 1H), 3.10 (m, 2H), 2.90 (m, 1H), 2.60 (m, 1H), 2.13 (m, 1H), 1.65 (m, 1H) | 478.3, 480.3 [M + H]⁺ |
| 374 | (structure) | 3 | Ex 37, 51, 130, 136, 158, 168, 399 | DMSO + D₂O: 7.80 (d, J = 7.6 Hz, 1H), 7.45 (m, 3H), 7.32 (m, 1H), 7.14 (d, J = 16.4, 1H), 7.10 (s, 1H), 6.96 (s, 1H), 6.88 (s, 1H), 6.05 (m, 1H), 5.40 (m, 1H), 5.27 (m, 1H), 4.57 (m, 2H), 3.95 (m, 2H), 3.65 (m, 4H), 2.90 (m, 1H), 2.73 (m, 2H) | 378.3 [M + H]⁺ |
| 375 | (structure) | 3 | Ex 37, 51, 130, 136, 158, 168, 399 | DMSO + D₂O: 7.79 (d, J = 8.0 Hz, 1H), 7.46 (m, 3H), 7.33 (m, 1H), 7.15 (m, 2H), 6.97 (s, 1H), 6.90 (s, 1H), 3.83 (s, 2H), 3.76 (m, 2H), 3.30 (m, 1H), 3.20 (m, 1H), 3.10 (m, 1H), 2.85 (m, 1H), 2.70 (m, 2H), 2.45 (m, 1H), 2.05 (m, 2H), 1.60 (m, 1H), 0.98 (d, J = 6.4 Hz, 6H) | 408.3 [M + H]⁺ |
| 376 | (structure) | 6 | Ex 37, 119, 130, 136, 354 | DMSO + D₂O: 9.04 (t, J = 5.6 Hz, 1H), 7.82 (s, J = 2.0 Hz, 1H), 7.54 (dd, J = 2.0 Hz, 8.0 Hz, 1H), 7.43 (d, J = 8.0 Hz, 1H), 7.00 (m, 3H), 6.05 (m, 1H), 5.38 (m, 1H), 5.27 (m, 1H), 4.56 (m, 2H), 4.40 (m, 2H), 4.07 (s, 2H), 4.00 (m, 2H), 3.82 (m, 2H), 3.22 (m, 2H), 3.11 (m, 1H) | 478.3, 480.3 [M + H]⁺ |
| 377 | (structure) | 6 | Ex 37, 130, 158, 354, 369, 399 | DMSO + D₂O: 8.93 (s, 1H), 7.70 (d, J = 6.4 Hz, 2H), 7.56 (d, J = 6.4 Hz, 2H), 7.44 (s, 1H), 7.00 (s, 1H), 6.97 (s, 1H), 6.88 (s, 1H), 4.16 (t, J = 7.2 Hz, 2H), 4.05 (s, 2H), 3.93 (s, 2H), 3.35 (m, 1H), 3.25 (m, 1H), 3.13 (m, 3H), 3.02 (m, 2H), 2.90 (m, 1H), 2.50 (m, 1H), 2.13 (m, 1H), 1.65 (m, 1H), 1.27 (s, 9H) | 526.4 [M + H]⁺ |
| 378 | (structure) | 5 | Ex 37, 119, 130, 158, 263 | DMSO + D₂O: 8.75 (d, J = 2.0 Hz, 1H), 8.22 (dd, J = 2.4 Hz, 8.4 Hz, 1H), 7.66 (s, 1H), 7.61 (s, 1H), 7.54 (d, J = 8.8 Hz, 1H), 7.33 (s, 1H), 6.07 (m, 1H), 5.43 (m, 1H), 5.31 (m, 1H), 4.67 (m, 2H), 4.21 (s, 2H), 3.35 (m, 1H), 3.25 (m, 1H), 3.15 (m, 1H), 3.10 (m, 2H), 2.88 (m, 1H), 2.58 (m, 1H), 2.11 (m, 1H), 1.67 (m, 1H) | 401.3 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 379 | | 5 | Ex 37, 119, 130, 158, 263 | DMSO + D$_2$O: 9.20 (t, J = 6.0 Hz, 1H), 8.36 (d, J = 2.0 Hz, 1H), 7.77 (dd, J = 2.4 Hz, 8.0 Hz, 1H), 7.56 (s, 1H), 7.49 (m, 2H), 7.26 (s, 1H), 6.04 (m, 1H), 5.40 (m, 1H), 5.29 (m, 1H), 4.63 (m, 2H), 4.48 (m, 2H), 4.16 (m, 2H), 3.35 (m, 1H), 3.25 (m, 1H), 3.15 (m, 1H), 3.10 (m, 2H), 2.88 (m, 1H), 2.57 (m, 1H), 2.13 (m, 1H), 1.67 (m, 1H) | 415.3 [M + H]$^+$ |
| 380 | | 5 | Ex 37, 119, 130, 158, 263 | DMSO + D$_2$O: 7.76 (d, J = 2.0 Hz, 1H), 7.60 (s, 1H), 7.55 (s, 1H), 7.45 (dd, J = 2.0 Hz, 8.4 Hz, 1H), 7.31 (d, J = 8.4 Hz, 1H), 7.28 (s, 1H), 6.05 (m, 1H), 5.42 (m, 1H), 5.30 (m, 1H), 4.63 (m, 2H), 4.48 (s, 2H), 4.17 (s, 2H), 3.35 (m, 1H), 3.25 (m, 1H), 3.13 (m, 1H), 3.07 (m, 2H), 2.88 (m, 1H), 2.57 (m, 1H), 2.12 (m, 1H), 1.62 (m, 1H) | 492.2, 494.2 [M + H]$^+$ |
| 381 | | 3 | Ex 37, 130, 136, 158, 168, 183 | DMSO + D$_2$O: 7.82 (m, 2H), 7.51 (dd, J = 2.4 Hz, 8.8 Hz, 1H), 7.23-7.42 (m, 4H), 7.12 (s, 1H), 5.13 (s, 2H), 4.16 (s, 2H), 3.36 (m, 1H), 3.25 (m, 1H), 3.13 (m, 1H), 3.06 (m, 2H), 2.88 (m, 1H), 2.58 (m, 1H), 2.13 (m, 1H), 1.65 (m, 1H) | 519.3, 521.3 [M + H]$^+$ |
| 382 | | 1 | Ex 37 & 387 | DMSO + D$_2$O: 7.82 (d, J = 2.0 Hz, 1H), 7.59 (d, J = 8.4 Hz, 1H), 7.52 (dd, J = 2.0 Hz, 8.4 Hz, 1H), 6.75 (m, 3H), 5.11 (s, 2H), 4.34 (s, 2H), 4.04 (m, 2H), 3.91 (m, 2H), 3.75 (m, 2H), 3.58 (m, 2H), 3.51 (m, 1H), 2.89 (s, 6H), 2.00 (m, 1H), 0.96 (d, J = 6.8 Hz, 6H) | 495.3, 497.3 [M]$^+$ |
| 383 | | 5 | Ex 37, 119, 130, 158, 263 | DMSO + D$_2$O: 7.77 (m, 2H), 7.33 (s, 1H), 6.82 (s, 1H), 6.10 (m, 1H), 5.43 (m, 1H), 5.31 (m, 1H), 4.70 (m, 2H), 4.19 (s, 2H), 3.35 (m, 1H), 3.25 (m, 1H), 3.15 (m, 1H), 3.10 (m, 2H), 2.88 (m, 1H), 2.57 (m, 1H), 2.13 (m, 1H), 1.68 (m, 1H), 1.28 (s, 9H) | 429.4 [M + H]$^+$ |
| 384 | | 6 | Ex 23, 37, 119, 130 | DMSO + D$_2$O: 7.92 (d, J = 8.0 Hz, 1H), 7.85 (d, J = 2.0 Hz, 1H), 7.55 (m, 2H), 7.20 (d, J = 2.0 Hz, 1H), 7.10 (dd, J = 2.0 Hz, 8.0 Hz, 1H), 6.07 (m, 1H), 5.41 (m, 1H), 5.26 (m, 1H), 4.62 (m, 2H), 4.13 (m, 2H), 3.37 (m, 1H), 3.25 (m, 1H), 3.13 (m, 1H), 3.05 (m, 2H), 2.88 (m, 1H), 2.57 (m 1H), 2.13 (m, 1H), 1.65 (m, 1H) | 478.2, 480.2 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 385 | | 6 | Ex 23, 37, 119, 130 | DMSO + D$_2$O: 8.88 (d, J = 2.0 Hz, 1H), 8.30 (dd, J = 2.0 Hz, 8.4 Hz, 1H), 7.70 (m, 2H), 7.22 (d, J = 2.0 Hz, 1H), 7.08 (d, J = 8.4 Hz, 1H), 6.05 (m, 1H), 5.39 (m, 1H), 5.25 (m, 1H), 4.62 (m, 2H), 4.13 (m, 2H), 3.37 (m, 1H), 3.25 (m, 1H), 3.13 (m, 1H), 3.05 (m, 2H), 2.88 (m, 1H), 2.57 (m, 1H), 2.15 (m, 1H), 1.65 (m, 1H) | 401.3 [M + H]$^+$ |
| 386 | | 6 | Ex 23, 37, 119, 130 | DMSO + D$_2$O: 8.27 (d, J = 8.0 Hz, 1H), 7.72 (s, 1H), 7.27 (d, J = 2.0 Hz, 1H), 7.13 (dd, J = 2.0 Hz, 8.0 Hz, 1H), 6.15 (m, 1H), 5.56 (m, 1H), 5.37 (m, 1H), 4.68 (m, 2H), 4.12 (m, 2H), 3.37 (m, 1H), 3.25 (m, 1H), 3.13 (m, 1H), 3.05 (m, 2H), 2.88 (m, 1H), 2.57 (m, 1H), 2.15 (m, 2H), 1.65 (m, 1H), 1.02 (m, 2H), 0.85 (m, 2H) | 413.3 [M + H]$^+$ |
| 387 | | 1 | Ex 37 & 158 | DMSO + D$_2$O: 7.81 (d, J = 2.0 Hz, 1H), 7.59 (d, J = 8.0 Hz, 1H), 7.51 (dd, J = 2.0 Hz, 8.0 Hz, 1H), 6.75 (m, 3H), 5.11 (s, 2H), 4.41 (s, 2H), 3.75 (m, 2H), 3.50 (m, 3H), 3.29 (m, 1H), 3.05 (m, 1H), 2.97 (s, 3H), 2.96 (s, 3H), 2.90 (m, 2H), 2.29 (m, 1H), 1.97 (m, 1H), 1.64 (m, 1H), 0.96 (d, J = 6.8 Hz, 6H) | 509.3, 511.3 [M]$^+$ |
| 388 | | 1 | Ex 37 & 387 | DMSO + D$_2$O: 7.81 (d, J = 2.0 Hz, 1H), 7.59 (d, J = 8.4 Hz, 1H), 7.51 (dd, J = 2.0 Hz, 8.0 Hz, 1H), 6.78 (m, 3H), 6.01 (m, 1H), 5.39 (m, 1H), 5.27 (m, 1H), 5.12 (s, 2H), 4.59 (m, 2H), 4.43 (s, 2H), 3.53 (m, 1H), 3.47 (m, 2H), 3.29 (m, 1H), 3.08 (m, 1H), 2.98 (s, 3H), 2.97 (s, 3H), 2.90 (m, 2H), 2.29 (m, 1H), 1.66 (m, 1H) | 493.2, 495.2 [M]$^+$ |
| 389 | | 1 | Ex 37, 130, 354, 387 | DMSO + D$_2$O: 8.92 (d, J = 1.2 Hz, 1H), 7.82 (d, J = 2.0 Hz, 1H), 7.58 (d, J = 8.4 Hz, 1H), 7.52 (dd, J = 2.0 Hz, 8.4 Hz, 1H), 7.45 (d, J = 1.2 Hz, 1H), 6.80 (m, 2H), 6.73 (s, 1H), 5.11 (s, 2H), 4.34 (s, 2H), 4.24 (t, J = 6.0 Hz, 2H), 4.06 (m, 2H), 3.92 (m, 2H), 3.60 (m, 2H), 3.55 (m, 1H), 2.13 (t, J = 6.0 Hz, 2H), 2.88 (s, 6H) | 533.2, 535.2 [M]$^+$ |
| 390 | | 3 | Ex 37, 130, 136, 158, 168, 183 | DMSO + D$_2$O: 7.85 (d, J = 8.8 Hz, 1H), 7.79 (d, J = 2.0 Hz, 1H), 7.51(dd, J = 2.0 Hz, 8.8 Hz, 1H), 7.38 (d, J = 16.0 Hz, 1H), 7.36 (s, 1H), 7.26 (d, J = 16.0 Hz, 1H), 7.17 (s, 1H), 7.07 (s, 1H), 4.23 (t, J = 6.0 Hz, 2H), 4.15 (s, 2H), 3.37 (m, 1H), 3.25 (m, 1H), 3.15 (m, 1H), 3.07 (m, 2H), 2.90 (m, 1H), 2.60 (m, 3H), 2.15 (m, 1H), 1.65 (m, 1H) | 492.2, 494.2 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 391 | | 6 | Ex 37, 119, 130, 158, 354, 399 | DMSO + D₂O: 8.97 (s, 1H), 7.55 (s, 1H), 7.49 (s, 1H), 7.12 (s, 1H), 7.01 (s, 1H), 6.95 (s, 1H), 4.42 (s, 2H), 4.24 (t, J = 6.0 Hz, 2H), 4.08 (s, 2H), 3.35 (m, 1H), 3.23 (m, 1H), 3.14 (m, 3H), 3.05 (m, 2H), 2.92 (m, 1H), 2.52 (m, 1H), 2.14 (m, 2H), 1.67 (m, 1H), 0.94 (m, 2H), 0.85 (m, 2H) | 481.3 [M + H]⁺ |
| 392 | | 5 | Ex 37, 51, 119, 130, 158, 263 | DMSO + D₂O: 7.73 (m, 2H), 7.39 (d, J = 1.6 Hz, 1H), 6.82 (s, 1H), 6.08 (m, 1H), 5.42 (m, 1H), 5.30 (m, 1H), 4.70 (m, 2H), 4.16 (s, 2H), 4.00 (m, 2H), 3.85 (m, 2H), 3.25 (m, 2H), 3.16 (m, 1H), 1.28 (s, 9H) | 415.3 [M + H]⁺ |
| 393 | | 6 | Ex 37, 119, 130, 158, 354, 399 | DMSO + D₂O: 8.96 (s, 1H), 7.80 (d, J = 2.0 Hz, 1H), 7.53 (dd, J = 2.0 Hz, 8.4 Hz, 1H), 7.47 (m, 2H), 7.10 (s, 1H), 7.04 (s, 1H), 6.98 (s, 1H), 4.41 (s, 2H), 4.24 (t, J = 6.4 Hz, 2H), 4.09 (s, 2H), 3.35 (m, 1H), 3.22 (m, 1H), 3.14 (m, 3H), 3.05 (m, 2H), 2.92 (m, 1H), 2.65 (m, 1H), 2.12 (m, 1H), 1.65 (m, 1H) | 546.2, 548.2 [M + H]⁺ |
| 394 | | 5 | Ex 158 | DMSO + D₂O: 7.83 (s, 1H), 7.62 (m, 2H), 7.53 (m, 2H), 7.35 (s, 1H), 6.07 (m, 1H), 5.40 (m, 1H), 5.30 (m, 1H), 4.66 (m, 2H), 4.16 (s, 2H), 4.00 (m, 2H), 3.84 (m, 2H), 3.26 (m, 2H), 3.15 (m, 1H) | 464.2, 466.2 [M + H]⁺ |
| 395 | | 1 | Ex 37 & 387 | DMSO + D₂O: 7.84 (d, J = 2.0 Hz, 1H), 7.62 (d, J = 8.0 Hz, 1H), 7.51 (dd, J = 2.0 Hz, 8.0 Hz, 1H), 6.78 (m, 2H), 6.75 (s, 1H), 6.02 (m, 1H), 5.39 (m, 1H), 5.27 (m, 1H), 5.12 (s, 2H), 4.59 (m, 2H), 4.36 (s, 2H), 4.06 (m, 2H), 3.92 (m, 2H), 3.59 (m, 2H), 3.56 (m, 1H), 2.89 (s, 6H) | 479.2, 481.2 [M]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 396 | (structure) | 3 | Ex 37, 158, 168, 387 | DMSO + D₂O: 7.82 (d, J = 8.4 Hz, 1H), 7.78 (d, J = 2.0 Hz, 1H), 7.49 (dd, J = 2.0 Hz, 8.4 Hz, 1H), 7.34-7.41 (m, 3H), 7.25 (d, J = 16.4 Hz, 1H), 7.10 (s, 1H), 6.03 (m, 1H), 5.44 (m, 1H), 5.29 (m, 1H), 4.65 (m, 2H), 4.50 (s, 2H), 3.52 (m, 3H), 3.30 (m, 1H), 3.11 (m, 1H), 3.01 (s, 3H), 2.99 (s, 3H), 2.92 (m, 2H), 2.33 (m, 1H), 1.68 (m, 1H) | 489.2, 491.2 [M]⁺ |
| 397 | (structure) | 3 | Ex 37, 136, 168, 399 | DMSO: 9.32 (br, 4H), 7.93 (d, J = 2.2 Hz, 1H), 7.83 (d, J = 8.6 Hz, 1H), 7.78 (d, J = 2.0 Hz, 1H), 7.60 (td, J = 2.2 Hz, 8.6 Hz, 2H), 7.33 (s, 2H), 7.15 (d, J = 8.6 Hz, 1H), 4.17 (m, 2H), 3.88 (d, J = 6.5 Hz, 2H), 3.40 (m, 1H), 3.25 (m, 1H), 3.12 (m, 3H), 3.00 (m, 2H), 2.71 (m, 1H), 2.12 (m, 1H), 1.72 (m, 1H), 1.02 (d, J = 6.7 Hz, 6H) | 477.1, 479.1 [M + H]⁺ |
| 398 | (structure) | 3 | Ex 37, 158, 168, 354, 387 | DMSO + D₂O: 8.93 (s, 1H), 7.82 (d, J = 8.4 Hz, 1H), 7.80 (d, J = 2.0 Hz, 1H), 7.50 (m, 2H), 7.40 (d, J = 16.0 Hz, 1H), 7.38 (s, 1H), 7.35 (s, 1H), 7.25 (d, J = 16.4 Hz, 1H), 7.13 (s, 1H), 4.52 (s, 2H), 4.32 (t, J = 6.4 Hz, 2H), 3.54 (m, 3H), 3.31 (m, 1H), 3.16 (t, J = 6.0 Hz, 2H), 3.12 (m, 1H), 3.02 (s, 3H), 3.00 (s, 3H), 2.93 (m, 2H), 2.30 (m, 1H), 1.68 (m, 1H) | 543.1, 545.1 [M]⁺ |
| 399 | (structure) | 6 | Ex 37, 130, 158, 369 | DMSO + D₂O: 8.94 (s, 1H), 7.58 (d, J = 8.4 Hz, 2H), 7.49 (d, J = 8.4 Hz, 2H), 7.46 (s, 1H), 7.33 (d, J = 8.4 Hz, 1H), 7.16 (s, 1H), 7.03 (d, J = 8.4 Hz, 1H), 4.03 (s, 2H), 3.92 (t, J = 6.0 Hz, 2H), 3.35 (m, 1H), 3.25 (m, 1H), 3.10 (m, 1H), 3.00 (m, 4H), 2.87 (m, 1H), 2.60 (m, 1H), 2.10 (m, 1H), 1.65 (m, 1H), 1.22 (s, 9H) | 512.2 [M + H]⁺ |
| 400 | (structure) | 6 | Ex 23, 37, 119, 130, 158, 399 | DMSO + D₂O: 8.93 (s, 1H), 8.19 (d, J = 8.4 Hz, 1H), 7.65 (s, 1H), 7.47 (s, 1H), 7.40 (s, 1H), 7.15 (d, J = 8.4 Hz, 1H), 4.42 (t, J = 6.4 Hz, 2H), 4.13 (s, 2H), 3.38 (m, 1H), 3.25 (m, 3H), 3.14 (m, 1H), 3.05 (m, 2H), 2.92 (m, 1H), 2.65 (m, 1H), 2.15 (m, 2H) 1.68 (m, 1H), 0.96 (m, 2H), 0.70 (m, 2H) | 467.3 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 401 | (structure) | 3 | Ex 37, 136, 168, 399 | DMSO: 9.49 (br, 2H), 9.15 (br, 2H), 7.94 (d, J = 2.2 Hz, 1H), 7.82 (d, J = 8.6 Hz, 1H), 7.77 (d, J = 2.0 Hz, 1H), 7.60 (td, J = 2.2 Hz, 8.6 Hz, 2H), 7.32 (s, 2H), 7.13 (d, J = 8.6 Hz, 1H), 4.14 (t, J = 5.7 Hz, 2H), 4.00 (m, 3H), 3.87 (m, 3H), 3.27 (m, 3H), 2.12 (m, 1H), 1.04 (d, J = 6.7 Hz, 6H) | 463.1, 465.1 [M + H]+ |
| 402 | (structure) | 3 | Ex 37, 158, 168, 387 | DMSO + D2O: 7.83 (d, J = 8.4 Hz, 1H), 7.78 (d, J = 2.0 Hz, 1H), 7.50 (dd, J = 2.0 Hz, 8.4 Hz, 1H), 7.39 (d, J = 16.0 Hz, 1H), 7.34 (s, 2H), 7.25 (d, J = 16.0 Hz, 1H), 7.08 (s, 1H), 6.04 (m, 1H), 5.42 (m, 1H), 5.30 (m, 1H), 4.66 (m, 2H), 4.43 (s, 2H), 4.08 (m, 2H), 3.93 (m, 2H), 3.61 (m, 2H), 3.56 (m, 1H), 2.92 (s, 6H) | 475.2, 477.2 [M]+ |
| 403 | (structure) | 6 | Ex 23, 37, 119, 130, 158, 399 | DMSO + D2O: 8.92 (s, 1H), 7.91 (d, J = 8.4 Hz, 1H), 7.85 (d, J = 2.0 Hz, 1H), 7.61 (dd, J = 2.0 Hz, 8.0 Hz, 1H), 7.47 (m, 2H), 7.39 (s, 1H), 7.13 (d, J = 8.4 Hz, 1H), 4.31 (t, J = 6.0 Hz, 2H), 4.13 (s, 2H), 3.37 (m, 1H), 3.25 (m, 1H), 3.20 (m, 3H), 3.05 (m, 2H), 2.93 (m, 1H), 2.65 (m, 1H), 2.15 (m, 1H), 1.68 (m, 1H) | 532.1, 534.1 [M + H]+ |
| 404 | (structure) | 1 | Ex 37, 130, 354, 387 | DMSO + D2O: 8.88 (s, 1H), 7.81 (d, J = 2.0 Hz, 1H), 7.58 (d, J = 8.4 Hz, 1H), 7.51 (dd, J = 2.0 Hz, 8.4 Hz, 1H), 7.45 (s, 1H), 6.79 (s, 2H), 6.73 (s, 1H), 5.10 (s, 2H), 4.39 (s, 2H), 4.23 (t, J = 6.0 Hz, 2H), 3.40-3.60 (m, 3H), 3.30 (m, 1H), 3.10 (m, 3H), 2.96 (s, 3H), 2.94 (s, 3H), 2.90 (m, 2H), 2.28 (m, 1H), 1.65 (m, 1H) | 547.2, 549.2 [M]+ |
| 405 | (structure) | 1 | Ex 37 | DMSO: 9.40 (br, 4H), 7.82 (d, J = 1.9 Hz, 1H), 7.63 (dd, J = 2.0 Hz, 8.3 Hz, 1H), 7.57 (d, J = 8.3 Hz, 1H), 7.38 (m, 1H), 7.05 (s, 2H), 6.10 (m, 1H), 5.44 (m, 1H), 5.29 (m, 1H), 5.11 (s, 2H), 4.61 (m, 2H), 4.12 (t, J = 5.6 Hz, 2H), 3.38 (m, 1H), 3.23 (m, 1H), 2.92-3.18 (m, 4H), 2.72 (m, 1H), 2.14 (m, 1H), 1.70 (m, 1H) | 465.0, 467.0 [M + H]+ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 406 | 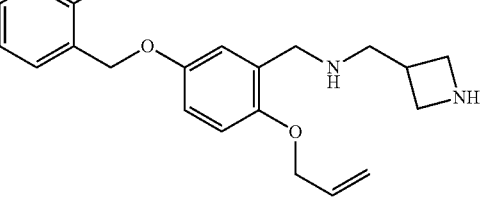 | 1 | Ex 37 | DMSO: 9.42 (br, 2H), 9.07 (br, 2H), 7.82 (d, J = 1.9 Hz, 1H), 7.64 (dd, J = 2.0 Hz, 8.3 Hz, 1H), 7.57 (d, J = 8.3 Hz, 1H), 7.38 (m, 1H), 7.06 (s, 2H), 6.10 (m, 1H), 5.44 (m, 1H), 5.29 (m, 1H), 5.11 (s, 2H), 4.61 (m, 2H), 4.09 (t, J = 5.6 Hz, 2H), 3.97 (m, 2H), 3.87 (m, 2H), 3.24 (m, 3H) | 451.0, 453.0 [M + H]+ |
| 407 | 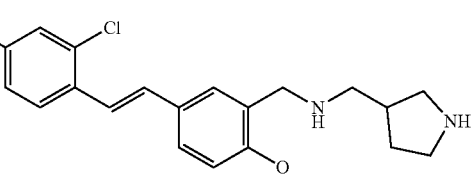 | 3 | Ex 37, 136, 168, 399 | DMSO: 9.35 (br, 4H), 7.93 (d, J = 2.2 Hz, 1H), 7.82 (d, J = 8.6 Hz, 1H), 7.78 (d, J = 2.0 Hz, 1H), 7.61 (td, J = 2.2 Hz, 8.6 Hz, 2H), 7.33 (s, 2H), 7.15 (d, J = 8.7 Hz, 1H), 6.13 (m, 1H), 5.48 (m, 1H), 5.33 (m, 1H), 4.72 (m, 2H), 4.18 (s, 2H), 3.40 (m, 1H), 3.24 (m, 1H), 3.11 (m, 3H), 2.99 (m, 1H), 2.72 (m, 1H), 2.16 (m, 1H), 1.72 (m, 1H) | 461.0, 463.0 [M + H]+ |
| 408 | 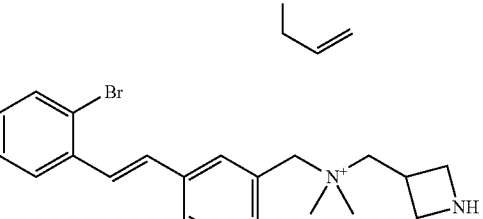 | 3 | Ex 37, 158, 168, 354, 387 | DMSO + D2O: 8.92 (d, J = 1.2 Hz, 1H), 7.80 (m, 2H), 7.50 (m, 2H), 7.30-7.42 (m, 3H), 7.24 (d, J = 16.4 Hz, 1H), 7.07 (s, 1H), 4.43 (s, 2H), 4.31 (t, J = 6.4 Hz, 2H), 4.08 (m, 2H), 3.93 (m, 2H), 3.63 (m, 2H), 3,57 (m, 1H), 3.16 (t, J = 6.0 Hz, 2H), 2.92 (s, 6H) | 529.2, 531.2 [M]+ |
| 409 | 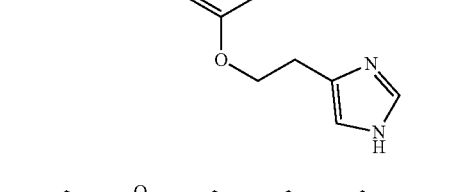 | 1 | Ex 37, 130, 354 | DMSO + D2O: 8.74 (m, 1H), 8.37 (m, 1H), 7.93 (m, 1H), 7.82 (m, 1H), 6.71 (s, 1H), 6.68 (s, 1H), 6.54 (s, 1H), 6.00 (m, 1H), 5.37 (m, 1H), 5.25 (m, 1H), 4.53 (m, 2H), 4.38 (t, J = 6.0 Hz, 2H), 4.01 (m, 4H), 3.83 (m, 2H), 3.43 (t, J = 6.0 Hz, 2H), 3.20 (m, 3H) | 354.2 [M + H]+ |
| 410 | 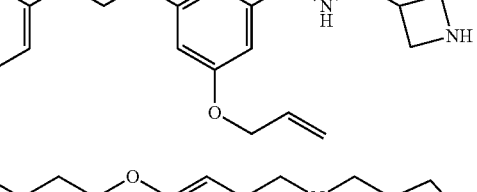 | 1 | Ex 37, 130, 354 | DMSO + D2O: 8.73 (m, 1H), 8.39 (m, 1H), 7.93 (m, 1H), 7.82 (m, 1H), 6.73 (s, 1H), 6.70 (s, 1H), 6.54 (s, 1H), 5.98 (m, 1H), 5.37 (m, 1H), 5.26 (m, 1H), 4.53 (m, 2H), 4.38 (t, J = 6.0 Hz, 2H), 4.04 (s, 2H), 3.43 (t, J = 6.0 Hz, 2H), 3.36 (m, 1H), 3.25 (m, 1H), 3.12 (m, 1H), 3.02 (m, 2H), 2.90 (m, 1H), 2.64 (m, 1H), 2.12 (m, 1H), 1.66 (m, 1H) | 368.3 [M + H]+ |
| 411 | 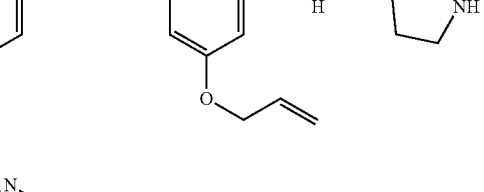 | 1 | Ex 37, 130, 158 | DMSO + D2O: 8.78 (s, 1H), 8.68 (d, J = 5.2 Hz, 1H), 8.26 (d, J = 8.0 Hz, 1H), 7.77 (dd, J = 5.6 Hz, 8.0 Hz, 1H), 6.79 (s, 1H), 6.74 (s, 1H), 6.68 (s, 1H), 6.00 (m, 1H), 5.37 (m, 1H), 5.27 (m, 3H), 4.55 (m, 2H), 4.03 (s, 2H), 3.98 (m, 2H), 3.85 (m, 2H), 3.18 (m, 3H) | 340.3 [M + H]+ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 412 | | 1 | Ex 37 | DMSO: 9.37 (br, 4H), 7.85 (d, J = 2.1 Hz, 1H), 7.63 (d, J = 8.3 Hz, 1H), 7.55 (dd, J = 2.1 Hz, 8.3 Hz, 1H), 7.37 (m, 1H), 7.05 (s, 2H), 6.10 (m, 1H), 5.44 (m, 1H), 5.30 (m, 1H), 5.09 (s, 2H), 4.61 (m, 2H), 4.12 (s, 2H), 3.39 (m, 1H), 3.23 (m, 1H), 2.93-3.17 (m, 4H), 2.72 (m, 1H), 2.14 (m, 1H), 1.70 (m, 1H) | 465.0, 467.0 [M + H]⁺ |
| 413 | | 1 | Ex 37 | DMSO: 9.46 (br, 2H), 9.15 (br, 2H), 7.85 (d, J = 1.9 Hz, 1H), 7.62 (d, J = 8.3 Hz, 1H), 7.54 (dd, J = 1.9 Hz, 8.3 Hz, 1H), 7.36 (s, 1H), 7.05 (s, 2H), 6.10 (m, 1H), 5.44 (m, 1H), 5.30 (m, 1H), 5.09 (s, 2H), 4.61 (m, 2H), 4.09 (m, 2H), 3.97 (m, 2H), 3.86 (m, 2H), 3.25 (m, 3H) | 451.0, 453.0 [M + H]⁺ |
| 414 | | 1 | Ex 37, 130, 354 | DMSO + D₂O: 8.84 (s, 1H), 8.73 (d, J = 5.6 Hz, 1H), 8.50 (d, J = 8.0 Hz, 1H), 7.96 (m, 1H), 6.72 (s, 1H), 6.71 (s, 1H), 6.55 (s, 1H), 6.00 (m, 1H), 5.37 (m, 1H), 5.26 (m, 1H), 4.53 (m, 2H), 4.28 (t, J = 6.4 Hz, 2H), 4.04 (s, 2H), 4.00 (m, 2H), 3.84 (m, 2H), 3.25 (m, 5H) | 354.3 [M + H]⁺ |
| 415 | | 1 | Ex 37 & 130 | DMSO + D₂O: 6.76 (s, 1H), 6.74 (s, 1H), 6.65 (s, 1H), 6.31 (s, 1H), 6.02 (m, 1H), 5.38 (m, 1H), 5.26 (m, 1H), 5.12 (s, 2H), 4.55 (m, 2H), 4.06 (s, 2H), 3.37 (m, 1H), 3.25 (m, 1H), 3.13 (m, 1H), 3.02 (m, 2H), 2.90 (m, 1H), 2.60 (m, 1H), 2.39 (s, 3H), 2.13 (m, 1H), 1.65 (m, 1H) | 358.3 [M + H]⁺ |
| 416 | | 1 | Ex 37 | DMSO: 9.41 (br, 4H), 7.85 (d, J = 2.1 Hz, 1H), 7.63 (d, J = 8.3 Hz, 1H), 7.54 (dd, J = 2.1 Hz, 8.3 Hz, 1H), 7.39 (m, 1H), 7.04 (m, 2H), 5.09 (s, 2H), 4.10 (m, 2H), 3.77 (d, J = 6.5 Hz, 2H), 3.39 (m, 1H), 3.25 (m, 1H), 2.92-3.18 (m, 4H), 2.72 (m, 1H), 2.11 (m, 2H), 1.71 (m, 1H), 1.01 (d, J = 6.7 Hz, 6H) | 481.2, 483.2 [M + H]⁺ |
| 417 | | 1 | Ex 37, 130, 158 | DMSO + D₂O: 8.87 (d, J = 1.2 Hz, 1H), 8.75 (dd, J = 1.2 Hz, 5.2 Hz, 1H), 8.36 (d, J = 8.0 Hz, 1H), 7.86 (dd, J = 6.0 Hz, 8.0 Hz, 1H), 6.87 (s, 1H), 6.81 (s, 1H), 6.69 (s, 1H), 6.01 (m, 1H), 5.38 (m, 1H), 5.25 (m, 3H), 4.57 (m, 2H), 4.08 (s, 2H), 3.37 (m, 2H), 3.25 (m, 1H), 3.15 (m, 1H), 3.02 (m, 2H), 2.90 (m, 1H), 2.65 (m, 1H), 2.12 (m, 1H), 1.65 (m, 1H) | 354.2 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 418 | | 1 | Ex 37, 130, 354 | DMSO + D$_2$O: 8.82 (s, 1H), 8.72 (d, J = 5.6 Hz, 1H), 8.47 (d, J = 8.0 Hz, 1H), 7.94 (m, 1H), 6.72 (s, 1H), 6.70 (s, 1H), 6.55 (s, 1H), 6.00 (m, 1H), 5.37 (m, 1H), 5.26 (m, 1H), 4.53 (m, 2H), 4.27 (t, J = 6.0 Hz, 2H), 4.04 (s, 2H), 3.35 (m, 1H), 3.25 (m, 3H), 3.13 (m, 1H), 3.00 (m, 2H), 2.86 (m, 1H), 2.60 (m, 1H), 2.11 (m, 1H), 1.65 (m, 1H) | 368.3 [M + H]$^+$ |
| 419 | | 3 | Ex 37, 136, 168, 399 | DMSO: 9.41 (br, 4H), 7.91 (d, J = 2.2 Hz, 1H), 7.86 (d, J = 8.6 Hz, 1H), 7.81 (d, J = 2.2 Hz, 1H0, 7.61 (dd, J = 2.2 Hz, 8.6 Hz, 1H), 7.51 (dd, J = 2.2 Hz, 8.5 Hz, 1H), 7.27 (s, 2H), 7.15 (d, J = 8.7 Hz, 1H), 6.13 (m, 1H), 5.47 (m, 1H), 5.33 (m, 1H), 4.72 (m, 2H), 4.18 (m, 2H), 3.40 (m, 1H), 3.25 (m, 1H), 3.10 (m, 3H), 3.00 (m, 1H), 2.73 (m, 1H), 2.15 (m, 1H), 1.72 (m, 1H) | 461.1, 463.1 [M + H]$^+$ |
| 420 | | 1 | Ex 37 & 130 | DMSO + D$_2$O: 6.74 (s, 1H), 6.72 (s, 1H), 6.65 (m, 1H), 6.31 (s, 1H), 6.01 (m, 1H), 5.38 (m, 1H), 5.27 (m, 1H), 5.12 (s, 2H), 4.55 (m, 2H), 3.95-4.05 (m, 4H), 3.82 (m, 2H), 3.21 (m, 2H), 3.15 (m, 1H), 2.39 (s, 3H) | 344.2 [M + H]$^+$ |
| 421 | | 3 | Ex 37, 136, 168, 399 | DMSO: 9.29 (br, 2H), 8.99 (br, 2H), 7.86 (m, 2H), 7.82 (d, J = 2.2 Hz, 1H), 7.61 (dd, J = 2.2 Hz, 8.6 Hz, 1H), 7.52 (dd, J = 2.2 Hz, 8.5 Hz, 1H), 7.27 (s, 2H), 7.16 (d, J = 8.7 Hz, 1H), 6.14 (m, 1H), 5.48 (m, 1H), 5.34 (m, 1H), 4.72 (m, 2H), 4.16 (m, 2H), 3.99 (m, 2H), 3.87 (m, 2H), 3.28 (m, 3H) | 447.0, 449.0 [M + H]$^+$ |
| 422 | | 1 | Ex 37 | DMSO: 9.41 (br, 2H), 9.07 (br, 2H), 7.85 (d, J = 2.1 Hz, 1H), 7.62 (d, J = 8.3 Hz, 1H), 7.55 (dd, J = 2.1 Hz, 8.3 Hz, 1H), 7.35 (m, 1H), 7.04 (s, 2H), 5.09 (s, 2H), 4.08 (m, 2H), 3.98 (m, 2H), 3.86 (m, 2H), 3.77 (d, J = 6.5 Hz, 2H), 3.25 (m, 3H), 2.08 (m, 1H), 1.02 (d, J = 6.7 Hz, 6H) | 467.1, 469.1 [M + H]$^+$ |
| 423 | | 1 | Ex 37, 130, 354 | DMSO + D$_2$O: 8.79 (d, J = 6.8 Hz, 2H), 8.01 (d, J = 6.8 Hz, 2H), 6.73 (s, 1H), 6.72 (s, 1H), 6.55 (s, 1H), 6.00 (m, 1H), 5.37 (m, 1H), 5.25 (m, 1H), 4.53 (m, 2H), 4.35 (t, J = 6.4 Hz, 2H), 4.02 (s, 2H), 3.98 (m, 2H), 3.84 (m, 2H), 3.35 (t, J = 6.0 Hz, 2H), 3.18 (m, 3H) | 354.2 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 424 | | 1 | Ex 37, 130, 354 | DMSO + D₂O: 8.80 (d, J = 6.8 Hz, 2H), 8.02 (d, J = 6.8 Hz, 2H), 6.75 (s, 1H), 6.73 (s, 1H), 6.55 (s, 1H), 6.00 (m, 1H), 5.38 (m, 1H), 5.25 (m, 1H), 4.54 (m, 2H), 4.35 (t, J = 6.0 Hz, 2H), 4.04 (s, 2H), 3.35 (m, 3H), 3.25 (m, 1H), 3.12 (m, 1H), 3.00 (m, 2H), 2.89 (m, 1H), 2.65 (m, 1H), 2.13 (m, 1H), 1.65 (m, 1H) | 368.3 [M + H]⁺ |
| 425 | | 1 | Ex 37 & 354 | DMSO + D₂O: 8.87 (s, 1H), 8.77 (m, 3H), 8.40 (d, J = 8.0 Hz, 1H), 8.02 (d, J = 6.4 Hz, 2H), 7.91 (m, 1H), 6.86 (s, 1H), 6.78 (s, 1H), 6.68 (s, 1H), 5.27 (s, 2H), 4.36 (t, J = 6.4 Hz, 2H), 4.04 (s, 2H), 4.00 (m, 2H), 3.82 (m, 2H), 3.35 (t, J = 6.0 Hz, 2H), 3.22 (m, 3H) | 405.4 [M + H]⁺ |
| 426 | | 3 | Ex 37, 130, 136, 158, 168, 183 | DMSO + D₂O: 7.82 (d, J = 8.4 Hz, 1H), 7.79 (d, J = 2.4 Hz, 1H), 7.51 (dd, J = 2.4 Hz, 8.4 Hz, 1H), 7.37 (m, 2H), 7.20 (m, 2H), 7.03 (s, 1H), 4.44 (t, J = 6.0 Hz, 2H), 4.13 (s, 2H), 3.30-3.45 (m, 3H), 3.25 (m, 1H), 3.12 (m, 1H), 3.05 (m, 2H), 2.90 (m, 1H), 2.60 (m, 1H), 2.15 (m, 1H), 1.65 (m, 1H) | 517.2, 519.1 [M + H]⁺ |
| 427 | | 1 | Ex 37 & 354 | DMSO + D₂O: 8.93 (s, 1H), 8.83 (m, 3H), 8.47 (d, J = 8.0 Hz, 1H), 8.06 (d, J = 6.8 Hz, 2H), 7.96 (m, 1H), 6.93 (s, 1H), 6.85 (s, 1H), 6.71 (s, 1H), 5.31 (s, 2H), 4.39 (t, J = 6.0 Hz, 2H), 4.09 (s, 2H), 3.40 (m, 3H), 3.25 (m, 1H), 3.15 (m, 1H), 3.05 (m, 2H), 2.95 (m, 1H), 2.69 (m, 1H), 2.18 (m, 1H), 1.68 (m, 1H) | 419.3 [M + H]⁺ |
| 428 | | 1 | Ex 37 & 158 | DMSO + D₂O: 8.94 (s, 1H), 8.82 (d, J = 5.2 Hz, 1H), 8.53 (d, J = 8.4 Hz, 1H), 8.00 (m, 1H), 6.94 (s, 1H), 6.88 (s, 1H), 6.77 (m, 1H), 5.33 (s, 2H), 4.40 (t, J = 4.4 Hz, 2H), 4.07 (s, 2H), 3.95 (m, 4H), 3.85 (m, 2H), 3.72 (m, 2H), 3.56 (t, J = 4.4 Hz, 2H), 3.46 (m, 2H), 3.23 (m, 5H) | 413.3 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 429 | 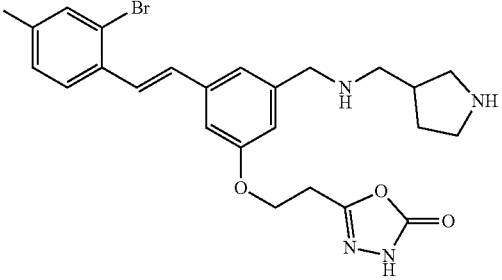 | 3 | Ex 37, 119, 130, 136, 158, 168, 183 | DMSO + $D_2O$: 7.83 (d, J = 8.8 Hz, 1H), 7.78 (d, J = 2.0 Hz, 1H), 7.51 (dd, J = 2.0 Hz, 8.8 Hz, 1H), 7.38 (m, 2H), 7.25 (d, J = 16.4 Hz, 1H), 7.19 (s, 1H), 7.08 (s, 1H), 4.33 (t, J = 6.0 Hz, 2H), 4.14 (s, 2H), 3.37 (m, 1H), 3.25 (m, 1H), 3.15 (m, 1H), 3.05 (m, 4H), 2.90 (m, 1H), 2.62 (m, 1H), 2.15 (m, 1H), 1.65 (m, 1H) | 533.2, 535.2 $[M + H]^+$ |
| 430 | 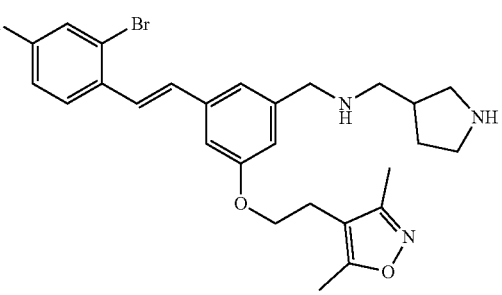 | 3 | Ex 37, 130, 136, 158, 168, 183 | DMSO + $D_2O$: 7.82 (d, J = 8.4 Hz, 1H), 7.78 (d, J = 2.0 Hz, 1H), 7.50 (dd, J = 2.0 Hz, 8.4 Hz, 1H), 7.37 (m, 2H), 7.24 (d, J = 16.4 Hz, 1H), 7.14 (s, 1H), 7.04 (s, 1H), 4.13 (s, 2H), 4.11 (t, J = 6.4 Hz, 2H), 3.37 (m, 1H), 3.25 (m, 1H), 3.15 (m, 1H), 3.05 (m, 2H), 2.90 (m, 1H), 2.78 (t, J = 6.4 Hz, 2H), 2.60 (m, 1H), 2.34 (s, 3H), 2.21 (s, 3H), 2.15 (m, 1H), 1.65 (m, 1H) | 544.2, 546.2 $[M + H]^+$ |
| 431 | 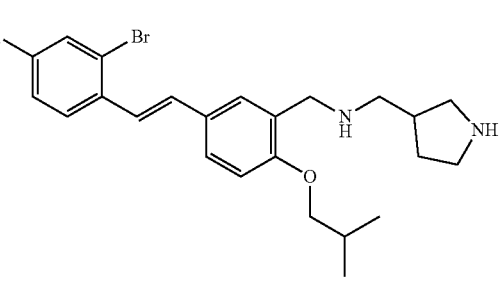 | 3 | Ex 37 & 136, 168, 399 | DMSO: 9.45 (br, 4H), 7.92 (m, 1H), 7.86 (d, J = 8.6 Hz, 1H), 7.81 (m, 1H), 7.60 (m, 1H), 7.51 (m, 1H), 7.27 (s, 2H), 7.14 (d, J = 8.6 Hz, 1H), 4.16 (m, 2H), 3.87 (d, J = 6.5 Hz, 2H), 3.40 (m, 1H), 3.24 (m, 1H), 3.11 (m, 3H), 2.99 (m, 1H), 2.73 (m, 1H), 2.14 (m, 2H), 1.72 (m, 1H), 1.04 (d, J = 6.7 Hz, 6H) | 477.1, 479.1 $[M + H]^+$ |
| 432 | 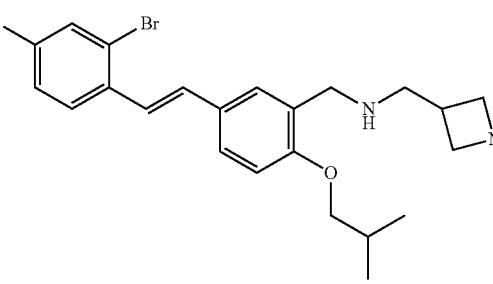 | 3 | Ex 37, 136, 168, 399 | DMSO: 9.36 (br, 2H), 9.03 (br, 2H), 7.85 (m, 3H), 7.61 (dd, J = 2.2 Hz, 8.6 Hz, 1H), 7.51 (dd, J = 2.2 Hz, 8.5 Hz, 1H), 7.27 (s, 2H), 7.14 (d, J = 8.7 Hz, 1H), 4.14 (m, 2H), 3.99 (m, 3H), 3.87 (m, 3H), 3.27 (m, 3H), 2.13 (m, 1H), 1.04 (d, J = 6.7 Hz, 6H) | 463.2, 465.2 $[M + H]^+$ |
| 433 | 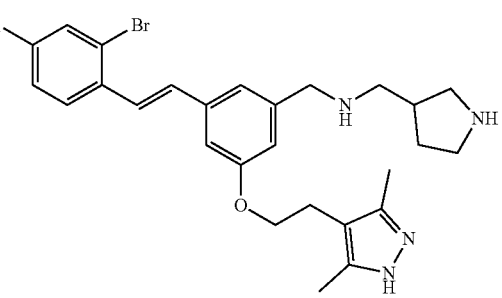 | 3 | Ex 37, 130, 136, 158, 168, 183, 354 | DMSO + $D_2O$: 7.83 (d, J = 8.4 Hz, 1H), 7.79 (d, J = 2.0 Hz, 1H), 7.51 (dd, J = 2.0 Hz, 8.4 Hz, 1H), 7.37 (m, 2H), 7.24 (d, J = 16.0 Hz, 1H), 7.14 (s, 1H), 7.06 (s, 1H), 4.13 (s, 2H), 4.08 (t, J = 6.0 Hz, 2H), 3.37 (m, 1H), 3.25 (m, 1H), 3.12 (m, 1H), 3.07 (m, 2H), 2.90 (m, 1H), 2.85 (t, J = 6.0 Hz, 2H), 2.63 (m, 1H), 2.26 (s, 6H), 2.15 (m, 1H), 1.65 (m, 1H) | 543.2, 545.2 $[M + H]^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 434 | | 2 & 5 | Ex 37 & 130 | DMSO + D₂O: 7.92 (d, J = 6.8 Hz, 1H), 6.96 (m, 1H), 6.88 (m, 1H), 6.80 (m, 3H), 6.66 (m, 1H), 6.03 (m, 1H), 5.39 (m, 1H), 5.26 (m, 1H), 4.75 (s, 2H), 4.57 (m, 2H), 4.08 (s, 2H), 3.36 (m, 1H), 3.23 (m, 1H), 3.11 (m, 1H), 3.04 (m, 2H), 2.90 (m, 1H), 2.61 (m, 1H), 2.13 (m, 1H), 1.65 (m, 1H) | 412.2 [M + H]⁺ |
| 435 | | 1 | Ex 37, 130, 354 | DMSO + D₂O: 9.01 (d, J = 2.0 Hz, 1H), 8.95 (d, J = 2.4 Hz, 1H), 8.40 (d, J = 2.0 Hz, 1H), 6.63 (s, 1H), 6.57 (s, 1H), 6.51 (s, 1H), 6.02 (m, 1H), 5.38 (m, 1H), 5.24 (m, 1H), 5.19 (s, 2H), 4.54 (m, 2H), 3.63 (s, 2H), 3.21 (m, 1H), 3.13 (m, 1H), 3.05 (m, 1H), 2.77 (m, 1H), 2.45 (m, 2H), 2.33 (m, 1H), 1.96 (m, 1H), 1.53 (m, 1H) | 379.5 [M + H]⁺ |
| 436 | | 1 | Ex 37, 130, 354 | DMSO + D₂O: 8.96 (d, J = 2.0 Hz, 1H), 8.90 (d, J = 2.0 Hz, 1H), 8.33 (t, J = 2.0 Hz, 1H), 6.73 (s, 1H), 6.69 (s, 2H), 6.00 (m, 1H), 5.36 (m, 1H), 5.25 (m, 1H), 5.20 (s, 2H), 4.55 (m, 2H), 4.04 (s, 2H), 3.99 (m, 2H), 3.80 (m, 2H), 3.20 (m, 2H), 3.12 (m, 1H) | 365.6 [M + H]⁺ |
| 437 | | 1 | Ex 37, 130, 354 | DMSO + D₂O: 8.97 (d, J = 2.0 Hz, 1H), 8.77 (d, J = 2.0 Hz, 1H), 8.26 (t, J = 2.0 Hz, 1H), 6.74 (s, 1H), 6.69 (s, 1H), 6.68 (s, 1H), 6.00 (m, 1H), 5.36 (m, 1H), 5.25 (m, 1H), 5.22 (s, 2H), 4.54 (m, 2H), 4.04 (s, 2H), 3.98 (m, 2H), 3.82 (m, 2H), 3.21 (m, 2H), 3.14 (m, 1H) | 383.2 [M + H]⁺ |
| 438 | | 3 | Ex 37, 130, 158, 168, 354 | DMSO + D₂O: 8.82 (s, 1H), 8.74 (d, J = 6.8 Hz, 2H), 8.55 (m, 1H), 8.25 (m, 1H), 7.89 (d, J = 6.0 Hz, 2H), 7.62 (m, 1H), 7.43 (d, J = 16.4 Hz, 1H), 7.33 (m, 2H), 7.27 (s, 1H), 7.00 (s, 1H), 4.40 (t, J = 6.0 Hz, 2H), 4.10 (s, 2H), 3.99 (m, 2H), 3.83 (m, 2H), 3.33 (t, J = 6.0 Hz, 2H), 3.25 (m, 2H), 3.16 (m, 1H) | 401.3 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 439 | | 3 | Ex 37, 130, 158, 168, 354 | DMSO + D$_2$O: 8.81 (s, 1H), 8.73 (d, J = 6.8 Hz, 2H), 8.55 (m, 1H), 8.28 (m, 1H), 7.90 (d, J = 6.8 Hz, 2H), 7.64 (m, 1H), 7.41 (d, J = 16.8 Hz, 1H), 7.34 (m, 2H), 7.27 (s, 1H), 7.01 (s, 1H), 4.40 (t, J = 6.0 Hz, 2H), 4.12 (s, 2H), 3.35 (m, 3H), 3.25 (m, 1H), 3.15 (m, 1H), 3.05 (m, 2H), 2.88 (m, 1H), 2.59 (m, 1H), 2.15 (m, 1H), 1.65 (m, 1H) | 415.3 [M + H]$^+$ |
| 440 | | 3 | Ex 37, 130, 158 | DMSO + D$_2$O: 8.99 (s, 1H), 8.67 (m, 2H), 7.94 (m, 1H), 7.56 (d, J = 16.4 Hz, 1H), 7.44 (m, 2H), 7.35 (s, 1H), 7.25 (s, 1H), 4.46 (t, J = 4.8 Hz, 2H), 4.17 (s, 2H), 3.98 (m, 2H), 3.79 (m, 2H), 3.59 (t, J = 4.8 Hz, 2H), 3.50 (m, 2H), 3.40 (m, 1H), 3.25 (m, 3H), 3.15 (m, 3H), 2.95 (m, 1H), 2.67 (m, 1H), 2.17 (m, 1H), 1.69 (m, 1H) | 423.3 [M + H]$^+$ |
| 441 | | 3 | Ex 37, 130, 158, 168 | DMSO: 9.71 (br, 2H), 9.39 (br, 2H), 9.11 (d, J = 2.1 Hz, 1H), 8.98 (d, J = 1.9 Hz, 1H), 8.66 (t, J = 2.1 Hz, 1H), 8.01 (d, J = 16.1 Hz, 1H), 7.61 (d, J = 16.1 Hz, 1H), 7.27 (d, J = 2.2 Hz, 1H), 7.19 (d, J = 2.2 Hz, 1H), 6.10 (m, 1H), 5.48 (m, 1H), 5.36 (m, 1H), 4.77 (m, 2H), 4.33 (m, 2H), 3.43 (m, 1H), 3.08-3.30 (m, 4H), 3.03 (m, 1H), 2.80 (m, 1H), 2.18 (m, 1H), 1.76 (m, 1H) | 376.3 [M + H]$^+$ |
| 442 | | 3 | Ex 37, 130, 158 | DMSO + D$_2$O: 8.85 (s, 1H), 8.59 (s, 1H), 8.23 (d, J = 8.1 Hz, 1H), 7.61 (m, 1H), 7.25-7.45 (m, 4H), 7.12 (s, 1H), 4.44 (t, J = 4.9 Hz, 2H), 4.16 (s, 2H), 4.02 (m, 4H), 3.87 (m, 4H), 3.40-3.70 (m, 6H), 3.30 (m, 2H), 3.22 (m, 1H) | 409.3 [M + H]$^+$ |
| 443 | | 3 | Ex 37, 119, 158, 168 | DMSO + D$_2$O: 7.83 (d, J = 8.8 Hz, 1H), 7.87 (d, J = 2.0 Hz, 1H), 7.49 (dd, J = 2.0 Hz, 8.4 Hz, 1H), 7.36 (m, 2H), 7.23 (d, J = 16.4 Hz, 1H), 7.19 (s, 1H), 7.06 (s, 1H), 6.05 (m, 1H), 5.41 (m, 1H), 5.29 (m, 1H), 4.61 (m, 2H), 4.15 (s, 2H), 3.94 (m, 2H), 3.68 (m, 4H), 3.34 (m, 2H), 2.89 (m, 1H) | 504.1, 506.1 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 444 | | 3 | Ex 37, 119, 158, 168, 387 | DMSO + D$_2$O: 8.82 (t, J = 5.6 Hz, 1H), 7.82 (d, J = 8.8 Hz, 1H), 7.79 (d, J = 2.0 Hz, 1H), 7.50 (dd, J = 2.0 Hz, 8.5 Hz, 1H), 7.30-7.42 (m, 3H), 7.26 (d, J = 16.0 Hz, 1H), 7.06 (s, 1H), 6.07 (m, 1H) 5.42 (m, 1H), 5.30 (m, 1H), 4.66 (m, 4H), 3.95 (m, 4H), 3.70 (m, 2H), 3.38 (m, 2H), 3.17 (s, 6H), 2.93 (m, 1H) | 532.1, 534.0 [M + H]$^+$ |
| 445 | | 3 | Ex 37, 119, 158, 168, 263, 399 | DMSO + D$_2$O: 7.85 (d, J = 8.1 Hz, 1H), 7.79 (d, J = 2.0 Hz, 1H), 7.74 (s, 1H), 7.50 (dd, J = 2.3 Hz, 8.5 Hz, 1H), 7.40 (m, 2H), 7.30 (m, 2H), 6.05 (m, 1H), 5.42 (m, 1H), 5.29 (m, 1H), 4.66 (m, 2H), 3.90 (m, 4H), 3.72 (m, 2H), 3.30 (m, 2H), 2.92 (m, 1H) | 518.1, 519.8 [M + H]$^+$ |
| 446 | | 3 | Ex 37, 130, 158, 168 | DMSO: 9.67 (br, 2H), 9.34 (br, 2H), 9.10 (d, J = 2.0 Hz, 1H), 8.98 (d, J = 1.8 Hz, 1H), 8.67 (t, J = 2.1 Hz, 1H), 8.00 (d, J = 16.0 Hz, 1H), 7.60 (d, J = 16.1 Hz, 1H), 7.35-7.55 (m, 5H), 7.32 (m, 1H), 7.25 (m, 1H), 5.30 (s, 2H), 4.33 (m, 2H), 3.42 (m, 1H), 3.08-3.30 (m, 4H), 3.02 (m, 1H), 2.79 (m, 1H), 2.18 (m, 1H), 1.76 (m, 1H) | 426.3 [M + H]$^+$ |
| 447 | | 3 | Ex 37, 119, 158, 168, 263, 399 | DMSO + D$_2$O: 7.82 (d, J = 8.4 Hz, 1H), 7.76 (d, J = 2.4 Hz, 1H), 7.74 (s, 1H), 7.50 (dd, J = 2.0 Hz, 8.4 Hz, 1H), 7.35-7.45 (m, 3H), 7.28 (d, J = 16.0 Hz, 1H), 6.05 (m, 1H), 5.42 (m, 1H), 5.28 (m, 1H), 4.67 (m, 2H), 4.05 (m, 4H), 3.90 (m, 4H), 3.63 (m, 2H), 3.45 (m, 4H), 3.30 (m, 2H), 3.16 (m, 2H) | 573.5, 575.4 [M + H]$^+$ |
| 448 | | 3 | Ex 37, 158, 168 | DMSO + D$_2$O: 7.83 (d, J = 8.4 Hz, 1H), 7.79 (d, J = 2.4 Hz, 1H), 7.50 (dd, J = 2.4 Hz, 8.4 Hz, 1H), 7.27-7.40 (m, 2H), 7.20-7.27 (m, 2H), 7.09 (s, 1H), 6.05 (m, 1H), 5.43 (m, 1H), 5.30 (m, 1H), 4.63 (m, 2H), 3.90-4.10 (m, 6H), 3.75 (m, 4H), 3.05-3.35 (m, 6H) | 516.0, 518.0 [M + H]$^+$ |
| 449 | | 3 | Ex 37, 130, 158, 168 | DMSO: 9.65 (br, 2H), 9.36 (br, 2H), 9.04 (d, J = 2.2 Hz, 1H), 8.99 (d, J = 1.9 Hz, 1H), 8.56 (t, J = 2.0 Hz, 1H), 7.51 (m, 3H), 7.31 (m, 2H), 6.11 (m, 1H), 5.47 (m, 1H), 5.32 (m, 1H), 4.67 (m, 2H), 4.14 (m, 2H), 3.39 (m, 1H), 3.24 (m, 1H), 2.95-3.20 (m, 4H), 2.73 (m, 1H), 2.15 (m, 1H), 1.73 (m, 1H) | 394.3 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 450 | | 3 | Ex 37, 119, 158, 168 | DMSO + D$_2$O: 7.83 (d, J = 8.4 Hz, 1H), 7.78 (d, J = 2.0 Hz, 1H), 7.48 (dd, J = 2.0 Hz, 8.4 Hz, 1H), 7.32 (d, J = 16.4 Hz, 1H), 7.22 (m, 2H), 7.05 (s, 1H), 6.93 (s, 1H), 6.04 (m, 1H), 5.41 (m, 1H), 5.27 (m, 1H), 4.59 (m, 2H), 3.96 (m, 4H), 3.75 (s, 2H), 3.49 (m, 1H), 3.23 (t, J = 6.4 Hz, 2H), 2.63 (t, J = 6.4 Hz, 2H) | 504.0, 505.9 [M + H]$^+$ |
| 451 | | 3 | Ex 37, 119, 158, 168, 263, 399 | DMSO + D$_2$O: 7.85 (d, J = 8.4 Hz, 1H), 7.79 (d, J = 2.4 Hz, 1H), 7.71 (s, 1H), 7.50 (dd, J = 2.0 Hz, 8.4 Hz, 1H), 7.33 (m, 3H), 7.29 (d, J = 16.0 Hz, 1H), 6.05 (m, 1H), 5.42 (m, 1H), 5.29 (m, 1H), 4.66 (m, 2H), 4.00 (m, 2H), 3.86 (m, 2H), 3.57 (t, J = 6.0 Hz, 2H), 3.26 (m, 2H), 3.12 (m, 3H) | 504.4, 506.3 [M + H]$^+$ |
| 452 | | 3 | Ex 37, 119, 158, 168, 387 | DMSO + D$_2$O: 9.07 (t, J = 5.8 Hz, Hz, 1H), 7.82 (d, J = 8.6 Hz, 1H), 7.78 (d, J = 2.3 Hz, 1H), 7.49 (dd, J = 2.0 Hz, 8.5 Hz, 1H), 7.32 (d, J = 16.3 Hz, 1H), 7.21 (d, J = 16.3 Hz, 1H), 7.12 (s, 1H), 7.08 (s, 1H), 6.83 (s, 1H), 6.03 (m, 1H), 5.40 (m, 1H), 5.28 (m, 1H), 4.59 (m, 2H), 4.34 (d, J = 5.8 Hz, 2H), 4.05 (m, 4H), 3.90 (m, 2H), 3.82 (m, 2H), 3.46 (m, 1H), 3.14 (s, 6H) | 532.0, 534.0 [M]$^+$ |
| 453 | | 3 | Ex 37, 158, 168 | DMSO + D$_2$O: 7.83 (d, J = 8.8 Hz, 1H), 7.79 (d, J = 2.0 Hz, 1H), 7.50 (dd, J = 2.0 Hz, 8.5 Hz, 1H), 7.39 (m, 2H), 7.23 (m, 2H), 7.12 (s, 1H), 6.05 (m, 1H), 5.44 (m, 1H), 5.29 (m, 1H), 4.63 (m, 2H), 4.21 (s, 2H), 4.00 (m, 2H), 3.87 (m, 2H), 3.28 (m, 6H), 3.14 (m, 1H) | 490.0, 492.0 [M + H]$^+$ |
| 454 | | 3 | Ex 37, 119, 158, 168, 263, 399 | DMSO + D$_2$O: 7.84 (d, J = 8.6 Hz, 1H), 7.78 (d, J = 2.3 Hz, 1H), 7.65 (s, 1H), 7.49 (dd, J = 2.3 Hz, 8.5 Hz, 1H), 7.38 (d, J = 16.3 Hz, 1H), 7.23-7.33 (m, 3H), 6.05 (m, 1H), 5.41 (m, 1H), 5.29 (m, 1H), 4.64 (m, 2H), 4.00 (m, 4H), 3.50 (m, 1H), 3.35 (m, 2H), 3.26 (m, 2H) | 518.0, 519.9 [M + H]$^+$ |
| 455 | | 3 | Ex 37, 158, 168 | DMSO + D$_2$O: 7.83 (d, J = 8.4 Hz, 1H), 7.78 (d, J = 2.0 Hz, 1H), 7.50 (dd, J = 2.0 Hz, 8.4 Hz, 1H), 7.38 (m, 2H), 7.20-7.30 (m, 2H), 7.12 (s, 1H), 6.05 (m, 1H), 5.42 (m, 1H), 5.29 (m, 1H), 4.64 (m, 2H), 4.17 (s, 2H), 4.00 (m, 4H), 3.73 (m, 4H), 3.23 (m, 2H), 3.12 (m, 2H), 2.96 (m, 6H) | 559.3, 561.2 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 456 | | 3 | Ex 37, 119, 158, 168, 263, 399 | DMSO + D$_2$O: 7.82 (d, J = 8.4 Hz, 1H), 7.80 (d, J = 2.0 Hz, 1H), 7.50 (dd, J = 2.4 Hz, 8.8 Hz, 1H), 7.43 (m, 3H), 7.27 (d, J = 16.4 Hz, 1H), 7.12 (s, 1H), 6.05 (m, 1H), 5.43 (m, 1H), 5.31 (m, 1H), 4.66 (m, 2H), 3.83 (m, 2H), 3.30-3.60 (m, 9H), 3.15 (m, 2H), 2.30 (m, 1H) | 530.3, 532.3 [M + H]$^+$ |
| 457 | | 3 | Ex 37, 130, 158, 168 | DMSO + D$_2$O: 9.01 (d, J = 2.0 Hz, 1H), 8.96 (d, J = 2.0 Hz, 1H), 8.52 (t, J = 2.0 Hz, 1H), 7.35-7.50 (m, 3H), 7.30 (s, 1H), 7.11 (s, 1H), 6.07 (m, 1H), 5.44 (m, 1H), 5.29 (m, 1H), 4.64 (m, 2H), 4.14 (s, 2H), 3.91 (s, 3H), 3.38 (m, 1H), 3.25 (m, 1H), 3.02-3.18 (m, 3H), 2.92 (m, 1H), 2.65 (m, 1H), 2.15 (m, 1H), 1.68 (m, 1H) HPLC: 473 min | 408.3 [M + H]$^+$ |
| 458 | | 3 | Ex 37, 130, 158, 168, 399 | DMSO: 9.74 (br, 2H), 9.45 (br, 2H), 9.04 (d, J = 2.0 Hz, 1H), 8.99 (d, J = 2.0 Hz, 1H), 8.81 (m, 1H), 8.48 (m, 1H), 7.85 (m, 1H), 7.61 (d, J = 16.5 Hz, 1H), 7.48 (m, 2H), 7.34 (s, 1H), 7.30 (s, 1H), 6.11 (m, 1H), 5.47 (m, 1H), 5.32 (m, 1H), 4.67 (m, 2H), 4.15 (t, J = 5.7 Hz, 2H), 3.39 (m, 1H), 3.23 (m, 1H), 2.95-3.18 (m, 4H), 2.75 (m, 1H), 2.15 (m, 1H), 1.73 (m, 1H) | 393.3 [M + H]$^+$ |
| 459 | | 3 | Ex 37, 158, 168, 387 | DMSO + D$_2$O: 8.75 (s, 1H), 8.47 (s, 1H), 8.05 (d, J = 8.0 Hz, 1H), 7.44 (m, 1H), 7.35 (m, 4H), 7.05 (s, 1H), 4.50 (s, 2H), 3.82 (d, J = 6.4 Hz, 2H), 3.48 (m, 3H), 3.24 (m, 1H), 3.06 (m, 1H), 2.99 (m, 6H), 2.83 (m, 2H), 2.28 (m, 1H), 2.03 (m, 1H), 1.65 (m, 1H), 0.99 (d, J = 6.8 Hz, 6H) HPLC: 3.92 min | 394.4 [M]$^+$ |
| 460 | | 3 | Ex 37, 158, 168, 387 | DMSO: 9.05 (d, J = 2.2 Hz, 1H), 8.99 (br, 2H), 8.94 (d, J = 1.9 Hz, 1H), 7.61 (t, J = 2.1 Hz, 1H), 7.59 (d, J = 16.5 Hz, 1H), 7.42 (m, 2H), 7.31 (s, 1H), 7.14 (s, 1H), 4.54 (m, 2H), 3.87 (d, J = 6.5 Hz, 2H), 3.50 (m, 4H), 3.05 (m, 7H), 2.94 (m, 2H), 2.33 (m, 1H), 2.08 (m, 1H), 1.69 (m, 1H), 1.04 (d, J = 6.7 Hz, 6H) | 419.4 [M]$^+$ |
| 461 | | 3 | Ex 37, 130, 158, 168 | DMSO: 9.76 (br, 2H), 9.43 (br, 2H), 8.98 (d, J = 1.7 Hz, 1H), 8.69 (s, 1H), 8.64 (s, 1H), 7.56 (m, 3H), 7.36 (s, 1H), 7.30 (s, 1H), 6.11 (m, 1H), 5.47 (m, 1H), 5.32 (m, 1H), 4.73 (s, 2H), 4.68 (d, J = 5.4 Hz, 2H), 4.15 (m, 2H), 3.38 (m, 1H), 3.24 (m, 1H), 2.95-3.18 (m, 4H), 2.77 (m, 1H), 2.15 (m, 1H), 1.73 (m, 1H) | 380.4 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 462 | | | Ex 37, 130, 158, 168 | DMSO: 9.75 (br, 2H), 9.46 (br, 2H), 8.97 (d, J = 1.9 Hz, 1H), 8.81 (s, J = 1.9 Hz, 1H), 8.77 (d, J = 1.9 Hz, 1H), 7.48 (m, 3H), 7.34 (s, 1H), 7.27 (s, 1H), 6.11 (m, 1H), 5.47 (m, 1H), 5.32 (m, 1H), 4.68 (d, J = 5.4 Hz, 2H), 4.46 (d, J = 4.9 Hz, 2H), 4.15 (t, J = 5.1 Hz, 2H), 3.39 (m, 1H), 3.23 (m, 1H), 2.95-3.18 (m, 4H), 2.77 (m, 7H), 2.15 (m, 1H), 1.73 (m, 1H) | 407.4 [M + H]+ |
| 463 | | 1 | Ex 37, 130, 183, 354, 399 | DMSO: 14.50 (br, 2H), 9.42 (br, 4H), 9.09 (d, J = 1.3 Hz, 1H), 7.85 (d, J = 2.1 Hz, 1H), 7.63 (m, 2H), 7.54 (dd, J = 2.1 Hz, 8.2 Hz, 1H), 7.37 (d, J = 2.1 Hz, 1H), 7.06 (s, 2H), 5.09 (s, 2H), 4.27 (t, J = 6.0 Hz, 2H), 4.04 (s, 2H), 2.95-3.30 (m, 8H), 2.69 (m, 1H), 2.14 (m, 1H), 1.71 (m, 1H) | 519.2, 521.2 [M + H]+ |
| 464 | | 3 | Ex 37, 130, 168, 354, 399 | DMSO: 14.50 (br, 2H), 9.42 (br, 4H), 9.08 (s, 1H), 7.85 (m, 3H), 7.63 (m, 2H), 7.51 (dd, J = 2.0 Hz, 8.5 Hz, 1H), 7.27 (s, 2H), 7.17 (d, J = 8.6 Hz, 1H), 4.37 (t, J = 6.0 Hz, 2H), 4.11 (s, 2H), 2.95-3.30 (m, 8H), 2.72 (m, 1H), 2.15 (m, 1H), 1.72 (m, 1H) | 515.2, 517.2 [M + H]+ |
| 465 | | 1 | Ex 37, 130, 183, 354, 399 | DMSO: 14.85 (br, 1H), 14.40 (br, 1H), 9.45 (br, 2H), 9.19 (br, 2H), 9.11 (d, J = 1.4 Hz, 1H), 7.84 (d, J = 2.1 Hz, 1H), 7.63 (m, 2H), 7.54 (dd, J = 2.1 Hz, 8.3 Hz, 1H), 7.35 (m, 1H), 7.06 (s, 2H), 5.08 (s, 2H), 4.27 (t, J = 6.1 Hz, 2H), 4.01 (m, 4H), 3.87 (m, 2H), 3.21 (m, 5H) | 505.2, 507.2 [M + H]+ |
| 466 | | 3 | Ex 37, 51, 130, 158, 168, 232 | DMSO: 9.71 (br, 2H), 9.39 (br, 2H), 8.89 (s, 1H), 8.74 (br, 5H), 8.64 (s, 1H), 7.47 (m, 3H), 7.32 (s, 1H), 7.27 (s, 1H), 6.11 (m, 1H), 5.47 (m, 1H), 5.32 (m, 1H), 4.68 (m, 2H), 4.17 (m, 2H), 3.39 (m, 1H), 3.24 (m, 1H), 2.95-3.18 (m, 4H), 2.77 (m, 1H), 2.15 (m, 1H), 1.74 (m, 1H) | 379.4 [M + H]+ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 467 | | 3 | Ex 14, 37, 130, 158, 168 | DMSO: 9.80 (br, 2H), 9.51 (br, 2H), 8.99 (s, 1H), 8.72 (s, 1H), 8.48 (s, 1H), 7.62 (d, J = 16.5 Hz, 1H), 7.47 (m, 2H), 7.37 (s, 1H), 7.27 (s, 1H), 6.10 (m, 1H), 5.47 (m, 1H), 5.31 (m, 1H), 4.67 (m, 2H), 4.14 (t, J = 5.6 Hz, 2H), 3.38 (m, 1H), 3.23 (m, 1H), 2.95-3.18 (m, 10H), 2.78 (m, 1H), 2.15 (m, 1H), 1.75 (m, 1H) | 421.4 [M + H]+ |
| 468 | | 6 | Ex 37, 119, 387, 399 | DMSO: 11.12 (s, 1H), 9.80 (br, 1H), 9.65 (br, 1H), 9.37 (dd, J = 0.8 Hz, 2.2 Hz, 1H), 8.93 (dd, J = 1.6 Hz, 5.1 Hz, 1H), 8.74 (dd, J = 1.8 Hz, 8.1 Hz, 1H), 7.86 (m, 1H), 7.72 (s, 1H), 7.65 (s, 1H) 6.99 (s, 1H), 4.59 (m, 2H), 3.81 (d, J = 6.5 Hz, 2H), 3.57 (m, 3H), 3.30 (m, 1H), 3.07 (m, 7H), 2.98 (m, 2H), 2.33 (m, 1H), 2.08 (m, 1H), 1.69 (m, 1H), 1.02 (d, J = 6.7 Hz, 6H) | 411.4 [M]+ |
| 469 | | 6 | Ex 37, 119, 387, 399 | DMSO + D2O: 9.28 (d, J = 2.0 Hz, 1H), 9.19 (d, J = 2.0 Hz, 1H), 8.74 (t, J = 2.0 Hz, 1H), 7.59 (s, 1H), 7.42 (s, 1H), 6.92 (s, 1H), 4.49 (s, 2H), 3.78 (d, J = 6.4 Hz, 2H), 3.40-3.60 (m, 3H), 3.31 (m, 1H), 3.12 (m, 1H), 3.00 (m, 6H), 2.90 (m, 2H), 2.33 (m, 1H), 2.03 (m, 1H), 1.67 (m, 1H), 0.98 (d, J = 6.8 Hz, 6H) HPLC: 3.64 min | 436.4 [M]+ |
| 470 | | 6 | Ex 37, 119, 387, 399 | DMSO + D2O: 9.17 (m, 2H), 8.68 (d, J = 2.0 Hz, 1H), 7.59 (s, 1H), 7.42 (s, 1H), 6.92 (s, 1H), 4.47 (s, 2H), 3.78 (m, 2H), 3.40-3.60 (m, 3H), 3.32 (m, 1H), 3.12 (m, 1H), 3.00 (m, 6H), 2.90 (m, 2H), 2.33 (m, 1H), 2.03 (m, 1H), 1.67 (m, 1H), 0.97 (d, J = 6.8 Hz, 6H) HPLC: 3.08 min | 454.4 [M]+ |
| 471 | | 3 | Ex 37, 130, 168, 354, 399 | DMSO + D2O: 7.81 (d, J = 8.8 Hz, 1H), 7.75 (m, 2H), 7.68 (d, J = 2.0 Hz, 1H), 7.60 (dd, J = 2.0 Hz, 8.4 Hz, 1H), 7.47 (dd, J = 2.4 Hz, 8.4 Hz, 1H), 7.22 (s, 2H), 7.12 (d, J = 8.8 Hz, 1H), 7.03 (s, 1H), 4.25 (t, J = 5.6 Hz, 2H), 4.08 (s, 2H), 4.00 (m, 2H), 3.81 (m, 2H), 3.15-3.30 (m, 3H), 3.00 (t, J = 5.6 Hz, 2H) HPLC: 5.46 min | 501.3, 503.3 [M + H]+ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 472 | | 6 | Ex 37, 119, 130, 158, 354 | DMSO: 9.49 (m, 3H), 9.32 (br, 2H), 9.22 (d, J = 2.1 Hz, 1H), 9.18 (d, J = 2.1 Hz, 1H), 8.84 (t, J = 2.1 Hz, 1H), 8.38 (s, 1H), 7.76 (s, 1H), 7.18 (s, 1H), 7.10 (s, 1H), 6.98 (s, 1H), 4.51 (d, J = 5.9 Hz, 2H), 4.10 (t, J = 5.7 Hz, 2H), 3.78 (d, J = 6.5 Hz, 2H), 3.36 (m, 1H), 3.24 (m, 1H), 3.11 (m, 1H), 2.92-3.07 (m, 3H), 2.70 (m, 1H), 2.12 (m, 1H), 2.04 (m, 1H), 1.69 (m, 1H), 0.99 (d, J = 6.7 Hz, 6H) | 440.4 [M + H]$^+$ |
| 473 | | 6 | Ex 37, 119, 130, 158, 354 | DMSO: 9.67 (t, J = 5.9 Hz, 1H), 9.59 (br, 2H), 9.46 (br, 2H), 9.30 (dd, J = 0.8 Hz, 2.1 Hz, 1H), 8.92 (dd, J = 1.5 Hz, 5.3 Hz, 1H), 8.72 (td, J = 1.8 Hz, 8.1 Hz, 1H), 7.89 (m, 1H), 7.20 (s, 1H), 7.12 (s, 1H), 6.98 (s, 1H), 4.51 (d, J = 5.9 Hz, 2H), 4.10 (t, J = 5.7 Hz, 2H), 3.78 (d, J = 6.5 Hz, 2H), 3.36 (m, 1H), 3.22 (m, 1H), 3.10 (m, 1H), 2.99 (m, 3H), 2.71 (m, 1H), 2.11 (m, 1H), 2.03 (m, 1H), 1.70 (m, 1H), 0.99 (d, J = 6.7 Hz, 6H) | 397.4 [M + H]$^+$ |
| 474 | | 3 | Ex 37, 68, 130, 158, 168 | DMSO: 9.08 (br, 2H), 9.05 (d, J = 2.2 Hz, 1H), 8.94 (d, J = 1.9 Hz, 1H), 8.87 (br, 2H), 8.63 (m, 2H), 7.90 (td, J = 1.8 Hz, 7.7 Hz, 1H), 7.57 (m, 2H), 7.35-7.43 (m, 4H), 7.24 (dd, J = 1.4 Hz, 2.4 Hz, 1H), 5.29 (s, 2H), 4.20 (t, J = 5.6 Hz, 2H), 3.40 (m, 1H), 3.27 (m, 1H), 3.05-3.20 (m, 3H), 2.93 (m, 1H), 2.65 (m, 1H), 2.15 (m, 1H), 1.69 (m, 1H) | 426.4 [M + H]$^+$ |
| 475 | | 3 | Ex 37, 130, 136, 158, 168, 399 | DMSO + D$_2$O: 7.85 (d, J = 16.0 Hz, 1H), 7.62 (d, J = 8.8 Hz, 2H), 7.28 (d, J = 2.0 Hz, 1H), 7.18 (d, J = 16.0 Hz, 1H), 7.12 (m, 3H), 6.05 (m, 1H), 5.44 (m, 1H), 5.32 (m, 1H), 4.75 (m, 2H), 4.33 (s, 2H), 4.40 (m, 1H), 3.25 (m, 1H), 3.05-3.20 (m, 3H), 2.95 (m, 1H), 2.70 (m, 1H), 2.18 (m, 1H), 1.72 (m, 1H)<br>HPLC: 4.52 min | 365.1 [M + H]$^+$ |
| 476 | | 1 | Ex 37, 130, 136, 137 | DMSO + D$_2$O: 7.83 (m, 1H), 7.66 (s, 1H), 7.55 (s, 1H), 7.47 (t, J = 1.6 Hz, 1H), 7.33-7.45 (m, 2H), 7.10 (t, J = 1.6 Hz, 1H), 4.74 (s, 2H), 4.18 (s, 2H), 3.71 (d, J = 6.4 Hz, 2H), 3.40 (m, 1H), 3.25 (m, 1H), 3.12 (m, 1H), 3.06 (m, 2H), 2.90 (m, 1H), 2.65 (m, 1H), 2.15 (m, 1H), 1.95 (m, 1H), 1.67 (m, 1H), 0.94 (d, J = 6.4 Hz, 6H)<br>HPLC: 4.95 min | 460.3 [M + H]$^+$ |
| 477 | | 6 | Ex 37, 119, 130, 158, 354 | DMSO + D$_2$O: 8.36 (t, J = 1.6 Hz, 1H), 8.00 (m, 2H), 7.58 (m, 1H), 7.01 (m, 2H), 6.95 (s, 1H), 4.47 (s, 2H), 4.08 (s, 2H), 3.74 (d, J = 6.8 Hz, 2H), 3.38 (m, 1H), 3.23 (m, 1H), 3.12 (m, 1H), 3.05 (m, 2H), 2.90 (m, 1H), 2.60 (m, 1H), 2.15 (m, 1H), 2.00 (m, 1H), 1.65 (m, 1H), 0.95 (d, J = 6.8 Hz, 6H)<br>HPLC: 4.65 min | 439.3 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 478 | | 1 | Ex 37, 130, 137, 476 | DMSO + D₂O: 8.97 (d, J = 2.0 Hz, 1H), 8.43 (d, J = 2.0 Hz, 1H), 8.03 (s, 1H), 7.51 (s, 1H), 7.47 (s, 1H), 7.15 (s, 1H), 4.85 (s, 2H), 4.17 (s, 2H), 3.73 (d, J = 6.8 Hz, 2H), 3.38 (m, 1H), 3.35 (m, 1H), 3.12 (m, 1H), 3.04 (m, 2H), 2.90 (m, 1H), 2.60 (m, 1H), 2.15 (m, 1H), 1.95 (m, 1H), 1.68 (m, 1H), 0.95 (d, J = 6.4 Hz, 6H) HPLC: 3.54 min | 461.2 [M + H]⁺ |
| 479 | | 6 | Ex 37, 119, 130, 158, 477 | DMSO + D₂O: 9.43 (t, J = 6.0 Hz, 1H), 9.23 (d, J = 2.0 Hz, 1H), 9.15 (d, J = 2.0 Hz, 1H), 8.65 (t, J = 2.0 Hz, 1H), 6.97 (m, 3H), 4.48 (d, J = 6.0 Hz, 2H), 4.08 (s, 2H), 3.73 (d, J = 6.4 Hz, 2H), 3.35 (m, 1H), 3.25 (m, 1H), 3.12 (m, 1H), 3.05 (m, 2H), 2.85 (m, 1H), 2.55 (m, 1H), 2.15 (m, 1H), 2.00 (m, 1H), 1.60 (m, 1H), 0.95 (d, J = 6.8 Hz, 6H) HPLC: 5.00 min | 422.3 [M + H]⁺ |
| 480 | | 3 | Ex 37, 130, 158, 168, 236 | DMSO + D₂O: 9.00 (d, J = 2.0 Hz, 1H), 8.85 (d, J = 2.0 Hz, 1H), 8.54 (t, J = 2.0 Hz, 1H), 7.50 (d, J = 16.4 Hz, 1H), 7.25 (m, 2H), 7.05 (d, J = 1.6 Hz, 1H), 6.89 (d, J = 1.6 Hz, 1H), 4.07 (s, 2H), 3.38 (m, 1H), 3.25 (m, 1H), 3.00-3.28 (m, 3H), 2.92 (m, 1H), 2.60 (m, 1H), 2.12 (m, 1H), 1.68 (m, 1H) HPLC: 4.17 min | 335.3 [M + H]⁺ |
| 481 | | 1 | Ex 37, 130, 137, 476 | DMSO + D₂O: 8.99 (d, J = 2.0 Hz, 1H), 8.53 (d, J = 2.0 Hz, 1H), 8.08 (t, J = 2.0 Hz, 1H), 7.45 (d, J = 2.0 Hz, 1H), 7.42 (s, 1H), 7.25 (t, J = 2.0 Hz, 1H), 4.87 (s, 2H), 4.17 (s, 2H), 3.79 (d, J = 6.8 Hz, 2H), 3.37 (m, 1H), 3.25 (m, 1H), 3.15 (m, 1H), 3.03 (m, 2H), 2.87 (m, 1H), 2.55 (m, 1H), 2.12 (m, 1H), 2.00 (m, 1H), 1.65 (m, 1H), 0.98 (d, J = 6.8 Hz, 6H) HPLC: 4.31 min | 443.2 [M + H]⁺ |
| 482 | | 3 | Ex 37, 130, 136, 168, 236, 480 | DMSO + D₂O: 9.03 (d, J = 2.0 Hz, 1H), 8.92 (d, J = 2.0 Hz, 1H), 8.60 (m, 2H), 7.91 (m, 1H), 7.82 (d, J = 16.0 Hz, 1H), 7.57 (m, 2H), 7.43 (m, 1H), 7.27 (d, J = 2.0 Hz, 1H), 7.10 (d, J = 2.0 Hz, 1H), 5.33 (s, 2H), 4.32 (s, 2H), 3.40 (m, 1H), 3.25 (m, 1H), 3.15 (m, 3H), 2.90 (m, 1H), 2.70 (m, 1H), 2.20 (m, 1H), 1.70 (m, 1H) HPLC: 4.69 min | 427.3 [M + H]⁺ |
| 483 | | 3 | Ex 37, 130, 136, 158, 168, 236 | DMSO + D₂O: 9.00 (d, J = 2.0 Hz, 1H), 8.87 (d, J = 2.0 Hz, 1H), 8.53 (t, J = 2.0 Hz, 1H), 7.49 (d, J = 16.4 Hz, 1H), 7.35 (m, 3H), 7.12 (s, 1H), 6.33 (s, 1H), 5.19 (s, 2H), 4.14 (s, 2H), 3.37 (m, 1H), 3.25 (m, 1H), 3.00-3.20 (m, 3H), 2.87 (m, 1H), 2.55 (m, 1H), 2.39 (s, 3H), 2.12 (m, 1H), 1.65 (m, 1H) HPLC: 5.15 min | 430.3 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 484 | | 3 | Ex 37, 130, 136, 158, 168, 236, 483 | DMSO + D$_2$O: 9.00 (d, J = 2.0 Hz, 1H), 8.88 (d, J = 2.0 Hz, 1H), 8.53 (t, J = 2.0 Hz, 1H), 7.50 (d, J = 16.4 Hz, 1H), 7.32 (m, 3H), 7.08 (s, 1H), 4.38 (t, J = 4.8 Hz, 2H), 4.15 (s, 2H), 3.68-4.05 (m, 4H), 3.55 (m, 2H), 3.20-3.50 (m, 6H), 3.00-3.20 (m, 3H), 2.88 (m, 1H), 2.60 (m, 1H), 2.15 (m, 1H), 1.65 (m, 1H) HPLC: 4.57 min | 448.3 [M + H]$^+$ |
| 485 | | 6 | Ex 37, 119, 130 | DMSO + D$_2$O: 9.14 (d, J = 2.0 Hz, 1H), 8.83 (dd, J = 1.6 Hz, 5.2 Hz, 1H), 8.49 (m, 1H), 7.75 (dd, J = 5.2 Hz, 8.0 Hz, 1H), 7.53 (s, 1H), 7.37 (t, J = 2.0 Hz, 1H), 6.94 (s, 1H), 4.10 (s, 2H), 3.75 (d, J = 6.8 Hz, 2H), 3.37 (m, 1H), 3.25 (m, 1H), 3.13 (m, 1H), 3.07 (m, 2H), 2.90 (m, 1H), 2.65 (m, 1H), 2.15 (m, 1H), 2.00 (m, 1H), 1.65 (m, 1H), 0.97 (d, J = 6.8 Hz, 6H) HPLC: 3.92 min | 383.3 [M + H]$^+$ |
| 486 | | 6 | Ex 37, 119, 130, 485 | DMSO + D$_2$O: 9.26 (d, J = 2.0 Hz, 1H), 9.18 (d, J = 2.0 Hz, 1H), 8.72 (t, J = 2.0 Hz, 1H), 7.56 (s, 1H), 7.28 (s, 1H), 6.90 (s, 1H), 4.10 (s, 2H), 3.75 (d, J = 6.4 Hz, 2H), 3.35 (m, 1H), 3.25 (m, 1H), 3.15 (m, 1H), 3.05 (m, 2H), 2.85 (m, 1H), 2.55 (m, 1H), 2.15 (m, 1H), 2.00 (m, 1H), 1.65 (m, 1H), 0.97 (d, J = 6.8 Hz, 6H) HPLC: 4.27 min | 408.3 [M + H]$^+$ |
| 487 | | 6 | Ex 37, 119, 130, 477, 485 | DMSO + D$_2$O: 8.42 (t, J = 2.0 Hz, 1H), 8.05 (m, 2H), 7.55-7.65 (m, 2H), 7.39 (d, J = 2.0 Hz, 1H), 6.93 (t, J = 2.0 Hz, 1H), 4.10 (s, 2H), 3.75 (d, J = 6.8 Hz, 2H), 3.37 (m, 1H), 3.25 (m, 1H), 3.12 (m, 1H), 3.05 (m, 2H), 2.90 (m, 1H), 2.65 (m, 1H), 2.15 (m, 1H), 2.05 (m, 1H), 1.65 (m, 1H), 0.97 (d J = 6.8 Hz, 6H) HPLC: 3.86 min | 425.3 [M + H]$^+$ |
| 488 | | 6 | Ex 37, 119, 130, 477, 485 | DMSO + D$_2$O: 9.17 (m, 2H), 8.72 (t, J = 2.0 Hz, 1H), 7.55 (s, 1H), 7.37 (t, J = 2.0 Hz, 1H), 6.94 (t, J = 2.0 Hz, 1H), 4.10 (s, 2H), 3.75 (d, J = 6.4 Hz, 2H), 3.37 (m, 1H), 3.25 (m, 1H), 3.12 (m, 1H), 3.07 (m, 2H), 2.90 (m, 1H), 2.63 (m, 1H), 2.15 (m, 1H), 2.02 (m, 1H), 1.65 (m, 1H), 0.97 (d, J = 6.8 Hz, 6H) HPLC: 3.55 min | 426.3 [M + H]$^+$ |
| 489 | | 3 | Ex 37, 119, 130, 136, 168 | DMSO + D$_2$O: 8.17 (d, J = 2.4 Hz, 1H), 7.74 (m, 3H), 7.46 (dd, J = 2.0 Hz, 8.8 Hz, 1H), 7.10 (m, 2H), 4.00 (m, 4H), 3.82 (m, 2H), 3.26 (m, 2H), 3.18 (m, 1H) HPLC: 4.37 min | 408.1, 410.1 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 490 | | 3 | Ex 37, 130, 158, 168, 263, 387 | DMSO: 8.84 (d, J = 1.6 Hz, 1H), 8.57 (dd, J = 1.6 Hz, 5.2 Hz, 1H), 8.34 (d, J = 7.6 Hz, 1H), 7.68 (m, 3H), 7.47 (d, J = 16.4 Hz, 1H), 7.38 (s, 1H), 7.32 (d, J = 16.4 Hz, 1H), 4.52 (s, 2H), 4.48 (m, 1H), 4.17 (s, 2H), 3.65 (m, 4H), 3.50 (m, 1H), 3.35 (m, 1H), 3.25 (m, 1H), 3.02-3.22 (m, 8H), 2.90 (m, 1H), 2.57 (m, 2H), 2.25 (m, 1H), 2.15 (m, 1H), 1.65 (m, 1H)<br>HPLC: 2.75 min | 421.3 [M]+ |
| 491 | | 3 | Ex 37, 130, 158, 168, 236, 480 | DMSO + D2O: 8.99 (d, J = 1.6 Hz, 1H), 8.85 (d, J = 1.6 Hz, 1H), 8.52 (t, J = 1.6 Hz, 1H), 7.49 (d, J = 16.4 Hz, 1H), 7.32-7.42 (m, 3H), 7.17 (s, 1H), 5.12 (s, 2H), 4.14 (s, 2H), 3.38 (m, 1H), 3.25 (m, 1H), 3.00-3.20 (m, 3H), 2.90 (m, 1H), 2.63 (m, 1H), 2.15 (m, 1H), 1.68 (m, 1H)<br>HPLC: 3.41 min | 433.1 [M + H]+ |
| 492 | | 3 | Ex 37, 130, 136, 168, 236, 399 | DMSO + D2O: 8.00 (d, J = 9.2 Hz, 1H), 7.93 (d, J = 2.8 Hz, 1H), 7.80 (d, J = 16.0 Hz, 1H), 7.61 (dd, J = 2.8 Hz, 9.2 Hz, 1H), 7.54 (d, J = 16.0 Hz, 1H), 7.18 (d, J = 2.0 Hz, 1H), 7.09 (d, J = 2.0 Hz, 1H), 6.05 (m, 1H), 5.42 (m, 1H), 5.32 (m, 1H), 4.71 (m, 2H), 4.29 (s, 2H), 3.42 (m, 1H), 3.27 (m, 1H), 3.15 (m, 3H), 2.97 (m, 1H), 2.72 (m, 1H), 2.20 (m, 1H), 1.70 (m, 1H)<br>HPLC: 3.57 min | 366.3 [M + H]+ |
| 493 | | 3 | Ex 37, 51, 130, 158, 168, 236, 480 | DMSO + D2O: 9.02 (d, J = 2.0 Hz, 1H), 8.88 (d, J = 2.0 Hz, 1H), 8.55 (t, J = 2.0 Hz, 1H), 7.53 (d, J = 16.8 Hz, 1H), 7.35 (m, 3H), 7.22 (s, 1H), 7.14 (s, 1H), 5.21 (s, 2H), 4.15 (s, 2H), 3.38 (m, 1H), 3.25 (m, 1H), 3.00-3.20 (m, 3H), 2.88 (m, 1H), 2.58 (m, 4H), 2.15 (m, 1H), 1.65 (m, 1H)<br>HPLC: 4.36 min | 446.2 [M + H]+ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 494 | (structure) | 3 | Ex 37, 119, 130, 136, 158, 168, 489 | DMSO + D₂O: 8.18 (d, J = 2.8 Hz, 1H), 7.75 (m, 3H), 7.47 (dd, J = 2.0 Hz, 8.4 Hz, 1H), 7.10 (m, 2H), 4.04 (s, 2H), 3.38 (m, 1H), 3.25 (m, 1H), 3.00-3.20 (m, 3H), 2.90 (m, 1H), 2.64 (m, 1H), 2.15 (m, 1h), 1.67 (m, 1H) HPLC: 4.29 min | 422.1, 424.1 [M + H]⁺ |
| 495 | (structure) | 1 | Ex 37, 130, 137, 476 | DMSO + D₂O: 8.81 (m, 1H), 8.68 (d, J = 1.2 Hz, 1H), 8.23 (m, 1H), 7.90 (dd, J = 5.6 Hz, 8.0 Hz, 1H), 7.58 (m, 2H), 7.22 (s, 1H), 5.02 (s, 2H), 4.20 (s, 2H), 3.82 (d, J = 6.4 Hz, 2H), 3.40 (m, 1H), 3.25 (m, 1H), 3.15 (m, 1H), 3.08 (m, 2H), 2.95 (m, 1H), 2.70 (m, 1H), 2.15 (m, 1H), 2.00 (m, 1H), 1.70 (m, 1H), 0.96 (d J = 6.4 Hz, 6H) HPLC: 3.99 min | 417.9 [M + H]⁺ |
| 496 | (structure) | 3 | Ex 37, 130, 158, 168, 483, 484 | DMSO + D₂O: 9.00 (d, J = 2.0 Hz, 1H), 8.88 (d, J = 2.0 Hz, 1H), 8.69 (d, J = 6.4 Hz, 2H), 8.52 (t, J = 2.0 Hz, 1H), 7.78 (d, J = 6.4 Hz, 2H), 7.50 (d, J = 16.4 Hz, 1H), 7.33 (d, J = 16.4 Hz, 1H), 7.30 (s, 1H), 7.27 (s, 1H), 7.03 (s, 1H), 4.38 (t, J = 6.0 Hz, 2H), 4.12 (s, 2H), 3.38 (m, 3H), 3.28 (m, 3H), 3.00-3.20 (m, 3H), 2.88 (m, 1H), 2.58 (m, 1H), 2.12 (m, 1H), 1.65 (m, 1H) HPLC: 4.04 min | 440.2 [M + H]⁺ |
| 497 | (structure) | 3 | Ex 37, 130, 136, 168, 480, 484 | DMSO + D₂O: 9.03 (d, J = 2.0 Hz, 1H), 8.93 (d, J = 2.0 Hz, 1H), 8.78 (d, J = 6.8 Hz, 2H), 8.55 (t, J = 2.0 Hz, 1H), 7.96 (d, J = 6.8 Hz, 2H), 7.82 (d, J = 16.0 Hz, 1H), 7.52 (d, J = 16.0 Hz, 1H), 7.17 (d, J = 2.0 Hz, 1H), 7.00 (d, J = 2.0 Hz, 1H), 4.50 (t, J = 6.0 Hz, 2H), 4.30 (s, 2H), 3.40 (m, 3H), 3.25 (m, 1H), 3.15 (m, 3H), 2.90 (m, 1H), 2.67 (m, 1H), 2.20 (m, 1H), 1.70 (m, 1H) HPLC: 3.72 min | 441.1 [M + H]⁺ |
| 498 | (structure) | 1 | Ex 37 & 130 | DMSO + D₂O: 8.87 (d, J = 1.6 Hz, 1H), 8.76 (dd, J = 1.6 Hz, 5.2 Hz, 1H), 8.37 (d, J = 8.0 Hz, 1H), 7.87 (dd, J = 5.2 Hz, 8.0 Hz, 1H), 6.73 (t, J = 1.6 Hz, 1H), 6.55 (t, J = 1.6 Hz, 1H), 6.50 (t, J = 1.6 Hz, 1H), 5.24 (s, 2H), 4.00 (m, 4H), 3.85 (m, 2H), 3.20 (m, 3H) HPLC: 2.59 min | 300.2 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 499 | | 3 | Ex 37, 130, 136, 168, 263 | DMSO + D₂O: 8.44 (d, J = 2.0 Hz, 1H), 8.19 (d, J = 2.0 Hz, 1H), 7.82 (t, J = 2.0 Hz, 1H), 7.43 (d, J = 16.4 Hz, 1H), 7.25-7.40 (m, 3H), 7.13 (s, 1H), 6.07 (m, 1H), 5.45 (m, 1H), 5.30 (m, 1H), 4.64 (m, 2H), 4.14 (s, 2H), 3.40 (m, 1H), 3.25 (m, 1H), 3.00-3.20 (m, 2H), 3.40 (m, 1H), 3.25 (m, 1H), 3.00-3.20 (m, 3H), 2.90 (m, 1H), 2.65 (m, 1H), 2.15 (m, 1H), 1.70 (m, 1H) HPLC: 3.67 min | 366.3 [M + H]⁺ |
| 500 | | 3 | Ex 37, 130, 136, 168, 263, 399 | DMSO + D₂O: 8.22 (d, J = 2.0 Hz, 1H), 7.92 (d, J = 2.0 Hz, 1H), 7.78 (t, J = 2.0 Hz, 1H), 7.42 (m, 2H), 7.30 (m, 2H), 7.19 (s, 1H), 6.07 (m, 1H), 5.42 (m, 1H), 5.29 (m, 1H), 4.64 (m, 2H), 4.14 (s, 2H), 3.40 (m, 1H), 3.25 (m, 1H), 3.00-3.20 (m, 3H), 2.95 (m, 1H), 2.70 (m, 1H), 2.15 (m, 1H), 1.70 (m, 1H) HPLC: 3.60 min | 365.3 [M + H]⁺ |
| 501 | | 6 | Ex 37, 119, 130, 135, 236, 399 | DMSO + D₂O: 9.16 (d, J = 1.6 Hz, 1H), 8.83 (dd, J = 1.6 Hz, 5.2 Hz, 1H), 8.45 (m, 1H), 8.07 (s, 1H), 7.73 (m, 2H), 7.31 (s, 1H), 4.80 (s, 2H), 3.84 (d, J = 6.4 Hz, 2H), 3.43 (m, 1H), 3.27 (m, 1H), 3.15 (m, 3H), 2.95 (m, 1H), 2.71 (m, 1H), 2.18 (m, 1H), 2.07 (m, 1H), 1.72 (m, 1H), 1.00 (d, J = 6.4 Hz, 6H) HPLC: 4.06 min | 411.2 [M + H]⁺ |
| 502 | | 3 | Ex 37, 130, 135, 158, 168, 183, 263, 490 | DMSO + D₂O: 8.96 (d, J = 1.6 Hz, 1H), 8.66 (d, J = 4.4 Hz, 1H), 8.55 (d, J = 8.4 Hz, 1H), 7.84 (m, 2H), 7.57 (m, 3H), 7.45 (m, 1H), 4.83 (s, 2H), 3.89 (d, J = 6.4 Hz, 2H), 3.44 (m, 1H), 3.28 (m, 1H), 3.14 (m, 3H), 2.96 (m, 1H), 2.73 (m, 1H), 2.20 (m, 1H), 2.06 (m, 1H), 1.72 (m, 1H), 1.01 (d, J = 6.8 Hz, 6H) HPLC: 4.79 min | 394.2 [M + H]⁺ |
| 503 | | 1 | Ex 37, 51, 130 | DMSO + D₂O: 8.97 (s, 1H), 8.86 (d, J = 2.0 Hz, 1H), 8.76 (dd, J = 2.0 Hz, 5.6 Hz, 1H), 8.34 (d, J = 8.4 Hz, 1H), 7.85 (dd, J = 5.6 Hz, 8.4 Hz, 1H), 7.49 (s, 1H), 6.87 (s, 1H), 6.80 (s, 1H), 6.71 (s, 1H), 5.26 (s, 2H), 4.24 (t, J = 6.4 Hz, 2H), 4.05 (s, 2H), 4.00 (m, 2H), 3.85 (m, 2H), 3.20 (m, 3H), 3.13 (t, J = 6.4 Hz, 2H) HPLC: 3.04 min | 394.3 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 504 | | 1 | Ex 37 | DMSO: 7.40 (m, 5H), 6.98 (d, J = 1.9 Hz, 1H), 6.94 (d, J = 8.2 Hz, 1H), 6.79 (dd, J = 1.9 Hz, 8.2 Hz, 1H), 5.07 (s, 2H), 4.03 (q, J = 7.0 Hz, 2H), 3.61 (s, 2H), 3.11 (m, 2H), 2.65 (m, 2H), 2.34 (d, J = 6.7 Hz, 2H), 1.80 (m, 2H), 1.61 (m, 1H), 1.33 (t, J = 7.0 Hz, 3H), 1.18 (m, 2H) HPLC: 3.88 min | 355.3 [M + H]+ |
| 505 | | 1 | Ex 37, 51, 119, 130, 263, 490 | DMSO + D2O: 8.98 (m, 2H), 8.84 (d, J = 5.2 Hz, 1H), 8.56 (d, J = 7.6 Hz, 1H), 8.02 (m, 1H), 7.51 (s, 1H), 7.26 (s, 1H), 7.18 (s, 1H), 6.86 (s, 1H), 5.38 (s, 2H), 4.30 (t, J = 6.0 Hz, 2H), 4.05 (m, 4H), 3.90 (m, 4H), 3.65 (m, 2H), 3.50 (m, 4H), 3.35 (m, 2H), 3.15 (m, 4H) HPLC: 2.72 min | 520.3 [M + H]+ |
| 506 | | 1 | Ex 37, 119, 263, 490 | DMSO + D2O: 8.88 (s, 1H), 8.80 (d, J = 6.4 Hz, 2H), 8.75 (m, 1H), 8.40 (d, J = 8.0 Hz, 1H), 8.03 (d, J = 6.4 Hz, 2H), 7.88 (m, 1H), 7.20 (s, 1H), 7.12 (s, 1H), 6.80 (s, 1H), 5.30 (s, 2H), 4.39 (t, J = 6.0 Hz, 2H), 4.00 (m, 4H), 3.90 (m, 4H), 3.55-3.80 (m, 2H), 3.45 (m, 4H), 3.30 (m, 4H), 3.17 (m, 2H) HPLC: 3.13 min | 531.2 [M + H]+ |
| 507 | | 6 | Ex 37, 119, 183, 263, 477, 490, 506 | DMSO + D2O: 9.28 (s, 1H), 8.96 (d, J = 5.6 Hz, 1H), 8.87 (m, 1H), 8.82 (d, J = 6.8 Hz, 2H), 8.08 (d, J = 6.8 Hz, 2H), 8.04 (m, 1H), 7.48 (s, 1H), 7.40 (s, 1H), 7.10 (s, 1H), 4.50 (s, 2H), 4.43 (t, J = 6.0 Hz, 2H), 4.05 (m, 4H), 3.90 (m, 4H), 3.64 (t, J = 6.0 Hz, 2H), 3.50 (m, 4H), 3.33 (m, 4H), 3.18 (m, 2H) HPLC: 2.74 min | 558.3 [M + H]+ |
| 508 | | 6 | Ex 37, 119, 183, 263, 477, 490, 507 | DMSO + D2O: 9.14 (d, J = 1.6 Hz, 1H), 8.96 (s, 1H), 8.83 (dd, J = 1.6 Hz, 5.2 Hz, 1H), 8.54 (m, 1H), 7.79 (m, 1H), 7.50 (s, 1H), 7.47 (s, 1H), 7.40 (s, 1H), 7.11 (s, 1H), 4.50 (s, 2H), 4.29 (t, J = 6.0 Hz, 2H), 4.05 (m, 4H), 3.90 (m, 4H), 3.64 (t, J = 6.0 Hz, 2H), 3.47 (m, 4H), 3.33 (m, 2H), 3.15 (m, 4H) HPLC: 2.32 min | 547.2 [M + H]+ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 509 | | 3 | Ex 37, 168, 183, 506 | DMSO + D₂O: 8.67 (d, J = 6.4 Hz, 2H), 7.78 (m, 4H), 7.49 (dd, J = 2.0 Hz, 8.4 Hz, 1H), 7.26 (d, J = 16.4 Hz, 1H), 7.18 (d, J = 16.4 Hz, 1H), 6.76 (m, 2H), 6.45 (s, 1H), 4.33 (t, J = 6.4 Hz, 2H), 3.95-4.05 (m, 4H), 3.83 (m, 2H), 3.23 (m, 4H), 3.00-3.15 (m, 3H), 2.00 (m, 2H) HPLC: 5.84 min | 555.8, 557.8 [M + H]⁺ |
| 510 | | 6 | Ex 37, 51, 119, 130, 136, 158, 506 | DMSO + D₂O: 9.15 (d, J = 1.6 Hz, 1H), 8.82 (m, 3H), 8.54 (m, 1H), 8.05 (d, J = 6.8 Hz, 2H), 7.79 (m, 1H), 7.10 (s, 1H), 7.05 (s, 1H), 6.94 (s, 1H), 4.46 (s, 2H), 4.37 (t, J = 6.0 Hz, 2H), 4.05 (s, 2H), 3.97 (m, 2H), 3.85 (m, 2H), 3.37 (t, J = 6.0 Hz, 2H), 3.20 (m, 3H) HPLC: 3.00 min | 431.9 [M + H]⁺ |
| 511 | | 6 | Ex 37, 119, 130, 136, 158, 183, 263, 354 | DMSO + D₂O: 9.02 (d, J = 1.6 Hz, 1H), 8.94 (s, 1H), 8.72 (dd, J = 1.6 Hz, 5.2 Hz, 1H), 8.23 (m, 1H), 7.55 (m, 1H), 7.45 (s, 1H), 6.99 (s, 1H), 6.96 (s, 1H), 6.93 (s, 1H), 4.47 (s, 2H), 4.20 (t, J = 6.4 Hz, 2H), 4.05 (s, 2H), 3.97 (m, 2H), 3.80 (m, 2H), 3.21 (d, J = 7.2 Hz, 2H), 3.12 (m, 3H) HPLC: 2.48 min | 421.1 [M + H]⁺ |
| 512 | | 3 | Ex 37, 158, 168, 236 | DMSO + D₂O: 7.79 (m, 2H), 7.48 (m, 2H), 7.31 (s, 1H), 7.25 (m, 1H), 6.99 (m, 2H), 6.32 (d, J = 0.8 Hz, 1H), 5.12 (s, 2H), 4.08 (t, J = 6.0 Hz, 2H), 3.97 (m, 2H), 3.81 (m, 2H), 3.22 (m, 2H), 3.09 (m, 3H), 2.39 (d, J = 0.8 Hz, 3H), 2.09 (m, 2H) HPLC: 5.91 min | 545.9, 547.9 [M + H]⁺ |
| 513 | | 3 | Ex 37, 158, 168, 236 | DMSO + D₂O: 7.79 (d, J = 8.8 Hz, 1H), 7.75 (d, J = 2.4 Hz, 1H), 7.46 (dd, J = 2.0 Hz, 8.4 Hz, 1H), 7.18 (m, 4H), 7.00 (d, J = 8.4 Hz, 1H), 4.10 (t, J = 6.0 Hz, 2H), 3.98 (m, 2H), 3.82 (m, 2H), 3.76 (d, J = 6.4 Hz, 2H), 3.23 (m, 2H), 3.09 (m, 3H), 2.04 (m, 3H), 0.98 (m, 6H) HPLC: 6.85 min | 507.1, 509.1 [M + H]⁺ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 514 | | 3 | Ex 37, 119, 136, 168, 263 | DMSO + D$_2$O: 8.00 (d, J = 2.4 Hz, 1H), 7.85 (d, J = 8.4 Hz, 1H), 7.77 (d, J = 2.0 Hz, 1H), 7.73 (dd, J = 2.4 Hz, 8.4 Hz, 1H), 7.48 (dd, J = 2.0 Hz, 8.4 Hz, 1H), 7.27 (m, 3H), 6.34 (s, 1H), 5.36 (s, 2H), 4.00 (m, 2H), 3.85 (m, 2H), 3.61 (m, 2H), 3.27 (d, J = 7.2 Hz, 2H), 3.10 (m, 3H), 2.41 (s, 3H) HPLC: 5.72 min | 558.8, 560.8 [M + H]$^+$ |
| 515 | | 3 | Ex 37, 119, 136, 158, 168, 263, 506 | DMSO + D$_2$O: 8.82 (d, J = 6.8 Hz, 2H), 8.08 (d, J = 6.8 Hz, 2H), 7.83 (d, J = 8.4 Hz, 1H), 7.79 (d, J = 2.4 Hz, 1H), 7.68 (s, 1H), 7.50 (dd, J = 2.4 Hz, 8.4 Hz, 1H), 7.38 (d, J = 16.4 Hz, 1H), 7.33 (s, 1H), 7.27 (s, 1H), 7.24 (d, J = 16.4 Hz, 1H), 4.45 (t, J = 6.0 Hz, 2H), 4.00 (m, 4H), 3.50 (m, 1H), 3.40 (t, J = 6.0 Hz, 2H), 3.33 (t, J = 6.4 Hz, 2H), 3.25 (t, J = 6.4 Hz, 2H) HPLC: 5.39 min | 582.7, 584.7 [M + H]$^+$ |
| 516 | | 3 | Ex 37, 119, 158, 168, 173, 183, 506 | DMSO + D$_2$O: 8.71 (d, J = 6.0 Hz, 2H), 7.80 (m, 4H), 7.48 (dd, J = 2.0 Hz, 8.4 Hz, 1H), 7.25 (d, J = 16.4 Hz, 1H), 7.18 (d, J = 16.4 Hz, 1H), 6.73 (m, 2H), 6.44 (m, 1H), 4.34 (t, J = 6.4 Hz, 2H), 3.98 (m, 6H), 3.49 (m, 1H), 3.25 (t, J = 6.0 Hz, 2H), 3.13 (t, J = 6.8 Hz, 2H), 1.69 (m, 2H), 1.54 (m, 2H) HPLC: 6.26 min | 583.7, 585.7 [M + H]$^+$ |
| 517 | | 3 | Ex 37, 158, 168, 173, 183, 506 | DMSO + D$_2$O: 8.68 (d, J = 6.4 Hz, 2H), 7.80 (m, 4H), 7.47 (dd, J = 2.4 Hz, 8.8 Hz, 1H), 7.25 (d, J = 16.4 Hz, 1H), 7.16 (d, J = 16.4 Hz, 1H), 6.73 (m, 2H), 6.43 (s, 1H), 4.34 (t, J = 6.0 Hz, 2H), 3.98 (m, 4H), 3.80 (m, 2H), 3.25 (t, J = 6.0 Hz, 2H), 3.18 (d, J = 7.2 Hz, 2H), 3.08 (m, 1H), 2.93 (m, 2H), 1.72 (m, 4H) HPLC: 5.96 min | 569.8, 571.8 [M + H]$^+$ |
| 518 | | 3 | Ex 37, 119, 136, 158, 168, 263, 506 | DMSO + D$_2$O: 8.83 (d, J = 6.4 Hz, 2H), 8.06 (d, J = 6.4 Hz, 2H), 7.80 (s, 3H), 7.50 (dd, J = 2.0 Hz, 8.4 Hz, 1H), 7.42 (s, 1H), 7.38 (s, 1H), 7.31 (s, 1H), 7.26 (d, J = 16.4 Hz, 1H), 4.47 (t, J = 6.0 Hz, 2H), 4.00 (m, 2H), 3.87 (m, 2H), 3.60 (t, J = 6.0 Hz, 2H), 3.39 (t, J = 6.0 Hz, 2H), 3.28 (d, J = 7.2 Hz, 2H), 3.18 (m, 1H), 3.10 (t, J = 6.0 Hz, 2H) HPLC: 5.36 min | 568.7, 570.7 [M + H]$^+$ |
| 519 | | 3 | Ex 37, 158, 168, 263 | DMSO + D$_2$O: 8.73 (m, 2H), 7.79 (m, 4H), 7.46 (m, 2H), 7.28 (m, 2H), 7.01 (m, 2H), 5.33 (s, 2H), 4.07 (t, J = 6.0 Hz, 2H), 3.97 (m, 2H), 3.80 (m, 2H), 3.22 (m, 2H), 3.09 (m, 3H), 2.09 (m, 2H) HPLC: 5.53 min | 541.8, 543.8 [M + H]$^+$ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 520 | | | 1 | Ex 37 DMSO: 9.50 (br, 2H), 9.15 (br, 2H), 8.00 (m, 2H), 7.60 (m, 2H), 7.52 (m, 2H), 7.08 (m, 2H), 5.26 (s, 2H), 4.04 (m, 2H), 3.96 (m, 2H), 3.87 (m, 5H), 3.23 (m, 3H) HPLC: 4.03 min | 341.2 [M + H]+ |
| 521 | | | 2 | Ex 37 & 263 DMSO + D2O: 8.85 (d, J = 1.6 Hz, 1H), 8.73 (d, J = 5.2 Hz, 1H), 8.34 (d, J = 8.0 Hz, 1H), 7.85 (m, 1H), 6.92 (s, 1H), 6.86 (s, 1H), 6.77 (s, 1H), 5.27 (s, 2H), 4.38 (t, J = 4.8 Hz, 2H), 4.09 (s, 2H), 3.95 (m, 2H), 3.78 (m, 2H), 3.55 (t, J = 4.8 Hz, 2H), 3.45 (m, 2H), 3.38 (m, 1H), 3.25 (m, 3H), 3.11 (m, 1H), 3.05 (m, 2H), 2.92 (m, 1H), 2.66 (m, 1H), 2.15 (m, 1H), 1.67 (m, 1H) HPLC: 3.22 min | 427.4 [M + H]+ |
| 522 | | | 3 | Ex 37, 119, 168, 485 DMSO + D2O: 8.81 (d, J = 6.8 Hz, 2H), 8.03 (d, J = 6.8 Hz, 2H), 7.80 (d, J = 8.4 Hz, 1H), 7.77 (d, J = 2.4 Hz, 1H), 7.45-7.52 (m, 2H), 7.30 (d, J = 16.4 Hz, 1H), 7.11 (d, J = 2.8 Hz, 1H), 6.96 (d, J = 8.8 Hz, 1H), 6.88 (dd, J = 2.8 Hz, 8.8 Hz, 1H), 4.33 (t, J = 6.4 Hz, 2H), 3.98 (m, 6H), 3.51 (m, 1H), 3.34 (t, J = 6.4 Hz, 2H), 3.28 (t, J = 6.4 Hz, 2H), 1.92 (m, 2H) HPLC: 5.84 min | 569.8, 571.8 [M + H]+ |
| 523 | | | 3 | Ex 37, 51, 165, 168 DMSO + D2O: 7.83 (d, J = 8.4 Hz, 1H), 7.78 (d, J = 2.4 Hz, 1H), 7.48 (dd, J = 2.4 Hz, 8.4 Hz, 1H), 7.31 (d, J = 16.4 Hz, 1H), 7.21 (d, J = 16.4 Hz, 1H), 7.12 (m, 2H), 6.86 (s, 1H), 6.32 (s, 1H), 5.16 (s, 2H), 4.27 (m, 2H), 3.31 (m, 2H), 3.18 (m, 3H), 2.39 (s, 3H), 2.21 (m, 1H), 1.97 (m, 1H) HPLC: 5.99 min | 529.9, 531.9 [M + H]+ |

TABLE 1-continued

Exemplified compounds
The Examples in the following table can be prepared using procedures described above, and detailed synthesis methodology is described in detail below. The Example number used in the leftmost column are used in the whole application text for identifying the respective compounds.

| Example | Formula | Reference Scheme | Reference for Preparation | 1H-NMR (400 MHz) δ ppm and/or HPLC Retention Time (min) | MS m/z (+ESI) |
|---|---|---|---|---|---|
| 524 | | 3 | Ex 37, 119, 168 | DMSO + D$_2$O: 7.90 (d, J = 2.0 Hz, 1H), 7.83 (d, J = 8.4 Hz, 1H), 7.76 (d, J = 2.4 Hz, 1H), 7.72 (dd, J = 2.0 Hz, 8.4 Hz, 1H), 7.47 (dd, J = 2.4 Hz, 8.4 Hz, 1H), 7.26 (m, 3H), 6.32 (s, 1H), 5.32 (s, 2H), 3.93 (m, 2H), 3.77 (m, 2H), 3.50 (d, J = 6.8 Hz, 2H), 3.01 (m, 1H), 2.41 (s, 3H) | 516.0, 518.0 [M + H]$^+$ |
| 525 | | 3 | Ex 37, 168, 263, 485 | DMSO + D$_2$O: 8.80 (d, J = 6.8 Hz, 2H), 8.02 (d, J = 6.8 Hz, 2H), 7.82 (d, J = 8.4 Hz, 1H), 7.77 (d, J = 2.0 Hz, 1H), 7.49 (dd, J = 2.0 Hz, 8.4 Hz, 1H), 7.44 (d, J = 16.4 Hz, 1H), 7.29 (d, J = 16.4 Hz, 1H), 7.13 (d, J = 2.8 Hz, 1H), 6.99 (d, J = 8.8 Hz, 1H), 6.90 (dd, J = 2.8 Hz, 8.8 Hz, 1H), 4.35 (t, J = 6.4 Hz, 2H), 4.06 (t, J = 6.4 Hz, 2H), 3.98 (m, 2H), 3.85 (m, 2H), 3.33 (t, J = 6.4 Hz, 2H), 3.23 (d, J = 7.2 Hz, 2H), 3.12 (m, 3H), 2.14 (m, 2H) HPLC: 5.64 min | 555.8, 557.8 [M + H]$^+$ |

Example 14: 4-benzyloxy-N-(4-piperidyl)benzamide

4-Aminopiperidine (215 mg, 2.15 mmol, 1.0 eq) [13035-19-3] is added at room temperature to a stirred solution of 4-benzyloxybenzoic acid (500 mg, 2.15 mmol, 1.0 eq) [1486-51-7] in N,N-dimethylformamide (10 mL), followed by N-(3-dimethylaminopropyl)-N'-ethylcarbodiimide hydrochloride (482 mg, 1.15 eq, 2.47 mmol), 1-hydroxybenzotriazole (362 mg, 2.36 mmol, 1.1 eq) and N,N-diisopropylethylamine (1.87 mL, 10.73 mmol, 5.0 eq). After 15 hours stirring at room temperature, solvent is evaporated and the residue is extracted with dichloromethane (3×20 mL) and water (20 mL). The combined organic layers are washed with brine (20 mL), dried over sodium sulfate, filtered and concentrated to give a residue that is purified by column chromatography (silica gel; dichloromethane:methanol, 9:1, v/v) to afford 4-benzyloxy-N-(4-piperidyl)benzamide as a yellow amorphous (130 mg, 18% yield).

Example 23: N-(azetidin-3-ylmethyl)-3-[(4-chlorophenyl)methoxy]aniline

Preparation of 1-[(4-chlorophenyl)methoxy]-3-nitrobenzene

The titled compound is prepared as a light yellow solid (1.7 g, 99% yield) following Scheme 1 and in analogy to Example 37 using 1-chloro-4-(chloromethyl)benzene (1.0 g, 6.2 mmol, 1.0 eq) [104-83-6] and 3-nitrophenol (0.86 g, 6.2 mmol, 1.0 eq) [554-84-7] as starting materials.

$^1$H-NMR (400 MHz, DMSO-d6) δ ppm: 7.80 (m, 2H), 7.58 (m, 1H), 7.45 (m, 5H), 5.25 (s, 2H).

Preparation of 3-[(4-chlorophenyl)methoxy]aniline

Zinc powder (1.6 g, 24.6 mmol, 10.0 eq) is added at room temperature to a stirred solution 1-[(4-chlorophenyl)methoxy]-3-nitro-benzene (650 mg, 2.46 mmol, 1.0 eq) in dichloromethane (10 mL), followed by acetic acid (1.4 mL, 24.6 mmol, 10.0 eq). After 5 hours stirring at 30° C., the reaction mixture is filtered through decalite and concentrated to give a residue that is extracted with ethyl acetate (3×30 mL) and water (30 mL). The combined organic layers are dried over sodium sulfate, filtered and concentrated to afford 3-[(4-chlorophenyl)methoxy]aniline as a light yellow solid (580 mg, 99% yield) that is directly engaged in the next step without further purification.

Preparation of N-(azetidin-3-ylmethyl)-3-[(4-chlorophenyl)methoxy]aniline

The titled compound is prepared as a white solid following Scheme 1 and in analogy to Example 158 using 3-[(4-chlorophenyl)methoxy]aniline and tert-butyl 3-formylazetidine-1-carboxylate as starting materials.

Example 27: N-(azetidin-3-ylmethyl)-1-[4-(4-chlorophenoxy)phenyl]methanamine Preparation of 4-(4-chlorophenoxy)benzonitrile Cesium carbonate (610 mg, 1.87 mmol, 2.0 eq) is added at room temperature to a stirred solution of 4-chlorophenol (0.11 mL, 1.13 mmol, 1.2 eq) [106-48-9] and 3-fluorobenzonitrile (0.1 mL, 0.94 mmol, 1.0 eq) [403-54-3] in N,N-dimethylformamide (5 mL). After 5 hours stirring at 160° C., solvent is evaporated and the residue is extracted with ethyl acetate (3×20 mL) and water (20 mL). The combined organic layers are washed with brine (20 mL), dried over sodium sulfate, filtered and concentrated to give a residue that is purified by column chromatography (silica gel; petroleum ether:dichloromethane, 100:1, v/v) to afford 4-(4-chlorophenoxy)benzonitrile as a white solid (200 mg, 93% yield).

$^1$H-NMR (400 MHz, DMSO-d6) δ ppm: 7.10 (m, 2H), 7.35 (m, 1H), 7.40-7.70 (m, 5H).

Preparation of N-(azetidin-3-ylmethyl)-1-[4-(4-chlorophenoxy)phenyl]methanamine

The titled compound is prepared as a white solid following Scheme 7 and in analogy to Examples 37, 158 and 183 using 4-(4-chlorophenoxy)benzonitrile and tert-butyl 3-(aminomethyl)azetidine-1-carboxylate as starting materials.

Example 37: N-(azetidin-3-ylmethyl)-1-[3-[(2-bromo-4-chloro-phenyl)methoxy]-5-chloro-phenyl]methanamine Preparation of 3-[(2-bromo-4-chloro-phenyl)methoxy]-5-chloro-benzaldehyde Potassium carbonate (194 mg, 1.41 mmol, 2.0 eq) is added at room temperature to a stirred solution of 2-bromo-1-(bromomethyl)-4-chloro-benzene (200 mg, 0.70 mmol, 1.0 eq) [33924-45-7] and 3-chloro-5-hydroxybenzaldehyde (110 mg, 0.70 mmol, 1.0 eq) [1829-33-0] in N,N-dimethylformamide (5 mL). After 5 hours stirring at 70° C., solvent is evaporated and the residue is extracted with ethyl acetate (3×20 mL) and water (20 mL). The combined organic layers are dried over magnesium sulfate, filtered and concentrated to give a residue that is purified by column chromatography (silica gel; petroleum ether:ethyl acetate, 10:1, v/v) to afford 3-[(2-bromo-4-chloro-phenyl)methoxy]-5-chloro-benzaldehyde as a white solid (210 mg, 83% yield).

$^1$H-NMR (400 MHz, CDCl$_3$) δ ppm: 9.94 (s, 1H), 7.65 (d, J=2.0 Hz, 1H), 7.50 (m, 2H), 7.37 (m, 2H), 7.26 (m, 1H), 5.15 (s, 2H).

Preparation of tert-butyl 3-[[[3-[(2-bromo-4-chloro-phenyl)methoxy]-5-chloro-phenyl]methylamino]methyl]azetidine-1-carboxylate tert-Butyl 3-(aminomethyl)azetidine-1-carboxylate (75 mg, 0.40 mmol, 1.1 eq) [325775-44-8] is added at room temperature to a stirred solution of 3-[(2-bromo-4-chloro-phenyl)methoxy]-5-chloro-benzaldehyde (120 mg, 0.33 mmol, 1.0 eq) in 1,2-dichloroethane (10 mL), followed by one drop of acetic acid and sodium triacetoxyborohydride (212 mg, 1.00 mmol, 3.0 eq). After 1 hour stirring at room temperature, the reaction mixture is concentrated to give a residue that is purified by column chromatography (silica gel; ethyl acetate) to afford tert-butyl 3-[[[3-[(2-bromo-4-chloro-phenyl)methoxy]-5-chloro-phenyl]methylamino]methyl]azetidine-1-carboxylate as a light yellow oil (150 mg, 85% yield).

MS m/z (+ESI): 528.9, 531.0 [M+H]$^+$.

Preparation of N-(azetidin-3-ylmethyl)-1-[3-[(2-bromo-4-chloro-phenyl)methoxy]-5-chloro-phenyl]methanamine Trifluoroacetic acid (1.0 mL, 13.06 mmol, 46.0 eq) is added at room temperature to a stirred solution of tert-butyl 3-[[[3-[(2-bromo-4-chloro-phenyl)methoxy]-5-chloro-phenyl]methylamino]methyl]azetidine-1-carboxylate (150 mg, 0.28 mmol, 1.0 eq) in dichloromethane (5 mL). After 2 hours stirring at room temperature, the reaction mixture is extracted with dichloromethane (3×10 mL) and water (10 mL) and the pH is adjusted to 9 by the addition of a saturated sodium hydrogen carbonate aqueous solution. The combined organic layers are dried over sodium sulfate, filtered and concentrated to give a residue that is dissolved in a 2N hydrochloric acid solution in ethyl acetate (2 mL). After 2 hours stirring at room temperature, the resulting precipitate is collected by centrifugation, washed with ethyl acetate and purified by preparative HPLC to afford N-(azetidin-3-ylmethyl)-1-[3-[(2-bromo-4-chloro-phenyl)methoxy]-5-chloro-phenyl]methanamine as a white solid (86 mg, 64% yield).

Example 51: N-(azetidin-3-ylmethyl)-1-[3-[(2-bromo-4-chloro-phenyl)methylsulfanyl]phenyl]methanamine Preparation of 3-[(2-bromo-4-chloro-phenyl)methylsulfanyl]benzoic acid Triethylamine (736 μL, 5.27 mmol, 3.0 eq) is added at room temperature to a stirred solution of 2-bromo-1-(bromomethyl)-4-chloro-benzene (500 mg, 1.76 mmol, 1.0 eq) [33924-45-7] and 3-sulfanylbenzoic acid (298 mg, 1.93 mmol, 1.1 eq) [4869-59-4] in acetonitrile (10 mL). After 20 hours stirring at 45° C., the reaction mixture is concentrated to afford 3-[(2-bromo-4-chloro-phenyl)methylsulfanyl]benzoic acid as an off-white solid (600 mg, 95% yield) that is directly engaged in the next step without further purification.

$^1$H-NMR (400 MHz, CDCl$_3$) δ ppm: 8.10 (d, J=1.6 Hz, 1H), 7.98 (d, J=7.6 Hz, 1H), 7.60 (d, J=0.9 Hz, 1H), 7.53 (d, J=7.6 Hz, 1H), 7.40 (m, 1H), 7.20 (m, 2H), 4.24 (s, 2H). MS m/z (+ESI): 355.0, 357.0 [M+H]$^+$.

Preparation of 3-[(2-bromo-4-chloro-phenyl)methylsulfanyl]phenyl]methanol

A solution of borane dimethyl sulphide complex in tetrahydrofuran (1.12 mL, 2.24 mmol, 2.0 eq) is added dropwise 0° C. to a stirred solution of 3-[(2-bromo-4-chlorophenyl)methylsulfanyl]benzoic acid (400 mg, 1.12 mmol, 1.0 eq) in tetrahydrofuran (20 mL). After 20 hours stirring at room temperature and 2 additional hours stirring at 60° C., a mixture of acetic acid (1 mL) and water (1 mL) is cautiously added to the reaction mixture that is then evaporated. The crude is extracted with ethyl acetate (3×30 mL) and a saturated sodium hydrogen carbonate aqueous solution (30 mL). The combined organic layers are dried over sodium sulfate, filtered and concentrated to give a residue that purified by column chromatography (silica gel; petroleum ether:ethyl acetate, 1:1, v/v) to afford 3-[(2-bromo-4-chlorophenyl)methylsulfanyl]phenyl]methanol as a white solid (360 mg, 94% yield).

$^1$H-NMR (400 MHz, CDCl$_3$) δ ppm: 7.59 (s, 1H), 7.35 (s, 1H), 7.18-7.31 (m, 5H), 4.67 (s, 2H), 4.20 (s, 2H).

Preparation of 3-[(2-bromo-4-chloro-phenyl)methylsulfanyl]phenyl]methyl methanesulfonate Methanesulfonyl chloride (118 μL, 1.53 mmol, 1.5 eq) is added at 0° C. to a stirred solution of 3-[(2-bromo-4-chlorophenyl)methylsulfanyl]phenyl]methanol (350 mg, 1.02 mmol, 1.0 eq), triethylamine (284 µL, 2.04 mmol, 2.0 eq) and 4-dimethylaminopyridine (12 mg, 0.10 mmol, 0.1 eq) in dichloromethane (10 mL). After 2 hours stirring at 0° C., the reaction mixture is concentrated and purified by column chromatography (silica gel; petroleum ether:ethyl acetate, 1:1, v/v) to afford 3-[(2-bromo-4-chloro-phenyl)methylsulfanyl]phenyl]methyl methanesulfonate as an off-white solid (350 mg, 81% yield).

MS m/z (+ESI): 443.1, 445.0 [M+H]$^+$.

Preparation of tert-butyl 3-[[[3-[(2-bromo-4-chloro-phenyl)methylsulfanyl]phenyl]methylamino]methyl]azetidine-1-carboxylate tert-Butyl 3-(aminomethyl)pyrrolidine-1-carboxylate (170 mg, 0.91 mmol, 1.1 eq) is added at room temperature to a stirred solution of 3-[(2-bromo-4-chloro-phenyl)methylsulfanyl]phenyl]methyl methanesulfonate (350 mg, 0.83 mmol, 1.0 eq) in N,N-dimethylformamide (10 mL), followed by potassium carbonate (229 mg, 1.66 mmol, 2.0 eq). After 5 hours stirring at 70° C., solvent is evaporated and the residue is extracted with ethyl acetate (3×20 mL) and water (20 mL). The combined organic layers are dried over sodium sulfate, filtered and concentrated to give a residue that is purified by column chromatography (silica gel; dichloromethane:methanol, 10:1, v/v) to afford tert-butyl 3-[[[3-[(2-bromo-4-chloro-phenyl)methylsulfanyl]phenyl]methylamino]methyl]azetidine-1-carboxylate as a colorless oil (300 mg, 71% yield).

MS m/z (+ESI): 511.2, 513.3 [M+H]$^+$.

Preparation of N-(azetidin-3-ylmethyl)-1-[3-[(2-bromo-4-chloro-phenyl)methylsulfanyl]phenyl]methanamine The titled compound is prepared as a white solid (80 mg, 60% yield) following Scheme 1 and in analogy to Example 37 using tert-butyl 3-[[[3-[(2-bromo-4-chloro-phenyl)methylsulfanyl]phenyl]methylamino]methyl]azetidine-1-carboxylate (150 mg, 0.29 mmol, 1.0 eq) as starting material.

Example 64: N-(azetidin-3-ylmethyl)-1-[3-[2-(2-bromo-4-chloro-phenyl)ethyl]phenyl]methanamine Preparation of (2-bromo-4-chloro-phenyl)methyl-triphenyl-phosphonium The titled compound is prepared as a white solid (900 mg, 64% yield) following Scheme 3 and in analogy to Example 236 using 2-bromo-1-(bromomethyl)-4-chloro-benzene (500 mg, 1.76 mmol, 1.0 eq) and triphenylphosphine (461 mg, 1.76 mmol, 1.0 eq) as starting materials.

Preparation of 3-[(E)-2-(2-bromo-4-chloro-phenyl)vinyl]benzaldehyde

Potassium carbonate (202 mg, 1.61 mmol, 1.1 eq) is added at room temperature to a stirred solution of (2-bromo-4-chloro-phenyl)methyl-triphenyl-phosphonium (800 mg, 1.46 mmol, 1.0 eq) and benzene-1,3-dicarbaldehyde (196 mg, 1.46 mmol, 1.0 eq) [626-19-7] in toluene (15 mL), followed by 18-crown-6 (193 mg, 0.73 mmol, 0.5 eq). After 15 hours stirring under reflux conditions, solvent is evaporated and the residue is extracted with ethyl acetate (3×20 mL) and water (20 mL). The combined organic layers are dried over sodium sulfate, filtered and concentrated to give a residue that is purified by column chromatography (silica gel; petroleum ether:ethyl acetate, 10:1, v/v) to afford 3-[(E)-2-(2-bromo-4-chloro-phenyl)vinyl]benzaldehyde as a white solid (360 mg, 76% yield).

$^1$H-NMR (400 MHz, CDCl$_3$) δ ppm: 10.09 (s, 1H), 8.05 (s, 1H), 7.83 (m, 2H), 7.56-7.65 (m, 3H), 7.50 (d, J=16.4 Hz, 1H), 7.34 (dd, J=2.0 Hz, 8.8 Hz, 1H), 7.08 (d, J=16.4 Hz, 1H).

Preparation of tert-butyl 3-[[[3-[(E)-2-(2-bromo-4-chloro-phenyl)vinyl]phenyl]methylamino]methyl]azetidine-1-carboxylate The titled compound is prepared as a light yellow oil (220 mg, 72% yield) following Scheme 3 and in analogy to Example 37 using 3-[(E)-2-(2-bromo-4-chloro-phenyl)vinyl]benzaldehyde (200 mg, 0.62 mmol, 1.0 eq) and tert-butyl 3-(aminomethyl)azetidine-1-carboxylate (139 mg, 0.75 mmol, 1.2 eq) as starting materials.

MS m/z (+ESI): 491.1, 493.2 [M+H]$^+$.

Preparation of tert-butyl 3-[[[3-[2-(2-bromo-4-chloro-phenyl)ethyl]phenyl]methylamino]methyl]azetidine-1-carboxylate A mixture of tert-butyl 3-[[[3-[(E)-2-(2-bromo-4-chloro-phenyl)vinyl]phenyl]methylamino]methyl]azetidine-1-carboxylate (200 mg, 0.41 mmol, 1.0 eq), zinc bromide (96 mg, 0.43 mmol, 1.0 eq), and 10% palladium on activated carbon (20 mg) in ethyl acetate (10 mL) is stirred under hydrogen flow at room temperature and 4 atm for 2 hours. The catalyst is then removed by filtration and the solution is evaporated to dryness to afford tert-butyl 3-[[[3-[2-(2-bromo-4-chloro-phenyl)ethyl]phenyl]methylamino]methyl]azetidine-1-carboxylate as a brown solid (202 mg, 99% yield) that is directly engaged in the next step without further purification.

Preparation of N-(azetidin-3-ylmethyl)-1-[3-[2-(2-bromo-4-chloro-phenyl)ethyl]phenyl]methanamine The titled compound is prepared as a white solid (130 mg, 82% yield) following Scheme 3 and in analogy to Example 37 using tert-butyl 3-[[[3-[2-(2-bromo-4-chloro-phenyl)ethyl]phenyl]methylamino]methyl]azetidine-1-carboxylate (200 mg, 0.40 mmol, 1.0 eq) as starting material.

Example 68: N-(azetidin-3-ylmethyl)-1-[4-(2-bromo-4-chloro-phenyl)phenyl]methanamine Preparation of 4-(2-bromo-4-chloro-phenyl)benzaldehyde Potassium carbonate (540 mg, 3.93 mmol, 2.5 eq) is added at room temperature to a stirred solution of 2-bromo-4-chloro-1-iodo-benzene (500 mg, 1.57 mmol, 1.0 eq) [31928-44-6] and (4-formylphenyl)boronic acid (260 mg, 1.73 mmol, 1.1 eq) [87199-17-5] in N,N-dimethylformamide (10 mL), followed by tetrakis(triphenylphosphine)palladium(0) (180 mg, 0.16 mmol, 0.1 eq). After 5 hours stirring at 80° C., the reaction mixture is filtered through decalite, concentrated and the residue is extracted with ethyl acetate (3×50 mL) and water (50 mL). The combined organic layers are washed with brine (50 mL), dried over sodium sulfate, filtered and concentrated to give a residue that is purified by column chromatography (silica gel; petroleum ether:ethyl acetate, 10:1, v/v) to afford 4-(2-bromo-4-chloro-phenyl)benzaldehyde as a grey solid (260 mg, 56% yield).

¹H-NMR (400 MHz, DMSO-d6) δ ppm: 10.08 (s, 1H), 8.01 (d, J=8.0 Hz, 2H), 7.94 (d, J=2.0 Hz, 1H), 7.63 (d, J=8.0 Hz, 2H), 7.60 (dd, J=2.0 Hz, 8.0 Hz, 1H), 7.47 (d, J=8.0 Hz, 1H).

Preparation of N-(azetidin-3-ylmethyl)-1-[4-(2-bromo-4-chloro-phenyl)phenyl]methanamine The titled compound is prepared as a white solid following Scheme 7 and in analogy to Examples 37 and 158 using 4-(2-bromo-4-chloro-phenyl)benzaldehyde and tert-butyl 3-(aminomethyl)azetidine-1-carboxylate as starting materials.

Example 88: 1-[3-(2-bromo-4-chloro-phenoxy)phenyl]-N-(pyrrolidin-3-ylmethyl)methanamine Preparation of 3-(2-bromo-4-chloro-phenoxy)benzaldehyde Triethylamine (3.48 mL, 24.1 mmol, 5.0 eq) is added at room temperature to a stirred solution of 2-bromo-4-chlorophenol (1.0 g, 4.82 mmol, 1.0 eq) [695-96-5], (3-formylphenyl)boronic acid (1.45 g, 9.64 mmol, 2.0 eq) [87199-16-4] and copper(II) acetate (880 mg, 4.82 mmol, 1.0 eq) in dichloromethane (30 mL). After 3 days stirring at room temperature, the reaction mixture is filtered through decalite, concentrated and the residue is purified by column chromatography (silica gel; petroleum ether:ethyl acetate, 10:1, v/v) to afford 3-(2-bromo-4-chloro-phenoxy)benzaldehyde as a yellow oil (1.3 g, 86% yield).

¹H-NMR (400 MHz, DMSO-d6) δ ppm: 9.95 (s, 1H), 7.91 (s, 1H), 7.67 (m, 1H), 7.61 (m, 1H,), 7.49 (m, 1H), 7.21 (m, 2H), 7.19 (m, 1H).

Preparation of 1-[3-(2-bromo-4-chloro-phenoxy)phenyl]-N-(pyrrolidin-3-ylmethyl)methanamine The titled compound is prepared as a white solid following Scheme 7 and in analogy to Examples 37 and 236 using 3-(2-bromo-4-chloro-phenoxy)benzaldehyde and tert-butyl 3-(aminomethyl)pyrrolidine-1-carboxylate as starting materials.

Example 119: 3-[(azetidin-3-ylmethylamino)methyl]-N-benzyl-5-[(2-bromo-4-chloro-phenyl)methoxy]-benzamide Preparation of tert-butyl 3-[[[3-[(2-bromo-4-chlorophenyl)methoxy]-5-methoxycarbonyl-phenyl]methyl-tert-butoxycarbonyl-amino]methyl]azetidine-1-carboxylate The titled compound is prepared as a white foam following Scheme 1 and in analogy to Examples 51 and 130 using dimethyl 5-[(2-bromo-4-chloro-phenyl)methoxy]benzene-1,3-dicarboxylate, 4-toluenesulfonyl chloride, tert-butyl 3-(aminomethyl)azetidine-1-carboxylate and di-tert-butyl dicarbonate as starting materials.

¹H-NMR (400 MHz, CDCl₃) δ ppm: 7.63 (s, 1H), 7.33-7.56 (m, 4H), 7.02 (s, 1H), 5.12 (s, 2H), 4.45 (m, 2H), 3.93 (s, 3H), 3.88 (m, 2H), 3.58 (m, 2H), 3.48 (m, 2H), 2.70 (m, 1H), 1.38-1.55 (m, 18H).

Preparation of 3-[(2-bromo-4-chloro-phenyl)methoxy]-5-[[tert-butoxycarbonyl-[(1-tert-butoxycarbonylazetidin-3-yl)methyl]amino]methyl]benzoic Acid Sodium hydroxide (31 mg, 0.78 mmol, 10.0 eq) is added at room temperature to a stirred solution of tert-butyl 3-[[[3-[(2-bromo-4-chloro-phenyl)methoxy]-5-methoxycarbonyl-phenyl]methyl-tert-butoxycarbonyl-amino]methyl]azetidine-1-carboxylate (50 mg, 0.08 mmol, 1.0 eq) in methanol (3 mL) and water (0.5 mL). After 5 hours stirring at 40° C., solvent is evaporated and the residue is extracted with ethyl acetate (3×10 mL) and saturated ammonium chloride aqueous solution (10 mL). The combined organic layers are dried over sodium sulfate, filtered and concentrated to give a residue that is purified by column chromatography (silica gel; ethyl acetate) to afford 3-[(2-bromo-4-chloro-phenyl)methoxy]-5-[[tert-butoxycarbonyl-[(1-tert-butoxycarbonylazetidin-3-yl)methyl]amino]methyl]benzoic acid as a colorless semi-solid (38 mg, 78% yield).

¹H-NMR (400 MHz, CDCl₃) δ ppm: 7.56-7.64 (m, 3H), 7.50 (d, J=8.0 Hz, 1H), 7.35 (d, J=8.0 Hz, 1H), 7.06 (s, 1H), 5.13 (s, 2H), 4.44 (m, 2H), 3.92 (m, 2H), 3.61 (m, 2H), 3.45 (m, 2H), 2.60-2.80 (m, 1H), 1.38-1.55 (m, 18H).

Preparation of tert-butyl 3-[[[3-(benzylcarbamoyl)-5-[(2-bromo-4-chloro-phenyl)methoxy]phenyl]methyl-tert-butoxycarbonyl-amino]methyl]azetidine-1-carboxylate O-(7-azabenzotriazol-1-yl)-N,N,N',N'-tetramethyluronium hexafluorophosphate (178 mg, 0.47 mmol, 1.5 eq) is added at room temperature to a stirred solution of 3-[(2-bromo-4-chloro-phenyl)methoxy]-5-[[tert-butoxycarbonyl-[(1-tert-butoxycarbonylazetidin-3-yl)methyl]amino]methyl]benzoic acid (200 mg, 0.31 mmol, 1.0 eq), N,N-diisopropylethylamine (109 μL, 0.62 mmol, 2.0 eq) and benzylamine (50 mg, 0.47 mmol, 1.5 eq) in N,N-dimethylformamide (5 mL). After 3 hours stirring at room temperature, solvent is evaporated and the residue is extracted with ethyl acetate (3×10 mL) and water (10 mL). The combined organic layers are washed with brine, dried over sodium sulfate, filtered and concentrated to give a residue that is purified by column chromatography (silica gel; petroleum ether:ethyl acetate, 2:1, v/v) to afford tert-butyl 3-[[[3-(benzylcarbamoyl)-5-[(2-bromo-4-chloro-phenyl)methoxy]phenyl]methyl-tert-butoxycarbonyl-amino]methyl]azetidine-1-carboxylate as a white foam (150 mg, 66% yield).

¹H-NMR (400 MHz, CDCl₃) δ ppm: 7.62 (s, 1H), 7.48 (d, J=8.0 Hz, 1H), 7.32-7.39 (m, 7H), 7.22 (s, 1H), 6.95 (s, 1H), 6.39 (s, 1H), 5.12 (s, 2H,), 4.67 (m, 2H), 4.44 (m, 2H), 3.90 (m, 2H), 3.59 (m, 2H), 3.43 (m, 2H), 2.73 (m, 1H), 1.42 (s, 18H).

Preparation of 3-[(azetidin-3-ylmethylamino)methyl]-N-benzyl-5-[(2-bromo-4-chloro-phenyl)methoxy]-benzamide A solution of tert-butyl 3-[[[3-(benzylcarbamoyl)-5-[(2-bromo-4-chloro-phenyl)methoxy]phenyl]methyl-tert-butoxycarbonyl-amino]methyl]azetidine-1-carboxylate (145 mg, 0.20 mmol, 1.0 eq) in trifluoroacetic acid (2 mL) is stirred at room temperature for 1 hour. Then the reaction mixture is concentrated to give a residue that is purified by preparative HPLC to afford 3-[(azetidin-3-ylmethylamino)

methyl]-N-benzyl-5-[(2-bromo-4-chloro-phenyl)methoxy]-benzamide as a white solid (40 mg, 38% yield).

Example 129: Ethyl (E)-3-[3-[(azetidin-3-ylmethyl-amino)methyl]-5-[(2-bromo-4-chloro-phenyl)methoxy]phenyl]prop-2-enoate Preparation of tert-butyl 3-[[[3-[(2-bromo-4-chloro-phenyl)methoxy]-5-[(E)-3-ethoxy-3-oxo-prop-1-enyl]phenyl]methyl-tert-butoxycarbonyl-amino]methyl]azetidine-1-carboxylate A solution of tert-butyl 3-[[[3-[(2-bromo-4-chloro-phenyl)methoxy]-5-formyl-phenyl]methyl-tert-butoxycarbonyl-amino]methyl]azetidine-1-carboxylate (50 mg, 0.08 mmol, 1.0 eq) in acetonitrile is added at 0° C. to a stirred mixture of ethyl 2-diethoxyphosphorylacetate (27 mg, 0.12 mmol, 1.5 eq), lithium chloride (17 mg, 0.40 mmol, 5.0 eq) and N,N-diisopropylethylamine (28 µL, 0.16 mmol, 2.0 eq) in acetonitrile. After 15 hours stirring at 5-10° C., the reaction mixture is concentrated to give a residue that is purified by column chromatography (silica gel; petroleum ether:ethyl acetate, 4:1, v/v) to afford tert-butyl 3-[[[3-[(2-bromo-4-chloro-phenyl)methoxy]-5-[(E)-3-ethoxy-3-oxo-prop-1-enyl]phenyl]methyl-tert-butoxycarbonyl-amino]methyl]azetidine-1-carboxylate as a colorless semi-solid (22 mg, 39% yield).

$^1$H-NMR (400 MHz, CDCl$_3$) δ ppm: 7.63 (m, 2H), 7.48 (d, J=8.4 Hz, 1H), 7.36 (dd, J=1.6 Hz, 8.4 Hz, 1H), 7.03 (s, 1H), 6.97 (s, 1H), 6.84 (s, 1H), 6.40 (d, J=16.0 Hz, 1H), 5.09 (s, 2H), 4.43 (m, 2H), 4.29 (q, J=7.2 Hz, 2H), 3.90 (m, 2H), 3.59 (m, 2H), 3.45 (m, 2H), 2.68 (m, 1H), 1.47 (m, 18H), 1.34 (t, J=7.2 Hz, 3H).

Preparation of ethyl (E)-3-[3-[(azetidin-3-ylmethyl-amino)methyl]-5-[(2-bromo-4-chloro-phenyl)methoxy]phenyl]prop-2-enoate (example 129)

The titled compound is prepared as a white solid following Scheme 1 and in analogy to Example 119 using tert-butyl 3-[[[3-[(2-bromo-4-chloro-phenyl)methoxy]-5-[(E)-3-ethoxy-3-oxo-prop-1-enyl]phenyl]methyl-tert-butoxycarbonyl-amino]methyl]azetidine-1-carboxylate as starting material.

Example 130: N-(azetidin-3-ylmethyl)-1-[3-[(2-bromo-4-chloro-phenyl)methoxy]-5-[(E)-2-(2-furyl)vinyl]phenyl]methanamine Preparation of dimethyl 5-[(2-bromo-4-chloro-phenyl)methoxy]benzene-1,3-dicarboxylate The titled compound is prepared as a white solid (1.8 g, 87% yield) following Scheme 1 and in analogy to Example 37 using 2-bromo-1-(bromomethyl)-4-chloro-benzene (1.4 g, 5.0 mmol, 1.0 eq) and dimethyl 5-hydroxybenzene-1,3-dicarboxylate (1.05 g, 5.0 mmol, 1.0 eq) [13036-02-7] as starting materials.

$^1$H-NMR (400 MHz, CDCl$_3$) δ ppm: 8.33 (s, 1H), 7.84 (s, 2H), 7.63 (s, 1H), 7.50 (d, J=8.0 Hz, 1H), 7.35 (d, J=8.0 Hz, 1H), 5.17 (s, 2H), 3.96 (s, 6H).

Preparation of [3-[(2-bromo-4-chloro-phenyl)methoxy]-5-(hydroxymethyl)phenyl]methanol and methyl 3-[(2-bromo-4-chloro-phenyl)methoxy]-5-(hydroxymethyl)benzoate Lithium borohydride (1.26 g, 58.02 mmol, 5.0 eq) is added at room temperature to a stirred solution of dimethyl 5-[(2-bromo-4-chloro-phenyl)methoxy]benzene-1,3-dicarboxylate (4.8 g, 11.6 mmol, 1.0 eq) in tetrahydrofuran (100 mL). After 18 hours stirring at room 30° C., the reaction mixture is quenched with a saturated sodium sulfate aqueous solution, filtered and concentrated to give a residue that is purified by column chromatography (silica gel; ethyl acetate) to afford [3-[(2-bromo-4-chloro-phenyl)methoxy]-5-(hydroxymethyl)phenyl]methanol (500 mg, 12% yield) and methyl 3-[(2-bromo-4-chloro-phenyl)methoxy]-5-(hydroxymethyl)benzoate (3.7 g, 83% yield).

[3-[(2-bromo-4-chloro-phenyl)methoxy]-5-(hydroxymethyl)phenyl]methanol $^1$H-NMR (400 MHz, CD$_3$OD) δ ppm: 7.70 (s, 1H), 7.57 (d, J=8.0 Hz, 1H), 7.42 (d, J=8.0 Hz, 1H), 6.97 (s, 1H), 6.94 (s, 2H), 5.15 (s, 2H), 4.60 (s, 4H).

methyl 3-[(2-bromo-4-chloro-phenyl)methoxy]-5-(hydroxymethyl)benzoate $^1$H-NMR (400 MHz, CDCl$_3$) δ ppm: 7.69 (s, 1H), 7.64 (s, 1H), 7.58 (s, 1H), 7.52 (d, J=8.0 Hz, 1H), 7.36 (d, J=8.0 Hz, 1H), 7.24 (s, 1H), 5.15 (s, 2H), 4.76 (s, 2H), 3.94 (s, 3H).

Preparation of tert-butyl 3-[[[3-[(2-bromo-4-chloro-phenyl)methoxy]-5-(hydroxymethyl)phenyl]methyl-amino]methyl]azetidine-1-carboxylate The titled compound is prepared as a white foam following Scheme 1 and in analogy to Example 51 using [3-[(2-bromo-4-chloro-phenyl)methoxy]-5-(hydroxymethyl)phenyl]methanol, methanesulfonyl chloride and tert-butyl 3-(aminomethyl)azetidine-1-carboxylate as starting materials.

$^1$H-NMR (400 MHz, CDCl$_3$) δ ppm: 7.60 (s, 1H), 7.47 (d, J=8.0 Hz, 1H), 7.33 (d, J=8.0 Hz, 1H), 7.25 (s, 1H), 6.98 (s, 1H), 6.90 (s, 1H), 5.15 (s, 2H), 4.65 (s, 2H), 3.95-4.20 (m, 4H), 3.70 (m, 2H), 3.20 (m, 2H), 2.90 (m, 1H), 1.40 (s, 9H).

MS m/z (+ESI): 525.2, 527.2 [M+H]$^+$.

Preparation of tert-butyl 3-[[[3-[(2-bromo-4-chloro-phenyl)methoxy]-5-(hydroxymethyl)phenyl]methyl-tert-butoxycarbonyl-amino]methyl]azetidine-1-carboxylate Triethylamine (637 µL, 4.56 mmol, 1.5 eq) is added at room temperature to a stirred solution of tert-butyl 3-[[[3-[(2-bromo-4-chloro-phenyl)methoxy]-5-(hydroxymethyl)phenyl]methylamino]methyl]azetidine-1-carboxylate (1.6 g, 3.04 mmol, 1.0 eq) in dichloromethane (60 mL), followed by di-tert-butyl dicarbonate (797 mg, 3.65 mmol, 1.2 eq). After 2 hours stirring at room temperature, the reaction mixture is concentrated to give a residue that is purified by column chromatography (silica gel; petroleum ether:ethyl acetate, 5:3, v/v) to afford tert-butyl 3-[[[3-[(2-bromo-4-chloro-phenyl)methoxy]-5-(hydroxymethyl)phenyl]methyl-tert-butoxycarbonyl-amino]methyl]azetidine-1-carboxylate as a white foam (1.17 g, 61% yield).

$^1$H-NMR (400 MHz, CDCl$_3$) δ ppm: 7.62 (s, 1H), 7.49 (d, J=8.0 Hz, 1H), 7.33 (d, J=8.0 Hz, 1H), 6.92 (s, 1H), 6.83 (s, 1H), 6.74 (s, 1H), 5.08 (s, 2H), 4.68 (s, 2H), 4.42 (s, 2H), 3.90 (m, 2H), 3.53 (m, 2H), 3.43 (m, 2H), 2.74 (m, 1H), 1.40-1.55 (m, 18H).

MS m/z (+ESI): 625.4, 627.4 [M+H]$^+$.

Preparation of tert-butyl 3-[[[3-[(2-bromo-4-chloro-phenyl)methoxy]-5-formyl-phenyl]methyl-tert-butoxycarbonyl-amino]methyl]azetidine-1-carboxylate Dess Martin periodinane solution (0.75 mL, 0.74 mmol, 1.5 eq) is added at 0° C. to a stirred solution of tert-butyl 3-[[[3-[(2-bromo-4-chloro-phenyl)methoxy]-5-(hydroxymethyl)phenyl]methyl-tert-butoxycarbonyl-amino]methyl] azetidine-1-carboxylate (310 mg, 0.49 mmol, 1.0 eq) in dichloromethane (20 mL). After 1 hour stirring at 0° C., the reaction mixture is quenched with a saturated sodium thiosulfate aqueous solution (20 mL). The organic layer is washed with water (20 mL), brine (20 mL), dried over sodium sulfate, filtered and concentrated to give a residue that is purified by column chromatography (silica gel; petroleum ether:ethyl acetate, 2:1, v/v) to afford tert-butyl 3-[[[3-[(2-bromo-4-chloro-phenyl)methoxy]-5-formyl-phenyl]methyl-tert-butoxycarbonyl-amino]methyl]azetidine-1-carboxylate as a white foam (260 mg, 84% yield).

$^1$H-NMR (400 MHz, CDCl$_3$) δ ppm: 9.98 (s, 1H), 7.65 (s, 1H), 7.49 (d, J=8.0 Hz, 1H), 7.37 (m, 3H), 7.10 (s, 1H), 5.15 (s, 2H), 4.50 (s, 2H), 3.90 (m, 2H), 3.62 (m, 2H), 3.48 (m, 2H), 2.76 (m, 1H), 1.40-1.55 (m, 18H).

Preparation of 2-furylmethyl(triphenyl)phosphonium bromide

Triphenylphosphine (1.63 g, 6.20 mmol, 1.0 eq) is added at room temperature to a stirred solution of 2-(bromomethyl)furan (1.0 g, 6.20 mmol, 1.0 eq) [4437-18-7] in toluene (15 mL). After 6 hours stirring at 80° C., the resulting suspension is filtered, washed with tetrahydrofuran (20 mL) and dried under vacuum to afford 2-furylmethyl(triphenyl)phosphonium bromide (2.0 g, 76% yield) that is directly engaged in the next step without further purification.

MS m/z (+ESI): 343.2 [M+H]$^+$.

Preparation of tert-butyl 3-[[[3-[(2-bromo-4-chloro-phenyl)methoxy]-5-[(E)-2-(2-furyl)vinyl]phenyl] methyl-tert-butoxycarbonyl-amino]methyl]azetidine-1-carboxylate A solution of potassium tert-butoxide (89 mg, 0.79 mmol, 1.5 eq) in tetrahydrofuran (5 mL) is added dropwise at 0° C. to a stirred solution of 2-furylmethyl(triphenyl)phosphonium bromide (336 mg, 0.79 mmol, 1.0 eq) in tetrahydrofuran (15 mL). After 15 minutes stirring at 0° C., a solution of tert-butyl 3-[[[3-[(2-bromo-4-chloro-phenyl)methoxy]-5-formyl-phenyl]methyl-tert-butoxycarbonyl-amino]methyl] azetidine-1-carboxylate (330 mg, 0.53 mmol, 1.0 eq) in tetrahydrofuran (5 mL) is added dropwise to the reaction mixture. After 30 minutes stirring at 0° C., the reaction mixture is quenched with a saturated ammonium chloride aqueous solution (10 mL). Tetrahydrofuran is evaporated and the residue is extracted with ethyl acetate (3×20 mL) and water (20 mL). The combined organic layers are dried over sodium sulfate, filtered and concentrated to give a residue that is purified by column chromatography (silica gel; petroleum ether:ethyl acetate, 5:2, v/v) to afford tert-butyl 3-[[[3-[(2-bromo-4-chloro-phenyl)methoxy]-5-[(E)-2-(2-furyl)vinyl]phenyl]methyl-tert-butoxycarbonyl-amino]methyl] azetidine-1-carboxylate (245 mg, 67% yield).

$^1$H-NMR (400 MHz, CDCl$_3$) δ ppm: 7.64 (s, 1H), 7.51 (d, J=8.0 Hz, 1H), 7.43 (s, 1H), 7.36 (d, J=8.0 Hz, 1H), 6.85-7.05 (m, 4H), 6.25-6.45 (m, 3H), 5.10 (s, 2H), 4.43 (m, 2H), 3.90 (m, 2H), 3.61 (m, 2H) 3.46 (m, 2H), 2.65-2.85 (m, 1H), 1.43-1.60 (m, 18H).

MS m/z (+ESI): 687.2, 689.2 [M+H]$^+$.

Preparation of N-(azetidin-3-ylmethyl)-1-[3-[(2-bromo-4-chloro-phenyl)methoxy]-5-[(E)-2-(2-furyl)vinyl]phenyl]methanamine The titled compound is prepared as a white solid (24 mg, 16% yield) following Scheme 1 and in analogy to Example 158 using tert-butyl 3-[[[3-[(2-bromo-4-chloro-phenyl) methoxy]-5-[(E)-2-(2-furyl)vinyl]phenyl]methyl-tert-butoxycarbonyl-amino]methyl]azetidine-1-carboxylate (200 mg, 0.30 mmol, 1.0 eq) as starting material.

Example 135: 2-(azetidin-3-ylmethylamino)-1-[3-[(2-bromo-4-chloro-phenyl)methoxy]phenyl]ethanone

Preparation of 1-[3-[(2-bromo-4-chloro-phenyl) methoxy]phenyl]ethanone

The titled compound is prepared as a white solid (260 mg, 56% yield) following Scheme 1 and in analogy to Example 136 using 2-bromo-1-(bromomethyl)-4-chloro-benzene (1.5 g, 5.27 mmol, 1.0 eq) and 1-(3-hydroxyphenyl)ethanone (0.26 g, 10.5 mmol, 2.0 eq) [121-71-1] as starting materials.

$^1$H-NMR (400 MHz, DMSO-d6) δ ppm: 7.82 (s, 1H), 7.40-7.65 (m, 5H), 7.42 (dd, J=1.6 Hz, 8.0 Hz, 1H), 5.17 (s, 2H), 2.60 (s, 3H).

MS m/z (+ESI): 338.9, 340.9 [M+H]$^+$.

Preparation of 2-bromo-1-[3-[(2-bromo-4-chloro-phenyl)methoxy]phenyl]ethanone Copper(II) bromide (1.05 g, 4.7 mmol, 2.0 eq) is added at room temperature to a stirred solution of 1-[3-[(2-bromo-4-chloro-phenyl)methoxy]phenyl]ethanone (800 mg, 2.35 mmol, 1.0 eq) in chloroform (10 mL) and ethyl acetate (10 mL). After 3 hours stirring at 90° C., ethyl acetate (100 mL) is added and the resulting mixture is filtered and concentrated to give a residue that is purified by column chromatography (silica gel; petroleum ether:ethyl acetate, 20:1, v/v) to afford 2-bromo-1-[3-[(2-bromo-4-chloro-phenyl) methoxy]phenyl]ethanone as a white solid (400 mg, 41% yield).

$^1$H-NMR (400 MHz, DMSO-d6) δ ppm: 7.84 (s, 1H), 7.45-7.65 (m, 5H), 7.33 (d, J=8.0 Hz, 1H), 5.18 (s, 2H), 4.94 (s, 2H).

Preparation of 2-(azetidin-3-ylmethylamino)-1-[3-[(2-bromo-4-chloro-phenyl)methoxy]phenyl]ethanone The titled compound is prepared as a white solid following Scheme 1 and in analogy to Example 158 using 2-bromo-1-[3-[(2-bromo-4-chloro-phenyl)methoxy]phenyl] ethanone and tert-butyl 3-(aminomethyl)azetidine-1-carboxylate as starting materials.

Example 136: 1-[3-[(2-bromo-4-chloro-phenyl) methylsulfanyl]phenyl]-N-(pyrrolidin-3-ylmethyl) methanamine

Preparation of methyl 3-[(2-bromo-4-chloro-phenyl) methylsulfanyl]benzoate 2-bromo-1-(bromomethyl)-4-chloro-benzene (845 mg, 2.97 mmol, 1.0 eq) is added at room temperature to a stirred solution of methyl 3-sulfanylbenzoate (500 mg, 2.97 mmol, 1.0 eq) [72886-42-1] in N,N-dimethylformamide (10 mL), followed by potassium carbonate (822 mg, 5.96 mmol, 2.0 eq). After 20 hours stirring at room temperature, solvent is evaporated and the residue is extracted with ethyl acetate (3×20 mL) and water (20 mL). The combined organic layers are washed with brine, dried over sodium sulfate, filtered and concentrated to afford methyl 3-[(2-bromo-4-chloro-phenyl)methylsulfanyl]benzoate as a light yellow oil (1.1 g, 99% yield) that is directly engaged in the next step without further purification.

$^1$H-NMR (400 MHz, DMSO-d6) δ ppm: 7.80 (m, 3H), 7.64 (d, J=8.0 Hz, 1H), 7.48 (t, J=8.0 Hz, 1H), 7.39 (s, 2H), 4.33 (s, 2H), 3.85 (s, 3H).

MS m/z (+ESI): 371.0, 373.0 [M+H]$^+$.

Preparation of [3-[(2-bromo-4-chloro-phenyl)methylsulfanyl]phenyl]methanol

Lithium borohydride (327 mg, 14.9 mmol, 5.0 eq) is added at room temperature to a stirred solution of methyl 3-[(2-bromo-4-chloro-phenyl)methylsulfanyl]benzoate (1.1 g, 2.97 mmol, 1.0 eq) in tetrahydrofuran (15 mL). After 20 hours stirring at room 15° C., the reaction mixture is quenched with a 2M hydrochloric acid aqueous solution (10 mL) and extracted with ethyl acetate (3×10 mL). The combined organic layers are dried over sodium sulfate, filtered and concentrated to afford [3-[(2-bromo-4-chloro-phenyl)methylsulfanyl]phenyl]methanol as a light yellow oil (970 mg, 95% yield) that is directly engaged in the next step without further purification.

$^1$H-NMR (400 MHz, DMSO-d6) δ ppm: 7.76 (s, 1H), 7.38 (s, 2H), 7.15-7.30 (m, 4H), 5.22 (t, J=5.6 Hz, 1H), 4.46 (d, J=6.0 Hz, 2H), 4.27 (s, 2H).

MS m/z (+ESI): 342.9, 344.9 [M+H]$^+$.

Preparation of 3-[(2-bromo-4-chloro-phenyl)methylsulfanyl]benzaldehyde

Manganese dioxide (2.38 g, 27.4 mmol, 10.0 eq) is added at room temperature to a stirred solution of [3-[(2-bromo-4-chloro-phenyl)methylsulfanyl]phenyl]methanol (940 mg, 2.74 mmol, 1.0 eq) in dichloromethane (20 mL). After 16 hours stirring at room temperature, manganese dioxide is removed by filtration and the solution is evaporated to afford 3-[(2-bromo-4-chloro-phenyl)methylsulfanyl]benzaldehyde as a light yellow oil (640 mg, 69% yield) that is directly engaged in the next step without further purification.

$^1$H-NMR (400 MHz, DMSO-d6) δ ppm: 9.98 (s, 1H), 7.87 (t, J=1.6 Hz, 1H), 7.77 (d, J=2.0 Hz, 1H), 7.65-7.75 (m, 2H), 7.55 (t, J=7.2 Hz, 1H), 7.40 (m, 1H), 4.37 (s, 2H).

Preparation of tert-butyl 3-[[[3-[(2-bromo-4-chloro-phenyl)methylsulfanyl]phenyl]methylamino]methyl]pyrrolidine-1-carboxylate The titled compound is prepared as a colorless oil (177 mg, 77% yield) following Scheme 1 and in analogy to Example 37 using 3-[(2-bromo-4-chloro-phenyl)methylsulfanyl]benzaldehyde (150 mg, 0.44 mmol, 1.0 eq) and tert-butyl 3-(aminomethyl)pyrrolidine-1-carboxylate (97 mg, 0.49 mmol, 1.1 eq) [270912-72-6] as starting materials.

$^1$H-NMR (400 MHz, DMSO-d6+D$_2$O) δ ppm: 7.70 (s, 1H), 7.31 (s, 2H), 7.15-7.25 (m, 4H), 4.22 (s, 2H), 3.63 (s, 2H), 3.35 (m, 1H), 3.25 (m, 1H), 3.13 (m, 1H), 2.85 (m, 1H), 2.40 (m, 2H), 2.23 (m, 1H), 1.88 (m, 1H), 1.45 (m, 1H), 1.35 (s, 9H).

MS m/z (+ESI): 525.1, 527.1 [M+H]$^+$.

Preparation of 1-[3-[(2-bromo-4-chloro-phenyl)methylsulfanyl]phenyl]-N-(pyrrolidin-3-ylmethyl)methanamine Trifluoroacetic acid (0.6 mL, 7.84 mmol, 25.0 eq) is added at room temperature to a stirred solution of tert-butyl 3-[[[3-[(2-bromo-4-chloro-phenyl)methylsulfanyl]phenyl]methylamino]methyl]pyrrolidine-1-carboxylate (170 mg, 0.32 mmol, 1.0 eq) in dichloromethane (2 mL). After 30 minutes stirring at room temperature, diethyl ether is added and the resulting precipitate is collected by filtration to afford 1-[3-[(2-bromo-4-chloro-phenyl)methylsulfanyl]phenyl]-N-(pyrrolidin-3-ylmethyl)methanamine as a white solid (190 mg, 99% yield).

Example 137: 1-[3-[(2-bromo-4-chloro-phenyl)methylsulfinyl]phenyl]-N-(pyrrolidin-3-ylmethyl)methanamine Preparation of 3-[(2-bromo-4-chloro-phenyl)methylsulfinyl]benzaldehyde meta-Chloroperoxybenzoic acid (337 mg, 1.5 mmol, 1.5 eq) is added at 0° C. to a stirred solution of 3-[(2-bromo-4-chloro-phenyl)methylsulfanyl]benzaldehyde (340 mg, 1.0 mmol, 1.0 eq) in dichloromethane (10 mL). After 16 hours stirring at room temperature, the reaction mixture is quenched with a saturated sodium thiosulfate aqueous solution (10 mL), extracted with ethyl acetate (3×20 mL) and a saturated sodium hydrogen carbonate aqueous solution (10 mL). The combined organic layers are dried over sodium sulfate, filtered and concentrated to give a residue that is purified by column chromatography (silica gel; petroleum ether:ethyl acetate, 10:1 to 3:1, v/v) to afford 3-[(2-bromo-4-chloro-phenyl)methylsulfinyl]benzaldehyde as a white solid (300 mg, 84% yield).

$^1$H-NMR (400 MHz, DMSO-d6) δ ppm: 10.06 (s, 1H), 8.09 (m, 1H), 8.30 (d, J=2.0 Hz, 1H), 7.77 (m, 3H), 7.45 (dd, J=2.0 Hz, 8.2 Hz, 1H), 7.24 (d, J=8.4 Hz, 1H), 4.42 (m, 2H).

MS m/z (+ESI): 357.1, 359.1 [M+H]$^+$.

Preparation of 1-[3-[(2-bromo-4-chloro-phenyl)methylsulfinyl]phenyl]-N-(pyrrolidin-3-ylmethyl)methanamine The titled compound is prepared as a white solid following Scheme 1 and in analogy to Examples 37 and 136 using 3-[(2-bromo-4-chloro-phenyl)methylsulfinyl]benzaldehyde and tert-butyl 3-(aminomethyl)pyrrolidine-1-carboxylate as starting materials.

Example 141: 1-[3-[(2-bromo-4-chloro-phenyl)methylsulfonyl]phenyl]-N-(pyrrolidin-3-ylmethyl)methanamine The titled compound is prepared as a white solid following Scheme 1 and in analogy to Example 137 using 3-[(2-bromo-4-chloro-phenyl)methylsulfinyl]benzaldehyde and tert-butyl 3-(aminomethyl)pyrrolidine-1-carboxylate as starting materials.

Example 149: N-(azetidin-3-ylmethyl)-1-[3-[2-(2-bromo-4-chlorophenyl)ethynyl]phenyl]methanamine Preparation of 3-[2-(2-bromo-4-chloro-phenyl)ethynylbenzaldehyde A solution of triphenylphosphine (230 mg, 0.88 mmol, 0.06 eq) in dioxane (1 mL), is added at room temperature to a stirred suspension of bis(benzonitrile)palladium(II) chloride (168 mg, 0.43 mmol, 0.03 eq) and copper(I) iodide (56 mg, 0.29 mmol, 0.02 eq) in dioxane (1 mL), followed by diisopropylamine (2.46 mL, 17.5 mmol, 1.2 eq), 2-bromo-4-chloro-1-iodo-benzene (4.63 g, 14.6 mmol, 1.0 eq) [31928-44-6] and 3-ethynylbenzaldehyde (1.9 g, 14.6 mmol, 1.0 eq) [77123-56-9]. After 15 hours stirring at room temperature, the reaction mixture is diluted with ethyl acetate, filtered through decalite and concentrated to give a residue that is purified by column chromatography (silica gel; petroleum ether:dichloromethane, 1:1, v/v) to afford 3-[2-(2-bromo-4-chloro-phenyl)ethynylbenzaldehyde as a yellow solid (4.35 g, 93% yield).

$^1$H-NMR (400 MHz, CDCl$_3$) δ ppm: 10.03 (s, 1H), 8.06 (s, 1H), 7.88 (d, J=7.6 Hz, 1H), 7.81 (d, J=7.6 Hz, 1H), 7.65 (d, J=2.0 Hz, 1H), 7.55 (m, 1H), 7.49 (d, J=8.0 Hz, 1H), 7.30 (dd, J=2.0 Hz, 8.0 Hz, 1H).

Preparation of N-(azetidin-3-ylmethyl)-1-[3-[2-(2-bromo-4-chlorophenyl)ethynyl]phenyl]methanamine The titled compound is prepared as a white solid following Scheme 4 and in analogy to Examples 37 and 136 using 3-[2-(2-bromo-4-chloro-phenyl)ethynylbenzaldehyde and tert-butyl 3-(aminomethyl)azetidine-1-carboxylate as starting materials.

Example 158: 3-[(azetidin-3-ylmethylamino)methyl]-N-[(2-bromo-4-chloro-phenyl)methyl]aniline Preparation of methyl 3-[(2-bromo-4-chloro-phenyl)methyl-tert-butoxycarbonyl-amino]benzoate Sodium hydride (200 mg, 4.8 mmol, 1.2 eq) is added at room temperature to a stirred solution of methyl 3-(tert-butoxycarbonylamino)benzoate (1.0 g, 4.0 mmol, 1.0 eq) [161111-23-5] in N,N-dimethylformamide (10 mL), followed by 2-bromo-1-(bromomethyl)-4-chloro-benzene (1.7 g, 4.8 mmol, 1.2 eq). After 1 hour stirring at room temperature, solvent is evaporated and the residue is extracted with ethyl acetate (3×20 mL) and water (20 mL). The combined organic layers are washed with brine, dried over sodium sulfate, filtered and concentrated to give a residue that is purified by column chromatography (silica gel; petroleum ether:ethyl acetate, 20:1, v/v) to afford methyl 3-[(2-bromo-4-chloro-phenyl)methyl-tert-butoxycarbonyl-amino]benzoate as a colorless oil (2.5 g, 94% yield).

$^1$H-NMR (400 MHz, DMSO-d6) δ ppm: 7.82 (s, 1H), 7.72 (m, 2H), 7.52 (d, J=8.0 Hz, 1H), 7.44 (m, 2H), 7.29 (d, J=8.4 Hz, 1H), 4.89 (s, 2H), 3.82 (s, 3H), 1.34 (s, 9H).
MS m/z (+ESI): 398.0, 400.0 [M-tBu+H]$^+$.

Preparation of tert-butyl N-[(2-bromo-4-chloro-phenyl)methyl]-N-[3-(hydroxymethyl)phenyl]carbamate Lithium aluminium hydride (130 mg, 3.3 mmol, 1.0 eq) is added at 0° C. to a stirred solution of methyl 3-[(2-bromo-4-chloro-phenyl)methyl-tert-butoxycarbonyl-amino]benzoate (1.5 g, 3.3 mmol, 1.0 eq) in tetrahydrofuran (10 mL). After 2 hours stirring at 0° C., the reaction mixture is quenched with brine (10 mL) and extracted with ethyl acetate (3×10 mL). The combined organic layers are dried over sodium sulfate, filtered and concentrated to give a residue that is purified by column chromatography (silica gel; petroleum ether:ethyl acetate, 5:1, v/v) to afford tert-butyl N-[(2-bromo-4-chloro-phenyl)methyl]-N-[3-(hydroxymethyl)phenyl]carbamate as a light yellow viscous oil (1.16 g, 41% yield).

$^1$H-NMR (400 MHz, DMSO-d6) δ ppm: 7.72 (s, 1H), 7.46 (d, J=8.4 Hz, 1H), 7.30 (d, J=8.4 Hz, 1H), 7.23 (m, 2H), 7.09 (m, 2H), 5.18 (t, J=5.6 Hz, 1H), 4.81 (s, 2H), 4.43 (d, J=5.6 Hz, 2H), 1.34 (s, 9H). MS m/z (+ESI): 370.0, 372.0 [M-tBu+H]$^+$.

Preparation of tert-butyl N-[(2-bromo-4-chloro-phenyl)methyl]-N-(3-formylphenyl)carbamate Manganese dioxide (1.6 g, 18.7 mmol, 10.0 eq) is added at room temperature to a stirred solution of tert-butyl N-[(2-bromo-4-chloro-phenyl)methyl]-N-[3-(hydroxymethyl)phenyl]carbamate (800 mg, 1.9 mmol, 1.0 eq) in acetone (20 mL). After 3 hours stirring at room temperature, manganese dioxide is removed by filtration and the solution is evaporated to give a residue that is purified by column chromatography (silica gel; petroleum ether:ethyl acetate, 20:1, v/v) to afford tert-butyl N-[(2-bromo-4-chloro-phenyl)methyl]-N-(3-formylphenyl)carbamate as a colorless oil (500 mg, 72% yield).

$^1$H-NMR (400 MHz, DMSO-d6) δ ppm: 9.95 (s, 1H), 7.79 (s, 1H), 7.70 (m, 2H), 7.59 (d, J=8.0 Hz, 1H), 7.53 (m, 1H), 7.44 (dd, J=2.0 Hz, 8.0 Hz, 1H), 7.31 (d, J=8.4 Hz, 1H), 4.90 (s, 2H), 1.35 (s, 9H).
MS m/z (+ESI): 368.0, 370.0 [M-tBu+H]$^+$.

Preparation of tert-butyl 3-[[[3-[(2-bromo-4-chloro-phenyl)methyl]-tert-butoxycarbonyl-amino]phenyl]methylamino]methyl]azetidine-1-carboxylate The titled compound is prepared as a colorless oil (200 mg, 71% yield) following Scheme 1 and in analogy to Example 37 using tert-butyl N-[(2-bromo-4-chloro-phenyl)methyl]-N-(3-formylphenyl)carbamate (200 mg, 0.47 mmol, 1.0 eq) and tert-butyl 3-(aminomethyl)azetidine-1-carboxylate (80 mg, 0.47 mmol, 1.0 eq) as starting materials.

$^1$H-NMR (400 MHz, DMSO-d6) δ ppm: 7.69 (s, 1H), 7.43 (d, J=8.0 Hz, 1H), 7.29 (d, J=8.4 Hz, 1H), 7.19 (m, 2H), 7.08 (m, 2H), 4.82 (s, 2H), 3.80 (m, 2H), 3.61 (s, 2H), 3.44 (m, 2H), 2.52 (m, 3H), 1.34 (s, 18H).
MS m/z (+ESI): 594.2, 596.2 [M+H]$^+$.

Preparation of 3-[(azetidin-3-ylmethylamino)methyl]-N-[(2-bromo-4-chloro-phenyl)methyl]aniline Trifluoroacetic acid (0.5 mL, 6.53 mmol, 19.0 eq) is added at room temperature to a stirred solution of tert-butyl 3-[[[3-[(2-bromo-4-chloro-phenyl)methyl]-tert-butoxycarbonyl-amino]phenyl]methylamino]methyl]azetidine-1-carboxylate (200 mg, 0.34 mmol, 1.0 eq) in dichloromethane (2 mL). After 3 hours stirring at room temperature, the reaction mixture is concentrated and the residue is purified by preparative HPLC to afford 3-[(azetidin-3-ylmethylamino)methyl]-N-[(2-bromo-4-chloro-phenyl)methyl]aniline as a white solid (48 mg, 36% yield).

Example 165: N-(azetidin-3-ylmethyl)-2-[3-[(E)-2-(2-bromo-4-chloro-phenyl)vinyl]phenyl]ethanamine Preparation of 3-[(E)-2-(2-bromo-4-chloro-phenyl)vinyl]benzonitrile The titled compound is prepared as a white solid (70 mg, 75% yield) following Scheme 3 and in analogy to Example 168 using 2-bromo-4-chloro-1-(diethoxyphosphorylmethyl) benzene (100 mg, 0.29 mmol, 1.0 eq) and 3-formylbenzonitrile (42 mg, 0.32 mmol, 1.1 eq) [24964-64-5] as starting materials.

$^1$H-NMR (400 MHz, DMSO-d6) δ ppm: 8.10 (s, 1H), 7.94 (d, J=8.4 Hz, 1H), 7.84 (d, J=8.4 Hz, 1H), 7.81 (d, J=1.6 Hz, 1H), 7.77 (d, J=7.6 Hz, 1H), 7.60 (dd, J=7.6 Hz, 8.4 Hz, 1H), 7.52 (dd, J=1.6 Hz, 8.4 Hz, 1H), 7.46 (d, J=16.4 Hz, 1H), 7.31 (d, J=16.4 Hz, 1H).

Preparation of 3-[(E)-2-(2-bromo-4-chloro-phenyl) vinyl]benzaldehyde

Diisobutylaluminium hydride (1M solution in tetrahydrofuran, 1.90 mL, 1.90 mmol, 1.5 eq) is added dropwise at 0° C. to a stirred solution of 3-[(E)-2-(2-bromo-4-chloro-phenyl)vinyl]benzonitrile (400 mg, 1.26 mmol, 1.0 eq) in dichloromethane (5 mL). After 16 hours stirring at room temperature, the reaction mixture is poured in 100 g of crushed ice and a 2N hydrochloric acid aqueous solution (10 mL). The phases are separated and the aqueous phase is extracted with ethyl acetate (3×15 mL). The combined organic layers are washed with brine (10 mL), dried over sodium sulfate, filtered and concentrated to afford 3-[(E)-2-(2-bromo-4-chloro-phenyl)vinyl]benzaldehyde as a yellow solid (330 mg, 82% yield) that is directly engaged in the next step without further purification.

$^1$H-NMR (400 MHz, DMSO-d6) δ ppm: 10.07 (s, 1H), 8.15 (s, 1H), 7.96 (d, J=8.4 Hz, 1H), 7.91 (d, J=8.4 Hz, 1H), 7.87 (d, J=7.6 Hz, 1H), 8.25 (d, J=2.0 Hz, 1H), 7.65 (dd, J=7.6 Hz, 8.4 Hz, 1H), 7.53 (dd, J=2.0 Hz, 8.4 Hz, 1H), 7.48 (m, 2H).

Preparation of 2-[3-[(E)-2-(2-bromo-4-chloro-phenyl)vinyl]phenyl]acetaldehyde

Lithium diisopropylamide (2M solution in tetrahydrofuran, 2.40 mL, 4.80 mmol, 3.0 eq) is added at 0° C. to as stirred suspension of (methoxymethyl)triphenylphosphonium chloride (800 mg, 2.33 mmol, 1.5 eq) in tetrahydrofuran (20 mL). After 1 hour stirring at room temperature, 3-[(E)-2-(2-bromo-4-chloro-phenyl)vinyl]benzaldehyde (500 mg, 1.55 mmol, 1.0 eq) is added at room temperature to the reaction mixture. After 1 hour stirring at room temperature, a saturated ammonium chloride aqueous solution (20 mL) is added to quench the reaction. The resulting mixture is extracted with ethyl acetate (3×20 mL). The combined organic layers are dried over sodium sulfate, filtered and concentrated to give a yellow oil that is dissolved in tetrahydrofuran (5 mL) and concentrated hydrochloric acid aqueous solution (2.0 mL). After 1 hour stirring at room temperature, the reaction mixture is extracted with ethyl acetate (3×20 mL) and water (20 mL). The combined organic layers are washed with brine (20 mL), dried over sodium sulfate, filtered and concentrated to give a residue that is purified by column chromatography (silica gel; petroleum ether:ethyl acetate, 20:1 to 10:1, v/v) to afford 2-[3-[(E)-2-(2-bromo-4-chloro-phenyl)vinyl]phenyl]acetaldehyde as a yellow oil (180 mg, 37% yield).

$^1$H-NMR (400 MHz, DMSO-d6) δ ppm: 9.75 (s, 1H), 7.78 (m, 2H), 7.48 (m, 3H), 7.30-7.43 (m, 2H), 7.25 (m, 2H), 3.83 (s, 2H).

Preparation of N-(azetidin-3-ylmethyl)-2-[3-[(E)-2-(2-bromo-4-chloro-phenyl)vinyl]phenyl]ethanamine The titled compound is prepared as a white solid following Scheme 3 and in analogy to Examples 37 and 158 using 2-[3-[(E)-2-(2-bromo-4-chloro-phenyl)vinyl]phenyl]acetaldehyde and tert-butyl 3-(aminomethyl)azetidine-1-carboxylate as starting materials.

Example 168: N-(azetidin-3-ylmethyl)-1-[3-[(Z/E)-3-(2-bromo-4-chloro-phenyl)allyl]phenyl]methanamine Preparation of 2-bromo-4-chloro-1-(diethoxyphosphorylmethyl)benzene Triethyl phosphite (30.03 mL, 175.82 mmol, 5.0 eq) is added at room temperature to a stirred solution of 2-bromo-1-(bromomethyl)-4-chloro-benzene (10.0 g, 35.16 mmol, 1.0 eq) in toluene (100 mL). After 4 hours stirring under reflux conditions, solvent is evaporated and the residue is purified by column chromatography (silica gel; petroleum ether:ethyl acetate, 10:1 to 1:1, v/v) to afford 2-bromo-4-chloro-1-(diethoxyphosphorylmethyl)benzene as a light yellow oil (12.0 g, 85% yield).

$^1$H-NMR (400 MHz, DMSO-d6) δ ppm: 7.75 (s, 1H), 7.44 (m, 2H), 4.97 (m, 4H), 3.39 (m, 2H), 1.19 (m, 6H).

MS m/z (+ESI): 341.0 [M+H]$^+$.

Preparation of 2-[3-[(Z/E)-3-(2-bromo-4-chloro-phenyl)allyl]phenyl]-1,3-dioxolane Sodium hydride (400 mg, 16.8 mmol, 2.6 eq) is added at room temperature to a stirred solution of 2-bromo-4-chloro-1-(diethoxyphosphorylmethyl)benzene (2.86 g, 8.39 mmol, 1.3 eq) in tetrahydrofuran (50 mL), followed by 2-[3-(1,3-dioxolan-2-yl)phenyl]acetaldehyde (1.24 g, 6.45 mmol, 1.0 eq) [88679-83-8]. After 24 hours stirring at room temperature, solvent is evaporated and the residue is extracted with ethyl acetate (3×50 mL) and water (50 mL). The combined organic layers are washed with brine, dried over sodium sulfate, filtered and concentrated to give a residue that is purified by column chromatography (silica gel; petroleum ether:ethyl acetate, 10:1, v/v) to afford 2-[3-[(Z/E)-3-(2-bromo-4-chloro-phenyl)allyl]phenyl]-1,3-dioxolane as a yellow oil (1.6 g, 65% yield).

$^1$H-NMR (400 MHz, DMSO-d6) δ ppm: 7.75 (m, 1H), 7.68 (d, J=8.4 Hz, 1H), 7.42 (m, 2H), 7.33 (m, 3H), 6.68 (d, J=16.0 Hz, 1H), 6.47 (m, 1H), 5.70 (s, 1H), 4.04 (m, 2H), 3.92 (m, 2H), 3.60 (m, 2H). MS m/z (+ESI): 379.1, 381.1 [M+H]$^+$.

Preparation of 3-[(Z/E)-3-(2-bromo-4-chloro-phenyl)allyl]benzaldehyde

1N Hydrochloric acid aqueous solution (30 mL) is added at room temperature to a stirred solution of 2-[3-[(Z/E)-3-(2-bromo-4-chloro-phenyl)allyl]phenyl]-1,3-dioxolane (1.5 g, 3.95 mmol, 1.0 eq) in tetrahydrofuran (30 mL). After 2 hours stirring at 60° C., the reaction mixture is extracted with ethyl acetate (3×30 mL) and water (20 mL) and the pH is adjusted to 7 by the addition of a saturated sodium hydrogen carbonate aqueous solution. The combined organic layers are dried over sodium sulfate, filtered and concentrated to give a residue that is purified by column chromatography (silica gel; petroleum ether:ethyl acetate, 15:1, v/v) to afford 3-[(Z/E)-3-(2-bromo-4-chloro-phenyl)allyl]benzaldehyde as a yellow oil (1.1 g, 84% yield).

$^1$H-NMR (400 MHz, DMSO-d6) δ ppm: 10.00 (s, 1H), 7.73 (m, 4H), 7.58 (m, 2H), 7.42 (m, 1H), 6.71 (d, J=16.0 Hz, 1H), 6.53 (m, 1H), 3.68 (m, 2H,).

MS m/z (+ESI): 334.9, 337.0 [M+H]$^+$.

Preparation of N-(azetidin-3-ylmethyl)-1-[3-[(Z/E)-3-(2-bromo-4-chloro-phenyl)allyl]phenyl]methanamine The titled compound is prepared as a white solid following Scheme 3 and in analogy to Examples 37 and 158 using 3-[(Z/E)-3-(2-bromo-4-chloro-phenyl)allyl]benzaldehyde and tert-butyl 3-(aminomethyl)azetidine-1-carboxylate as starting materials.

Example 173: N-(azetidin-3-ylmethyl)-1-[3-[(2-bromo-4-chloro-phenyl)methoxymethyl]phenyl]methanamine Preparation of [3-[(2-bromo-4-chloro-phenyl)methoxymethyl]phenyl]methanol Sodium hydride (125 mg, 3.13 mmol, 1.2 eq) is added at room temperature to a stirred solution of [3-(hydroxymethyl)phenyl]methanol (360 mg, 2.60 mmol, 1.0 eq) [626-18-6] in N,N-dimethylformamide (3 mL), followed by 2-bromo-1-(bromomethyl)-4-chloro-benzene (738 mg, 2.60 mmol, 1.0 eq). After 15 hours stirring at room temperature, solvent is evaporated and the residue is extracted with ethyl acetate (3×20 mL) and water (20 mL). The combined organic layers are washed with brine, dried over sodium sulfate, filtered and concentrated to give a residue that is purified by column chromatography (silica gel; petroleum ether:ethyl acetate, 8:1, v/v) to afford [3-[(2-bromo-4-chloro-phenyl)methoxymethyl]phenyl]methanol as a light yellow oil (300 mg, 34% yield) that is directly engaged in the next step without further purification.

Preparation of N-(azetidin-3-ylmethyl)-1-[3-[(2-bromo-4-chloro-phenyl)methoxymethyl]phenyl]methanamine The titled compound is prepared as a white solid following Scheme 1 and in analogy to Example 158 using [3-[(2-bromo-4-chloro-phenyl)methoxymethyl]phenyl]methanol and tert-butyl 3-(aminomethyl)azetidine-1-carboxylate as starting materials.

Example 183: 1-[3-allyloxy-5-[[4-chloro-2-(trifluoromethyl)phenyl]sulfanylmethyl]phenyl]-N-azetidin-3-ylmethyl)methanamine Preparation of dimethyl 5-[tert-butyl(dimethyl)silyl]oxybenzene-1,3-dicarboxylate tert-Butyl-chloro-dimethyl-silane (8.61 g, 57.1 mmol, 1.2 eq) is added at room temperature to a stirred solution of dimethy 5-hydroxybenzene-1,3-dicarboxylate (10 g, 47.6 mmol, 1.0 eq) and imidazole (3.89 g, 57.1 mmol, 1.2 eq) in dichloromethane (60 mL). After 6 hours stirring at room temperature, the solid is filtered off and the filtrate is washed with brine (50 mL), dried over sodium sulfate, filtered and concentrated to afford dimethyl 5-[tert-butyl(dimethyl)silyl]oxybenzene-1,3-dicarboxylate as a white solid (13.75 g, 89% yield).
$^1$H-NMR (400 MHz, CDCl$_3$) δ ppm: 8.10 (s, 1H), 7.58 (s, 2H), 3.88 (s, 6H), 0.96 (s, 9H), 0.22 (s, 6H).

Preparation of methyl 3-[tert-butyl(dimethyl)silyl]oxy-5-(methylsulfonyloxymethyl)benzoate The titled compound is prepared as a white solid following Scheme 2 and in analogy to Examples 51 and 158 using dimethyl 5-[tert-butyl(dimethyl)silyl]oxybenzene-1,3-dicarboxylate and methanesulfonyl chloride as starting materials. This compound is directly engaged in the next step without further purification.

Preparation of methyl 3-[tert-butyl(dimethyl)silyl]oxy-5-[[4-chloro-2-(trifluoromethyl)phenyl]sulfanylmethyl]benzoate 4-chloro-2-(trifluoromethyl)benzenethiol (1.25 g, 5.87 mmol, 1.1 eq) is added at room temperature to a stirred solution of methyl 3-[tert-butyl(dimethyl)silyl]oxy-5-(methylsulfonylmethyl)benzoate (2.00 g, 5.34 mmol, 1.0 eq) in N,N-dimethylformamide (50 mL), followed by cesium carbonate (3.48 g, 10.68 mmol, 2.0 eq). After 4 hours stirring at 30° C., the reaction mixture is concentrated and extracted with ethyl acetate (3×50 mL) and water (50 mL). The combined organic layers are washed with brine (50 mL), dried over sodium sulfate, filtered and concentrated to afford methyl 3-[tert-butyl(dimethyl)silyl]oxy-5-[[4-chloro-2-(trifluoromethyl)phenyl]sulfanylmethyl]benzoate as a colorless oil (2.10 g, 80% yield).
$^1$H-NMR (400 MHz, CDCl$_3$) δ ppm: 7.64 (s, 1H), 7.02-7.51 (m, 5H), 4.11 (s, 2H), 3.94 (s, 3H), 0.93 (s, 9H), 0.12 (s, 6H).

Preparation of methyl 3-[[4-chloro-2-(trifluoromethyl)phenyl]sulfanylmethyl]-5-hydroxy-benzoate Tetra-n-butylammonium fluoride (1M solution in tetrahydrofuran, 8.55 mL, 8.55 mmol, 1.1 eq) is added at room temperature to a stirred solution of methyl 3-[tert-butyl(dimethyl)silyl]oxy-5-[[4-chloro-2-(trifluoromethyl)phenyl]sulfanylmethyl]benzoate (2.10 g, 4.28 mmol, 1.0 eq) in tetrahydrofuran (20 mL). After 2 hours stirring at 30° C., the reaction mixture is concentrated and extracted with ethyl acetate (3×20 mL) and water (20 mL). The combined organic layers are washed with a saturated ammonium chloride aqueous solution (20 mL), brine (50 mL), dried over sodium sulfate, filtered and concentrated to afford methyl 3-[[4-chloro-2-(trifluoromethyl)phenyl]sulfanylmethyl]-5-hydroxy-benzoate as a colorless oil (1.60 g, 99% yield).
$^1$H-NMR (400 MHz, CDCl$_3$) δ ppm: 7.65 (s, 1H), 7.03-7.51 (m, 5H), 4.11 (s, 2H), 3.92 (s, 3H).

Preparation of methyl 3-allyloxy-5-[[4-chloro-2-(trifluoromethyl)phenyl]sulfanylmethyl]benzoate The titled compound is prepared as a colorless oil (1.32 g, 75% yield) following Scheme 2 and in analogy to Example 37 using methyl 3-[[4-chloro-2-(trifluoromethyl)phenyl]sulfanylmethyl]-5-hydroxy-benzoate (1.60 g, 4.23 mmol, 1.0 eq) and allyl bromide (550 μL, 6.37 mmol, 1.5 eq) as starting materials.
$^1$H-NMR (400 MHz, CDCl$_3$) δ ppm: 7.63 (s, 1H), 7.05-7.53 (m, 5H), 5.97-6.07 (m, 1H), 5.40 (m, 1H), 5.29 (m, 1H), 4.53 (m, 2H), 4.13 (s, 2H), 3.90 (s, 3H).

Preparation of [3-allyloxy-5-[[4-chloro-2-(trifluoromethyl)phenyl]sulfanylmethyl]phenyl]methanol Diisobutylaluminium hydride (1M solution in tetrahydrofuran, 9.40 mL, 9.40 mmol, 3.0 eq) is added dropwise at −78° C. to a stirred solution of methyl 3-allyloxy-5-[[4-chloro-2-(trifluoromethyl)phenyl]sulfanylmethyl]benzoate (1.30 g, 3.12 mmol, 1.0 eq) in tetrahydrofuran (30 mL).

After 4 hours stirring at −78° C., the reaction mixture is poured in a 1N hydrochloric acid aqueous solution (10 mL). The phases are separated and the aqueous phase is extracted with ethyl acetate (3×50 mL). The combined organic layers are washed with brine (50 mL), dried over sodium sulfate, filtered and concentrated to afford [3-allyloxy-5-[[4-chloro-2-(trifluoromethyl)phenyl]sulfanylmethyl]phenyl]methanol as a colorless oil (1.20 g, 99% yield).

$^1$H-NMR (400 MHz, CDCl$_3$) δ ppm: 7.64 (s, 1H), 7.30-7.39 (m, 2H), 6.80-6.90 (m, 3H), 5.99-6.09 (m, 1H), 5.41 (m, 1H), 5.30 (m, 1H), 4.64 (s, 2H), 4.52 (m, 2H), 4.13 (s, 2H).

Preparation of 1-[3-allyloxy-5-[[4-chloro-2-(trifluoromethyl)phenyl]sulfanylmethyl]phenyl]-N-azetidin-3-ylmethyl)methanamine The titled compound is prepared as a light yellow solid following Scheme 2 and in analogy to Examples 51 and 158 using [3-allyloxy-5-[[4-chloro-2-(trifluoromethyl)phenyl]sulfanylmethyl]phenyl]methanol, methanesulfonyl chloride and tert-butyl 3-(aminomethyl)azetidine-1-carboxylate as starting materials.

Example 201: N-(azetidin-3-ylmethyl)-3-[3-[(E)-2-(2-bromo-4-chloro-phenyl)vinyl]phenoxy]propan-1-amine Preparation of 3-[tert-butyl(dimethyl)silyl]oxybenzaldehyde The titled compound is prepared as a colorless oil (1.9 g, 99% yield) following Scheme 3 and in analogy to Example 183 using 3-hydroxybenzaldehyde (1.0 g, 8.19 mmol, 1.0 eq) [100-83-4] and tert-butyl-chloro-dimethyl-silane (1.48 g, 9.09 mmol, 1.1 eq) as starting materials.

$^1$H-NMR (400 MHz, CDCl$_3$) δ ppm: 9.95 (s, 1H), 7.47 (d, J=7.6 Hz, 1H), 7.40 (m, 1H), 7.36 (s, 1H), 7.10 (m, 1H), 0.99 (s, 9H), 0.22 (s, 6H).

Preparation of 3-[(E)-2-(2-bromo-4-chloro-phenyl)vinyl]phenol

A solution of 2-bromo-4-chloro-1-(diethoxyphosphorylmethyl)benzene (305 mg, 0.89 mmol, 1.0 eq) in tetrahydrofuran (3 mL) is added dropwise at 0° C. to a stirred solution of potassium tert-butoxide (106 mg, 0.94 mmol, 1.05 eq) in tetrahydrofuran (5 mL). After 30 minutes stirring at 0° C., 3-[tert-butyl(dimethyl)silyl]oxybenzaldehyde (190 mg, 0.80 mmol, 0.9 eq) is added at 0° C. to the reaction mixture. After 1 hour stirring at 0° C. and 15 hours stirring at room temperature, the reaction mixture is extracted with ethyl acetate (3×30 mL) and a saturated ammonium chloride aqueous solution (30 mL). The combined organic layers are washed with brine (30 mL), dried over sodium sulfate, filtered and concentrated to give a residue that is dissolved in tetrahydrofuran (5 mL) before the addition of tetra-n-butylammonium fluoride (233 mg, 0.89 mmol, 1.0 eq). After 4 hours stirring at room temperature the reaction mixture is concentrated to give a residue that is purified by column chromatography (silica gel; petroleum ether:ethyl acetate, 5:1, v/v) to afford 3-[(E)-2-(2-bromo-4-chloro-phenyl)vinyl]phenol as a light yellow solid (180 mg, 65% yield).

$^1$H-NMR (400 MHz, CDCl$_3$) δ ppm: 7.58 (m, 2H), 7.36 (d, J=16.0 Hz, 1H), 7.26 (m, 2H), 7.10 (d, J=8.0 Hz, 1H), 7.03 (s, 1H), 6.96 (d, J=16.0 Hz, 1H), 6.78 (dd, J=2.0 Hz, 8.0 Hz, 1H).

Preparation of 2-bromo-4-chloro-1-[(E)-2-[3-(3-chloropropoxy)phenyl)vinyl]benzene The titled compound is prepared as a light yellow oil (374 mg, 95% yield) following Scheme 3 and in analogy to Example 37 using 3-[(E)-2-(2-bromo-4-chloro-phenyl)vinyl]phenol (317 mg, 1.02 mmol, 1.0 eq) and 1-bromo-3-chloro-propane (322 mg, 2.05 mmol, 2.0 eq) as starting materials.

$^1$H-NMR (400 MHz, CDCl$_3$) δ ppm: 7.58 (m, 2H), 7.37 (d, J=16.0 Hz, 1H), 7.24 (m, 2H), 7.16 (d, J=7.6 Hz, 1H), 7.10 (s, 1H), 7.00 (d, J=16.0 Hz, 1H), 6.87 (dd, J=2.4 Hz, 8.0 Hz, 1H), 4.17 (t, J=6.0 Hz, 2H), 3.77 (t, J=6.0 Hz, 2H), 2.26 (m, 2H).

Preparation of 2-bromo-4-chloro-1-[(E)-2-[3-(3-iodopropoxy)phenyl)vinyl]benzene

Sodium iodide (1.71 g, 11.4 mmol, 20.0 eq) is added at room temperature to a stirred solution of 2-bromo-4-chloro-1-[(E)-2-[3-(3-chloropropoxy)phenyl)vinyl]benzene (220 mg, 0.57 mmol, 1.0 eq) in acetone (18 mL) and the resulting mixture is stirred at 60° C. for 36 hours. Then solvent is evaporated to afford 2-bromo-4-chloro-1-[(E)-2-[3-(3-iodopropoxy)phenyl)vinyl]benzene as a light yellow solid (272 mg, 99% yield) that is directly engaged in the next step without further purification.

$^1$H-NMR (400 MHz, CDCl$_3$) δ ppm: 7.57 (m, 2H), 7.36 (d, J=16.0 Hz, 1H), 7.28 (m, 2H), 7.13 (d, J=7.6 Hz, 1H), 7.06 (s, 1H), 6.97 (d, J=16.0 Hz, 1H), 6.84 (dd, J=2.0 Hz, 7.6 Hz, 1H), 4.08 (t, J=5.8 Hz, 2H), 3.38 (t, J=6.6 Hz, 2H), 2.29 (m, 2H).

Preparation of N-(azetidin-3-ylmethyl)-3-[3-[(E)-2-(2-bromo-4-chloro-phenyl)vinyl]phenoxy]propan-1-amine The titled compound is prepared as a white solid following Scheme 3 and in analogy to Examples 51 and 158 using 2-bromo-4-chloro-1-[(E)-2-[3-(3-iodopropoxy)phenyl)vinyl]benzene and tert-butyl 3-(aminomethyl)azetidine-1-carboxylate as starting materials.

Example 232: [3-[(azetidin-3-ylmethylamino)methyl]-5-[(2-bromo-4-chloro-phenyl))methoxy]phenyl]methyl-(carboxymethyl)-dimethyl-ammonium Preparation of tert-butyl 3-[[[3-[(2-bromo-4-chloro-phenyl)methoxy]-5-(methylsulfonyloxymethyl)phenyl]methyl-tert-butoxycarbonyl-amino]methyl]azetidine-1-carboxylate The titled compound is prepared following Scheme 1 and in analogy to Examples 51 and 130 using [3-[(2-bromo-4-chloro-phenyl)methoxy]-5-(hydroxymethyl)phenyl]methyl methanesulfonate, tert-butyl 3-(aminomethyl)azetidine-1-carboxylate, di-tert-butyl dicarbonate and methanesulfonyl chloride as starting materials. $^1$H-NMR (400 MHz, CDCl$_3$) δ ppm: 7.61 (s, 1H), 7.52 (d, J=8.0 Hz, 1H), 7.46 (d, J=8.0 Hz, 1H), 6.91 (s, 1H), 6.84 (s, 1H), 6.81 (s, 1H), 5.23 (s, 2H), 5.14 (s, 2H), 4.41 (s, 2H), 3.90 (m, 2H), 3.58 (m, 2H), 3.44 (m, 2H), 3.08 and 2.97 (2s, 3H), 2.73 (m, 1H), 1.67 and 1.40 (2s, 18H).

Preparation of tert-butyl 3-[[[3-[(2-bromo-4-chloro-phenyl)methoxy]-5-(methylaminomethyl)phenyl]methyl-tert-butoxycarbonyl-amino]methyl]azetidine-1-carboxylate A 2N solution of methylamine in tetrahydrofuran (8 mL, 16 mmol, 16.3 eq) is added at room temperature to a stirred solution of tert-butyl 3-[[[3-[(2-bromo-4-chloro-phenyl)methoxy]-5-(methylsulfonyloxymethyl)phenyl]methyl-tert-butoxycarbonyl-amino]methyl]azetidine-1-carboxylate (693 mg, 0.98 mmol, 1.0 eq). After 2 hours stirring at room temperature, solvent is evaporated and the residue is purified by column chromatography (silica gel; dichloromethane:methanol, 8:1, v/v) to afford tert-butyl 3-[[[3-[(2-bromo-4-chloro-phenyl)methoxy]-5-(methylaminomethyl)phenyl]methyl-tert-butoxycarbonyl-amino]methyl]azetidine-1-carboxylate as a light yellow semi-solid (263 mg, 42% yield).

MS m/z (+ESI): 638.1, 640.1 [M+H]$^+$.

Preparation of [3-[(azetidin-3-ylmethylamino)methyl]-5-[(2-bromo-4-chloro-phenyl))methoxy]phenyl]methyl-(carboxymethyl)-dimethyl-ammonium The titled compound is prepared as a white semi-solid following Scheme 1 and in analogy to Examples 37 and 387 using tert-butyl 3-[[[3-[(2-bromo-4-chloro-phenyl)methoxy]-5-(methylaminomethyl)phenyl]methyl-tert-butoxycarbonyl-amino]methyl]azetidine-1-carboxylate, tert-butyl 2-bromoacetate, and iodomethane as starting materials.

Example 236: 1-[3-[(Z)-2-(4-tert-butylphenyl)vinyl]phenyl]-N-(pyrrolidin-3-ylmethyl)methanamine

Preparation of (4-tert-butylphenyl)methyl-triphenyl-phenphosphonium

A mixture of 1-(bromomethyl)-4-tert-butyl-benzene (500 mg, 1.76 mmol, 1.0 eq) [18880-00-7] and triphenylphosphine (461 mg, 1.76 mmol, 1.0 eq) in xylene (10 mL) is heated under reflux conditions at 140° C. for 20 hours. The resulting precipitate is collected by filtration and washed with diethyl ether to afford (4-tert-butylphenyl)methyl-triphenyl-phosphonium as a white solid (4.0 g, 93% yield).

$^1$H-NMR (400 MHz, CDCl$_3$) δ ppm: 7.59-7.78 (m, 15H), 7.14 (d, J=8.0 Hz, 2H), 6.98 (d, J=8.0 Hz, 2H), 5.29 (d, J=14.0 Hz, 1H), 1.22 (s, 9H).

MS m/z (+ESI): 409.2 [M+H]$^+$.

Preparation of 3-[(E)-2-(4-tert-butylphenyl)vinyl]benzaldehyde and 3-[(Z)-2-(4-tert-butylphenyl)vinyl]benzaldehyde Silver(I) oxide (616 mg, 2.65 mmol, 1.0 eq) is added at room temperature to a stirred solution of (4-tert-butylphenyl)methyl-triphenyl-phosphonium (1.3 g, 2.65 mmol, 1.0 eq) and benzene-1,3-dicarbaldehyde (356 mg, 2.65 mmol, 1.0 eq) [626-19-7] in dioxane (40 mL). After 30 minutes stirring at 100° C., the reaction mixture is filtered and the filtrate is concentrated to give a residue that is purified by column chromatography (silica gel; petroleum ether:ethyl acetate, 50:1, v/v) to afford 3-[(E)-2-(4-tert-butylphenyl)vinyl]benzaldehyde as a white solid (250 mg, 36% yield) and 3-[(Z)-2-(4-tert-butylphenyl)vinyl]benzaldehyde as a yellow oil (260 mg, 37% yield). 3-[(E)-2-(4-tert-butylphenyl)vinyl]benzaldehyde $^1$H-NMR (400 MHz, CDCl$_3$) δ ppm: 10.05 (s, 1H), 8.02 (s, 1H), 7.63 (d, J=7.6 Hz, 2H), 7.52 (m, 1H), 7.49 (d, J=8.4 Hz, 2H), 7.42 (d, J=8.4 Hz, 2H), 7.09-7.22 (m, J=16.4 Hz, 2H), 1.34 (s, 9H).

3-[(Z)-2-(4-tert-butylphenyl)vinyl]benzaldehyde $^1$H-NMR (400 MHz, CDCl$_3$) δ ppm: 9.90 (s, 1H), 7.72 (m, 2H), 7.55 (d, J=7.2 Hz, 1H), 7.41 (m, 1H), 7.25 (d, J=8.8 Hz, 2H), 715 (d, J=8.8 Hz, 2H), 6.57-6.69 (m, J=12.4 Hz, 2H), 1.29 (s, 9H).

Preparation of tert-butyl 3-[[[3-[(Z)-2-(4-tert-butylphenyl)vinyl]phenyl]methylamino]methyl]pyrrolidine-1-carboxylate The titled compound is prepared as a colorless oil (150 mg, 68% yield) following Scheme 3 and in analogy to Example 37 using 3-[(Z)-2-(4-tert-butylphenyl)vinyl]benzaldehyde (130 mg, 0.49 mmol, 1.0 eq) and tert-butyl 3-(aminomethyl)pyrrolidine-1-carboxylate (99 mg, 0.49 mmol, 1.0 eq) as starting materials.

$^1$H-NMR (400 MHz, CDCl$_3$) δ ppm: 7.15-7.26 (m, 8H), 6.56-6.64 (m, J=12.4 Hz, 2H), 3.76 (s, 2H), 3.59 (m, 6H), 2.37 (m, 1H), 2.10 (m, 1H), 1.59 (m, 1H), 1.44 (s, 9H), 1.28 (s, 9H).

MS m/z (+ESI): 449.6 [M+H]$^+$.

Preparation of 1-[3-[(Z)-2-(4-tert-butylphenyl)vinyl]phenyl]-N-(pyrrolidin-3-ylmethyl)methanamine A solution of tert-butyl 3-[[[3-[(Z)-2-(4-tert-butylphenyl)vinyl]phenyl]methylamino]methyl]pyrrolidine-1-carboxylate (150 mg, 0.33 mmol, 1.0 eq) in a 2N hydrochloric acid solution in ethyl acetate (5 mL) is stirred at room temperature for 1 hour. Then the reaction mixture is concentrated to give a residue that is triturated with ethyl acetate to give a precipitate that is collected by filtration to afford 1-[3-[(Z)-2-(4-tert-butylphenyl)vinyl]phenyl]-N-(pyrrolidin-3-ylmethyl)methanamine as a white solid (110 mg, 92% yield).

Example 263: 4-113-[(2-bromo-4-chloro-phenyl)methoxyl-5-[(pyrrolidin-3-ylmethylamino)methyl]phenyl]methoxyl-1,1-dimethyl-pyrrolidin-1-ium-2-carboxylic acid

Preparation of 3-[(2-bromo-4-chloro-phenyl)methoxy]-5-(hydroxymethyl)benzaldehyde The titled compound is prepared as a white solid (2.2 g, 76% yield) following Scheme 1 and in analogy to Example 136 using [3-[(2-bromo-4-chloro-phenyl)methoxy]-5-(hydroxymethyl)phenyl]methanol (2.9 mg, 8.11 mmol, 1.0 eq) as starting material.

$^1$H-NMR (400 MHz, CD$_3$OD) δ ppm: 9.95 (s, 1H), 7.71 (s, 1H), 7.56 (m, 2H), 7.42 (m, 2H), 7.34 (s, 1H), 5.20 (s, 2H), 4.59 (s, 2H).

Preparation of 3-[(2-bromo-4-chloro-phenyl)methoxy]-5-(bromomethyl)benzaldehyde N-Bromosuccinimide (7.16 g, 40.21 mmol, 1.2 eq) is added at 0° C. to a stirred solution of 3-[(2-bromo-4-chloro-phenyl)methoxy]-5-(hydroxymethyl)benzaldehyde (13.0 g, 36.56 mmol, 1.0 eq) and triphenylphosphine (10.55 g, 40.21 mmol, 1.2 eq) in dichloromethane (600 mL). After 4 hours stirring at room temperature, solvent is evaporated and the residue is purified by column chromatography (silica gel; petroleum ether:dichloromethane, 2:1, v/v) to afford 3-[(2-bromo-4-chloro-phenyl)methoxy]-5-(bromomethyl)benzaldehyde as a white solid (2.2 g, 76% yield).

$^1$H-NMR (400 MHz, CDCl$_3$) δ ppm: 9.99 (s, 1H), 7.65 (d, J=2.0 Hz, 1H), 7.56 (s, 1H), 7.50 (d, J=8.0 Hz, 1H), 7.43 (s, 1H), 7.36 (dd, J=2.0 Hz, 8.4 Hz, 1H), 7.30 (s, 1H), 5.16 (s, 2H), 4.53 (s, 2H).

Preparation of O1-tert-butyl O2-ethyl 4-[[3-[(2-bromo-4-chloro-phenyl)methoxy]-5-formyl-phenyl]methoxy]pyrrolidine-1,2-dicarboxylate Sodium hydride (380 mg, 9.64 mmol, 1.0 eq) is added at −20° C. to a stirred solution of O1-tert-butyl O2-ethyl (2R,4R)-4-hydroxypyrrolidine-1,2-dicarboxylate (2.5 g, 9.64 mmol, 1.0 eq) [77450-00-1] in N,N-dimethylformamide (60 mL), followed by 3-[(2-bromo-4-chloro-phenyl)methoxy]-5-(bromomethyl)benzaldehyde (4.84 g, 11.57 mmol, 1.2 eq) and tetrabutylammonium iodide (178 mg, 0.48 mmol, 0.05 eq). After 15 hours stirring at 10° C., solvent is evaporated and the residue is extracted with ethyl acetate (3×40 mL) and a saturated ammonium chloride aqueous solution (40 mL). The combined organic layers are washed with brine, dried over sodium sulfate, filtered and concentrated to give a residue that is purified by column chromatography (silica gel; petroleum ether:ethyl acetate, 3:1, v/v) to afford O1-tert-butyl O2-ethyl 4-[[3-[(2-bromo-4-chloro-phenyl)methoxy]-5-formyl-phenyl]methoxy]pyrrolidine-1,2-dicarboxylate as a light yellow semi-solid (3.55 g, 62% yield).

$^1$H-NMR (400 MHz, CDCl$_3$) δ ppm: 9.98 (s, 1H), 7.64 (d, J=2.0 Hz, 1H), 7.50 (d, J=8.0 Hz, 1H), 7.45 (s, 1H), 7.35 (m, 2H), 7.24 (s, 1H), 5.16 (s, 2H), 4.50 (m, 2H), 4.35 (m, 1H), 4.18 (m, 3H), 3.60 (m, 2H), 2.30 (m, 2H), 1.45 (m, 9H), 1.2 (t, J=7.2 Hz, 3H).

MS m/z (+ESI): 596.1, 598.1 [M+H]$^+$.

Preparation of ethyl 4-[[3-[(2-bromo-4-chloro-phenyl)methoxy]-5-formyl-phenyl]methoxy]pyrrolidine-2-carboxylate Trifluoroacetic acid (0.3 mL, 2.29 mmol, 12.7 eq) is added at room temperature to a stirred solution of O1-tert-butyl O2-ethyl 4-[[3-[(2-bromo-4-chloro-phenyl)methoxy]-5-formyl-phenyl]methoxy]pyrrolidine-1,2-dicarboxylate (110 mg, 0.18 mmol, 1.0 eq) in dichloromethane (2 mL). After 2 hours stirring at room temperature, the reaction mixture is concentrated to afford ethyl 4-[[3-[(2-bromo-4-chloro-phenyl)methoxy]-5-formyl-phenyl]methoxy]pyrrolidine-2-carboxylate as a light red solid (90 mg, 98% yield).

$^1$H-NMR (400 MHz, CDCl$_3$) δ ppm: 9.97 (s, 1H), 7.63 (d, J=2.0 Hz, 1H), 7.47 (d, J=8.0 Hz, 1H), 7.40 (m, 2H), 7.34 (dd, J=2.0 Hz, 8.0 Hz, 1H), 7.13 (s, 1H), 5.14 (s, 2H), 4.65 (m, 1H), 4.52 (m, 2H), 4.35 (m, 1H), 4.4 (q, J=6.8 Hz, 2H), 3.55-3.75 (m, 2H), 2.55 (m, 2H), 1.22 (t, J=7.2 Hz, 3H).

MS m/z (+ESI): 496.0, 498.0 [M+H]$^+$.

Preparation of ethyl 4-[[3-[(2-bromo-4-chloro-phenyl)methoxy]-5-formyl-phenyl]methoxy]-1,1-dimethyl-pyrrolidin-1-ium-2-carboxylate The titled compound is prepared as a colorless oil (90 mg, 95% yield) following Scheme 1 and in analogy to Example 387 using ethyl 4-[[3-[(2-bromo-4-chloro-phenyl)methoxy]-5-formyl-phenyl]methoxy]pyrrolidine-2-carboxylate (90 mg, 0.17 mmol, 1.0 eq) and iodomethane (50 μL, 0.86 mmol, 5.0 eq) as starting materials.

MS m/z (+ESI): 524.3, 526.3 [M+H]$^+$.

Preparation of ethyl 4-[[3-[(2-bromo-4-chloro-phenyl)methoxy]-5-[[(1-tert-butoxycarbonylpyrrolidin-3-yl)methylamino]methyl]phenyl]methoxy]-1,1-dimethyl-pyrrolidin-1-ium-2-carboxylate tert-Butyl 3-(aminomethyl)pyrrolidine-1-carboxylate (51 mg, 0.26 mmol, 1.5 eq) is added at room temperature to a stirred solution of ethyl 4-[[3-[(2-bromo-4-chloro-phenyl)methoxy]-5-formyl-phenyl]methoxy]-1,1-dimethyl-pyrrolidin-1-ium-2-carboxylate (90 mg, 0.17 mmol, 1.0 eq) in dichloromethane (3 mL), followed by one drop of acetic acid. After 30 minutes stirring at room temperature, sodium cyanoborohydride (22 mg, 0.34 mmol, 2.0 eq) is added. After 12 hours stirring at room temperature, the reaction mixture is concentrated to give a residue that is purified by column chromatography (silica gel; dichloromethane:methanol, 10:1, v/v) to afford ethyl 4-[[3-[(2-bromo-4-chloro-phenyl)methoxy]-5-[[(1-tert-butoxycarbonylpyrrolidin-3-yl)methylamino]methyl]phenyl]methoxy]-1,1-dimethyl-pyrrolidin-1-ium-2-carboxylate as a colorless semi-solid (110 mg, 90% yield).

MS m/z (+ESI): 708.2, 710.2 [M+H]$^+$.

Preparation of 4-[[3-[(2-bromo-4-chloro-phenyl)methoxy]-5-[[(1-tert-butoxycarbonylpyrrolidin-3-yl)methylamino]methyl]phenyl]methoxy]-1,1-dimethyl-pyrrolidin-1-ium-2-carboxylic acid Lithium hydroxide (80 mg, 1.9 mmol, 5.0 eq) is added at room temperature to a stirred solution of ethyl 4-[[3-[(2-bromo-4-chloro-phenyl)methoxy]-5-[[(1-tert-butoxycarbonylpyrrolidin-3-yl)methylamino]methyl]phenyl]methoxy]-1,1-dimethyl-pyrrolidin-1-ium-2-carboxylate (270 mg, 0.38 mmol, 1.0 eq) in tetrahydrofuran (10 mL) and water (5 mL). After 2 hours stirring at room temperature, the reaction mixture is concentrated to afford 4-[[3-[(2-bromo-4-chloro-phenyl)methoxy]-5-[[(1-tert-butoxycarbonylpyrrolidin-3-yl)methylamino]methyl]phenyl]methoxy]-1,1-dimethyl-pyrrolidin-1-ium-2-carboxylic acid as a white semi-solid (260 mg, 99% yield) that is directly engaged in the next step without further purification.

MS m/z (+ESI): 680.2, 682.2 [M+H]$^+$.

Preparation of 4-[[3-[(2-bromo-4-chloro-phenyl)methoxy]-5-[(pyrrolidin-3-ylmethylamino)methyl]phenyl]methoxy]-1,1-dimethyl-pyrrolidin-1-ium-2-carboxylic Acid The titled compound is prepared as a white solid (58 mg, 27% yield) following Scheme 1 and in analogy to Example 158 using 4-[[3-[(2-bromo-4-chloro-phenyl)methoxy]-5-[[(1-tert-butoxycarbonylpyrrolidin-3-yl)methylamino]methyl]phenyl]methoxy]-1,1-dimethyl-pyrrolidin-1-ium-2-carboxylic acid (250 mg, 0.37 mmol, 1.0 eq) as starting material.

Example 354: N-[[3-allyloxy-5-[(E)-2-(2-bromo-4-chloro-phenyl)vinyl]phenyl]methyl]piperidine-4-carboxamide Preparation of [3-allyloxy-5-[(E)-2-(2-bromo-4-chloro-phenyl)vinyl]phenyl]methanol The titled compound is prepared as a white solid following Scheme 3 and in analogy to Examples 158 and 168 using

[3-allyloxy-5-(hydroxymethyl)phenyl]methanol and 2-bromo-4-chloro-1-(diethoxyphosphorylmethyl)benzene as starting materials.

$^1$H-NMR (400 MHz, CDCl$_3$) δ ppm: 7.60 (m, 2H), 7.39 (d, J=16.4 Hz, 1H), 7.28 (m, 1H), 7.15 (s, 1H), 7.04 (s, 1H), 6.98 (d, J=16.4 Hz, 1H), 6.91 (s, 1H), 6.11 (m, 1H), 5.47 (m, 1H), 5.33 (m, 1H), 4.72 (m, 2H), 4.61 (m, 2H).

Preparation of 2-[[3-allyloxy-5-[(E)-2-(2-bromo-4-chloro-phenyl)vinyl]phenyl]methyl]isoindoline-1,3-dione Diisopropyl azodicarboxylate (8.3 mL, 42.14 mmol, 2.0 eq) is added at 0° C. to a stirred solution of [3-allyloxy-5-[(E)-2-(2-bromo-4-chloro-phenyl)vinyl]phenyl]methanol (8.0 g, 21.07 mmol, 1.0 eq), triphenylphosphine (11.05 g, 42.14 mmol, 2.0 eq) and phthalimide (4.65 g, 31.06 mmol, 1.5 eq) in tetrahydrofuran (200 mL). After 1 hour stirring at 50° C., the reaction mixture is concentrated to give a residue that is purified by column chromatography (silica gel; dichloromethane:petroleum ether, 2:1, v/v) to afford 2-[[3-allyloxy-5-[(E)-2-(2-bromo-4-chloro-phenyl)vinyl]phenyl]methyl]isoindoline-1,3-dione as a white solid (8.5 g, 79% yield).

$^1$H-NMR (400 MHz, DMSO-d6) δ ppm: 7.92 (m, 4H), 7.85 (d, J=8.8 Hz, 1H), 7.79 (d, J=2.0 Hz, 1H), 7.48 (dd, J=2.4 Hz, 8.4 Hz, 1H), 7.28 (m, 2H), 7.11 (m, 2H), 6.86 (s, 1H), 6.07 (m, 1H), 5.40 (m, 1H), 5.25 (m, 1H), 4.78 (m, 2H), 4.61 (m, 2H).

MS m/z (+ESI): 508.0, 510.0 [M+H]$^+$.

Preparation of [3-allyloxy-5-[(E)-2-(2-bromo-4-chloro-phenyl)vinyl]phenyl]methanamine Hydrazine monohydrate (0.28 mL, 5.7 mmol, 2.0 eq) is added at room temperature to a stirred solution of 2-[[3-allyloxy-5-[(E)-2-(2-bromo-4-chloro-phenyl)vinyl]phenyl]methyl]isoindoline-1,3-dione (1.45 g, 2.85 mmol, 1.0 eq) in ethanol (50 mL). After 2 hours stirring under reflux conditions, the reaction mixture is filtered and concentrated to afford [3-allyloxy-5-[(E)-2-(2-bromo-4-chloro-phenyl)vinyl]phenyl]methanamine as a light yellow semi-solid (8.5 g, 79% yield) that is directly engaged in the next step without further purification.

$^1$H-NMR (400 MHz, DMSO-d6) δ ppm: 7.85 (d, J=8.8 Hz, 1H), 7.80 (d, J=2.0 Hz, 1H), 7.48 (dd, J=2.4 Hz, 8.8 Hz, 1H), 7.33 (d, J=16.4 Hz, 1H), 7.22 (m, 2H), 7.02 (s, 1H), 6.95 (s, 1H), 6.08 (m, 1H), 5.42 (m, 1H), 5.28 (m, 1H), 4.60 (m, 2H), 3.74 (m, 2H).

Preparation of tert-butyl 4-[[3-allyloxy-5-[(E)-2-(2-bromo-4-chloro-phenyl)vinyl]phenyl]methylcarbamoyl]piperidine-1-carboxylate 1-tert-Butoxycarbonylpiperidine-4-carboxylic acid (121 mg, 0.53 mmol, 1.0 eq) [84358-13-4] is added at room temperature to a stirred solution of [3-allyloxy-5-[(E)-2-(2-bromo-4-chloro-phenyl)vinyl]phenyl]methanamine (200 mg, 0.53 mmol, 1.0 eq) in ethyl acetate (10 mL), followed by 4-(4,6-dimethoxy-1,3,5-triazin-2-yl)-4-methylmorpholinium chloride (301 mg, 0.79 mmol, 1.5 eq). After 15 hours stirring at room temperature, the reaction mixture is concentrated to give a residue that is purified by column chromatography (silica gel; petroleum ether:ethyl acetate, 1:1, v/v) to afford tert-butyl 4-[[3-allyloxy-5-[(E)-2-(2-bromo-4-chloro-phenyl)vinyl]phenyl]methylcarbamoyl]piperidine-1-carboxylate as a white solid (300 mg, 96% yield).

$^1$H-NMR (400 MHz, DMSO-d6+D$_2$O) δ ppm: 8.38 (m, 1H), 7.85 (d, J=8.4 Hz, 1H), 7.80 (d, J=2.0 Hz, 1H), 7.51 (dd, J=2.0 Hz, 8.4 Hz, 1H), 7.30 (d, J=16.4 Hz, 1H), 7.25 (d, J=17.6 Hz, 1H), 7.07 (m, 2H), 6.79 (s, 1H), 6.05 (m, 1H), 5.41 (m, 1H), 5.27 (m, 1H), 4.61 (m, 2H), 4.26 (d, J=6.0 Hz, 2H), 3.95 (m, 2H), 2.73 (m, 2H), 2.37 (m, 1H), 1.71 (m, 2H), 1.50 (m, 2H), 1.42 (m, 9H).

MS m/z (+ESI): 533.0, 535.0 [M+H]$^+$.

Preparation of N-[[3-allyloxy-5-[(E)-2-(2-bromo-4-chloro-phenyl)vinyl]phenyl]methyl]piperidine-4-carboxamide The titled compound is prepared as a white solid (130 mg, 53% yield) following Scheme 3 and in analogy to Example 37 using tert-butyl 4-[[3-allyloxy-5-[(E)-2-(2-bromo-4-chloro-phenyl)vinyl]phenyl]methylcarbamoyl]piperidine-1-carboxylate (290 mg, 0.49 mmol, 1.0 eq) as starting material.

Example 369: N-[[3-allyloxy-5-[(azetidin-3-ylmethylamino)methyl]phenyl]methyl]-4-tert-butyl-benzenesulfonamide

Preparation of tert-butyl 3-[[[3-allyloxy-5-(aminomethyl)phenyl]methyl-tert-butoxycarbonyl-amino]methyl]azetidine-1-carboxylate The titled compound is prepared as a colorless oil following Scheme 6 and in analogy to Examples 37, 130, 136 and 354 using methyl 3-formylbenzoate, tert-butyl 3-(aminomethyl)azetidine-1-carboxylate, di-tert-butyl dicarbonate and phthalimide as starting materials.

$^1$H-NMR (400 MHz, CDCl$_3$) δ ppm: 6.80 (s, 1H), 6.73 (s, 1H), 6.64 (s, 1H), 6.09 (m, 1H), 5.42 (m, 1H), 5.31 (m, 1H), 4.54 (m, 2H), 4.40 (s, 2H), 3.88 (m, 2H), 3.74 (m, 6H), 3.41 (m, 2H), 2.74 (m, 1H), 1.45 (m, 18H).

Preparation of tert-butyl 3-[[[3-allyloxy-5-[[(4-tert-butylphenyl)sulfonylamino]methyl]phenyl]methyl-tert-butoxycarbonyl-amino]methyl]azetidine-1-carboxylate 4-tert-Butylbenzenesulfonyl chloride (230 mg, 0.97 mmol, 1.5 eq) [15084-51-2] is added at 0° C. to a stirred solution of tert-butyl 3-[[[3-allyloxy-5-(aminomethyl)phenyl]methyl-tert-butoxycarbonyl-amino]methyl]azetidine-1-carboxylate (300 mg, 0.65 mmol, 1.0 eq) and triethylamine (179 μL, 1.30 mmol, 2.0 eq) in dichloromethane (15 mL). After 12 hours stirring at room temperature, the reaction mixture is concentrated to give a residue that is purified by column chromatography (silica gel; petroleum ether:ethyl acetate, 6:1, v/v) to afford tert-butyl 3-[[[3-allyloxy-5-[[(4-tert-butylphenyl)sulfonylamino]methyl]phenyl]methyl-tert-butoxycarbonyl-amino]methyl]azetidine-1-carboxylate as a colorless oil (410 mg, 96% yield).

$^1$H-NMR (400 MHz, DMSO-d6) δ ppm: 8.98 (s, 1H), 8.06 (s, 1H), 7.93 (s, 2H), 7.74 (d, J=8.0 Hz, 2H), 7.53 (d, J=8.8 Hz, 2H), 5.95 (m, 1H), 5.33 (m, 1H), 5.22 (m, 1H), 4.42 (m, 2H), 4.25 (s, 2H), 4.01 (m, 2H), 3.91 (s, 2H), 3.74 (m, 2H), 3.47 (m, 2H), 2.66 (m, 1H), 1.36 (m, 18H), 1.27 (s, 9H).

MS m/z (+ESI): 658.4 [M+H]$^+$.

Preparation of N-[[3-allyloxy-5-[(azetidin-3-ylmethylamino)methyl]phenyl]methyl]-4-tert-butyl-benzenesulfonamide The titled compound is prepared as a white solid (123 mg, 43% yield) following Scheme 6 and in analogy to Example 158 using tert-butyl 3-[[[3-allyloxy-5-[[(4-tert-butylphenyl)sulfonylamino]methyl]phenyl]methyl-tert-butoxycarbonylamino]methyl]azetidine-1-carboxylate (410 mg, 0.62 mmol, 1.0 eq) as starting material.

Example 387: [3-[(2-bromo-4-chloro-phenyl)methoxy]-5-isobutoxy-phenyl]methyl-dimethyl-(pyrrolidin-3-ylmethyl) ammonium Preparation of tert-butyl 3-[[[3-[(2-bromo-4-chlorophenyl)methoxy]-5-isobutoxy-phenyl]methylamino]methyl]pyrrolidine-1-carboxylate The titled compound is prepared as a white solid following Scheme 1 and in analogy to Example 37 using 2-bromo-1-(bromomethyl)-4-chloro-benzene, 3,5-dihydroxybenzaldehyde, 1-bromo-2-methyl-propane and tert-butyl 3-(aminomethyl)pyrrolidine-1-carboxylate as starting materials.

$^1$H-NMR (400 MHz, DMSO-d6) δ ppm: 7.82 (d, J=2.0 Hz, 1H), 7.58 (d, J=8.4 Hz, 1H), 7.52 (dd, J=2.0 Hz, 8.4 Hz, 1H), 6.57 (s, 1H), 6.53 (s, 1H), 6.42 (s, 1H), 5.08 (s, 2H), 3.71 (m, 2H), 3.61 (s, 2H), 3.26 (m, 1H), 3.15 (m, 1H), 2.88 (m, 1H), 2.40 (m, 3H), 2.24 (m, 1H), 1.95 (m, 1H), 1.88 (m, 1H), 1.50 (m, 1H), 1.38 (s, 9H), 0.97 (d, J=6.8 Hz, 6H).

MS m/z (+ESI): 581.1, 583.1 [M+H]$^+$.

Preparation of [3-[(2-bromo-4-chloro-phenyl)methoxy]-5-isobutoxy-phenyl]methyl-[(1-tert-butoxycarbonylpyrrolidin-3-yl)methyl]-dimethyl-ammonium Potassium carbonate (209 mg, 1.51 mmol, 2.0 eq) is added at room temperature to a stirred solution of tert-butyl 3-[[[3-[(2-bromo-4-chloro-phenyl)methoxy]-5-isobutoxy-phenyl]methylamino]methyl]pyrrolidine-1-carboxylate (440 mg, 0.76 mmol, 1.0 eq) in N,N-dimethylformamide (10 mL), followed by iodomethane (190 μL, 3.02 mmol, 4.0 eq). After 3 hours stirring at room temperature, solvent is evaporated and the residue is extracted with ethyl acetate (3×10 mL) and water (10 mL). The combined organic layers are washed with brine (10 mL), dried over sodium sulfate, filtered and concentrated to afford [3-[(2-bromo-4-chloro-phenyl)methoxy]-5-isobutoxy-phenyl]methyl-[(1-tert-butoxycarbonylpyrrolidin-3-yl)methyl]-dimethyl-ammonium as a light yellow semi-solid (501 mg, 99% yield).

$^1$H-NMR (400 MHz, DMSO-d6) δ ppm: 7.85 (d, J=2.0 Hz, 1H), 7.62 (d, J=8.0 Hz, 1H), 7.54 (dd, J=2.0 Hz, 8.0 Hz, 1H), 6.80 (s, 3H), 5.15 (s, 2H), 4.47 (s, 2H), 3.78 (m, 2H), 3.72 (m, 1H), 3.42 (m, 3H), 3.14 (m, 1H), 3.00 (s, 6H), 2.80-2.95 (m, 2H), 2.12 (m, 1H), 2.03 (m, 1H), 1.62 (m, 1H), 1.40 (s, 9H), 0.99 (d, J=6.8 Hz, 6H).

MS m/z (+ESI): 609.2, 611.2 [M+H]$^+$.

Preparation of [3-[(2-bromo-4-chloro-phenyl)methoxy]-5-isobutoxy-phenyl]methyl-dimethyl-(pyrrolidin-3-ylmethyl)ammonium The titled compound is prepared as a light yellow semi-solid (205 mg, 55% yield) following Scheme 1 and in analogy to Example 158 using [3-[(2-bromo-4-chloro-phenyl)methoxy]-5-isobutoxy-phenyl]methyl-[(1-tert-butoxycarbonylpyrrolidin-3-yl)methyl]-dimethyl-ammonium (450 mg, 0.74 mmol, 1.0 eq) as starting material.

Example 394: 3-allyloxy-5-[(azetidin-3-ylmethylamino)methyl]-N-(2-bromo-4-chloro-phenyl)benzamide Preparation of tert-butyl 3-[[[3-allyloxy-5-[(2-bromo-4-chloro-phenyl)carbamoyl]phenyl]methyl]-tert-butoxycarbonyl-amino]methyl]azetidine-1-carboxylate 1-Chloro-N,N,2-trimethyl-1-propenylamine (40 μL, 0.34 mmol, 1.6 eq) is added at 0° C. to a stirred solution of 3-allyloxy-5-[[tert-butoxycarbonyl-[(1-tert-butoxycarbonylazetidin-3-yl)methyl]amino]methyl]benzoic acid (100 mg, 0.21 mmol, 1.0 eq) and dichloromethane (10 mL). After 1 hour stirring at 0° C., 2-bromo-4-chloro-aniline (70 mg, 0.31 mmol, 1.5 eq) [874482-95-8] and 2,4,6-trimethylpyridine (80 μL, 0.63 mmol, 3.0 eq) are added at 0° C. After 12 hours stirring at room temperature, the reaction mixture is concentrated to give a residue that is purified by column chromatography (silica gel; petroleum ether:ethyl acetate, 6:1, v/v) to afford tert-butyl 3-[[[3-allyloxy-5-[(2-bromo-4-chloro-phenyl)carbamoyl]phenyl]methy]-tert-butoxycarbonyl-amino]methyl]azetidine-1-carboxylate as a colorless oil (60 mg, 46% yield).

$^1$H-NMR (400 MHz, DMSO-d6) δ ppm: 10.06 (s, 1H), 7.88 (d, J=2.4 Hz, 1H), 7.62 (d, J=8.4 Hz, 1H), 7.40-7.60 (m, 3H), 7.00 (s, 1H), 6.08 (m, 1H), 5.42 (m, 1H), 5.29 (m, 1H), 4.64 (m, 2H), 4.42 (s, 2H), 3.78 (m, 2H), 3.52 (m, 2H), 3.34 (m, 2H), 2.75 (m, 1H), 1.37 (m, 18H).

Preparation of 3-allyloxy-5-[(azetidin-3-ylmethylamino)methyl]-N-(2-bromo-4-chloro-phenyl)benzamide The titled compound is prepared as a light yellow solid (20 mg, 9% yield) following Scheme 5 and in analogy to Example 158 using tert-butyl 3-[[[3-allyloxy-5-[(2-bromo-4-chloro-phenyl)carbamoyl]phenyl]methy]-tert-butoxycarbonyl-amino]methyl]azetidine-1-carboxylate (300 mg, 0.45 mmol, 1.0 eq) as starting material.

Example 399: 4-tert-butyl-N-[2-[2-(1H-imidazol-4-yl)ethoxy]-4-[(pyrrolidin-3-ylmethylamino)methyl]phenyl]benzenesulfonamide Preparation of 2-(1-tritylimidazol-4-yl)ethanol Triphenylmethyl chloride (29.84 g, 107.0 mmol, 1.2 eq) is added at room temperature to a stirred solution of 2-(1H-imidazol-4-yl)ethanol (10.0 g, 89.18 mmol, 1.0 eq) [872-82-2] in N,N-dimethylformamide (300 mL), followed by triethylamine (14.92 mL, 107.0 mmol, 1.2 eq). After 12 hours stirring at room temperature, the reaction mixture is poured into crushed ice and the resulting solid is collected by filtration, washed with water and acetone to afford 2-(1-tritylimidazol-4-yl)ethanol as a white solid (12.5 g, 40% yield).

$^1$H-NMR (400 MHz, DMSO-d6) δ ppm: 7.38 (m, 9H), 7.24 (s, 1H), 7.08 (m, 6H), 6.65 (s, 1H), 4.52 (t, J=5.6 Hz, 1H), 3.57 (m, 2H), 2.58 (t, J=7.2 Hz, 2H).

MS m/z (+ESI): 355.2 [M+H]$^+$.

Preparation of methyl 4-nitro-3-[2-(1-tritylimidazol-4-yl)ethoxy]benzoate

Sodium hydride (1.08 g, 27.09 mmol, 1.2 eq) is added at 0° C. to a stirred solution of 2-(1-tritylimidazol-4-yl)ethanol (8.0 g, 22.57 mmol, 1.0 eq) in N,N-dimethylformamide (150 mL), followed by methyl 3-fluoro-4-nitro-benzoate (5.39 g, 27.09 mmol, 1.2 eq) [185629-31-6]. After 4 hours stirring at 70° C., solvent is evaporated and the residue is extracted with ethyl acetate (3×100 mL) and water (100 mL). The combined organic layers are washed with brine, dried over sodium sulfate, filtered and concentrated to give a residue that is purified by column chromatography (silica gel; petroleum ether:ethyl acetate, 2:1, v/v) to afford methyl 4-nitro-3-[2-(1-tritylimidazol-4-yl)ethoxy]benzoate as a yellow solid (3.40 g, 28% yield).

$^1$H-NMR (400 MHz, DMSO-d6) δ ppm: 7.80 (d, J=8.4 Hz, 1H), 7.76 (d, J=1.2 Hz, 1H), 7.66 (dd, J=1.2 Hz, 8.0 Hz, 1H), 7.37 (m, 10H), 7.14 (m, 6H), 6.74 (s, 1H), 4.46 (t, J=6.8 Hz, 2H), 3.95 (s, 3H), 3.08 (t, J=6.8 Hz, 2H).

Preparation of [4-nitro-3-[2-(1-tritylimidazol-4-yl)ethoxy]phenyl]methanol

The titled compound is prepared as a yellow solid (3.10 g, 73% yield) following Scheme 6 and in analogy to Example 158 using methyl 4-nitro-3-[2-(1-tritylimidazol-4-yl)ethoxy]benzoate (4.50 g, 8.43 mmol, 1.0 eq) as starting material.

$^1$H-NMR (400 MHz, CDCl$_3$) δ ppm: 7.81 (d, J=8.0 Hz, 1H), 7.32 (m, 9H), 7.22 (s, 1H), 7.17 (s, 1H), 7.12 (m, 6H), 6.93 (d, J=8.4 Hz, 1H), 6.66 (s, 1H), 4.71 (s, 2H), 4.41 (t, J=6.4 Hz, 2H), 3.84 (m, 1H), 3.06 (t, J=6.4 Hz, 2H).

MS m/z (+ESI): 506.2[M+H]$^+$.

Preparation of 4-nitro-3-[2-(1-tritylimidazol-4-yl)ethoxy]benzaldehyde

Pyridinium chlorochromate (2.64 g, 12.26 mmol, 2.0 eq) is added at room temperature to a stirred solution of [4-nitro-3-[2-(1-tritylimidazol-4-yl)ethoxy]phenyl]methanol (3.10 g, 6.13 mmol, 1.0 eq) in dichloromethane (120 mL). After 2 hours stirring at room temperature, the reaction mixture is filtered and concentrated to give a residue that is purified by column chromatography (silica gel; petroleum ether:ethyl acetate, 2:1, v/v) to afford 4-nitro-3-[2-(1-tritylimidazol-4-yl)ethoxy]benzaldehyde as a light yellow solid (1.20 g, 39% yield).

$^1$H-NMR (400 MHz, CDCl$_3$) δ ppm: 10.07 (s, 1H), 7.92 (d, J=8.0 Hz, 1H), 7.72 (s, 1H), 7.58 (d, J=8.0 Hz, 1H), 7.47 (m, 9H), 7.32 (s, 1H), 7.14 (m, 6H), 7.00 (s, 1H), 4.66 (m, 2H), 3.32 (m, 2H).

MS m/z (+ESI): 504.1 [M+H]$^+$.

Preparation of tert-butyl 3-[[tert-butoxycarbonyl-[[4-nitro-3-[2-(1-tritylimidazol-4-yl)ethoxy]phenyl]methyl]amino]methyl]pyrrolidine-1-carboxylate The titled compound is prepared as a white solid following Scheme 6 and in analogy to Examples 37 and 130 using 4-nitro-3-[2-(1-tritylimidazol-4-yl)ethoxy]benzaldehyde, tert-butyl 3-(aminomethyl)pyrrolidine-1-carboxylate and di-tert-butyl dicarbonate as starting materials.

$^1$H-NMR (400 MHz, CDCl$_3$) δ ppm: 7.83 (d, J=8.4 Hz, 1H), 7.41 (s, 1H), 7.34 (m, 9H), 7.15 (m, 6H), 6.96 (m, 1H), 6.82 (m, 1H), 6.78 (s, 1H), 4.47 (m, 2H), 4.37 (t, J=6.0 Hz, 2H), 3.20-3.50 (m, 6H), 3.09 (t, J=6.0 Hz, 2H), 2.36 (m, 1H), 1.90 (m, 1H) 1.54 (m, 1H), 1.45 (m, 18H).

Preparation of tert-butyl 3-[[[4-amino-3-[2-(1-tritylimidazol-4-yl)ethoxy]phenyl]methyl-tert-butoxycarbonylamino]methyl]pyrrolidine-1-carboxylate Ammonium chloride (160 mg, 3.05 mmol, 2.0 eq) is added at room temperature to a stirred solution of tert-butyl 3-[[tert-butoxycarbonyl-[[4-nitro-3-[2-(1-tritylimidazol-4-yl)ethoxy]phenyl]methyl]amino]methyl]pyrrolidine-1-carboxylate (1.20 g, 1.52 mmol, 1.0 eq) in ethanol (40 mL) and water (5 mL), followed by iron powder (850 mg, 15.2 mmol, 10.0 eq). After 3 hours stirring under reflux conditions, the reaction mixture is filtered through decalite and concentrated to give a residue that is purified by column chromatography (silica gel; dichloromethane:methanol, 100:5, v/v) to afford tert-butyl 3-[[[4-amino-3-[2-(1-tritylimidazol-4-yl)ethoxy]phenyl]methyl-tert-butoxycarbonylamino]methyl]pyrrolidine-1-carboxylate as a light yellow solid (950 mg, 82% yield).

$^1$H-NMR (400 MHz, CDCl$_3$) δ ppm: 7.38 (s, 1H), 7.32 (m, 9H), 7.15 (m, 6H), 6.72 (m, 2H), 6.62 (s, 2H), 4.32 (m, 2H), 4.23 (t, J=6.4 Hz, 2H), 3.13-3.45 (m, 6H), 3.05 (t, J=6.0 Hz, 2H), 2.40 (m, 1H), 1.87 (m, 1H) 1.52 (m, 1H), 1.47 (s, 9H), 1.46 (s, 9H).

Preparation of 4-tert-butyl-N-[2-[2-(1H-imidazol-4-yl)ethoxy]-4-[(pyrrolidin-3-ylmethylamino)methyl]phenyl]benzenesulfonamide The titled compound is prepared as a light yellow oil following Scheme 6 and in analogy to Examples 158 and 369 using tert-butyl 3-[[[4-amino-3-[2-(1-tritylimidazol-4-yl)ethoxy]phenyl]methyl-tert-butoxycarbonylamino]methyl]pyrrolidine-1-carboxylate and 4-tert-butylbenzenesulfonyl chloride as starting materials.

Example 476: 3-[[3-isobutoxy-5-[(pyrrolidin-3-ylmethylamino)methyl]phenyl]sulfonylmethyl]benzamide Preparation of 1,3-dibromo-5-isobutoxy-benzene The titled compound is prepared as a colorless oil (5.45 g, 90% yield) following Scheme 1 and in analogy to Example 37 using 3,5-dibromophenol (5.0 g, 19.45 mmol, 1.0 eq) [626-41-5] and 1-bromo-2-methyl-propane (2.99 g, 21.40 mmol, 1.1 eq) [78-77-3] as starting materials.

$^1$H-NMR (400 MHz, DMSO-d6) δ ppm: 7.36 (t, J=2.0 Hz, 1H), 7.19 (d, J=2.0 Hz, 2H), 3.79 (d, J=6.4 Hz, 2H), 2.00 (m, 1H), 0.96 (d, J=6.8 Hz, 6H).

Preparation of 3-bromo-5-isobutoxy-benzaldehyde n-Butyllithium (1.6 M in n-hexane, 2.0 mL, 3.20 mmol, 1.2 eq) is added dropwise at −78° C. to a stirred solution of 1,3-dibromo-5-isobutoxy-benzene (815 mg, 2.62 mmol, 1.0 eq) in tetrahydrofuran (13 mL). After 20 minutes stirring at −78° C., N,N-dimethylformamide (2.0 mL, 26.2 mmol, 10.0 eq) is added. After 30 minutes stirring at −78° C., the reaction is allowed to warm at −30° C. before the addition of a 1N hydrochloric acid aqueous solution (3 mL). The resulting mixture is extracted with ethyl acetate (3×20 mL) and water (30 mL). The combined organic layers are washed with brine (30 mL), dried over sodium sulfate, filtered and concentrated to give a residue that is purified by column chromatography (silica gel; petroleum ether:ethyl acetate, 20:1, v/v) to afford 3-bromo-5-isobutoxy-benzaldehyde as a colorless oil (639 mg, 94% yield).

$^1$H-NMR (400 MHz, DMSO-d6) δ ppm: 9.93 (s, 1H), 7.63 (t, J=1.2 Hz, 1H), 7.49 (t, J=1.2 Hz, 1H), 7.44 (t, J=1.2 Hz, 1H), 3.85 (d, J=6.4 Hz, 2H), 2.03 (m, 1H), 0.99 (d, J=6.8 Hz, 6H).

Preparation of tert-butyl 3-[[(3-bromo-5-isobutoxy-phenyl)methyl-tert-butoxycarbonyl-amino]methyl]pyrrolidine-1-carboxylate The titled compound is prepared as a colorless gum following Scheme 1 and in analogy to Examples 37 and 130 using 3-bromo-5-isobutoxy-benzaldehyde, tert-butyl 3-(aminomethyl)pyrrolidine-1-carboxylate and di-tert-butyl dicarbonate as starting material.

$^1$H-NMR (400 MHz, DMSO-d6) δ ppm: 7.03 (s, 1H), 6.97 (s, 1H), 6.79 (s, 1H), 4.34 (s, 2H), 3.74 (d, J=6.4 Hz, 2H), 3.02-3.40 (m, 5H), 2.97 (m, 1H), 2.40 (m, 1H), 2.00 (m, 1H), 1.83 (m, 1H), 1.52 (m, 1H), 1.38 (s, 18H), 0.96 (d, J=6.8 Hz, 6H).

MS m/z (+ESI): 541.2, 543.2 [M+H]$^+$.

Preparation of tert-butyl 3-[[(3-acetylsulfanyl-5-isobutoxy-phenyl)methyl-tert-butoxycarbonyl-amino]methyl]pyrrolidine-1-carboxylate N,N-diisopropylethylamine (235 µL, 1.35 mmol, 2.0 eq) is added at room temperature to a stirred solution of tert-butyl 3-[[(3-bromo-5-isobutoxy-phenyl)methyl-tert-butoxycarbonyl-amino]methyl]pyrrolidine-1-carboxylate (370 mg, 0.68 mmol, 1.0 eq) in dioxane (3 mL), followed by potassium thioacetate (117 mg, 1.01 mmol, 1.5 eq), 4,5-bis(diphenylphosphino)-9,9-dimethylxanthene (40 mg, 0.068 mmol, 0.1 eq) and tris(dibenzylideneacetone)dipalladium(0) (31 mg, 0.034 mmol, 0.05 eq). The resulting mixture is irradiated by microwaves at 120° C. for 6 minutes, then solvent is evaporated, and the residue is extracted with ethyl acetate (3×20 mL) and water (20 mL). The combined organic layers are washed with brine (20 mL), dried over sodium sulfate, filtered and concentrated to give a residue that is purified by column chromatography (silica gel; petroleum ether:ethyl acetate, 5:1, v/v) to afford tert-butyl 3-[[(3-acetylsulfanyl-5-isobutoxy-phenyl)methyl-tert-butoxycarbonyl-amino]methyl]pyrrolidine-1-carboxylate as a light yellow gum (179 mg, 49% yield).

$^1$H-NMR (400 MHz, DMSO-d6) δ ppm: 6.88 (s, 2H), 6.85 (s, 1H), 4.37 (s, 2H), 3.74 (d, J=6.8 Hz, 2H), 3.00-3.30 (m, 5H), 2.95 (m, 1H), 2.41 (s, 3H), 2.35 (m, 1H), 2.00 (m, 1H), 1.82 (m, 1H), 1.50 (m, 1H), 1.38 (s, 18H), 0.97 (d, J=6.4 Hz, 6H).

MS m/z (+ESI): 537.3 [M+H]$^+$.

Preparation of 3-[[3-isobutoxy-5-[(pyrrolidin-3-ylmethylamino)methyl]phenyl]sulfonylmethyl]benzamide The titled compound is prepared as a white solid following Scheme 1 and in analogy to Examples 37, 136 and 137 using tert-butyl 3-[[(3-acetylsulfanyl-5-isobutoxy-phenyl)methyl-tert-butoxycarbonyl-amino]methyl]pyrrolidine-1-carboxylate and 3-(chloromethyl)benzamide [135654-16-9] as starting materials.

Example 477: N1-[[3-isobutoxy-5-[(pyrrolidin-3-ylmethylamino)methyl]phenyl]methyl]benzene-1,3-dicarboxamide

Preparation of 3-[[3-[[tert-butoxycarbonyl-[(1-tert-butoxycarbonylpyrrolidin-3-yl)methyl]amino]methyl]-5-isobutoxy-phenyl]methylcarbamoyl]benzoic Acid The titled compound is prepared as a yellow gum following Scheme 6 and in analogy to Examples 37, 119, 130, 158 and 354 using dimethyl 5-hydroxybenzene-1,3-dicarboxylate, 1-bromo-2-methyl-propane, tert-butyl 3-(aminomethyl)pyrrolidine-1-carboxylate, phthalimide and isophthalic acid as starting materials.

MS m/z (+ESI): 640.3 [M+H]$^+$.

Preparation of tert-butyl 3-[[tert-butoxycarbonyl-[[3-[[(3-carbamoylbenzoyl)amino]methyl]-5-isobutoxy-phenyl]methyl]amino]methyl]pyrrolidine-1-carboxylate Ammonium chloride (377 mg, 6.98 mmol, 5.0 eq) is added at room temperature to a stirred solution of 3-[[3-[[tert-butoxycarbonyl-[(1-tert-butoxycarbonylpyrrolidin-3-yl)methyl]amino]methyl]-5-isobutoxy-phenyl]methylcarbamoyl]benzoic acid (902 mg, 1.40 mmol, 1.0 eq) in N,N-dimethylformamide (15 mL), followed by N,N-diisopropylethylamine (1.72 mL, 9.77 mmol, 7.0 eq) and N,N,N',N'-tetramethyl-O-(1H-benzotriazol-1-yl)uronium hexafluorophosphate (802 mg, 2.09 mmol, 1.5 eq). After 20 hours stirring at room temperature, solvent is evaporated and the residue is extracted with ethyl acetate (3×30 mL) and water (30 mL). The combined organic layers are washed with brine (30 mL), dried over sodium sulfate, filtered and concentrated to give a residue that is purified by column chromatography (silica gel; petroleum ether:ethyl acetate, 1:2, v/v) to afford tert-butyl 3-[[tert-butoxycarbonyl-[[3-[[(3-carbamoylbenzoyl)amino]methyl]-5-isobutoxy-phenyl]methyl]amino]methyl]pyrrolidine-1-carboxylate as a light yellow foam (535 mg, 59% yield).

$^1$H-NMR (400 MHz, DMSO-d6) δ ppm: 9.10 (t, J=5.6 Hz, 1H), 8.39 (s, 1H), 8.05 (s, 1H), 8.00 (m, 2H), 7.54 (t, J=7.6 Hz, 1H), 7.49 (s, 1H), 6.77 (m, 2H), 6.65 (s, 1H), 4.43 (d, J=5.6 Hz, 2H), 4.25-4.40 (m, 2H), 3.69 (d, J=6.0 Hz, 2H), 3.10-3.30 (m, 5H), 2.95 (m, 1H), 2.35 (m, 1H), 2.00 (m, 1H), 1.77 (m, 1H), 1.47 (m, 1H), 1.25-1.40 (m, 18H), 0.95 (d, J=6.8 Hz, 6H).

MS m/z (+ESI): 639.4 [M+H]$^+$.

Preparation of N1-[[3-isobutoxy-5-[(pyrrolidin-3-ylmethylamino)methyl]phenyl]methyl]benzene-1,3-dicarboxamide The titled compound is prepared as a white solid (125 mg, 62% yield) following Scheme 6 and in analogy to Example 37 using tert-butyl 3-[[tert-butoxycarbonyl-[[3-[[(3-carbamoylbenzoyl)amino]methyl]-5-isobutoxy-phenyl]methyl]amino]methyl]pyrrolidine-1-carboxylate (291 mg, 0.45 mmol, 1.0 eq) as starting material.

Example 478: 5-[[3-isobutoxy-5-[(pyrrolidin-3-ylmethylamino)methyl]phenyl]sulfonylmethyl]pyridine-3-carboxamide

Preparation of 5-[[3-isobutoxy-5-[(pyrrolidin-3-ylmethylamino)methyl]phenyl]sulfonylmethyl]pyridine-3-carbonitrile The titled compound is prepared as a white solid following Scheme 1 and in analogy to Examples 37, 137 and 476 using tert-butyl 3-[[(3-acetylsulfanyl-5-isobutoxy-phenyl)methyl-tert-butoxycarbonyl-amino]methyl]pyrrolidine-1-carboxylate and 5-(bromomethyl)pyridine-3-carbonitrile [1211530-54-9] as starting materials.

$^1$H-NMR (400 MHz, DMSO-d6+D$_2$O) δ ppm: 8.99 (d, J=2.0 Hz, 1H), 8.53 (d, J=2.0 Hz, 1H), 8.08 (t, J=2.0 Hz, 1H), 7.45 (d, J=2.0 Hz, 1H), 7.42 (s, 1H), 7.25 (t, J=2.0 Hz, 1H), 4.87 (s, 2H), 4.17 (s, 2H), 3.79 (d, J=6.8 Hz, 2H), 3.37 (m, 1H), 3.25 (m, 1H), 3.15 (m, 1H), 3.03 (m, 2H), 2.87 (m, 1H), 2.55 (m, 1H), 2.12 (m, 1H), 2.00 (m, 1H), 1.65 (m, 1H), 0.98 (d, J=6.8 Hz, 6H)

MS m/z (+ESI): 443.2 [M+H]+.

Preparation of 5-[[3-isobutoxy-5-[(pyrrolidin-3-ylmethylamino)methyl]phenyl]sulfonylmethyl]pyridine-3-carboxamide A solution of 5-[[3-isobutoxy-5-[(pyrrolidin-3-ylmethylamino)methyl]phenyl]sulfonylmethyl]pyridine-3-carbonitrile (69 mg, 0.16 mmol, 1.0 eq) in a 0.5N hydrochloric acid solution in ethyl acetate (2 mL) is stirred at room temperature for 20 hours. The reaction mixture is then concentrated and purified by preparative HPLC to afford 5-[[3-isobutoxy-5-[(pyrrolidin-3-ylmethylamino)methyl]phenyl]sulfonylmethyl]pyridine-3-carboxamide as a white solid (37 mg, 51% yield).

Example 480: 5-[(E)-2-[3-hydroxy-5-[(pyrrolidin-3-ylmethylamino)methyl]phenyl]vinyl]pyridine-3-carbonitrile Preparation of tert-butyl 3-[[[3-allyloxy-5-[(E)-2-(5-cyano-3-pyridyl)vinyl]phenyl]methyl-tert-butoxycarbonyl-amino]methyl]pyrrolidine-1-carboxylate The titled compound is prepared as a light yellow semi-solid following Scheme 3 and in analogy to Examples 37, 130, 158 and 168 using dimethyl 5-hydroxybenzene-1,3-dicarboxylate, allyl bromide, di-tert-butyl dicarbonate, tert-butyl 3-(aminomethyl)pyrrolidine-1-carboxylate, 5-(bromomethyl)pyridine-3-carbonitrile and triethyl phosphite as starting materials.

1H-NMR (400 MHz, CDCl3) δ ppm: 8.80 (s, 1H), 7.91 (d, J=8.0 Hz, 1H), 7.68 (d, J=8.0 Hz, 1H), 7.20 (m, 1H), 6.90-7.10 (m, 3H), 6.78 (m, 1H), 6.05 (m, 1H), 5.46 (m, 1H), 5.34 (m, 1H), 4.59 (m, 2H), 4.25-4.45 (m, 2H), 3.00-3.40 (m, 6H), 2.40-2.50 (m, 1H), 1.90 (m, 1H), 1.45-1.60 (m, 19H).

MS m/z (+ESI): 475.2 [M-Boc+H]+.

Preparation of tert-butyl 3-[[tert-butoxycarbonyl-[[3-[(E)-2-(5-cyano-3-pyridyl)vinyl]-5-hydroxy-phenyl]methyl]amino]methyl]pyrrolidine-1-carboxylate Potassium carbonate (289 mg, 2.09 mmol, 2.0 eq) is added at room temperature to a stirred solution of tert-butyl 3-[[[3-allyloxy-5-[(E)-2-(5-cyano-3-pyridyl)vinyl]phenyl]methyl-tert-butoxycarbonyl-amino]methyl]pyrrolidine-1-carboxylate (600 mg, 1.04 mmol, 1.0 eq) in methanol (30 mL), followed by tetrakis(triphenylphosphine)palladium(0) (121 mg, 0.10 mmol, 0.1 eq). After 2 hours stirring at 70° C., solvent is evaporated and the residue is purified by column chromatography (silica gel; dichloromethane:methanol, 80:1 to 60:1, v/v) to afford tert-butyl 3-[[tert-butoxycarbonyl-[[3-[(E)-2-(5-cyano-3-pyridyl)vinyl]-5-hydroxy-phenyl]methyl]amino]methyl]pyrrolidine-1-carboxylate as a light yellow solid (180 mg, 26% yield).

MS m/z (+ESI): 535.3 [M+H]+.

Preparation of 5-[(E)-2-[3-hydroxy-5-[(pyrrolidin-3-ylmethylamino)methyl]phenyl]vinyl]pyridine-3-carbonitrile The titled compound is prepared as a light yellow solid (50 mg, 45% yield) following Scheme 3 and in analogy to Example 236 using tert-butyl 3-[[tert-butoxycarbonyl-[[3-[(E)-2-(5-cyano-3-pyridyl)vinyl]-5-hydroxy-phenyl]methyl]amino]methyl]pyrrolidine-1-carboxylate (180 mg, 0.32 mmol, 1.0 eq) as starting material.

Example 483: 5-[(E)-2-[3-[(5-methylisoxazol-3-yl)methoxy]-5-[(pyrrolidin-3-ylmethylamino)methyl]phenyl]vinyl]pyridine-3-carbonitrile Preparation of tert-butyl 3-[[(3-benzyloxy-5-methoxycarbonyl-phenyl)methyl-tert-butoxycarbonyl-amino]methyl]pyrrolidine-1-carboxylate The titled compound is prepared as a yellow oil following Scheme 3 and in analogy to Examples 37, 130 and 158 using dimethyl 5-hydroxybenzene-1,3-dicarboxylate, benzyl bromide, tert-butyl 3-(aminomethyl)pyrrolidine-1-carboxylate and di-tert-butyl dicarbonate as starting materials.

MS m/z (+ESI): 555.2 [M+H]+.

Preparation of tert-butyl 3-[[tert-butoxycarbonyl-[(3-hydroxy-5-methoxycarbonyl-phenyl)methyl]amino]methyl]pyrrolidine-1-carboxylate A mixture of tert-butyl 3-[[(3-benzyloxy-5-methoxycarbonyl-phenyl)methyl-tert-butoxycarbonyl-amino]methyl]pyrrolidine-1-carboxylate (1.30 g, 2.34 mmol, 1.0 eq) and 10% palladium on activated carbon (250 mg, 0.23 mmol, 0.1 eq) in ethyl acetate (30 mL) is stirred under hydrogen flow at room temperature and 4 atm for 20 hours. The catalyst is then removed by filtration and the solution is evaporated to dryness to afford tert-butyl 3-[[tert-butoxycarbonyl-[(3-hydroxy-5-methoxycarbonyl-phenyl)methyl]amino]methyl]pyrrolidine-1-carboxylate as a white solid (1.08 g, 95% yield) that is directly engaged in the next step without further purification.

MS m/z (+ESI): 465.1 [M+H]+.

Preparation of 5-[(E)-2-[3-[(5-methylisoxazol-3-yl)methoxy]-5-[(pyrrolidin-3-ylmethylamino)methyl]phenyl]vinyl]pyridine-3-carbonitrile The titled compound is prepared as a white solid following Scheme 3 and in analogy to Examples 37, 136, 168 and 236 using tert-butyl 3-[[tert-butoxycarbonyl-[(3-hydroxy-5-methoxycarbonyl-phenyl)methyl]amino]methyl]pyrrolidine-1-carboxylate, 3-(bromomethyl)-5-methyl-isoxazole [130628-75-0] and 5-(bromomethyl)pyridine-3-carbonitrile as starting materials.

Example 484: 5-[(E)-2-[3-(2-morpholinoethoxy)-5-[(pyrrolidin-3-ylmethylamino)methyl]phenyl]vinyl]pyridine-3-carbonitrile Preparation of tert-butyl 3-[[tert-butoxycarbonyl-[[3-methoxycarbonyl-5-(2-morpholinoethoxy)phenyl]methyl]amino]methyl]pyrrolidine-1-carboxylate 2-Morpholinoethanol (85 mg, 0.65 mmol, 1.5 eq) [622-40-2] is added at room temperature to a stirred solution of tert-butyl 3-[[tert-butoxycarbonyl-[(3-hydroxy-5-methoxycarbonyl-phenyl)methyl]amino]methyl]pyrrolidine-1-carboxylate (200 mg, 0.43 mmol, 1.0 eq) in toluene (10 mL), followed by tributylphosphine (160 µL, 0.65 mmol, 1.5 eq) and 1,1'-(azodicarbonyl)dipiperidine (164 mg, 0.65 mmol, 1.5 eq). After 5 hours stirring at 100° C., solvent is evaporated and the residue is purified by column chromatography (silica gel; dichloromethane:methanol, 60:1 to 40:1, v/v) to afford tert-butyl 3-[[tert-butoxycarbonyl-[[3-methoxycarbonyl-5-(2-morpholinoethoxy)phenyl]methyl]amino]methyl]pyrrolidine-1-carboxylate as a white solid (200 mg, 80% yield).

MS m/z (+ESI): 578.2 [M+H]+.

Preparation of 5-[(E)-2-[3-(2-morpholinoethoxy)-5-[(pyrrolidin-3-ylmethylamino)methyl]phenyl]vinyl]pyridine-3-carbonitrile The titled compound is prepared as a light yellow solid following Scheme 3 and in analogy to Examples 136, 168 and 236 using tert-butyl 3-[[tert-butoxycarbonyl-[[3-methoxycarbonyl-5-(2-morpholinoethoxy)phenyl]methyl]amino]methyl]pyrrolidine-1-carboxylate and 5-(bromomethyl)pyridine-3-carbonitrile as starting materials.

Example 485: N-[3-isobutoxy-5-[(pyrrolidin-3-ylmethylamino)methyl]phenyl]pyridine-3-carboxamide Preparation of tert-butyl 3-[[tert-butoxycarbonyl-[(3-isobutoxy-5-nitro-phenyl)methyl]amino]methyl]pyrrolidine-1-carboxylate The titled compound is prepared as a light yellow solid following Scheme 6 and in analogy to Examples 37 and 130 using 3-hydroxy-5-nitro-benzaldehyde [193693-95-7], 1-bromo-2-methyl-propane, tert-butyl 3-(aminomethyl)pyrrolidine-1-carboxylate and di-tert-butyl dicarbonate as starting materials.

$^1$H-NMR (400 MHz, DMSO-d6) δ ppm: 7.67 (s, 1H), 7.59 (s, 1H), 7.26 (s, 1H), 4.47 (s, 2H), 3.85 (d, J=6.4 Hz, 2H), 3.05-3.30 (m, 5H), 2.95 (m, 1H), 2.40 (m, 1H), 2.05 (m, 1H), 1.84 (m, 1H), 1.52 (m, 1H), 1.30-1.50 (m, 18H), 0.98 (d, J=6.8 Hz, 6H).

MS m/z (+ESI): 508.2 [M+H]+.

Preparation of tert-butyl 3-[[(3-amino-5-isobutoxyphenyl)methyl-tert-butoxycarbonyl-amino]methyl]pyrrolidine-1-carboxylate A mixture of tert-butyl 3-[[tert-butoxycarbonyl-[(3-isobutoxy-5-nitro-phenyl)methyl]amino]methyl]pyrrolidine-1-carboxylate (7.76 g, 15.14 mmol, 1.0 eq) and 10% palladium on activated carbon (2.40 g, 2.21 mmol, 0.1 eq) in isopropanol (150 mL) is stirred under hydrogen flow at room temperature and 1 atm for 4 hours. The catalyst is then removed by filtration and the solution is evaporated to dryness to afford tert-butyl 3-[[(3-amino-5-isobutoxy-phenyl)methyl-tert-butoxycarbonyl-amino]methyl]pyrrolidine-1-carboxylate as a light yellow solid (6.28 g, 87% yield) that is directly engaged in the next step without further purification.

$^1$H-NMR (400 MHz, DMSO-d6) δ ppm: 6.01 (s, 1H), 5.99 (s, 1H), 5.93 (s, 1H), 5.05 (s, 2H), 4.20 (m, 2H), 3.59 (d, J=6.8 Hz, 2H), 3.05-3.30 (m, 5H), 2.95 (m, 1H), 2.40 (m, 1H), 1.95 (m, 1H), 1.80 (m, 1H), 1.50 (m, 1H), 1.30-1.45 (m, 18H), 0.93 (d, J=6.8 Hz, 6H).

MS m/z (+ESI): 478.2 [M+H]+.

Preparation of N-[3-isobutoxy-5-[(pyrrolidin-3-ylmethylamino)methyl]phenyl]pyridine-3-carboxamide The titled compound is prepared as a white solid following Scheme 6 and in analogy to Examples 37 and 119 using tert-butyl 3-[[(3-amino-5-isobutoxy-phenyl)methyl-tert-butoxycarbonyl-amino]methyl]pyrrolidine-1-carboxylate and nicotinic acid [59-67-6] as starting materials.

Example 489: 3-[(azetidin-3-ylmethylamino)methyl]-5-[(E)-2-(2-bromo-4-chloro-phenyl)vinyl]pyridin-2-ol Preparation of methyl 5-bromo-6-oxo-1-(2-trimethylsilylethoxymethyl)pyridine-3-carboxylate 2-(Chloromethoxy)ethyl-trimethyl-silane (11.0 g, 66.3 mmol, 1.1 eq) [76513-69-4] is added at 0° C. to a stirred solution of methyl 5-bromo-6-hydroxy-pyridine-3-carboxylate (14.0 g, 60.3 mmol, 1.0 eq) [381247-99-0] in N,N-dimethylformamide (130 mL), followed by sodium hydride (4.8 g, 120.0 mmol, 2.0 eq). After 2 hours stirring at 0° C., solvent is evaporated and the residue is extracted with ethyl acetate (3×200 mL) and water (200 mL). The combined organic layers are washed with brine, dried over sodium sulfate, filtered and concentrated to give a residue that is purified by column chromatography (silica gel; petroleum ether:ethyl acetate, 10:1, v/v) to afford methyl 5-bromo-6-oxo-1-(2-trimethylsilylethoxymethyl)pyridine-3-carboxylate as a white solid (19.2 g, 88% yield).

$^1$H-NMR (400 MHz, DMSO-d6) δ ppm: 8.53 (d, J=2.4 Hz, 1H), 8.20 (d, J=2.4 Hz, 1H), 5.40 (s, 2H), 3.80 (s, 3H), 3.60 (t, J=8.0 Hz, 2H), 0.86 (t, J=8.0 Hz, 2H), 0.04 (s, 9H).

Preparation of methyl 6-oxo-1-(2-trimethylsilylethoxymethyl)-5-vinyl-pyridine-3-carboxylate Potassium vinyltrifluoroborate (5.80 g, 43.4 mmol, 1.5 eq) [13682-77-4] is added at room temperature to a stirred solution of methyl 5-bromo-6-oxo-1-(2-trimethylsilylethoxymethyl)pyridine-3-carboxylate (10.5 g, 28.9 mmol, 1.0 eq) in isopropanol (100 mL), followed by triethylamine (8 mL, 57.9 mmol, 2.0 eq) and [1,1'-bis(diphenylphosphino)ferrocene]palladium(II) dichloride (1.06 g, 1.45 mmol, 0.05 eq). After 3 hours stirring at 90° C., the catalyst is removed by filtration and the solution is extracted with ethyl acetate (3×300 mL) and water (300 mL). The combined organic layers are washed with brine (300 mL), dried over sodium sulfate, filtered and concentrated to give a residue that is purified by column chromatography (silica gel; petroleum ether:ethyl acetate, 5:1, v/v) to afford methyl 6-oxo-1-(2-trimethylsilylethoxymethyl)-5-vinyl-pyridine-3-carboxylate as a yellow oil (5.63 g, 62% yield).

$^1$H-NMR (400 MHz, DMSO-d6) δ ppm: 8.44 (d, J=2.4 Hz, 1H), 7.93 (d, J=2.4 Hz, 1H), 6.73 (dd, J=11.2 Hz, 17.6 Hz, 1H), 6.20 (dd, J=1.6 Hz, 17.6 Hz, 1H), 5.39 (s, 2H), 5.36 (dd, J=1.6 Hz, 11.2 Hz, 1H), 3.81 (s, 3H), 3.59 (t, J=8.0 Hz, 2H), 0.86 (t, J=8.0 Hz, 2H), 0.05 (s, 9H).

MS m/z (+ESI): 310.2 [M+H]+.

Preparation of methyl 5-formyl-6-oxo-1-(2-trimethylsilylethoxymethyl)pyridine-3-carboxylate Ozone is introduced at −78° C. to a stirred solution of methyl 6-oxo-1-(2-trimethylsilylethoxymethyl)-5-vinyl-pyridine-3-carboxylate (5.60 g, 18.1 mmol, 1.0 eq) in dichloromethane (120 mL) and methanol (40 mL). Then triphenylphosphine (7.12 g, 27.25 mmol, 1.5 eq) is added and the resulting mixture is stirred at room temperature for 7 hours. Solvent is evaporated and the residue is purified by column chromatography (silica gel; petroleum ether:ethyl acetate, 3:1, v/v) to afford methyl 5-formyl-6-oxo-1-(2-trimethylsilylethoxymethyl)pyridine-3-carboxylate as a yellow oil (5.10 g, 90% yield).

¹H-NMR (400 MHz, DMSO-d6) δ ppm: 10.09 (s, 1H), 8.83 (d, J=2.8 Hz, 1H), 8.29 (d, J=2.8 Hz, 1H), 5.43 (s, 2H), 3.84 (s, 3H), 3.64 (t, J=8.0 Hz, 2H), 0.88 (t, J=8.0 Hz, 2H), 0.04 (s, 9H).

MS m/z (+ESI): 312.1 [M+H]⁺.

Preparation of 5-[[tert-butoxycarbonyl-[(1-tert-butoxycarbonylazetidin-3-yl)methyl]amino]methyl]-6-oxo-1-(2-trimethylsilylethoxymethyl)pyridine-3-carboxylic acid The titled compound is prepared as a white foam following Scheme 3 and in analogy to Examples 37, 119 and 130 using methyl 5-formyl-6-oxo-1-(2-trimethylsilylethoxymethyl)pyridine-3-carboxylate, tert-butyl 3-(aminomethyl)azetidine-1-carboxylate and di-tert-butyl dicarbonate as starting materials.

¹H-NMR (400 MHz, DMSO-d6) δ ppm: 12.92 (br, 1H), 8.37 (d, J=2.0 Hz, 1H), 7.48 (m, 1H), 5.37 (s, 2H), 4.02 (m, 2H), 3.40-4.20 (m, 8H), 2.69 (m, 1H), 1.30-1.43 (m, 18H), 0.84 (t, J=8.0 Hz, 2H), −0.05 (s, 9H).

MS m/z (+ESI): 568.3 [M+H]⁺.

Preparation of tert-butyl 3-[[tert-butoxycarbonyl-[[5-(hydroxymethyl)-2-oxo-1-(2-trimethylsilylethoxymethyl)-3-pyridyl]methyl]amino]methyl]azetidine-1-carboxylate Isobutyl chloroformate (361 mg, 2.64 mmol, 1.5 eq) [543-27-1] is added at 0° C. to a stirred solution of 5-[[tert-butoxycarbonyl-[(1-tert-butoxycarbonylazetidin-3-yl)methyl]amino]methyl]-6-oxo-1-(2-trimethylsilylethoxymethyl)pyridine-3-carboxylic acid (1.0 g, 1.76 mmol, 1.0 eq) in tetrahydrofuran 20 mL), followed by 4-methylmorpholine (267 mg, 2.64 mmol, 1.5 eq) [109-02-4]. After 1 hour stirring at 0° C. the reaction mixture is filtered and sodium borohydride (333 mg, 8.81 mmol, 5.0 eq) is added at room temperature to the filtrate. After 12 hours stirring at room temperature, solvent is evaporated and the residue is purified by column chromatography (silica gel; petroleum ether:ethyl acetate, 1:1, v/v) to afford tert-butyl 3-[[tert-butoxycarbonyl-[[5-(hydroxymethyl)-2-oxo-1-(2-trimethylsilylethoxymethyl)-3-pyridyl]methyl]amino]methyl]azetidine-1-carboxylate as a white foam (490 mg, 50% yield).

¹H-NMR (400 MHz, DMSO-d6) δ ppm: 7.49 (d, J=2.0 Hz, 1H), 7.10 (br, 1H), 5.26 (s, 2H), 5.16 (br, 1H), 4.22 (d, J=5.2 Hz, 2H), 4.12 (s, 2H), 3.40-3.80 (m, 8H), 2.71 (m, 1H), 1.43-1.32 (m, 18H), 1.18 (t, J=7.2 Hz, 2H), −0.02 (s, 9H).

MS m/z (+ESI): 554.2 [M+H]⁺.

Preparation of 3-[(azetidin-3-ylmethylamino)methyl]-5-[(E)-2-(2-bromo-4-chloro-phenyl)vinyl]pyridin-2-ol The titled compound is prepared as a light yellow solid following Scheme 3 and in analogy to Examples 37, 136 and 168 using tert-butyl 3-[[tert-butoxycarbonyl-[[5-(hydroxymethyl)-2-oxo-1-(2-trimethylsilylethoxymethyl)-3-pyridyl]methyl]amino]methyl]azetidine-1-carboxylate and 2-bromo-4-chloro-1-(diethoxyphosphorylmethyl)benzene as starting materials.

Example 490: 1-[3-[(1,1-dimethylpyrrolidin-1-ium-3-yl)oxymethyl]-5-[(E)-2-(3-pyridyl)vinyl]phenyl]-N-(pyrrolidin-3-ylmethyl)methanamine Preparation of benzyl 3-[[3,5-bis(bromomethyl)phenyl]methoxy]pyrrolidine-1-carboxylate The titled compound is prepared as a colorless oil (420 mg, 29% yield) following Scheme 3 and in analogy to Example 263 using 1,3,5-tris(bromomethyl)benzene (1.02 g, 2.86 mmol, 1.0 eq) [18226-42-1] and benzyl 3-hydroxypyrrolidine-1-carboxylate (630 mg, 2.86 mmol, 1.0 eq) [95656-88-5] as starting materials.

¹H-NMR (400 MHz, DMSO-d6) δ ppm: 7.29-7.43 (m, 8H), 5.06 (s, 2H), 4.70 (s, 4H), 4.49 (s, 2H), 4.16 (m, 1H), 3.33-3.45 (m, 4H), 2.02 (m, 2H).

MS m/z (+ESI): 496.0, 498.0, 500.0 [M+H]⁺.

Preparation of benzyl 3-[[3,5-bis(acetoxymethyl)phenyl]methoxy]pyrrolidine-1-carboxylate Sodium acetate (66 mg, 0.80 mmol, 4.0 eq) is added at room temperature to a stirred solution of benzyl 3-[[3,5-bis(bromomethyl)phenyl]methoxy]pyrrolidine-1-carboxylate (100 mg, 0.20 mmol, 1.0 eq) in N,N-dimethylformamide (2 mL). After 2 hours stirring at 100° C., the reaction mixture is extracted with ethyl acetate (3×20 mL) and water (20 mL). The combined organic layers are washed with brine (20 mL), dried over sodium sulfate, filtered and concentrated to afford benzyl 3-[[3,5-bis(acetoxymethyl)phenyl]methoxy]pyrrolidine-1-carboxylate as a colorless oil (85 mg, 93% yield).

¹H-NMR (400 MHz, DMSO-d6) δ ppm: 7.35 (m, 5H), 7.26 (s, 3H), 5.06 (s, 6H), 4.50 (s, 2H), 4.15 (m, 1H), 3.33-3.45 (m, 4H), 2.05 (s, 6H), 2.00 (m, 2H).

MS m/z (+ESI): 456.2 [M+H]⁺.

Preparation of benzyl 3-[[3,5-bis(hydroxymethyl)phenyl]methoxy]pyrrolidine-1-carboxylate Sodium methoxide (830 mg, 15.35 mmol, 3.0 eq) is added at room temperature to a stirred solution of benzyl 3-[[3,5-bis(acetoxymethyl)phenyl]methoxy]pyrrolidine-1-carboxylate (2.33 g, 5.12 mmol, 1.0 eq) in methanol (40 mL). After 1 hour stirring at room temperature, solvent is evaporated and the residue is extracted with ethyl acetate (3×40 mL) and water (40 mL). The combined organic layers are washed with brine (40 mL), dried over sodium sulfate, filtered and concentrated to afford benzyl 3-[[3,5-bis(hydroxymethyl)phenyl]methoxy]pyrrolidine-1-carboxylate as a yellow oil (1.61 g, 85% yield).

¹H-NMR (400 MHz, DMSO-d6) δ ppm: 7.35 (m, 5H), 7.17 (s, 1H), 7.12 (s, 2H), 5.16 (t, J=5.6 Hz, 2H), 5.06 (s, 2H), 4.46 (m, 6H), 4.14 (m, 1H), 3.33-3.45 (m, 4H), 2.00 (m, 2H).

MS m/z (+ESI): 372.2 [M+H]⁺.

Preparation of tert-butyl 3-[[[3-[(1-benzyloxycarbonylpyrrolidin-3-yl)oxymethyl]-5-(hydroxymethyl)phenyl]methyl-tert-butoxycarbonyl-amino]methyl]pyrrolidine-1-carboxylate The titled compound is prepared as a light yellow oil following Scheme 3 and in analogy to Examples 37, 130 and 158 using benzyl 3-[[3,5-bis(hydroxymethyl)phenyl]

methoxy]pyrrolidine-1-carboxylate, tert-butyl 3-(aminomethyl)pyrrolidine-1-carboxylate and di-tert-butyl dicarbonate as starting materials.

$^1$H-NMR (400 MHz, DMSO-d6) δ ppm: 7.36 (m, 5H), 7.14 (s, 1H), 7.08 (s, H), 7.04 (s, 1H), 5.18 (t, J=6.0 Hz, 1H), 5.05 (s, 2H), 4.47 (s, 4H), 4.35 (s, 2H), 4.12 (m, 1H), 2.95-3.45 (m, 1OH), 2.39 (m, 1H, H-3), 2.00 (m, 3H), 1.80 (m, 1H), 1.42 (s, 9H), 1.37 (s, 9H).

Preparation of tert-butyl 3-[[tert-butoxycarbonyl-[[3-(hydroxymethyl)-5-(pyrrolidin-3-yloxymethyl)phenyl]methyl]amino]methyl]pyrrolidine-1-carboxylate A mixture of tert-butyl 3-[[[3-[(1-benzyloxycarbonylpyrrolidin-3-yl)oxymethyl]-5-(hydroxymethyl)phenyl]methyl-tert-butoxycarbonyl-amino]methyl]pyrrolidine-1-carboxylate (840 mg, 1.28 mmol, 1.0 eq) and 10% palladium on activated carbon (270 mg, 0.26 mmol, 0.2 eq) in methanol (20 mL) is stirred under hydrogen flow at room temperature and 4 atm for 20 hours. The catalyst is then removed by filtration and the solution is evaporated to dryness to afford tert-butyl 3-[[tert-butoxycarbonyl-[[3-(hydroxymethyl)-5-(pyrrolidin-3-yloxymethyl)phenyl]methyl]amino]methyl]pyrrolidine-1-carboxylate as a white gum (633 mg, 85% yield) that is directly engaged in the next step without further purification.

MS m/z (+ESI): 520.3 [M+H]$^+$.

Preparation of 1-[3-[(1,1-dimethylpyrrolidin-1-ium-3-yl)oxymethyl]-5-[(E)-2-(3-pyridyl)vinyl]phenyl]-N-(pyrrolidin-3-ylmethyl)methanamine The titled compound is prepared as a colorless gum following Scheme 3 and in analogy to Examples 37, 158, 168 and 387 using tert-butyl 3-[[tert-butoxycarbonyl-[[3-(hydroxymethyl)-5-(pyrrolidin-3-yloxymethyl)phenyl]methyl]amino]methyl]pyrrolidine-1-carboxylate and 3-(bromomethyl)pyridine [69966-55-8] as starting materials.

Example 491: 5-[(E)-2-[3-[(2-oxo-3H-1,3,4-oxadiazol-5-yl)methoxy]-5-[(pyrrolidin-3-ylmethylamino)methyl]phenyl]vinyl]pyridine-3-carbonitrile Preparation of tert-butyl 3-[[tert-butoxycarbonyl-[[3-[(E)-2-(5-cyano-3-pyridyl)vinyl]-5-(2-methoxy-2-oxo-ethoxy)phenyl]methyl]amino]methyl]pyrrolidine-1-carboxylate The titled compound is prepared as a light yellow oil following Scheme 3 and in analogy to Examples 37, 130, 158, 168 and 480 using dimethyl 5-hydroxybenzene-1,3-dicarboxylate, allyl bromide, di-tert-butyl dicarbonate, tert-butyl 3-(aminomethyl)pyrrolidine-1-carboxylate, 5-(bromomethyl)pyridine-3-carbonitrile, triethyl phosphite and methyl 2-bromoacetate [96-32-2] as starting materials.

MS m/z (+ESI): 607.2 [M+H]$^+$.

Preparation of tert-butyl 3-[[tert-butoxycarbonyl-[[3-[(E)-2-(5-cyano-3-pyridyl)vinyl]-5-(2-hydrazino-2-oxo-ethoxy)phenyl]methyl]amino]methyl]pyrrolidine-1-carboxylate Hydrazine monohydrate (0.13 mL, 2.75 mmol, 5.0 eq) is added at room temperature to a stirred solution tert-butyl 3-[[tert-butoxycarbonyl-[[3-[(E)-2-(5-cyano-3-pyridyl)vinyl]-5-(2-methoxy-2-oxo-ethoxy)phenyl]methyl]amino]methyl]pyrrolidine-1-carboxylate (350 mg, 0.55 mmol, 1.0 eq) in ethanol (10 mL). After 20 hours stirring at room temperature, the reaction mixture is concentrated to give a residue that is purified by column chromatography (silica gel; dichloromethane:methanol, 20:1, v/v) to afford tert-butyl 3-[[tert-butoxycarbonyl-[[3-[(E)-2-(5-cyano-3-pyridyl)vinyl]-5-(2-hydrazino-2-oxo-ethoxy)phenyl]methyl]amino]methyl]pyrrolidine-1-carboxylate as a white solid (310 mg, 89% yield).

MS m/z (+ESI): 607.2 [M+H]$^+$.

Preparation of tert-butyl 3-[[tert-butoxycarbonyl-[[3-[(E)-2-(5-cyano-3-pyridyl)vinyl]-5-[(2-oxo-3H-1,3,4-oxadiazol-5-yl)methoxy]phenyl]methyl]amino]methyl]pyrrolidine-1-carboxylate Triethylamine (400 μL, 2.91 mmol, 6.0 eq) is added at room temperature to a stirred solution of tert-butyl 3-[[tert-butoxycarbonyl-[[3-[(E)-2-(5-cyano-3-pyridyl)vinyl]-5-(2-hydrazino-2-oxo-ethoxy)phenyl]methyl]amino]methyl]pyrrolidine-1-carboxylate (310 mg, 0.49 mmol, 1.0 eq) in tetrahydrofuran (10 mL), followed by carbonyldiimidazole (252 mg, 1.55 mmol, 3.5 eq). After 3 hours stirring at 65° C., the reaction mixture is concentrated to give a residue that is purified by column chromatography (silica gel; dichloromethane:methanol, 40:1, v/v) to afford tert-butyl 3-[[tert-butoxycarbonyl-[[3-[(E)-2-(5-cyano-3-pyridyl)vinyl]-5-[(2-oxo-3H-1,3,4-oxadiazol-5-yl)methoxy]phenyl]methyl]amino]methyl]pyrrolidine-1-carboxylate as a white solid (260 mg, 80% yield).

MS m/z (+ESI): 633.3 [M+H]$^+$.

Preparation of 5-[(E)-2-[3-[(2-oxo-3H-1,3,4-oxadiazol-5-yl)methoxy]-5-[(pyrrolidin-3-ylmethylamino)methyl]phenyl]vinyl]pyridine-3-carbonitrile The titled compound is prepared as a light yellow solid (55 mg, 32% yield) following Scheme 3 and in analogy to Example 236 using tert-butyl 3-[[tert-butoxycarbonyl-[[3-[(E)-2-(5-cyano-3-pyridyl)vinyl]-5-[(2-oxo-3H-1,3,4-oxadiazol-5-yl)methoxy]phenyl]methyl]amino]methyl]pyrrolidine-1-carboxylate (260 mg, 0.39 mmol, 1.0 eq) as starting material.

Example 494: 5-[(E)-2-(2-bromo-4-chloro-phenyl)vinyl]-3-[(pyrrolidin-3-ylmethylamino)methyl]pyridin-2-ol Preparation of tert-butyl 3-[[[5-[(E)-2-(2-bromo-4-chloro-phenyl)vinyl]-2-oxo-1-(2-trimethylsilylethoxymethyl)-3-pyridyl]methyl-tert-butoxycarbonyl-amino]methyl]pyrrolidine-1-carboxylate The titled compound is prepared as a colorless oil following Scheme 3 and in analogy to Examples 37, 119, 130, 136, 158, 168 and 489 using 2-(chloromethoxy)ethyl-trimethyl-silane, methyl 5-bromo-6-hydroxy-pyridine-3-carboxylate [381247-99-0], potassium vinyltrifluoroborate, tert-butyl 3-(aminomethyl)pyrrolidine-1-carboxylate, di-tert-butyl dicarbonate and isobutyl chloroformate as starting materials.

$^1$H-NMR (400 MHz, DMSO-d6) δ ppm: 7.88 (s, 1H), 7.78 (m, 2H), 7.52 (m, 2H), 7.17 (d, J=16.0 Hz, 1H), 6.97 (m, 1H), 5.32 (s, 2H), 4.21 (s, 2H), 3.59 (t, J=8.0 Hz, 2H), 3.00-3.30 (m, 6H), 2.41 (m, 1H), 1.87 (m, 1H), 1.56 (m, 1H), 1.35-1.45 (m, 18H), 0.88 (t, J=8.0 Hz, 2H), 0.04 (s, 9H).

MS m/z (+ESI): 752.2, 754.1 [M+H]$^+$.

Preparation of tert-butyl 3-[[[5-[(E)-2-(2-bromo-4-chloro-phenyl)vinyl]-2-hydroxy-3-pyridyl]methyl-tert-butoxycarbonyl-amino]methyl]pyrrolidine-1-carboxylate A solution of tert-butyl 3-[[[5-[(E)-2-(2-bromo-4-chloro-phenyl)vinyl]-2-oxo-1-(2-trimethylsilylethoxymethyl)-3-pyridyl]methyl-tert-butoxycarbonyl-amino]methyl]pyrrolidine-1-carboxylate (2.40 g, 3.18 mmol, 1.0 eq) in a 1 M solution of tetrabutylammonium fluoride in tetrahydrofuran (20 mL, 20.0 mmol, 6.2 eq) is stirred at 60° C. for 4 hours. Solvent is removed and the residue is extracted with ethyl acetate (3×30 mL) and water (30 mL). The combined organic layers are washed with brine (30 mL), dried over sodium sulfate, filtered and concentrated to afford tert-butyl 3-[[[5-[(E)-2-(2-bromo-4-chloro-phenyl)vinyl]-2-hydroxy-3-pyridyl]methyl-tert-butoxycarbonyl-amino]methyl]pyrrolidine-1-carboxylate as a white solid (1.30 g, 65% yield).

$^1$H-NMR (400 MHz, DMSO-d6) δ ppm: 11.91 (s, 1H), 7.77 (s, 1H), 7.76 (d, J=7.6 Hz, 1H), 7.50 (m, 3H), 7.17 (d, J=16.0 Hz, 1H), 6.92 (m, 1H), 4.18 (s, 2H), 3.00-3.30 (m, 6H), 2.41 (m, 1H), 1.87 (m, 1H), 1.58 (m, 1H), 1.35-1.45 (m, 18H).

MS m/z (+ESI): 622.1 [M+H]$^+$.

Preparation of 5-[(E)-2-(2-bromo-4-chloro-phenyl)vinyl]-3-[(pyrrolidin-3-ylmethylamino)methyl]pyridin-2-ol The titled compound is prepared as a light yellow solid (65 mg, 43% yield) following Scheme 3 and in analogy to Example 158 using tert-butyl 3-[[[5-[(E)-2-(2-bromo-4-chloro-phenyl)vinyl]-2-hydroxy-3-pyridyl]methyl-tert-butoxycarbonyl-amino]methyl]pyrrolidine-1-carboxylate (200 mg, 0.32 mmol, 1.0 eq) as starting material.

Example 502: 1-[3-isobutoxy-5-[(E)-2-(3-pyridyl)vinyl]phenyl]-2-(pyrrolidin-3-ylmethylamino)ethanone

Preparation of 3-(hydroxymethyl)-5-isobutoxy-benzoic Acid

The titled compound is prepared as a light yellow oil following Scheme 3 and in analogy to Examples 37, 158, 183 and 263 using dimethyl 5-hydroxybenzene-1,3-dicarboxylate, 1-bromo-2-methyl-propane and tert-butyl-chloro-dimethyl-silane as starting materials.

MS m/z (+ESI): 225.3 [M+H]$^+$.

Preparation of 3-(hydroxymethyl)-5-isobutoxy-N-methoxy-N-methyl-benzamide

O-(7-azabenzotriazol-1-yl)-N,N,N',N'-tetramethyluronium hexafluorophosphate (6.36 g, 16.72 mmol, 1.5 eq) is added at room temperature to a stirred solution of 3-(hydroxymethyl)-5-isobutoxy-benzoic acid (2.50 g, 11.15 mmol, 1.0 eq), N,N-diisopropylethylamine (5.53 mL, 33.45 mmol, 3.0 eq) and N-methoxymethanamine hydrochloride (1.63 g, 16.72 mmol, 1.5 eq) [6638-79-5] in N,N-dimethylformamide (50 mL). After 16 hours stirring at room temperature, solvent is evaporated and the residue is extracted with ethyl acetate (3×50 mL) and water (50 mL). The combined organic layers are washed with brine, dried over sodium sulfate, filtered and concentrated to give a residue that is purified by column chromatography (silica gel; petroleum ether:ethyl acetate, 10:1, v/v) to afford 3-(hydroxymethyl)-5-isobutoxy-N-methoxy-N-methyl-benzamide as a yellow oil (3.0 g, 95% yield).

$^1$H-NMR (400 MHz, DMSO-d6) δ ppm: 7.06 (s, 1H), 6.99 (s, 1H), 6.93 (s, 1H), 5.26 (t, J=5.6 Hz, 1H), 4.49 (d, J=6.0 Hz, 2H), 3.75 (d, J=6.4 Hz, 2H), 3.55 (s, 3H), 3.22 (s, 3H), 2.00 (m, 1H), 0.97 (d, J=6.4 Hz, 6H).

Preparation of 1-[3-(hydroxymethyl)-5-isobutoxy-phenyl]ethanone

Methylmagnesium bromide (1M solution in tetrahydrofuran, 30.9 mL, 30.9 mmol, 3.0 eq) [75-16-1] is added at 0° C. to a stirred solution of 3-(hydroxymethyl)-5-isobutoxy-N-methoxy-N-methyl-benzamide (2.90 g, 10.30 mmol, 1.0 eq) in tetrahydrofuran (100 mL). After 1 hour stirring at room temperature, a saturated ammonium chloride aqueous solution (50 mL) is added to quench the reaction. Tetrahydrofuran is evaporated and the resulting mixture is extracted with ethyl acetate (3×50 mL) and water (50 mL). The combined organic layers are washed with brine, dried over sodium sulfate, filtered and concentrated to afford 1-[3-(hydroxymethyl)-5-isobutoxy-phenyl]ethanone as a light yellow oil (1.60 g, 70% yield) that is directly engaged in the next step without further purification.

$^1$H-NMR (400 MHz, DMSO-d6) δ ppm: 7.50 (s, 1H), 7.30 (s, 1H), 7.16 (s, 1H), 5.32 (t, J=5.6 Hz, 1H), 4.53 (d, J=6.0 Hz, 2H), 3.80 (d, J=6.4 Hz, 2H), 2.57 (s, 3H), 2.04 (m, 1H), 1.00 (d, J=6.4 Hz, 6H).

Preparation of (3-acetyl-5-isobutoxy-phenyl)methyl acetate

Triethylamine (750 μL, 5.40 mmol, 1.5 eq) is added at room temperature to a stirred solution of 1-[3-(hydroxymethyl)-5-isobutoxy-phenyl]ethanone (800 mg, 3.60 mmol, 1.0 eq) in dichloromethane (30 mL), followed by acetic anhydride (510 μL, 5.40 mmol, 1.5 eq). After 16 hours stirring at room temperature, solvent is evaporated and the residue is purified by column chromatography (silica gel; petroleum ether:ethyl acetate, 4:1, v/v) to afford (3-acetyl-5-isobutoxy-phenyl)methyl acetate as a yellow oil (900 mg, 92% yield).

$^1$H-NMR (400 MHz, DMSO-d6) δ ppm: 7.52 (s, 1H), 7.39 (s, 1H), 7.20 (s, 1H), 5.09 (s, 2H), 3.81 (d, J=6.4 Hz, 2H), 2.57 (s, 3H), 2.21 (s, 3H), 2.08 (m, 1H), 0.99 (d, J=6.8 Hz, 6H).

Preparation of 1-[3-isobutoxy-5-[(E)-2-(3-pyridyl)vinyl]phenyl]-2-(pyrrolidin-3-ylmethylamino)ethanone The titled compound is prepared as a white solid following Scheme 3 and in analogy to Examples 37, 130, 135, 158, 168 and 490 using (3-acetyl-5-isobutoxy-phenyl)methyl acetate, tert-butyl 3-(aminomethyl)pyrrolidine-1-carboxylate, di-tert-butyl dicarbonate and 3-(bromomethyl)pyridine as starting materials.

Example 506: N-[2-[bis(azetidin-3-ylmethyl)amino]ethyl]-3-[2-(4-pyridyl)ethoxy]-5-(3-pyridylmethoxy)benzamide

Preparation of methyl 3-hydroxy-5-(3-pyridylmethoxy)benzoate

The titled compound is prepared as an off-white solid (400 mg, 26% yield) following Scheme 1 and in analogy to Example 37 using methyl 3,5-dihydroxybenzoate (1 g, 5.95 mmol, 1.0 eq) [2150-44-9] and 3-(chloromethyl)pyridine hydrochloride (980 mg, 5.95 mmol, 1.0 eq) [6959-48-4] as starting materials.

$^1$H-NMR (400 MHz, CDCl$_3$) δ ppm: 8.77 (s, 1H), 8.62 (m, 1H), 7.81 (d, J=7.6 Hz, 1H), 7.39 (dd, J=4.8 Hz, 7.6 Hz, 1H), 7.24 (s, 1H), 7.22 (s, 1H), 6.73 (s, 1H), 5.14 (s, 2H), 3.93 (s, 3H).

Preparation of methyl 3-[2-(4-pyridyl)ethoxy]-5-(3-pyridylmethoxy)benzoate 4-(2-Hydroxyethyl)pyridine (530 mg, 4.20 mmol, 1.2 eq) [5344-27-4] is added at room temperature to a stirred solution of methyl 3-hydroxy-5-(3-pyridylmethoxy)benzoate (910 mg, 3.50 mmol, 1.0 eq) in tetrahydrofuran (30 mL), followed by triphenylphosphine (1.86 g, 7.00 mmol, 2.0 eq). Then a solution of diisopropyl azodicarboxylate (1.49 g, 7.00 mmol, 2.0 eq) in tetrahydrofuran (5 mL) is added dropwise at room temperature and the resulting mixture is stirred at 80° C. for 16 hours. Solvent is evaporated and the residue is extracted with ethyl acetate (3×40 mL) and water (40 mL). The combined organic layers are washed with brine, dried over sodium sulfate, filtered and concentrated to give a residue that is purified by column chromatography (silica gel; petroleum ether:ethyl acetate, 1:2, v/v) to afford methyl 3-[2-(4-pyridyl)ethoxy]-5-(3-pyridylmethoxy)benzoate as a light yellow gum (290 mg, 22% yield).

$^1$H-NMR (400 MHz, CDCl$_3$) δ ppm: 8.70 (s, 1H), 8.61 (d, J=4.8 Hz, 1H), 8.55 (d, J=5.6 Hz, 2H), 7.79 (d, J=7.6 Hz, 1H), 7.35 (dd, J=4.8 Hz, 7.6 Hz, 1H), 7.29 (s, 1H), 7.24 (d, J=5.6 Hz, 2H), 7.22 (s, 1H), 6.71 (s, 1H), 5.10 (s, 2H), 4.25 (t, J=6.4 Hz, 2H), 3.92 (s, 3H), 3.11 (t, J=6.4 Hz, 2H).

MS m/z (+ESI): 365.1 [M+H]$^+$.

Preparation of N-[2-[bis(azetidin-3-ylmethyl)amino] ethyl]-3-[2-(4-pyridyl)ethoxy]-5-(3-pyridylmethoxy) benzamide The titled compound is prepared as a colorless solid following Scheme 1 and in analogy to Examples 37, 119, 263 and 490 using methyl 3-[2-(4-pyridyl)ethoxy]-5-(3-pyridylmethoxy)benzoate, tert-butyl 3-formylazetidine-1-carboxylate [177947-96-5], tert-butyl 3-(aminomethyl)azetidine-1-carboxylate [325775-44-8] and benzyl N-(2-oxoethyl)carbamate [67561-03-9] as starting materials.

Example 507: N-[[3-[2-[bis(azetidin-3-ylmethyl) amino]ethylcarbamoyl]-5-[2-(4-pyridyl)ethoxyl] phenyl]methyl]pyridine-3-carboxamide Preparation of methyl 3-[tert-butyl(dimethyl)silyl] oxy-5-carbamoyl-benzoate The titled compound is prepared as a white solid (3.42 g, 21% yield) following Scheme 6 and in analogy to Examples 183 and 477 using dimethyl 5-hydroxybenzene-1,3-dicarboxylate and tert-butyl-chloro-dimethyl-silane as starting materials.

$^1$H-NMR (400 MHz, DMSO-d6) δ ppm: 8.17 (br, 1H), 8.08 (s, 1H), 7.58 (s, 1H), 7.50 (br, 1H), 7.46 (s, 1H), 3.85 (s, 3H), 0.95 (s, 9H), 0.20 (s, 6H).

MS m/z (+ESI): 310.1 [M+H]$^+$.

Preparation of methyl 3-(aminomethyl)-5-[tert-butyl (dimethyl)silyl]oxy-benzoate A 1.0 M borane tetrahydrofuran complex solution (21.2 mL, 21.2 mmol, 4.0 eq) [14044-65-6] is added at 0° C. to a stirred solution of methyl 3-[tert-butyl(dimethyl)silyl]oxy-5-carbamoyl-benzoate (1.66 g, 5.30 mmol, 1.0 eq) in tetrahydrofuran (40 mL). After 16 hours stirring at 15° C., methanol (5 mL) is cautiously added to the reaction mixture that is then evaporated. The crude is purified by column chromatography (silica gel; dichloromethane:methanol, 40:1 to 20:1, v/v) to afford methyl 3-(aminomethyl)-5-[tert-butyl(dimethyl)silyl]oxy-benzoate as a light yellow gum (210 mg, 13% yield).

$^1$H-NMR (400 MHz, DMSO-d6) δ ppm: 7.52 (s, 1H), 7.21 (s, 1H), 7.13 (s, 1H), 3.83 (s, 3H), 3.76 (s, 2H), 0.95 (s, 9H), 0.20 (s, 6H).

MS m/z (+ESI): 296.2 [M+H]$^+$.

Preparation of N-[[3-[2-[bis(azetidin-3-ylmethyl) amino]ethylcarbamoyl]-5-[2-(4-pyridyl) ethoxy] phenyl]methyl]pyridine-3-carboxamide The titled compound is prepared as a colorless solid following Scheme 6 and in analogy to Examples 37, 119, 183, 263, 490 and 506 using methyl 3-(aminomethyl)-5-[tert-butyl(dimethyl)silyl]oxy-benzoate, 4-(2-hydroxyethyl) pyridine, tert-butyl 3-formylazetidine-1-carboxylate, tert-butyl 3-(aminomethyl)azetidine-1-carboxylate and benzyl N-(2-oxoethyl)carbamate as starting materials.

Example 511: N-[[3-[(azetidin-3-ylmethylamino) methyl]-5-[2-(1H-imidazol-4-yl)ethoxy]phenyl] methyl]pyridine-3-carboxamide Preparation of methyl 3-[tert-butyl(dimethyl)silyl] oxy-5-(hydroxymethyl)benzoate The titled compound is prepared as a colorless oil following Scheme 6 and in analogy to Examples 130 and 183 using dimethyl 5-hydroxybenzene-1,3-dicarboxylate and tert-butyl-chloro-dimethyl-silane as starting materials.

$^1$H-NMR (400 MHz, CDCl$_3$) δ ppm: 7.58 (s, 1H), 7.36 (s, 1H), 7.03 (s, 1H), 4.63 (s, 2H), 3.86 (s, 3H), 0.96 (s, 9H), 0.18 (s, 6H).

Preparation of methyl 3-[tert-butyl(dimethyl)silyl] oxy-5-(tetrahydropyran-2-yloxymethyl)benzoate p-Toluenesulfonic acid (11 mg, 0.06 mmol, 0.01 eq) [104-15-4] is added at 0° C. to a stirred solution of methyl 3-[tert-butyl(dimethyl)silyl]oxy-5-(hydroxymethyl)benzoate (2.0 g, 6.48 mmol, 1.0 eq) and 3,4-dihydro-2H-pyran (1.52 mL, 16.2 mmol, 2.5 eq) [110-87-2] in dichloromethane (20 mL). After 2 hours stirring at 15° C., solvent is evaporated and the residue is purified by column chromatography (silica gel; petroleum ether:ethyl acetate, 12:1, v/v) to afford methyl 3-[tert-butyl(dimethyl)silyl]oxy-5-(tetrahydropyran-2-yloxymethyl)benzoate as a colorless oil (2.43 g, 89% yield).

$^1$H-NMR (400 MHz, CDCl$_3$) δ ppm: 7.64 (s, 1H), 7.41 (s, 1H), 7.07 (s, 1H), 4.78 (d, J=12.4 Hz, 1H), 4.71 (t, J=3.6 Hz, 1H), 4.52 (d, J=12.4 Hz, 1H), 3.85-3.95 (m, 4H), 3.50-3.60 (m, 1H), 1.50-1.93 (m, H-6), 1.00 (s, 9H), 0.22 (s, 6H).

Preparation of N-[[3-(tetrahydropyran-2-yloxymethyl)-5-[2-(1-tritylimidazol-4-yl)ethoxy]phenyl] methyl]pyridine-3-carboxamide The titled compound is prepared as a white solid following Scheme 6 and in analogy to Examples 37, 119, 158, 183 and 354 using methyl 3-[tert-butyl(dimethyl)silyl]oxy-5-

(tetrahydropyran-2-yloxymethyl)benzoate, 2-(1H-imidazol-4-yl)ethanol [872-82-2], trityl chloride [76-83-5], 4-toluenesulfonyl chloride, phthalimide and nicotinic acid as starting materials.

$^1$H-NMR (400 MHz, CDCl$_3$) δ ppm: 9.21 (t, J=6.0 Hz, 1H), 9.04 (d, J=1.6 Hz, 1H), 8.71 (dd, J=1.6 Hz, 4.8 Hz, 1H), 8.21 (m, 1H), 7.51 (m, 1H), 7.33-7.49 (m, 11H), 7.04-7.12 (m, 6H), 6.87 (s, 1H), 6.77 (s, 1H), 6.72 (s, 1H), 4.58-4.65 (m, 2H), 4.46 (d, J=6.0 Hz, 2H), 4.38 (d, J=12.4 Hz, 1H), 4.15 (t, J=6.8 Hz, 2H), 3.70-3.80 (m, 1H), 3.40-3.47 (m, 1H), 2.89 (t, J=6.8 Hz, 2H), 1.55-1.74 (m, 2H), 1.36-1.54 (m, 4H).

MS m/z (+ESI): 679.3 [M+H]$^+$.

Preparation of N-[[3-(hydroxymethyl)methyl]-5-[2-(1-tritylimidazol-4-yl)ethoxy]phenyl]methyl]pyridine-3-carboxamide p-Toluenesulfonic acid (27 mg, 0.16 mmol, 0.6 eq) is added at room temperature to a stirred solution of N-[[3-(tetrahydropyran-2-yloxymethyl)-5-[2-(1-tritylimidazol-4-yl)ethoxy]phenyl]methyl]pyridine-3-carboxamide (200 mg, 0.26 mmol, 1.0 eq) in methanol (10 mL). After 5 hours stirring at 40° C., the pH is adjusted to 7 by the addition of a saturated sodium hydrogen carbonate aqueous solution. Solvent is evaporated and the residue is extracted with dichloromethane (3×10 mL) and water (10 mL). The combined organic layers are washed with brine (10 mL), dried over sodium sulfate, filtered and concentrated to afford N-[[3-(hydroxymethyl)methyl]-5-[2-(1-tritylimidazol-4-yl)ethoxy]phenyl]methyl]pyridine-3-carboxamide as a white solid (110 mg, 59% yield) that is directly engaged in the next step without further purification.

MS m/z (+ESI): 595.3 [M+H]$^+$.

Preparation of N-[[3-[(azetidin-3-ylmethylamino)methyl]-5-[2-(1H-imidazol-4-yl)ethoxy]phenyl]methyl]pyridine-3-carboxamide The titled compound is prepared as a light grey gum following Scheme 6 and in analogy to Examples 136, 158 and 263 using N-[[3-(hydroxymethyl)methyl]-5-[2-(1-tritylimidazol-4-yl)ethoxy]phenyl]methyl]pyridine-3-carboxamide and tert-butyl 3-(aminomethyl)azetidine-1-carboxylate as starting materials.

Biological Examples

Efflux Inhibition Assay

In vitro efflux-pump inhibition was measured with *P. aeruginosa* based on Alamar Blue accumulation following a published procedure (F. Vidal-Aroca et al. 2009. J. Microbiol. Methods 79: 232-237). *P. aeruginosa* PAO1 was grown on Müller-Hinton agar plates. Bacteria were resuspended in Dulbecco's phosphate buffered saline to OD625=1. Assays were performed in 96-well microtiter plates. Each well contained 100 μL assay mixture with 84 μL bacteria suspension, 5 μl succinic acid 40 mM, 10 μL Alamar Blue (Biosource DAL1100) and 1 μL test compound in DMSO. Fluorescence was measured every 5 minutes for 1 h with a Spectramax microtiter plate reader (ex at 530 nm, em at 590 nm).

Inhibition of efflux pumps caused increased accumulation of Alamar Blue compared to controls without inhibitor (i.e. uninhibited control). Results were expressed as relative fluorescence intensity (% of uninhibited control). Efflux inhibition caused increased relative fluorescence.

Antibacterial activity in combination with minocycline or with linezolid

Inhibition of growth was measured with *E. coli* ATCC25922 and *P. aeruginosa* PAO1 in a 96-well plate format. Cation-adjusted Müller-Hinton broth (caMHB) was inoculated with an overnight culture and incubated at 37° C. on a shaker until OD625 reached 0.6 to 0.7. Density was adjusted to OD600=0.5 by addition of caMHB. 35 μL of the suspension were diluted to 35 mL with caMHB and supplemented with minocycline at the subinhibitory doses of 0.25 μg/mL for *E. coli* and 8 μg/mL for *P. aeruginosa* or with linezolid at the subinhibitory dose of 128 μg/mL for *E. coli* and *P. aeruginosa*. Each well contained 1 μL of test compound in 100 μL caMHB with minocycline or with linezolid.

Plates were incubated at 37° C. on a plate shaker. OD625 was measured at 1 h, 6 h, and at 23 h.

The difference between OD at 23 h and at 1 h was taken as measure for cell density and compared to controls without inhibitor (i.e. uninhibited control). Results were expressed as residual growth (% of uninhibited control). Enhancement of minocycline or linezolid activity caused reduced residual growth.

The following compounds provide at least 115% inhibition in the efflux inhibition assay when the compound of formula I is present at 50 μM or less
1-525

The following compounds reduce growth of *E. coli* ATCC25922 to no more than 50% growth of the uninhibited control in the antibacterial activity assay with minocycline when the compound is present at 50 μM:

1, 3, 4, 5, 6, 7, 8, 9, 13, 18, 21, 22, 23, 25, 26, 27, 28, 29, 30, 31, 32, 33, 34, 35, 36, 37, 38, 39, 40, 41, 42, 43, 44, 45, 46, 47, 49, 50, 51, 52, 53, 54, 55, 56, 57, 58, 59, 60, 61, 62, 63, 64, 65, 66, 67, 68, 69, 70, 71, 72, 73, 74, 75, 80, 81, 82, 84, 85, 87, 88, 89, 90, 91, 92, 94, 95, 96, 97, 98, 99, 100, 103, 104, 105, 106, 108, 109, 111, 112, 113, 114, 115, 116, 117, 118, 119, 120, 121, 122, 123, 124, 125, 126, 127, 128, 129, 130, 131, 132, 133, 134, 136, 137, 138, 142, 146, 147, 148, 149, 150, 157, 158, 159, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 233, 234, 235, 236, 237, 238, 239, 240, 241, 242, 243, 245, 246, 247, 248, 249, 250, 251, 252, 253, 254, 255, 256, 257, 258, 259, 260, 261, 262, 264, 265, 266, 267, 268, 269, 270, 271, 272, 273, 274, 275, 276, 277, 278, 280, 281, 282, 283, 284, 285, 286, 288, 289, 290, 291, 292, 294, 295, 296, 297, 298, 299, 300, 301, 302, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 359, 360, 361, 362, 363, 364, 365, 366, 367, 369, 370, 371, 373, 374, 375, 376, 377, 378, 380, 381, 382, 383, 384, 386, 387, 388, 389, 390, 391, 392, 393, 394, 395, 396, 397, 398, 399, 400, 401, 402, 404, 405, 406, 407, 408, 409, 410, 411, 412, 413, 414, 416, 417, 418, 419, 421, 422, 423, 424, 426, 429, 430, 431, 432, 433, 434, 435, 436, 438, 439, 443, 444, 445, 446, 447, 448, 450, 451, 452, 453, 454, 455, 456, 457, 459, 460, 463, 464, 465, 471, 475, 485, 486, 489, 494, 499, 509, 512, 513, 514, 515, 516, 517, 518, 519, 522, 523, 524, 525.

The following compounds reduce growth of *P. aeruginosa* PAO1 to no more than 50% growth of the uninhibited control in the antibacterial activity assay with minocycline when the compound is present at 50 µM:
1, 13, 18, 21, 22, 25, 26, 27, 28, 29, 30, 31, 32, 33, 34, 35, 36, 37, 38, 40, 41, 42, 43, 44, 45, 46, 47, 48, 49, 50, 51, 52, 53, 55, 56, 57, 58, 61, 62, 63, 64, 66, 68, 70, 73, 74, 75, 81, 82, 85, 87, 89, 93, 94, 96, 98, 100, 101, 102, 103, 104, 105, 106, 107, 108, 109, 111, 112, 113, 114, 115, 116, 117, 119, 120, 121, 122, 123, 124, 125, 126, 127, 128, 129, 130, 131, 133, 134, 136, 142, 147, 149, 150, 157, 158, 159, 163, 164, 165, 166, 167, 168, 169, 170, 171, 172, 173, 175, 177, 178, 179, 180, 181, 182, 183, 184, 185, 186, 187, 188, 189, 190, 191, 192, 193, 194, 196, 197, 198, 199, 200, 201, 202, 203, 204, 205, 206, 207, 208, 209, 210, 211, 212, 213, 214, 215, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 271, 272, 273, 274, 275, 276, 277, 280, 281, 282, 285, 288, 290, 292, 294, 295, 296, 297, 299, 300, 305, 308, 309, 310, 311, 313, 314, 316, 317, 318, 319, 320, 321, 322, 323, 327, 328, 330, 331, 332, 340, 341, 342, 343, 344, 345, 346, 347, 348, 349, 350, 353, 354, 356, 357, 360, 361, 366, 367, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 416, 419, 420, 421, 422, 423, 424, 425, 426, 429, 430, 431, 432, 433, 434, 435, 436, 437, 438, 439, 440, 443, 444, 445, 446, 447, 448, 450, 451, 452, 453, 454, 455, 456, 458, 460, 461, 462, 463, 464, 465, 466, 467, 468, 469, 471, 474, 475, 477, 480, 487, 489, 494, 496, 499, 500, 502, 503, 505, 506, 507, 509, 510, 512, 513, 514, 515, 516, 517, 518, 519, 523, 524, 525.

The following compounds reduce growth of *E. coli* ATCC25922 to no more than 10% growth of the uninhibited control in the antibacterial activity assay with minocycline when the compound is present at 50 µM:
1, 3, 4, 6, 7, 9, 18, 21, 25, 27, 28, 29, 30, 31, 32, 33, 34, 35, 36, 37, 38, 39, 40, 41, 42, 43, 44, 45, 46, 47, 49, 51, 52, 53, 54, 55, 56, 57, 58, 59, 60, 61, 62, 63, 64, 65, 66, 67, 68, 70, 71, 72, 73, 74, 75, 80, 81, 82, 84, 85, 88, 90, 91, 92, 94, 95, 96, 97, 98, 99, 100, 103, 104, 105, 106, 108, 109, 111, 112, 113, 114, 115, 116, 117, 118, 119, 120, 121, 122, 123, 124, 125, 126, 127, 128, 129, 130, 131, 132, 133, 134, 136, 142, 146, 147, 148, 149, 150, 157, 158, 159, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 233, 234, 235, 236, 237, 238, 239, 240, 241, 242, 243, 245, 246, 247, 248, 249, 250, 251, 252, 253, 254, 255, 256, 257, 258, 259, 260, 261, 262, 264, 265, 266, 267, 268, 269, 270, 271, 272, 273, 274, 275, 276, 277, 280, 281, 282, 283, 284, 285, 286, 289, 290, 291, 292, 294, 295, 296, 297, 298, 299, 300, 301, 302, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 347, 348, 349, 350, 351, 352, 353, 354, 355, 356, 357, 359, 360, 361, 362, 363, 364, 365, 366, 367, 369, 370, 371, 373, 374, 375, 376, 377, 378, 380, 381, 382, 383, 384, 386, 387, 388, 389, 390, 392, 394, 395, 396, 397, 398, 399, 400, 401, 402, 404, 405, 406, 407, 408, 411, 412, 413, 416, 419, 421, 422, 424, 426, 429, 430, 431, 432, 433, 434, 435, 436, 439, 443, 444, 445, 446, 447, 448, 450, 451, 452, 453, 454, 455, 456, 457, 459, 460, 463, 464, 465, 471, 486, 489, 494, 509, 512, 513, 514, 515, 516, 517, 518, 519, 522, 523, 524, 525.

The following compounds reduce growth of *P. aeruginosa* PAO1 to no more than 10% growth of the uninhibited control in the antibacterial activity assay with minocycline when the compound is present at 50 µM:
13, 18, 21, 22, 25, 27, 29, 30, 31, 32, 33, 34, 35, 36, 37, 38, 40, 41, 42, 43, 44, 45, 46, 47, 48, 49, 51, 52, 53, 55, 56, 58, 61, 62, 63, 64, 66, 68, 70, 73, 75, 81, 85, 94, 96, 98, 100, 101, 103, 104, 105, 106, 107, 108, 109, 111, 112, 113, 114, 115, 116, 117, 119, 120, 121, 122, 123, 125, 126, 127, 128, 129, 130, 133, 134, 136, 142, 147, 149, 150, 157, 158, 159, 163, 164, 165, 166, 167, 168, 169, 171, 172, 175, 178, 179, 180, 181, 182, 183, 184, 185, 186, 187, 188, 189, 190, 191, 193, 194, 196, 197, 198, 199, 200, 201, 202, 203, 204, 205, 207, 209, 210, 211, 212, 213, 214, 215, 217, 218, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 271, 272, 273, 274, 275, 280, 281, 282, 290, 292, 294, 295, 296, 297, 299, 300, 305, 308, 309, 310, 311, 313, 317, 318, 321, 322, 327, 328, 330, 340, 341, 342, 343, 344, 345, 346, 347, 348, 350, 354, 356, 357, 360, 361, 367, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 416, 419, 421, 422, 423, 426, 429, 430, 431, 432, 433, 434, 435, 436, 438, 439, 443, 444, 446, 447, 448, 450, 451, 452, 453, 454, 455, 456, 460, 461, 462, 463, 464, 465, 466, 468, 469, 471, 487, 489, 494, 499, 500, 503, 505, 506, 509, 512, 513, 514, 515, 516, 517, 518, 519, 523, 524, 525.

The following compounds reduce growth of *E. coli* ATCC25922 to no more than 10% growth of the uninhibited control in the antibacterial activity assay with minocycline when the compound is present at 25 µM:
18, 25, 27, 28, 29, 30, 31, 32, 33, 34, 35, 36, 37, 38, 39, 40, 41, 42, 43, 44, 45, 46, 47, 49, 51, 52, 53, 55, 56, 57, 58, 59, 60, 61, 62, 63, 64, 65, 66, 67, 68, 70, 71, 72, 73, 74, 75, 80, 81, 82, 84, 85, 88, 90, 94, 95, 96, 97, 9899, 100, 103, 104, 105, 106, 108, 109, 111, 112, 113, 114, 116, 117, 119, 120, 121, 122, 123, 124, 125, 126, 127, 128, 129, 130, 131, 132, 133, 134, 136, 142, 147, 148, 149, 150, 157, 158, 159, 163, 164, 165, 166, 167, 168, 169, 170, 171, 172, 173, 174, 175, 176, 177, 178, 180, 181, 182, 183, 184, 185, 186, 187, 188, 189, 190, 191, 192, 193, 194, 196, 197, 198, 199, 200, 201, 202, 203, 205, 207, 209, 210, 211, 212, 213, 214, 215, 216, 217, 218, 219, 221, 222, 223, 224, 225, 226, 227, 228, 229, 230, 231, 233, 234, 235, 236, 237, 238, 239, 240, 241, 242, 243, 246, 247, 248, 249, 250, 251, 252, 253, 254, 255, 256, 257, 258, 259, 260, 261, 262, 264, 265, 266, 267, 268, 269, 271, 272, 273, 274, 275, 276, 277, 280, 281, 282, 283, 284, 285, 289, 290, 291, 292, 294, 295, 296, 297, 299, 300, 301, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 344, 345, 346, 347, 348, 353, 354, 355, 356, 357, 359, 360, 361, 362, 364, 366, 367, 369, 370, 371, 373, 375, 376, 377, 380, 381, 382, 387, 388, 389, 390, 392, 394, 395, 396, 397, 398, 399, 401, 402, 404, 405, 406, 407, 408, 412, 413, 416, 419, 421, 422, 426, 429, 430, 431, 432, 433, 443, 444, 445, 446, 447, 448, 450, 451, 452, 453, 454, 455, 456, 457, 459, 460, 463, 464, 465, 471, 494, 509, 512, 513, 514, 515, 517, 518, 519, 523, 524, 525.

The following compounds reduce growth of *P. aeruginosa* PAO1 to no more than 10% growth of the uninhibited control in the antibacterial activity assay with minocycline when the compound is present at 25 µM:
18, 25, 27, 28, 29, 30, 33, 34, 36, 37, 38, 40, 41, 42, 43, 44, 45, 47, 48, 49, 51, 52, 55, 56, 58, 61, 62, 64, 73, 96, 98, 100, 103, 104, 106, 107, 108, 109, 111, 112, 113, 114, 116, 117, 119, 120, 121, 122, 125, 126, 128, 129, 130, 133, 134, 142, 147, 157, 158, 159, 164, 165, 167, 168, 169, 171, 175, 178, 179, 180, 181, 182, 183, 184, 185, 186, 187, 188, 189, 190, 191, 193, 194, 196, 197, 198, 199, 200, 201, 202, 203, 204, 207, 209, 210, 211, 212, 213, 214, 215, 217, 218, 224, 225, 226, 227, 228, 229, 230, 231, 233, 234, 236, 237, 238, 239, 240, 241, 242, 243, 246, 251, 252, 253, 254, 255, 256, 257, 258, 259, 260, 261, 262, 263, 264, 265, 268, 271, 272, 273, 274, 275, 280, 281, 282, 290, 294, 295, 296, 297, 309, 310, 311, 321, 341, 342, 344, 345, 346, 347, 354, 360, 361, 371, 373, 374, 375, 376, 377, 378, 379, 380, 381, 382, 383, 384, 386, 387, 388, 389, 390, 391, 393, 395, 396, 397, 398, 399, 400, 401, 402, 403, 404, 405, 406, 407, 408, 412, 413, 416, 419, 421, 422, 426, 429, 430, 431, 432, 433, 435, 443, 444, 447, 448, 450, 451, 452, 453, 455, 460, 462, 463, 464, 465, 466, 471, 489, 494, 505, 509, 512, 513, 514, 515, 517, 518, 519, 525.

The following compounds reduce growth of E. coli ATCC25922 to no more than 50% growth of the uninhibited control in the antibacterial activity assay with linezolid when the compound is present at 50 µM:
1, 2, 3, 4, 5, 6, 7, 8, 9, 10, 11, 12, 13, 15, 16, 17, 18, 19, 20, 21, 22, 23, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 84, 85, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 136, 137, 138, 141, 142, 143, 144, 146, 147, 148, 149, 150, 151, 152, 153, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 336, 337, 338, 339, 340, 341, 342, 343, 344, 345, 346, 347, 348, 349, 350, 351, 352, 353, 354, 355, 356, 357, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 416, 417, 418, 419, 420, 421, 422, 423, 424, 425, 426, 427, 428, 429, 430, 431, 432, 433, 434, 435, 436, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 479, 480, 481, 482, 483, 484, 485, 486, 487, 488, 489, 491, 492, 493, 494, 495, 496, 497, 499, 500, 502, 503, 504, 505, 506, 507, 509, 510, 512, 513, 514, 515, 516, 517, 518, 519, 522, 523, 524, 525.

The following compounds reduce growth of P. aeruginosa PAO1 to no more than 50% growth of the uninhibited control in the antibacterial activity assay with linezolid when the compound is present at 50 µM:
13, 29, 32, 36, 37, 38, 51, 58, 61, 63, 73, 100, 104, 106, 108, 109, 111, 112, 113, 114, 116, 117, 119, 120, 121, 122, 123, 125, 126, 129, 130, 133, 134, 142, 147, 149, 150, 157, 159, 164, 165, 166, 167, 168, 169, 171, 175, 178, 179, 180, 181, 182, 183, 184, 185, 186, 187, 188, 189, 190, 191, 192, 193, 194, 196, 197, 198, 199, 200, 201, 202, 203, 204, 209, 210, 211, 212, 213, 214, 217, 218, 224, 228, 229, 231, 234, 243, 246, 251, 252, 253, 254, 255, 256, 257, 258, 259, 260, 261, 262, 264, 265, 268, 271, 272, 273, 274, 275, 280, 281, 282, 290, 292, 295, 296, 297, 299, 305, 308, 309, 310, 311, 312, 313, 314, 317, 319, 320, 321, 322, 323, 327, 328, 330, 331, 332, 337, 341, 344, 345, 346, 347, 354, 359, 360, 361, 371, 381, 382, 387, 388, 389, 390, 395, 396, 397, 398, 401, 402, 404, 406, 407, 408, 413, 416, 419, 421, 422, 426, 429, 430, 431, 432, 433, 443, 444, 447, 448, 450, 451, 452, 453, 454, 455, 456, 464, 467, 471, 494, 509, 512, 513, 514, 515, 517, 518, 519, 525.

The following compounds reduce growth of E. coli ATCC25922 to no more than 10% growth of the uninhibited control in the antibacterial activity assay with linezolid when the compound is present at 50 µM:
2, 3, 4, 5, 6, 7, 8, 9, 10, 11, 12, 13, 15, 16, 17, 18, 19, 20, 21, 22, 23, 25, 26, 27, 28, 29, 30, 31, 32, 33, 34, 35, 36, 37, 38, 39, 40, 41, 42, 43, 44, 45, 46, 47, 49, 50, 51, 52, 53, 54, 55, 56, 57, 58, 59, 60, 61, 62, 63, 64, 65, 66, 67, 68, 69, 70, 71, 72, 73, 74, 75, 77, 79, 80, 81, 82, 84, 85, 87, 88, 89, 90, 91, 92, 93, 94, 95, 96, 97, 98, 99, 10, 101, 102, 103, 104, 105, 106, 107, 108, 109, 111, 112, 113, 114, 115, 116, 117, 118, 119, 120, 121, 122, 123, 124, 125, 126, 127, 128, 129, 130, 131, 132, 133, 134, 136, 137, 138, 141, 142, 144, 146, 147, 148, 149, 150, 151, 152, 153, 155, 156, 157, 158, 159, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 233, 234, 235, 236, 237, 238, 239, 240, 241, 242, 243, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 336, 337, 338, 339, 340, 341, 342, 343, 344, 345, 346, 347, 348, 349, 350, 351, 352, 353, 354, 355, 356, 357, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 416, 417, 418, 419, 420, 421, 422, 423, 424, 425, 426, 429, 430, 431, 432, 433, 434, 435, 436, 438, 439, 440, 441, 443, 444, 445, 446, 448, 450, 451, 452, 453, 454, 455, 456, 457, 458, 459, 460, 461, 462, 463, 464, 465, 466, 467, 468, 469, 470, 471, 472, 473, 474, 475, 476, 479, 480, 481, 483, 485, 486, 487, 488, 489, 492, 493, 494, 496, 497, 499, 500, 503, 504, 505, 509, 510, 512, 513, 514, 515, 516, 517, 518, 519, 522, 523, 524, 525.

The following compounds reduce growth of P. aeruginosa PAO1 to no more than 10% growth of the uninhibited control in the antibacterial activity assay with linezolid when the compound is present at 50 µM:

13, 29, 32, 37, 38, 51, 58, 61, 73, 100, 104, 106, 108, 109, 111, 112, 113, 114, 116, 117, 119, 120, 121, 122, 123, 125, 126, 129, 130, 133, 134, 142, 147, 149, 150, 157, 159, 164, 165, 168, 169, 171, 175, 178, 179, 180, 181, 182, 183, 184, 185, 186, 187, 188, 189, 190, 191, 193, 194, 196, 197, 198, 199, 200, 201, 202, 203, 204, 209, 210, 211, 212, 213, 214, 217, 218, 224, 228, 229, 231, 234, 243, 246, 252, 253, 254, 255, 256, 257, 258, 259, 260, 261, 262, 264, 265, 268, 271, 272, 274, 275, 280, 281, 282, 290, 292, 295, 296, 297, 299, 308, 309, 310, 311, 312, 313, 314, 317, 319, 320, 321, 322, 323, 327, 328, 330, 331, 341, 344, 345, 346, 347, 354, 359, 360, 361, 371, 381, 382, 387, 388, 390, 395, 396, 397, 398, 401, 402, 406, 407, 408, 413, 416, 419, 421, 422, 426, 429, 430, 431, 433, 443, 444, 447, 448, 450, 451, 452, 453, 455, 456, 464, 471, 509, 512, 513, 514, 515, 517, 518, 519, 525.

The invention claimed is:

1. A compound of formula I or pharmaceutically acceptable salt, solvate or hydrate thereof:

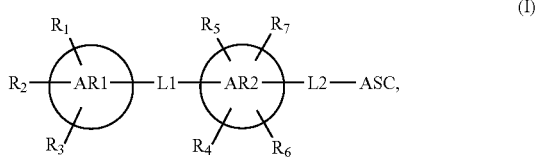

wherein
ASC is —N(R8)(R9)ASC-1;
ASC-1 is

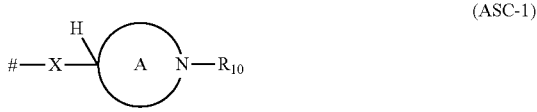

Ring A represents a 4- to 6-membered saturated ring containing carbon atoms as ring members in addition to the nitrogen atom and wherein one CH2 moiety in ring A is optionally replaced by CH(R21) and wherein one carbon atom in ring A that is not adjacent to the nitrogen atom is optionally replaced by O, and wherein ring A is connected to X via a carbon atom;
X represents a bond, —CH2- or —C(=O)—;
AR1 and AR2 are phenyl;
R1, R2, R3 represent independently hydrogen, halogen, cyano, hydroxyl, C1-C6alkyl, C1-C6haloalkyl, C3-C8cycloalkyl, C1-C6alkoxy, C1-C6haloalkoxy, —C1-C6alkylene-N(R12)R13, —N(R12)R13, —C(O)OR11, —C(O)N(R12)R13, or —S(O)OR11;
R4 represents hydrogen, hydroxyl, halogen, nitro, cyano, amino, C1-C6alkyl optionally substituted by 1 to 5 R14, C2-C6alkenyl optionally substituted by 1 to 5 R14, C2-C6alkynyl optionally substituted by 1 to 5 R14, C1-C6alkoxy optionally substituted by 1 to 5 R14, C2-C6alkenyloxy optionally substituted by 1 to 5 R14, C2-C6alkynyloxy optionally substituted by 1 to 5 R14, —C(O)OR15, —CHO, —C(O)N(R16)R17, —C1-C6alkylene-N(R9)(R16)R17, —O-Cycle-P or —O-Cycle-Q;
R5, R6, R7 represent independently hydrogen, halogen, cyano, C1-C6alkyl, C1-C6haloalkyl, C1-C6alkoxy or C1-C6haloalkoxy;
R8 represents hydrogen, methyl or ASC-1;
R9 is methyl or absent, and wherein when R9 is present the respective nitrogen atom carries a positive charge;
R10 represents hydrogen or methyl;
R11 represents independently at each occurrence hydrogen or C1-C6alkyl;
R12, R13 represent independently at each occurrence hydrogen or C1-C6alkyl;
R14 represents independently at each occurrence halogen, cyano, hydroxyl, C1-C6alkoxy, C1-C6haloalkoxy, C3-C8cycloalkyl, —C(O)OR11, —CHO, —C(O)N(R12)R13, —C1-C6alkylene-N(R12)R13, Cycle-P, O-Cycle-P, Cycle-Q or O-Cycle-Q;
Cycle-P represents independently at each occurrence a saturated or partially unsaturated C3-C8 carbocyclic ring optionally substituted by 1 to 3 R18, or a saturated or partially unsaturated C3-C8 heterocyclic ring optionally substituted by 1 to 3 R18 containing carbon atoms as ring members and one or two ring members independently selected from N(R9)(R12) and O;
Cycle-Q represents independently at each occurrence phenyl optionally substituted by 1 to 3 R19 or a 5- to 6-membered heteroaryl ring containing one to four heteroatoms selected from O, S and N, optionally substituted by 1 to 3 R19;
R15 represents independently at each occurrence hydrogen or C1-C6alkyl optionally substituted by 1 to 5 R14;
R16 and R17 represent independently at each occurrence hydrogen or C1-C6alkyl optionally substituted by 1 to 5 R14;
R18 and R19 represent independently at each occurrence halogen, cyano, hydroxyl, oxo, amino, C1-C4alkyl, C1-C4haloalkyl, C1-C4alkoxy, C1-C4haloalkoxy or —CO(O)R11;
R20 represents independently at each occurrence hydrogen or methyl;
R21 represents N(R20)2 or CH2-N(R20)2;
L1 represents —CH=CH—, —CH2-O—, —O—CH2-, —CH2-O—CH2-, —CH2-S—, —S—CH2-, —CH2-S(O)—, —CH2-S(O2)-, —S(O)—CH2-, —S(O2)-CH2-, —C(CH3)(CH3)-, —C(=O)—NH—, —NH—C(=O)—, —CH2-CH2-, —CH=CH—CH2-, —CH2-NH—C(=O)—, —C(=O)—NH—CH2, —S(O2)-NH—CH2, —S(O2)-NH—, —O—CH2-CH2-O—, —O—, —NH—CH2-, —CH2-NH—, —CH2-CH2-O—, —NH—C(=O)—CH2-O— or a bond;
L2 represents C1-C7alkylene, wherein one or more CH2 moieties in the alkylene are optionally replaced independently by —N(R9)(R20)-, —CH(N(R9)(R20)(R20))-, or —C(=O)—, wherein within L2 there are no adjacent C(=O) moieties or adjacent —N(R9)(R20)- moieties, and wherein the terminal moiety of L2 is not —N(R9)(R20)-, or L2 represents —O—C1-C6alkylene-, or L2 represents a bond, providing that X represents —CH2- when L2 is a bond;
wherein
when L2 is C(=O), then R8 is ASC-1;
when L1 is a bond, then R1 is Br or C2-C6alkyl, and/or R4 is O—C2-C6alkenyl, O—C1-C6alkylene-Cycle-P1 or O—C1-C6alkylene-Cycle-Q1, wherein Cycle-P1 represents a saturated or partially unsaturated C3-C8 heterocyclic ring optionally substituted by 1 to 3 R18 containing carbon atoms as ring members and one or two ring members independently selected from N(R9)(R12) and O and Cycle-Q1 represents a 5- to 6-membered heteroaryl ring containing one to four heteroatoms selected from O, S and N, optionally substituted by 1 to 3 R19;
when L1 is —CH2-O— or —NH—C(=O)—CH2-O—, L2 is C1-C7alkylene as defined above, ring A is a 6-membered ring, and R8 is hydrogen or methyl, then R1 is Br or C2-C6alkyl, and/or R4 is O—C2-C6alkenyl, O—C1-C6alkylene-Cycle-P1 or O—C1-C6alkylene-Cycle-Q1;
when L1 is —CH2-O— or —NH—C(=O)—CH2-O—, L2 is —CH2- or CH2-CH2-, ring A is a 4- or 5-membered ring, X is C(=O) and R8 is hydrogen or methyl, then R1 is Br or C2-C6alkyl, and/or R4 is O—C2-C6alkenyl, O—C1-C6alkylene-Cycle-P1 or O—C1-C6alkylene-Cycle-Q1;
when L1 is —O—CH2-, —CH2-O—CH2-, —C(=O)—NH—, —NH—C(=O)—, —CH2-NH—C(=O)—, —O—CH2-CH2-O— or —O—, L2 is —CH2-, X is C(=O) and R8 is hydrogen or methyl, then R1 is Br or C2-C6alkyl, and/or R4 is O—C2-C6alkenyl, O—C1-C6alkylene-Cycle-P1 or O—C1-C6alkylene-Cycle-Q1;
when L1 is —O—, then ring A is a 4- or 5-membered ring;
wherein the compound of formula I is not
2-Pyrrolidinemethanamine-[[4-[(4-bromophenyl)methoxy]-3-methoxyphenyl]methyl]-1-methyl-;
2-Pyrrolidinemethanamine, N-[[3-bromo-4-(phenylmethoxy)phenyl]methyl]-1-methyl-;
2-Pyrrolidinemethanamine, N-[[3-[(2-chlorophenyl)methoxy]phenyl]methyl]-1-methyl-;
2-Pyrrolidinemethanamine, N-[[3-methoxy-4-[[3-(trifluoromethyl)phenyl]methoxy]phenyl]methyl]-1-methyl-;
2-Pyrrolidinemethanamine, N-[[4-[(4-chlorophenyl)methoxy]-3-methoxyphenyl]methyl]-1-methyl-;
2-Pyrrolidinemethanamine, N-[[4-(4-bromophenoxy)phenyl]methyl]-N-methyl-;
Benzamide, N-(2,4-difluorophenyl)-3-[[methyl(3-piperidinylmethyl)amino]methyl]-;
2-Pyrrolidinemethanamine, 1-methyl-N-[(3-phenoxyphenyl)methyl]-;
3-Azetidinamine, N-methyl-N-[(3-phenoxyphenyl)methyl]-;
3-Pyrrolidinamine, N-methyl-N-[(3-phenoxyphenyl)methyl]-; and
3-Pyrrolidinamine, 1-methyl-N-[(3-phenoxyphenyl)methyl]-.

2. The compound according to claim 1 or pharmaceutically acceptable salt, solvate or hydrate thereof, wherein L1 represents —CH=CH—.

3. The compound according to claim 1 or pharmaceutically acceptable salt, solvate or hydrate thereof, wherein L1 represents —CH2-O—.

4. The compound according to claim 1 or pharmaceutically acceptable salt, solvate or hydrate thereof, wherein L1 represents —C(CH3)(CH3)-.

5. The compound according to claim 1 or pharmaceutically acceptable salt, solvate or hydrate thereof, wherein L2 represents C1-C7alkylene, wherein one or more CH2 moieties in the alkylene are optionally replaced independently by —N(R9)(R20)-, —CH(N(R9)(R20)(R20))-, or —C(=O)—, wherein within 0.2 there are no adjacent C(=O) moieties or adjacent —N(R9)(R20)- moieties, and wherein the terminal moiety of L2 is not —N(R9)(R20)-, or L2 represents —O—C1-C6alkylene-.

6. The compound according to claim 1 or pharmaceutically acceptable salt, solvate or hydrate thereof, wherein ring A is a 4- to 6-membered saturated ring containing only CH2 moieties as ring members in addition to the nitrogen atom.

7. The compound according to claim 1, or pharmaceutically acceptable salt, solvate or hydrate thereof, wherein X is CH2;
L2 represents C1-C7alkylene, wherein one or more CH2 moieties in the alkylene are optionally replaced independently by —N(R9)(R20)-, —CH(N(R9)(R20)(R20))-, or —C(=O)—, wherein within L2 there are no adjacent C(=O) moieties or adjacent —N(R9)(R20)- moieties, and wherein the terminal moiety of L2 is not —N(R9)(R20)- and wherein the terminal moiety of L2 connected to ASC is —CH2-, or L2 represents —O—C1-C6alkylene-.

8. The compound according to claim 1 or pharmaceutically acceptable salt, solvate or hydrate thereof, wherein L2 represents C1-C7alkylene, wherein one or two CH2 moieties in the alkylene are optionally replaced independently by —N(R9)(R20)- or —C(=O)—, and wherein the terminal moiety of L2 connected to ASC is —CH2-.

9. The compound according to claim 1 or pharmaceutically acceptable salt, solvate or hydrate thereof, wherein L2 represents —CH2-, —CH2-CH2-, —CH2-CH2-CH2-, —CH(CH3)-, —CH2-NH—CH2-CH2-, —C(=O)—, —C(=O)—CH2, —C(=O)—NH—CH2-C(=O)—, —C(=O)—NH—CH2-CH2-, —CH2-N(CH3)2-CH2-C(=O)—, —CH2-NH—C(=O)—CH2-, —CH2-NH—CH2-C(=O)—, —O—CH2-CH2-, —O—CH2-CH2-CH2- or —O—CH2-CH2-CH2-CH2-.

10. The compound according to claim 1 or pharmaceutically acceptable salt, solvate or hydrate thereof, wherein L2 represents —CH2-, —CH2-CH2-, —CH(CH3)-, —CH2-CH2-CH2-, —CH2-NH—CH2-CH2-, —C(=O)—, —C(=O)—NH—CH2-CH2-, —O—CH2-CH2-, —O—CH2-CH2-CH2- or —O—CH2-CH2-CH2-CH2-.

11. The compound according to claim 1 or pharmaceutically acceptable salt, solvate or hydrate thereof, wherein L2 represents —O—CH2-, —O—CH2-CH2-, —O—CH2-CH2-CH2-, —O—CH2-CH2-CH2-CH2-, —O—CH2-CH2-CH2-CH2-CH2- or —O—CH2-CH2-CH2-CH2-CH2-CH2-.

12. The compound according to claim 1 or pharmaceutically acceptable salt, solvate or hydrate thereof, wherein R8 represents ASC-1, and preferably wherein ASC is ASC-o

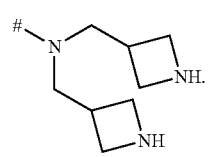

(ASC-o)

13. The compound according to claim 12, or pharmaceutically acceptable salt, solvate or hydrate thereof, wherein L2 represents —C(=O)—.

14. The compound according to claim 1 or pharmaceutically acceptable salt, solvate or hydrate thereof, wherein ASC-1 is ASC-1a or ASC-1b

(ASC-1a)

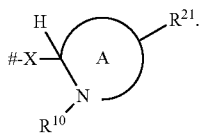

(ASC-1b)

15. The compound according to claim 14 or pharmaceutically acceptable salt, solvate or hydrate thereof, wherein ring A represents a 4- to 6-membered saturated ring containing carbon atoms as ring members in addition to the nitrogen atom.

16. The compound according to claim 15 or pharmaceutically acceptable salt, solvate or hydrate thereof, wherein ASC-1 is ASC-1a wherein ring A represents a 4- to 5-membered saturated ring containing carbon atoms as ring members in addition to the nitrogen atom and X represents CH2, and preferably wherein ASC is ASC-a or ASC-g

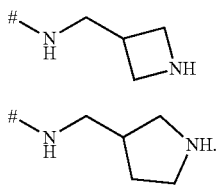

(ASC-a)

(ASC-g)

17. The compound according to claim 16 or pharmaceutically acceptable salt, solvate or hydrate thereof, wherein L2 represents —CH2-, —CH2-CH2-, —CH1(CH3)-, —CH2-CH2-CH2-, —CH2-NH—CH2-CH2-, —C(=O)—NH—CH2-CH2-, —O—CH2-CH2- —O—CH2-CH2-CH2- or —O—CH2-CH12-CH2-CH2-.

18. The compound according to claim 1 or pharmaceutically acceptable salt, solvate or hydrate thereof, wherein
ASC is —N(R8a)ASC-1 or —N(R8b)(R9)ASC-1;
Ring A represents a 4- to 5-membered saturated ring containing carbon atoms as ring members in addition to the nitrogen atom;
X represents CH2;
L1 represents —CH=CH—, —CH2-O—, —O—CH2-, —CH2-O—CH2-, —CH2-S—, —S—CH2-, —CH2-S(O)—, —CH2-S(O2)-, —S(O)—CH2-, —S(O2)-CH2-, —C(CH3)(CH3)-, —C(=O)—NH—, —NH—C(=O)—, —CH2-CH2-, —CH=CH—CH2-, —CH2-NH—C(=O)—, —C(=O)—NH—CH2, —C≡C—, —S(O2)-NH—CH2-, —S(O2)-NH—, —O—CH2-CH2-O—, —O—, —NH—CH2-, —CH2-NH—, —CH2-CH2-O—, or —NH—C(=O)—CH2-O—;
R8a represents hydrogen or ASC-1;
R8b represents methyl or ASC-1;
R9 represents methyl; and
R10 represents hydrogen.

19. The compound according to claim 1 or pharmaceutically acceptable salt, solvate or hydrate thereof, wherein R4 represents O—R22 and wherein R22 is C3-C6alkyl, C2-C6alkenyl, C1-C6alkyl-Cycle-P1, C1-C6alkyl-Cycle-Q1.

20. The compound according to claim 1 or pharmaceutically acceptable salt, solvate or hydrate thereof, wherein R4 represents O—R22 and wherein R22 is C2-C6alkenyl.

21. The compound according to claim 1 or pharmaceutically acceptable salt, solvate or hydrate thereof, wherein ASC-1 is ASC1a

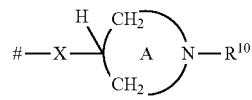

(ASC-1a)

Ring A represents a 4- to 5-membered saturated ring containing carbon atoms as ring members in addition to the nitrogen atom;

X represents CH2;

AR1 represents phenyl;

AR2 represents phenyl;

R1 and R2 represent independently hydrogen, halogen, cyano, C1-C6alkyl, C1-C6haloalkyl, C3-C8cycloalkyl, C1-C6alkoxy, C1-C6haloalkoxy, —C(O)OR11 or —C(O)N(R12)R13;

R3 is hydrogen;

R4 represents hydrogen, halogen, cyano, C1-C6alkyl, C1-C6haloalkyl or O—R22;

R5, R6, R7 are hydrogen or halogen;

R8 represents hydrogen, methyl or ASC-1;

R9 is methyl or absent;

R10 represents hydrogen;

R11 represents independently at each occurrence hydrogen or C1-C6alkyl;

R12 and R13 represent independently at each occurrence hydrogen or C1-C6alkyl;

R18 and R19 represent independently at each occurrence halogen, cyano, methyl, halomethyl, methoxy or halomethoxy;

R22 represents C1-C6alkyl, C2-C6alkenyl, C1-C6haloalkyl, C2-C6haloalkenyl, C1-C6alkyl-Cycle-P, C1-C6alkyl-Cycle-Q, C2-C6alkenyl-Cycle-P or C2-C6alkenyl-Cycle-Q;

Cycle-P represents independently at each occurrence tetrahydrofuranyl, pyrrolidinyl, piperidinyl, piperazinyl, dioxanyl, or morpholinyl, each optionally substituted by 1 to 3 R18;

Cycle-Q represents independently at each occurrence phenyl, pyridinyl, pyrimidinyl, pyrazinyl, pyridazinyl, pyrrolyl, pyrazolyl, imidazolyl, triazolyl, isoxazolyl, oxazolyl, isothiazolyl, thiazolyl, tetrazolyl, furanyl, or thiophenyl, each optionally substituted by 1 to 3 R19;

L1 represents —CH=CH—, —CH2-O— or —C(CH3)(CH3)-;

L2 represents —CH2-, —CH-12-CH2-, —CH(CH3)-, —CH2-CH2-CH2-, —CH2-NH—CH2-CH2-, —C(=O)—, —C(=O)—NH—CH2-CH2, —O—CH2-, —O—CH2-CH2-CH2-, —O—CH2-CH2-CH2- or —O—CH2-CH2-CH-2-CH2-.

22. The compound according to claim 21 or pharmaceutically acceptable salt, solvate or hydrate thereof, wherein R8 represents ASC-1 and L2 represents —C(=O)—.

23. The compound according to claim 1 or pharmaceutically acceptable salt, solvate or hydrate thereof, wherein the compound is a compound of formula I-20

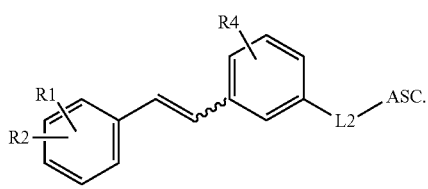
(I-20)

24. The compound according to claim 1 or pharmaceutically acceptable salt, solvate or hydrate thereof, wherein the compound is a compound of formula I-21

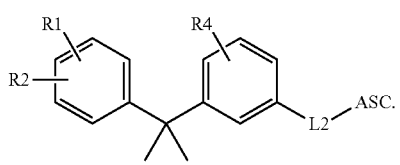
(I-21)

25. The compound according to claim 1 or pharmaceutically acceptable salt, solvate or hydrate thereof, wherein the compound is a compound of formula I-22

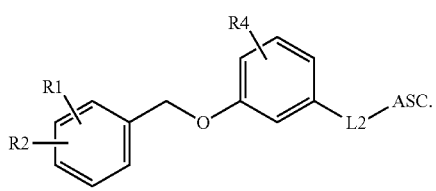
(I-22)

26. The compound according to claim 1 or pharmaceutically acceptable salt, solvate or hydrate thereof, wherein the compound is a compound of formula I-23

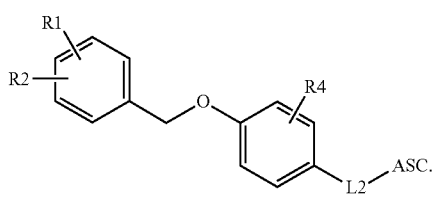
(I-23)

27. The compound according to claim 1 or pharmaceutically acceptable salt, solvate or hydrate thereof, wherein the compound is a compound of formula I-24

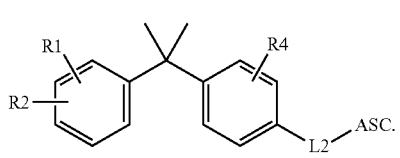
(I-24)

28. The compound according to claim 1 or pharmaceutically acceptable salt, solvate or hydrate thereof, wherein the compound is a compound of formula I-25

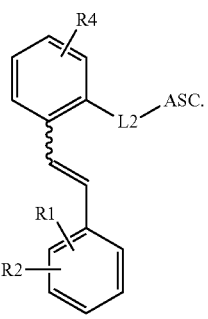
(I-25)

29. The compound according to claim 1 or pharmaceutically acceptable salt, solvate or hydrate thereof, wherein the compound is a compound of formula I-26

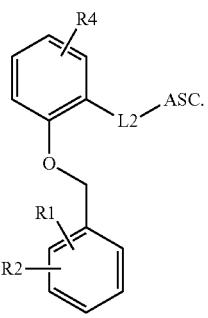
(I-26)

30. The compound according to claim 1 or pharmaceutically acceptable salt, solvate or hydrate thereof, wherein the compound is a compound of formula I-33

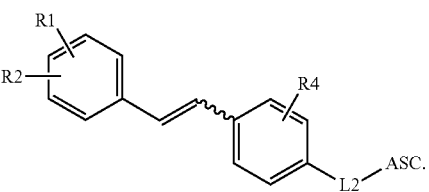
(I-33)

31. A pharmaceutical composition, comprising (i) a compound of formula I or pharmaceutically acceptable salt, solvate or hydrate thereof according to claim 1, and (ii) an antimicrobial agent.

32. A method of treating a subject with a microbial infection or susceptible to a microbial infection, said method comprising the step of administering the compound of formula I or pharmaceutically acceptable salt, solvate or hydrate thereof according to claim 1 to said subject, and wherein said subject is receiving the compound of formula I or pharmaceutically acceptable salt, solvate or hydrate thereof in combination with an antimicrobial agent.

33. The pharmaceutical composition according to claim 31, wherein the antimicrobial agent is a tetracycline antibiotic.

34. The pharmaceutical composition according to claim 31, wherein the antimicrobial agent is an oxazolidinone antibiotic.

35. The pharmaceutical composition according to claim 33, wherein said tetracycline antibiotic is minocycline.

36. The pharmaceutical composition according to claim 34, wherein said oxazolidinone antibiotic is linezolid.

37. The method according to claim 32, wherein the antimicrobial agent is a tetracycline antibiotic.

38. The method according to claim 37, wherein the tetracycline antibiotic is minocycline.

39. The method according to claim 32, wherein the antimicrobial agent is an oxazolidinone antibiotic.

40. The method according to claim 39, wherein the oxazolidinone antibiotic is linezolid.

41. A method of treating a subject with a microbial infection or susceptible to a microbial infection, said method comprising the step of administering the compound of formula I or pharmaceutically acceptable salt, solvate or hydrate thereof:

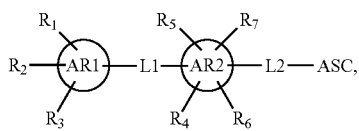

(I)

wherein:
ASC is —N(R8)(R9)ASC-1;
ASC-1 is

(ASC-1)

Ring A represents a 4- to 6-membered saturated ring containing carbon atoms as ring members in addition to the nitrogen atom and wherein one CH2 moiety in ring A is optionally replaced by CH(R21) and wherein one carbon atom in ring A that is not adjacent to the nitrogen atom is optionally replaced by O, and wherein ring A is connected to X via a carbon atom;
X represents a bond, —CH2- or —C(=O)—;
AR1 and AR2 are phenyl;
R1, R2, R3 represent independently hydrogen, halogen, cyano, hydroxyl, C1-C6alkyl, C1-C6haloalkyl, C3-C8cycloalkyl, C1-C6alkoxy, C1-C6haloalkoxy, —C1-C6alkylene-N(R12)R13, —N(R12)R13, —C(O)OR11, —C(O)N(R12)R13, —S(O)OR11 or phenyl;
R4 represents hydroxyl, hydrogen, halogen, nitro, cyano, amino, C1-C6alkyl optionally substituted by 1 to 5 R14, C2-C6alkenyl optionally substituted by 1 to 5 R14, C2-C6alkynyl optionally substituted by 1 to 5 R14, C1-C6alkoxy optionally substituted by 1 to 5 R14, C2-C6alkenyloxy optionally substituted by 1 to 5 R14, C2-C6alkynyloxy optionally substituted by 1 to 5 R14, —C(O)OR15, —CHO, —C(O)N(R16)R17, —C1-C6alkylene-N(R9)(R16)R17, —O-Cycle-P or —O-Cycle-Q;
R5, R6, R7 represent independently hydrogen, halogen, cyano, C1-C6alkyl, C1-C6haloalkyl, C1-C6alkoxy or C1-C6haloalkoxy;
R8 represents hydrogen, methyl or ASC-1;
R9 is methyl or absent, and wherein when R9 is present the respective nitrogen atom carries a positive charge;
R10 represents hydrogen or methyl;
R11 represents independently at each occurrence hydrogen or C1-C6alkyl;
R12, R13 represent independently at each occurrence hydrogen or C1-C6alkyl;
R14 represents independently at each occurrence halogen, cyano, hydroxyl, C1-C6alkoxy, C1-C6haloalkoxy, C3-C8cycloalkyl, —C(O)OR11, —CHO, —C(O)N(R12)R13, —C1-C6alkylene-N(R12)R13, Cycle-P, O-Cycle-P, Cycle-Q or O-Cycle-Q;
Cycle-P represents independently at each occurrence a saturated or partially unsaturated C3-C8 carbocyclic ring optionally substituted by 1 to 3 R18, or a saturated or partially unsaturated C3-C8 heterocyclic ring optionally substituted by 1 to 3 R18 containing carbon atoms as ring members and one or two ring members independently selected from N(R9)(R12)- and O;
Cycle-Q represents independently at each occurrence phenyl optionally substituted by 1 to 3 R19 or a 5- to 6-membered heteroaryl ring containing one to four heteroatoms selected from O, S and N, optionally substituted by 1 to 3 R19;
R15 represents independently at each occurrence hydrogen or C1-C6alkyl optionally substituted by 1 to 5 R14;
R16 and R17 represent independently at each occurrence hydrogen or C1-C6alkyl optionally substituted by 1 to 5 R14;
R18 and R19 represent independently at each occurrence halogen, cyano, hydroxyl, oxo, amino, C1-C4alkyl, C1-C4haloalkyl, C1-C4alkoxy, C1-C4haloalkoxy or —CO(O)R11;
R20 represents independently at each occurrence hydrogen or methyl;
R21 represents N(R20)2 or CH2-N(R20)2;
L1 represents —CH=CH—, —CH2-O—, —O—CH2-, —CH2-O—CH2-, —CH2-S—, —S—CH2-, —CH2-S(O)—, —CH2-S(O2)-, —S(O)—CH2-, —S(O2)-CH2-, —C(CH3)(CH3)-, —C(=O)—NH—, —NH—C(=O)—, —CH2-CH2-, —CH=CH—CH2-, —CH2-NH—C(=O)—, —C(=O)—NH—CH2, —C≡C—, —S(O2)-NH—CH2-, —S(O2)-NH—, —O—CH2-CH2-O—, —O—, —NH—CH2-, —CH2-NH—, —CH2-CH2-O—, or —NH—C(=O)—CH2-O—, or a bond;
L2 represents C1-C7alkylene, wherein one or more CH2 moieties in the alkylene are optionally replaced independently by —N(R9)(R20)-, —CH(N(R9)(R20)(R20))-, or —C(=O)—, wherein within L2 there are no adjacent C(=O) moieties or adjacent —N(R9)(R20)- moieties, and wherein the terminal moiety of L2 is not —N(R9)(R20)-, or L2 represents —O—C1-C6alkylene-, or L2 represents a bond, providing that X represents —CH2- when L2 is a bond,
to said subject, and wherein said subject is receiving the compound of formula I or pharmaceutically acceptable salt, solvate or hydrate thereof in combination with an antimicrobial agent.

42. The method according to claim 41, wherein the antimicrobial agent is a tetracycline antibiotic.

43. The method according to claim 42, wherein the tetracycline antibiotic is minocycline.

44. The method according to claim 41, wherein the antimicrobial agent is an oxazolidinone antibiotic.

45. The method according to claim 44, wherein the oxazolidinone antibiotic is linezolid.

46. A compound according to claim 1, wherein the compounds is selected from the group of compounds consisting of

| Example | Formula |
|---|---|
| 13 | 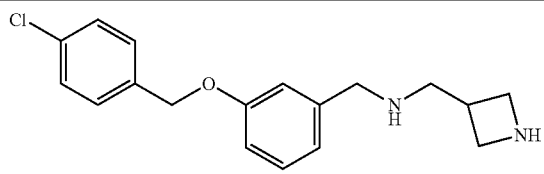 |
| 16 | 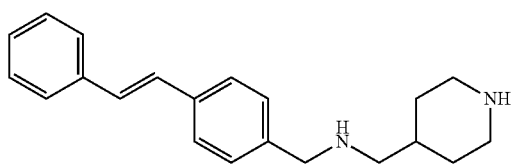 [SMILES: C(=C\c1ccc(CNCC2CCNCC2)cc1)/c1ccccc1] |
| 17 | 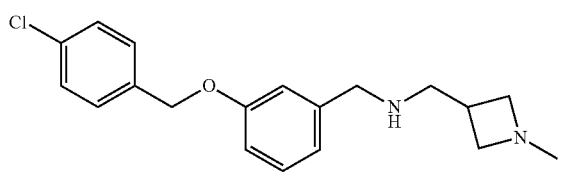 [SMILES: CN1CC(CNCc2cccc(OCc3ccc(Cl)cc3)c2)C1] |
| 18 | 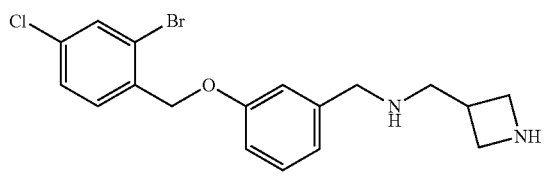 |
| 19 | 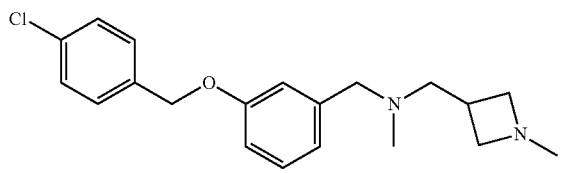 [SMILES: CN(Cc1cccc(OCc2ccc(Cl)cc2)c1)CC1CN(C)C1] |
| 20 | 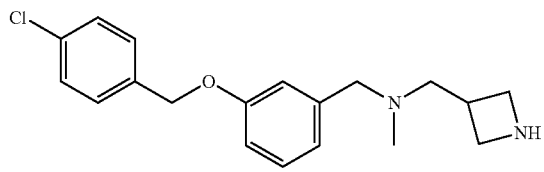 |
| 21 | 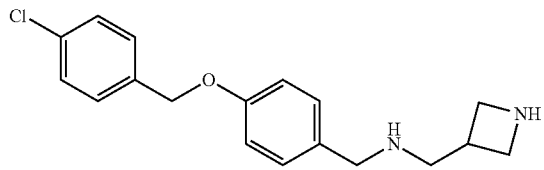 [SMILES: Clc1ccc(COc2ccc(CNCC3CNC3)cc2)cc1] |
| 22 | 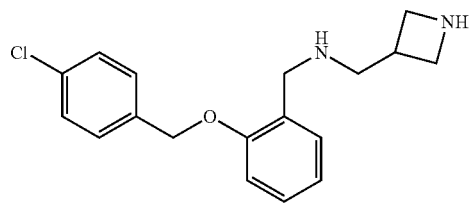 [SMILES: Clc1ccc(COc2ccccc2CNCC2CNC2)cc1] |
| 23 | 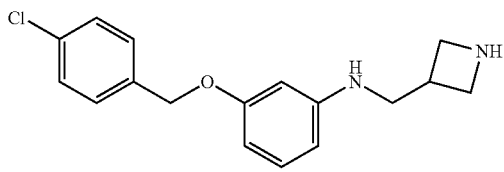 [SMILES: Clc1ccc(COc2cccc(NCC3CNC3)c2)cc1] |

-continued
| Example | Formula |
|---|---|
| 24 | 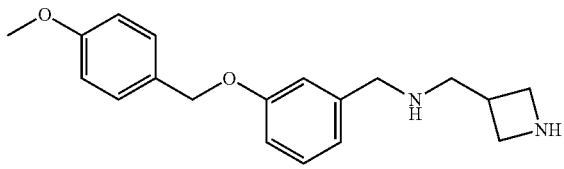 [SMILES: COc1ccc(COc2cccc(CNCC3CNC3)c2)cc1] |
| 25 | 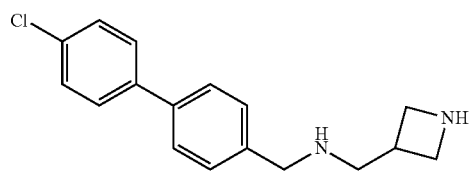 [SMILES: Clc1ccc(-c2ccc(CNCC3CNC3)cc2)cc1] |
| 26 | 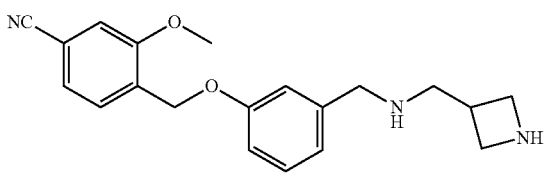 [SMILES: COc1cc(C#N)ccc1COc1cccc(CNCC2CNC2)c1] |
| 27 | 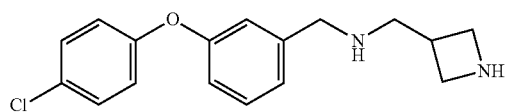 [SMILES: Clc1ccc(Oc2cccc(CNCC3CNC3)c2)cc1] |
| 28 | 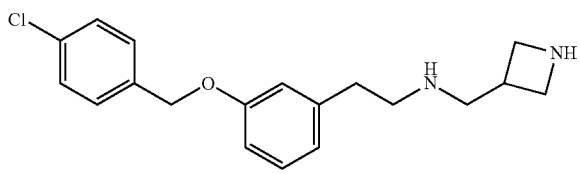 [SMILES: Clc1ccc(COc2cccc(CCNCC3CNC3)c2)cc1] |
| 29 | 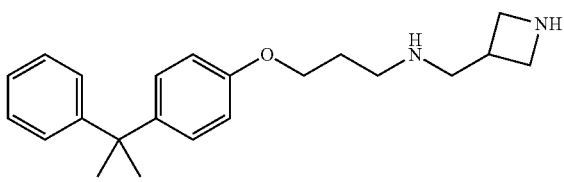 [SMILES: CC(C)(c1ccccc1)c1ccc(OCCCNCC2CNC2)cc1] |
| 30 | 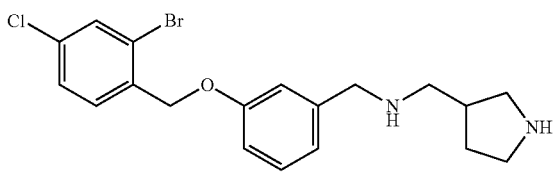 |
| 31 | 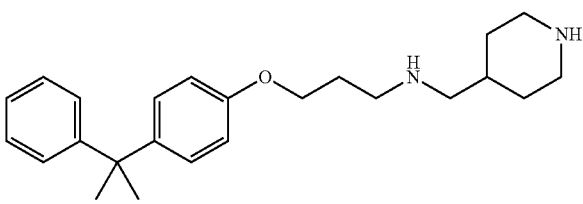 [SMILES: CC(C)(c1ccccc1)c1ccc(OCCCNCC2CCNCC2)cc1] |

-continued
| Example | Formula |
|---|---|
| 32 | 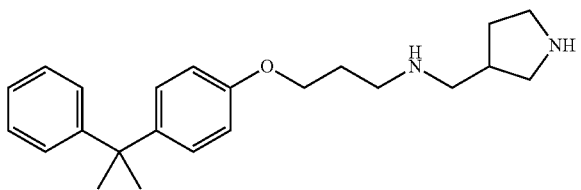 [SMILES: CC(C)(c1ccccc1)c1ccc(OCCCNCC2CCNC2)cc1] |
| 33 | 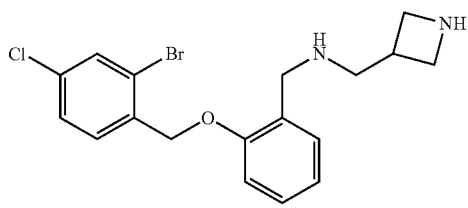 [SMILES: Clc1ccc(COc2ccccc2CNCC2CNC2)c(Br)c1] |
| 34 | 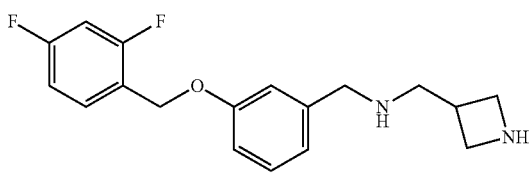 [SMILES: Fc1ccc(COc2cccc(CNCC3CNC3)c2)c(F)c1] |
| 35 | 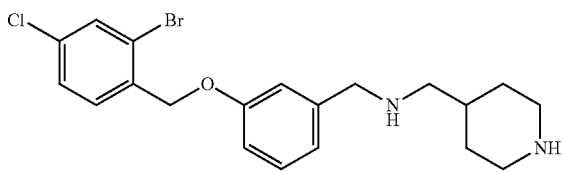 [SMILES: Clc1ccc(COc2cccc(CNCC3CCNCC3)c2)c(Br)c1] |
| 36 | 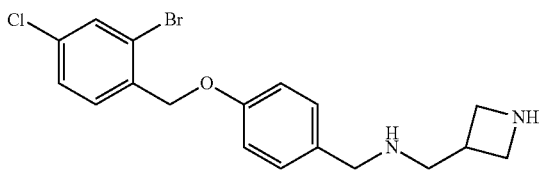 [SMILES: Clc1ccc(COc2ccc(CNCC3CNC3)cc2)c(Br)c1] |
| 37 | 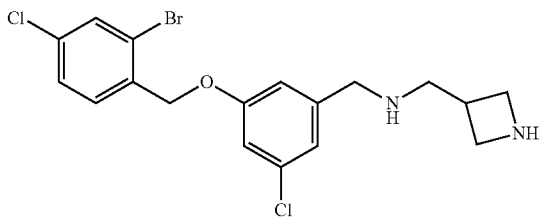 |
| 38 | 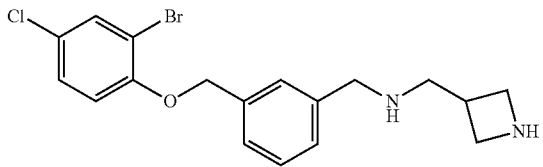 [SMILES: Clc1ccc(OCc2cccc(CNCC3CNC3)c2)c(Br)c1] |
| 39 | 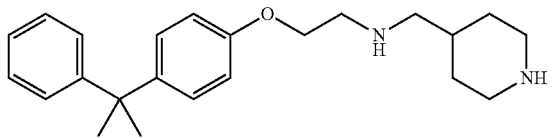 [SMILES: CC(C)(c1ccccc1)c1ccc(OCCNCC2CCNCC2)cc1] |

-continued
| Example | Formula |
|---|---|
| 40 | 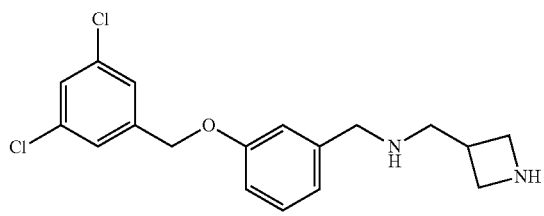 [SMILES: Clc1cc(Cl)cc(COc2cccc(CNCC3CNC3)c2)c1] |
| 41 | 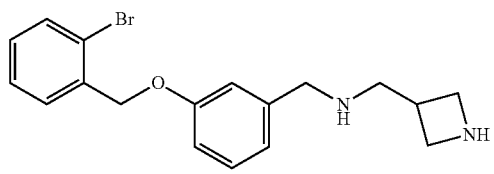 |
| 42 | 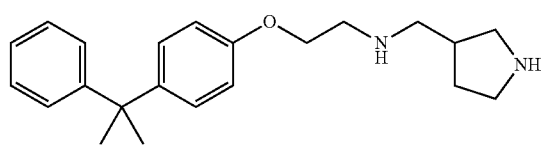 [SMILES: CC(C)(c1ccccc1)c1ccc(OCCNCC2CCNC2)cc1] |
| 43 | 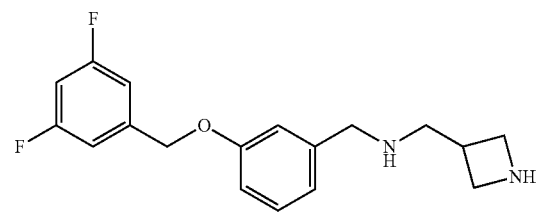 [SMILES: Fc1cc(F)cc(COc2cccc(CNCC3CNC3)c2)c1] |
| 44 | 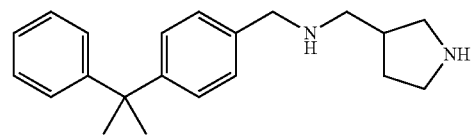 [SMILES: CC(C)(c1ccccc1)c1ccc(CNCC2CCNC2)cc1] |
| 45 | 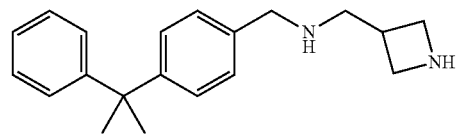 [SMILES: CC(C)(c1ccccc1)c1ccc(CNCC2CNC2)cc1] |
| 46 | 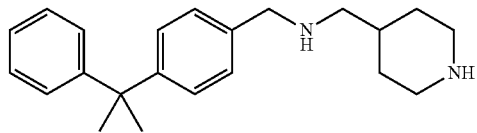 [SMILES: CC(C)(c1ccccc1)c1ccc(CNCC2CCNCC2)cc1] |
| 47 | 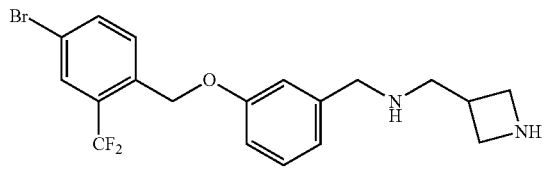 |
| 49 | 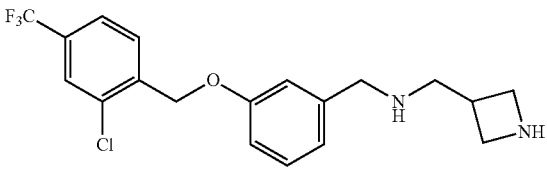 [SMILES: FC(F)(F)c1ccc(COc2cccc(CNCC3CNC3)c2)c(Cl)c1] |

-continued
| Example | Formula |
|---|---|
| 50 | 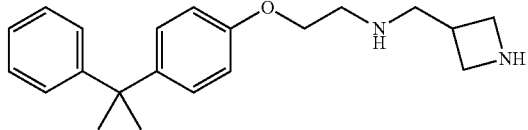 [SMILES: CC(C)(c1ccccc1)c1ccc(OCCNCC2CNC2)cc1] |
| 51 | 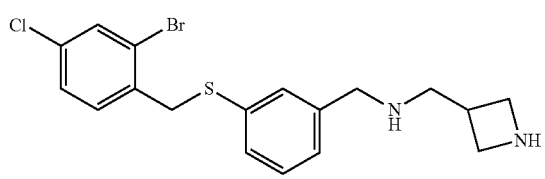 |
| 52 | 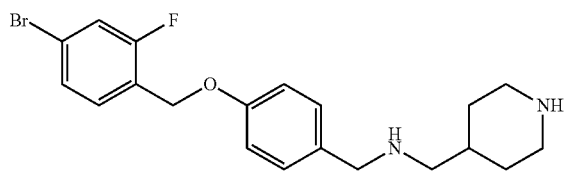 [SMILES: Fc1cc(Br)ccc1COc1ccc(CNCC2CCNCC2)cc1] |
| 53 | 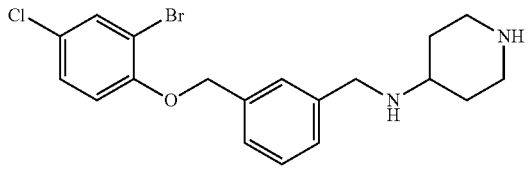 [SMILES: Clc1ccc(OCc2cccc(CNC3CCNCC3)c2)c(Br)c1] |
| 54 | 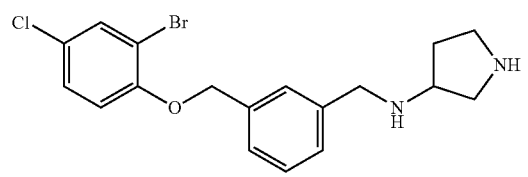 [SMILES: Clc1ccc(OCc2cccc(CNC3CCNC3)c2)c(Br)c1] |
| 55 | 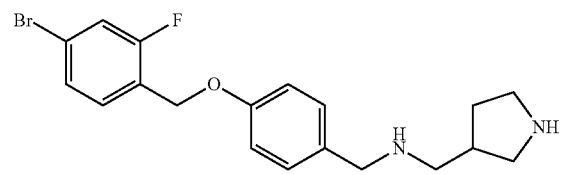 |
| 56 | 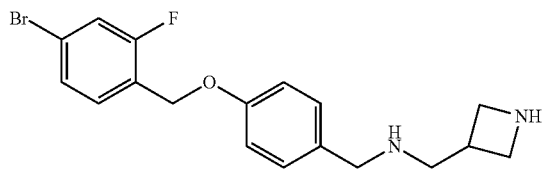 [SMILES: Fc1cc(Br)ccc1COc1ccc(CNCC2CNC2)cc1] |
| 57 | 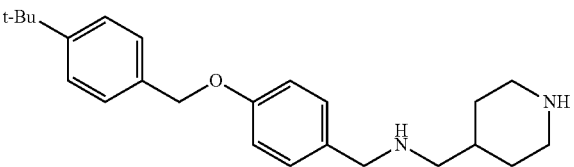 [SMILES: CC(C)(C)c1ccc(COc2ccc(CNCC3CCNCC3)cc2)cc1] |
| 58 | 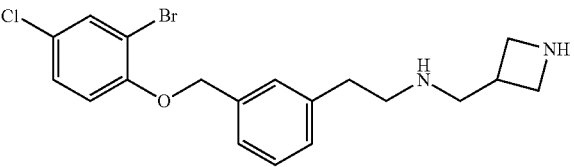 [SMILES: Clc1ccc(OCc2cccc(CCNCC3CNC3)c2)c(Br)c1] |

-continued
| Example | Formula |
|---|---|
| 59 | 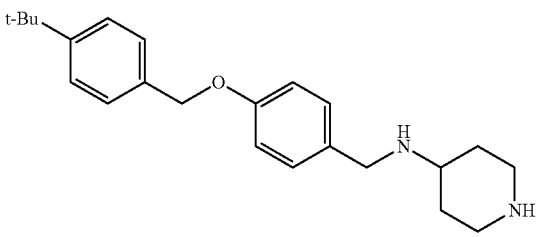 [SMILES: CC(C)(C)c1ccc(COc2ccc(CNC3CCNCC3)cc2)cc1] |
| 60 | 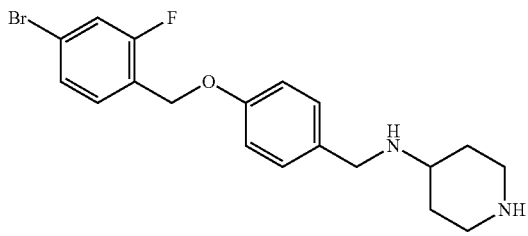 [SMILES: Fc1cc(Br)ccc1COc1ccc(CNC2CCNCC2)cc1] |
| 61 | 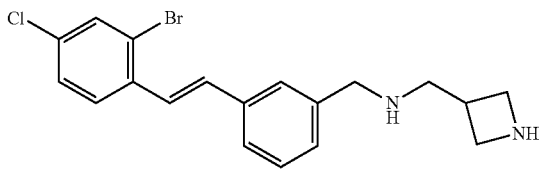 [SMILES: Clc1ccc(/C=C/c2cccc(CNCC3CNC3)c2)c(Br)c1] |
| 62 | 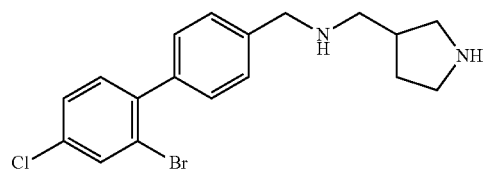 [SMILES: Clc1ccc(-c2ccc(CNCC3CCNC3)cc2)c(Br)c1] |
| 63 | 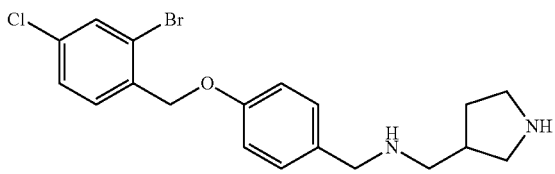 [SMILES: Clc1ccc(COc2ccc(CNCC3CCNC3)cc2)c(Br)c1] |
| 64 | 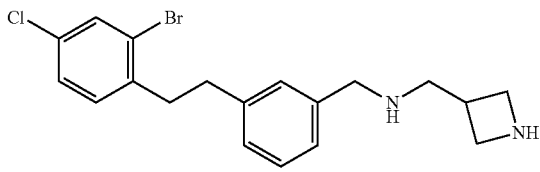 [SMILES: Clc1ccc(CCc2cccc(CNCC3CNC3)c2)c(Br)c1] |
| 65 | 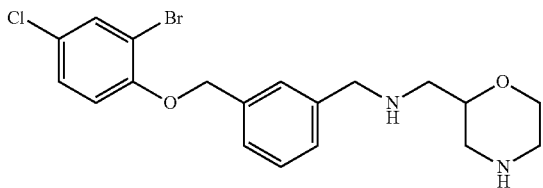 [SMILES: Clc1ccc(OCc2cccc(CNCC3CNCCO3)c2)c(Br)c1] |
| 66 | 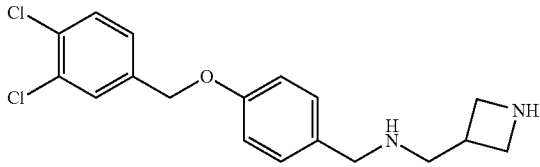 [SMILES: Clc1ccc(COc2ccc(CNCC3CNC3)cc2)cc1Cl] |

US 10,464,896 B2
| Example | Formula |
|---|---|
| 68 | 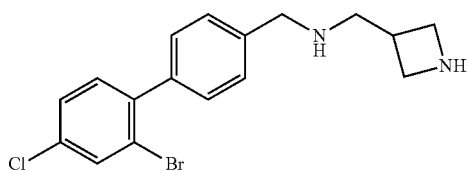 [SMILES: Clc1ccc(-c2ccc(CNCC3CNC3)cc2)c(Br)c1] |
| 69 | 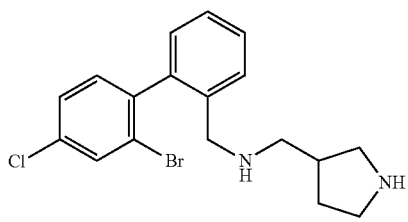 [SMILES: Clc1ccc(-c2ccccc2CNCC2CCNC2)c(Br)c1] |
| 70 | 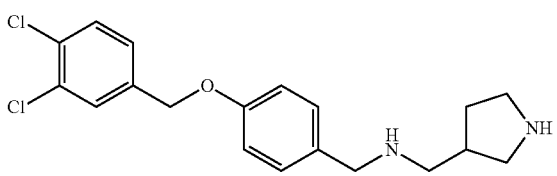 [SMILES: Clc1ccc(COc2ccc(CNCC3CCNC3)cc2)cc1Cl] |
| 71 | 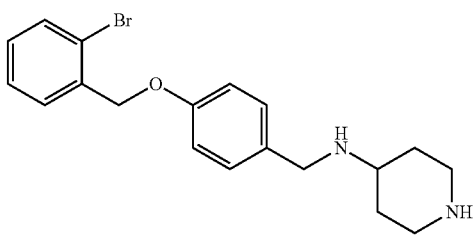 [SMILES: Brc1ccccc1COc1ccc(CNC2CCNCC2)cc1] |
| 72 | 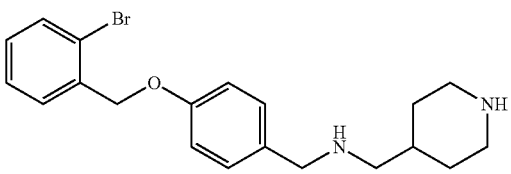 [SMILES: Brc1ccccc1COc1ccc(CNCC2CCNCC2)cc1] |
| 73 | 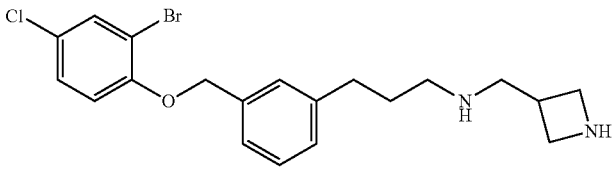 [SMILES: Clc1ccc(OCc2cccc(CCCNCC3CNC3)c2)c(Br)c1] |
| 74 | 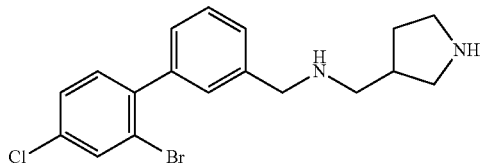 [SMILES: Clc1ccc(-c2cccc(CNCC3CCNC3)c2)c(Br)c1] |
| 75 | 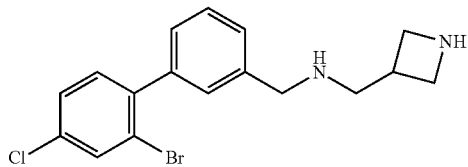 [SMILES: Clc1ccc(-c2cccc(CNCC3CNC3)c2)c(Br)c1] |

-continued
| Example | Formula |
|---|---|
| 76 | 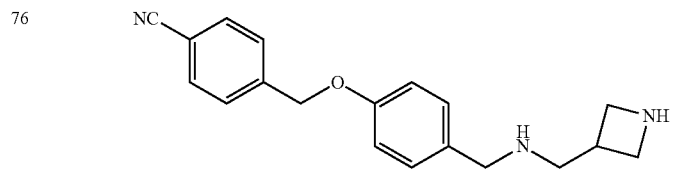 |
| 77 | 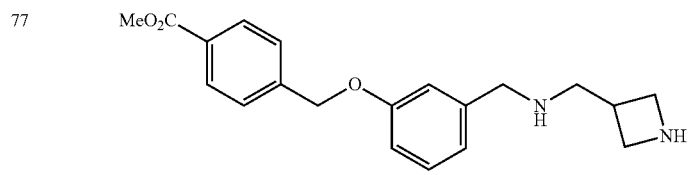 |
| 78 | 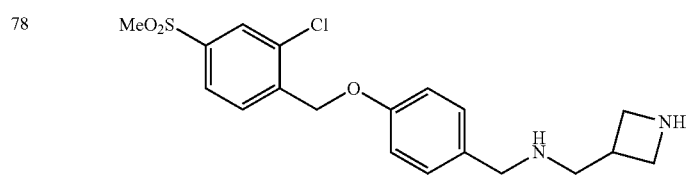 |
| 79 | 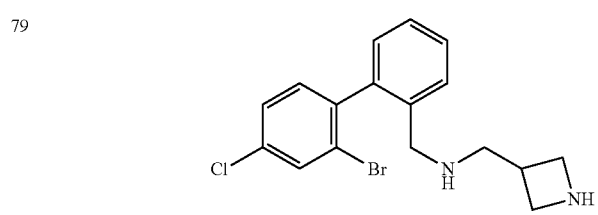 |
| 80 | 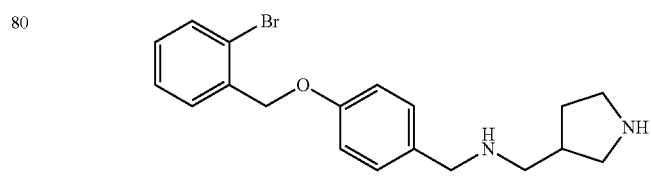 |
| 81 | 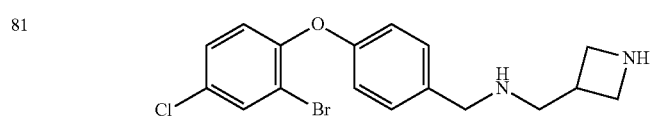 |
| 82 | 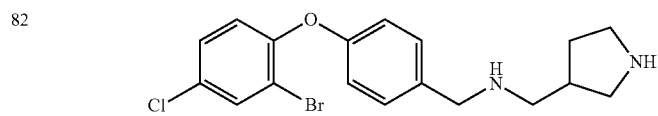 |
| 83 | 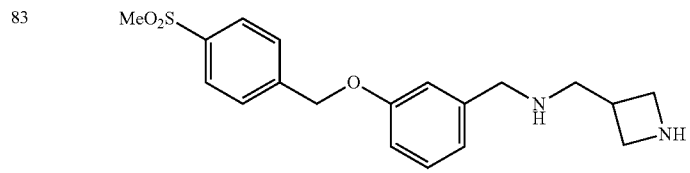 |
| 84 | 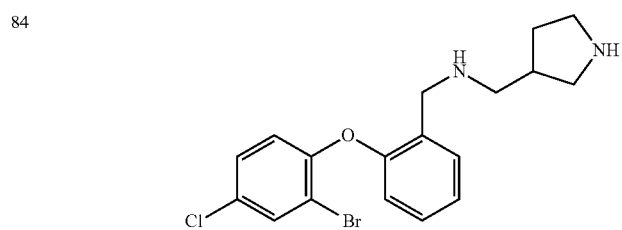 |

| Example | Formula |
|---|---|
| 85 | 3-bromo-4-((4-(((azetidin-3-ylmethyl)amino)methyl)phenoxy)methyl)benzonitrile |
| 86 | N-(4-((4-(methylsulfonyl)benzyl)oxy)benzyl)-1-(azetidin-3-yl)methanamine |
| 87 | methyl 3-bromo-4-((4-(((azetidin-3-ylmethyl)amino)methyl)phenoxy)methyl)benzoate |
| 88 | N-(3-(2-bromo-4-chlorophenoxy)benzyl)-1-(pyrrolidin-3-yl)methanamine |
| 89 | N-(2-(2-bromo-4-chlorophenoxy)benzyl)-1-(azetidin-3-yl)methanamine |
| 90 | N-(3-(2-bromo-4-chlorophenoxy)benzyl)-1-(azetidin-3-yl)methanamine |
| 91 | 4-((3-(((azetidin-3-ylmethyl)amino)methyl)phenoxy)methyl)benzonitrile |
| 92 | methyl 3-bromo-4-((3-(((azetidin-3-ylmethyl)amino)methyl)phenoxy)methyl)benzoate |
| 96 | N-(4-(2-(2-bromo-4-chlorophenoxy)ethoxy)benzyl)-1-(azetidin-3-yl)methanamine |

Note: The table above shows example numbers with chemical structures. The structures are depicted as chemical diagrams showing various substituted aromatic compounds linked via ether/methylene linkages to azetidine or pyrrolidine-containing amine moieties.

| Example | Formula |
|---------|---------|
| 97 | 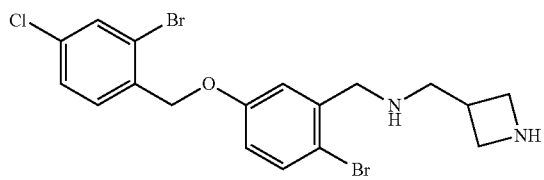 [SMILES: Clc1ccc(COc2ccc(Br)c(CNCC3CNC3)c2)c(Br)c1] |
| 98 | 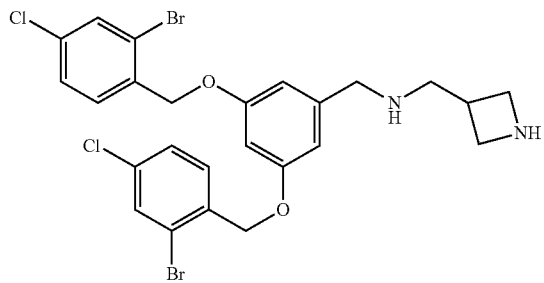 [SMILES: Clc1ccc(COc2cc(CNCC3CNC3)cc(OCc3ccc(Cl)cc3Br)c2)c(Br)c1] |
| 99O | 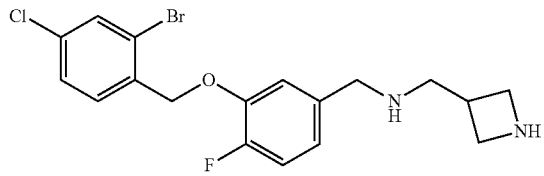 [SMILES: Fc1ccc(CNCC2CNC2)cc1OCc1ccc(Cl)cc1Br] |
| 100 | 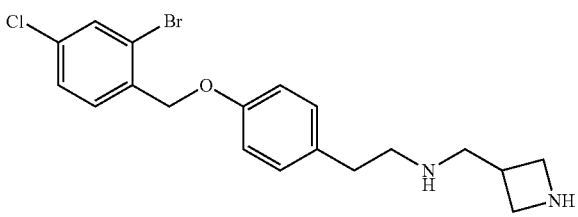 [SMILES: Clc1ccc(COc2ccc(CCNCC3CNC3)cc2)c(Br)c1] |
| 101 | 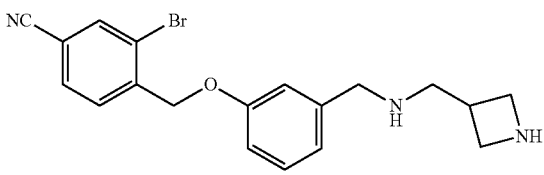 [SMILES: N#Cc1ccc(COc2cccc(CNCC3CNC3)c2)c(Br)c1] |
| 102 | 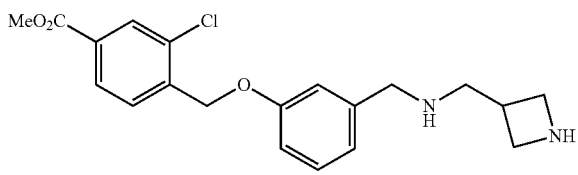 [SMILES: COC(=O)c1ccc(COc2cccc(CNCC3CNC3)c2)c(Cl)c1] |
| 103 | 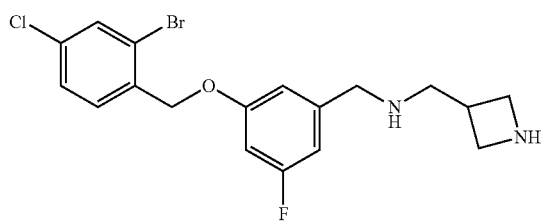 [SMILES: Fc1cc(CNCC2CNC2)cc(OCc2ccc(Cl)cc2Br)c1] |

| Example | Formula |
|---------|---------|
| 104 | 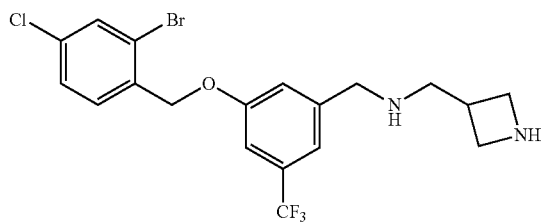 [SMILES: FC(F)(F)c1cc(CNCC2CNC2)cc(OCc2ccc(Cl)cc2Br)c1] |
| 105 | 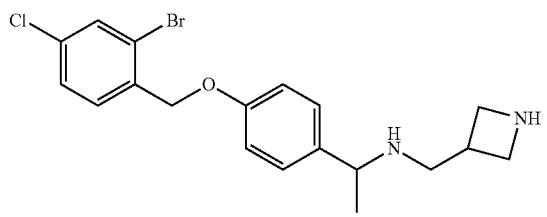 [SMILES: CC(NCC1CNC1)c1ccc(OCc2ccc(Cl)cc2Br)cc1] |
| 106 | 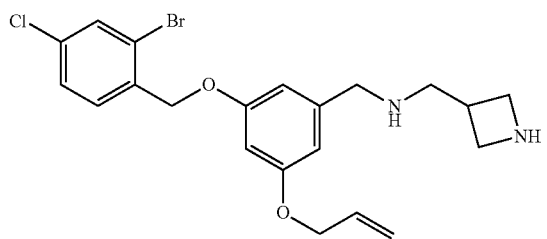 [SMILES: C=CCOc1cc(CNCC2CNC2)cc(OCc2ccc(Cl)cc2Br)c1] |
| 107 | 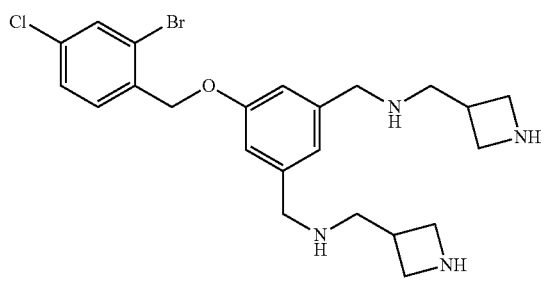 [SMILES: Clc1ccc(COc2cc(CNCC3CNC3)cc(CNCC3CNC3)c2)c(Br)c1] |
| 108 | 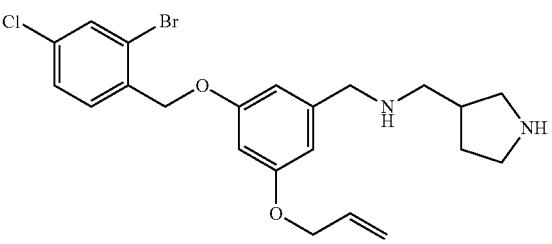 [SMILES: C=CCOc1cc(CNCC2CCNC2)cc(OCc2ccc(Cl)cc2Br)c1] |
| 109 | 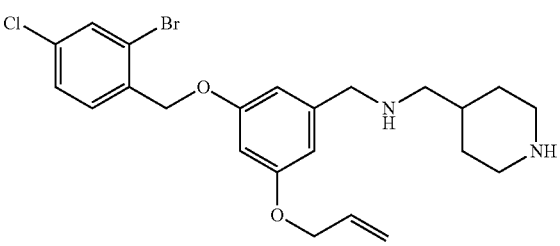 [SMILES: C=CCOc1cc(CNCC2CCNCC2)cc(OCc2ccc(Cl)cc2Br)c1] |

| Example | Formula |
|---------|---------|
| 110 | 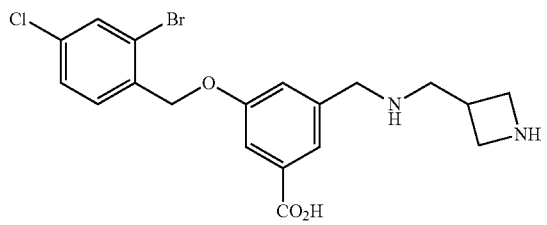 [SMILES: O=C(O)c1cc(CNCC2CNC2)cc(OCc2ccc(Cl)cc2Br)c1] |
| 111 | 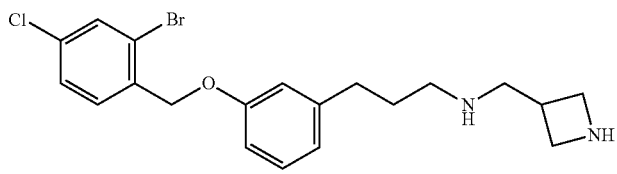 [SMILES: Clc1ccc(COc2cccc(CCCNCC3CNC3)c2)c(Br)c1] |
| 112 | 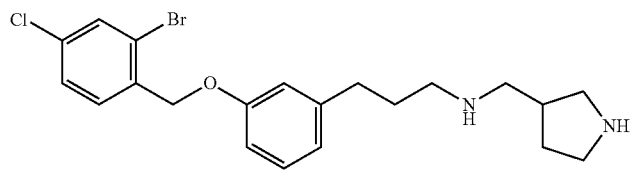 [SMILES: Clc1ccc(COc2cccc(CCCNCC3CCNC3)c2)c(Br)c1] |
| 113 | 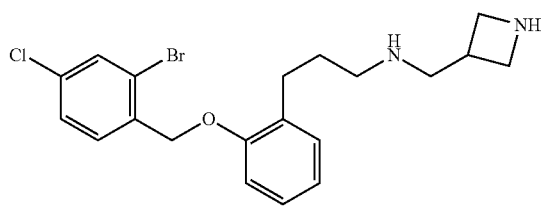 [SMILES: Clc1ccc(COc2ccccc2CCCNCC2CNC2)c(Br)c1] |
| 114 | 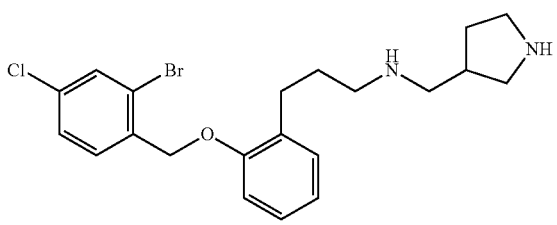 [SMILES: Clc1ccc(COc2ccccc2CCCNCC2CCNC2)c(Br)c1] |
| 115 | 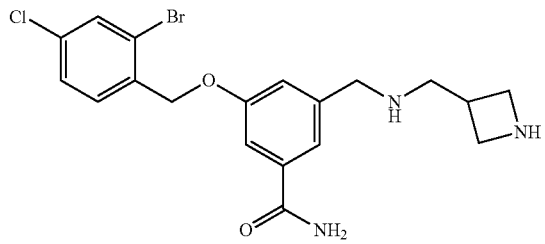 [SMILES: NC(=O)c1cc(CNCC2CNC2)cc(OCc2ccc(Cl)cc2Br)c1] |
| 116 | 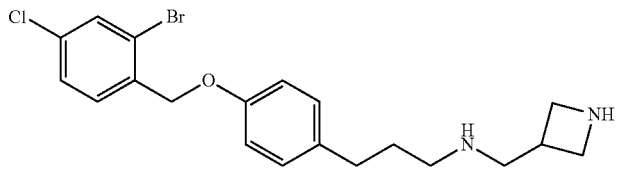 [SMILES: Clc1ccc(COc2ccc(CCCNCC3CNC3)cc2)c(Br)c1] |

| Example | Formula |
|---|---|
| 117 | 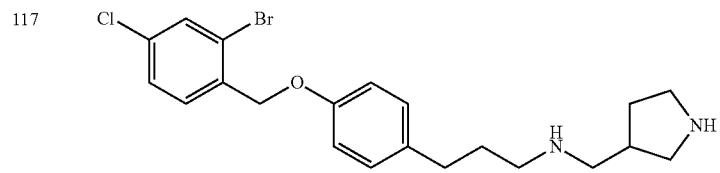 |
| 118 | 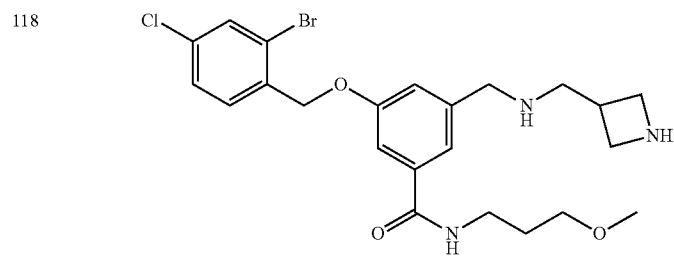 |
| 119 | 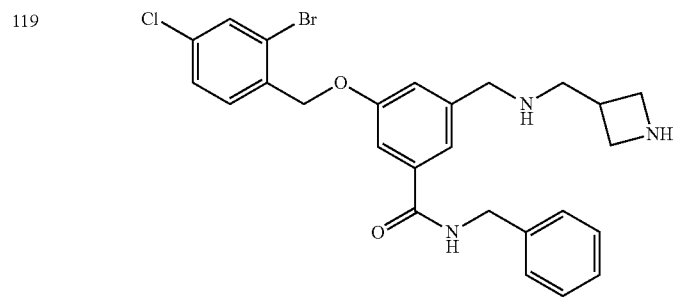 |
| 120 | 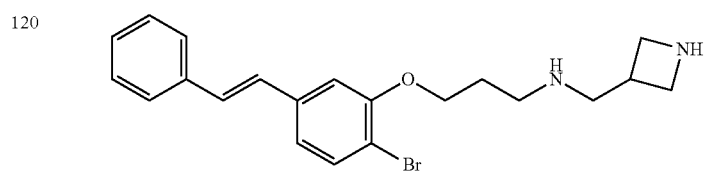 |
| 121 | 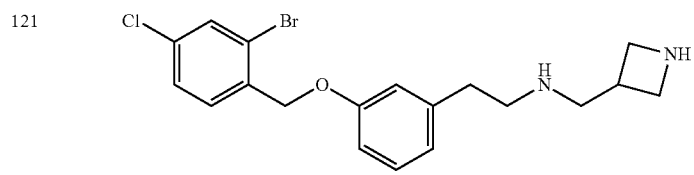 |
| 122 | 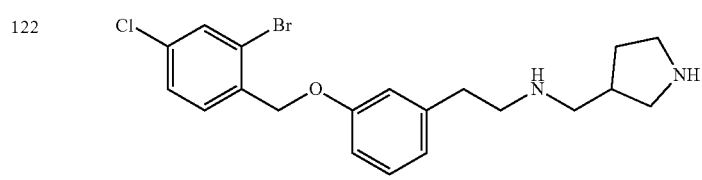 |
| 123 | 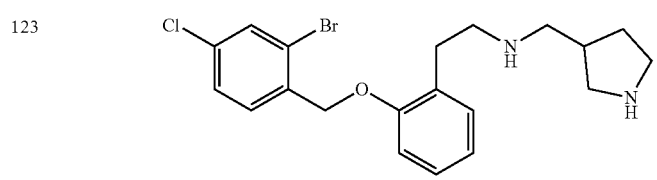 |

| Example | Formula |
|---|---|
| 124 | 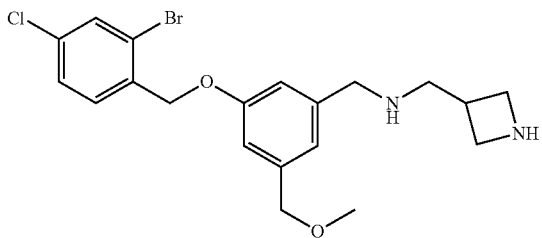 [SMILES: COCc1cc(CNCC2CNC2)cc(OCc2ccc(Cl)cc2Br)c1] |
| 125 | 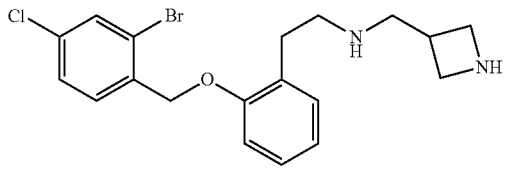 [SMILES: Clc1ccc(COc2ccccc2CCNCC2CNC2)c(Br)c1] |
| 126 | 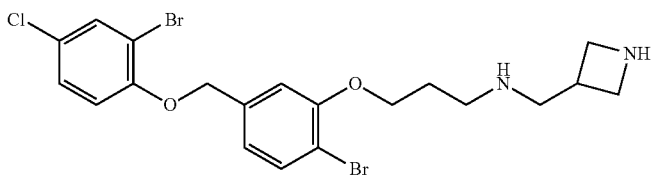 [SMILES: Clc1ccc(OCc2ccc(Br)c(OCCCNCC3CNC3)c2)c(Br)c1] |
| 127 | 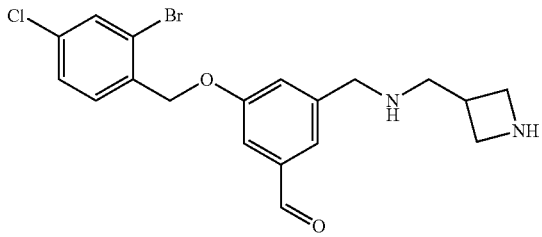 [SMILES: O=Cc1cc(CNCC2CNC2)cc(OCc2ccc(Cl)cc2Br)c1] |
| 128 | 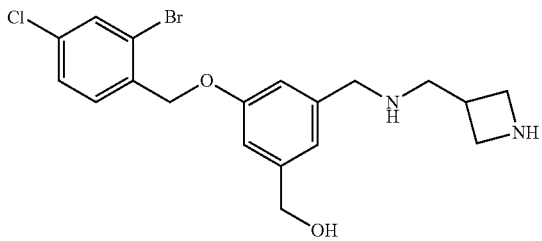 [SMILES: OCc1cc(CNCC2CNC2)cc(OCc2ccc(Cl)cc2Br)c1] |
| 129 | 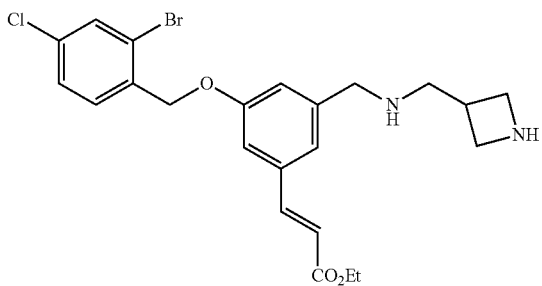 [SMILES: CCOC(=O)/C=C/c1cc(CNCC2CNC2)cc(OCc2ccc(Cl)cc2Br)c1] |

| Example | Formula |
|---------|---------|
| 130 | 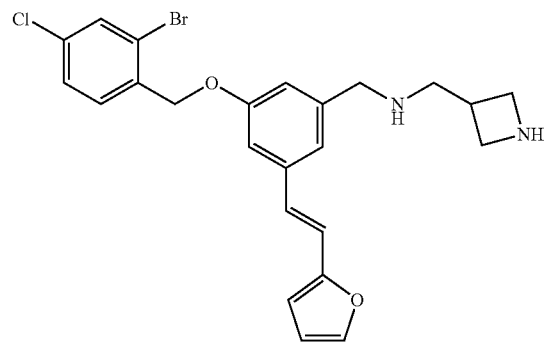 [SMILES: Clc1ccc(COc2cc(/C=C/c3ccco3)cc(CNCC3CNC3)c2)c(Br)c1] |
| 131 | 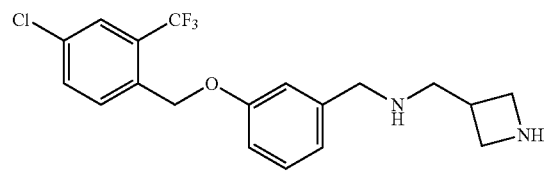 [SMILES: FC(F)(F)c1cc(Cl)ccc1COc1cccc(CNCC2CNC2)c1] |
| 132 | 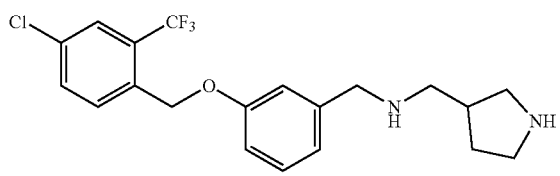 [SMILES: FC(F)(F)c1cc(Cl)ccc1COc1cccc(CNCC2CCNC2)c1] |
| 133 | 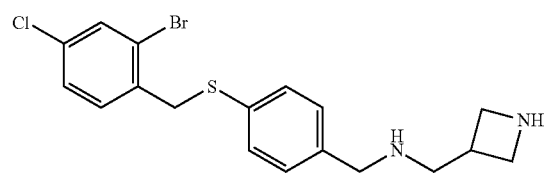 [SMILES: Clc1ccc(CSc2ccc(CNCC3CNC3)cc2)c(Br)c1] |
| 134 | 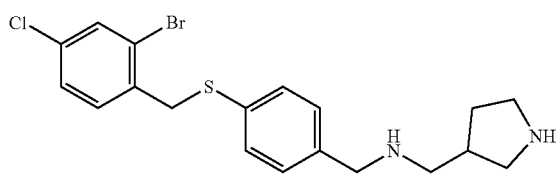 [SMILES: Clc1ccc(CSc2ccc(CNCC3CCNC3)cc2)c(Br)c1] |
| 135 | 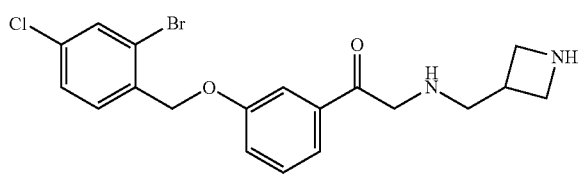 [SMILES: O=C(CNCC1CNC1)c1cccc(OCc2ccc(Cl)cc2Br)c1] |
| 136 | 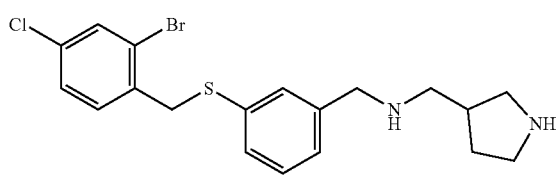 [SMILES: Clc1ccc(CSc2cccc(CNCC3CCNC3)c2)c(Br)c1] |
| 137 | 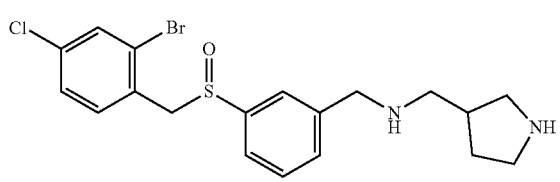 [SMILES: O=S(Cc1ccc(Cl)cc1Br)c1cccc(CNCC2CCNC2)c1] |

| Example | Formula |
|---|---|
| 138 | 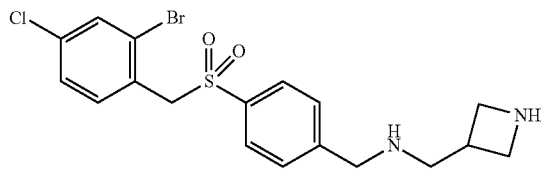 [SMILES: O=S(=O)(Cc1ccc(Cl)cc1Br)c1ccc(CNCC2CNC2)cc1] |
| 139 | 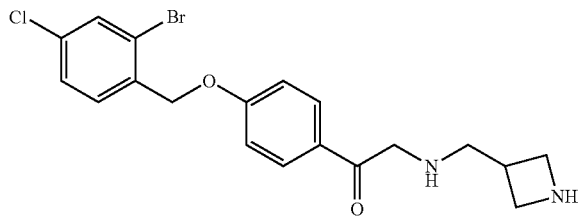 [SMILES: O=C(CNCC1CNC1)c1ccc(OCc2ccc(Cl)cc2Br)cc1] |
| 140 | 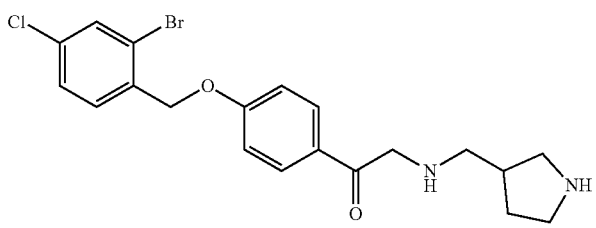 [SMILES: O=C(CNCC1CCNC1)c1ccc(OCc2ccc(Cl)cc2Br)cc1] |
| 141 | 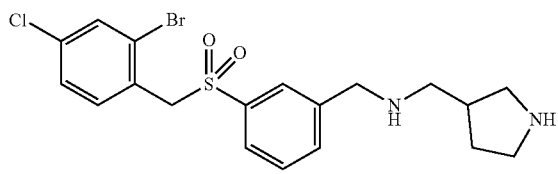 [SMILES: O=S(=O)(Cc1ccc(Cl)cc1Br)c1cccc(CNCC2CCNC2)c1] |
| 142 | 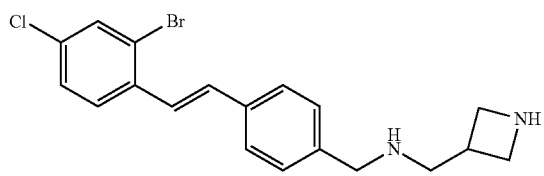 [SMILES: Clc1ccc(/C=C/c2ccc(CNCC3CNC3)cc2)c(Br)c1] |
| 143 | 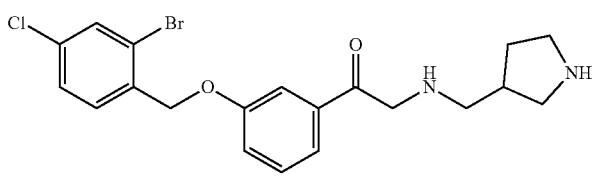 [SMILES: O=C(CNCC1CCNC1)c1cccc(OCc2ccc(Cl)cc2Br)c1] |
| 145 | 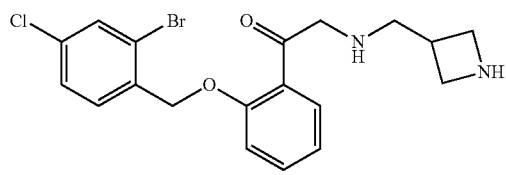 [SMILES: O=C(CNCC1CNC1)c1ccccc1OCc1ccc(Cl)cc1Br] |
| 147 | 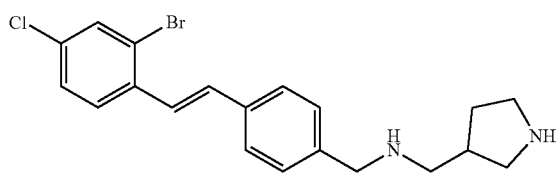 [SMILES: Clc1ccc(/C=C/c2ccc(CNCC3CCNC3)cc2)c(Br)c1] |

| Example | Formula |
|---------|---------|
| 148 | 4-chloro-2-bromobenzyl ether of 2-nitro-phenol linked via CH2-NH-CH2-pyrrolidin-3-yl |
| 151 | 4-chloro-2-bromo-N-(2-chloro-4-((pyrrolidin-3-ylmethylamino)methyl)phenyl)benzamide |
| 152 | 2,4-dichloro-N-(2-chloro-4-((pyrrolidin-3-ylmethylamino)methyl)phenyl)benzamide |
| 153 | 4-chloro-2-(trifluoromethyl)-N-(2-chloro-4-((pyrrolidin-3-ylmethylamino)methyl)phenyl)benzamide |
| 154 | 4-chloro-2-bromobenzyl ether linked to phenyl-C(O)-CH2-NH-CH2-pyrrolidin-3-yl |
| 155 | 2,4-bis(trifluoromethyl)-N-(2-chloro-4-((azetidin-3-ylmethylamino)methyl)phenyl)benzamide |
| 156 | 2,4-dichloro-N-(2-chloro-4-((azetidin-3-ylmethylamino)methyl)phenyl)benzamide |
| 157 | (E)-4-chloro-2-bromostyryl linked to 3-chloro-5-((pyrrolidin-3-ylmethylamino)methyl)phenyl |

-continued
| Example | Formula |
|---|---|
| 158 | 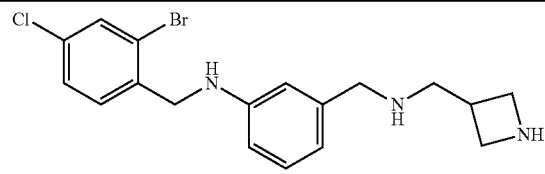 |
| 159 | 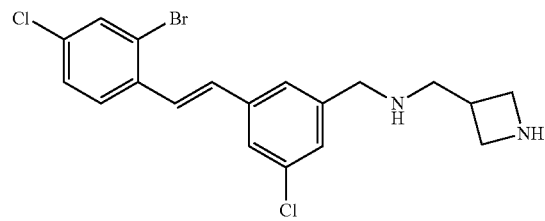 [SMILES: Clc1cc(/C=C/c2ccc(Cl)cc2Br)cc(CNCC2CNC2)c1] |
| 160 | 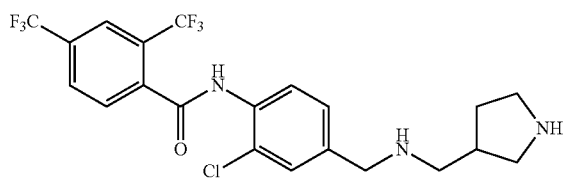 [SMILES: O=C(Nc1ccc(CNCC2CCNC2)cc1Cl)c1ccc(C(F)(F)F)cc1C(F)(F)F] |
| 161 | 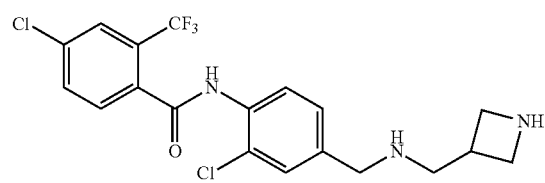 |
| 162 | 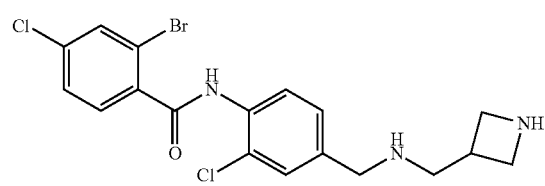 [SMILES: O=C(Nc1ccc(CNCC2CNC2)cc1Cl)c1ccc(Cl)cc1Br] |
| 163 | 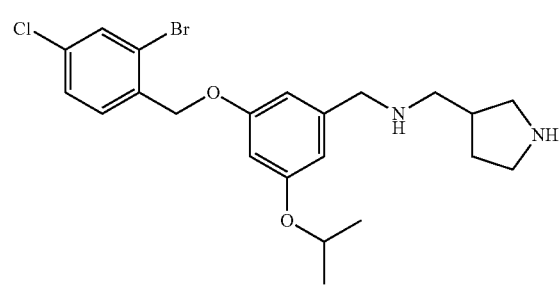 [SMILES: CC(C)Oc1cc(CNCC2CCNC2)cc(OCc2ccc(Cl)cc2Br)c1] |
| 164 | 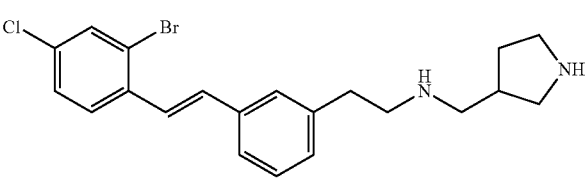 [SMILES: Clc1ccc(/C=C/c2cccc(CCNCC3CCNC3)c2)c(Br)c1] |
| 165 | 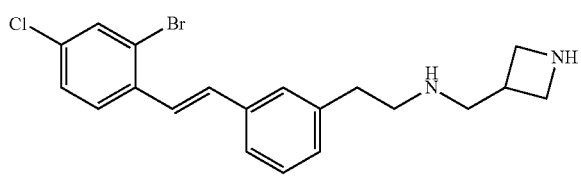 [SMILES: Clc1ccc(/C=C/c2cccc(CCNCC3CNC3)c2)c(Br)c1] |

| Example | Formula |
|---|---|
| 166 | 2,4-dichlorobenzyl ether of 3-(cyclopropylmethoxy)-5-({[(azetidin-3-yl)methyl]amino}methyl)phenol |
| 167 | 4-chloro-2-bromobenzyl ether of 3-isopropoxy-5-{[dimethyl({(pyrrolidin-3-yl)methyl})ammonio]methyl}phenol |
| 168 | (E)-1-(4-chloro-2-bromophenyl)-3-{3-[({(azetidin-3-yl)methyl}amino)methyl]phenyl}prop-1-ene |
| 169 | (E)-1-(4-chloro-2-bromophenyl)-3-{3-[({(pyrrolidin-3-yl)methyl}amino)methyl]phenyl}prop-1-ene |
| 170 | N-(4-chloro-2-bromophenyl)-3-[({(azetidin-3-yl)methyl}amino)methyl]benzylamine |
| 171 | (E)-1-(4-chloro-2-bromophenyl)-2-{3-[({((2S,4S)-4-aminopyrrolidin-2-yl)methyl}amino)methyl]phenyl}ethene |
| 172 | 4-chloro-2-bromobenzyl ether of 3-[({((2S,4S)-4-aminopyrrolidin-2-yl)methyl}amino)methyl]phenol |
| 173 | 4-chloro-2-bromobenzyl 3-[({(azetidin-3-yl)methyl}amino)methyl]benzyl ether |
| 174 | 4-chloro-2-bromobenzyl 3-[({(pyrrolidin-3-yl)methyl}amino)methyl]benzyl ether |

| Example | Formula |
|---|---|
| 175 | 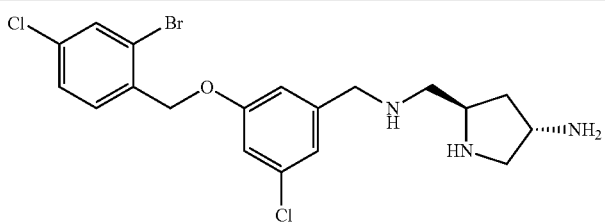 [SMILES: N[C@@H]1CN[C@@H](CNCc2cc(Cl)cc(OCc3ccc(Cl)cc3Br)c2)C1] |
| 176 | 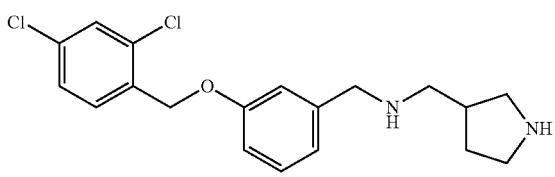 |
| 177 | 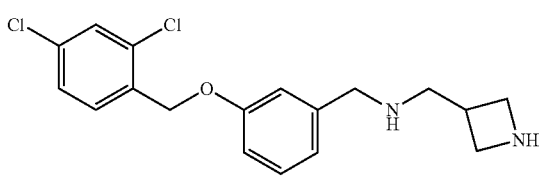 |
| 178 | 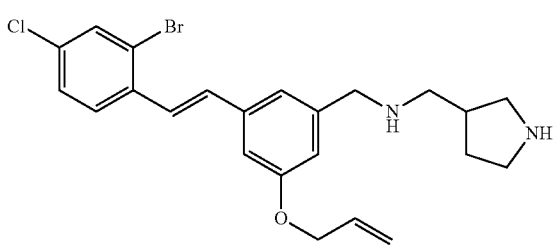 [SMILES: C=CCOc1cc(/C=C/c2ccc(Cl)cc2Br)cc(CNCC2CCNC2)c1] |
| 179 | 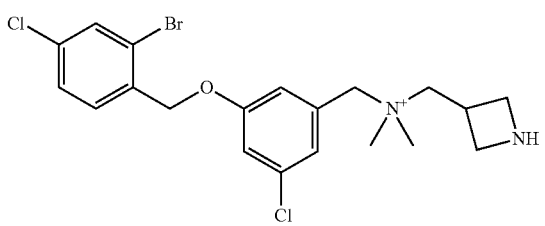 [SMILES: C[N+](C)(Cc1cc(Cl)cc(OCc2ccc(Cl)cc2Br)c1)CC1CNC1] |
| 180 | 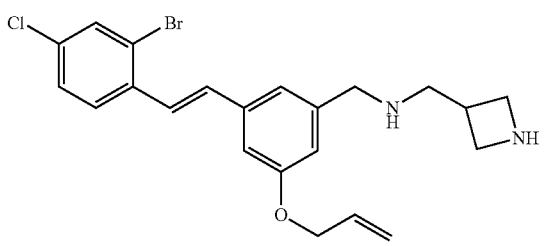 [SMILES: C=CCOc1cc(/C=C/c2ccc(Cl)cc2Br)cc(CNCC2CNC2)c1] |
| 181 | 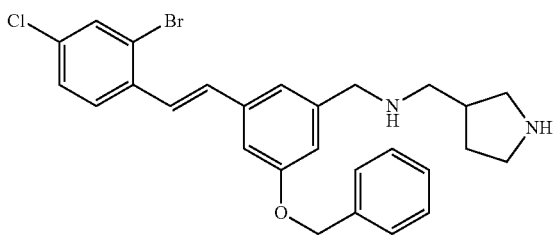 [SMILES: Clc1ccc(/C=C/c2cc(CNCC3CCNC3)cc(OCc3ccccc3)c2)c(Br)c1] |

-continued

| Example | Formula |
|---|---|
| 182 | 4-Cl, 2-Br-phenyl-CH=CH-[3-(OCH2CH(CH3)2)-5-yl]-CH2-NH-CH2-(pyrrolidin-3-yl) |
| 183 | 4-Cl, 2-CF3-phenyl-S-CH2-[3-(O-allyl)-5-yl]-CH2-NH-CH2-(azetidin-3-yl) |
| 184 | 4-Cl, 2-CF3-phenyl-S-CH2-[3-(O-allyl)-5-yl]-CH2-NH-CH2-(pyrrolidin-3-yl) |
| 185 | 4-Cl, 2-Br-phenyl-CH=CH-[2-(O(CH2)3NH-CH2-(pyrrolidin-3-yl))-4-Cl-phenyl] |
| 186 | 4-Cl, 2-Br-phenyl-CH=CH-[2-(O(CH2)3NH-CH2-(pyrrolidin-3-yl))-5-Cl-phenyl] |
| 187 | 4-Cl, 2-Br-phenyl-CH=CH-[2-(O(CH2)3NH-CH2-(azetidin-3-yl))-4-Cl-phenyl] |
| 188 | 4-Cl, 2-Br-phenyl-CH=CH-[3-(O(CH2)3NH-CH2-(azetidin-3-yl))-5-Cl-phenyl] |

Note: Structural formulas shown as images in original; textual representations approximated.

-continued
| Example | Formula |
|---|---|
| 189 | 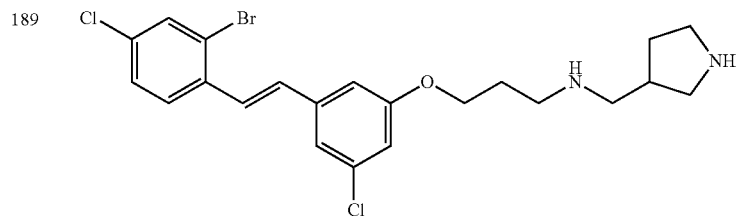 |
| 190 | 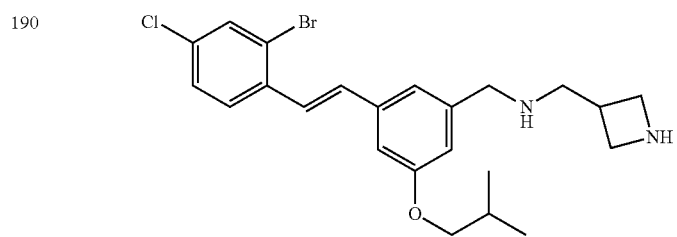 |
| 191 | 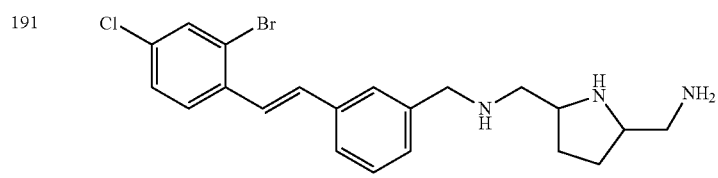 |
| 192 | 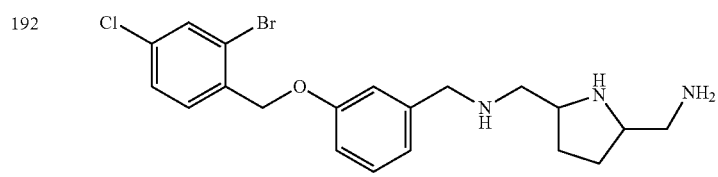 |
| 193 | 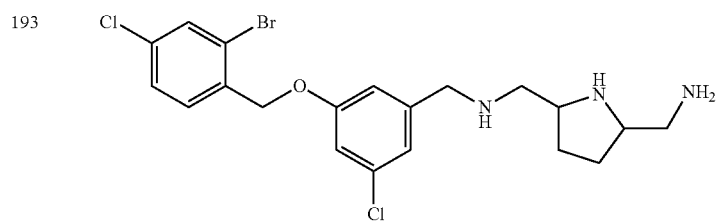 |
| 194 | 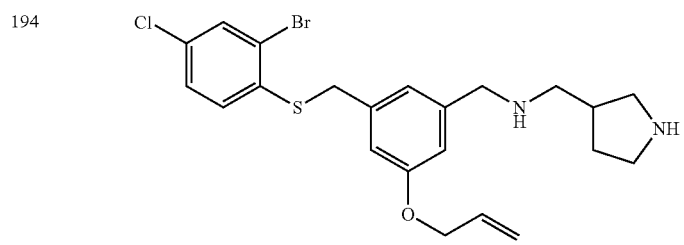 |
| 195 | 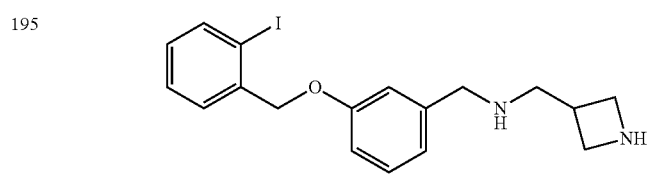 |

| Example | Formula |
|---|---|
| 196 | 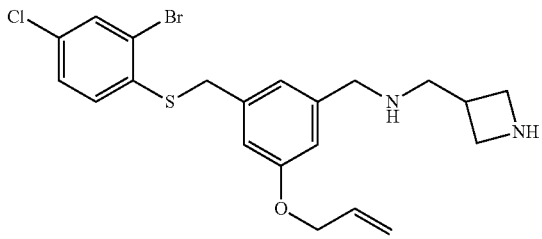 [SMILES: C=CCOc1cc(CNCC2CNC2)cc(CSc2ccc(Cl)cc2Br)c1] |
| 197 | 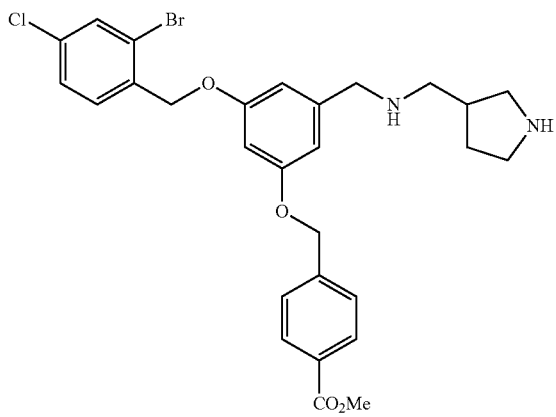 [SMILES: COC(=O)c1ccc(COc2cc(CNCC3CCNC3)cc(OCc3ccc(Cl)cc3Br)c2)cc1] |
| 198 | 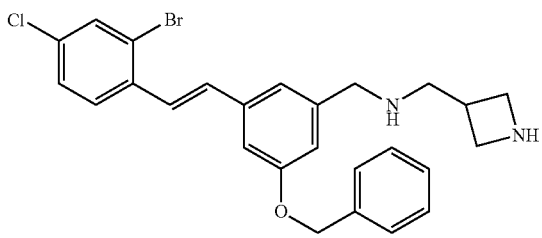 [SMILES: Clc1ccc(/C=C/c2cc(CNCC3CNC3)cc(OCc3ccccc3)c2)c(Br)c1] |
| 199 | 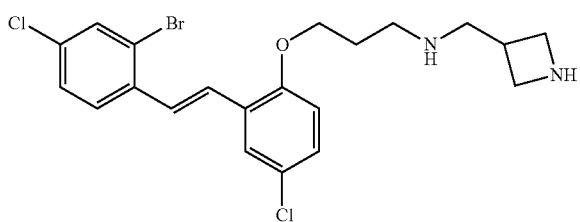 [SMILES: Clc1ccc(/C=C/c2cc(Cl)ccc2OCCCNCC2CNC2)c(Br)c1] |
| 200 | 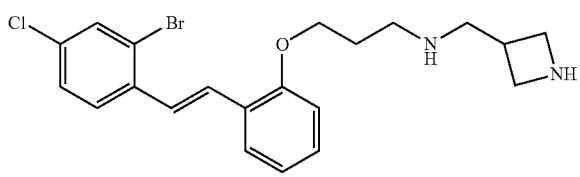 [SMILES: Clc1ccc(/C=C/c2ccccc2OCCCNCC2CNC2)c(Br)c1] |
| 201 | 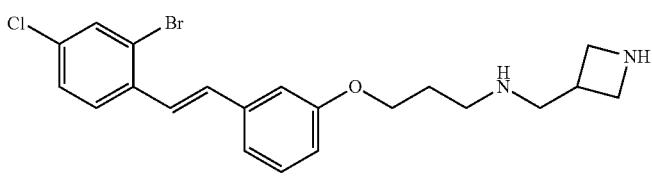 [SMILES: Clc1ccc(/C=C/c2cccc(OCCCNCC3CNC3)c2)c(Br)c1] |

-continued
| Example | Formula |
|---|---|
| 202 | 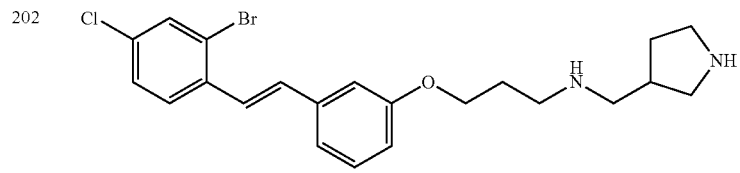 |
| 203 | 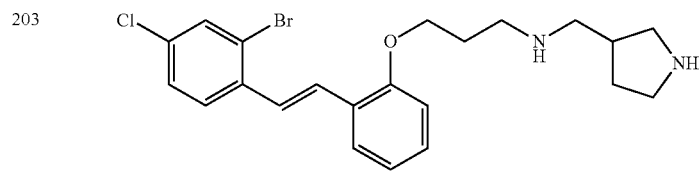 |
| 204 | 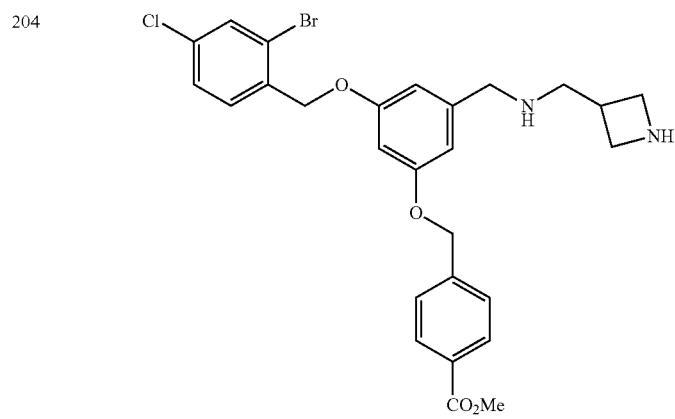 |
| 205 | 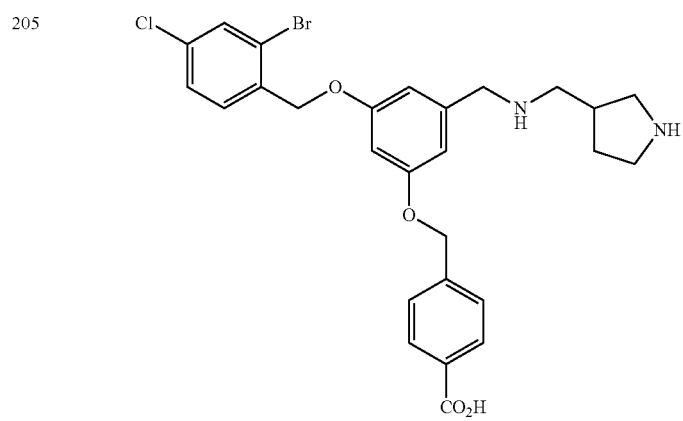 |
| 206 | 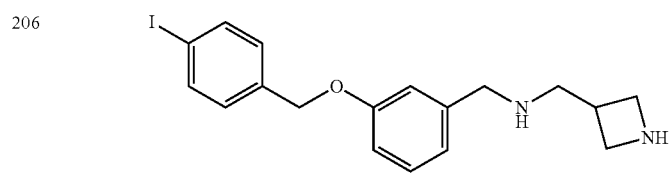 |
| 207 | 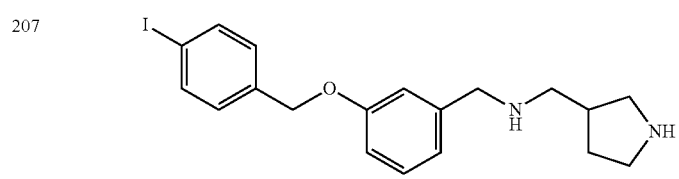 |

| Example | Formula |
|---|---|
| 208 | 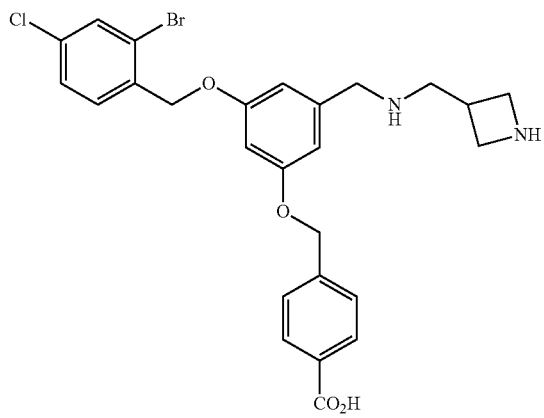 [SMILES: O=C(O)c1ccc(COc2cc(CNCC3CNC3)cc(OCc3ccc(Cl)cc3Br)c2)cc1] |
| 209 | 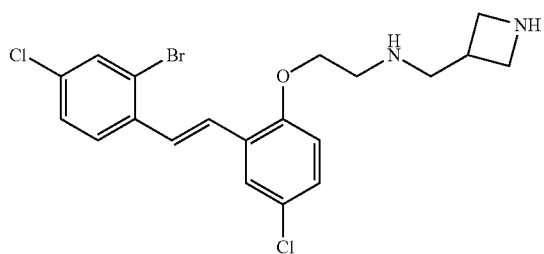 [SMILES: Clc1ccc(/C=C/c2cc(Cl)ccc2OCCNCC2CNC2)c(Br)c1] |
| 210 | 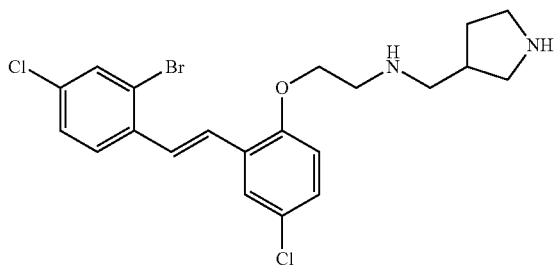 [SMILES: Clc1ccc(/C=C/c2cc(Cl)ccc2OCCNCC2CCNC2)c(Br)c1] |
| 211 | 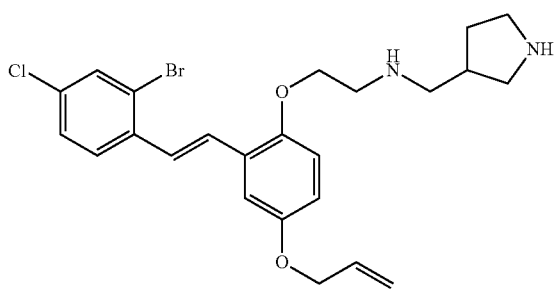 [SMILES: C=CCOc1ccc(OCCNCC2CCNC2)c(/C=C/c2ccc(Cl)cc2Br)c1] |
| 212 | 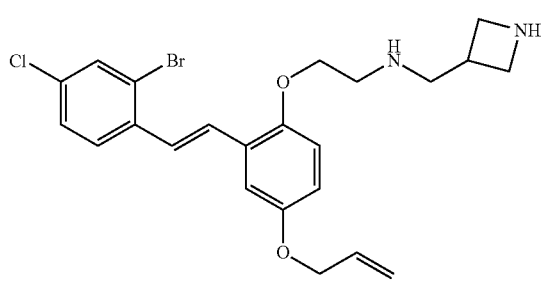 [SMILES: C=CCOc1ccc(OCCNCC2CNC2)c(/C=C/c2ccc(Cl)cc2Br)c1] |

| Example | Formula |
|---|---|
| 213 | (4-chloro-2-bromophenyl)-CH=CH-[phenyl with O-CH2CH2CH2-NH-CH2-(pyrrolidin-3-yl) and O-allyl substituents] |
| 214 | (4-chloro-2-bromophenyl)-CH=CH-[phenyl with O-CH2CH2CH2-NH-CH2-(azetidin-3-yl) and O-allyl substituents] |
| 215 | (4-t-Bu-phenyl)-CH2-O-(4-phenyl)-CH2-NH-CH2-(pyrrolidin-3-yl) |
| 216 | (4-t-Bu-phenyl)-CH2-O-(3-phenyl)-CH2-NH-CH2-(pyrrolidin-3-yl) |
| 217 | (4-chloro-2-bromophenyl)-CH2-O-[phenyl with CH2-NH-CH2-(pyrrolidin-3-yl) and isopropyl substituents] |
| 218 | (4-chloro-2-bromophenyl)-CH2-O-[phenyl with CH2-NH-CH2-(pyrrolidin-3-yl) and t-Bu substituents] |
| 219 | (3-iodophenyl)-CH2-O-(3-phenyl)-CH2-NH-CH2-(azetidin-3-yl) |

-continued
| Example | Formula |
|---------|---------|
| 220 | 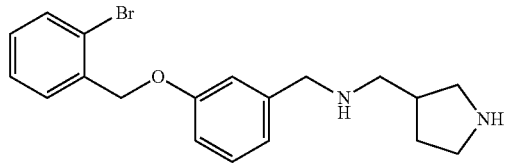 [SMILES: Brc1ccccc1COc1cccc(CNCC2CCNC2)c1] |
| 221 | 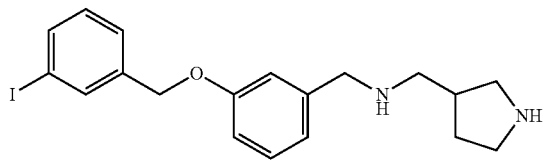 [SMILES: Ic1cccc(COc2cccc(CNCC3CCNC3)c2)c1] |
| 222 | 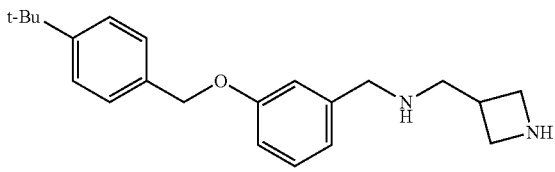 [SMILES: CC(C)(C)c1ccc(COc2cccc(CNCC3CNC3)c2)cc1] |
| 223 | 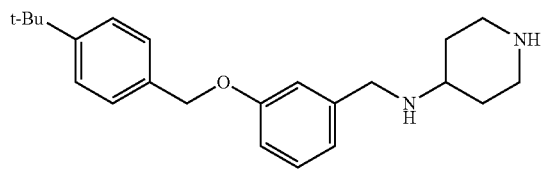 [SMILES: CC(C)(C)c1ccc(COc2cccc(CNC3CCNCC3)c2)cc1] |
| 224 | 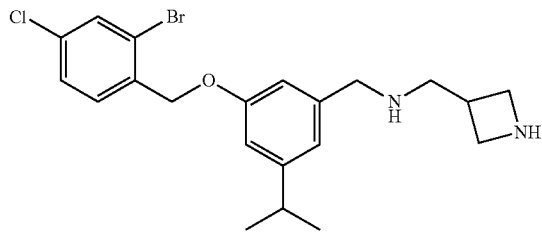 [SMILES: CC(C)c1cc(CNCC2CNC2)cc(OCc2ccc(Cl)cc2Br)c1] |
| 225 | 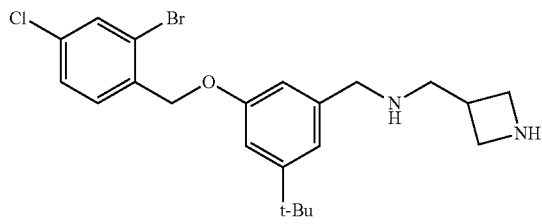 [SMILES: CC(C)(C)c1cc(CNCC2CNC2)cc(OCc2ccc(Cl)cc2Br)c1] |
| 226 | 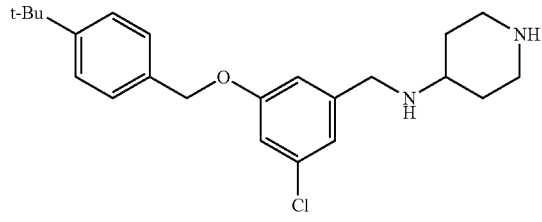 [SMILES: CC(C)(C)c1ccc(COc2cc(Cl)cc(CNC3CCNCC3)c2)cc1] |

| Example | Formula |
|---|---|
| 227 | 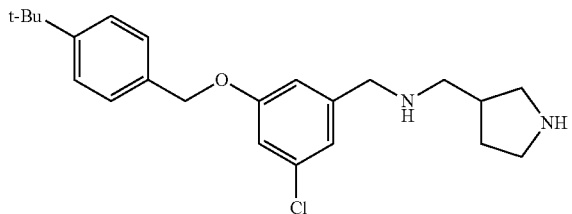 [SMILES: CC(C)(C)c1ccc(COc2cc(Cl)cc(CNCC3CCNC3)c2)cc1] |
| 228 | 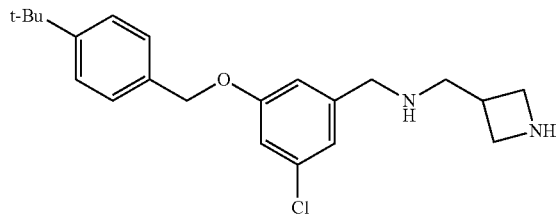 [SMILES: CC(C)(C)c1ccc(COc2cc(Cl)cc(CNCC3CNC3)c2)cc1] |
| 229 | 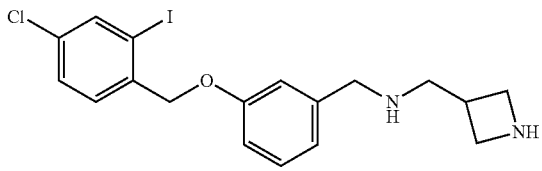 [SMILES: Clc1ccc(COc2cccc(CNCC3CNC3)c2)c(I)c1] |
| 230 | 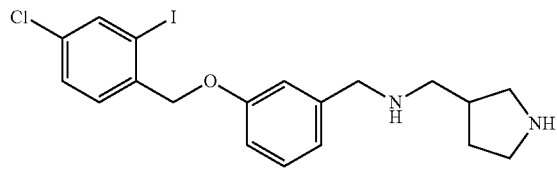 |
| 231 | 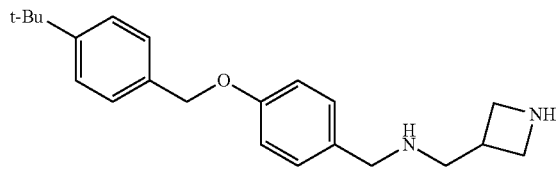 [SMILES: CC(C)(C)c1ccc(COc2ccc(CNCC3CNC3)cc2)cc1] |
| 232 | 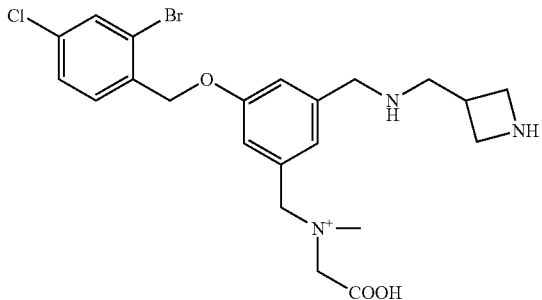 [SMILES: C[NH+](CC(=O)O)Cc1cc(CNCC2CNC2)cc(OCc2ccc(Cl)cc2Br)c1] |
| 233 | 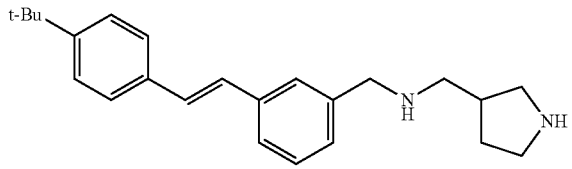 [SMILES: CC(C)(C)c1ccc(/C=C/c2cccc(CNCC3CCNC3)c2)cc1] |

-continued
| Example | Formula |
|---------|---------|
| 234 | 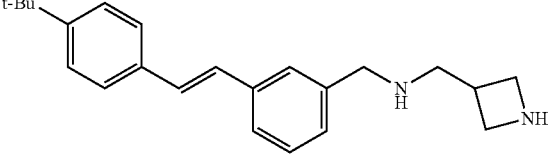 |
| 235 | 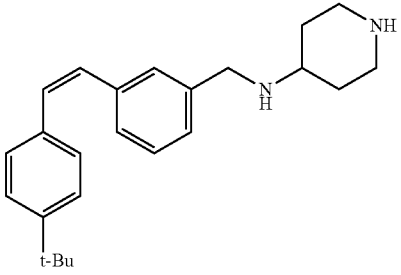 [SMILES: CC(C)(C)c1ccc(/C=C\c2cccc(CNC3CCNCC3)c2)cc1] |
| 236 | 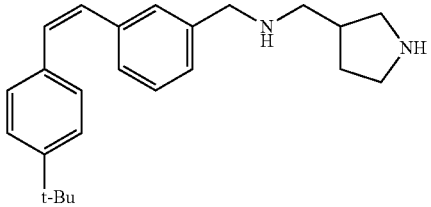 [SMILES: CC(C)(C)c1ccc(/C=C\c2cccc(CNCC3CCNC3)c2)cc1] |
| 237 | 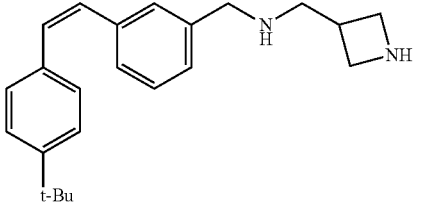 [SMILES: CC(C)(C)c1ccc(/C=C\c2cccc(CNCC3CNC3)c2)cc1] |
| 238 | 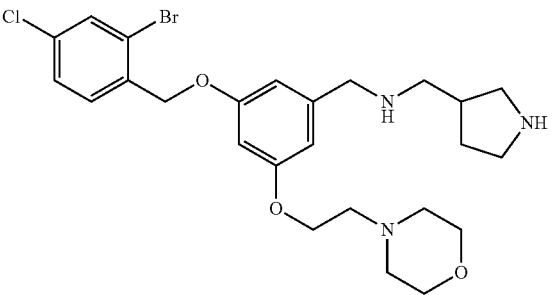 [SMILES: Clc1ccc(COc2cc(CNCC3CCNC3)cc(OCCN3CCOCC3)c2)c(Br)c1] |
| 239 | 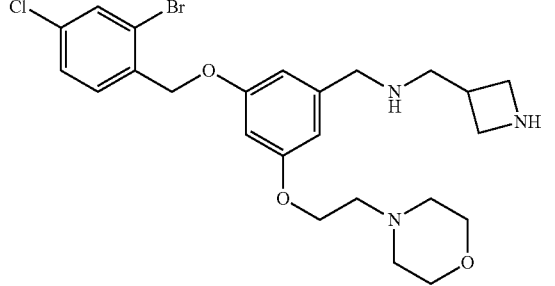 [SMILES: Clc1ccc(COc2cc(CNCC3CNC3)cc(OCCN3CCOCC3)c2)c(Br)c1] |

| Example | Formula |
|---|---|
| 240 | 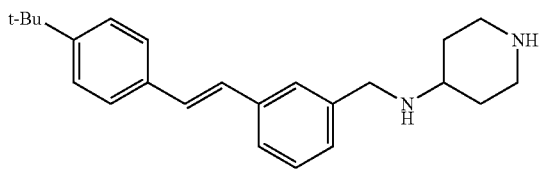 [SMILES: CC(C)(C)c1ccc(/C=C/c2cccc(CNC3CCNCC3)c2)cc1] |
| 241 | 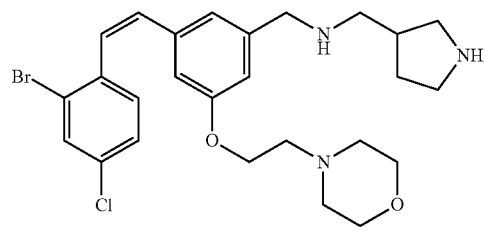 [SMILES: Clc1ccc(/C=C\c2cc(CNCC3CCNC3)cc(OCCN3CCOCC3)c2)c(Br)c1] |
| 242 | 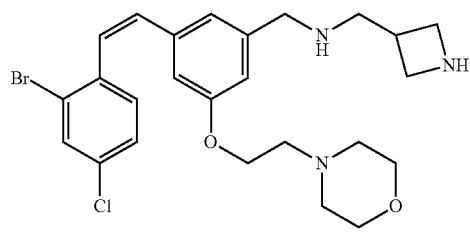 [SMILES: Clc1ccc(/C=C\c2cc(CNCC3CNC3)cc(OCCN3CCOCC3)c2)c(Br)c1] |
| 243 | 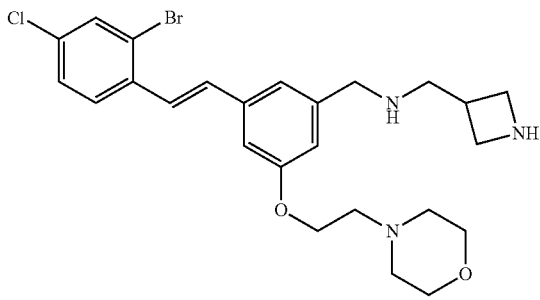 [SMILES: Clc1ccc(/C=C/c2cc(CNCC3CNC3)cc(OCCN3CCOCC3)c2)c(Br)c1] |
| 244 | 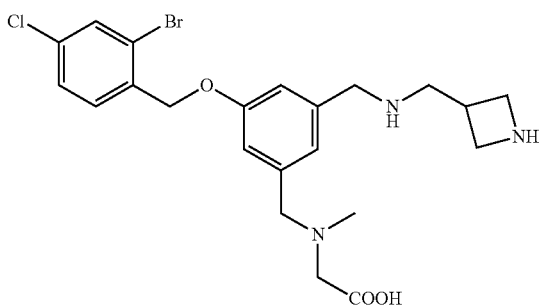 [SMILES: CN(CC(=O)O)Cc1cc(CNCC2CNC2)cc(OCc2ccc(Cl)cc2Br)c1] |

-continued

| Example | Formula |
|---------|---------|
| 245 | |
| 246 | |
| 247 | |
| 248 | |

-continued
| Example | Formula |
|---------|---------|
| 249 | 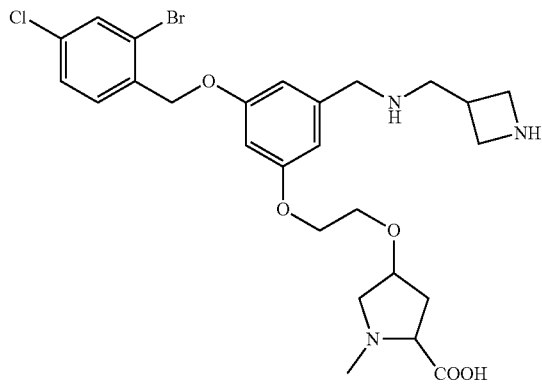 [SMILES: CN1CC(OCCOc2cc(CNCC3CNC3)cc(OCc3ccc(Cl)cc3Br)c2)CC1C(=O)O] |
| 250 | 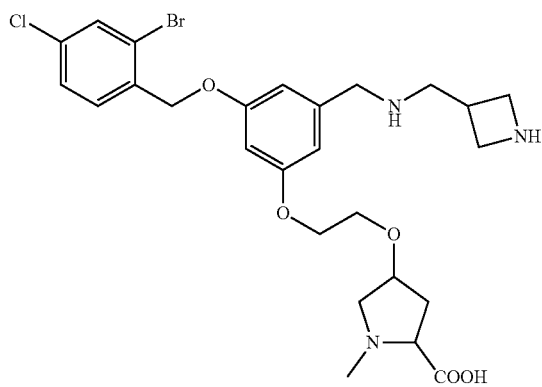 [SMILES: CN1CC(OCCOc2cc(CNCC3CNC3)cc(OCc3ccc(Cl)cc3Br)c2)CC1C(=O)O] |
| 251 | 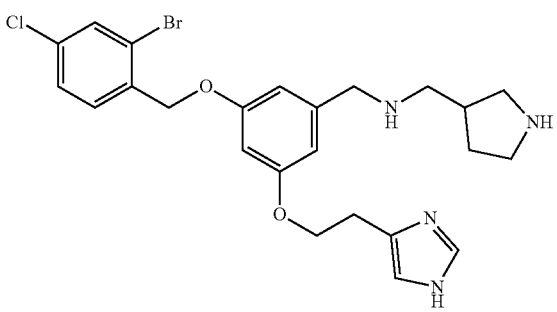 |
| 252 | 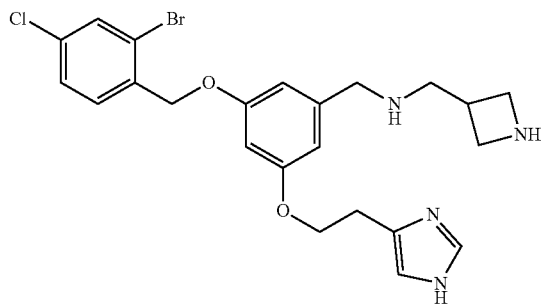 [SMILES: Clc1ccc(COc2cc(CNCC3CNC3)cc(OCCc3c[nH]cn3)c2)c(Br)c1] |
| 253 | 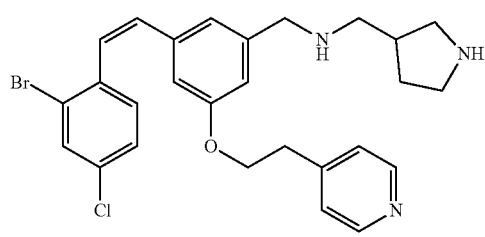 [SMILES: Clc1ccc(/C=C\c2cc(CNCC3CCNC3)cc(OCCc3ccncc3)c2)c(Br)c1] |

| Example | Formula |
|---|---|
| 254 | 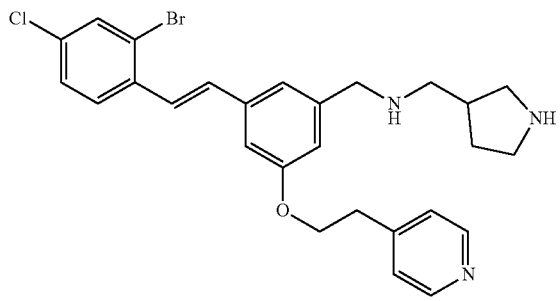 |
| 255 | 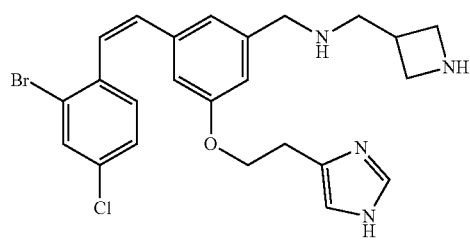 [SMILES: Clc1ccc(/C=C\c2cc(CNCC3CNC3)cc(OCCc3c[nH]cn3)c2)c(Br)c1] |
| 256 | 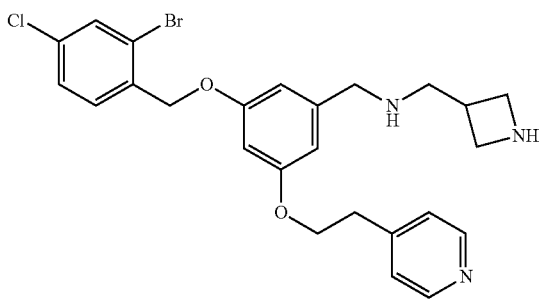 |
| 257 | 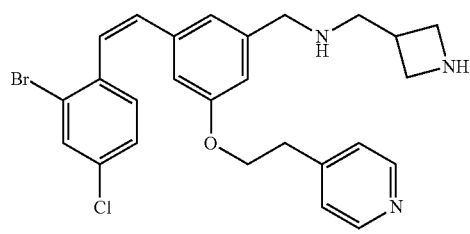 [SMILES: Clc1ccc(/C=C\c2cc(CNCC3CNC3)cc(OCCc3ccncc3)c2)c(Br)c1] |
| 258 | 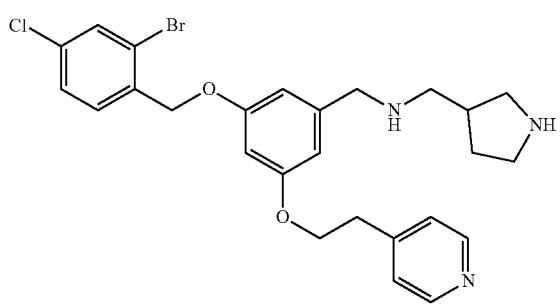 [SMILES: Clc1ccc(COc2cc(CNCC3CCNC3)cc(OCCc3ccncc3)c2)c(Br)c1] |

| Example | Formula |
|---|---|
| 259 | *(structure: 2-bromo-4-chlorophenyl cis-vinyl linked to phenyl with CH2NH-CH2-pyrrolidine substituent and O-CH2CH2-imidazole substituent)* |
| 260 | *(structure: 4-chloro-2-bromophenyl trans-vinyl linked to phenyl with CH2NH-CH2-azetidine and O-CH2CH2-pyridin-4-yl)* |
| 261 | *(structure: 4-chloro-2-bromophenyl trans-vinyl linked to phenyl with CH2NH-CH2-azetidine and O-CH2CH2-imidazole)* |
| 262 | *(structure: 4-chloro-2-bromophenyl trans-vinyl linked to phenyl with CH2NH-CH2-pyrrolidine and O-CH2CH2-imidazole)* |
| 263 | *(structure: 4-chloro-2-bromobenzyloxy-phenyl with CH2NH-CH2-pyrrolidine and CH2-O-pyrrolidine bearing N,N-dimethyl and COOH)* |

| Example | Formula |
|---|---|
| 264 | 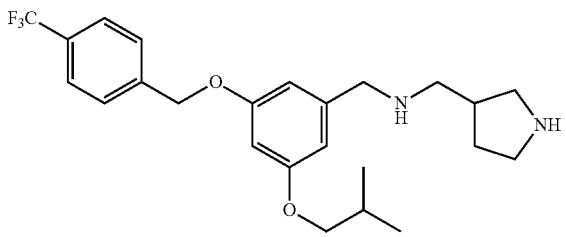 [SMILES: CC(C)COc1cc(CNCC2CCNC2)cc(OCc2ccc(C(F)(F)F)cc2)c1] |
| 265 | 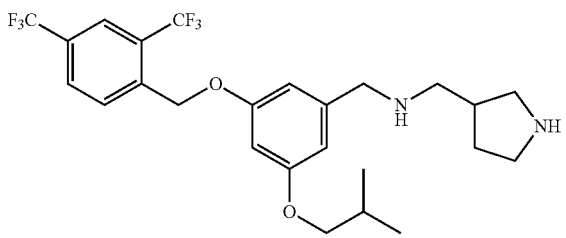 |
| 266 | 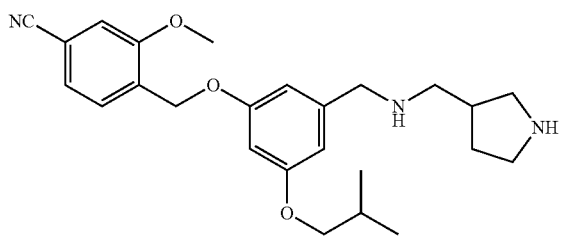 [SMILES: COc1cc(C#N)ccc1COc1cc(CNCC2CCNC2)cc(OCC(C)C)c1] |
| 268 | 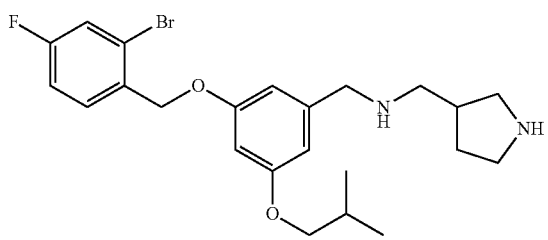 [SMILES: CC(C)COc1cc(CNCC2CCNC2)cc(OCc2ccc(F)cc2Br)c1] |
| 271 | 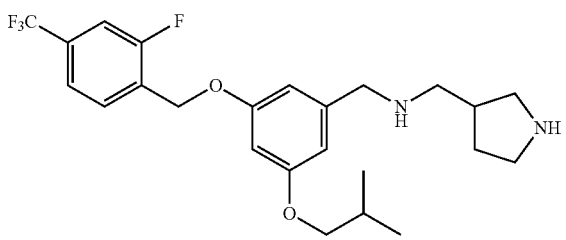 [SMILES: CC(C)COc1cc(CNCC2CCNC2)cc(OCc2ccc(C(F)(F)F)cc2F)c1] |
| 272 | 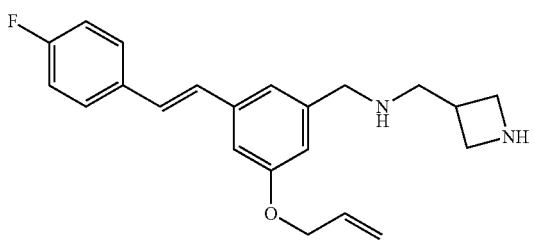 [SMILES: C=CCOc1cc(/C=C/c2ccc(F)cc2)cc(CNCC2CNC2)c1] |

| Example | Formula |
|---|---|
| 273 | 4-t-Bu-benzyloxy-3-CF3-benzyl-NH-CH2-azetidine |
| 274 | 4-t-Bu-benzyloxy-3-isobutoxy-benzyl-NH-CH2-azetidine |
| 275 | 4-CF3-styryl-3-allyloxy-benzyl-NH-CH2-azetidine |
| 276 | 3-methoxy-styryl-3-allyloxy-benzyl-NH-CH2-azetidine |
| 277 | 4-t-Bu-benzyloxy-3-(2-morpholinoethoxy)-benzyl-NH-CH2-azetidine |
| 279 | 3,4,5-trimethoxy-styryl-3-allyloxy-benzyl-NH-CH2-azetidine |

-continued
| Example | Formula |
|---|---|
| 280 | 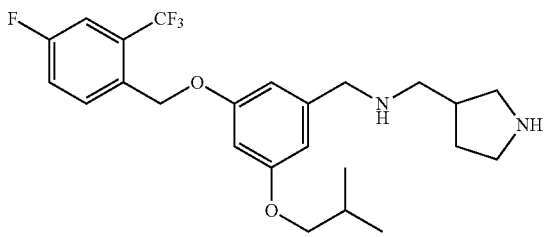 [SMILES: CC(C)COc1cc(CNCC2CCNC2)cc(OCc2ccc(F)cc2C(F)(F)F)c1] |
| 281 | 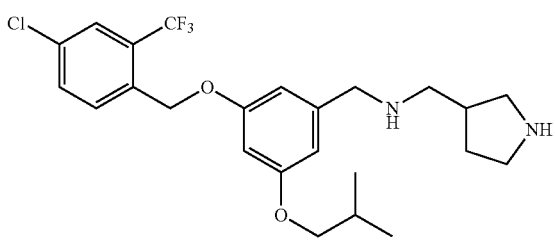 |
| 282 | 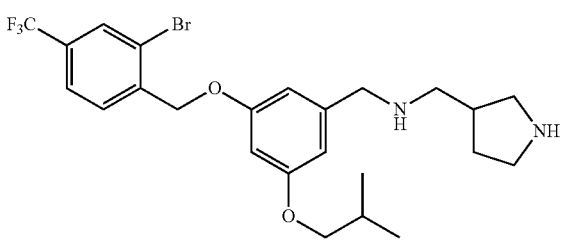 [SMILES: CC(C)COc1cc(CNCC2CCNC2)cc(OCc2ccc(C(F)(F)F)cc2Br)c1] |
| 284 | 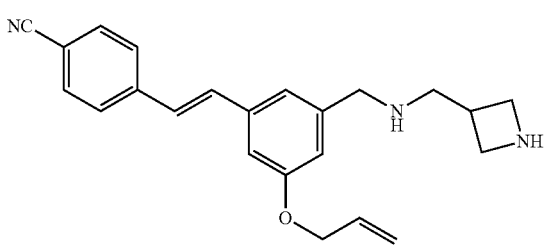 [SMILES: C=CCOc1cc(/C=C/c2ccc(C#N)cc2)cc(CNCC2CNC2)c1] |
| 285 | 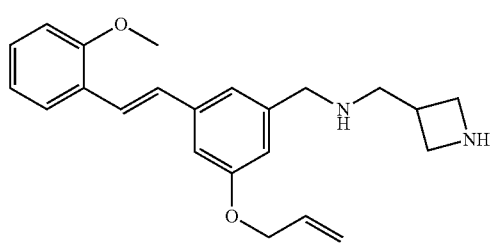 [SMILES: C=CCOc1cc(/C=C/c2ccccc2OC)cc(CNCC2CNC2)c1] |
| 286 | 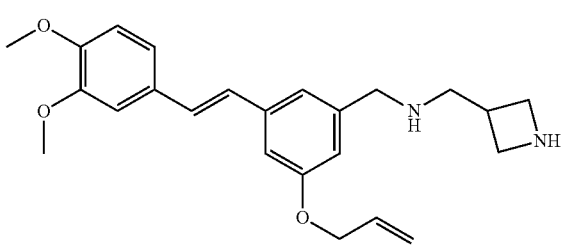 [SMILES: C=CCOc1cc(/C=C/c2ccc(OC)c(OC)c2)cc(CNCC2CNC2)c1] |

| Example | Formula |
|---|---|
| 287 | 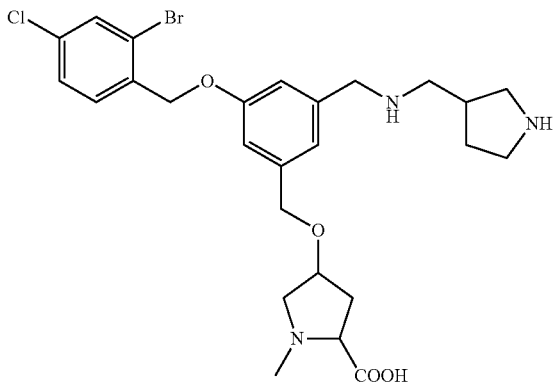 [SMILES: CN1CC(OCc2cc(CNCC3CCNC3)cc(OCc3ccc(Cl)cc3Br)c2)CC1C(=O)O] |
| 288 | 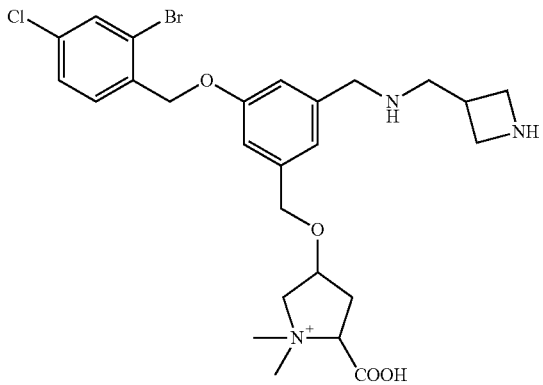 |
| 290 | 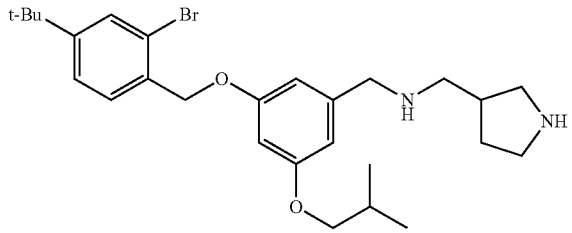 [SMILES: CC(C)COc1cc(CNCC2CCNC2)cc(OCc2ccc(C(C)(C)C)cc2Br)c1] |
| 292 | 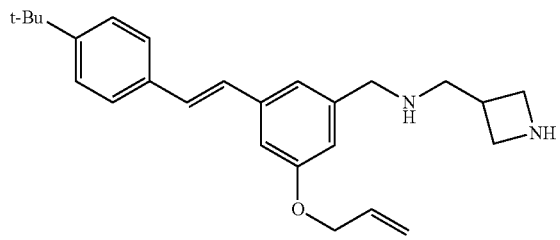 [SMILES: C=CCOc1cc(/C=C/c2ccc(C(C)(C)C)cc2)cc(CNCC2CNC2)c1] |

-continued
| Example | Formula |
|---|---|
| 293 | 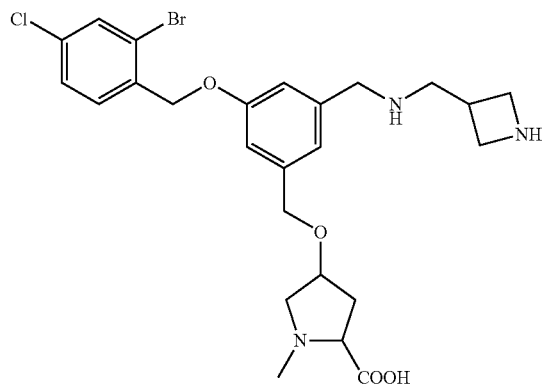 [SMILES: CN1CC(OCc2cc(CNCC3CNC3)cc(OCc3ccc(Cl)cc3Br)c2)CC1C(=O)O] |
| 294 | 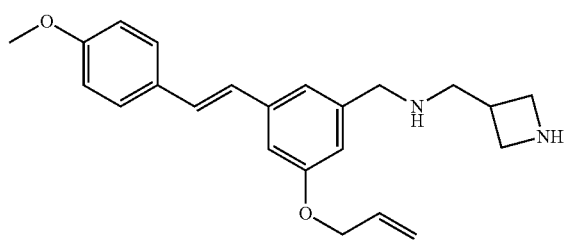 [SMILES: C=CCOc1cc(/C=C/c2ccc(OC)cc2)cc(CNCC2CNC2)c1] |
| 295 | 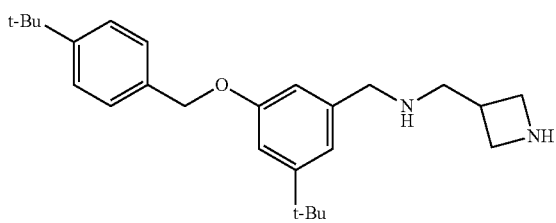 [SMILES: CC(C)(C)c1ccc(COc2cc(CNCC3CNC3)cc(C(C)(C)C)c2)cc1] |
| 296 | 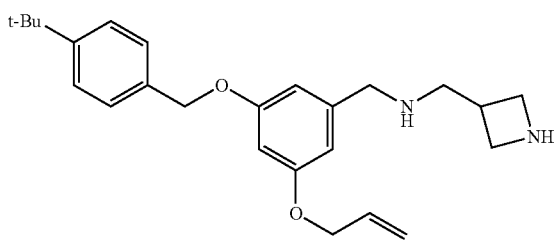 [SMILES: C=CCOc1cc(CNCC2CNC2)cc(OCc2ccc(C(C)(C)C)cc2)c1] |
| 297 | 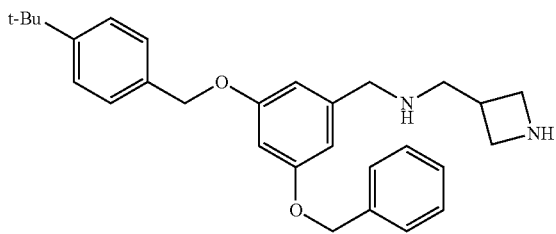 [SMILES: CC(C)(C)c1ccc(COc2cc(CNCC3CNC3)cc(OCc3ccccc3)c2)cc1] |
| 298 | 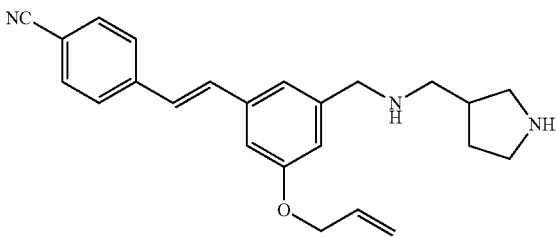 [SMILES: C=CCOc1cc(/C=C/c2ccc(C#N)cc2)cc(CNCC2CCNC2)c1] |

| Example | Formula |
|---------|---------|
| 299 | 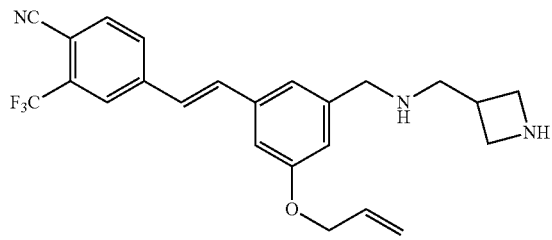 [SMILES: C=CCOc1cc(/C=C/c2ccc(C#N)c(C(F)(F)F)c2)cc(CNCC2CNC2)c1] |
| 300 | 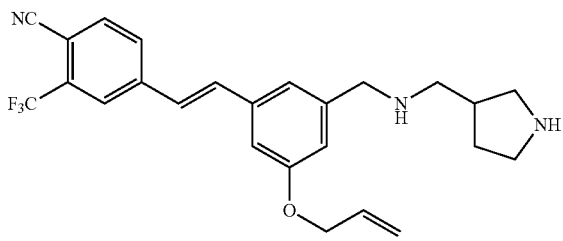 [SMILES: C=CCOc1cc(/C=C/c2ccc(C#N)c(C(F)(F)F)c2)cc(CNCC2CCNC2)c1] |
| 301 | 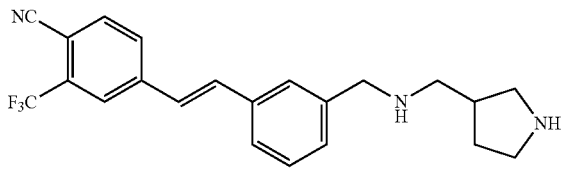 [SMILES: N#Cc1ccc(/C=C/c2cccc(CNCC3CCNC3)c2)cc1C(F)(F)F] |
| 302 | 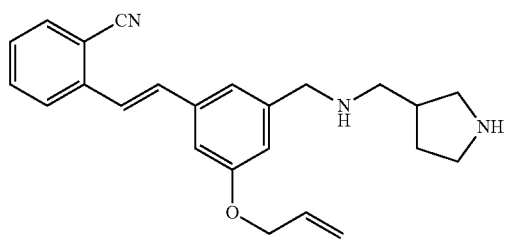 [SMILES: C=CCOc1cc(/C=C/c2ccccc2C#N)cc(CNCC2CCNC2)c1] |
| 305 | 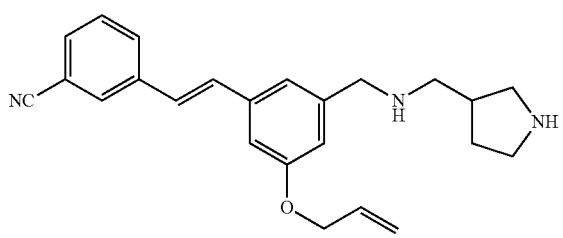 [SMILES: C=CCOc1cc(/C=C/c2cccc(C#N)c2)cc(CNCC2CCNC2)c1] |
| 308 | 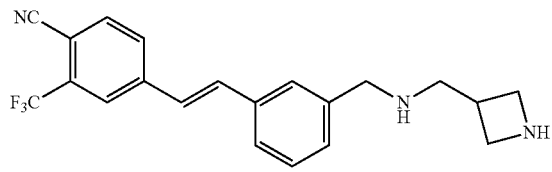 [SMILES: N#Cc1ccc(/C=C/c2cccc(CNCC3CNC3)c2)cc1C(F)(F)F] |
| 309 | 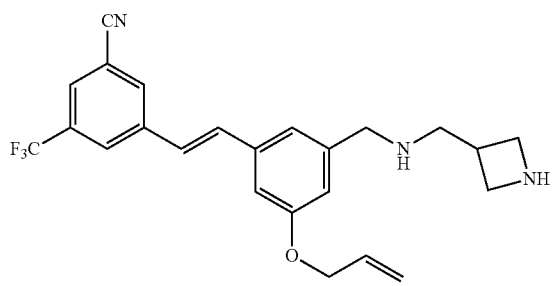 [SMILES: C=CCOc1cc(/C=C/c2cc(C#N)cc(C(F)(F)F)c2)cc(CNCC2CNC2)c1] |

| Example | Formula |
|---|---|
| 310 | 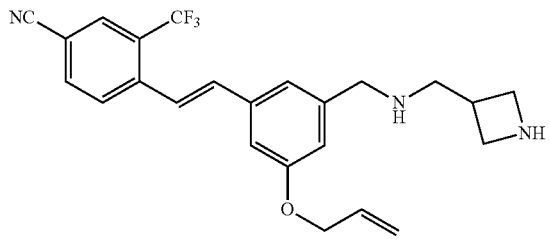 [SMILES: C=CCOc1cc(/C=C/c2ccc(C#N)cc2C(F)(F)F)cc(CNCC2CNC2)c1] |
| 311 | 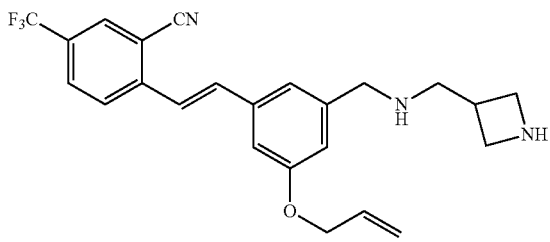 [SMILES: C=CCOc1cc(/C=C/c2ccc(C(F)(F)F)cc2C#N)cc(CNCC2CNC2)c1] |
| 312 | 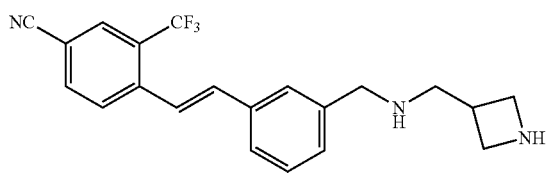 [SMILES: N#Cc1ccc(/C=C/c2cccc(CNCC3CNC3)c2)c(C(F)(F)F)c1] |
| 313 | 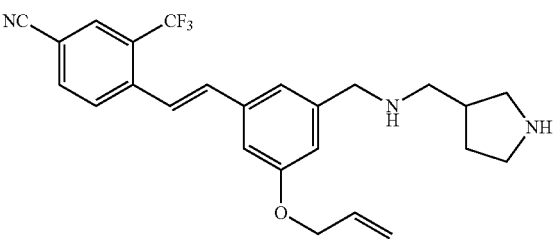 [SMILES: C=CCOc1cc(/C=C/c2ccc(C#N)cc2C(F)(F)F)cc(CNCC2CCNC2)c1] |
| 314 | 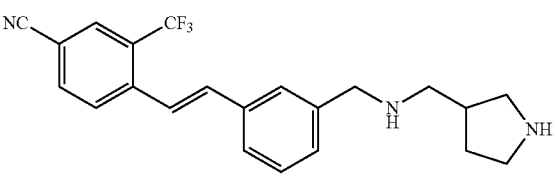 [SMILES: N#Cc1ccc(/C=C/c2cccc(CNCC3CCNC3)c2)c(C(F)(F)F)c1] |
| 321 | 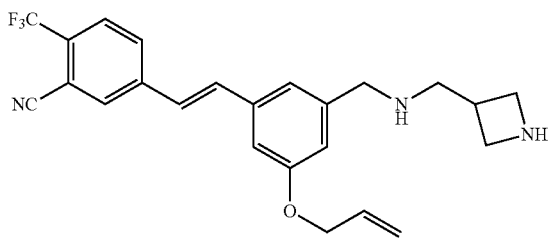 [SMILES: C=CCOc1cc(/C=C/c2ccc(C(F)(F)F)c(C#N)c2)cc(CNCC2CNC2)c1] |
| 322 | 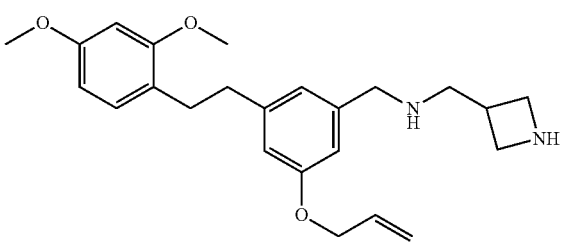 [SMILES: C=CCOc1cc(CCc2ccc(OC)cc2OC)cc(CNCC2CNC2)c1] |

-continued
| Example | Formula |
|---|---|
| 323 | 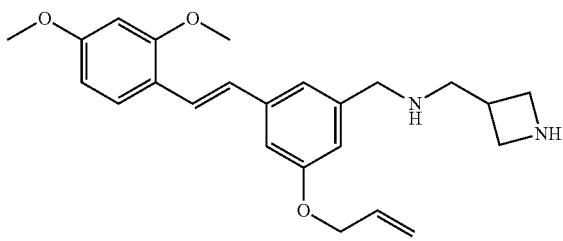 [SMILES: C=CCOc1cc(/C=C/c2ccc(OC)cc2OC)cc(CNCC2CNC2)c1] |
| 328 | 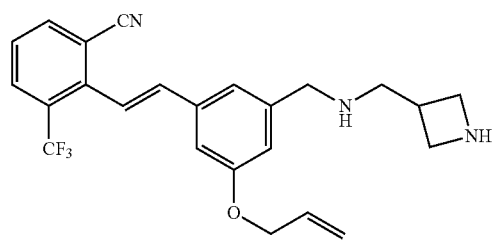 [SMILES: C=CCOc1cc(/C=C/c2c(C#N)cccc2C(F)(F)F)cc(CNCC2CNC2)c1] |
| 331 | 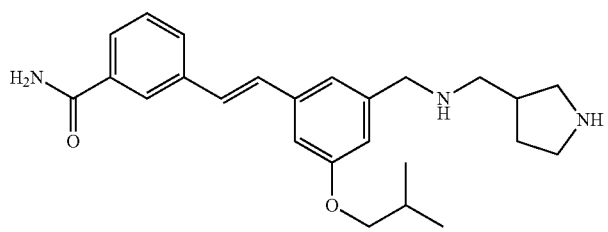 [SMILES: CC(C)COc1cc(/C=C/c2cccc(C(N)=O)c2)cc(CNCC2CCNC2)c1] |
| 337 | 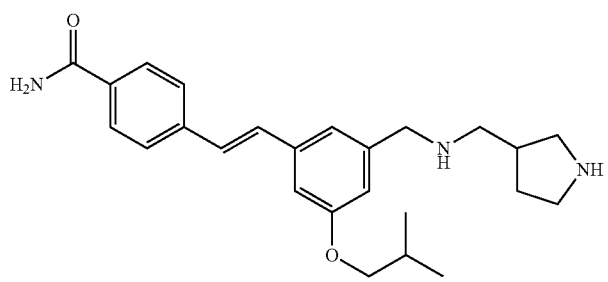 [SMILES: CC(C)COc1cc(/C=C/c2ccc(C(N)=O)cc2)cc(CNCC2CCNC2)c1] |
| 339 | 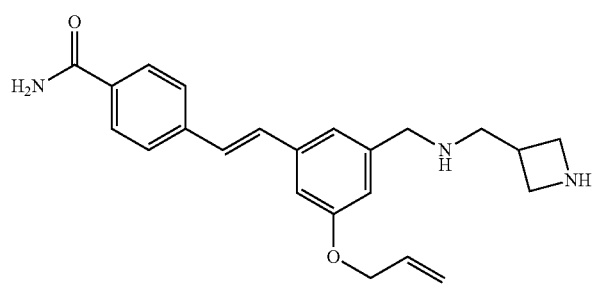 [SMILES: C=CCOc1cc(/C=C/c2ccc(C(N)=O)cc2)cc(CNCC2CNC2)c1] |
| 340 | 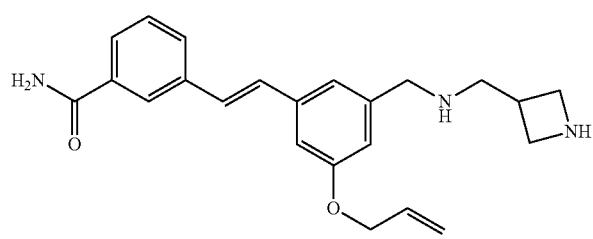 [SMILES: C=CCOc1cc(/C=C/c2cccc(C(N)=O)c2)cc(CNCC2CNC2)c1] |

| Example | Formula |
|---|---|
| 341 | 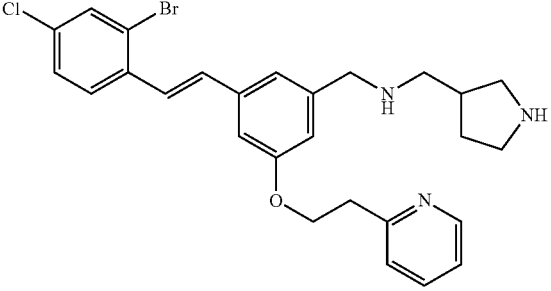 [SMILES: Clc1ccc(/C=C/c2cc(CNCC3CCNC3)cc(OCCc3ccccn3)c2)c(Br)c1] |
| 342 | 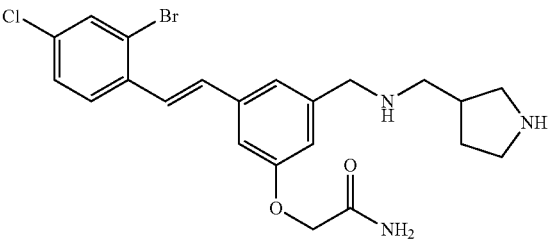 [SMILES: NC(=O)COc1cc(/C=C/c2ccc(Cl)cc2Br)cc(CNCC2CCNC2)c1] |
| 343 | 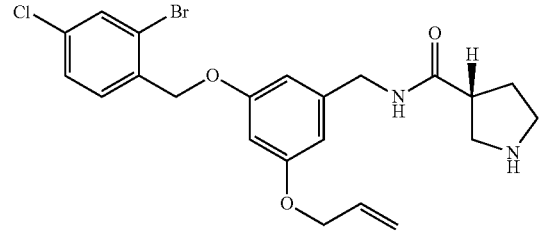 [SMILES: C=CCOc1cc(CNC(=O)[C@@H]2CCNC2)cc(OCc2ccc(Cl)cc2Br)c1] |
| 344 | 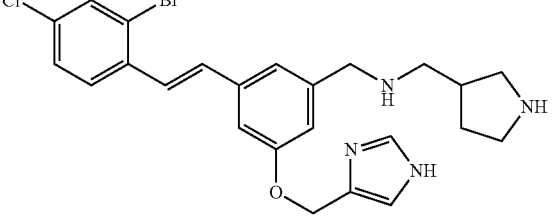 |
| 345 | 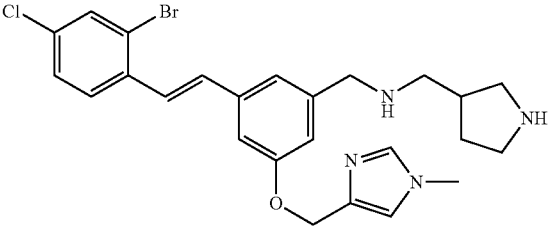 [SMILES: Cn1cnc(COc2cc(/C=C/c3ccc(Cl)cc3Br)cc(CNCC3CCNC3)c2)c1] |
| 346 | 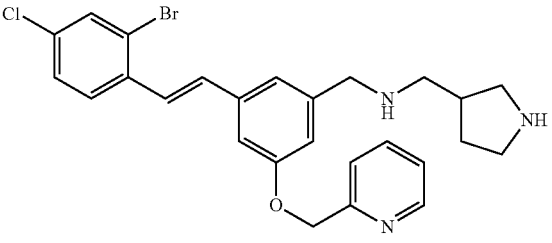 [SMILES: Clc1ccc(/C=C/c2cc(CNCC3CCNC3)cc(OCc3ccccn3)c2)c(Br)c1] |

-continued
| Example | Formula |
|---|---|
| 347 | 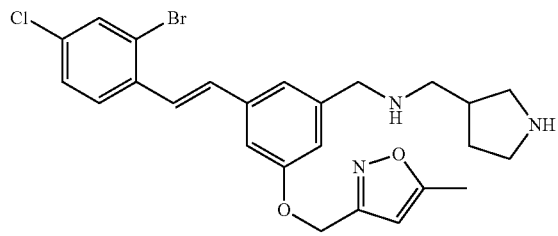 [SMILES: Cc1cc(COc2cc(/C=C/c3ccc(Cl)cc3Br)cc(CNCC3CCNC3)c2)no1] |
| 349 | 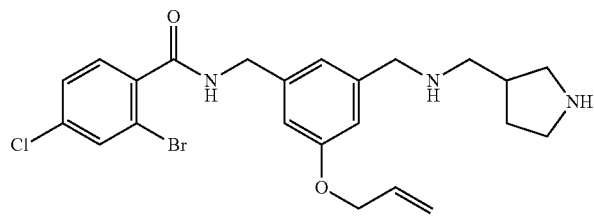 [SMILES: C=CCOc1cc(CNCC2CCNC2)cc(CNC(=O)c2ccc(Cl)cc2Br)c1] |
| 350 | 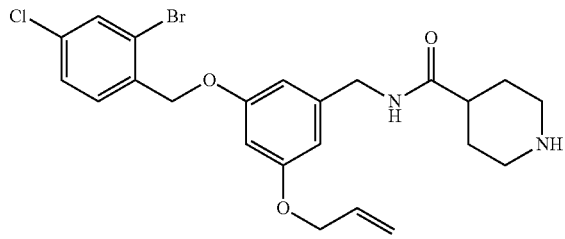 [SMILES: C=CCOc1cc(CNC(=O)C2CCNCC2)cc(OCc2ccc(Cl)cc2Br)c1] |
| 354 | 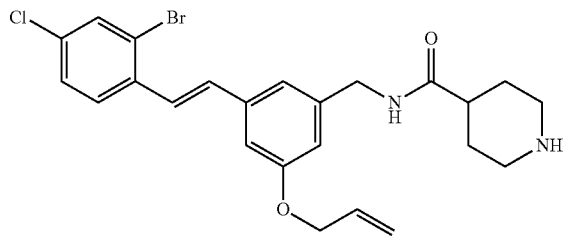 [SMILES: C=CCOc1cc(/C=C/c2ccc(Cl)cc2Br)cc(CNC(=O)C2CCNCC2)c1] |
| 357 | 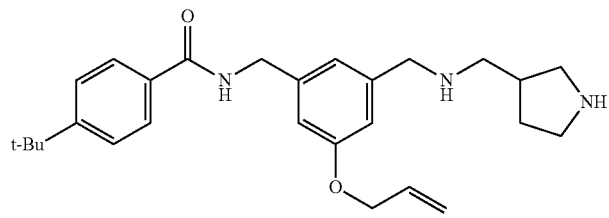 [SMILES: C=CCOc1cc(CNCC2CCNC2)cc(CNC(=O)c2ccc(C(C)(C)C)cc2)c1] |
| 359 | 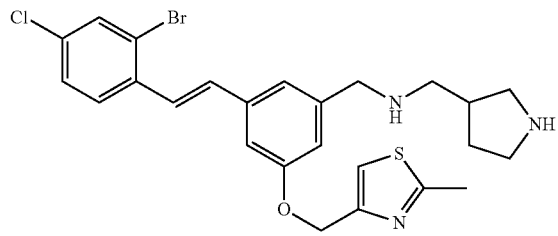 |

| Example | Formula |
|---------|---------|
| 360 | 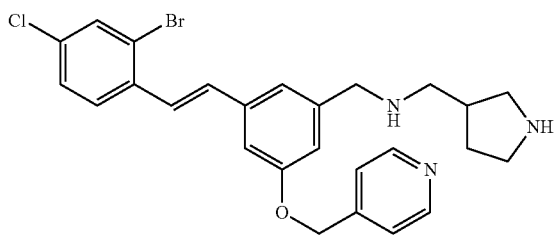 [SMILES: Clc1ccc(/C=C/c2cc(CNCC3CCNC3)cc(OCc3ccncc3)c2)c(Br)c1] |
| 361 | 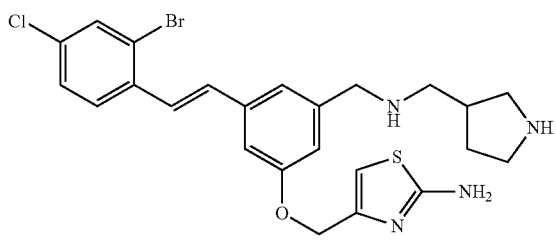 [SMILES: Nc1nc(COc2cc(/C=C/c3ccc(Cl)cc3Br)cc(CNCC3CCNC3)c2)cs1] |
| 364 | 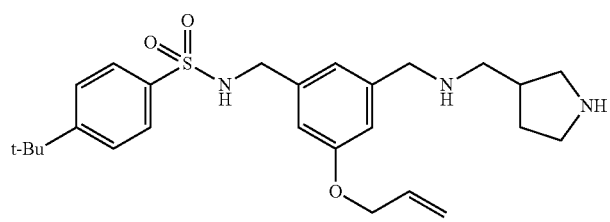 [SMILES: C=CCOc1cc(CNCC2CCNC2)cc(CNS(=O)(=O)c2ccc(C(C)(C)C)cc2)c1] |
| 365 | 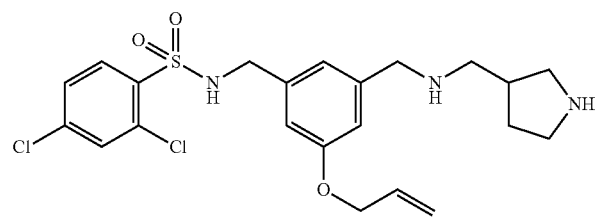 [SMILES: C=CCOc1cc(CNCC2CCNC2)cc(CNS(=O)(=O)c2ccc(Cl)cc2Cl)c1] |
| 366 | 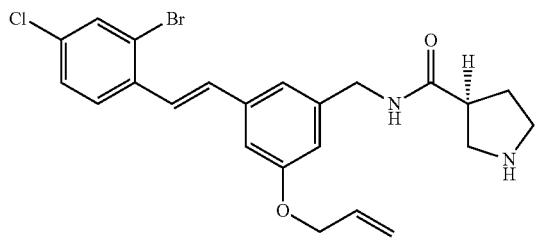 [SMILES: C=CCOc1cc(/C=C/c2ccc(Cl)cc2Br)cc(CNC(=O)[C@H]2CCNC2)c1] |
| 367 | 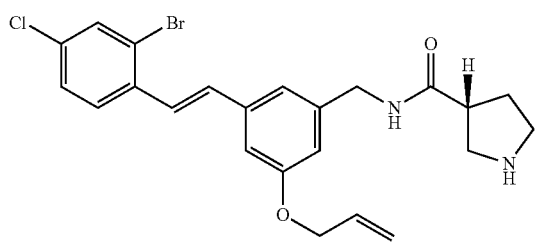 [SMILES: C=CCOc1cc(/C=C/c2ccc(Cl)cc2Br)cc(CNC(=O)[C@@H]2CCNC2)c1] |

-continued
| Example | Formula |
|---|---|
| 369 | 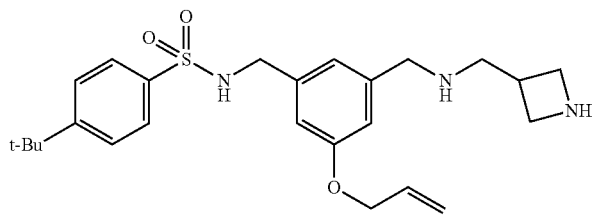 [SMILES: C=CCOc1cc(CNCC2CNC2)cc(CNS(=O)(=O)c2ccc(C(C)(C)C)cc2)c1] |
| 370 | 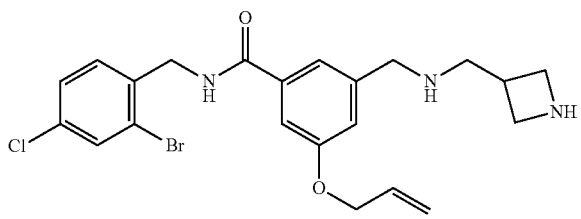 [SMILES: C=CCOc1cc(CNCC2CNC2)cc(C(=O)NCc2ccc(Cl)cc2Br)c1] |
| 371 | 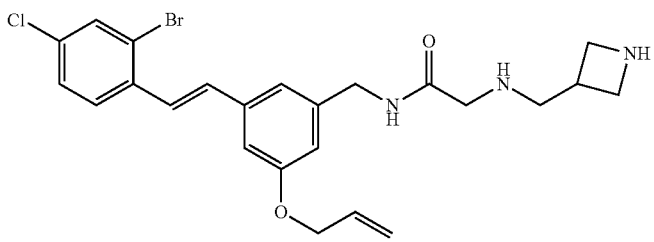 [SMILES: C=CCOc1cc(/C=C/c2ccc(Cl)cc2Br)cc(CNC(=O)CNCC2CNC2)c1] |
| 373 | 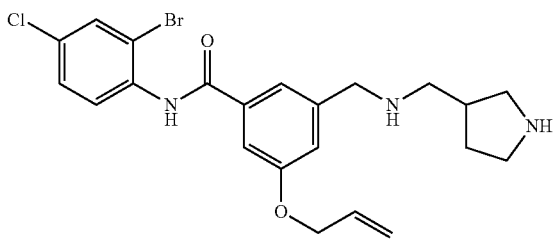 [SMILES: C=CCOc1cc(CNCC2CCNC2)cc(C(=O)Nc2ccc(Cl)cc2Br)c1] |
| 374 | 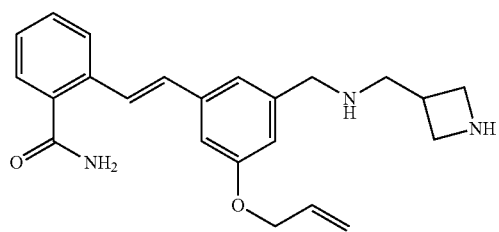 [SMILES: C=CCOc1cc(/C=C/c2ccccc2C(N)=O)cc(CNCC2CNC2)c1] |
| 375 | 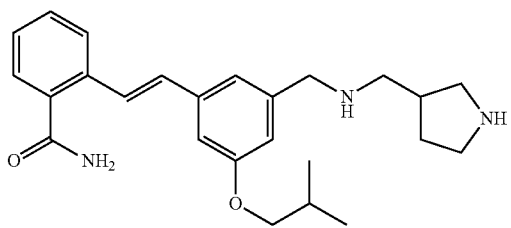 [SMILES: CC(C)COc1cc(/C=C/c2ccccc2C(N)=O)cc(CNCC2CCNC2)c1] |

-continued
| Example | Formula |
|---|---|
| 376 | 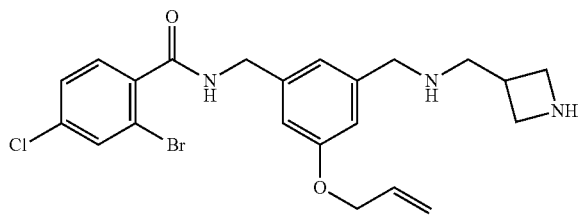 [SMILES: C=CCOc1cc(CNCC2CNC2)cc(CNC(=O)c2ccc(Cl)cc2Br)c1] |
| 377 | 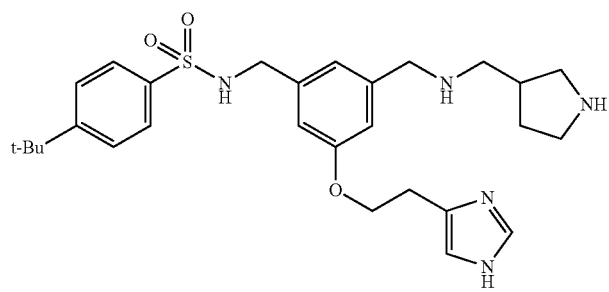 [SMILES: CC(C)(C)c1ccc(S(=O)(=O)NCc2cc(CNCC3CCNC3)cc(OCCc3c[nH]cn3)c2)cc1] |
| 380 | 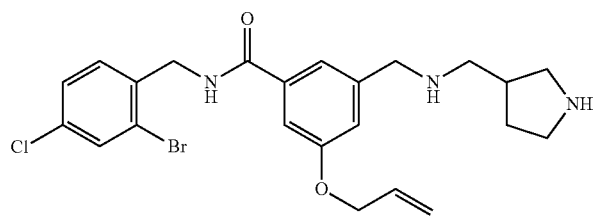 [SMILES: C=CCOc1cc(CNCC2CCNC2)cc(C(=O)NCc2ccc(Cl)cc2Br)c1] |
| 381 | 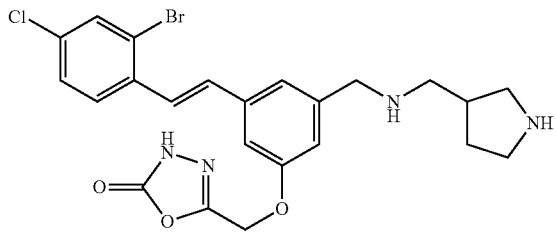 [SMILES: O=c1[nH]nc(COc2cc(/C=C/c3ccc(Cl)cc3Br)cc(CNCC3CCNC3)c2)o1] |
| 382 | 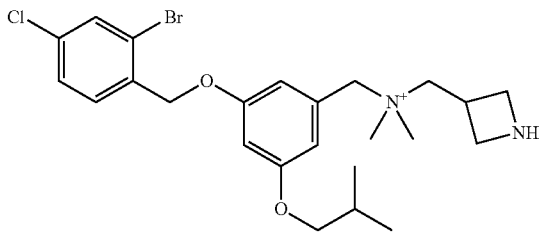 [SMILES: CC(C)COc1cc(C[N+](C)(C)CC2CNC2)cc(OCc2ccc(Cl)cc2Br)c1] |
| 384 | 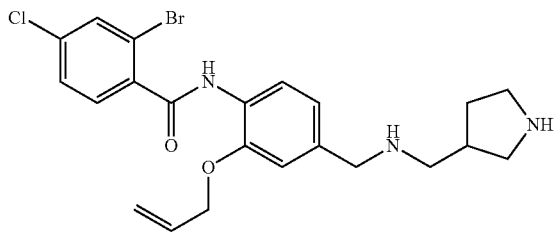 [SMILES: C=CCOc1cc(CNCC2CCNC2)ccc1NC(=O)c1ccc(Cl)cc1Br] |

-continued
| Example | Formula |
|---|---|
| 387 | 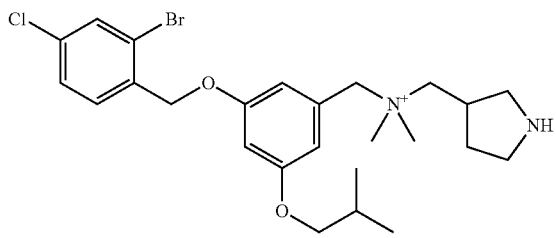 [SMILES: CC(C)COc1cc(C[N+](C)(C)CC2CCNC2)cc(OCc2ccc(Cl)cc2Br)c1] |
| 388 | 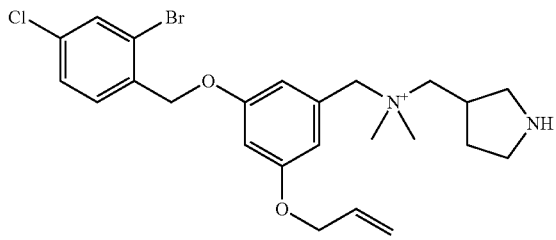 [SMILES: C=CCOc1cc(C[N+](C)(C)CC2CCNC2)cc(OCc2ccc(Cl)cc2Br)c1] |
| 389 | 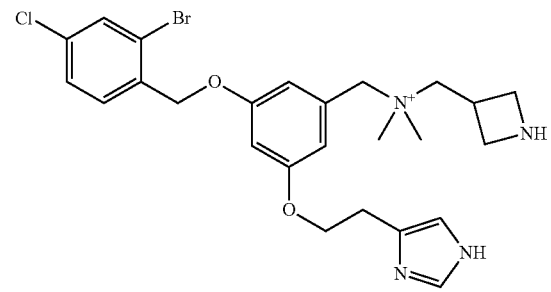 [SMILES: C[N+](C)(Cc1cc(OCCc2c[nH]cn2)cc(OCc2ccc(Cl)cc2Br)c1)CC1CNC1] |
| 390 | 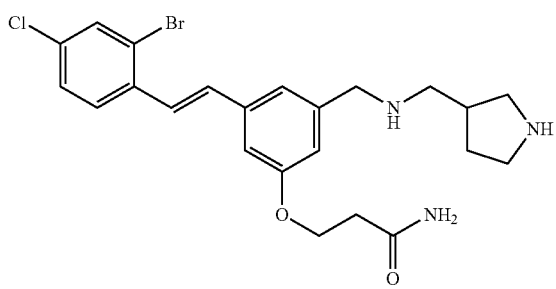 [SMILES: NC(=O)CCOc1cc(/C=C/c2ccc(Cl)cc2Br)cc(CNCC2CCNC2)c1] |
| 393 | 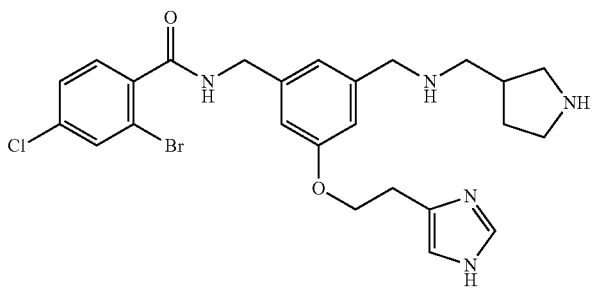 [SMILES: O=C(NCc1cc(CNCC2CCNC2)cc(OCCc2c[nH]cn2)c1)c1ccc(Cl)cc1Br] |
| 394 | 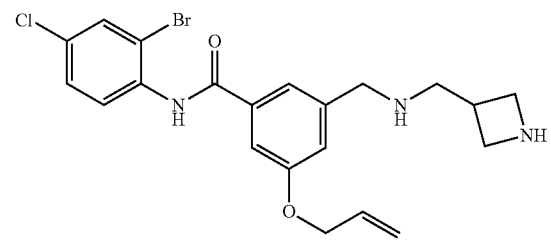 [SMILES: C=CCOc1cc(CNCC2CNC2)cc(C(=O)Nc2ccc(Cl)cc2Br)c1] |

-continued
| Example | Formula |
|---------|---------|
| 395 | 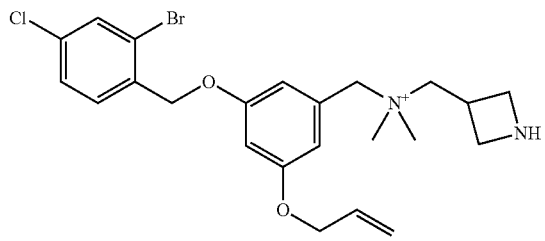 [SMILES: C=CCOc1cc(C[N+](C)(C)CC2CNC2)cc(OCc2ccc(Cl)cc2Br)c1] |
| 396 | 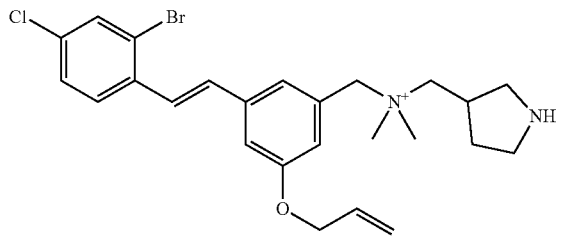 [SMILES: C=CCOc1cc(/C=C/c2ccc(Cl)cc2Br)cc(C[N+](C)(C)CC2CCNC2)c1] |
| 397 | 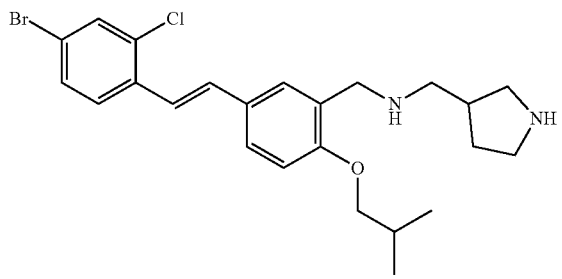 |
| 398 | 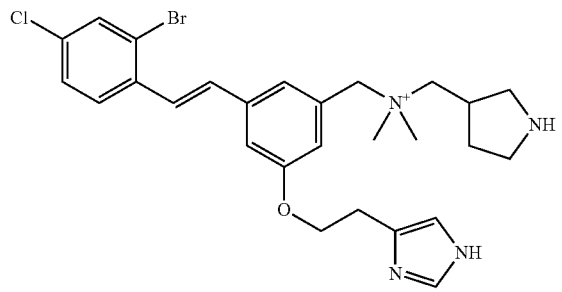 [SMILES: C[N+](C)(Cc1cc(/C=C/c2ccc(Cl)cc2Br)cc(OCCc2c[nH]cn2)c1)CC1CCNC1] |
| 399 | 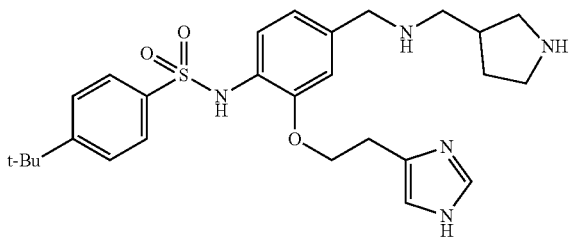 [SMILES: CC(C)(C)c1ccc(S(=O)(=O)Nc2ccc(CNCC3CCNC3)cc2OCCc2c[nH]cn2)cc1] |
| 401 | 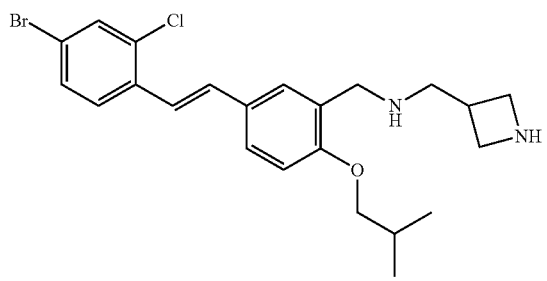 [SMILES: CC(C)COc1ccc(/C=C/c2ccc(Br)cc2Cl)cc1CNCC1CNC1] |

| Example | Formula |
|---|---|
| 402 | 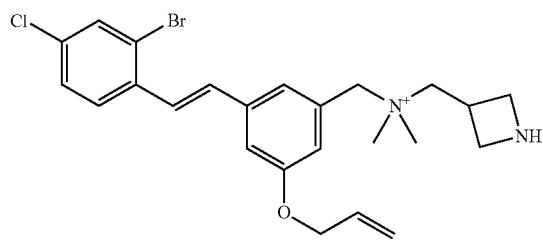 [SMILES: C=CCOc1cc(/C=C/c2ccc(Cl)cc2Br)cc(C[N+](C)(C)CC2CNC2)c1] |
| 403 | 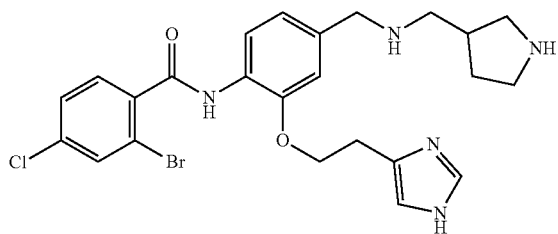 [SMILES: O=C(Nc1ccc(CNCC2CCNC2)cc1OCCc1c[nH]cn1)c1ccc(Cl)cc1Br] |
| 404 | 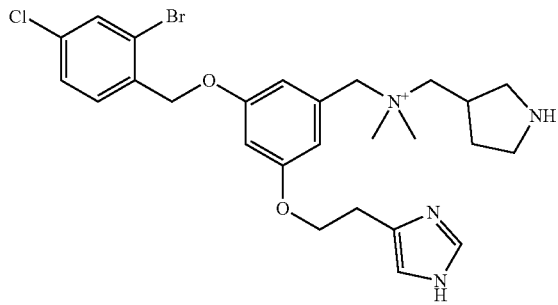 [SMILES: C[N+](C)(Cc1cc(OCCc2c[nH]cn2)cc(OCc2ccc(Cl)cc2Br)c1)CC1CCNC1] |
| 405 | 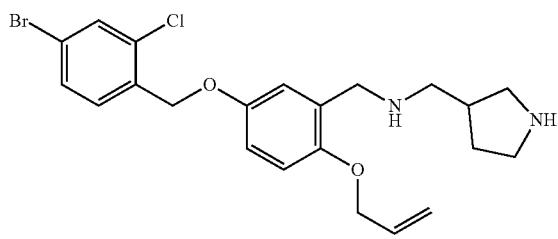 [SMILES: C=CCOc1ccc(OCc2ccc(Br)cc2Cl)cc1CNCC1CCNC1] |
| 406 | 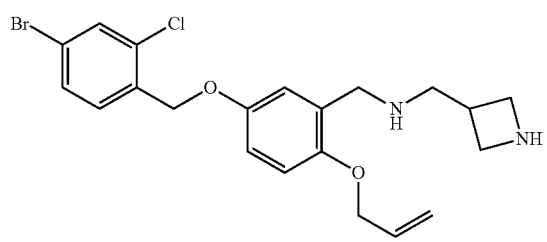 |
| 407 | 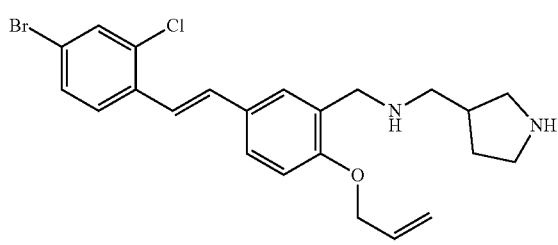 |

-continued
| Example | Formula |
|---|---|
| 408 | 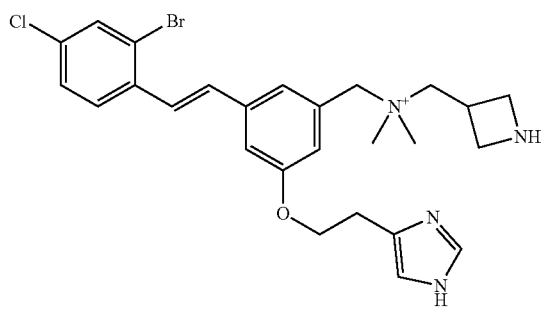 [SMILES: C[N+](C)(Cc1cc(/C=C/c2ccc(Cl)cc2Br)cc(OCCc2c[nH]cn2)c1)CC1CNC1] |
| 412 | 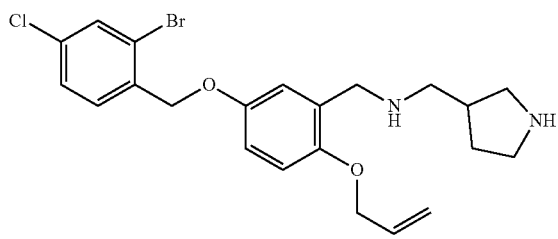 [SMILES: C=CCOc1ccc(OCc2ccc(Cl)cc2Br)cc1CNCC1CCNC1] |
| 413 | 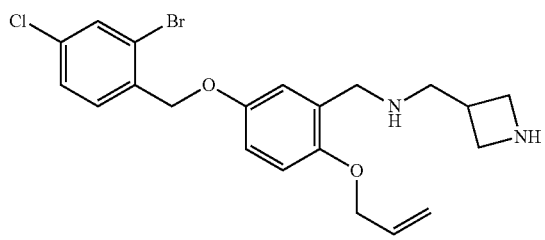 [SMILES: C=CCOc1ccc(OCc2ccc(Cl)cc2Br)cc1CNCC1CNC1] |
| 416 | 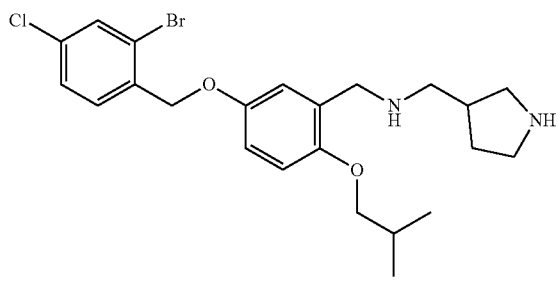 [SMILES: CC(C)COc1ccc(OCc2ccc(Cl)cc2Br)cc1CNCC1CCNC1] |
| 419 | 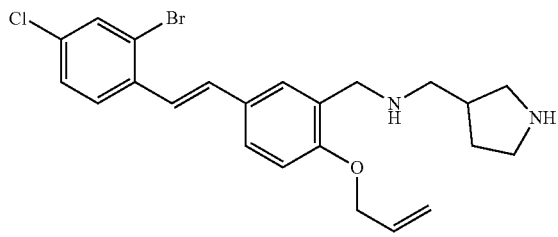 [SMILES: C=CCOc1ccc(/C=C/c2ccc(Cl)cc2Br)cc1CNCC1CCNC1] |
| 421 | 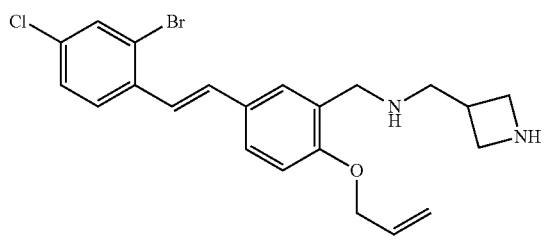 [SMILES: C=CCOc1ccc(/C=C/c2ccc(Cl)cc2Br)cc1CNCC1CNC1] |

| Example | Formula |
|---|---|
| 422 | 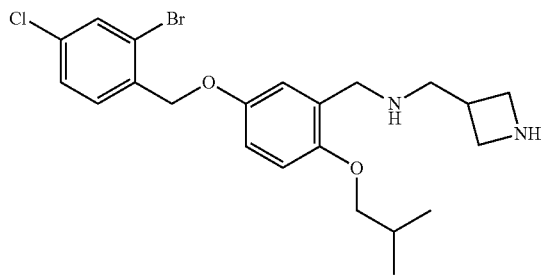 [SMILES: CC(C)COc1ccc(OCc2ccc(Cl)cc2Br)cc1CNCC1CNC1] |
| 426 | 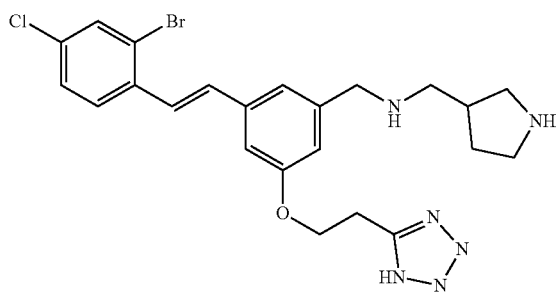 [SMILES: Clc1ccc(/C=C/c2cc(CNCC3CCNC3)cc(OCCC3=NNNN3)c2)c(Br)c1] |
| 429 | 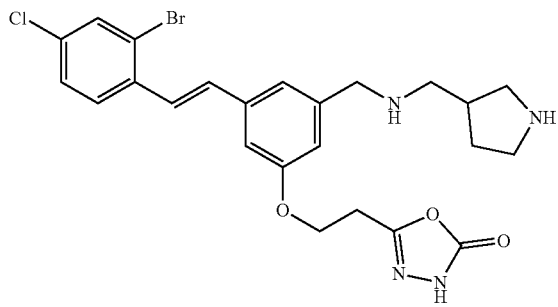 [SMILES: O=c1[nH]nc(CCOc2cc(/C=C/c3ccc(Cl)cc3Br)cc(CNCC3CCNC3)c2)o1] |
| 430 | 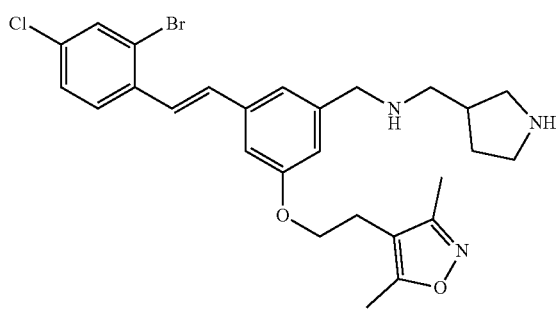 [SMILES: Cc1noc(C)c1CCOc1cc(/C=C/c2ccc(Cl)cc2Br)cc(CNCC2CCNC2)c1] |
| 431 | 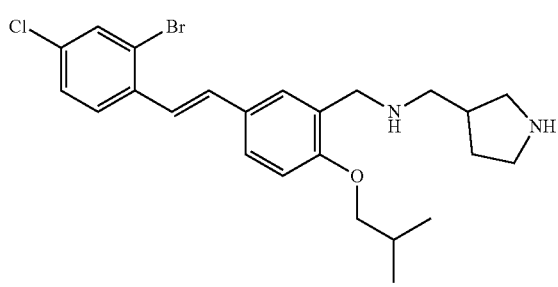 [SMILES: CC(C)COc1ccc(/C=C/c2ccc(Cl)cc2Br)cc1CNCC1CCNC1] |

-continued
| Example | Formula |
|---|---|
| 432 | 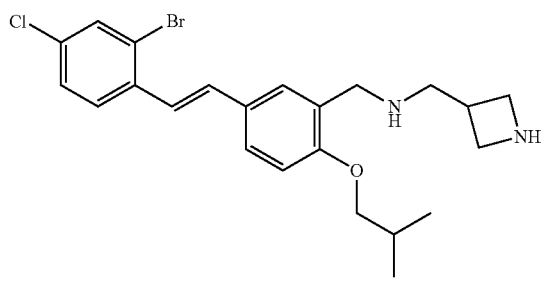 [SMILES: CC(C)COc1ccc(/C=C/c2ccc(Cl)cc2Br)cc1CNCC1CNC1] |
| 433 | 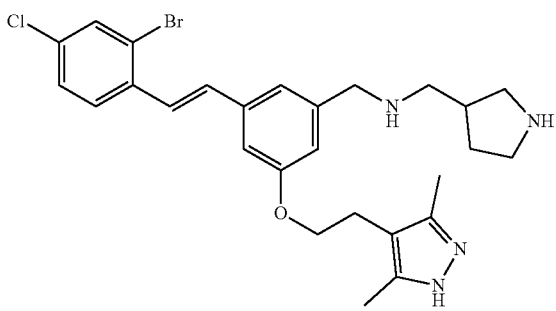 [SMILES: Cc1n[nH]c(C)c1CCOc1cc(/C=C/c2ccc(Cl)cc2Br)cc(CNCC2CCNC2)c1] |
| 434 | 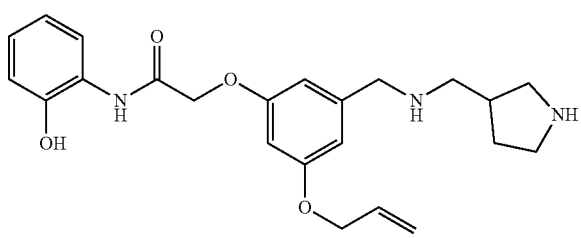 [SMILES: C=CCOc1cc(CNCC2CCNC2)cc(OCC(=O)Nc2ccccc2O)c1] |
| 443 | 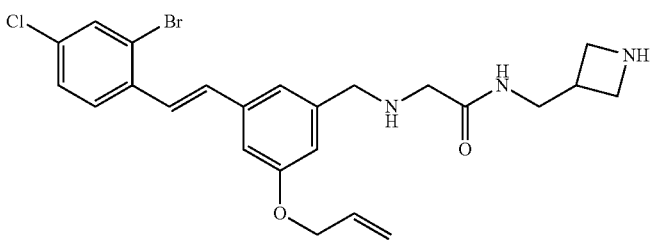 [SMILES: C=CCOc1cc(/C=C/c2ccc(Cl)cc2Br)cc(CNCC(=O)NCC2CNC2)c1] |
| 444 | 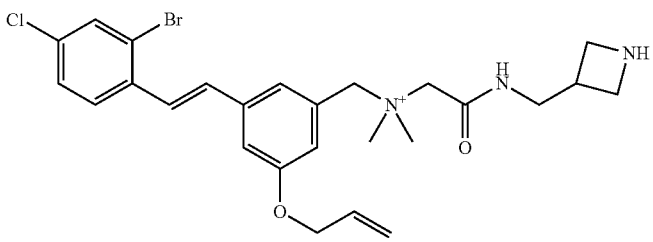 [SMILES: C=CCOc1cc(/C=C/c2ccc(Cl)cc2Br)cc(C[N+](C)(C)CC(=O)NCC2CNC2)c1] |
| 445 | 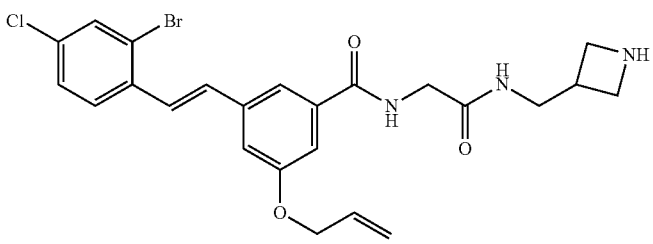 [SMILES: C=CCOc1cc(/C=C/c2ccc(Cl)cc2Br)cc(C(=O)NCC(=O)NCC2CNC2)c1] |

-continued
| Example | Formula |
|---|---|
| 447 | 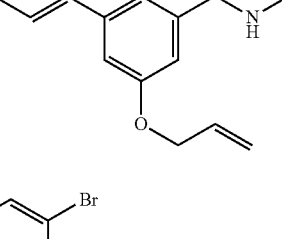 |
| 448 | 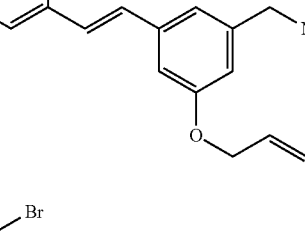 |
| 450 | 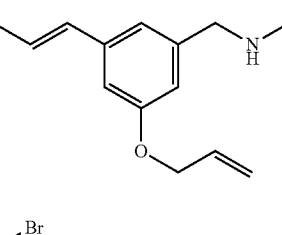 |
| 451 | 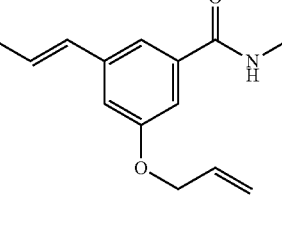 |
| 452 | 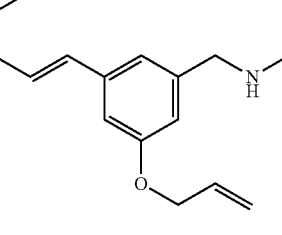 |
| 453 | 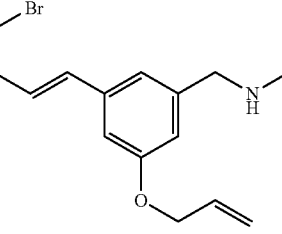 |

| Example | Formula |
|---------|---------|
| 454 | 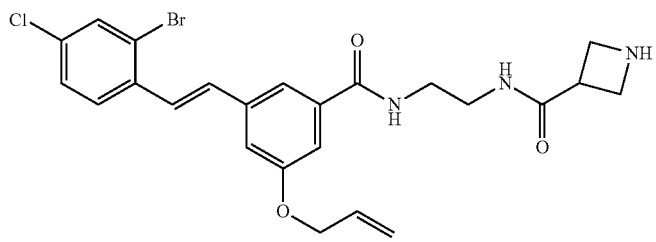 [SMILES: C=CCOc1cc(/C=C/c2ccc(Cl)cc2Br)cc(C(=O)NCCNC(=O)C2CNC2)c1] |
| 455 | 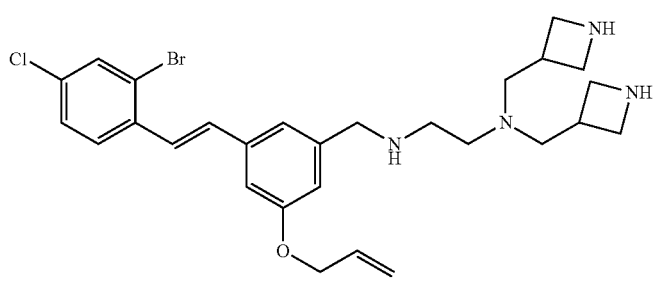 [SMILES: C=CCOc1cc(/C=C/c2ccc(Cl)cc2Br)cc(CNCCN(CC2CNC2)CC2CNC2)c1] |
| 456 | 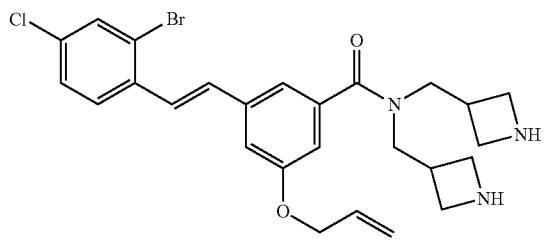 [SMILES: C=CCOc1cc(/C=C/c2ccc(Cl)cc2Br)cc(C(=O)N(CC2CNC2)CC2CNC2)c1] |
| 463 | 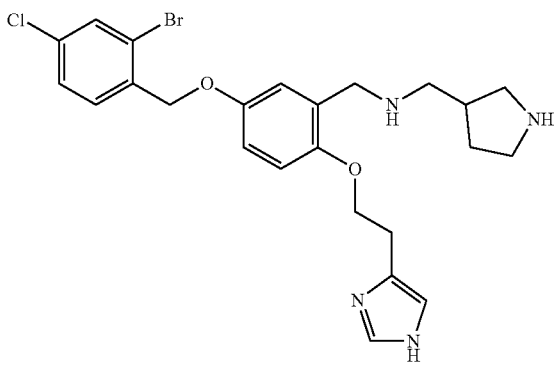 [SMILES: Clc1ccc(COc2ccc(OCCc3c[nH]cn3)c(CNCC3CCNC3)c2)c(Br)c1] |
| 464 | 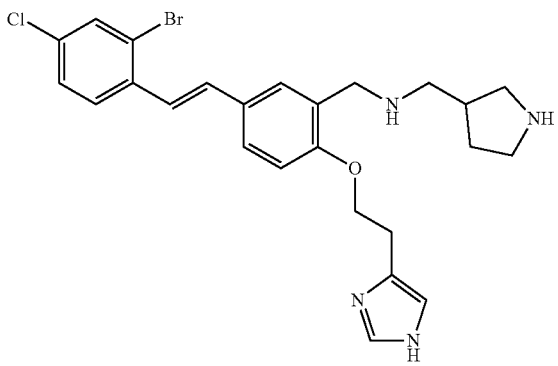 [SMILES: Clc1ccc(/C=C/c2ccc(OCCc3c[nH]cn3)c(CNCC3CCNC3)c2)c(Br)c1] |

-continued
| Example | Formula |
|---|---|
| 465 | 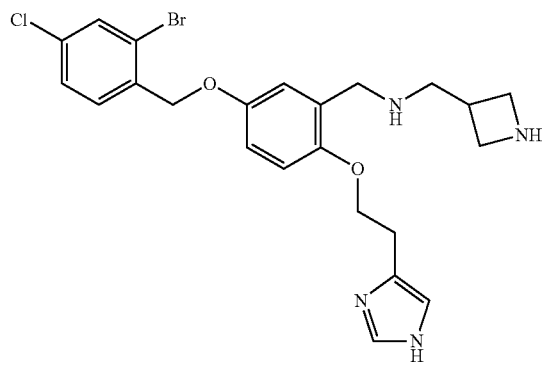 [SMILES: Clc1ccc(COc2ccc(OCCc3c[nH]cn3)c(CNCC3CNC3)c2)c(Br)c1] |
| 471 | 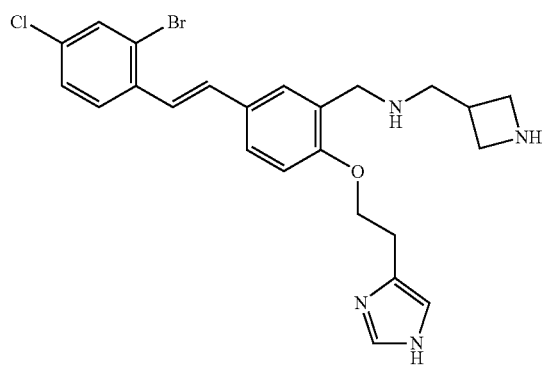 [SMILES: Clc1ccc(/C=C/c2ccc(OCCc3c[nH]cn3)c(CNCC3CNC3)c2)c(Br)c1] |
| 476 | 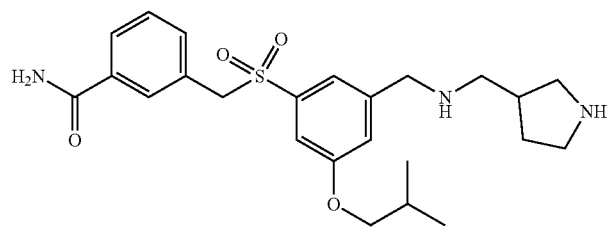 [SMILES: CC(C)COc1cc(CNCC2CCNC2)cc(S(=O)(=O)Cc2cccc(C(N)=O)c2)c1] |
| 477 | 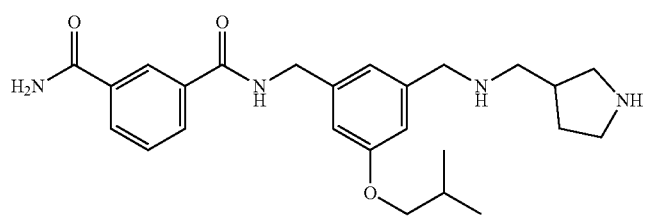 [SMILES: CC(C)COc1cc(CNCC2CCNC2)cc(CNC(=O)c2cccc(C(N)=O)c2)c1] |
| 487 | 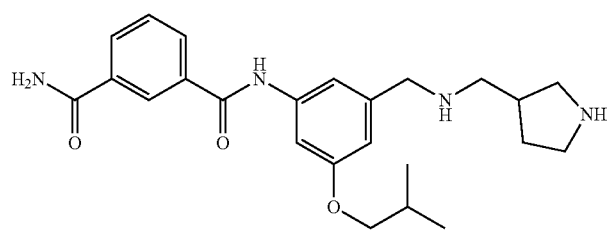 [SMILES: CC(C)COc1cc(CNCC2CCNC2)cc(NC(=O)c2cccc(C(N)=O)c2)c1] |
| 489 | 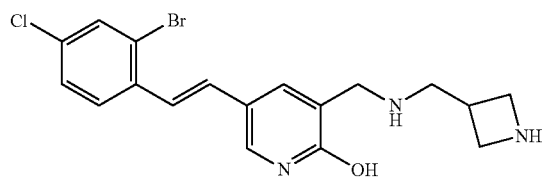 [SMILES: Oc1ncc(/C=C/c2ccc(Cl)cc2Br)cc1CNCC1CNC1] |

| Example | Formula |
|---|---|
| 504 | 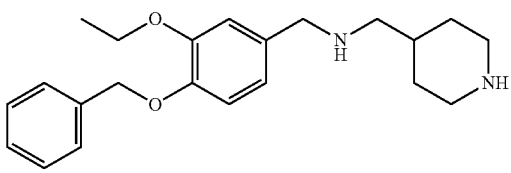 [SMILES: CCOc1cc(CNCC2CCNCC2)ccc1OCc1ccccc1] |
| 509 | 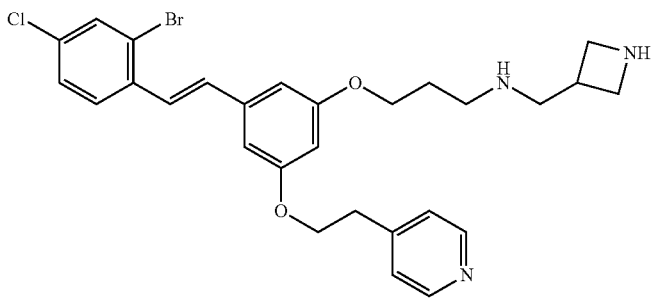 [SMILES: Clc1ccc(/C=C/c2cc(OCCCNCC3CNC3)cc(OCCc3ccncc3)c2)c(Br)c1] |
| 512 | 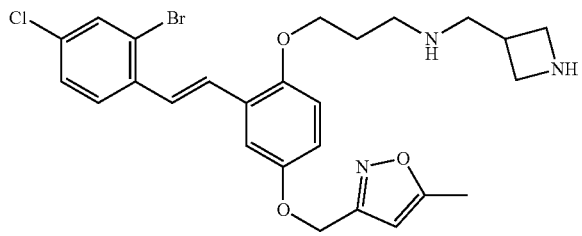 [SMILES: Cc1cc(COc2ccc(OCCCNCC3CNC3)c(/C=C/c3ccc(Cl)cc3Br)c2)no1] |
| 513 | 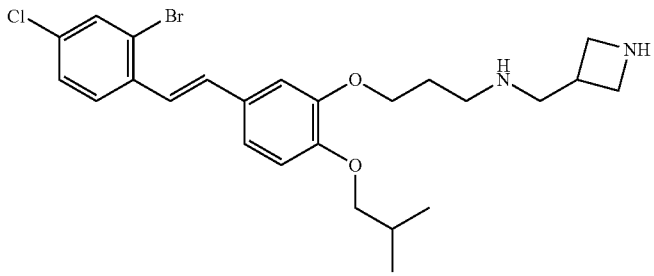 [SMILES: CC(C)COc1ccc(/C=C/c2ccc(Cl)cc2Br)cc1OCCCNCC1CNC1] |
| 514 | 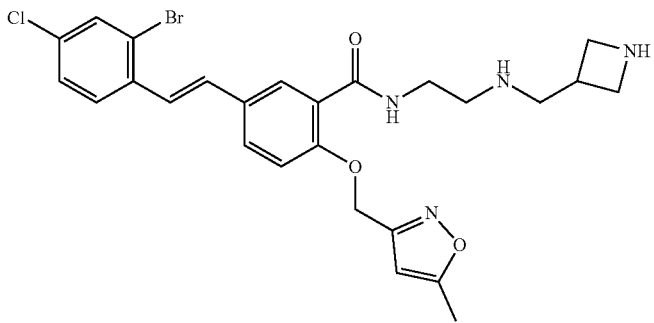 [SMILES: Cc1cc(COc2ccc(/C=C/c3ccc(Cl)cc3Br)cc2C(=O)NCCNCC2CNC2)no1] |

| Example | Formula |
|---------|---------|
| 515 | |
| 516 | |
| 517 | |
| 518 | |
| 519 | |

-continued
| Example | Formula |
|---|---|
| 520 | 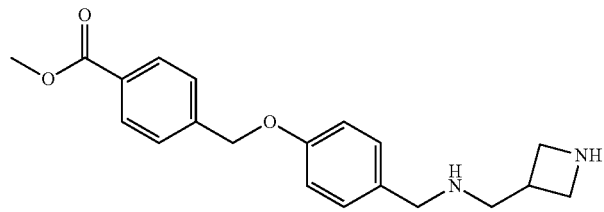 [SMILES: COC(=O)c1ccc(COc2ccc(CNCC3CNC3)cc2)cc1] |
| 522 | 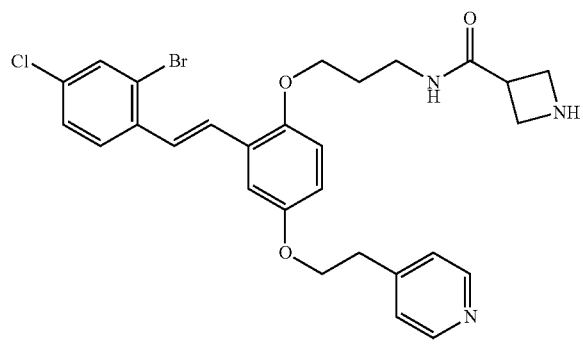 [SMILES: O=C(NCCCOc1ccc(OCCc2ccncc2)cc1/C=C/c1ccc(Cl)cc1Br)C1CNC1] |
| 523 | 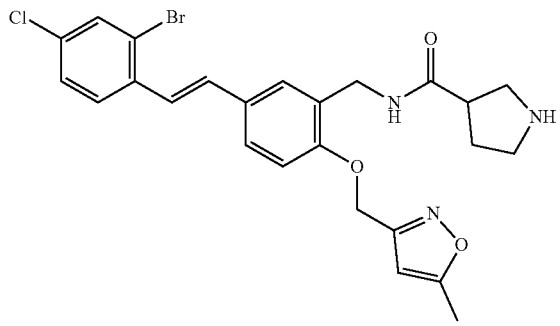 [SMILES: Cc1cc(COc2ccc(/C=C/c3ccc(Cl)cc3Br)cc2CNC(=O)C2CCNC2)no1] |
| 524 | 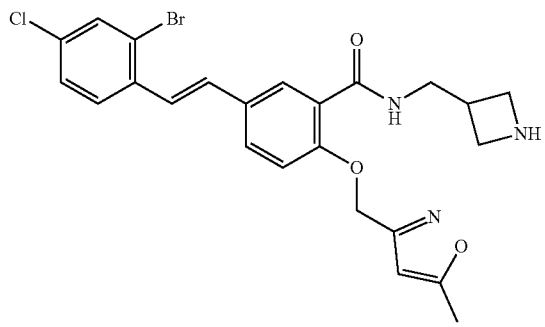 [SMILES: C/C(O)=C/C(=N)COc1ccc(/C=C/c2ccc(Cl)cc2Br)cc1C(=O)NCC1CNC1] |
| 525 | 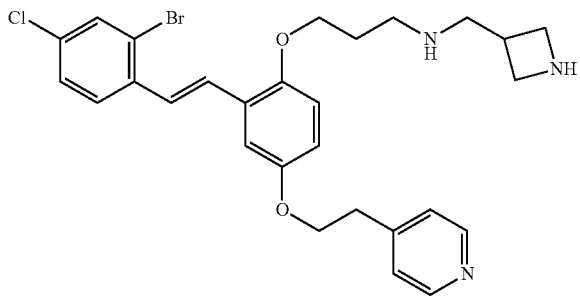 [SMILES: Clc1ccc(/C=C/c2cc(OCCc3ccncc3)ccc2OCCCNCC2CNC2)c(Br)c1] | or pharmaceutically acceptable salt, solvate or hydrate thereof.

47. A pharmaceutical composition according to claim 31, wherein the compound is a compound as defined in claim 46.

48. A method of treating a subject according to claim 41, wherein the compound is a compound as defined in claim 46.

* * * * *